(12) United States Patent
Mizojiri et al.

(10) Patent No.: US 7,659,263 B2
(45) Date of Patent: Feb. 9, 2010

(54) THIENOPYRROLE COMPOUND AND USE THEREOF AS HCV POLYMERASE INHIBITOR

(75) Inventors: Ryo Mizojiri, Takatsuki (JP); Takahiro Oka, Takatsuki (JP); Kenta Aoki, Takatsuki (JP); Satoru Noji, Takatsuki (JP); Yoko Matsumoto, Takatsuki (JP); Toshihiro Sato, Takatsuki (JP); Izuru Ando, Takatsuki (JP); Yasushi Niwa, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 383 days.

(21) Appl. No.: 11/271,136

(22) Filed: Nov. 10, 2005

(65) Prior Publication Data

US 2006/0167246 A1 Jul. 27, 2006

Related U.S. Application Data

(60) Provisional application No. 60/630,597, filed on Nov. 23, 2004.

(30) Foreign Application Priority Data

Nov. 12, 2004 (JP) .............................. 2004-329780

(51) Int. Cl.
| | | |
|---|---|---|
| A61P 1/16 | (2006.01) | |
| A61P 31/12 | (2006.01) | |
| A61P 43/00 | (2006.01) | |
| A61K 31/553 | (2006.01) | |
| A61K 31/5517 | (2006.01) | |
| C07D 498/12 | (2006.01) | |
| C07D 267/02 | (2006.01) | |
| C07D 495/14 | (2006.01) | |

(52) U.S. Cl. .................... 514/211.1; 514/219; 540/467; 540/480; 540/494; 540/546; 540/555

(58) Field of Classification Search .............. 514/211.1, 514/219; 540/467, 480, 494, 546, 555
See application file for complete search history.

(56) References Cited

U.S. PATENT DOCUMENTS

| | | | |
|---|---|---|---|
| 5,620,973 A | 4/1997 | Goto et al. | |
| 5,633,388 A | 5/1997 | Diana et al. | |
| 5,814,642 A | 9/1998 | Goto et al. | |
| 5,830,905 A | 11/1998 | Diana et al. | |
| 5,866,684 A | 2/1999 | Attwood et al. | |
| 5,932,743 A | 8/1999 | Collini et al. | |
| 5,990,276 A | 11/1999 | Zhang et al. | |
| 6,127,384 A | 10/2000 | Diana et al. | |
| 6,387,938 B1 | 5/2002 | Mizuguchi et al. | |
| 6,727,267 B2 | 4/2004 | Jaen et al. | |
| 6,770,666 B2 | 8/2004 | Hashimoto et al. | |
| 6,809,101 B2 | 10/2004 | Fujishita et al. | |
| 6,867,284 B1 | 3/2005 | Matassa et al. | |
| 7,091,209 B2 | 8/2006 | Gardelli et al. | |
| 7,153,848 B2 | 12/2006 | Hudyma et al. | |
| 7,285,551 B2 | 10/2007 | Hashimoto et al. | |
| 7,348,425 B2 | 3/2008 | Hudyma et al | |
| 7,399,758 B2 | 7/2008 | Meanwell et al | |
| 7,452,876 B2 | 11/2008 | Yeung et al. | |
| 7,456,166 B2 | 11/2008 | Bender et al. | |
| 7,456,167 B2 | 11/2008 | Bergstrom | |
| 7,485,633 B2 | 2/2009 | Meanwell et al. | |
| 2004/0082635 A1 | 4/2004 | Hashimoto et al. | |
| 2004/0097438 A1 | 5/2004 | Hashimoto et al. | |
| 2006/0046983 A1 | 3/2006 | Hudyma et al. | |
| 2006/0100262 A1 | 5/2006 | Conte et al. | |
| 2006/0167246 A1 | 7/2006 | Mizojiri et al. | |
| 2007/0049593 A1 | 3/2007 | Oka et al. | |
| 2007/0185083 A1 | 8/2007 | Bergstrom et al. | |
| 2007/0270406 A1 | 11/2007 | Gentles et al. | |
| 2007/0275930 A1 | 11/2007 | Gentles et al. | |
| 2008/0045498 A1 | 2/2008 | Griffith et al. | |
| 2008/0146537 A1 | 6/2008 | Bender et al. | |
| 2008/0153895 A1 | 6/2008 | Stansfield et al. | |
| 2008/0171015 A1 | 7/2008 | Bender et al. | |

(Continued)

FOREIGN PATENT DOCUMENTS

EP 0 145 095 A2 6/1985

(Continued)

OTHER PUBLICATIONS

Battistuzzi et al., *Organic Letters*, 4(8): 1355-1358 (2002).

(Continued)

*Primary Examiner*—Brenda L Coleman
(74) *Attorney, Agent, or Firm*—Leydig, Voit & Mayer, Ltd.

(57) ABSTRACT

The present invention relates to a thienopyrrole compound represented by the following formula [I]

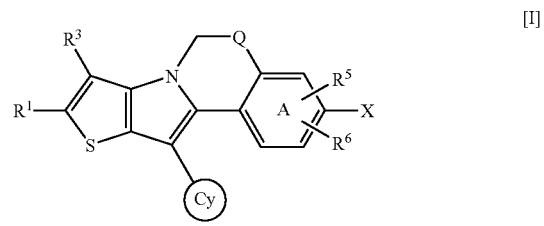

wherein each symbol is as defined in the specification, or a pharmaceutically acceptable a salt thereof, and a hepatitis C virus (HCV) polymerase inhibitor and a therapeutic agent for hepatitis C containing this compound as an active ingredient. The compound of the present invention shows an anti-HCV activity based on the HCV polymerase inhibitory activity, and useful as an agent for the prophylaxis or treatment of hepatitis C.

25 Claims, No Drawings

U.S. PATENT DOCUMENTS

| | | |
|---|---|---|
| 2008/0188458 A1 | 8/2008 | Yeung et al. |
| 2008/0214522 A1 | 9/2008 | Stansfield et al. |
| 2008/0221090 A1 | 9/2008 | Yeung et al. |
| 2008/0226590 A1 | 9/2008 | Bender et al. |
| 2008/0226591 A1 | 9/2008 | Gentles et al. |
| 2008/0226592 A1 | 9/2008 | Yeung et al. |
| 2008/0226593 A1 | 9/2008 | Hewawasam et al. |
| 2008/0227769 A1 | 9/2008 | Gentles et al. |
| 2009/0036444 A1 | 2/2009 | Mizojiri et al. |
| 2009/0042860 A1 | 2/2009 | Bergstrom et al. |
| 2009/0074715 A1 | 3/2009 | Martin et al. |

FOREIGN PATENT DOCUMENTS

| | | |
|---|---|---|
| EP | 0 226 508 A1 | 6/1987 |
| EP | 0 906 097 | 4/1999 |
| EP | 0 932 617 B1 | 8/1999 |
| EP | 1 162 196 A1 | 12/2001 |
| EP | 1 688 420 A1 | 8/2006 |
| JP | 57-123175 A1 | 7/1982 |
| JP | 61-275271 A | 12/1986 |
| JP | 04-329547 A | 11/1992 |
| JP | 07-069899 A | 3/1995 |
| JP | 07-309835 A | 11/1995 |
| JP | 08-268890 A | 10/1996 |
| JP | 10-101591 A | 4/1998 |
| JP | 10-298151 A | 11/1998 |
| JP | 11-127861 A | 5/1999 |
| JP | 11-180981 | 7/1999 |
| JP | 11-292840 A | 10/1999 |
| JP | 2000-511899 A | 9/2000 |
| JP | 2001-103993 A | 4/2001 |
| JP | 2001-247550 A | 9/2001 |
| JP | 2003-212846 A | 7/2003 |
| WO | WO 93/15730 A1 | 8/1993 |
| WO | 97/25041 A1 | 7/1997 |
| WO | WO 97/36554 A1 | 10/1997 |
| WO | WO 97/36866 A1 | 10/1997 |
| WO | WO 97/43310 A1 | 11/1997 |
| WO | 97/46237 A1 | 12/1997 |
| WO | WO 98/17679 A1 | 4/1998 |
| WO | WO 98/22496 A2 | 5/1998 |
| WO | WO 98/46597 A1 | 10/1998 |
| WO | WO 98/46630 A1 | 10/1998 |
| WO | 99/09007 A1 | 2/1999 |
| WO | WO 99/07733 A2 | 2/1999 |
| WO | WO 99/07734 A2 | 2/1999 |
| WO | 99/51619 A1 | 10/1999 |
| WO | WO 99/50230 A1 | 10/1999 |
| WO | WO 99/61613 A2 | 12/1999 |
| WO | WO 99/64442 A1 | 12/1999 |
| WO | WO 00/04141 A2 | 1/2000 |
| WO | WO 00/06529 A1 | 2/2000 |
| WO | WO 00/09543 A2 | 2/2000 |
| WO | WO 00/09558 A1 | 2/2000 |
| WO | WO 00/10573 A1 | 3/2000 |
| WO | WO 00/13708 A1 | 3/2000 |
| WO | WO 00/18231 A1 | 4/2000 |
| WO | WO 00/20400 A1 | 4/2000 |
| WO | WO 00/24725 A1 | 5/2000 |
| WO | WO 00/31129 A1 | 6/2000 |
| WO | WO 00/59929 A1 | 10/2000 |
| WO | WO 01/07027 A2 | 2/2001 |
| WO | WO 01/07027 A3 | 2/2001 |
| WO | WO 01/07407 A1 | 2/2001 |
| WO | WO 01/12214 A2 | 2/2001 |
| WO | WO 01/16379 A1 | 3/2001 |
| WO | WO 01/32153 A2 | 5/2001 |
| WO | WO 01/32691 A1 | 5/2001 |
| WO | WO 01/40262 A1 | 6/2001 |
| WO | 01/47883 A1 | 7/2001 |
| WO | WO 01/58877 A1 | 8/2001 |
| WO | WO 01/58929 A1 | 8/2001 |
| WO | WO 01/60315 A2 | 8/2001 |
| WO | WO 01/64678 A2 | 9/2001 |
| WO | WO 01/74768 A2 | 10/2001 |
| WO | WO 01/77091 A2 | 10/2001 |
| WO | WO 01/77113 A2 | 10/2001 |
| WO | WO 02/04425 A2 | 1/2002 |
| WO | WO 02/06246 A1 | 1/2002 |
| WO | WO 02/07761 A1 | 1/2002 |
| WO | WO 02/08187 A1 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/20497 A1 | 3/2002 |
| WO | 03/000254 A1 | 1/2003 |
| WO | WO 03/007945 A1 | 1/2003 |
| WO | 03/010140 A2 | 2/2003 |
| WO | WO 03/010141 A2 | 2/2003 |
| WO | 03/026587 A2 | 4/2003 |
| WO | 03/099824 A1 | 12/2003 |
| WO | 2004/064925 A1 | 8/2004 |
| WO | 2004/065367 A1 | 8/2004 |
| WO | 2004/087714 A1 | 10/2004 |
| WO | WO 2005/023819 A1 | 3/2005 |
| WO | WO 2005/049622 A1 | 6/2005 |
| WO | WO 2005/080399 A1 | 9/2005 |
| WO | WO 2006/008556 A1 | 1/2006 |
| WO | 2006/020082 A1 | 2/2006 |
| WO | 2006/046030 A1 | 5/2006 |
| WO | 2006/046039 A2 | 5/2006 |
| WO | 2006/052013 A1 | 5/2006 |
| WO | WO 2006/119975 A1 | 11/2006 |
| WO | 2007/029029 A2 | 3/2007 |
| WO | 2007/029029 A3 | 3/2007 |
| WO | 2007/033032 A1 | 3/2007 |
| WO | 2007/033175 A1 | 3/2007 |
| WO | 2007/054741 A1 | 5/2007 |
| WO | 2007/092000 A1 | 8/2007 |
| WO | 2007/129119 A1 | 11/2007 |
| WO | 2007/136982 A1 | 11/2007 |
| WO | 2007/140109 A1 | 12/2007 |
| WO | 2007/140200 A2 | 12/2007 |
| WO | 2007/140200 A3 | 12/2007 |
| WO | 2007/140254 A2 | 12/2007 |
| WO | 2007/140254 A3 | 12/2007 |
| WO | 2007/143521 A1 | 12/2007 |
| WO | 2008/008907 A2 | 1/2008 |
| WO | 2008/008912 A1 | 1/2008 |
| WO | 2008/011521 A2 | 1/2008 |
| WO | 2008/011521 A3 | 1/2008 |
| WO | 2009/023487 A1 | 2/2008 |
| WO | 2008/075103 A1 | 6/2008 |
| WO | 2008/089027 A1 | 7/2008 |
| WO | 2008/097796 A1 | 8/2008 |
| WO | 2008/109584 A1 | 9/2008 |
| WO | 2008/111978 A1 | 9/2008 |
| WO | 2008/112473 A1 | 9/2008 |
| WO | 2008/112841 A1 | 9/2008 |
| WO | 2008/112848 A1 | 9/2008 |
| WO | 2008/112851 A1 | 9/2008 |
| WO | 2008/112863 A1 | 9/2008 |
| WO | 2009/029384 A2 | 3/2009 |

OTHER PUBLICATIONS

Behrens et al., *EMBO Journal*, 15(1):12-22 (1996).
Gatta et al., *Bollettino Chimico Farmaceutico*, 120(2): 102-107 (1981).
Minami et al., *Japanese Journal of Dermatology*, 111(7): 1075-1081 (2001).
Roesch et al., *Journal of Organic Chemistry*, 66(2): 412-420 (2001).

Shvedov et al., *Chemistry of Heterocyclic Compounds*, 10: 1324-1327 (1975) [Translation pp. 1133-1136 (1975)].

Takamizawa et al., *Journal of Virology*, 65(3): 1105-1113 (Mar. 1991).

Buscemi et al., *Journal of Organic Chemistry*, 61(24): 8397-8401 (1996).

Campo et al., *Journal of the American Chemical Society*, 125(38): 11506-11507 (2003).

Chen et al., *Journal of Organic Chemistry*, 61(19): 6639-6645 (1996).

De Koning et al., *Tetrahedron Letters*, 39: 8725-8728 (1998).

Dorwald, F. Zaragoza, *Side Reactions in Organic Synthesis: a Guide to Successful Synthesis Design*, Weinheim: WILEY-VCH Verlag GmbH & Co. KGaA, 2005, Preface.

Foye et al., *Journal of Organic Chemistry*, 31:2417-2418 (Jul. 1966).

Greig et al., *Tetrahedron Letters*, 23(51): 5453-5354 (1982).

Heubach, *Liebigs Annalen der Chemie*, 9: 1376-1383 (1980).

Hiremath et al., *Journal of Heterocyclic Chemistry*, 30(3): 603-609 (May-Jun. 1993).

Höft et al, *Journal for Praktische Chemie*, 314(1): 145-156 (1972).

Jordan, V. Craig, *Nature Reviews: Drug Discovery*, 2:205-213 (2003).

Kauffman, *Journal of Organic Chemistry*, 39(16): 2472-2473 (1974).

Kohara et al., *Journal of Medicinal Chemistry*, 39(26): 5228-5235 (1996).

Kozikowski et al, *Tetrahedron Letters*, 32(28): 3317-3320 (1991).

Michel et al., *Helvetica Chimica Acta*, 48(8): 1973-1983 (1965).

Sauer et al., *Tetrahedron Letters*, 3: 319-324 (1968).

Sheehan et al., *Journal of the American Chemical Society*, 73: 4752-4755 (Oct. 1951).

Shvedov et al., *Chemistry of Heterocyclic Compounds*, 1133-1136(1976).

Sohda et al., *Chem Pharm Bull*, 30(10): 3563-3573 (1982).

Stempel et al., *Journal of Organic Chemistry*, 20: 412-418 (Apr. 1955).

Thiel et al., *Journal für Praktische Chemie*, 332(1): 55-64 (1990).

Unangst et al., *Journal of Medicinal Chemistry*, 35(20): 3691-3698 (1992).

Wolthuis et al., *Journal of Organic Chemistry*, 31(6): 2009-2011 (Jun. 1966).

Zou et al., *Heterocycles*, 43(1): 49-52 (1996).

THIENOPYRROLE COMPOUND AND USE THEREOF AS HCV POLYMERASE INHIBITOR

This application claims the benefit of U.S. provisional application Ser. No. 60/630,597 filed Nov. 23, 2004.

TECHNICAL FIELD

The present invention relates to a thienopyrrole compound or a pharmaceutically acceptable salt thereof, which shows anti-hepatitis C virus (HCV) activity, particularly anti-HCV activity based on an RNA-dependent RNA polymerase inhibitory activity. In addition, the present invention relates to a hepatitis C virus polymerase inhibitor, an anti-hepatitis C virus agent and a therapeutic agent for hepatitis C containing said thienopyrrole compound or a pharmaceutically acceptable salt thereof.

BACKGROUND ART

In 1989, a main causative virus of non-A non-B posttransfusion hepatitis was found and named hepatitis C virus (HCV). Since then, several types of hepatitis viruses have been found besides type A, type B and type C, wherein hepatitis caused by HCV is called hepatitis C.

The patients infected with HCV are considered to involve several percent of the world population, and the infection with HCV characteristically becomes chronic.

HCV is an envelope RNA virus, wherein the genome is a single strand plus-strand RNA, and belongs to the genus Hepacivirus of Flavivirus (from The International Committee on Taxonomy of Viruses, International Union of Microbiological Societies). Of the same hepatitis viruses, for example, hepatitis B virus (HBV), which is a DNA virus, is eliminated by the immune system and the infection with this virus ends in an acute infection except for neonates and infants having yet immature immunological competence. In contrast, HCV somehow avoids the immune system of the host due to an unknown mechanism. Once infected with this virus, even an adult having a mature immune system frequently develops persistent infection.

When chronic hepatitis is associated with the persistent infection with HCV, it advances to cirrhosis or hepatic cancer in a high rate. Enucleation of tumor by operation does not help much, because the patient often develops recurrent hepatic cancer due to the sequela inflammation in non-cancerous parts. In addition, there is a report on the involvement of HCV infection in dermatosis such as chronic urticaria, lichen planus, cryoglobulinemic purpura and the like (The Japanese Journal of Dermatology, Vol. 111, No. 7, pages 1075-1081, 2001).

Thus, an effective therapeutic method of hepatitis C is desired. Apart from the symptomatic therapy to suppress inflammation with an anti-inflammatory agent, the development of a therapeutic agent that reduces HCV to a low level free from inflammation and that eradicates HCV has been strongly demanded.

At present, a treatment with interferon is the only effective method known for the eradication of HCV. However, interferon can eradicate the virus only in about one-third of the patient population. For the rest of the patients, it has no effect or provides only a temporary effect. In recent years, polyethylene glycolated interferon has been put to practical use, and enhanced effects and reduced side effects have been achieved. However, complete response rate still remains at a low level, and therefore, an anti-HCV drug to be used in the place of or concurrently with interferon is awaited in great expectation.

In recent years, Ribavirin (1-β-D-ribofuranosyl-1H-1,2,4-triazole-3-carboxamide) has become commercially available as a therapeutic agent for hepatitis C, which is to be used concurrently with interferon. It enhances the efficacy of interferon but only to a low efficacy rate, and a different novel therapeutic agent for hepatitis C is desired.

Also, an attempt has been made to potentiate the immunocompetence of the patient with an interferon agonist, an interleukin-12 agonist and the like, thereby to eradicate the virus, but an effective pharmaceutical agent has not been found yet.

In addition, the inhibition of HCV growth, wherein HCV-specific protein is targeted, has been drawing attention these days.

The gene of HCV encodes a protein such as serine protease, RNA helicase, RNA-dependent RNA polymerase and the like. These proteins function as a specific protein essential for the growth of HCV.

One of the specific proteins, RNA-dependent RNA polymerase (hereinafter to be also briefly referred to as an HCV polymerase), is an enzyme essential for the growth of the virus. The gene replication of HCV having a plus-strand RNA gene is considered to involve synthesis of a complementary minus-strand RNA by the use of the plus-strand RNA as a template and using the obtained minus-strand RNA as a template, amplifying the plus-strand RNA. The portion called NS5B of a protein precursor, that HCV codes for, has been found to show an RNA-dependent RNA polymerase activity (EMBO J., Vol. 15, pages 12-22, 1996), and is considered to play a central role in the HCV gene replication.

Therefore, an HCV polymerase inhibitor can be a target in the development of an anti-HCV drug, and the development thereof is eagerly awaited. However, an effective HCV polymerase inhibitor has not been developed yet, like in other attempts to develop an anti-HCV drug based on other action mechanisms. As the situation stands, no pharmaceutical agent can treat hepatitis C satisfactorily.

The following describes known compounds comparatively similar to the present invention.

As anti-HCV agents, which are thieno[3,2-b]pyrrole derivatives, the following compound e and the like are known (WO2005/23819, page 71, Table 1, compound No. 113).

While this reference describes that the compound and the like have HCV polymerase inhibitory activity, it does not disclose the compound of the present invention, nor does it contain a description suggesting that the compound of the present invention has an anti-HCV activity.

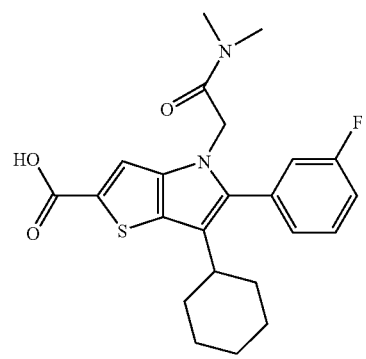

compound e
(Compound# 113)

As the thieno[3,2-b]pyrrole derivative, moreover, the following compound a etc. are also known (Chemistry of Heterocyclic Compounds, pages 1133-1136, 1976, compound IIc (page 1134, Table 1)).

This reference includes descriptions relating to the synthetic methods of thieno[3,2-b]pyrrole derivative, but does not disclose the compound of the present invention, nor does it contain a description relating to use as a pharmaceutical product. In addition, it does not contain a description suggesting such use.

compound a
(Compound# 11c)

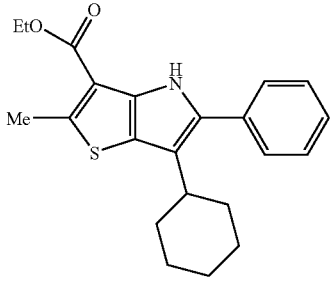

As tetracyclic fused heterocyclic compounds having known pharmaceutical use, the following compound b and the like are known, and synthetic methods of said compounds usable as central nervous system agents are known (Bollettino Chimico Farmaceutico, Vol. 120, No. 2, pages 102-107, 1981).

compound b

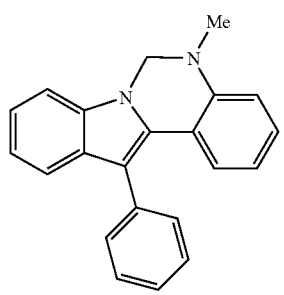

However, this reference does not disclose the compound of the present invention, not to mention use of the compound of this reference as an antiviral agent or a description suggestive thereof.

As tetracyclic fused heterocyclic compounds for use other than pharmaceutical use, the following compound c and the like are known, wherein its synthetic method is described (J. Org. Chem., Vol. 66, No. 2, pages 412-420, 2001, Table 3, No. 19 (page 415)).

compound c

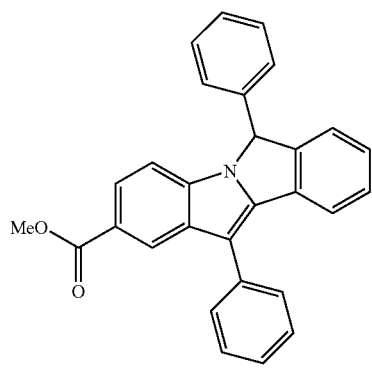

A different reference discloses the following compound d etc., wherein its synthetic method is described (Organic Letters, Vol. 4, No. 8, pages 1355-1358, 2002, Table 1, No. 17 (page 1357), Scheme 4 (page 1356)).

compound d

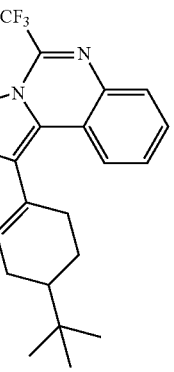

DISCLOSURE OF THE INVENTION

Based on the findings from the preceding studies, it has been elucidated that a compound having an anti-HCV activity is effective for the prophylaxis and treatment of hepatitis C, and particularly an anti-HCV agent having an inhibitory activity on RNA-dependent RNA polymerase of HCV can be a prophylactic and therapeutic agent effective against hepatitis C and a prophylactic and therapeutic agent for the disease caused by hepatitis C.

Accordingly, the present invention provides a compound having an anti-HCV activity, particularly a compound having an RNA-dependent RNA polymerase inhibitory activity.

The present inventors have made an in-depth study of compounds having an anti-HCV activity, particularly RNA-dependent RNA polymerase inhibitory activity, and completed the present invention.

Thus, the present invention provides the following [1] to [40].

[1] A thienopyrrole compound represented by the following formula [I] or a pharmaceutically acceptable salt thereof:

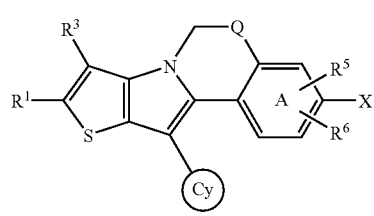

[I]

wherein
Q is
(1) —CH$_2$—O—#,
(2) —CH$_2$—N(R$^2$)—# or
(3) —CO—N(R$^2$)—# wherein # shows the side to be bonded to ring A, ring A is a benzene ring,
R$^1$ is
(1) a carboxyl group,
(2) a carboxylic acid equivalent,
(3) —CONR$^{11}$R$^{12}$ (wherein $R^{11}$ and $R^{12}$ are each independently
- (1') a hydrogen atom,
- (2') a $C_{1-6}$ alkyl group optionally substituted by 1 to 3 substituents selected from the following group E,
- (3') a $C_{2-6}$ alkenyl group optionally substituted by 1 to 3 substituents selected from the following group E,
- (4') a $C_{6-14}$ aryl group optionally substituted by 1 to 5 substituents selected from the following group E,
- (5') a heterocyclic group optionally substituted by 1 to 5 substituents selected from the following group E (wherein said heterocyclic group comprises 1 to 4 heteroatoms selected from oxygen atom, nitrogen atom and sulfur atom),
- (6') a $C_{3-10}$ cycloalkyl group optionally substituted by 1 to 5 substituents selected from the following group E,
- (7') —$NR^{131}R^{132}$,
- (8') —$NHCOOR^{133}$,
- (9') —$NHCOR^{134}$ (wherein $R^{131}$, $R^{132}$, $R^{133}$ and $R^{134}$ are each independently a hydrogen atom or a group selected from the following group F),
- (10') —$CR^{135}R^{136}$-$L^{101}$-$R^{137}$,
- (11') —$CR^{135}R^{136}$-$L^{101}$-$CONR^{140}$—$R^{137}$,
- (12')

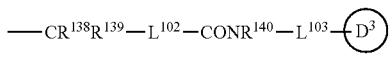

- (13')

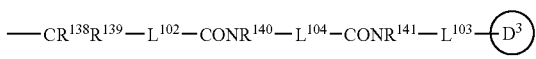

or
- (14')

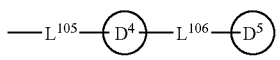

(wherein $R^{135}$, $R^{136}$, $R^{138}$ and $R^{139}$ are each independently
- (1") a hydrogen atom,
- (2") a cyano group,
- (3") —$COOR^{142}$ (wherein $R^{142}$ is a hydrogen atom or a group selected from the following group F),
- (4") —$CONR^{143}R^{144}$ (wherein $R^{143}$ and $R^{144}$ are each independently a hydrogen atom or a group selected from the following group F),
- (5") a $C_{1-6}$ alkyl group optionally substituted by 1 to 3 substituents selected from the following group A,
- (6") a $C_{2-6}$ alkenyl group optionally substituted by 1 to 3 substituents selected from the following group A,
- (7") a $C_{6-14}$ aryl group optionally substituted by 1 to 5 substituents selected from the following group B,
- (8") a heterocyclic group optionally substituted by 1 to 5 substituents selected from the following group B (wherein said heterocyclic group comprises 1 to 4 heteroatoms selected from oxygen atom, nitrogen atom and sulfur atom),
- (9") a $C_{3-10}$ cycloalkyl group optionally substituted by 1 to 5 substituents selected from the following group B,
- (10") a $C_{6-14}$ aryl $C_{1-6}$ alkyl group optionally substituted by 1 to 5 substituents selected from the following group B,
- (11") a heterocycle $C_{1-6}$ alkyl group optionally substituted by 1 to 5 substituents selected from the following group B or
- (12") a $C_{3-10}$ cycloalkyl $C_{1-6}$ alkyl group optionally substituted by 1 to 5 substituents selected from the following group B; or $R^{135}$ and $R^{136}$, or, $R^{138}$ and $R^{139}$ are bonded to each other, and optionally form, together with the carbon atom bonded thereto,
- (1") a $C_{3-10}$ cycloalkyl group optionally substituted by 1 to 5 substituents selected from the following group B or
- (2") a heterocyclic group optionally substituted by 1 to 5 substituents selected from the following group B (wherein said heterocyclic group comprises 1 to 4 heteroatoms selected from oxygen atom, nitrogen atom and sulfur atom), $R^{137}$ is
- (1") a hydrogen atom,
- (2") a carboxyl group,
- (3") a $C_{1-6}$ alkyl group optionally substituted by 1 to 3 substituents selected from the following group E,
- (4") a $C_{2-6}$ alkenyl group optionally substituted by 1 to 3 substituents selected from the following group E,
- (5") a $C_{6-14}$ aryl group optionally substituted by 1 to 5 substituents selected from the following group E,
- (6") a heterocyclic group optionally substituted by 1 to 5 substituents selected from the following group E (wherein said heterocyclic group comprises 1 to 4 heteroatoms selected from oxygen atom, nitrogen atom and sulfur atom) or
- (7") a $C_{3-10}$ cycloalkyl group optionally substituted by 1 to 5 substituents selected from the following group E, $R^{140}$ and $R^{141}$ are each independently
- (1") a hydrogen atom or
- (2") a $C_{1-6}$ alkyl group, $L^{101}$ and $L^{102}$ are each independently
- (1") a bond,
- (2") —CO—,
- (3") a $C_{1-6}$ alkylene optionally substituted by hydroxyl group or
- (4") a $C_{2-6}$ alkenylene, $L^{103}$ is
- (1") a bond or
- (2") a $C_{1-6}$ alkylene, $L^{104}$ is a $C_{1-6}$ alkylene, $L^{105}$ is
- (1") a bond or
- (2") a $C_{1-6}$ alkylene, $L^{106}$ is
- (1") a bond,
- (2") a $C_{1-6}$ alkylene,
- (3") —NH—,
- (4") —NH—$CH_2$— or
- (5") —$CH_2$—CONH—, ring $D^3$, ring $D^4$ and ring $D^5$ are each independently
- (1") a $C_{6-14}$ aryl group optionally substituted by 1 to 5 substituents selected from the following group E,
- (2") a $C_{3-10}$ cycloalkyl group optionally substituted by 1 to 5 substituents selected from the following group E or (3") a heterocyclic group optionally substituted by 1 to 5 substituents selected from the following group E
(wherein said heterocyclic group comprises 1 to 4 heteroatoms selected from oxygen atom, nitrogen atom and sulfur atom))),
(4) —COOR$^{103}$
(wherein R$^{103}$ is a group selected from the following group C or a glucuronic acid residue),
(5)

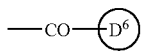

or
(6)

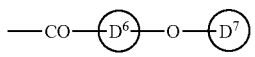

(wherein ring D$^6$ is a heterocyclic group optionally substituted by 1 to 5 substituents selected from the following group E
(wherein said heterocyclic group comprises 1 to 4 heteroatoms selected from oxygen atom, nitrogen atom and sulfur atom),
ring D$^7$ is a C$_{6-14}$ aryl group optionally substituted by 1 to 5 substituents selected from the following group E),
R$^2$ is
(1) a hydrogen atom,
(2) a group selected from the following group E,
(3) a C$_{1-6}$ alkyl group optionally substituted by 1 to 3 substituents selected from the following group E,
(4) a C$_{2-6}$ alkenyl group optionally substituted by 1 to 3 substituents selected from the following group E,
(5)

(6)

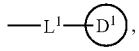

(7)

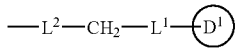

or
(8)

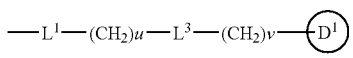

{wherein u and v are each independently 0 or an integer of 1 to 6,
L$^1$ and L$^2$ are each independently
(1') a bond,
(2') C$_{1-6}$ alkylene,
(3') C$_{2-6}$ alkenylene,
(4') —(CH$_2$)$_{u1}$—O—(CH$_2$)$_{v1}$—,
(5') —(CH$_2$)$_{u1}$—S—(CH$_2$)$_{v1}$—,
(6') —(CH$_2$)$_{u1}$—NR$^{L1}$—(CH$_2$)$_{v1}$—,
(7') —(CH$_2$)$_{u1}$—CO—(CH$_2$)$_{v1}$—,
(8') —(CH$_2$)$_{u1}$—CONR$^{L2}$—(CH$_2$)$_{v1}$—,
(9') —(CH$_2$)$_{u1}$—NR$^{L2}$CO$_2$—(CH$_2$)$_{v1}$—,
(10') —(CH$_2$)$_{u1}$—NR$^{L2}$CONR$^{L3}$—(CH$_2$)$_{v1}$—,
(11') —(CH$_2$)$_{u1}$—NR$^{L2}$CO (CH$_2$)$_{v1}$—,
(12') —(CH$_2$)$_{u1}$—NR$^{L2}$SO$_2$—(CH$_2$)$_{v1}$—,
(13') —(CH$_2$)$_{u1}$—SO$_2$—(CH$_2$)$_{v1}$—,
(14') —(CH$_2$)$_{u1}$—SO$_2$NR$^{L2}$—(CH$_2$)$_{v1}$— or
(15') —(CH$_2$)$_{u1}$—N$^+$R$^{L2}$R$^{L2'}$—(CH$_2$)$_{v1}$—, (wherein u1 and v1 are each independently 0 or an integer of 1 to 6,
R$^{L1}$ is
(1") a hydrogen atom,
(2") a group selected from the following group C,
(3") —COR$^{L11}$,
(4") —CONR$^{L11}$R$^{L12}$,
(5") —COOR$^{L11}$ or
(6") —SO$_2$R$^{L3}$ (wherein R$^{L11}$ and R$^{L12}$ are each independently a hydrogen atom or a group selected from the following group C, and R$^{L13}$ is a group selected from the following group C),
R$^{L2}$, R$^{L2'}$ and R$^{L3}$ are each independently
(1") a hydrogen atom,
(2") a group selected from the following group C,
(3 ") —COR$^{L11}$ or
(4") —SO$_2$R$^{L13}$ (wherein R$^{L11}$ and R$^{L13}$ are as defined above)),
L$^3$ is
(1') —CHR$^{L14}$— or
(2') —NR$^{L14}$—

(wherein R$^{L14}$ is a group selected from the following group F), ring D$^1$ and ring D$^2$ are each independently
(1') a C$_{6-14}$ aryl group optionally substituted by 1 to 5 substituents selected from the following group E,
(2') a C$_{3-10}$ cycloalkyl group optionally substituted by 1 to 5 substituents selected from the following group E or
(3') a heterocyclic group optionally substituted by 1 to 5 substituents selected from the following group E (wherein said heterocyclic group comprises 1 to 4 heteroatoms selected from oxygen atom, nitrogen atom and sulfur atom)},
R$^3$ is
(1) a hydrogen atom,
(2) a halogen atom,
(3) a C$_{1-6}$ alkanoyl group,
(4) a carboxyl group,
(5) a cyano group,
(6) a nitro group,
(7) a C$_{1-6}$ alkyl group optionally substituted by 1 to 3 substituents selected from the following group A,
(8) —OR$^{101}$ (wherein R$^{101}$ is a hydrogen atom or a group selected from the following group C),
(9) —NR$^{102}$R$^{119}$ (wherein $R^{102}$ and $R^{119}$ are each independently a hydrogen atom, a $C_{1-6}$ alkanoyl group or a $C_{1-6}$ alkylsulfonyl group),

(10) —COOR$^{103}$ (wherein $R^{103}$ is a group selected from the following group C or a glucuronic acid residue),

(11) —CONR$^{104}$R$^{105}$ (wherein $R^{104}$ and $R^{105}$ are each independently a hydrogen atom, a hydroxyl group, a cyano group, a $C_{1-6}$ alkoxy group or a $C_{1-6}$ alkyl group optionally substituted by 1 to 3 substituents selected from the following group A),

(12) —SO$_2$R$^{106}$ (wherein $R^{106}$ is a hydroxyl group, an amino group, a $C_{1-6}$ alkyl group or a $C_{1-6}$ alkylamino group),

(13) —NHCOR$^{107}$ (wherein $R^{107}$ is an amino group or a $C_{1-6}$ alkylamino group),

(14) —C(=NR$^{108}$)—NH$_2$ (wherein $R^{108}$ is a hydrogen atom, a $C_{1-6}$ alkyl group optionally substituted by 1 to 3 substituents selected from the following group A, a hydroxyl group or a $C_{1-6}$ alkoxy group),

(15) —P(=O) (OR$^{109}$)$_2$ (wherein $R^{109}$ are each independently a hydrogen atom or a group selected from the following group C),

(16) —P(=O) (OR$^{110}$) NR$^{111}$R$^{112}$ (wherein $R^{110}$, $R^{111}$ and $R^{112}$ are each independently a hydrogen atom or a group selected from the following group C),

(17) —CONHCO—R$^{113}$ (wherein $R^{113}$ is a group selected from the following group C),

(18) —CONHSO$_2$—R$^{114}$ (wherein $R^{114}$ is a group selected from the following group C),

(19) —SO$_2$NHCO—R$^{115}$ (wherein $R^{115}$ is a group selected from the following group C) or

(20) a heterocyclic group optionally substituted by 1 to 5 substituents selected from the following group B (wherein said heterocyclic group comprises 1 to 4 heteroatoms selected from oxygen atom, nitrogen atom and sulfur atom), $R^5$ and $R^6$ are each independently
(1) a hydrogen atom,
(2) a halogen atom,
(3) a $C_{1-6}$ alkyl group optionally substituted by 1 to 3 substituents selected from the following group A,
(4) —OR$^{120}$ (wherein $R^{120}$ is a hydrogen atom or a group selected from the following group C) or
(5) —NR$^{121}$R$^{122}$ (wherein $R^{121}$ and $R^{122}$ are each independently a hydrogen atom, a $C_{1-6}$ alkanoyl group or a group selected from the following group C), ring Cy is
(1) a $C_{3-10}$ cycloalkyl group optionally substituted by 1 to 5 substituents selected from the following group B,
(2) a $C_{3-10}$ cycloalkenyl group optionally substituted by 1 to 5 substituents selected from the following group B or
(3) a heterocyclic group optionally substituted by 1 to 5 substituents selected from the following group B (wherein said heterocyclic group comprises 1 to 4 heteroatoms selected from oxygen atom, nitrogen atom and sulfur atom), X is
(1) a group selected from the following group D,
(2) a $C_{2-6}$ alkenyl group optionally substituted by 1 to 3 substituents selected from the following group A or
(3)

wherein ring B is
(1') a $C_{6-14}$ aryl group,
(2') a $C_{3-10}$ cycloalkyl group or
(3') a heterocyclic group comprising 1 to 4 heteroatoms selected from oxygen atom, nitrogen atom and sulfur atom, each Z is independently
(1') a group selected from the following group D,
(2') a $C_{6-14}$ aryl group optionally substituted by 1 to 5 substituents selected from the following group D,
(3') a $C_{3-10}$ cycloalkyl group optionally substituted by 1 to 5 substituents selected from the following group D,
(4') a $C_{6-14}$ aryl $C_{1-6}$ alkyl group optionally substituted by 1 to 5 substituents selected from the following group D,
(5') a heterocyclic group optionally substituted by 1 to 5 substituents selected from the following group D (wherein said heterocyclic group comprises 1 to 4 heteroatoms selected from oxygen atom, nitrogen atom and sulfur atom) or
(6') a heterocycle $C_{1-6}$ alkyl group optionally substituted by 1 5 substituents selected from the following group D (wherein said heterocycle $C_{1-6}$ alkyl group is a $C_{1-6}$ alkyl group substituted by "a heterocyclic group optionally substituted by 1 to 5 substituents selected from group D" as defined above), w is an integer of 1 to 3,
Y is
(a) $C_{1-6}$ alkylene,
(b) $C_{2-6}$ alkenylene or
(c) —Y$^1$—(CH$_2$)$_m$—Y$^2$—(CH$_2$)$_n$—

(wherein m and n are each independently 0 or an integer of 1 to 6, $Y^1$ and $Y^2$ are each independently
(1') a bond,
(2') —O—,
(3') —NR$^{y1}$—,
(4') —S—,
(5') —CO—,
(6') —SO—,
(7') —SO$_2$—,
(8') —CO$_2$—,
(9') —OCO—,
(10') —CONR$^{y2}$—,
(11') —NR$^{y2}$CO—,
(12') —SO$_2$NR$^{y2}$—,
(13') —NR$^{y2}$SO$_2$—,
(14') —NR$^{y2}$CO$_2$—,
(15') —OCONR$^{y2}$—,
(16') —NR$^{y2}$CONR$^{y3}$—,
(17') —CR$^{y4}$R$^{y5}$— or
(18') —CH=CH—

(wherein $R^{y1}$ is
  (1″) a hydrogen atom,
  (2″) a group selected from the following group C,
  (3″) —COOR$^{y11}$,
  (4″) —CONR$^{y11}$R$^{y12}$,
  (5″) —COR$^{y11}$ or
  (6″) —SO$_2$R$^{y13}$ (wherein $R^{y11}$ and $R^{y12}$ are each independently a hydrogen atom or a group selected from the following group C, and $R^{y13}$ is a group selected from the following group C),
  $R^{y2}$ and $R^{y3}$ are each independently
    (1″) a hydrogen atom,
    (2″) a group selected from the following group C,
    (3″) —COR$^{y11}$ or
    (4″) —SO$_2$R$^{y13}$ (wherein $R^{y11}$ and $R^{y13}$ are as defined above),
  $R^{y4}$ and $R^{y5}$ are each independently
    (1″) a hydrogen atom,
    (2″) a carboxyl group,
    (3″) a group selected from group F,
    (4″) —OR$^{y14}$ or
    (5″) —NHR$^{y15}$ (wherein $R^{y14}$ is a group selected from the following group C, and $R^{y15}$ is a hydrogen atom, a C$_{1-6}$ alkyl group, a C$_{1-6}$ alkanoyl group or a C$_{6-14}$ aryl C$_{1-6}$ alkyloxycarbonyl group)))
  group A:
    (1) a halogen atom,
    (2) a C$_{1-6}$ alkoxy C$_{1-6}$ alkoxy group,
    (3) a cyano group,
    (4) —OR$^{a1}$,
    (5) —SR$^{a1}$,
    (6) —NR$^{a1}$R$^{a2}$,
    (7) —COOR$^{a1}$,
    (8) —CONR$^{a1}$R$^{a2}$,
    (9) —SO$_3$H,
    (10) —SO$_2$NR$^{a1}$R$^{a2}$,
    (11) —NHCOR$^{a1}$,
    (12) —NHSO$_2$R$^{a3}$,
    (13) —NHCO$_2$R$^{a4}$ and
    (14) —COR$^{a1}$ (wherein $R^{a1}$ and $R^{a2}$ are each a hydrogen atom or a C$_{1-6}$ alkyl group, $R^{a3}$ is a C$_{1-6}$ alkyl group and $R^{a4}$ is a C$_{1-6}$ alkyl group)
  group B:
    (1) a halogen atom,
    (2) a cyano group,
    (3) a nitro group,
    (4) a C$_{1-6}$ alkyl group,
    (5) a C$_{2-6}$ alkenyl group optionally substituted by carboxyl group,
    (6) a halogenated C$_{1-6}$ alkyl group,
    (7) —(CH$_2$)$_r$—OR$^{b1}$,
    (8) —(CH$_2$)$_r$—SR$^{b1}$,
    (9) —(CH$_2$)$_r$—NR$^{b1}$R$^{b2}$,
    (10) —(CH$_2$)$_r$—COOR$^{b1}$,
    (11) —(CH$_2$)$_r$—CONR$^{b1}$R$^{b2}$,
    (12) —(CH$_2$)$_r$—COR$^{b1}$,
    (13) —(CH$_2$)$_r$—NR$^{b1}$—COR$^{b2}$,
    (14) —(CH$_2$)$_r$—NR$^{b1}$—SO$_2$R$^{b3}$,
    (15) —(CH$_2$)$_r$—SO$_2$R$^{b3}$,
    (16) —(CH$_2$)$_r$—SO$_2$NR$^{b1}$R$^{b2}$,
    (17) —(CH$_2$)$_r$—CONR$^{b1}$—SO$_2$R$^{b3}$,
    (18) —(CH$_2$)$_r$—SO$_2$NR$^{b1}$—COR$^{b2}$,
    (19) —(CH$_2$)$_r$—NR$^{b1}$—COOR$^3$,
    (20) —(CH$_2$)$_r$—NR$^{b1}$—CONR$^{b2}$R$^{b4}$,
    (21) —O—(CH$_2$)$_r$—COOR$^{b1}$ and
    (22) —CO—(CH$_2$)$_r$—R$^{b5}$ (wherein $R^{b1}$, $R^{b2}$ and $R^{b4}$ are each independently a hydrogen atom or a C$_{1-6}$ alkyl group, $R^{b3}$ is a C$_{1-6}$ alkyl group, and $R^{b5}$ is a heterocyclic group and r is 0 or an integer of 1 to 6)
  group C:
    (1) a C$_{1-6}$ alkyl group optionally substituted by 1 to 3 substituents selected from the aforementioned group A,
    (2) a C$_{6-14}$ aryl group optionally substituted by 1 to 5 substituents selected from the aforementioned group B,
    (3) a C$_{6-14}$ aryl C$_{1-6}$ alkyl group optionally substituted by 1 to 5 substituents selected from the aforementioned group B,
    (4) a heterocyclic group optionally substituted by 1 to 5 substituents selected from the aforementioned group B and
    (5) a heterocycle C$_{1-6}$ alkyl group optionally substituted by 1 to 5 substituents selected from the aforementioned group B
  group D:
    (a) a hydrogen atom,
    (b) a halogen atom,
    (c) a cyano group,
    (d) a nitro group,
    (e) a C$_{1-6}$ alkyl group optionally substituted by 1 to 3 substituents selected from the aforementioned group A,
    (f) —(CH$_2$)$_t$—OR$^{d1}$, wherein $R^{d1}$ is
  (1) a hydrogen atom,
  (2) a group selected from the following group F,
  (3) a C$_{2-6}$ alkenyl group optionally substituted by 1 to 3 substituents selected from the aforementioned group A or
  (4) a C$_{2-6}$ alkynyl group optionally substituted by 1 to 3 substituents selected from the aforementioned group A, hereinafter each t is independently 0 or an integer of 1 to 6,
  (g) —(CH$_2$)$_t$—S(O)$_q$—R$^{d2}$, wherein $R^{d2}$ is
  (1) a hydrogen atom or
  (2) a group selected from the following group F,
  q is 0, 1, 2 or 3,
  (h) —(CH$_2$)$_t$—NR$^{d3}$R$^{d4}$, wherein $R^{d3}$ and $R^{d4}$ are each independently
  (1) a hydrogen atom or
  (2) a group selected from the following group F,
  (i) —(CH$_2$)$_t$—COOR$^{d5}$, wherein $R^{d5}$ is
  (1) a hydrogen atom or
  (2) a group selected from the following group F,
  (j) —(CH$_2$)$_t$—CONR$^{d6}$R$^{d7}$, wherein $R^{d6}$ and $R^{d7}$ are each independently
  (1) a hydrogen atom,
  (2) a hydroxyl group,
  (3) a group selected from the following group F or
  (4) a C$_{1-6}$ alkoxy group,
  (k) —(CH$_2$)$_t$—COR$^{d8}$, wherein $R^{d8}$ is a group selected from the following group F,
  (l) —(CH$_2$)$_t$—NR$^{d9}$CO—R$^{d10}$, wherein $R^{d9}$ is
- (1) a hydrogen atom,
- (2) a $C_{1-6}$ alkyl group optionally substituted by 1 to 3 substituents selected from the aforementioned group A or
- (3) a $C_{1-6}$ alkanoyl group, $R^{d10}$ is
- (1) an amino group,
- (2) a $C_{1-6}$ alkylamino group or
- (3) a group selected from the following group F,
- (m) —$(CH_2)_t$—$NR^{d11}SO_2$—$R^{d12}$, wherein $R^{d11}$ is
- (1) a hydrogen atom,
- (2) a $C_{1-6}$ alkyl group optionally substituted by 1 to 3 substituents selected from the aforementioned group A or
- (3) a $C_{1-6}$ alkanoyl group, $R^{d12}$ is
- (1) a hydrogen atom or
- (2) a group selected from the following group F,
- (n) —$(CH_2)_t$—$SO_2$—$NR^{d13}R^{d14}$, wherein $R^{d13}$ and $R^{d14}$ are each independently
- (1) a hydrogen atom or
- (2) a group selected from the following group F,
- (o) —$(CH_2)_t$—$CONR^{d15}$—$SO_2R^{d16}$, wherein $R^{d15}$ and $R^{d16}$ are each independently
- (1) a hydrogen atom or
- (2) a group selected from the following group F,
- (p) —$(CH_2)_t$—$SO_2NR^{d17}$—$COR^{d18}$, wherein $R^{d17}$ is
- (1) a hydrogen atom or
- (2) a group selected from the following group F, $R^{d18}$ is a group selected from the following group F,
- (q) —$(CH_2)_t$—$NR^{d19}$—$COOR^{d20}$, wherein $R^{d19}$ and $R^{d20}$ are each independently
- (1) a hydrogen atom or
- (2) a group selected from the following group F,
- (r) —$(CH_2)_t$—$NR^{d21}CONR^{d22}R^{d23}$, wherein $R^{d21}$, $R^{d22}$ and $R^{c23}$ are each independently
- (1) a hydrogen atom or
- (2) a group selected from the following group F,
- (s) —$(CH_2)_t$—$C(=NR^{d24})NH_2$, wherein $R^{d24}$ is
- (1) a hydrogen atom,
- (2) a hydroxyl group,
- (3) a $C_{1-6}$ alkyl group optionally substituted by 1 to 3 substituents selected from the aforementioned group A or
- (4) $C_{1-6}$ alkoxy group,
- (t) —$(CH_2)_t$—$O$—$(CH_2)_p$—$COR^{d25}$, wherein $R^{d5}$ is
- (1) an amino group,
- (2) a $C_{1-6}$ alkylamino group or
- (3) a heterocyclic group optionally substituted by 1 to 5 substituents selected from the aforementioned group B, p is 0 or an integer of 1 to 6, and
- (u) a heterocyclic group optionally substituted by 1 to 5 substituents selected from the aforementioned group B (wherein said heterocyclic group comprises 1 to 4 heteroatoms selected from oxygen atom, nitrogen atom and sulfur atom)

group E:
- (a) a halogen atom,
- (b) a cyano group,
- (c) a nitro group,
- (d) an azido group,
- (e) —$OP(=O)(OH)_2$,
- (f) —$OR^{e1}$, wherein $R^{e1}$ is
- (1) a hydrogen atom,
- (2) a group selected from the following group F,
- (3) a $C_{2-6}$ alkenyl group optionally substituted by 1 to 3 substituents selected from the aforementioned group A or
- (4) a $C_{2-6}$ alkynyl group optionally substituted by 1 to 3 substituents selected from the aforementioned group A,
- (g) —$S(O)_q$—$R^{e2}$ wherein $R^{e2}$ is
- (1) a hydrogen atom or
- (2) a group selected from the following group F, q is 0, 1, 2 or 3,
- (h) —$NR^{e3}R^{e4}$, wherein $R^{e3}$ and $R^{e4}$ are each independently
- (1) a hydrogen atom,
- (2) a cyano group or
- (3) a group selected from the following group F,
- (i) —$COOR^{e5}$, wherein $R^{e5}$ is
- (1) a hydrogen atom or
- (2) a group selected from the following group F,
- (j) —$CONR^{e6}R^{e7}$, wherein $R^{e6}$ and $R^{e7}$ are each independently
- (1) a hydrogen atom,
- (2) a hydroxyl group,
- (3) a group selected from the following group F or
- (4) a $C_{1-6}$ alkoxy group,
- (k) —$COR^{e8}$, wherein $R^{e8}$ is a group selected from the following group F,
- (1) —$NR^{e9}CO$—$R^{e10}$, wherein $R^{e9}$ is
- (1) a hydrogen atom,
- (2) a $C_{1-6}$ alkyl group or
- (3) a $C_{1-6}$ alkanoyl group, $R^{e10}$ is
- (1) a hydrogen atom,
- (2) an amino group,
- (3) a $C_{1-6}$ alkylamino group,
- (4) a $C_{2-6}$ alkenyl group optionally substituted by 1 to 3 substituents selected from the aforementioned group A or
- (5) a group selected from the following group F,
- (m) —$NR^{e11}SO_2$—$R^{e12}$, wherein $R^{e11}$ is
- (1) a hydrogen atom,
- (2) a $C_{1-6}$ alkyl group or
- (3) a $C_{1-6}$ alkanoyl group, $R^{e12}$ is
- (1) a hydrogen atom or
- (2) a group selected from the following group F,
- (n) —$SO_2$—$NR^{e13}R^{e14}$, wherein $R^{e13}$ and $R^{e14}$ are each independently
(1) a hydrogen atom or
(2) a group selected from the following group F,
(o) —CONR$^{e15}$—SO$_2$R$^{e16}$, wherein $R^{e15}$ and $R^{e16}$ are each independently
(1) a hydrogen atom or
(2) a group selected from the following group F,
(p) —SO$_2$NR$^{e17}$—COR$^{e18}$, wherein $R^{e17}$ is
(1) a hydrogen atom or
(2) a group selected from the following group F,
$R^{e18}$ is a group selected from the following group F,
(q) —NR$^{e19}$—COOR$^{e20}$, wherein $R^{e19}$ and $R^{e20}$ are each independently
(1) a hydrogen atom or
(2) a group selected from the following group F,
(r) —NR$^{e21}$—CONR$^{e22}$R$^{e23}$ wherein $R^{e21}$, $R^{e22}$ and $R^{e23}$ are each independently
(1) a hydrogen atom or
(2) a group selected from the following group F,
(s) —NHCO—OOR$^{e24}$ wherein $R^{e24}$ is
(1) a hydrogen atom or
(2) a group selected from the following group F,
(t) —NHCO—CONR$^{e25}$R$^{e26}$ wherein $R^{e25}$ and $R^{e26}$ are each independently
(1) a hydrogen atom,
(2) a hydroxyl group or
(3) a group selected from the following group F.
(u) —CONH—COOH, (v)

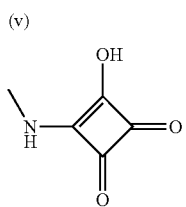

(w)

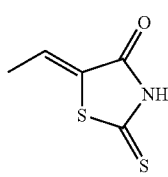

(x)

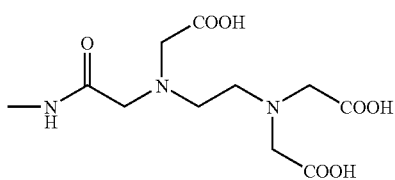

(y) a $C_{6-14}$ aryl group optionally substituted by 1 to 5 substituents selected from the aforementioned group B,
(z) a $C_{3-10}$ cycloalkyl group optionally substituted by 1 to 5 substituents selected from the aforementioned group B,
(aa) a heterocyclic group optionally substituted by 1 to 5 substituents selected from the aforementioned group B (wherein said heterocyclic group comprises 1 to 4 heteroatoms selected from oxygen atom, nitrogen atom and sulfur atom),
(bb) a $C_{3-10}$ cycloalkylidene group optionally substituted by 1 to 5 substituents selected from the aforementioned group B, and
(cc) a heterocycle ylidene group optionally substituted by 1 to 5 substituents selected from the aforementioned group B (wherein said heterocycle ylidene group comprises 1 to 4 heteroatoms selected from oxygen atom, nitrogen atom and sulfur atom), when group E is a substituent on a $C_{6-14}$ aryl group, a $C_{3-10}$ cycloalkyl group or a heterocyclic group, it may be
(dd) a $C_{1-6}$ alkyl group optionally substituted by 1 to 3 substituents selected from the aforementioned group A,
(ee) a $C_{2-6}$ alkenyl group optionally substituted by 1 to 3 substituents selected from the aforementioned group A,
(ff) a $C_{2-6}$ alkynyl group optionally substituted by 1 to 3 substituents selected from the aforementioned group A,
(gg) $C_{1-6}$ alkylidene group optionally substituted by 1 to 3 substituents selected from the aforementioned group A,
(hh) a $C_{6-14}$ aryl $C_{1-6}$ alkyl group optionally substituted by 1 to 5 substituents selected from the aforementioned group B,
(ii) a $C_{3-10}$ cycloalkyl $C_{1-6}$ alkyl group optionally substituted by 1 to 5 substituents selected from the aforementioned group B, or
(jj) a heterocycle $C_{1-6}$ alkyl group optionally substituted by 1 to 5 substituents selected from the aforementioned group B group F:
(1) a $C_{1-6}$ alkyl group optionally substituted by 1 to 3 substituents selected from the aforementioned group A,
(2) a $C_{6-14}$ aryl group optionally substituted by 1 to 5 substituents selected from the aforementioned group B,
(3) a heterocyclic group optionally substituted by 1 to 5 substituents selected from the aforementioned group B (wherein said heterocyclic group comprises 1 to 4 heteroatoms selected from oxygen atom, nitrogen atom and sulfur atom),
(4) a $C_{3-10}$ cycloalkyl group optionally substituted by 1 to 5 substituents selected from the aforementioned group B,
(5) a $C_{6-14}$ aryl $C_{1-6}$ alkyl group optionally substituted by 1 to 5 substituents selected from the aforementioned group B,
(6) a heterocycle $C_{1-6}$ alkyl group optionally substituted by 1 to 5 substituents selected from the aforementioned group B (wherein said heterocycle $C_{1-6}$ alkyl group is a $C_{1-6}$ alkyl group substituted by "a heterocyclic group optionally substituted by 1 to 5 substituents selected from group B" as defined above) and
(7) a $C_{3-10}$ cycloalkyl $C_{1-6}$ alkyl group optionally substituted by 1 to 5 substituents selected from the aforementioned group B.

[2] The thienopyrrole compound of [1], wherein Q is —CH$_2$—O—# or —CH$_2$—N(R$^2$)—# wherein R$^2$ is as defined in [1], or a pharmaceutically acceptable salt thereof.

[3] The thienopyrrole compound of [2], wherein Q is —CH$_2$—O—#, or a pharmaceutically acceptable salt thereof.

[4] The thienopyrrole compound of [2], wherein Q is —CH$_2$—N(R$^2$)—# wherein R$^2$ is as defined in [1], or a pharmaceutically acceptable salt thereof.

[5] The thienopyrrole compound of [1], wherein R$^1$ is a carboxyl group, or a pharmaceutically acceptable salt thereof.

[6] The thienopyrrole compound of [1], wherein R$^1$ is —CONHR$^{12}$ wherein R$^{12}$ is as defined in [1], or a pharmaceutically acceptable salt thereof.

[7] The thienopyrrole compound of [6], wherein R$^{12}$ is a hydrogen atom or

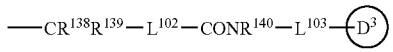

wherein each symbol is as defined in [1], or a pharmaceutically acceptable salt thereof.

[8] The thienopyrrole compound of [4], wherein R$^2$ is selected from
a hydrogen atom,
a C$_{1-6}$ alkyl group optionally substituted by 1 to 3 substituents selected from group E and

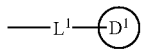

wherein L$^1$ and ring D$^1$ are as defined in [1], or a pharmaceutically acceptable salt thereof.

[9] The thienopyrrole compound of [8], wherein R$^2$ is a C$_{1-6}$ alkyl group optionally substituted by 1 to 3 substituents selected from group E, or a pharmaceutically acceptable salt thereof.

[10] The thienopyrrole compound of [8], wherein R$^2$ is

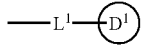

wherein L$^1$ and ring D$^1$ are as defined in [1], or a pharmaceutically acceptable salt thereof.

[11] The thienopyrrole compound of [1], wherein R$^3$ is a hydrogen atom, or a pharmaceutically acceptable salt thereof.

[12] The thienopyrrole compound of [1], wherein R$^5$ and R$^6$ are each a hydrogen atom, or a pharmaceutically acceptable salt thereof.

[13] The thienopyrrole compound of [1], wherein R5 is —NR$^{121}$R$^{122}$ wherein R$^{121}$ and R$^{122}$ are each independently a heterocycle C$_{1-6}$ alkyl group optionally substituted by 1 to 5 substituents selected from group B, and R is a hydrogen atom, or a pharmaceutically acceptable salt thereof.

[14] The thienopyrrole compound of [1], wherein ring Cy is a C$_{3-10}$ cycloalkyl group optionally substituted by 1 to 5 substituents selected from group B, or a pharmaceutically acceptable salt thereof.

[15] The thienopyrrole compound of [1], wherein X is a group selected from group D, or a pharmaceutically acceptable salt thereof.

[16] The thienopyrrole compound of [15], wherein X is a hydrogen atom, a halogen atom, a C$_{1-6}$ alkyl group optionally substituted by 1 to 3 substituents selected from group A or —OR$^{d1}$ wherein R$^{d1}$ is as defined in [1], or a pharmaceutically acceptable salt thereof.

[17] The thienopyrrole compound of [1], wherein X is

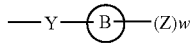

wherein each symbol is as defined in [1], or a pharmaceutically acceptable salt thereof.

[18] The thienopyrrole compound of [17], wherein Y is —(CH$_2$)$_m$—O—(CH$_2$)$_n$— wherein each symbol is as defined in [1], or a pharmaceutically acceptable salt thereof.

[19] The thienopyrrole compound of [17], wherein ring B is a C$_{6-14}$ aryl group or a heterocyclic group comprising 1 to 4 heteroatoms selected from oxygen atom, nitrogen atom and sulfur atom, or a pharmaceutically acceptable salt thereof.

[20] The thienopyrrole compound of [17], wherein Z is 1 to 3 substituents selected from
(1) a hydrogen atom,
(2) a heterocyclic group optionally substituted by 1 to 5 substituents selected from group D,
(3) —(CH$_2$)$_t$—S(O)$_q$—R$^{d2}$ and
(4) —(CH$_2$)$_t$—COOR$^{d5}$ wherein each symbol is as defined in [1], or a pharmaceutically acceptable salt thereof.

[21] The thienopyrrole compound of [1] or a pharmaceutically acceptable salt thereof, which is selected from the group consisting of
(1) methyl 11-cyclohexyl-8-hydroxy-4,5-dihydro-6-oxa-1-thia-3b-azabenzo[e]cyclopenta[a]azulene-2-carboxylate,
(2) methyl 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylate,
(3) 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylic acid,
(4) 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxamide,
(5) methyl 11-cyclohexyl-5-oxo-5,6-dihydro-4H-1-thia-3b,6-diazabenzo[e]cyclopenta[a]azulene-2-carboxylate,
(6) methyl 11-cyclohexyl-5-oxo-6-[2-oxo-2-(piperidin-1-yl)ethyl]-5,6-dihydro-4H-1-thia-3b,6-diazabenzo[e]cyclopenta[a]azulene-2-carboxylate,
(7) methyl 11-cyclohexyl-6-[2-(piperidin-1-yl)ethyl]-5,6-dihydro-4H-1-thia-3b,6-diazabenzo[e]cyclopenta[a]azulene-2-carboxylate,
(8) 11-cyclohexyl-6-[2-(piperidin-1-yl)ethyl]-5,6-dihydro-4H-1-thia-3b,6-diazabenzo[e]cyclopenta[a]azulene-2-carboxylic acid dihydrochloride,
(9) methyl 6-[2-(4-tert-butoxycarbonylpiperazin-1-yl)-2-oxoethyl]-11-cyclohexyl-5-oxo-5,6-dihydro-4H-1-thia-3b,6-diazabenzo[e]cyclopenta[a]azulene-2-carboxylate,
(10) methyl 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylate,
(11) 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylic acid hydrochloride,

(12) methyl 11-cyclohexyl-5,6-dihydro-4H-1-thia-3b,6-diazabenzo[e]cyclopenta[a]azulene-2-carboxylate,

(13) methyl 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylate,

(14) 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylic acid dihydrochloride,

(15) 11-cyclohexyl-4,5-dihydro-6-oxa-1-thia-3b-azabenzo[e]cyclopenta[a]azulene-2-carboxylic acid,

(16) 11-cyclohexyl-8-[2-(morpholin-4-yl)-5-(2-oxopyrrolidin-1-yl)benzyloxy]-4,5-dihydro-6-oxa-1-thia-3b-azabenzo[e]cyclopenta[a]azulene-2-carboxylic acid hydrochloride,

(17) 11-cyclohexyl-8-(1-methoxycarbonylpiperidin-3-yloxy)-4,5-dihydro-6-oxa-1-thia-3b-azabenzo[e]cyclopenta[a]azulene-2-carboxylic acid,

(18) 11-cyclohexyl-8-[2-(4-methanesulfonylpiperazin-1-yl)-5-(2-oxopyrrolidin-1-yl)benzyloxy]-4,5-dihydro-6-oxa-1-thia-3b-azabenzo[e]cyclopenta[a]azulene-2-carboxylic acid,

(19) 11-cyclohexyl-8-methyl-6-[2-(piperidin-1-yl)ethyl]-5,6-dihydro-4H-1-thia-3b,6-diazabenzo[e]cyclopenta[a]azulene-2-carboxylic acid dihydrochloride,

(20) 8-chloro-11-cyclohexyl-6-[2-(piperidin-1-yl)ethyl]-5,6-dihydro-4H-1-thia-3b,6-diazabenzo[e]cyclopenta[a]azulene-2-carboxylic acid dihydrochloride,

(21) 6-[2-(azocan-1-yl)ethyl]-11-cyclohexyl-5,6-dihydro-4H-1-thia-3b,6-diazabenzo[e]cyclopenta[a]azulene-2-carboxylic acid dihydrochloride,

(22) 11-cyclohexyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride,

(23) (S)-11-cyclohexyl-6-{2-[3-(2-methoxyethyl)piperidin-1-yl]ethyl}-5,6-dihydro-4H-1-thia-3b,6-diazabenzo[e]cyclopenta[a]azulene-2-carboxylic acid dihydrochloride,

(24) 11-cyclohexyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride,

(25) 6-[2-(azocan-1-yl)ethyl]-11-cyclohexyl-8-methyl-5,6-dihydro-4H-1-thia-3b,6-diazabenzo[e]cyclopenta[a]azulene-2-carboxylic acid dihydrochloride,

(26) 11-cyclohexyl-8-methyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride,

(27) (S)-11-cyclohexyl-6-{2-[3-(2-methoxyethyl)piperidin-1-yl]ethyl}-8-methyl-5,6-dihydro-4H-1-thia-3b,6-diazabenzo[e]cyclopenta[a]azulene-2-carboxylic acid dihydrochloride,

(28) 11-cyclohexyl-8-methyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride,

(29) 6-[2-(azocan-1-yl)ethyl]-8-chloro-11-cyclohexyl-5,6-dihydro-4H-1-thia-3b,6-diazabenzo[e]cyclopenta[a]azulene-2-carboxylic acid dihydrochloride,

(30) 8-chloro-11-cyclohexyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride,

(31) (S)-8-chloro-11-cyclohexyl-6-{2-[3-(2-methoxyethyl)piperidin-1-yl]ethyl}-5,6-dihydro-4H-1-thia-3b,6-diazabenzo[e]cyclopenta[a]azulene-2-carboxylic acid dihydrochloride,

(32) 8-chloro-11-cyclohexyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride,

(33) 6-[2-(4-tert-butoxycarbonylpiperazin-1-yl)ethyl]-11-cyclohexyl-8-methyl-5,6-dihydro-4H-1-thia-3b,6-diazabenzo[e]cyclopenta[a]azulene-2-carboxylic acid hydrochloride,

(34) 6-[2-(4-tert-butoxycarbonylpiperazin-1-yl)ethyl]-8-chloro-11-cyclohexyl-5,6-dihydro-4H-1-thia-3b,6-diazabenzo[e]cyclopenta[a]azulene-2-carboxylic acid hydrochloride,

(35) 11-cyclohexyl-6-[2-(4-ethylpiperazin-1-yl)-2-oxoethyl]-8-methyl-5,6-dihydro-4H-1-thia-3b,6-diazabenzo[e]cyclopenta[a]azulene-2-carboxylic acid dihydrochloride, and

(36) 8-chloro-11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylic acid dihydrochloride.

[22] The thienopyrrole compound of [1] or a pharmaceutically acceptable salt thereof, which is selected from the group consisting of

(37) (E)-3-[4-({1-[(11-cyclohexyl-8-methoxy-4,5-dihydro-6-oxa-1-thia-3b-azabenzo[e]cyclopenta[a]azulene-2-carbonyl)amino]cyclobutanecarbonyl}amino)phenyl]acrylic acid,

(38) (E)-3-[4-({1-[(11-cyclohexyl-6,8-dimethyl-5,6-dihydro-4H-1-thia-3b,6-diazabenzo[e]cyclopenta[a]azulene-2-carbonyl)amino]cyclobutanecarbonyl)amino)phenyl]acrylic acid,

(39) (E)-3-[4-({1-[(8-chloro-11-cyclohexyl-6-methyl-5,6-dihydro-4H-1-thia-3b,6-diazabenzo[e]cyclopenta[a]azulene-2-carbonyl)amino]cyclobutanecarbonyl}amino)phenyl]acrylic acid,

(40) (E)-3-[3-({1-[(11-cyclohexyl-8-methoxy-4,5-dihydro-6-oxa-1-thia-3b-azabenzo[e]cyclopenta[a]azulene-2-carbonyl)amino]cyclobutanecarbonyl}amino)phenyl]acrylic acid,

(41) 11-cyclohexyl-8-ethoxy-4,5-dihydro-6-oxa-1-thia-3b-azabenzo[e]cyclopenta[a]azulene-2-carboxylic acid,

(42) 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid trihydrochloride,

(43) (E)-3-[4-({1-[(11-cyclohexyl-8-ethoxy-4,5-dihydro-6-oxa-1-thia-3b-azabenzo[e]cyclopenta[a]azulene-2-carbonyl)amino]cyclobutanecarbonyl}amino)phenyl]acrylic acid,

(44) 11-cyclohexyl-8-ethoxy-6-methyl-5,6-dihydro-4H-1-thia-3b,6-diazabenzo[e]cyclopenta[a]azulene-2-carboxylic acid,

(45) (E)-3-[4-({1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino)phenyl]acrylic acid, and

(46) 7-{bis[2-(morpholin-4-yl)ethyl]amino}-11-cyclohexyl-4,5-dihydro-6-oxa-1-thia-3b-azabenzo[e]cyclopenta[a]azulene-2-carboxylic acid trihydrochloride.

[23] A pharmaceutical composition comprising a thienopyrrole compound of any of [1] to [22], or a pharmaceutically acceptable salt thereof, and a pharmaceutically acceptable carrier.

[24] A hepatitis C virus polymerase inhibitor comprising a thienopyrrole compound of any of [1] to [22] or a pharmaceutically acceptable salt thereof as an active ingredient.

[25] An anti-hepatitis C virus agent comprising a thienopyrrole compound of any of [1] to [22] or a pharmaceutically acceptable salt thereof as an active ingredient.

[26] A therapeutic agent for hepatitis C comprising a thienopyrrole compound of any of [1] to [22] or a pharmaceutically acceptable salt thereof as an active ingredient.

[27] A therapeutic agent for hepatitis C comprising (a) a thienopyrrole compound of any of [1] to [22] or a pharmaceutically acceptable salt thereof, and (b) at least one pharmaceutical agent selected from the group consisting of a different antiviral agent, an antiinflammatory agent and an immunostimulant.

[28] A therapeutic agent for hepatitis C comprising (a) a thienopyrrole compound of any of [1] to [22] or a pharmaceutically acceptable salt thereof, and (b) interferon.

[29] An anti-hepatitis C virus agent comprising (a) a thienopyrrole compound of any of [1] to [22] or a pharmaceutically acceptable salt thereof, and (b) at least one pharmaceutical agent selected from the group consisting of a different antiviral agent, an antiinflammatory agent and an immunostimulant.

[30] An anti-hepatitis C virus agent comprising (a) a thienopyrrole compound of any of [1] to [22] or a pharmaceutically acceptable salt thereof and (b) interferon.

[31] A pharmaceutical composition comprising (a) a thienopyrrole compound of any of [1] to [22] or a pharmaceutically acceptable salt thereof, and (b) at least one pharmaceutical agent selected from the group consisting of a different antiviral agent, an antiinflammatory agent and an immunostimulant.

[32] A pharmaceutical composition comprising (a) a thienopyrrole compound of any of [1] to [22] or a pharmaceutically acceptable salt thereof, and (b) interferon.

[33] Use of a thienopyrrole compound of any of [1] to [22] or a pharmaceutically acceptable salt thereof for the production of a pharmaceutical agent for treating hepatitis C.

[34] Use of a thienopyrrole compound of any of [1] to [22] or a pharmaceutically acceptable salt thereof for the production of a hepatitis C virus polymerase inhibitor.

[35] A method for treating hepatitis C, which comprises administering an effective amount of a thienopyrrole compound of any of [1] to [22] or a pharmaceutically acceptable salt thereof to a mammal.

[36] The method of [35], further comprising administering an effective amount of at least one pharmaceutical agent selected from the group consisting of a different antiviral agent, an antiinflammatory agent and an immunostimulant to the mammal.

[37] The method of [35], further comprising administering an effective amount of interferon to the mammal.

[38] A method for inhibiting hepatitis C virus polymerase, which comprises administering an effective amount of a thienopyrrole compound of any of [1] to [22] or a pharmaceutically acceptable salt thereof to a mammal.

[39] The method of [38], further comprising administering an effective amount of at least one pharmaceutical agent selected from the group consisting of a different antiviral agent, an antiinflammatory agent and an immunostimulant to the mammal.

[40] The method of [38], further comprising administering an effective amount of interferon to the mammal.

BEST MODE OF EMBODIMENT OF THE INVENTION

The definitions of respective substituents and moieties used in the present specification are as follows.

The "halogen atom" is a fluorine atom, chlorine atom, bromine atom or iodine atom, preferably fluorine atom, chlorine atom or bromine atom.

The "$C_{1-6}$ alkyl group" is a linear or branched chain alkyl group having 1 to 6 carbon atoms, preferably a linear or branched chain alkyl group having 1 to 4 carbon atoms. Specifically, methyl group, ethyl group, propyl group, isopropyl group, butyl group, isobutyl group, sec-butyl group, tert-butyl group, pentyl group, isopentyl group, tert-pentyl group, hexyl group and the like can be mentioned.

The "$C_{2-6}$ alkenyl group" is a linear or branched chain alkenyl group having 2 to 6 carbon atoms. Specifically, vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group and the like can be mentioned.

The "$C_{2-6}$ alkynyl group" is a linear or branched chain alkynyl group having 2 to 6 carbon atoms. Specifically, ethynyl group, 1-propynyl group, 2-propynyl group, 3-butynyl group and the like can be mentioned.

The "halogenated $C_{1-6}$ alkyl group" is the above-defined "$C_{1-6}$ alkyl group" substituted by the above-defined -halogen atom, which is preferably a halogenated alkyl group wherein the alkyl moiety is a linear or branched chain alkyl group having 1 to 4 carbon atoms. Specifically, fluoromethyl group, difluoromethyl group, trifluoromethyl group, bromomethyl group, chloromethyl group, 1,2-dichloroethyl group, 2,2-dichloroethyl group, 2,2,2-trifluoroethyl group and the like can be mentioned.

The "$C_{1-6}$ alkylene" is a straight chain alkylene having 1 to 6 carbon atoms, and methylene, ethylene, trimethylene, tetramethylene, pentamethylene, hexamethylene and the like can be mentioned.

The "$C_{2-6}$ alkenylene" is a straight chain alkenylene having 2 to 6 carbon atoms, and vinylene, propenylene, 1-butenylene, 1,3-butadienylene and the like can be mentioned.

The "$C_{1-6}$ alkoxy group" is an alkyl-oxy group wherein the alkyl moiety is the above-defined "$C_{1-6}$ alkyl group", preferably an alkoxy group wherein the alkyl moiety is a linear or branched chain alkyl group having 1 to 4 carbon atoms. Specifically, methoxy group, ethoxy group, propoxy group, isopropyloxy group, butoxy group, isobutyloxy group, tert-butyloxy group, pentyloxy group, hexyloxy group and the like can be mentioned.

The "$C_{1-6}$ alkoxy $C_{1-6}$ alkoxy group" is an alkyl-oxy-alkyl-oxy group wherein the above-defined "$C_{1-6}$ alkoxy group" is substituted by the above-defined "$C_{1-6}$ alkoxy group", preferably that wherein the alkyl moiety is a linear or branched chain alkyl group having 1 to 4 carbon atoms. Specifically, methoxymethoxy group, ethoxymethoxy group, 1-(methoxy)ethoxy group, 2-(methoxy)ethoxy group, methoxypropoxy group, isopropyloxyethoxy group and the like can be mentioned.

The "$C_{1-6}$ alkanoyl group" is an alkyl-carbonyl group wherein the alkyl moiety is the above-defined "$C_{1-6}$ alkyl group", preferably an alkyl-carbonyl group wherein the alkyl moiety is a linear or branched chain alkyl group having 1 to 4 carbon atoms. Specifically, acetyl group, propionyl group, butyryl group, isobutyryl group, pivaloyl group and the like can be mentioned.

The "$C_{1-6}$ alkoxycarbonyl group" is an alkyl-oxy-carbonyl group wherein the alkoxy moiety is the above-defined "$C_{1-6}$ alkoxy group", preferably an alkyl-oxy-carbonyl group wherein the alkyl moiety is a linear or branched chain alkyl group having 1 to 4 carbon atoms. Specifically, methoxycarbonyl group, ethoxycarbonyl group, propoxycarbonyl group, isopropyloxycarbonyl group, butoxycarbonyl group, isobutyloxycarbonyl group, tert-butyloxycarbonyl group, pentyloxycarbonyl group, hexyloxycarbonyl group and the like can be mentioned.

The "$C_{1-6}$ alkylamino group" is an alkyl-amino group or a dialkyl-amino group wherein the alkyl moiety is the above-defined "$C_{1-6}$ alkyl group", preferably an alkyl-amino group or a dialkyl-amino group wherein the alkyl moiety is a linear or branched chain alkyl group having 1 to 4 carbon atoms. Specifically, methylamino group, ethylamino group, propylamino group, isopropylamino group, butylamino group, isobutylamino group, tert-butylamino group, pentylamino group, hexylamino group, dimethylamino group, diethylamino group, N-ethyl-N-methylamino group, N-isobutyl-N-isopropylamino group and the like can be mentioned.

The "$C_{1-6}$ alkanoylamino group" is an alkyl-carbonyl-amino group wherein the alkanoyl moiety is the above-defined "$C_{1-6}$ alkanoyl group", preferably an alkyl-carbonyl-amino group wherein the alkyl moiety is a linear or branched chain alkyl group having 1 to 4 carbon atoms. Specifically, acetylamino group, propionylamino group, butyrylamino group, isobutyrylamino group, pivaloylamino group and the like can be mentioned.

The "$C_{1-6}$ alkylsulfonyl group" is an alkyl-sulfonyl group wherein the alkyl moiety is the above-defined "$C_{1-6}$ alkyl group", preferably an alkyl-sulfonyl group wherein the alkyl moiety is a linear or branched chain alkyl group having 1 to 4 carbon atoms. Specifically, methanesulfonyl group, ethylsulfonyl group, propylsulfonyl group, isopropylsulfonyl group, butylsulfonyl group, isobutylsulfonyl group, tert-butylsulfonyl group, pentylsulfonyl group, hexylsulfonyl group and the like can be mentioned.

The "$C_{6-14}$ aryl group" is an aromatic hydrocarbon group having 6 to 14 carbon atoms. Specifically, phenyl group, naphthyl group, anthryl group, indenyl group, azulenyl group, fluorenyl group, phenanthryl group and the like can be mentioned, with preference given to phenyl group.

The "$C_{3-10}$ cycloalkyl group" is a saturated cycloalkyl group having 3 to 10, preferably 3 to 8, more preferably 5 to 7, carbon atoms, and includes monocycle and fused ring. Specifically, cyclopropyl group, cyclobutyl group, cyclopentyl group, cyclohexyl group, cycloheptyl group, cyclooctyl group, adamantyl group and the like can be mentioned.

The "$C_{3-10}$ cycloalkenyl group" is a cycloalkenyl group having 3 to 10, preferably 3 to 8, more preferably 5 to 7, carbon atoms, and includes at least one, preferably 1 or 2, double bonds. Specifically, cyclopropenyl group, cyclobutenyl group, cyclopentenyl group, cyclopentadienyl group, cyclohexenyl group, 2,4-cyclohexadien-1-yl group, 2,5-cyclohexadien-1-yl group, cycloheptenyl group, cyclooctenyl group and the like can be mentioned. It does not include aryl group such as phenyl group and completely saturated cycloalkyl group.

The "$C_{6-14}$ aryl $C_{1-6}$ alkyloxycarbonyl group" is an aryl-alkyl-oxy-carbonyl group wherein the alkyl moiety is the above-defined "$C_{1-6}$ alkyl group", and the aryl moiety is the above-defined "$C_{6-14}$ aryl group". Preferred is an aryl-alkyl-oxy-carbonyl group wherein the alkyl moiety is a linear or branched chain alkyl group having 1 to 4 carbon atoms and the aryl moiety is a phenyl group. Specifically, benzyloxycarbonyl group, phenethyloxycarbonyl group, 3-phenylpropyloxycarbonyl group, 2-phenylpropyloxycarbonyl group, 4-phenylbutyloxycarbonyl group and the like can be mentioned.

The "bond" means a direct connection. For example, when $L^1$ is a "bond" in —O-$L^1$-Ph, it means —O-Ph.

The "glucuronic acid residue" is a group remaining after removing any hydroxyl group from glucuronic acid, and preferably substitutes at the 1-position of β-D-glucuronic acid.

The "heterocyclic group" and "heterocyclic group comprising 1 to 4 heteroatoms selected from oxygen atom, nitrogen atom and sulfur atom" has, as a ring-constituting atom, 1 to 4 heteroatoms selected from oxygen atom, nitrogen atom and sulfur atom besides carbon atom, wherein the number of atom constituting the ring is 3 to 14, includes saturated ring and unsaturated ring, monocycle and fused ring, and may be a spiro ring.

As the monocyclic heterocyclic group, specifically, pyridyl group, pyrazinyl group, pyrimidinyl group, pyridazinyl group, 1,3,5-triazinyl group, pyrrolyl group, pyrazolyl group, imidazolyl group, triazolyl group (1,2,3-triazolyl group, 1,2,4-triazolyl group), tetrazolyl group, thienyl group, furyl group, oxazolyl group, isoxazolyl group, thiazolyl group, isothiazolyl group, oxadiazolyl group (1,2,4-oxadiazolyl group, 1,3,4-oxadiazolyl group, 1,2,5-oxadiazolyl group), thiadiazolyl group (1,2,4-thiadiazolyl group, 1,3,4-thiadiazolyl group, 1,2,5-thiadiazolyl group), pyrrolinyl group (1-pyrrolinyl group, 2-pyrrolinyl group, 3-pyrrolinyl group), pyrrolidinyl group, 4,5-dihydro-1H-imidazolyl group, 4,5-dihydro-1H-oxazolyl group, 4,5-dihydro-1H-thiazolyl group, imidazolidinyl group, azetidinyl group, piperidyl group, piperazinyl group, 1,2,3,6-tetrahydropyridyl group, morpholinyl group, thiomorpholinyl group, 3,6-dihydro-2H-pyranyl group, tetrahydropyranyl group, tetrahydrofuranyl group, azepanyl group (e.g., azepan-1-yl group), azocanyl group (e.g., azocan-1-yl group), azonanyl group (e.g., azonan-1-yl group), 1,4-diazepanyl group (e.g., 1,4-diazepan-1-yl group), 1,4-oxazepanyl group (e.g., 1,4-oxazepan-4-yl group) and the like can be mentioned.

This heterocyclic group includes the groups represented by the following formulas.

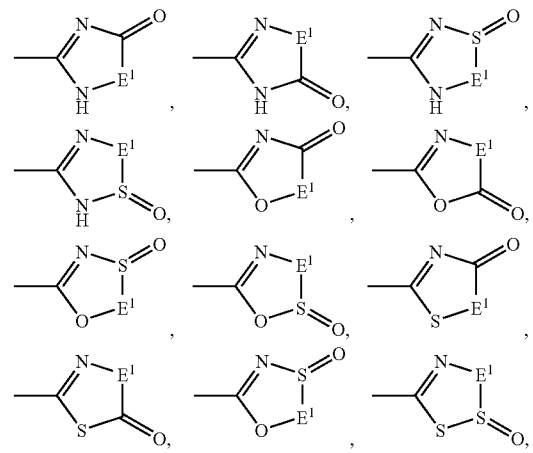

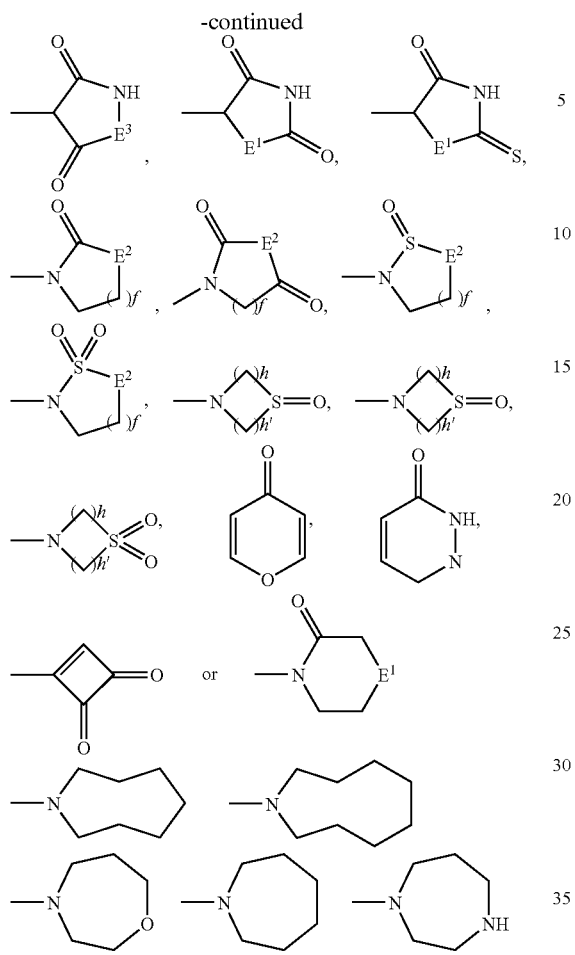

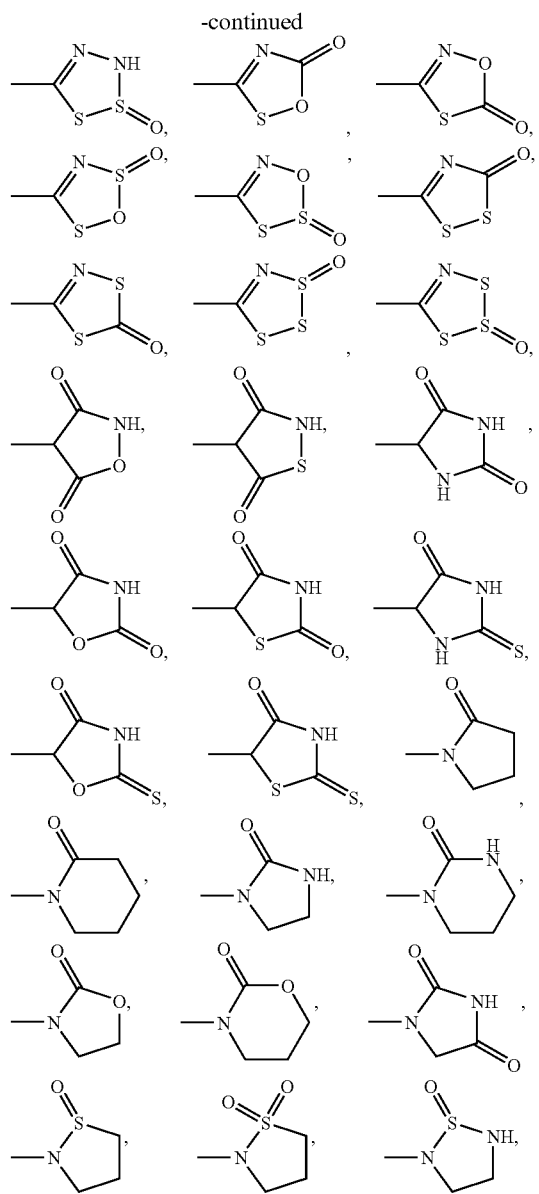

wherein $E^1$ is an oxygen atom, a sulfur atom or NH, $E^2$ is an oxygen atom, $CH_2$ or NH, $E^3$ is an oxygen atom or a sulfur atom, wherein f is an integer of 1 to 3, h and h' are the same or different and each is an integer of 1 to 3.

Specifically,

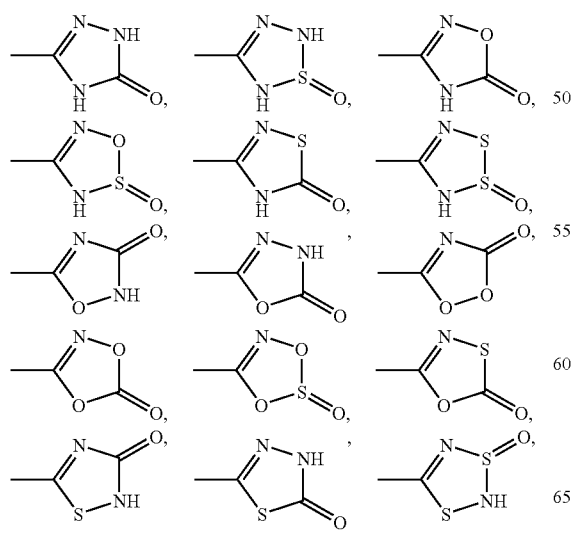

and the like can be mentioned.

As a fused heterocyclic group, specifically, quinolyl group, isoquinolyl group, quinazolinyl group, quinoxalinyl group, phthalazinyl group, cinnolinyl group, naphthyridinyl group, 1,2,3,4-tetrahydroquinolyl group, 5,6,7,8-tetrahydroquinolyl group, 1,2,3,4-tetrahydroisoquinolyl group, 5,6,7,8-tetrahydroisoquinolyl group, indolyl group, benzimidazolyl group, 2,3-dihydrobenzimidazolyl group, 2,3-dihydro-2-oxobenzimidazolyl group, indolinyl group, isoindolinyl group, octahydroindolyl group, octahydroisoindolyl group, benzofuranyl group, benzothienyl group, benzoxazolyl group, benzothiazolyl group, 3,4-dihydro-2H-benzo[1,4]oxazinyl group, 3-oxo-3,4-dihydro-2H-benzo[1,4]oxazinyl group, octahydrocyclopenta[c]pyrrolyl group, 2-oxo-2H-chromenyl group, benzo[1,3]dioxolanyl group, 4-oxo-1H-quinolinyl group, 2-oxohexahydrothieno[3,4-d]imidazolyl group,

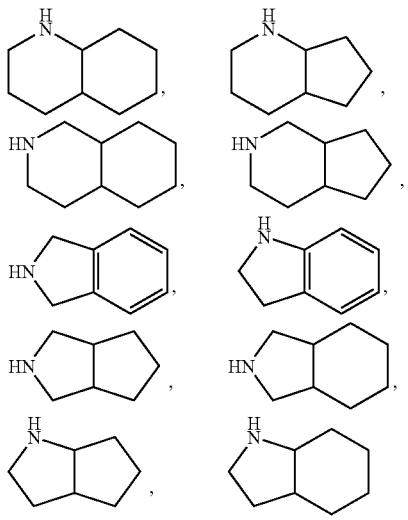

and the like can be mentioned.

As a Spiro heterocyclic group, specifically,

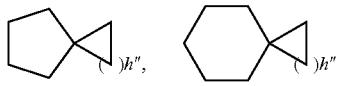

wherein h" is an integer of 1 to 6 and the like can be mentioned.

The "group A" means the substituent groups of the following (1) to (14).

($R^{a1}$ and $R^{a2}$ are each independently a hydrogen atom or the above-defined "$C_{1-6}$ alkyl group", $R^{a3}$ is the above-defined "$C_{1-6}$ alkyl group" and $R^{a4}$ is the above-defined "$C_{1-6}$ alkyl group")

(1) the above-defined "halogen atom",
(2) the above-defined "$C_{1-6}$ alkoxy $C_{1-6}$ alkoxy group",
(3) a cyano group,
(4) —$OR^{a1}$ (e.g., hydroxyl group, methoxy group, ethoxy group, isopropyloxy group, tert-butyloxy group etc.),
(5) —$SR^{a1}$ (e.g., mercapto group, methylsulfanyl group etc.),
(6) —$NR^{a1}R^{a2}$ (e.g., amino group, methylamino group, ethylamino group, isopropylamino group, dimethylamino group, diethylamino group, diisopropylamino group, di-tert-butylamino group, N-ethyl-N-methylamino group etc.),
(7) —$COOR^{a1}$ (e.g., carboxyl group, methoxycarbonyl group, ethoxycarbonyl group, isopropyloxycarbonyl group, tert-butoxycarbonyl group etc.),
(8) —$CONR^{a1}R^{a2}$ (e.g., carbamoyl group, methylcarbamoyl group, ethylcarbamoyl group, isopropylcarbamoyl group, dimethylcarbamoyl group, diethylcarbamoyl group, diisopropylcarbamoyl group, di-tert-butylcarbamoyl group, N-ethyl-N-methylcarbamoyl group etc.),
(9) —$SO_3H$,
(10) —$SO_2NR^{a1}R^{a2}$ (e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, N-ethyl-N-methylsulfamoyl group etc.),
(11) —$NHCOR^{a1}$ (e.g., formylamino group, acetylamino group, propionylamino group, isobutyrylamino group, pivaloylamino group etc.),
(12) —$NHSO_2R^{a3}$ (e.g., methanesulfonylamino group, ethylsulfonylamino group, isopropylsulfonylamino group, tert-butylsulfonylamino group etc.),
(13) —$NHCO_2R^{a4}$ (e.g., tert-butoxycarbonylamino group etc.) and
(14) —$COR^{a1}$ (e.g., formyl group, acetyl group, propionyl group, isobutyryl group, pivaloyl group etc.).

The "group B" means the substituent groups of the following (1) to (22).

(the following $R^{b1}$, $R^{b2}$ and $R^{b4}$ are each independently a hydrogen atom or the above-defined "$C_{1-6}$ alkyl group", $R^{b3}$ is the above-defined "$C_{1-6}$ alkyl group", and $R^{b5}$ is the above-defined "heterocyclic group" and r is 0 or an integer of 1 to 6)

(1) the above-defined "halogen atom",
(2) a cyano group,
(3) a nitro group,
(4) the above-defined "$C_{1-6}$ alkyl group",
(5) the above-defined "$C_{2-6}$ alkenyl group" optionally substituted by carboxyl group (e.g., vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group, 2-carboxyethenyl group etc.),
(6) the above-defined "halogenated $C_{1-6}$ alkyl group",
(7) —$(CH_2)_r$—$OR^{b1}$ (e.g., hydroxyl group, methoxy group, ethoxy group, isopropyloxy group, tert-butyloxy group, hydroxymethyl group, methoxymethyl group, 2-(methoxy)ethyl group etc.),
(8) —$(CH_2)_r$—$SR^{b1}$ (e.g., mercapto group, methylsulfanyl group, mercaptomethyl group, 2-(methylsulfanyl)ethyl group etc.),
(9) —$(CH_2)_r$—$NR^{b1}R^{b2}$ (e.g., amino group, methylamino group, ethylamino group, isopropylamino group, dimethylamino group, diethylamino group, diisopropylamino group, di-tert-butylamino group, N-ethyl-N-methylamino group, aminomethyl group, 2-(methylamino)ethyl group etc.),
(10) —$(CH_2)_r$—$COOR^{b1}$ (e.g., carboxyl group, methoxycarbonyl group, ethoxycarbonyl group, isopropyloxycarbonyl group, tert-butoxycarbonyl group, carboxymethyl group, 2-(carboxy)ethyl group etc.),
(11) —$(CH_2)_r$—$CONR^{b1}R^{b2}$ (e.g., carbamoyl group, methylcarbamoyl group, ethylcarbamoyl group, isopropylcarbamoyl group, dimethylcarbamoyl group, diethylcarbamoyl group, diisopropylcarbamoyl group, di-tert-butylcarbamoyl group, N-ethyl-N-methylcarbamoyl group, carbamoylmethyl group, dimethylcarbamoylmethyl group, 2-(methylcarbamoyl)ethyl group etc.),
(12) —$(CH_2)_r$—$COR^{b1}$ (e.g., formyl group, acetyl group, propionyl group, isobutyryl group, pivaloyl group, acetylmethyl group, 2-pivaloylethyl group etc.),

(13) —(CH$_2$)$_r$—NR$^{b1}$—COR$^{b2}$ (e.g., formylamino group, acetylamino group, propionylamino group, isobutyrylamino group, pivaloylamino group, N-acetyl-N-methylamino group, acetylaminomethyl group, 2-(isobutyrylamino)ethyl group etc.),

(14) —(CH$_2$)$_r$—NR$^{b1}$—SO$_2$R$^{b3}$ (e.g., methanesulfonylamino group, ethylsulfonylamino group, isopropylsulfonylamino group, tert-butylsulfonylamino group, N-methyl-N-(methanesulfonyl)amino group, methanesulfonylaminomethyl group, 2-(tert-butylsulfonylamino)ethyl group etc.),

(15) —(CH$_2$)$_r$—SO$_2$R$^{b3}$ (e.g., methanesulfonyl group, ethylsulfonyl group, isopropylsulfonyl group, tert-butylsulfonyl group, methanesulfonylmethyl group, 2-(ethylsulfonyl)ethyl group etc.),

(16) —(CH$_2$)$_r$—SO$_2$NR$^{b1}$R$^{b2}$ (e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, N-ethyl-N-methylsulfamoyl group, sulfamoylmethyl group, 2-(methylsulfamoyl)ethyl group etc.),

(17) —(CH$_2$)$_r$—CONR$^{b1}$—SO$_2$R$^{b3}$ (e.g., methanesulfonylcarbamoyl group, ethylsulfonylcarbamoyl group, isopropylsulfonylcarbamoyl group, tert-butylsulfonylcarbamoyl group, N-methyl-N-(methanesulfonyl)carbamoyl group, methanesulfonylcarbamoylmethyl group, 2-(ethylsulfonylcarbamoyl)ethyl group etc.),

(18) —(CH$_2$)$_r$—SO$_2$NR$^{b1}$—COR$^{b2}$ (e.g., acetylsulfamoyl group, propionylsulfamoyl group, isobutyrylsulfamoyl group, pivaloylsulfamoyl group, N-acetyl-N-methylsulfamoyl group, acetylsulfamoylmethyl group, 2-(pivaloylsulfamoyl)ethyl group etc.),

(19) —(CH$_2$)$_r$—NR$^{b1}$—COOR$^{b3}$ (e.g., methoxycarbonylamino group, ethoxycarbonylamino group, isopropyloxycarbonylamino group, tert-butoxycarbonylamino group, methoxycarbonylaminomethyl group, 2-(tert-butoxycarbonylamino)ethyl group etc.),

(20) —(CH$_2$)$_r$—NR$^{b1}$—CONR$^{b2}$R$^{b4}$ (e.g., ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group, ureidomethyl group, 2-(3,3-dimethylureido)ethyl group etc.),

(21) —O—(CH$_2$)$_r$—COOR$^{b1}$ (e.g., carboxymethoxy group, 2-carboxyethoxy group, 3-carboxypropoxy group, 4-carboxybutoxy group, 5-carboxypentyloxy group, methoxycarbonylmethoxy group, 2-ethoxycarbonylethoxy group etc.) and

(22) —CO—(CH$_2$)$_r$—R$^{b5}$ (e.g., 1-oxo-5-(2-oxohexahydrothieno[3,4-d]imidazol-6-yl)pentyl group etc.).

The "C$_{1-6}$ alkyl group optionally substituted by 1 to 3 substituents selected from group A" is a group wherein the above-defined "C$_{1-6}$ alkyl group" is optionally substituted by 1 to 3 substituents selected from the above-defined "group A", which includes non-substituted alkyl group.

Specifically, methyl group, ethyl group, propyl group, isopropyl group, butyl group, isobutyl group, sec-butyl group, tert-butyl group, pentyl group, isopentyl group, tert-pentyl group, neopentyl group, 1-ethylpropyl group, hexyl group, trifluoromethyl group, hydroxymethyl group, 2-hydroxyethyl group, 3-hydroxypropyl group, 4-hydroxybutyl group, 1-hydroxy-1-methylethyl group, 1-hydroxypropan-2-yl group, 1,3-dihydroxypropan-2-yl group, 1-hydroxy-2-methylpropan-2-yl group, carboxymethyl group, ethoxycarbonylmethyl group, 2-carboxyethyl group, methoxymethyl group, methoxyethyl group, methoxyethoxyethyl group, ethoxycarbonylmethyl group, 2-ethoxycarbonylethyl group, 2-dimethylaminoethyl group, carbamoylmethyl group, methylcarbamoylmethyl group, sulfomethyl group, sulfamoylmethyl group, 2-sulfamoylethyl group, methylsulfamoylmethyl group and the like can be mentioned.

The "C$_{2-6}$ alkenyl group optionally substituted by 1 to 3 substituents selected from group A" is the above-defined "C$_{2-6}$ alkenyl group" optionally substituted by 1 to 3 substituents selected from the above-defined "group A", which includes non-substituted alkenyl group.

Specifically, vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group, 2-carboxyethenyl group and the like can be mentioned.

The "C$_{2-6}$ alkynyl group optionally substituted by 1 to 3 substituents selected from group A" is the above-defined "C$_{2-6}$ alkynyl group" optionally substituted by 1 to 3 substituents selected from the above-defined "group A", which includes non-substituted alkynyl group.

Specifically, ethynyl group, 1-propynyl group, 2-propynyl group, 3-butynyl group and the like can be mentioned.

The "C$_{6-14}$ aryl group optionally substituted by 1 to 5 substituents selected from group B" is the above-defined "C$_{6-14}$ aryl group" optionally substituted by 1 to 5 substituents selected from the above-defined "group B", which includes non-substituted aryl group.

Specifically, phenyl group, naphthyl group, anthryl group, indenyl group, azulenyl group, fluorenyl group, phenanthryl group, 3-fluorophenyl group, 4-fluorophenyl group, 3-chlorophenyl group, 4-chlorophenyl group, 2,4-dichlorophenyl group, 3,5-dichlorophenyl group, pentafluorophenyl group, 4-tolyl group, 4-tert-butylphenyl group, 2-trifluoromethylphenyl group, 4-trifluoromethylphenyl group, 4-nitrophenyl group, 4-cyanophenyl group, 4-acetylphenyl group, 4-carboxyphenyl group, 4-carbamoylphenyl group, 4-aminophenyl group, 4-dimethylaminophenyl group, 4-acetylaminophenyl group, 4-(methylsulfonylamino)phenyl group, 4-methoxyphenyl group, 3,4,5-trimethoxyphenyl group, 4-methylthiophenyl group, 4-methylsulfonylphenyl group, 4-aminosulfonylphenyl group, 3-nitro-4-methoxyphenyl group and 4-nitro-3-methoxyphenyl group can be mentioned.

The "C$_{3-10}$ cycloalkyl group optionally substituted by 1 to 5 substituents selected from group B" is the above-defined "C$_{3-10}$ cycloalkyl group" optionally substituted by 1 to 5 substituents selected from the above-defined "group B", which includes non-substituted cycloalkyl group.

Specifically, cyclopropyl group, cyclobutyl group, cyclopentyl group, cyclohexyl group, cycloheptyl group, 1-adamantyl group, 4-fluorocyclohexyl group, 2-methylcyclopentyl group, 3-methylcyclohexyl group, 4-methylcyclohexyl group, 4,4-dimethylcyclohexyl group, 3,5-dimethylcyclohexyl group, 4-tert-butylcyclohexyl group, 4-hydroxycyclohexyl group, 4-methoxycyclohexyl group and 2,3,4,5,6-pentafluorocyclohexyl group can be mentioned.

The "C$_{3-10}$ cycloalkenyl group optionally substituted by 1 to 5 substituents selected from group B" is the above-defined "C$_{3-10}$ cycloalkenyl group" optionally substituted by 1 to 5 substituents selected from the above-defined "group B", which includes non-substituted cycloalkenyl group.

Specifically, cyclopropenyl group, cyclobutenyl group, cyclopentenyl group, cyclopentadienyl group, cyclohexenyl group (cyclohex-1-enyl group, cyclohex-2-enyl group, cyclohex-3-enyl group), 5-methylcyclohex-3-enyl group, 5-methoxycyclohex-3-enyl group, 5-acetylcyclohex-3-enyl group, 2,4-cyclohexadien-1-yl group, 2,5-cyclohexadien-1-yl group, cycloheptenyl group and cyclooctenyl group and the like can be mentioned.

The "heterocyclic group optionally substituted by 1 to 5 substituents selected from group B" is the above-defined "heterocyclic group" optionally substituted by 1 to 5 substituents selected from the above-defined "group B", which includes non-substituted heterocyclic group.

Specifically, 2-pyridyl group, 3-pyridyl group, 4-pyridyl group, 3-fluoropyridin-4-yl group, 3-chloropyridin-4-yl group, 4-chloropyridin-3-yl group, pyrazinyl group, pyrimidinyl group, pyridazinyl group, 1,3,5-triazinyl group, pyrrolyl group, pyrazolyl group, imidazolyl group, 1,2,4-triazolyl group, tetrazolyl group, 2-thienyl group, 3-thienyl group, furyl group, oxazolyl group, 2-methyloxazol-4-yl group, isoxazolyl group, thiazolyl group, 2-methylthiazol-4-yl group, 2,5-dimethylthiazol-4-yl group, 2,4-dimethylthiazol-5-yl group, isothiazolyl group, thiadiazolyl group, pyrrolinyl group, pyrrolidinyl group, 3-hydroxypyrrolidinyl group, imidazolidinyl group, azetidinyl group, piperidyl group, 3-hydroxypiperidino group, 4-hydroxypiperidino group, 3,4-dihydroxypiperidino group, 4-methoxypiperidino group, 4-carboxypiperidino group, 4-(hydroxymethyl)piperidino group, 2,2,6,6-tetramethylpiperidino group, 2,2,6,6-tetramethyl-4-hydroxypiperidino group, N-methylpiperidin-4-yl group, N-(tert-butoxycarbonyl)piperidin-4-yl group, N-acetylpiperidin-4-yl group, N-methylsulfonylpiperidin-4-yl group, piperazinyl group, 4-methylpiperazinyl group, 4-methylsulfonylpiperazinyl group, morpholinyl group, thiomorpholinyl group, 1-oxothiomorpholin-4-yl group, 1,1-dioxothiomorpholin-4-yl group, tetrahydropyranyl group, tetrahydrofuranyl group, azepanyl group, azocanyl group, azonanyl group, 1,4-diazepanyl group, 1,4-oxazepanyl group, quinolyl group, isoquinolyl group, quinazolinyl group, quinoxalinyl group, phthalazinyl group, cinnolinyl group, naphthyridinyl group, 1,2,3,4-tetrahydroquinolyl group, 5,6,7,8-tetrahydroquinolyl group, 1,2,3,4-tetrahydroisoquinolyl group, 5,6,7,8-tetrahydroisoquinolyl group, indolyl group, benzimidazolyl group, indolinyl group, isoindolinyl group, octahydroindolyl group, octahydroisoindolyl group, benzofuranyl group, benzothienyl group, benzoxazolyl group, benzothiazolyl group, octahydrocyclopenta[c]pyrrolyl group,

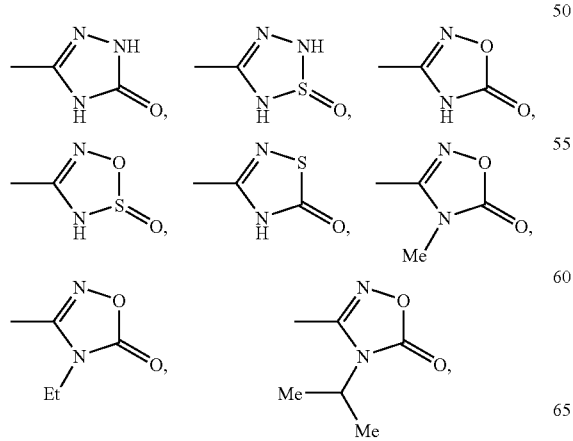

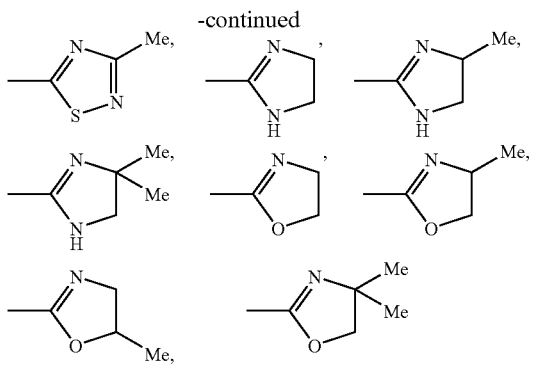

and the like can be mentioned.

For ring Cy, preferable "heterocyclic group optionally substituted by 1 to 5 substituents selected from group B" is

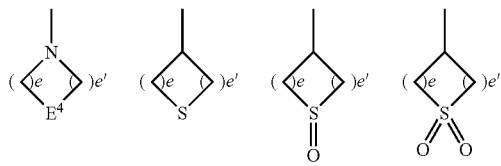

wherein $E^4$ is an oxygen atom, a sulfur atom, $CH_2$ or $N(-R^{Cy1})$, wherein $R^{Cy1}$ is a hydrogen atom or a $C_{1-6}$ alkyl group, and e and e' are each independently an integer of 1 to 3.

Specifically, pyrrolidinyl group, imidazolidinyl group, piperidyl group, piperazinyl group, morpholinyl group, thiomorpholinyl group, tetrahydropyranyl group, tetrahydrothiopyranyl group, 1-oxotetrahydrothiopyranyl group, 1,1-dioxotetrahydrothiopyranyl group and the like can be mentioned.

The "$C_{6-14}$ aryl $C_{1-6}$ alkyl group optionally substituted by 1 to 5 substituents selected from group B" is the above-defined "$C_{1-6}$ alkyl group" substituted by the above-defined "$C_{6-14}$ aryl group optionally substituted by 1 to 5 substituents selected from group B".

Specifically, benzyl group, 1-naphthylmethyl group, 2-naphthylmethyl group, phenethyl group, 3-phenylpropyl group, 2-phenylpropyl group, 3-fluorobenzyl group, 4-fluorobenzyl group, 3-chlorobenzyl group, 4-chlorobenzyl group, 2,4-dichlorobenzyl group, 3,5-dichlorobenzyl group, pentafluorobenzyl group, 4-methylbenzyl group, 4-tert-butylbenzyl group, 2-trifluoromethylbenzyl group, 4-trifluoromethylbenzyl group, 4-nitrobenzyl group, 4-cyanobenzyl group, 4-acetylbenzyl group, 4-carboxybenzyl group, 4-carbamoylbenzyl group, 4-aminobenzyl group, 4-dimethylaminobenzyl group, 4-acetylaminobenzyl group, 4-(methylsulfonylamino)benzyl group, 4-methoxybenzyl group, 3,4,5-trimethoxybenzyl group, 4-methylthiobenzyl group, 4-methylsulfonylbenzyl group, 4-aminosulfonylbenzyl group, 3-nitro-4-methoxybenzyl group, 4-nitro-3-methoxybenzyl group and the like can be mentioned.

The "heterocycle $C_{1-6}$ alkyl group optionally substituted by 1 to 5 substituents selected from group B" is the above-defined "$C_{1-6}$ alkyl group" substituted by the above-defined "heterocyclic group optionally substituted by 1 to 5 substituents selected from group B".

Specifically, 2-pyridylmethyl group, 3-pyridylmethyl group, 2-chloropyridin-4-ylmethyl group, 4-pyridylmethyl group, pyrrolylmethyl group, imidazolylmethyl group, 2-thienylmethyl group, 3-thienylmethyl group, 2-furylmethyl group, 2-oxazolylmethyl group, 5-isothiazolylmethyl group, 2-methyloxazol-4-ylmethyl group, 2-thiazolylmethyl group, 4-thiazolylmethyl group, 5-thiazolylmethyl group, 2-methylthiazol-4-ylmethyl group, 2-methylthiazol-5-ylmethyl group, 2,5-dimethylthiazol-4-ylmethyl group, 4-methylthiazol-2-ylmethyl group, 2,4-dimethylthiazol-5-ylmethyl group, 2-isothiazolylmethyl group, 2-pyrrolinylmethyl group, pyrrolidinylmethyl group, piperidylmethyl group, 4-piperidylmethyl group, 1-methylpiperidin-4-ylmethyl group, 4-hydroxypiperidinomethyl group, 3-hydroxypyrrolidinylmethyl group, 2-(4-hydroxypiperidino)ethyl group, 1-(tert-butoxycarbonyl)piperidin-4-ylmethyl group, 1-acetylpiperidin-4-ylmethyl group, 1-methylsulfonylpiperidin-4-ylmethyl group, piperazinylmethyl group, morpholinomethyl group, thiomorpholinylmethyl group, 2-tetrahydropyranylmethyl group, 2-quinolylmethyl group, 1-isoquinolylmethyl group and the like can be mentioned.

The "$C_{3-10}$ cycloalkyl $C_{1-6}$ alkyl group optionally substituted by 1 to 5 substituents selected from group B" is the above-defined "$C_{1-6}$ alkyl group" substituted by the above-defined "$C_{3-10}$ cycloalkyl group optionally substituted by 1 to 5 substituents selected from group B".

Specifically, cyclopropylmethyl group, cyclobutylmethyl group, cyclopentylmethyl group, cyclohexylmethyl group, 2-(cyclopentyl)ethyl group, 2-(cyclohexyl)ethyl group, cycloheptylmethyl group, 4-fluorocyclohexylmethyl group, 2-methylcyclopentylmethyl group, 3-methylcyclohexylmethyl group, 4-methylcyclohexylmethyl group, 4,4-dimethylcyclohexylmethyl group, 3,5-dimethylcyclohexylmethyl group, 4-tert-butylcyclohexylmethyl group, 4-hydroxycyclohexylmethyl group, 4-methoxycyclohexylmethyl group, 2,3,4,5,6-pentafluorocyclohexylmethyl group, 1-adamantylmethyl group and the like can be mentioned.

The "$C_{3-10}$ cycloalkylidene group optionally substituted by 1 to 5 substituents selected from group B" is such group wherein $C_{3-10}$ cycloalkylidene group is optionally substituted by 1 to 5 substituents selected from the above-defined "group B", which includes non-substituted cycloalkylidene group.

Specifically, cyclopropylidene group, cyclobutylidene group, cyclopentylidene group, cyclohexylidene group, cycloheptylidene group, 4-fluorocyclohexylidene group, 2-methylcyclopentylidene group, 3-methylcyclohexylidene group, 4-methylcyclohexylidene group, 4-ethylcyclohexylidene group, 4,4-dimethylcyclohexylidene group, 3,5-dimethylcyclohexylidene group, 4-tert-butylcyclohexylidene group, 4-hydroxycyclohexylidene group, 4-methoxycyclohexylidene group, 4-methoxycarbonylcyclohexylidene group, 2,3,4,5,6-pentafluorocyclohexylidene group and the like can be mentioned.

In addition, a group wherein the cyclopentylidene group or cyclohexylidene group is substituted by fluorine atom, chlorine atom, bromine atom, nitro group, methyl group, ethyl group, isopropyl group, tert-butyl group, carboxyl group, methoxycarbonyl group, acetyl group, trifluoromethyl group, hydroxymethyl group, methoxymethyl group, 2-carboxyethyl group, methoxy group, carbamoyl group, methylthio group, dimethylaminocarbonyl group, methylsulfonyl group or acetylamino group can be mentioned.

For group E for $R^2$, it is preferably a cyclohexylidene group.

The "heterocycle ylidene group optionally substituted by 1 to 5 substituents selected from group B" is such group wherein the heterocycle ylidene group is optionally substituted by 1 to 5 substituents selected from the above-defined "group B", which includes non-substituted heterocycle ylidene group.

The heterocycle ylidene group contains, as ring-constituting atom, 1 to 4 heteroatoms selected from oxygen atom, nitrogen atom and sulfur atom besides carbon atom, wherein the number of atom constituting the ring is 3 to 14, which includes saturated ring and unsaturated ring, monocycle and fused ring.

As the "heterocycle ylidene group optionally substituted by 1 to 5 substituents selected from group B", specifically, dihydrofuran-3-ylidene group, pyrrolidin-3-ylidene group, tetrahydropyran-4-ylidene group, piperidin-3-ylidene group, piperidin-4-ylidene group, 1-methylpiperidin-4-ylidene group, 1-ethylpiperidin-4-ylidene group, 1-isopropylpiperidin-4-ylidene group, 1-tert-butylpiperidin-4-ylidene group, 1-acetylpiperidin-4-ylidene group, 1-methanesulfonylpiperidin-4-ylidene group, 1-methoxycarbonylpiperidin-4-ylidene group, tetrahydrothiopyran-4-ylidene group, pyran-4-ylidene group, 1H-pyridin-4-ylidene group, 2,3-dihydro-1H-quinolin-4-ylidene group, 4-oxocyclohexylidene group and the like can be mentioned.

For group E for $R^2$, it is preferably 1-methylpiperidin-4-ylidene group, 1-ethylpiperidin-4-ylidene group, 1-acetylpiperidin-4-ylidene group, 1-methanesulfonylpiperidin-4-ylidene group, 1-methoxypiperidin-4-ylidene group or 1-methoxycarbonylpiperidin-4-ylidene group.

The "$C_{1-6}$ alkylidene group optionally substituted by 1 to 3 substituents selected from group A" is such group wherein a linear or branched chain having 1 to 6 carbon atoms, preferably having 1 to 4 carbon atoms, preferably a branched chain alkylidene group, is optionally substituted by 1 to 3 substituents selected from the above-defined "group A", which includes non-substituted alkylidene group.

Specifically, methylidene group, ethylidene group, propylidene group, isopropylidene group, butylidene group, pentylidene group, dimethylaminomethylidene group, methoxycarbonylmethylidene group, 2-methoxyethylidene group, diaminomethylidene group and the like can be mentioned.

For group E for $R^2$, it is preferably an isopropylidene group.

The "group C" means the substituent groups of the following (1) to (5).
(1) the above-defined "$C_{1-6}$ alkyl group optionally substituted by 1 to 3 substituents selected from group A",
(2) the above-defined "$C_{6-14}$ aryl group optionally substituted by 1 to 5 substituents selected from group B",
(3) the above-defined "$C_{6-14}$ aryl $C_{1-6}$ alkyl group optionally substituted by 1 to 5 substituents selected from group B",
(4) the above-defined "heterocyclic group optionally substituted by 1 to 5 substituents selected from group B" and
(5) the above-defined "heterocycle $C_{1-6}$ alkyl group optionally substituted by 1 to 5 substituents selected from group B".

The "group F" means the substituent groups of the following (1) to (7).
(1) the above-defined "$C_{1-6}$ alkyl group optionally substituted by 1 to 3 substituents selected from group A",
(2) the above-defined "$C_{6-14}$ aryl group optionally substituted by 1 to 5 substituents selected from group B",
(3) the above-defined "heterocyclic group optionally substituted by 1 to 5 substituents selected from group B",
(4) the above-defined "$C_3$-10 cycloalkyl group optionally substituted by 1 to 5 substituents selected from group B",
(5) the above-defined "$C_{6-14}$ aryl $C_{1-6}$ alkyl group optionally substituted by 1 to 5 substituents selected from group B",
(6) the above-defined "heterocycle $C_{1-6}$ alkyl group optionally substituted by 1 to 5 substituents selected from group B" and
(7) the above-defined "$C_{3-10}$ cycloalkyl $C_{1-6}$ alkyl group optionally substituted by 1 to 5 substituents selected from group B".

The "group D" means the substituent groups of the following (a) to (u).

(in the following, each t independently means 0 or an integer of 1 to 6)
(a) a hydrogen atom,
(b) the above-defined "halogen atom",
(c) a cyano group,
(d) a nitro group,
(e) the above-defined "$C_{1-6}$ alkyl group optionally substituted by 1 to 3 substituents selected from group A",
(f) —$(CH_2)_t$—$OR^{d1}$, wherein $R^{d1}$ is
(1) a hydrogen atom,
(2) the above-defined "group selected from group F",
(3) the above-defined "$C_{2-6}$ alkenyl group optionally substituted by 1 to 3 substituents selected from group A" or
(4) the above-defined "$C_{2-6}$ alkynyl group optionally substituted by 1 to 3 substituents selected from group A",
(e.g., substituent exemplified for "—$(CH_2)_t$—$OR^{b1}$" in group B, trifluoromethyloxy group, methoxymethoxy group, phenoxy group, benzyloxy group, 4-pyridylmethoxy group, 4-carboxybenzyloxy group, vinyloxy group, ethynyloxy group etc.)

(g) —$(CH_2)_t$—$S(O)_q$—$R^{d2}$, wherein $R^{d2}$ is
(1) a hydrogen atom or
(2) the above-defined "group selected from group F",
q is 0, 1, 2 or 3

(e.g., substituent exemplified for "—$(CH_2)_t$—$SR^{b1}$" and "—$(CH_2)_t$—$SO_2R^{b3}$" in group B, methylsulfinyl group, sulfo group, trifluoromethanesulfonyl group, 2-(methylamino)ethylsulfonyl group, 2-(dimethylamino)ethylsulfonyl group, 3-(dimethylamino)propylsulfonyl group, phenylsulfonyl group, 4-tolylsulfonyl group, benzylsulfonyl group etc.)

(h) —$(CH_2)_t$—$NR^{d3}R^{d4}$, wherein $R^{d3}$ and $R^{d4}$ are each independently
(1) a hydrogen atom or
(2) the above-defined "group selected from group F",
(e.g., substituent exemplified for "—$(CH_2)_t$—$NR^{b1}R^{b2}$" in group B, phenylamino group, benzyloxyamino group, methoxymethylamino group, N-ethyl-N-(carbamoylmethyl)amino group, N-ethyl-N-[2-(acetylamino)ethyl]amino group, N-[2-amino-2-(dimethylcarbamoyl)ethyl]-N-ethylamino group, N,N-bis(aminomethyl)amino group etc.)

(i) —$(CH_2)_t$—$COOR^{d5}$, wherein $R^{d5}$ is
(1) a hydrogen atom or
(2) the above-defined "group selected from group F",
(e.g., substituent exemplified for "—$(CH_2)_t$—$COOR^{b1}$" in group B, trifluoromethyloxycarbonyl group, phenoxycarbonyl group, benzyloxycarbonyl group, 2-morpholinoethoxycarbonyl group, 2-(dimethylamino)ethoxycarbonyl group etc.)

(j) —$(CH_2)_r$—$CONR^{d6}R^{d7}$, wherein $R^{d6}$ and $R^{d7}$ are each independently
(1) a hydrogen atom,
(2) a hydroxyl group,
(3) the above-defined "group selected from group F" or
(4) the above-defined "$C_{1-6}$ alkoxy group",
(e.g., substituent exemplified for "—$(CH_2)_r$—$CONR^{b1}R^{b2}$" in group B, hydroxycarbamoyl group, methoxycarbamoyl group, phenylcarbamoyl group, benzylcarbamoyl group, 2-morpholinoethylcarbamoyl group, 2-(dimethylamino)ethylcarbamoyl group, methoxymethylcarbamoyl group etc.)

(k) —$(CH_2)_r$—$COR^{d8}$, wherein $R^{d8}$ d is the above-defined "group selected from group F",
(e.g., substituent exemplified for "—$(CH_2)_r$—$COR^{b1}$" in group B, trifluoroacetyl group, methoxyacetyl group, carboxyacetyl group, benzoyl group, phenylacetyl group, 3-(dimethylamino)propionyl group, 3-morpholinopropionyl group etc.)

(l) —$(CH_2)_r$—$NR^{d9}CO$—$R^{d10}$, wherein $R^{d9}$ is
(1) a hydrogen atom,
(2) the above-defined "$C_{1-6}$ alkyl group optionally substituted by 1 to 3 substituents selected from group A" or
(3) the above-defined "$C_{1-6}$ alkanoyl group",
$R^{d10}$ is
(1) an amino group,
(2) the above-defined "$C_{1-6}$ alkylamino group" or
(3) the above-defined "group selected from group F",
(e.g., substituent exemplified for "—$(CH_2)_r$—$NR^{b1}$—$COR^{b2}$" in group B, ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group, ureidomethyl group, 2-(3,3-dimethylureido)ethyl group, benzoylamino group, phenylacetylamino group, trifluoroacetylamino group, methylaminoacetylamino group, N-acetyl-N-methylamino group, N-isopropyl-N-pivaloylamino group, dimethylaminoacetylamino group, N-(dimethylaminoacetyl)-N-methylamino group, morpholinoacetylamino group, N-methyl-N-(morpholinoacetyl)amino group etc.)

(m) —$(CH_2)_r$—$NR^{d11}SO_2$—$R^{d12}$, wherein $R^{d11}$ is
(1) a hydrogen atom,
(2) the above-defined "$C_{1-6}$ alkyl group optionally substituted by 1 to 3 substituents selected from group A" or
(3) the above-defined "$C_{1-6}$ alkanoyl group",
$R^{d12}$ is
(1) a hydrogen atom or
(2) the above-defined "group selected from group F",
(e.g., substituent exemplified for "—$(CH_2)_r$—$NR^{b1}$—$SO_2R^{b3}$" in group B, trifluoromethylsulfonylamino group, phenylsulfonylamino group, benzylsulfonylamino group, 2-(dimethylamino)ethylsulfonylamino group, 2-morpholinoethylsulfonylamino group, N-acetyl-N-methanesulfonylamino group, N-benzyl-N-methanesulfonylamino group etc.)

(n) —$(CH_2)_r$—$SO_2$—$NR^{d13}R^{d14}$, wherein $R^{d13}$ and $R^{d14}$ are each independently
(1) a hydrogen atom or
(2) the above-defined "group selected from group F",
(e.g., substituent exemplified for "—$(CH_2)_r$—$SO_2NR^{b1}R^{b2}$" in group B, trifluoromethylsulfamoyl group, 2-(dimethylamino)ethylsulfamoyl group, phenylsulfamoyl group, benzylsulfamoyl group, 2-morpholinoethylsulfamoyl group etc.)

(o) —$(CH_2)_r$—$CONR^{d15}$—$SO_2R^{d16}$, wherein $R^{d15}$ and $R^{d16}$ are each independently
(1) a hydrogen atom or
(2) the above-defined "group selected from group F",
(e.g., substituent exemplified for "—$(CH_2)_r$—$CONR^{b1}$—$SO_2R^{b3}$" in group B, trifluoromethylsulfonylcarbamoyl group, 2-(dimethylamino)ethylsulfonylcarbamoyl group, phenylsulfonylcarbamoyl group, benzylsulfonylcarbamoyl group, 2-morpholinoethylsulfonylcarbamoyl group, N-benzyl-N-(methanesulfonyl)carbamoyl group etc.)

(p) —$(CH_2)_r$—$SO_2NR^{d17}$—$COR^{d18}$, wherein $R^{d17}$ is
(1) a hydrogen atom or
(2) the above-defined "group selected from group F",
$R^{d18}$ is the above-defined "group selected from group F",
(e.g., substituent exemplified for "—$(CH_2)_r$—$SO_2N^{b1}$—$COR^{b2}$" in group B, trifluoroacetylsulfamoyl group, 2-(dimethylamino)ethylcarbonylsulfamoyl group, benzoylsulfamoyl group, phenylacetylsulfamoyl group, 3-morpholinopropionylsulfamoyl group, N-acetyl-N-benzylsulfamoyl group etc.)

(q) —$(CH_2)_r$—$NR^{d19}$—$COOR^{d20}$, wherein $R^{d19}$ and $R^{d20}$ are each independently
(1) a hydrogen atom or
(2) the above-defined "group selected from group F",
(e.g., substituent exemplified for "—$(CH_2)_r$—$NR^{b1}$—$COR^{b3}$" in group B, trifluoromethyloxycarbonylamino group, 2-(dimethylamino)ethoxycarbonylamino group, phenoxycarbonylamino group, benzyloxycarbonylamino group, 2-morpholinoethoxycarbonylamino group, N-ethoxycarbonyl-N-benzylamino group etc.)

(r) —$(CH_2)_r$—$NR^{d21}$—$CONR^{d22}R^{d23}$, wherein $R^{d21}$, $R^{d22}$ and $R^{d23}$ are each independently
(1) a hydrogen atom or
(2) the above-defined "group selected from group F",
(e.g., substituent exemplified for "—$(CH_2)_r$—$NR^{b1}$—$CONR^{b2}R^{b4}$" in group B etc.)

(s) —$(CH_2)_r$—$C(=NR^{d24})NH_2$, wherein $R^{d24}$ is
(1) a hydrogen atom,
(2) a hydroxyl group,
(3) the above-defined "$C_{1-6}$ alkyl group optionally substituted by 1 to 3 substituents selected from group A" or
(4) the above-defined "$C_{1-6}$ alkoxy group",
(e.g., carbamimidoyl group, N-hydroxycarbamimidoyl group, N-methylcarbamimidoyl group, N-methoxycarbamimidoyl group, N-(2-methoxyethyl)carbamimidoyl group etc.)

(t) —$(CH_2)_t$—O—$(CH_2)_p$—$COR^{d25}$, wherein $R^{d25}$ is
(1) an amino group,
(2) the above-defined "$C_{1-6}$ alkylamino group" or
(3) the above-defined "heterocyclic group optionally substituted by 1 to 5 substituents selected from group B",
p is 0 or an integer of 1 to 6

(e.g., carbamoylmethoxy group, methylcarbamoylmethoxy group, 2-(dimethylcarbamoyl)ethoxy group, 2-oxo-2-(pyridin-2-yl)ethoxy group, 2-oxo-2-(piperidin-1-yl)ethoxy group, 2-oxo-2-(piperazin-1-yl)ethoxy group, 2-oxo-2-(pyrrolidin-1-yl)ethoxy group, 2-(morpholin-4-yl)-2-oxoethoxy group etc.)

and (u) the above-defined "heterocyclic group optionally substituted by 1 to 5 substituents selected from group B".

The "group E" means the substituent groups of the following (a) to (jj).

(a) the above-defined "halogen atom",
(b) a cyano group,
(c) a nitro group,
(d) an azido group,
(e) —OP(=O) (OH)$_2$,
(f) —OR$^{e1}$, wherein R$^{e1}$ is
(1) a hydrogen atom,
(2) the above-defined "group selected from group F",
(3) the above-defined "C$_{2-6}$ alkenyl group optionally substituted by 1 to 3 substituents selected from group A" or
(4) the above-defined "C$_{2-6}$ alkynyl group optionally substituted by 1 to 3 substituents selected from group A",
(e.g., hydroxyl group, methoxy group, ethoxy group, isopropyloxy group, tert-butyloxy group, trifluoromethyloxy group, methoxymethoxy group, phenoxy group, benzyloxy group, 4-pyridylmethoxy group, 4-carboxybenzyloxy group, vinyloxy group, ethynyloxy group etc.)

(g) —S(O)$_q$—R$^{e2}$, wherein R$^{e2}$ is
(1) a hydrogen atom or
(2) the above-defined "group selected from group F",
q is 0, 1, 2 or 3
(e.g., mercapto group, methylsulfanyl group, methanesulfonyl group, ethylsulfonyl group, isopropylsulfonyl group, tert-butylsulfonyl group, methylsulfinyl group, sulfo group, trifluoromethanesulfonyl group, 2-(methylamino)ethylsulfonyl group, 2-(dimethylamino)ethylsulfonyl group, 3-(dimethylamino)propylsulfonyl group, phenylsulfonyl group, 4-tolylsulfonyl group, benzylsulfonyl group etc.)

(h) —NR$^{e3}$R$^{e4}$,
wherein R$^{e3}$ and R$^{e4}$ are each independently
(1) a hydrogen atom,
(2) a cyano group or
(3) the above-defined "group selected from group F",
(e.g., amino group, methylamino group, ethylamino group, isopropylamino group, dimethylamino group, diethylamino group, diisopropylamino group, di-tert-butylamino group, N-ethyl-N-methylamino group, phenylamino group, benzyloxyamino group, methoxymethylamino group, N-ethyl-N-(carbamoylmethyl)amino group, N-ethyl-N-[2-(acetylamino)ethyl] amino group, N-[2-amino-2-(dimethylcarbamoyl) ethyl]-N-ethylamino group, N,N-bis(aminomethyl) amino group etc.)

(i) —COOR$^{e5}$,
wherein R$^{e5}$ is
(1) a hydrogen atom or
(2) the above-defined "group selected from group F",
(e.g., carboxyl group, methoxycarbonyl group, ethoxycarbonyl group, isopropyloxycarbonyl group, tert-butoxycarbonyl group, trifluoromethyloxycarbonyl group, phenoxycarbonyl group, benzyloxycarbonyl group, 2-morpholinoethoxycarbonyl group, 2-(dimethylamino)ethoxycarbonyl group etc.)

(j) —CONR$^{e6}$R$^{e7}$,
wherein R$^{e6}$ and R$^{e7}$ are each independently
(1) a hydrogen atom,
(2) a hydroxyl group,
(3) the above-defined "group selected from group F" or
(4) the above-defined "C$_{1-6}$ alkoxy group",
(e.g., carbamoyl group, methylcarbamoyl group, ethylcarbamoyl group, isopropylcarbamoyl group, dimethylcarbamoyl group, diethylcarbamoyl group, diisopropylcarbamoyl group, di-tert-butylcarbamoyl group, N-ethyl-N-methylcarbamoyl group, hydroxycarbamoyl group, methoxycarbamoyl group, phenylcarbamoyl group, benzylcarbamoyl group, 2-morpholinoethylcarbamoyl group, 2-(dimethylamino)ethylcarbamoyl group, methoxymethylcarbamoyl group etc.)

(k) —COR$^{e8}$,
wherein R$^{e8}$ is the above-defined "group selected from group F",
(e.g., formyl group, acetyl group, propionyl group, isobutyryl group, pivaloyl group, trifluoroacetyl group, methoxyacetyl group, carboxyacetyl group, benzoyl group, phenylacetyl group, 3-(dimethylamino)propionyl group, 3-morpholinopropionyl group etc.)

(1) —NR$^{e9}$CO—R$^{e10}$,
wherein R$^{e9}$ is
(1) a hydrogen atom,
(2) the above-defined "C$_{1-6}$ alkyl group" or
(3) the above-defined "C$_{1-6}$ alkanoyl group",
R$^{e10}$ is
(1) a hydrogen atom,
(2) an amino group,
(3) the above-defined "C$_{1-6}$ alkylamino group",
(4) the above-defined "C$_{2-6}$ alkenyl group optionally substituted by 1 to 3 substituents selected from group A" or
(5) the above-defined "group selected from group F",
(e.g., formylamino group, acetylamino group, propionylamino group, isobutyrylamino group, pivaloylamino group, N-acetyl-N-methylamino group, ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group, benzoylamino group, phenylacetylamino group, trifluoroacetylamino group, methylaminoacetylamino group, N-acetyl-N-methylamino group, N-isopropyl-N-pivaloylamino group, 3-carboxy-3-butenoylamino group etc.)

(m) —NR$^{e11}$SO$_2$—R$^{e12}$,
wherein R$^{e11}$ is
(1) a hydrogen atom,
(2) the above-defined "C$_{1-6}$ alkyl group" or
(3) the above-defined "C$_{1-6}$ alkanoyl group",
R$^{e12}$ is
(1) a hydrogen atom or
(2) the above-defined "group selected from group F",
(e.g., methanesulfonylamino group, ethylsulfonylamino group, isopropylsulfonylamino group, tert-butylsulfonylamino group, N-methyl-N-(methanesulfonyl)amino group, trifluoromethylsulfonylamino group, phenylsulfonylamino group, benzylsulfonylamino group, 2-(dimethylamino)ethylsulfonylamino group, 2-morpholinoethylsulfonylamino group, N-acetyl-N- methanesulfonylamino group, N-benzyl-N-methanesulfonylamino group etc.)

(n) —SO$_2$—NR$^{e13}$R$^{e14}$, wherein R$^{e13}$ and R$^{e14}$ are each independently
(1) a hydrogen atom or
(2) the above-defined "group selected from group F",
(e.g., sulfamoyl group, methylsulfamoyl group, ethylsulfamoyl group, isopropylsulfamoyl group, dimethylsulfamoyl group, diethylsulfamoyl group, diisopropylsulfamoyl group, di-tert-butylsulfamoyl group, trifluoromethylsulfamoyl group, 2-(dimethylamino)ethylsulfamoyl group, phenylsulfamoyl group, benzylsulfamoyl group, 2-morpholinoethylsulfamoyl group etc.)

(o) —CONR$^{e15}$—SO$_2$R$^{e16}$, wherein R$^{e15}$ and R$^{e16}$ are each independently
(1) a hydrogen atom or
(2) the above-defined "group selected from group F",
(e.g., methanesulfonylcarbamoyl group, ethylsulfonylcarbamoyl group, isopropylsulfonylcarbamoyl group, tert-butylsulfonylcarbamoyl group, N-methyl-N-(methanesulfonyl)carbamoyl group, trifluoromethylsulfonylcarbamoyl group, 2-(dimethylamino)ethylsulfonylcarbamoyl group, phenylsulfonylcarbamoyl group, benzylsulfonylcarbamoyl group, 2-morpholinoethylsulfonylcarbamoyl group, N-benzyl-N-(methanesulfonyl)carbamoyl group etc.)

(p) —SO$_2$NR$^{e17}$COR$^{e18}$, wherein R$^{e17}$ is
(1) a hydrogen atom or
(2) the above-defined "group selected from group F",
R$^{e18}$ is the above-defined "group selected from group F",
(e.g., acetylsulfamoyl group, propionylsulfamoyl group, isobutyrylsulfamoyl group, pivaloylsulfamoyl group, N-acetyl-N-methylsulfamoyl group, trifluoroacetylsulfamoyl group, 2-(dimethylamino)ethylsulfamoyl group, benzoylsulfamoyl group, phenylacetylsulfamoyl group, 3-morpholinopropionylsulfamoyl group, N-acetyl-N-benzylsulfamoyl group etc.)

(q) —NR$^{e19}$—COOR$^{e20}$, wherein R$^{e19}$ and R$^{e20}$ are each independently
(1) a hydrogen atom or
(2) the above-defined "group selected from group F",
(e.g., methoxycarbonylamino group, ethoxycarbonylamino group, isopropyloxycarbonylamino group, tert-butoxycarbonylamino group, trifluoromethyloxycarbonylamino group, 2-(dimethylamino)ethyloxycarbonylamino group, phenoxycarbonylamino group, benzyloxycarbonylamino group, 2-morpholinoethoxycarbonylamino group, N-ethoxycarbonyl-N-benzylamino group etc.)

(r) —NR$^{e21}$—CONR$^{e22}$R$^{e23}$
wherein R$^{e21}$, R$^{e22}$ and R$^{e23}$ are each independently
(1) a hydrogen atom or
(2) the above-defined "group selected from group F",
(e.g., ureido group, 3-methylureido group, 3-ethylureido group, 3-isopropylureido group, 3,3-dimethylureido group, 3,3-diethylureido group, 3,3-diisopropylureido group, 3,3-di-tert-butylureido group, 3-ethyl-3-methylureido group, 1,3-dimethylureido group, trimethylureido group etc.)

(5) —NHCO—COOR$^{e24}$ wherein R$^{e24}$ is
(1) a hydrogen atom or
(2) the above-defined "group selected from group F",
(e.g., —NHCO—COOH etc.)

(t) —NHCO—CONR$^{e25}$R$^{e26}$ wherein R$^{e25}$ and R$^{e26}$ are each independently
(1) a hydrogen atom,
(2) a hydroxyl group or
(3) the above-defined "group selected from group F",
(e.g., —NHCO—CONH$_2$, —NHCO—CONHCH$_3$, —NHCO—CONHOH etc.)

(u) —CONH—COOH, (v)

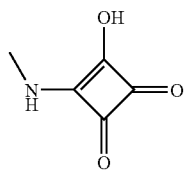

(w)

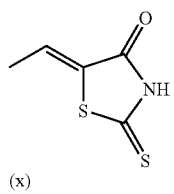

(x)

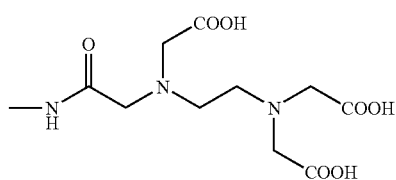

(y) the above-defined "C$_{6-14}$ aryl group optionally substituted by 1 to 5 substituents selected from group B",
(z) the above-defined "C$_3$-10 cycloalkyl group optionally substituted by 1 to 5 substituents selected from group B",
(aa) the above-defined "heterocyclic group optionally substituted by 1 to 5 substituents selected from group B",
(bb) the above-defined "C$_3$-10 cycloalkylidene group optionally substituted by 1 to 5 substituents selected from group B", and
(cc) the above-defined "heterocycle ylidene group optionally substituted by 1 to 5 substituents selected from group B",
when group E is a substituent on a C$_{6-14}$ aryl group, a C$_{3-10}$ cycloalkyl group or a heterocyclic group, it may be
(dd) the above-defined "C$_{1-6}$ alkyl group optionally substituted by 1 to 3 substituents selected from group A",
(ee) the above-defined "C$_{2-6}$ alkenyl group optionally substituted by 1 to 3 substituents selected from group A",
(ff) the above-defined "C$_{2-6}$ alkynyl group optionally substituted by 1 to 3 substituents selected from group A",
(gg) the above-defined "C$_{1-6}$ alkylidene group optionally substituted by 1 to 3 substituents selected from group A",
(hh) the above-defined "C$_{6-14}$ aryl C$_{1-6}$ alkyl group optionally substituted by 1 to 5 substituents selected from group B",
(ii) the above-defined "C$_{3-10}$ cycloalkyl C$_{1-6}$ alkyl group optionally substituted by 1 to 5 substituents selected from group B", or (jj) the above-defined "heterocycle C$_{1-6}$ alkyl group optionally substituted by 1 to 5 substituents selected from group B".

The "C$_{6-14}$ aryl group optionally substituted by 1 to 5 substituents selected from group D" is the above-defined "C$_{6-14}$ aryl group" optionally substituted by 1 to 5 substituents selected from the above-defined "group D", which includes non-substituted aryl group.

Specifically, phenyl group, naphthyl group, anthryl group, indenyl group, azulenyl group, fluorenyl group, phenanthryl group, 3-fluorophenyl group, 4-fluorophenyl group, 3-chlorophenyl group, 4-chlorophenyl group, 2,4-dichlorophenyl group, 3,5-dichlorophenyl group, 4-bromophenyl group, 4-nitrophenyl group, pentafluorophenyl group, 4-methylphenyl group, 4-tert-butylphenyl group, 2-trifluoromethylphenyl group, 4-trifluoromethylphenyl group, 4-(hydroxymethyl)phenyl group, 4-(methoxymethyl)phenyl group, 4-(2-carboxyethyl)phenyl group, 3-carboxyphenyl group, 4-carboxyphenyl group, 4-methoxyphenyl group, 3,4,5-trimethoxyphenyl group, 4-carbamoylphenyl group, 4-methylthiophenyl group, 4-(dimethylaminocarbonyl)phenyl group, 4-methylsulfonylphenyl group, 4-acetylaminophenyl group, 4-cyanophenyl group, 4-acetylphenyl group, 4-aminophenyl group, 4-dimethylaminophenyl group, 4-(methylsulfonylamino)phenyl group, 4-methylsulfinylphenyl group, 4-aminosulfonylphenyl group, 3-nitro-4-methoxyphenyl group, 4-nitro-3-methoxyphenyl group, 4-(tetrazol-5-yl)phenyl group and the like can be mentioned.

The "C$_{3-10}$ cycloalkyl group optionally substituted by 1 to 5 substituents selected from group D" is the above-defined "C$_{3-10}$ cycloalkyl group" optionally substituted by 1 to 5 substituents selected from the above-defined "group D", which includes non-substituted cycloalkyl group.

Specifically, cyclopropyl group, cyclobutyl group, cyclopentyl group, cyclohexyl group, cycloheptyl group, 4-fluorocyclohexyl group, 2-methylcyclopentyl group, 3-methylcyclohexyl group, 4-methylcyclohexyl group, 4,4-dimethylcyclohexyl group, 3,5-dimethylcyclohexyl group, 4-tert-butylcyclohexyl group, 4-hydroxycyclohexyl group, 4-methoxycyclohexyl group, 2,3,4,5,6-pentafluorocyclohexyl group, 1-adamantylmethyl group and the like can be mentioned.

In addition, such group wherein cyclopentyl group or cyclohexyl group is substituted by fluorine atom, chlorine atom, bromine atom, nitro group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group or acetylamino group can be mentioned.

The "heterocyclic group optionally substituted by 1 to 5 substituents selected from group D" is the above-defined "heterocyclic group" optionally substituted by 1 to 5 substituents selected from the above-defined "group D", which includes non-substituted heterocyclic group.

Specifically, 2-pyridyl group, 3-pyridyl group, 4-pyridyl group, 3-fluoropyridin-4-yl group, 3-chloropyridin-4-yl group, 4-chloropyridin-3-yl group, pyrazinyl group, pyrimidinyl group, pyridazinyl group, 1,3,5-triazinyl group, pyrrolyl group, pyrazolyl group, imidazolyl group, 1,2,4-triazolyl group, tetrazolyl group, 2-thienyl group, 3-thienyl group, furyl group, oxazolyl group, 2-methyloxazol-4-yl group, isoxazolyl group, thiazolyl group, 2-methylthiazol-4-yl group, 2,5-dimethylthiazol-4-yl group, 2,4-dimethylthiazol-5-yl group, isothiazolyl group, thiadiazolyl group, pyrrolinyl group, pyrrolidinyl group, imidazolidinyl group, piperidyl group, N-methylpiperidin-4-yl group, N-(tert-butoxycarbonyl)piperidin-4-yl group, N-acetylpiperidin-4-yl group, N-methylsulfonylpiperidin-4-yl group, piperazinyl group, 4-ethylpiperazin-1-yl group, 4-methanesulfonylpiperazin-1-yl group, 4-dimethylcarbamoylmethylpiperazin-1-yl group, morpholinyl group, thiomorpholinyl group, tetrahydropyranyl group, quinolyl group, isoquinolyl group, quinazolinyl group, quinoxalinyl group, phthalazinyl group, cinnolinyl group, naphthyridinyl group, 5,6,7,8-tetrahydroquinolyl group, indolyl group, benzimidazolyl group, indolinyl group, benzofuranyl group, benzothienyl group, benzoxazolyl group, benzothiazolyl group,

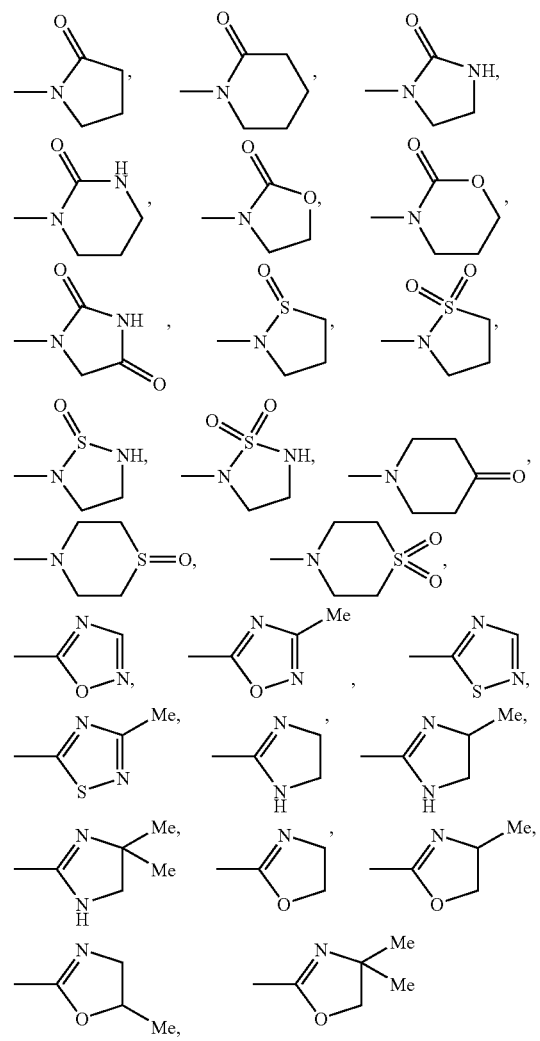

and the like can be mentioned.

In addition, such group wherein the 3, 4, 5 or 6-position of 2-pyridyl group, 2, 4, 5 or 6-position of 3-pyridyl group, 2, 3, 5 or 6-position of 4-pyridyl group, 3, 4 or 5-position of 2-thienyl group, and 2, 4 or 5-position of 3-thienyl group are substituted by fluorine atom, chlorine atom, bromine atom, nitro group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group, amino group or acetylamino group can be mentioned.

The "$C_{6-14}$ aryl $C_{1-6}$ alkyl group optionally substituted by 1 to 5 substituents selected from group D" is the above-defined "$C_{1-6}$ alkyl group" substituted by the above-defined "$C_{6-14}$ aryl group optionally substituted by 1 to 5 substituents selected from group D".

Specifically, benzyl group, 1-naphthylmethyl group, 2-naphthylmethyl group, phenethyl group, 3-phenylpropyl group, 2-phenylpropyl group, 3-fluorobenzyl group, 4-fluorobenzyl group, 3-chlorobenzyl group, 4-chlorobenzyl group, 2,4-dichlorobenzyl group, 3,5-dichlorobenzyl group, 4-bromobenzyl group, 4-nitrobenzyl group, pentafluorobenzyl group, 4-methylbenzyl group, 4-tert-butylbenzyl group, 2-trifluoromethylbenzyl group, 4-trifluoromethylbenzyl group, 4-(hydroxymethyl)benzyl group, 4-(methoxymethyl)benzyl group, 4-(2-carboxyethyl)benzyl group, 3-carboxybenzyl group, 4-carboxybenzyl group, 4-methoxybenzyl group, 3,4,5-trimethoxybenzyl group, 4-carbamoylbenzyl group, 4-methylthiobenzyl group, 4-(dimethylaminocarbonyl)benzyl group, 4-methylsulfonylbenzyl group, 4-(acetylamino)benzyl group, 4-cyanobenzyl group, 4-acetylbenzyl group, 4-aminobenzyl group, 4-dimethylaminobenzyl group, 4-(methylsulfonylamino)benzyl group, 4-methylsulfinylbenzyl group, 4-aminosulfonylbenzyl group, (3-nitro-4-methoxyphenyl)methyl group, (4-nitro-3-methoxyphenyl)methyl group and the like can be mentioned.

The "heterocycle $C_{1-6}$ alkyl group optionally substituted by 1 to 5 substituents selected from group D" is the above-defined "$C_{1-6}$ alkyl group" substituted by the above-defined "heterocyclic group optionally substituted by 1 to 5 substituents selected from group D".

Specifically, 2-pyridylmethyl group, 3-pyridylmethyl group, 2-chloropyridin-4-ylmethyl group, 4-pyridylmethyl group, pyrrolylmethyl group, imidazolylmethyl group, 2-thienylmethyl group, 3-thienylmethyl group, 2-furylmethyl group, 2-oxazolylmethyl group, 5-isothiazolylmethyl group, 2-methyloxazol-4-ylmethyl group, 2-thiazolylmethyl group, 4-thiazolylmethyl group, 5-thiazolylmethyl group, 2-methylthiazol-4-ylmethyl group, 2-methylthiazol-5-ylmethyl group, 2,5-dimethylthiazol-4-ylmethyl group, 4-methylthiazol-2-ylmethyl group, 2,4-dimethylthiazol-5-ylmethyl group, 2-isothiazolylmethyl group, 2-pyrrolinylmethyl group, pyrrolidinylmethyl group, piperidylmethyl group, 4-piperidylmethyl group, 1-methylpiperidin-4-ylmethyl group, 4-hydroxypiperidinomethyl group, 2-(4-hydroxypiperidino)ethyl group, 1-(tert-butoxycarbonyl)piperidin-4-ylmethyl group, 1-acetylpiperidin-4-ylmethyl group, 1-methylsulfonylpiperidin-4-ylmethyl group, piperazinylmethyl group, morpholinomethyl group, thiomorpholinylmethyl group, 1-tetrahydropyranylmethyl group, 2-quinolylmethyl group, 1-isoquinolylmethyl group and the like can be mentioned.

The "$C_{1-6}$ alkyl group optionally substituted by 1 to 3 substituents selected from group E" is the above-defined "$C_{1-6}$ alkyl group" optionally substituted by 1 to 3 substituents selected from the above-defined "group E", which includes non-substituted alkyl group.

Specifically, methyl group, ethyl group, propyl group, isopropyl group, butyl group, isobutyl group, sec-butyl group, tert-butyl group, pentyl group, isopentyl group, tert-pentyl group, neopentyl group, 1-ethylpropyl group, hexyl group, trifluoromethyl group, hydroxymethyl group, 2-hydroxyethyl group, 3-hydroxypropyl group, 4-hydroxybutyl group, 1-hydroxy-1-methylethyl group, 1-hydroxypropan-2-yl group, 1,3-dihydroxypropan-2-yl group, 1-hydroxy-2-methylpropan-2-yl group, 1,1-dimethyl-2-hydroxyethyl group, carboxymethyl group, ethoxycarbonylmethyl group, 2-carboxyethyl group, methoxymethyl group, methoxyethyl group, methoxyethoxyethyl group, ethoxycarbonylmethyl group, 2-ethoxycarbonylethyl group, 2-dimethylaminoethyl group, carbamoylmethyl group, methylcarbamoylmethyl group, sulfomethyl group, sulfamoylmethyl group, 2-sulfamoylethyl group, methylsulfamoylmethyl group and the like can be mentioned.

The "$C_{2-6}$ alkenyl group optionally substituted by 1 to 3 substituents selected from group E" is the above-defined "$C_{2-6}$ alkenyl group" optionally substituted by 1 to 3 substituents selected from the above-defined "group E", which includes non-substituted alkenyl group.

Specifically, vinyl group, allyl group, 1-propenyl group, isopropenyl group, 1-butenyl group, 2-butenyl group, 1,3-butadienyl group, 2-isopentenyl group, 3-isohexenyl group, 4-methyl-3-pentenyl group and the like can be mentioned.

The "$C_{6-14}$ aryl group optionally substituted by 1 to 5 substituents selected from group E" is the above-defined "$C_{6-14}$ aryl group" optionally substituted by 1 to 5 substituents selected from the above-defined "group E", which includes non-substituted aryl group.

Specifically, phenyl group, naphthyl group, anthryl group, indenyl group, azulenyl group, fluorenyl group, phenanthryl group, 3-fluorophenyl group, 4-fluorophenyl group, 3-chlorophenyl group, 4-chlorophenyl group, 2,4-dichlorophenyl group, 3,5-dichlorophenyl group, 4-bromophenyl group, 4-nitrophenyl group, pentafluorophenyl group, 4-methylphenyl group, 4-tert-butylphenyl group, 2-trifluoromethylphenyl group, 4-trifluoromethylphenyl group, 4-(hydroxymethyl)phenyl group, 4-(methoxymethyl)phenyl group, 4-(2-carboxyethyl)phenyl group, 3-carboxyphenyl group, 4-carboxyphenyl group, 4-methoxyphenyl group, 3,4,5-trimethoxyphenyl group, 4-carbamoylphenyl group, 4-methylthiophenyl group, 4-(dimethylaminocarbonyl)phenyl group, 4-methylsulfonylphenyl group, 4-acetylaminophenyl group, 4-cyanophenyl group, 4-acetylphenyl group, 4-aminophenyl group, 4-dimethylaminophenyl group, 4-(methylsulfonylamino)phenyl group, 4-methylsulfinylphenyl group, 4-aminosulfonylphenyl group, 3-nitro-4-methoxyphenyl group, 4-nitro-3-methoxyphenyl group, 4-(tetrazol-5-yl)phenyl group and the like can be mentioned.

The "$C_{3-10}$ cycloalkyl group optionally substituted by 1 to 5 substituents selected from group E" is the above-defined "$C_{3-10}$ cycloalkyl group" optionally substituted by 1 to 5 substituents selected from the above-defined "group E", which includes non-substituted cycloalkyl group.

Specifically, cyclopropyl group, cyclobutyl group, cyclopentyl group, cyclohexyl group, cycloheptyl group, 1-adamantyl group, 4-fluorocyclohexyl group, 2-methylcyclopentyl group, 3-methylcyclohexyl group, 4-methylcyclohexyl group, 4,4-dimethylcyclohexyl group, 3,5-dimethylcyclohexyl group, 4-tert-butylcyclohexyl group, 4-hydroxycyclohexyl group, 4-methoxycyclohexyl group, 2,3,4,5,6-pentafluorocyclohexyl group and the like can be mentioned.

In addition, such group wherein the cyclopentyl group or cyclohexyl group is substituted by fluorine atom, chlorine atom, bromine atom, nitro group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group or acetylamino group can be mentioned.

The "heterocyclic group optionally substituted by 1 to 5 substituents selected from group E" is the above-defined "heterocyclic group" optionally substituted by 1 to 5 substituents selected from the above-defined "group E", which includes non-substituted heterocyclic group.

Specifically, 2-pyridyl group, 3-pyridyl group, 4-pyridyl group, 3-fluoropyridin-4-yl group, 3-chloropyridin-4-yl group, 4-chloropyridin-3-yl group, pyrazinyl group, pyrimidinyl group, pyridazinyl group, 1,3,5-triazinyl group, pyrrolyl group, pyrazolyl group, imidazolyl group, 2-methylimidazol-1-yl group, 1,2,4-triazolyl group, tetrazolyl group, 2-thienyl group, 3-thienyl group, furyl group, oxazolyl group, 2-methyloxazol-4-yl group, isoxazolyl group, thiazolyl group, 2-methylthiazol-4-yl group, 2,5-dimethylthiazol-4-yl group, 2,4-dimethylthiazol-5-yl group, 2-(dimethylamino)thiazol-4-yl group, isothiazolyl group, thiadiazolyl group, pyrrolinyl group, pyrrolidinyl group, 1-methylpyrrolidin-3-yl group, 1-acetylpyrrolidin-3-yl group, 1-methanesulfonylpyrrolidin-3-yl group, 1-methoxycarbonylpyrrolidin-3-yl group, imidazolidinyl group, piperidyl group, 4-methylpiperidin-1-yl group, 2-methylpiperidin-1-yl group, 3-methylpiperidin-1-yl group, 4-ethylpiperidin-1-yl group, 4-propylpiperidin-1-yl group, 4-isopropylpiperidin-1-yl group, 4,4-dimethylpiperidin-1-yl group, 2,2,6,6-tetramethylpiperidin-1-yl group, 4-trifluoromethylpiperidin-1-yl group, 4-hydroxypiperidin-1-yl group, 3-hydroxypiperidin-1-yl group, 4-methoxypiperidin-1-yl group, 3-methoxypiperidin-1-yl group, 4-(dimethylamino)piperidin-1-yl group, 4-methylenepiperidin-1-yl group, 4-ethylidenepiperidin-1-yl group, 4-isopropylidenepiperidin-1-yl group, 1-methylpiperidin-4-yl group, 1-ethylpiperidin-4-yl group, 1-methoxypiperidin-4-yl group, 1-methoxycarbonylpiperidin-4-yl group, 1-(tert-butoxycarbonyl)piperidin-4-yl group, 1-acetylpiperidin-4-yl group, 1-methanesulfonylpiperidin-4-yl group, 1-methylpiperidin-3-yl group, 1-ethylpiperidin-3-yl group, 1-acetylpiperidin-3-yl group, 1-methanesulfonylpiperidin-3-yl group, 1-methoxypiperidin-3-yl group, 1-methoxycarbonylpiperidin-3-yl group, 1-methylpiperidin-2-yl group, 1-ethylpiperidin-2-yl group, 1-acetylpiperidin-2-yl group, 1-methanesulfonylpiperidin-2-yl group, 1-methoxypiperidin-2-yl group, 1-methoxycarbonylpiperidin-2-yl group, piperazinyl group, 4-methylpiperazin-1-yl group, 4-ethylpiperazin-1-yl group, 4-isopropylpiperazin-1-yl group, 4-methoxypiperazin-1-yl group, 4-phenylpiperazin-1-yl group, 4-benzylpiperazin-1-yl group, 4-methoxycarbonylpiperazin-1-yl group, 4-ethoxycarbonylpiperazin-1-yl group, 4-(tert-butoxycarbonyl)piperazin-1-yl group, 4-cyclopentyloxycarbonylpiperazin-1-yl group, 4-acetylpiperazin-1-yl group, 4-isobutyrylpiperazin-1-yl group, 4-benzoylpiperazin-1-yl group, 4-(2-methoxyacetyl)piperazin-1-yl group, 4-methylcarbamoylpiperazin-1-yl group, 4-dimethylcarbamoylpiperazin-1-yl group, 4-methanesulfonylpiperazin-1-yl group, 1,2,3,6-tetrahydropyridyl group, morpholinyl group, thiomorpholinyl group, tetrahydropyranyl group, tetrahydrofuranyl group, azepanyl group, azocanyl group, azonanyl group, 1,4-diazepanyl group, 4-methyl-1,4-diazepan-4-yl group, 4-ethyl-1,4-diazepan-4-yl group, 1,4-oxazepanyl group, quinolyl group, isoquinolyl group, quinazolinyl group, quinoxalinyl group, phthalazinyl group, cinnolinyl group, naphthyridinyl group, 1,2,3,4-tetrahydroquinolyl group, 5,6,7,8-tetrahydroquinolyl group, 1,2,3,4-tetrahydroisoquinolyl group, 5,6,7,8-tetrahydroisoquinolyl group, indolyl group, benzimidazolyl group, indolinyl group, isoindolinyl group, octahydroindolyl group, octahydroisoindolyl group, benzofuranyl group, benzothienyl group, benzoxazolyl group, benzothiazolyl group, octahydrocyclopenta[c]pyrrolyl group,

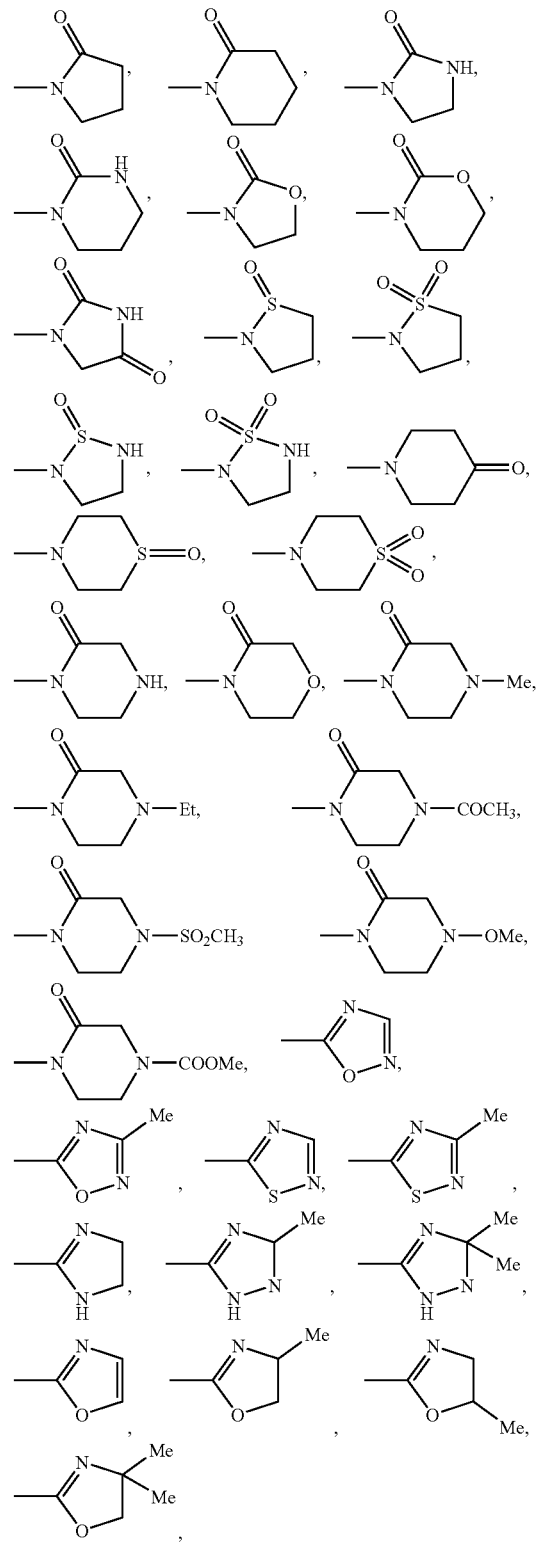

and the like can be mentioned.

In addition, such group wherein the 3, 4, 5 or 6-position of 2-pyridyl group, 2, 4, 5 or 6-position of 3-pyridyl group, 2, 3, 5 or 6-position of 4-pyridyl group, 3, 4 or 5-position of 2-thienyl group, and 2, 4 or 5-position of 3-thienyl group are substituted by fluorine atom, chlorine atom, bromine atom, nitro group, methyl group, tert-butyl group, carboxyl group, trifluoromethyl group, hydroxymethyl group, methoxymethyl group, 2-carboxyethyl group, methoxy group, carbamoyl group, methylthio group, dimethylaminocarbonyl group, methylsulfonyl group, amino group or acetylamino group can be mentioned.

The "carboxylic acid equiv ent" means a bioisostere and may only be a substituent having a similar polar effect as carboxylic acid. Specifically, a chain substituent such as
—CONHR$^{105}$, (wherein R$^{105}$, is a hydroxy group, a cyano group, a C$_{1-6}$ alkoxy group or a C$_{6-14}$ anyloxy group),
—SO$_2$R$^{106}$, (wherein R$^{106}$, is a hydroxyl group, an amino group or a C$_{1-6}$ alkylamino group),
—NHCOR$^{107}$, (wherein R$^{107}$, is an amino group or a C$_{1-6}$ alkylamino group),
—P(=O)(OH)(OR$^{109}$)

(wherein R$^{109}$ is a hydrogen atom or a substituent selected from the above-mentioned group C),
—P(=O)(OH)NR$^{111}$R$^{112}$ (wherein R$^{111}$ and R$^{112}$ are each independently a hydrogen atom or a substituent selected from the above-mentioned group C),
—CONHCO—R$^{113}$ (wherein R$^{113}$ is a substituent selected from the above-mentioned group C),
—CONHSO$_2$—R$^{114}$, (wherein R$^{114}$ is a substituent selected from the above-mentioned group C),
—SO$_2$NHCO—R$^{115}$ (wherein R$^{115}$ is a substituent selected from the above-mentioned group C) and the like, or a cyclic substituent such as a heterocyclic group having a hydrogen atom donor such as

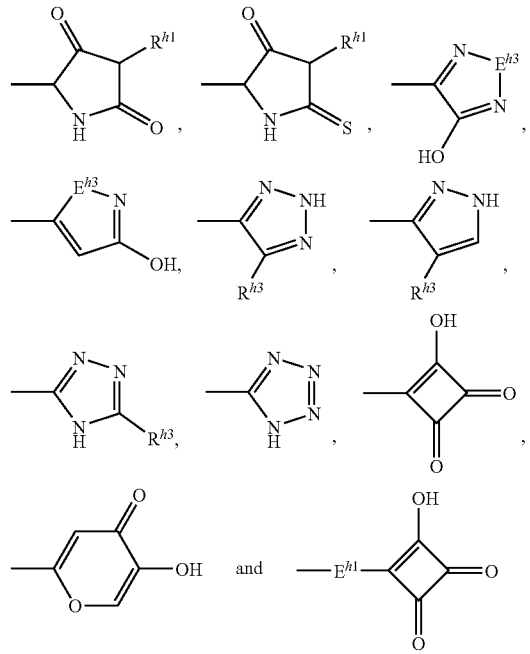

(wherein E$^{h1}$ is an oxygen atom, a sulfur atom or N(—R$^{h1}$, R$^{h1}$ is a hydrogen atom or a C$_{1-6}$ alkyl group, E$^{h3}$ is an oxygen atom or a sulfur atom, R$^{h2}$ is a C$_{1-6}$ alkyl group, R$^{h3}$ is an electron-withdrawing group such as halogen atom, a cyano group, a C$_{1-6}$ alkyl group, a trifluoromethyl group, a formyl group, a chlorocarbonyl group, a nitro group, an acetyl group, an ethoxycarbonyl group, a carbamoyl group and the like)

and the like, and said heterocyclic group substituted by an electron-withdrawing group and the like can be mentioned.

More specifically,
—CONHCN, —CONHOH, —CONHOMe,
—CONHOt-Bu, —CONHOBn,
—SO$_3$H, —SO$_2$NH$_2$, —SO$_2$NHMe,
—NHCONH$_2$, —NHCON(Me)$_2$,
—P(=O)(OH)$_2$, —P(=O)(OH)(OEt),
—P(=O)(OH)NH$_2$, —P(=O)(OH)NHMe,
—CONHCOMe, —CONHCOBn,
—CONHSO$_2$Me, —CONHSO$_2$Pr, —CONHSO$_2$Ph,

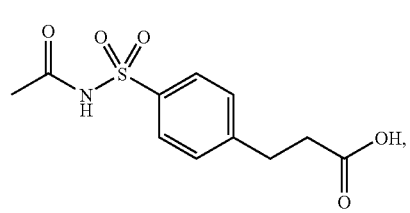

—SO$_2$NHCOMe, —SO$_2$NHCOPh wherein Me is a methyl group, Et is an ethyl group, Pr is a propyl group, t-Bu is a tert-butyl group, Ph is a phenyl group and Bn is a benzyl group, and

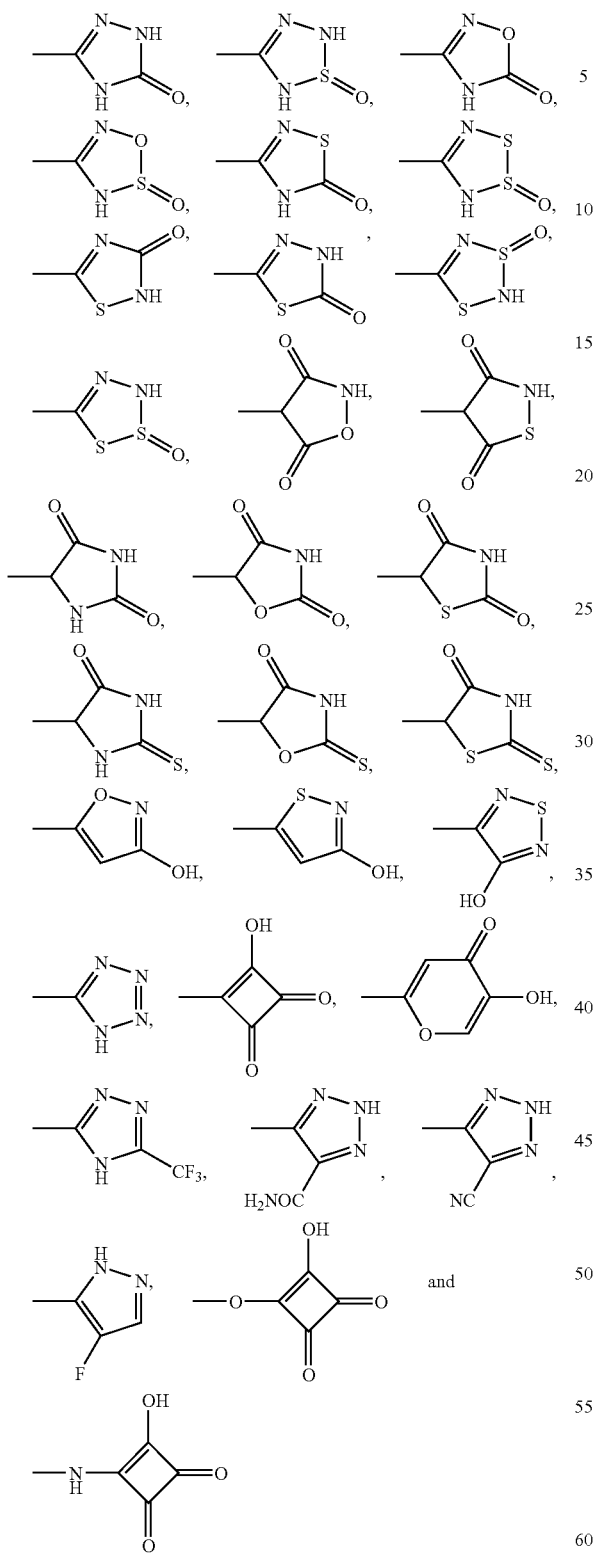

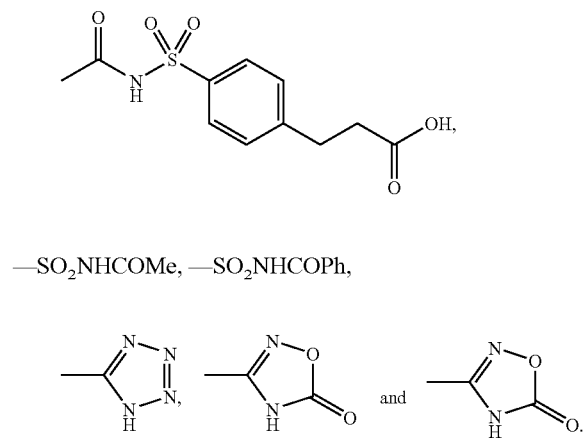

—SO₂NHCOMe, —SO₂NHCOPh,

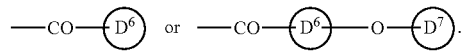

In the formula [I], ring A may be a 6-membered aromatic heterocycle containing 1 to 3 nitrogen atoms. As the "6-membered aromatic heterocycle containing 1 to 3 nitrogen atoms", pyridine, pyrimidine and the like can be mentioned.

For Q, preferred is —CH₂—O—# or —CH₂—N(R²)—#, particularly preferred is —CH₂—N(R²)—#.

For $R^1$, preferred is a carboxyl group, —CONR¹¹R¹², —COOR¹⁰³,

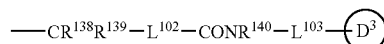

For $R^{11}$, preferred is a hydrogen atom or a $C_{1-6}$ alkyl group, more preferred is a hydrogen atom.

For $R^{12}$, preferred is a hydrogen atom, "a $C_{1-6}$ alkyl group optionally substituted by 1 to 3 substituents selected from group E", "a $C_{6-14}$ aryl group optionally substituted by 1 to 5 substituents selected from group E", "a heterocyclic group optionally substituted by 1 to 5 substituents selected from group E", "a $C_{3-10}$ cycloalkyl group optionally substituted by 1 to 5 substituents selected from group E", —NR¹³¹R¹³², —NHCOOR¹³³, —NHCOR¹³⁴, —CR¹³⁵R¹³⁶-L¹⁰¹-R¹³⁷,

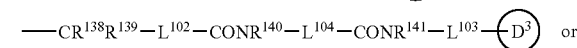

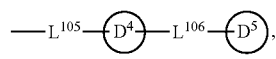

more preferred is a hydrogen atom or

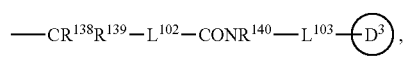

particularly preferred is

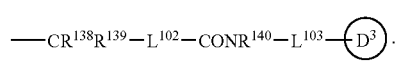

and the like can be mentioned.

As the carboxylic acid equivalent, preferred are —CONHOt-Bu, —CONHOBn, —SO₃H, —CONHSO₂Me, —CONHSO₂Pr, —CONHSO₂Ph, For $R^{103}$, preferred is "a $C_{1-6}$ alkyl group optionally substituted by 1 to 3 substituents selected from group A", "a $C_{6-14}$ aryl group optionally substituted by 1 to 5 substituents selected from group B" or "a $C_{6-14}$ aryl $C_{1-6}$ alkyl group optionally substituted by 1 to 5 substituents selected from group B".

As the "heterocyclic group" of "a heterocyclic group optionally substituted by 1 to 5 substituents selected from group E" for ring $D^6$, preferred is a pyrrolidinyl group, a piperidyl group, a piperazinyl group, a 2,6-dioxopiperazinyl group or a 2,3,4,9-tetrahydro-1H-p-carbolinyl group.

As the "$C_{6-14}$ aryl group" of "a $C_{6-14}$ aryl group optionally substituted by 1 to 5 substituents selected from group E" for ring $D^7$, preferred is a phenyl group.

For group E in ring $D^6$ and ring $D^7$, preferred is a hydroxyl group, a carboxyl group or a $C_{2-6}$ alkenyl group optionally substituted by carboxyl group.

For $R^{131}$, $R^{132}$, $R^{133}$ and $R^{134}$, preferred for each independently is a hydrogen atom, "a $C_{1-6}$ alkyl group optionally substituted by 1 to 3 substituents selected from group A", "a $C_{6-14}$ aryl group optionally substituted by 1 to 5 substituents selected from group B" or "a $C_{6-14}$ aryl $C_{1-6}$ alkyl group optionally substituted by 1 to 5 substituents selected from group B".

More preferably, $R^{131}$ and $R^{132}$ are each a $C_{1-6}$ alkyl group, $R^{133}$ is a $C_{6-14}$ aryl $C_{1-6}$ alkyl group, $R^{134}$ is a $C_{6-14}$ aryl group optionally substituted by carboxyl group.

For $R^{135}$ and $R^{136}$, preferred for each independently is a hydrogen atom, —$COOR^{42}$, —$CONR^{143}R^{144}$, "a $C_{1-6}$ alkyl group optionally substituted by 1 to 3 substituents selected from group A" or "a heterocyclic group optionally substituted by 1 to 5 substituents selected from group B", or $R^{135}$ and $R^{136}$ are bonded to each other, and form, together with the carbon atom bonded thereto, "a $C_{3-10}$ cycloalkyl group optionally substituted by 1 to 5 substituents selected from group B".

For $R^{142}$, preferred is a hydrogen atom or "a $C_{1-6}$ alkyl group optionally substituted by 1 to 3 substituents selected from group A". More preferably, $R^{142}$ is a hydrogen atom or a $C_{1-6}$ alkyl group.

For $R^{143}$ and $R^{144}$, preferred for each independently is a hydrogen atom, "a $C_{1-6}$ alkyl group optionally substituted by 1 to 3 substituents selected from group A", "a heterocyclic group optionally substituted by 1 to 5 substituents selected from group B" or "a heterocycle $C_{1-6}$ alkyl group optionally substituted by 1 to 5 substituents selected from group B". More preferably, $R^{143}$ is a hydrogen atom, $R^{144}$ is a hydrogen atom, "a $C_{1-6}$ alkyl group optionally substituted by 1 to 3 substituents selected from group A", "a heterocyclic group optionally substituted by 1 to 5 substituents selected from group B" or "a heterocycle $C_{1-6}$ alkyl group optionally substituted by 1 to 5 substituents selected from group B". For "a $C_{1-6}$ alkyl group optionally substituted by 1 to 3 substituents selected from group A" represented by $R^{144}$, preferred is a $C_{1-6}$ alkyl group optionally substituted by 1 to 3 substituents selected from a hydroxyl group and —$NR^{a1}R^{a2}$ (wherein $R^{a1}$ and $R^{a2}$ are each independently a hydrogen atom or a $C_{1-6}$ alkyl group). For the "heterocyclic group" of "a heterocyclic group optionally substituted by 1 to 5 substituents selected from group B" represented by $R^{144}$, preferred is a pyridyl group. For the "heterocycle" moiety of "a heterocycle $C_{1-6}$ alkyl group optionally substituted by 1 to 5 substituents selected from group B" represented by $R^{144}$, preferred is a morpholinyl group, pyrrolidinyl group or a pyridyl group.

For the "heterocyclic group" of "a heterocyclic-group optionally substituted by 1 to 5 substituents selected from group B" represented by $R^{135}$ and $R^{136}$, preferred is a thiazolyl group or a pyridyl group.

For the "$C_{3-10}$ cycloalkyl group" of "a $C_{3-10}$ cycloalkyl group optionally substituted by 1 to 5 substituents selected from group B" which is formed by $R^{135}$ and $R^{136}$ bonded to each other, together with the carbon atom bonded thereto, preferred is "a $C_{3-7}$ cycloalkyl group", more preferably a cyclopropyl group, a cyclobutyl group, a cyclopentyl group or a cyclohexyl group.

For $L^{101}$, preferred is a bond or methylene.

For $R^{137}$, preferred is "a $C_{6-14}$ aryl group optionally substituted by 1 to 5 substituents selected from group E" or "a heterocyclic group optionally substituted by 1 to 5 substituents selected from group E".

For the "$C_{6-14}$ aryl group" of "a $C_{6-14}$ aryl group optionally substituted by 1 to 5 substituents selected from group E" represented by $R^{137}$, preferred is a phenyl group.

For the "heterocyclic group" of "a heterocyclic group optionally substituted by 1 to 5 substituents selected from group E" represented by $R^{137}$, preferred is an indolyl group, a 2-oxo-2H-chromenyl group, a benzo[1,3]dioxolanyl group, a benzimidazolyl group, a benzofuranyl group, a benzothienyl group, a benzothiazolyl group, a pyridyl group, a pyrimidinyl group, a pyrazolyl group, a 4-oxo-1H-quinolinyl group, a furyl group, a thienyl group, an oxazolyl group or a thiazolyl group, more preferably, an indolyl group, a benzimidazolyl group, a benzofuranyl group or a benzothienyl group, and particularly preferably, an indolyl group.

For $R^{138}$ and $R^{139}$, preferred for each independently is a hydrogen atom or "a $C_{1-6}$ alkyl group optionally substituted by 1 to 3 substituents selected from group A", or $R^{138}$ and $R^{139}$ are bonded to each other, and form, together with the carbon atom bonded thereto, "a $C_{3-10}$ cycloalkyl group optionally substituted by 1 to 5 substituents selected from group B" or "a heterocyclic group optionally substituted by 1 to 5 substituents selected from group B".

For the "$C_{3-10}$ cycloalkyl group" of "a $C_{3-10}$ cycloalkyl group optionally substituted by 1 to 5 substituents selected from group B", which is formed by $R^{138}$ and $R^{139}$ bonded to each other, together with the carbon atom bonded thereto, preferred is "a $C_{3-7}$ cycloalkyl group", more preferred is a cyclopropyl group, a cyclobutyl group, a cyclopentyl group or a cyclohexyl group.

For the "heterocyclic group" of "a heterocyclic group optionally substituted by 1 to 5 substituents selected from group B", which is formed by $R^{138}$ and $R^{139}$ bonded to each other, together with the carbon atom bonded thereto, preferred is a "4-, 5- or 6-membered heterocyclic group comprising 1 to 3 heteroatoms selected from oxygen atom, nitrogen atom and sulfur atom", more preferably, a piperidyl group, a pyrrolidinyl group, a tetrahydropyranyl group or a tetrahydrothiopyranyl group.

Particularly preferably, $R^{138}$ and $R^{139}$ are each independently a hydrogen atom or a $C_{1-6}$ alkyl group, or $R^{138}$ and $R^{139}$ are bonded to each other, and form, together with the carbon atom bonded thereto, a cyclobutyl group or a cyclopentyl group.

For $R^{140}$ and $R^{141}$, preferred is a hydrogen atom.

For $L^{120}$, preferred is a bond or vinylene, more preferred is a bond.

For $L^{103}$, preferred is a bond.

For $L^{104}$, preferred is propylene.

For ring $D^3$, preferred is "a $C_{6-14}$ aryl group optionally substituted by 1 to 5 substituents selected from group E" or "a heterocyclic group optionally substituted by 1 to 5 substituents selected from group E", more preferred is "a $C_{6-14}$ aryl group optionally substituted by 1 to 5 substituents selected from group E".

For the "$C_{6-14}$ aryl group" of "a $C_{6-14}$ aryl group optionally substituted by 1 to 5 substituents selected from group E" represented by ring $D^3$, preferred is a phenyl group.

For the "heterocyclic group" of "a heterocyclic group optionally substituted by 1 to 5 substituents selected from group E" represented by ring $D^3$, preferred is an indolyl group, a 2-oxo-2H-chromenyl group, a benzo[1,3]dioxolanyl group, a benzimidazolyl group, a benzofuranyl group, a benzothienyl group, a benzothiazolyl group, a pyridyl group, a pyrimidinyl group, a pyrazolyl group, a 4-oxo-1H-quinolinyl group, a furyl group, a thienyl group, an oxazolyl group or a thiazolyl group, more preferably, an indolyl group, a benzimidazolyl group, a benzofuranyl group or a benzothienyl group, particularly preferably, an indolyl group.

For ring $D^4$, preferred is "a $C_{3-10}$ cycloalkyl group optionally substituted by 1 to 5 substituents selected from group E" or "a heterocyclic group optionally substituted by 1 to 5 substituents selected from group E".

For ring $D^5$, preferred is "a $C_{6-14}$ aryl group optionally substituted by 1 to 5 substituents selected from group E".

For the "$C_{3-10}$ cycloalkyl group" of "a $C_{3-10}$ cycloalkyl group optionally substituted by 1 to 5 substituents selected from group E" represented by ring $D^4$ and ring $D^5$, preferred is a cyclohexyl group.

For the "heterocyclic group" of "a heterocyclic group optionally substituted by 1 to 5 substituents selected from group E" represented by ring $D^4$ and ring $D^5$, preferred is a piperidyl group or a pyrrolidinyl group.

For the "$C_{6-14}$ aryl group" of "a $C_{6-14}$ aryl group optionally substituted by 1 to 5 substituents selected from group E" represented by ring $D^4$ and ring $D^5$, preferred is a phenyl group.

For the group E in $R^{137}$, ring $D^3$, ring $D^4$ and ring $D^5$, preferred is a halogen atom, a cyano group, a nitro group, an azido group, —OP(=O)(OH)$_2$, —OR$^{e1}$, —S(O)$_q$—R$^{e1}$, —NR$^{e3}$R$^{e4}$, —COOR$^{e5}$, —CONR$^{e6}$R$^{e7}$, —COR$^{e8}$, —NR$^{e9}$CO—R$^{e10}$, —NR$^{e11}$SO$_2$—R$^{e12}$, —NR$^{e21}$—CONR$^{e22}$R$^{e23}$, —NHCO—COOR$^{e24}$, —NHCO—CONR$^{e25}$R$^{e25}$, —CONH—COOH,

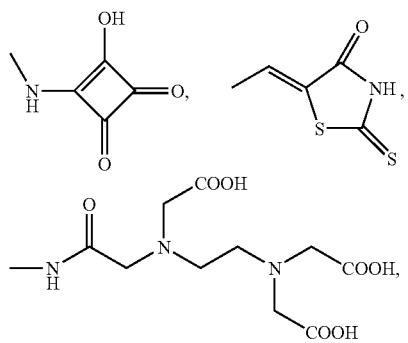

"a $C_{6-14}$ aryl group optionally substituted by 1 to 5 substituents selected from group B", "a $C_{3-10}$ cycloalkyl group optionally substituted by 1 to 5 substituents selected from group B", "a heterocyclic group optionally substituted by 1 to 5 substituents selected from group B", "a $C_{1-6}$ alkyl group optionally substituted by 1 to 3 substituents selected from group A", "a $C_{2-6}$ alkenyl group optionally substituted by 1 to 3 substituents selected from group A", "a $C_{2-6}$ alkynyl group optionally substituted by 1 to 3 substituents selected from group A" or "a $C_{6-14}$ aryl $C_{1-6}$ alkyl group optionally substituted by 1 to 5 substituents selected from group B", more preferably, a carboxyl group, —OR$^{e1}$ (wherein R$^{e1}$ is a hydrogen atom or a $C_{1-6}$ alkyl group substituted by carboxyl group), a $C_{1-6}$ alkyl group substituted by carboxyl group or a $C_{2-6}$ alkenyl group substituted by carboxyl group, particularly preferably, a carboxyl group, a hydroxyl group, —OCH$_2$COOH, —CH=CH—COOH or —CH$_2$CH$_2$COOH.

Preferably, $R^{12}$ is

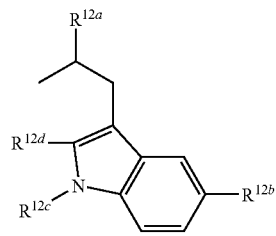

wherein $R^{12a}$ is preferably selected from a hydrogen atom, a 5- to 10-membered heterocyclic group comprising 1 to 4 heteroatoms selected from oxygen atom, nitrogen atom and sulfur atom (wherein the heterocyclic group is optionally substituted by 1 to 4 substituents selected from the group consisting of —CH$_3$, —CF$_3$, —OH, —CH$_2$COOH, —COOH, —NHCH(CH$_3$)$_2$, —NHCOCH$_3$, —NH$_2$, —NHCH$_3$ and —N(CH$_3$)$_2$), —COOH, —COO($C_{1-6}$ alkyl), —CONH$_2$, —COCH$_3$, —(CH$_2$)$_{p1}$COOH (wherein p1 is an integer of 1 to 4), benzyloxy, —CH$_2$—($C_{6-14}$ aryl)-COOH, pyridylcarbamoyl, pyridylmethylcarbamoyl and —CONH—($C_{2-4}$ alkyl)-N(CH$_3$)$_2$.

More preferably, $R^{12a}$ is —COOR$^{12g}$, —CONHR$^{12f}$ or

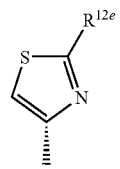

wherein, $R^{12e}$ is preferably a hydrogen atom, a $C_{1-6}$ alkyl group, an amino group, —NH ($C_{1-6}$ alkyl), —N($C_{1-6}$ alkyl)$_2$ or —NHCO ($C_{1-6}$ alkyl).

Preferably, $R^{12f}$ is a hydrogen atom, a heterocycle $C_{1-6}$ alkyl group (wherein the heterocycle is selected from morpholinyl, pyrrolidinyl and N-methylpyrrolidinyl), —($C_{1-6}$ alkyl)-N(CH$_3$)$_2$, —($C_{1-6}$ alkyl)-OH, —CH(CH$_2$OH)$_2$ or —CH$_2$CH(OH)CH$_2$OH. More preferably, $R^{12f}$ is a hydrogen atom.

Preferably, $R^{12g}$ is a hydrogen atom or a $C_{1-6}$ alkyl group. More preferably, $R^{12g}$ is a hydrogen atom or —CH$_3$.

Preferably, $R^{12b}$ is selected from a hydrogen atom, a hydroxyl group, an amino group, a 5- to 10-membered heterocyclic group comprising 1 to 4 heteroatoms selected from oxygen atom, nitrogen atom and sulfur atom (wherein the heterocyclic group is optionally substituted by hydroxyl group), —COOH, —CH$_3$, —CF$_3$, —CH$_2$COOH, —O($C_{1-6}$ alkyl) —COOH, —NHCOCOOH, —NHSO$_2$CH$_3$, —NHSO$_2$CF$_3$,

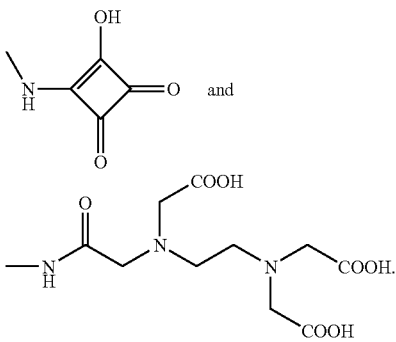 and

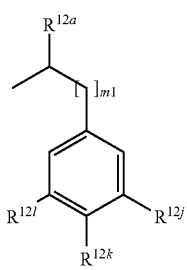

More preferably, $R^{12b}$ is —OCH$_2$COOH or a hydroxyl group.

Preferably, $R^{12c}$ is selected from a hydrogen atom, a C$_{1-6}$ alkyl group and —(CH$_2$)$_{p1}$COOH (wherein p1 is an integer of 1 to 4). More preferably, $R^{12c}$ is a hydrogen atom, —CH$_3$ or —CH$_2$COOH.

Preferably, $R^{12d}$ is a hydrogen atom or a C$_{1-6}$ alkyl group. More preferably, $R^{12d}$ is a hydrogen atom or —CH$_3$. Still more preferably, $R^{12d}$ is a hydrogen atom.

Alternatively, $R^{12}$ is preferably

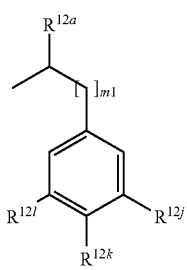

wherein $R^{12a}$ is as defined above.

Preferably, $R^{12j}$ is a C$_{1-6}$ alkoxy group, a hydroxyl group, —O(C$_{1-6}$ alkyl)-COOH, a C$_{1-6}$ alkyl group, a halogen atom, —(C$_{2-6}$ alkenyl)-COOH, —(C$_{1-6}$ alkyl)-OH, —COOH or an azido group.

Preferably, $R^{12k}$ is a hydroxyl group, —(CH$_2$)$_{p1}$COOH (wherein p1 is an integer of 1 to 4), an amino group, a C$_{1-6}$ alkoxy group, —NHCOCOOH, —NH(C$_{1-6}$ alkyl)-COOH, —O(C$_{1-6}$ alkyl)-COOH, —COOH, a 5- or 6-membered heterocyclic group comprising 1 to 4 heteroatoms selected from oxygen atom, nitrogen atom and sulfur atom (wherein the 5- or 6-membered heterocyclic group is optionally substituted by 1 to 4 substituents selected from the group consisting of —CH$_3$, —CF$_3$, —OH, —CH$_2$COOH and —COOH), —O(C$_{1-6}$ alkyl)-COOH,

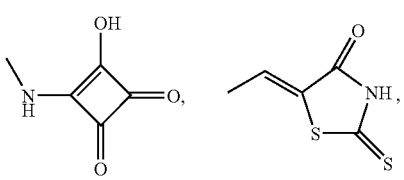

—NHCONH$_2$, —NHCN, —NHCHO, —NHSO$_2$CF$_3$, —NHCOCH$_3$, —NHSO$_2$CH$_3$, —CONH$_2$, —(C$_{3-10}$ cycloalkyl)-COOH, —(C$_{2-6}$ alkenyl)-COOH or —NHCOCH$_2$CH(OH)COOH.

Preferably, $R^{12i}$ is —O(C$_{1-6}$ alkyl)-COOH, a C$_{1-6}$ alkyl group or a halogen atom.

Preferably, m1 is 0 or an integer of 1 to 4. More preferably, m1 is 1.

Alternatively, $R^{12}$ is preferably

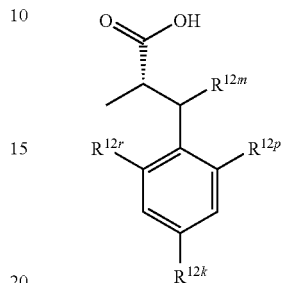

wherein $R^{12k}$ is as defined above.

Preferably, $R^{12m}$ is a hydrogen atom or a hydroxyl group.

Preferably, $R^{12p}$ is a hydrogen atom, a halogen atom or a C$_{1-6}$ alkyl group.

Preferably, $R^{12r}$ is a hydrogen atom, a halogen atom or a C$_{1-6}$ alkyl group.

Alternatively, $R^{12}$ is preferably

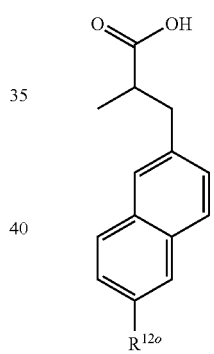

wherein $R^{12}$, is preferably a hydroxyl group or —O(C$_{1-6}$ alkyl)-COOH.

Alternatively, $R^{12}$ is preferably

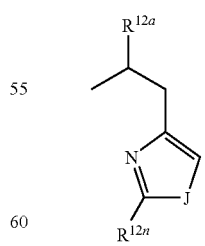

wherein $R^{12a}$ is as defined above.

Preferably, J is S or N(C$_{1-6}$ alkyl). More preferably, J is S or N(CH$_3$).

Preferably, $R^{12n}$ is a hydrogen atom or an amino group.

Alternatively, $R^{12}$ is more preferably

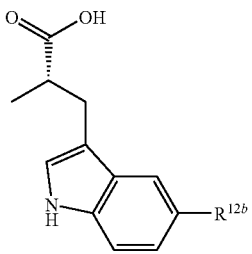

wherein $R^{12b}$ is as defined above.

Alternatively, $R^{12}$ is more preferably

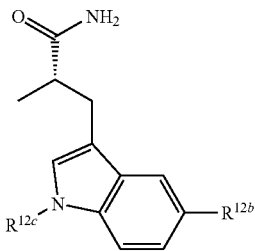

wherein $R^{12b}$ and $R^{12c}$ are as defined above.

Alternatively, $R^{12}$ is more preferably

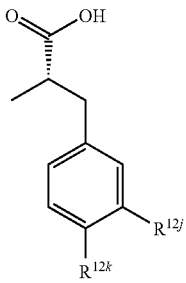

wherein $R^{12j}$ and $R^{12k}$ are as defined above.

Alternatively, $R^{12}$ is preferably

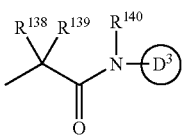

wherein $R^{138}$ and $R^{139}$ are each independently a hydrogen atom, "a $C_{1-6}$ alkyl group optionally substituted by 1 to 3 substituents selected from group A", "a $C_{3-10}$ cycloalkyl group optionally substituted by 1 to 5 substituents selected from group B", "a $C_{6-14}$ aryl group optionally substituted by 1 to 5 substituents selected from group B", "a heterocyclic group optionally substituted by 1 to 5 substituents selected from group B", "a $C_{6-14}$ aryl $C_{1-6}$ alkyl group optionally substituted by 1 to 5 substituents selected from group B", "a heterocycle $C_{1-6}$ alkyl group optionally substituted by 1 to 5 substituents selected from group B" or "a $C_{3-10}$ cycloalkyl $C_{1-6}$ alkyl group optionally substituted by 1 to 5 substituents selected from group B"; or $R^{138}$ and $R^{139}$ are bonded to each other and optionally form, together with the carbon atom bonded thereto, "a $C_{3-10}$ cycloalkyl group optionally substituted by 1 to 5 substituents selected from group B" or "a heterocyclic group optionally substituted by 1 to 5 substituents selected from group B".

Here, as the substituent selected from group A, preferred are 1 to 3 substituents selected from a halogen atom, $-OR^{a1}$, $-NR^{a1}R^{a2}$, $-COOR^{a1}$, $-CONR^{a1}R^{a2}$ and $-COR^{a1}$ (wherein $R^{a1}$ and $R^{a2}$ are each independently a hydrogen atom or a $C_{1-6}$ alkyl group), and as the substituent selected from group B, preferred are 1 to 5 substituents selected from a halogen atom, a $C_{1-6}$ alkyl group, a $C_{2-6}$ alkenyl group, $-OR^{b1}$, $-NR^{b1}R^{b2}$, $-COOR^{b1}$, $-CONR^{b1}R^{b2}$, $-COR^{b1}$ and $-SO_2R^{b3}$ (wherein $R^{b1}$ and $R^{b2}$ are each independently a hydrogen atom or a $C_{1-6}$ alkyl group and $R^{b3}$ is a $C_{1-6}$ alkyl group).

Preferably, $R^{140}$ is a hydrogen atom.

Preferably, ring $D^3$ is "a $C_{6-14}$ aryl group optionally substituted by 1 to 5 substituents selected from group E" or "a heterocyclic group optionally substituted by 1 to 5 substituents selected from group E".

Here, as the substituent selected from group E, preferred are 1 to 5 substituent selected from
a halogen atom,
a cyano group,
a nitro group,
an azido group,
$-OR^{e1}$ (wherein $R^{e1}$ is a hydrogen atom or a $C_{1-6}$ alkyl group optionally substituted by carboxyl group),
$-S(O)_q-R^{e2}$ (wherein $R^{e2}$ is a hydrogen atom or a $C_{1-6}$ alkyl group optionally substituted by carboxyl group and q is 0, 1, 2 or 3),
$-NR^{e3}R^{e4}$ (wherein $R^{e3}$ and $R^{e4}$ is independently a hydrogen atom, a $C_{1-6}$ alkyl group or a heterocyclic group optionally substituted by 1 to 5 substituents selected from group B),
$-COOR^{e5}$ (wherein $R^{e5}$ is a hydrogen atom or a $C_{1-6}$ alkyl group),
$-CONR^{e6}R^{e7}$ (wherein $R^{e6}$ and $R^{e7}$ are each independently a hydrogen atom or a $C_{1-6}$ alkyl group optionally substituted by carboxyl group),
$-NR^{e9}CO-R^{e10}$ (wherein $R^{e9}$ is a hydrogen atom or a $C_{1-6}$ alkyl group, and $R^{e10}$ is a hydrogen atom, an amino group, a $C_{1-6}$ alkylamino group or a $C_{1-6}$ alkyl group),
$-SO_2-NR^{e13}R^{e14}$ (wherein $R^{e13}$ and $R^{e14}$ are each a hydrogen atom or a $C_{1-6}$ alkyl group),
$-NR^{e21}-CONR^{e22}R^{e23}$ (wherein $R^{e21}$, $R^{e22}$ and $R^{e23}$ are each independently a hydrogen atom or a $C_{1-6}$ alkyl group),
$-NHCO-COOR^{e24}$ (wherein $R^{e24}$ is a hydrogen atom or a $C_{1-6}$ alkyl group),
$-NHCO-CONR^{e25}R^{e26}$ (wherein $R^{e25}$ and $R^{e26}$ are each independently a hydrogen atom, a hydroxyl group or a $C_{1-6}$ alkyl group), a $C_{6-14}$ aryl group optionally substituted by 1 to 5 substituents selected from group B, a $C_{3-10}$ cycloalkyl group optionally substituted by 1 to 5 substituents selected from group B, a heterocyclic group optionally substituted by 1 to 5 substituents selected from group B, a $C_{1-6}$ alkyl group optionally substituted by 1 to 3 substituents selected from group A, a $C_{2-6}$ alkenyl group optionally substituted by 1 to 3 substituents selected from group A, a $C_{2-6}$ alkynyl group optionally substituted by 1 to 3 substituents selected from group A, a $C_{6-14}$ aryl $C_{1-6}$ alkyl group optionally substituted by 1 to 5 substituents selected from group B, a $C_{3-10}$ cycloalkyl $C_{1-6}$ alkyl group optionally substituted by 1 to 5 substituents selected from group B, and a heterocycle $C_{1-6}$ alkyl group optionally substituted by 1 to 5 substituents selected from group B.

Here, as the substituent selected from group A, preferred are 1 to 3 substituents selected from a halogen atom, a cyano group, —$OR^{a1}$, —$NR^{a1}R^{a2}$, —$COOR^{a1}$, —$CON^{a1}R^{a2}$, —$SO_2NR^{a1}R^{a2}$ and —$NHCOR^{a1}$ (wherein $R^{a1}$ and $R^{a2}$ are each independently a hydrogen atom or a $C_{1-6}$ alkyl group), and as the substituent selected from group B, preferred are 1 to 5 substituent selected from a halogen atom, a $C_{1-6}$ alkyl group, a halogenated $C_{1-6}$ alkyl group, —$(CH_2)_r$—$OR^{b1}$, —$(CH_2)_r$—$NR^{b1}R^{b2}$, —$(CH_2)_r$—$COOR^{b1}$, —$(CH_2)_r$—$CONR^{b1}R^{b2}$, —$(CH_2)r$—$SO_2NR^{b1}R^{b2}$ and —$(CH_2)_r$—$NR^{b1}$—$COR^{b2}$ (wherein $R^{b1}$ and $R^{b2}$ are each independently a hydrogen atom or a $C_{1-6}$ alkyl group, and r is 0 or an integer of 1 to 6).

For $R^1$, more preferred are carboxyl group, —$CONR^{11}R^{12}$ and —$COOR^{103}$, further preferred are carboxyl group and —$CONR^{11}R^{12}$.

For $R^{11}$, preferred is hydrogen atom.

For $R^{12}$, preferred are hydrogen atom and

, and further preferred is

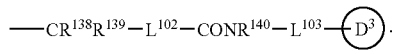.

$R^{138}$ and $R^{139}$ are preferably bonded to each other, and form, together with the carbon atom bonded thereto, a $C_{3-10}$ cycloalkyl group optionally substituted by 1 to 5 substituents selected from group B. As the "$C_{3-10}$ cycloalkyl group", preferred is "$C_{3-7}$ cycloalkyl group" and more preferred is cyclobutyl group.

For $L^{102}$ and $L^{103}$, preferred is bond.

For $R^{140}$, preferred is hydrogen atom.

For ring $D^3$, preferred is "$C_{6-14}$ aryl group optionally substituted by 1 to 5 substituents selected from group E". As the "$C_{6-14}$ aryl group", preferred is phenyl group. As the substituent selected from group E, preferred is "$C_{2-6}$ alkenyl group optionally substituted by 1 to 3 substituents selected from group A" and more preferred is $C_{2-6}$ alkenyl group (preferably vinyl group) substituted by —COOH.

For $R^1$, specific examples include carboxyl group, methoxycarbonyl group, ethoxycarbonyl group, phenoxycarbonyl group, benzyloxycarbonyl group, carbamoyl group, methylcarbamoyl group, (2-hydroxyethyl)carbamoyl group, (1,1-dimethyl-2-hydroxyethyl)carbamoyl group, carboxymethylcarbamoyl group, N-carboxymethyl-N-methylcarbamoyl group, (1-carboxy-3-methylbutyl)carbamoyl group, (1-carboxy-2-methoxyethyl)carbamoyl group, (1-carboxy-2-methylthioethyl)carbamoyl group, (1-carboxy-2-dimethylaminoethyl)carbamoyl group, 5-carboxypentylcarbamoyl group, (1-carboxy-1,3-dimethylbutyl)carbamoyl group, (1-carboxy-2-methyl-2-methylthiopropyl)carbamoyl group and (1-carboxy-2,2-dimethylpropyl)carbamoyl group, particularly preferred is carboxyl group.

$R^1$ may be a "carboxylic acid equivalent" which is a substituent biologically equivalent to a carboxyl group, and as a specific "carboxylic acid equivalent", the aforementioned substituent and the like can be mentioned.

Moreover, an example of $R^1$ is a group represented by

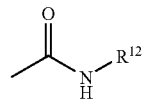

wherein $R^{12}$ is selected from the following formulas, can be mentioned.

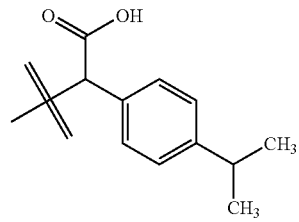

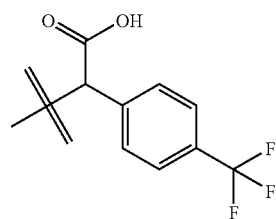

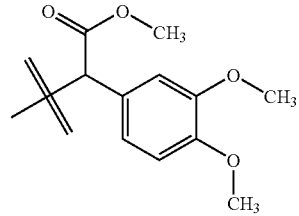

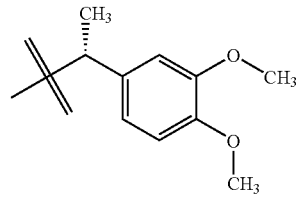
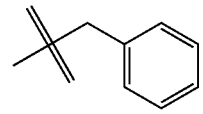

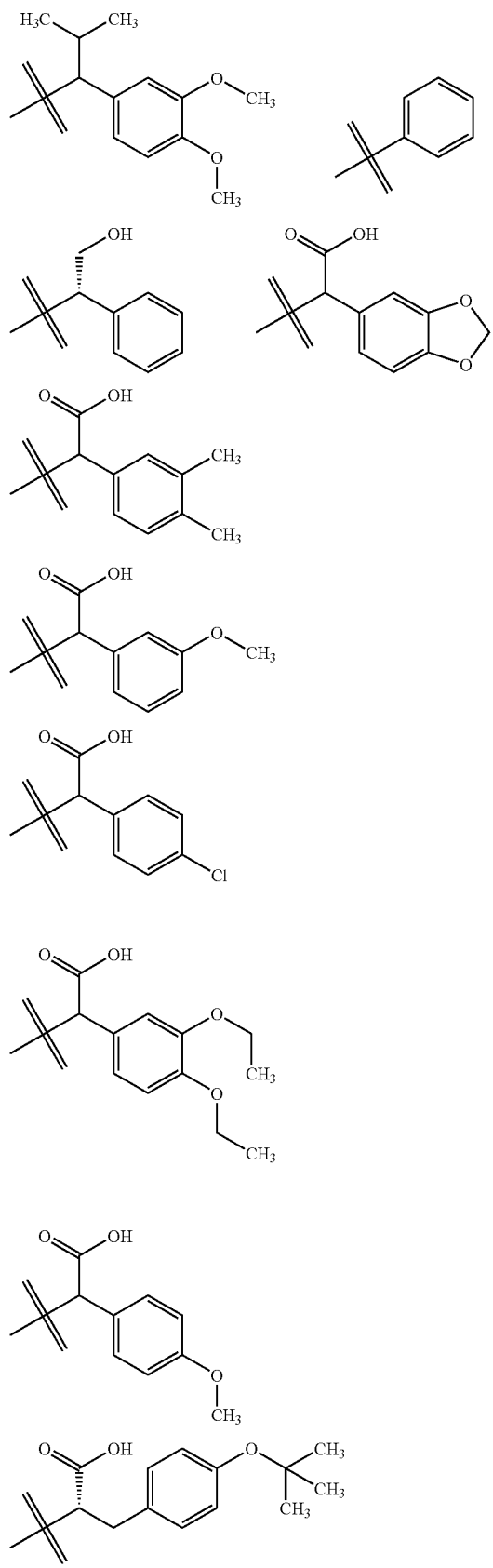
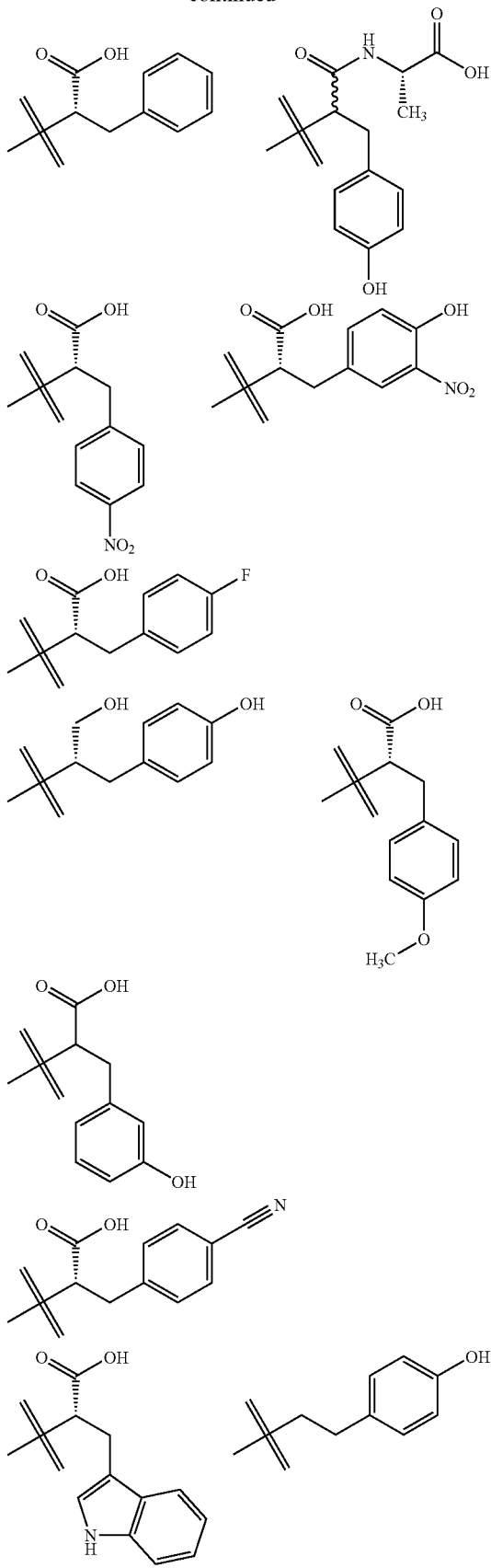

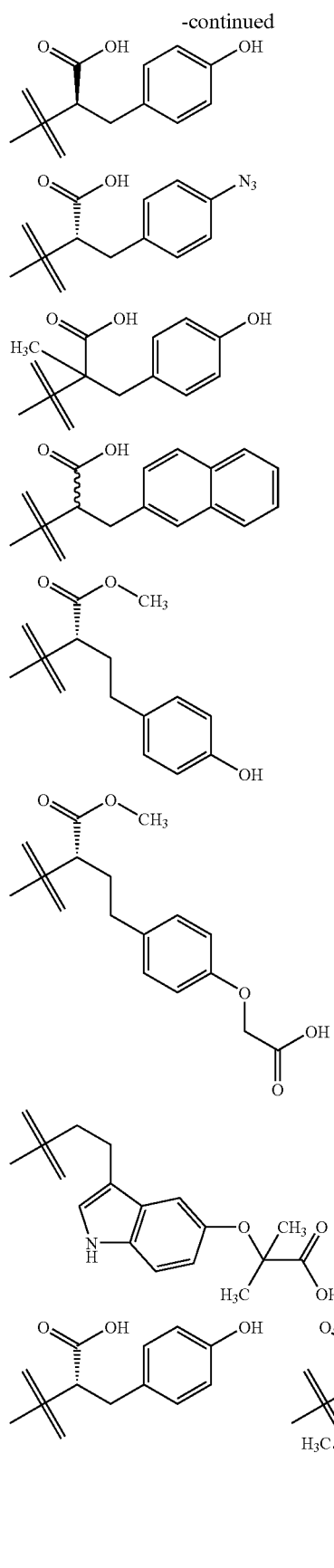
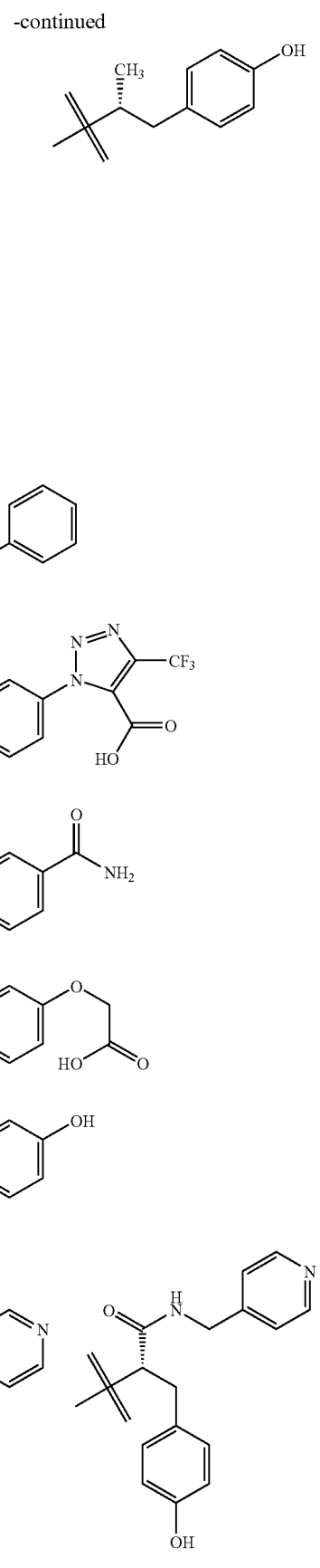

-continued
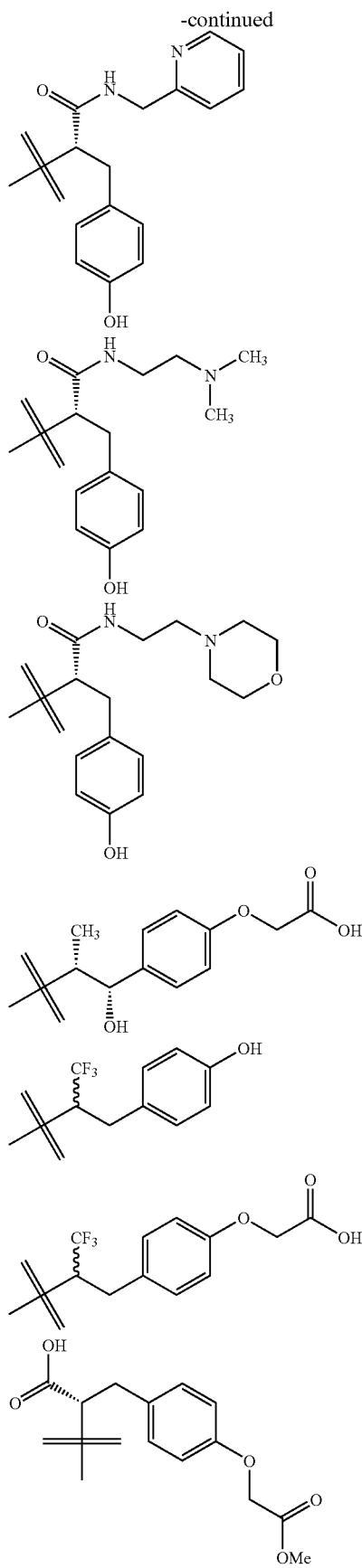
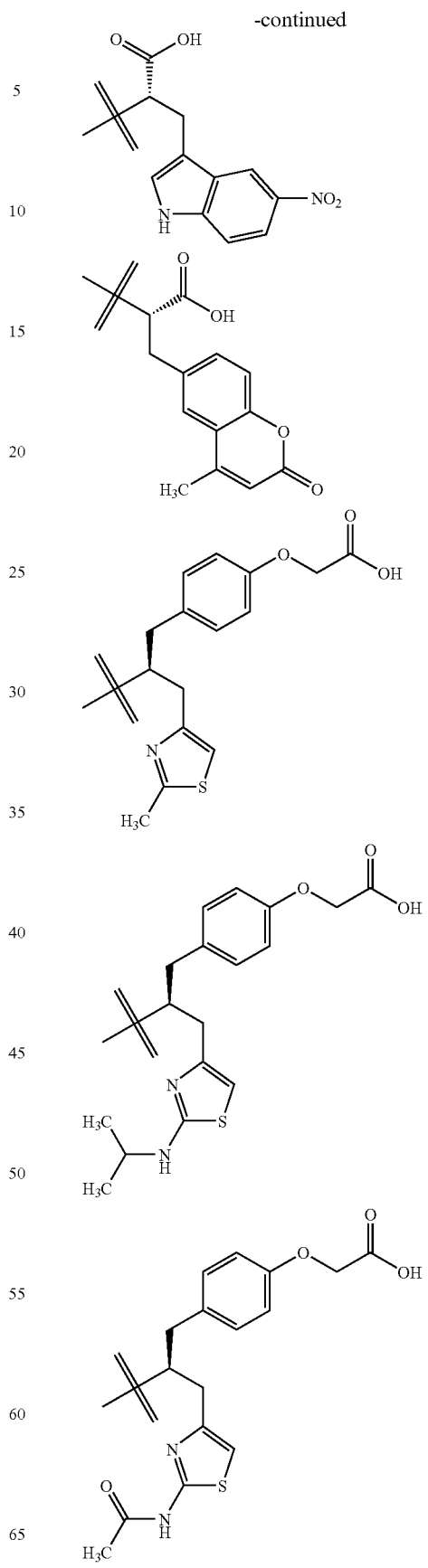

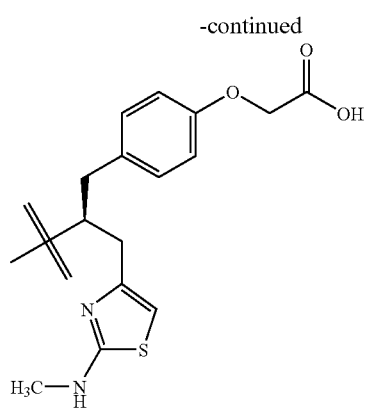
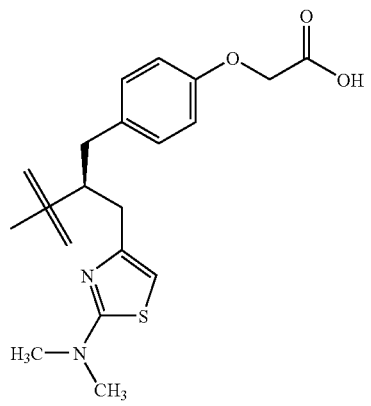
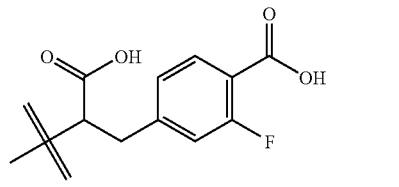
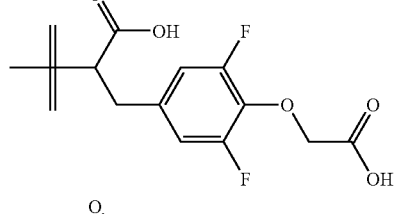
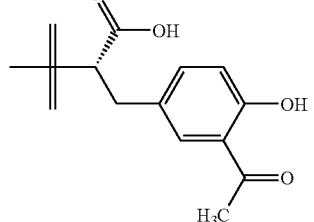
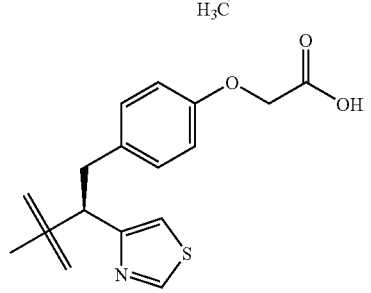
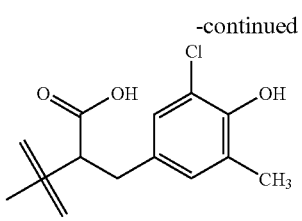
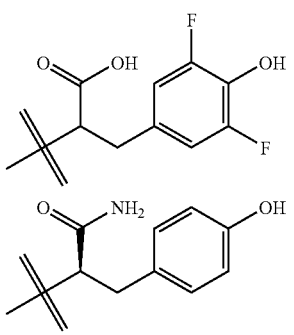
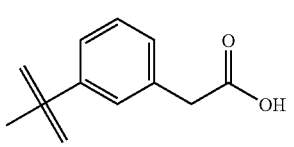
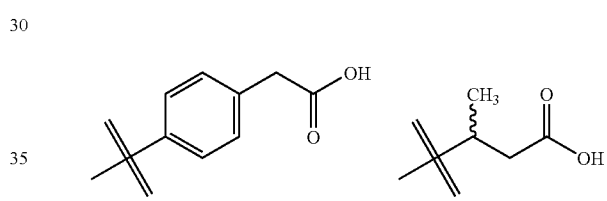
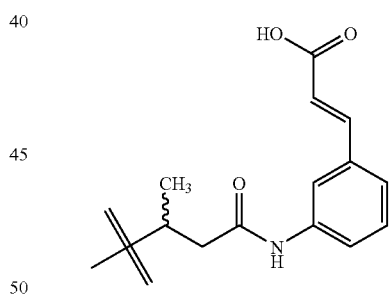
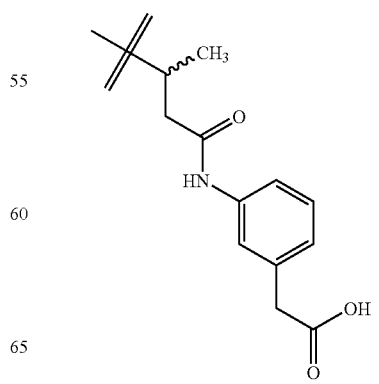

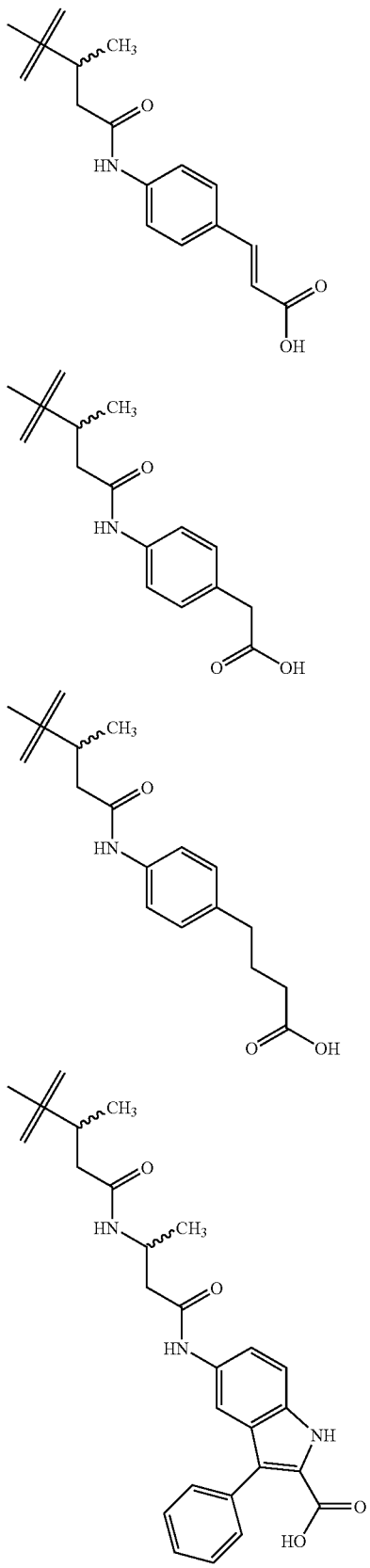
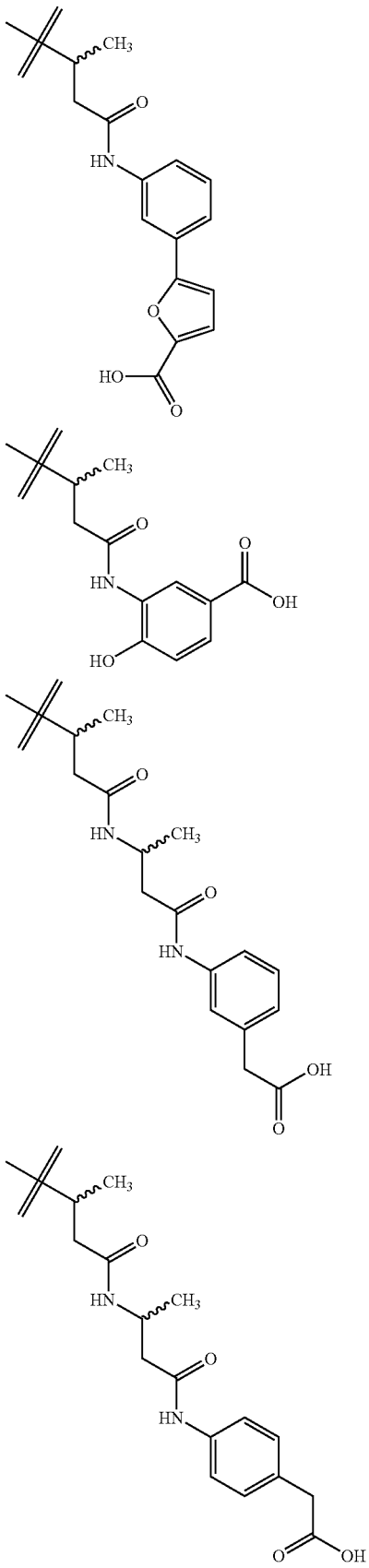

-continued
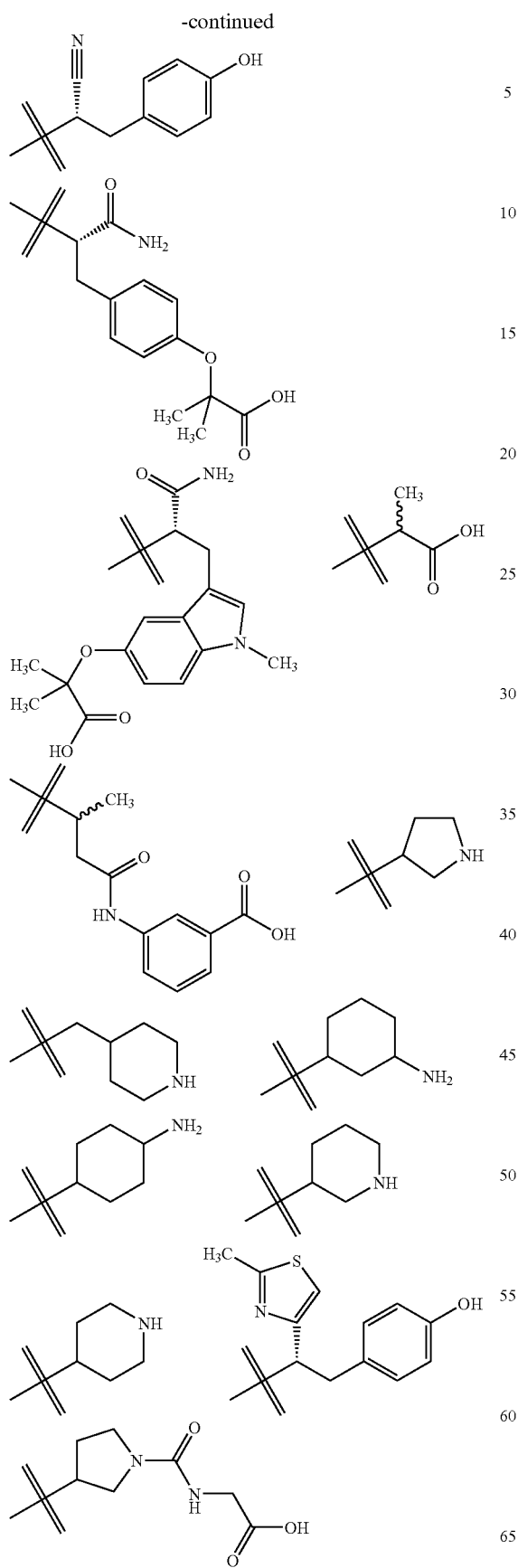
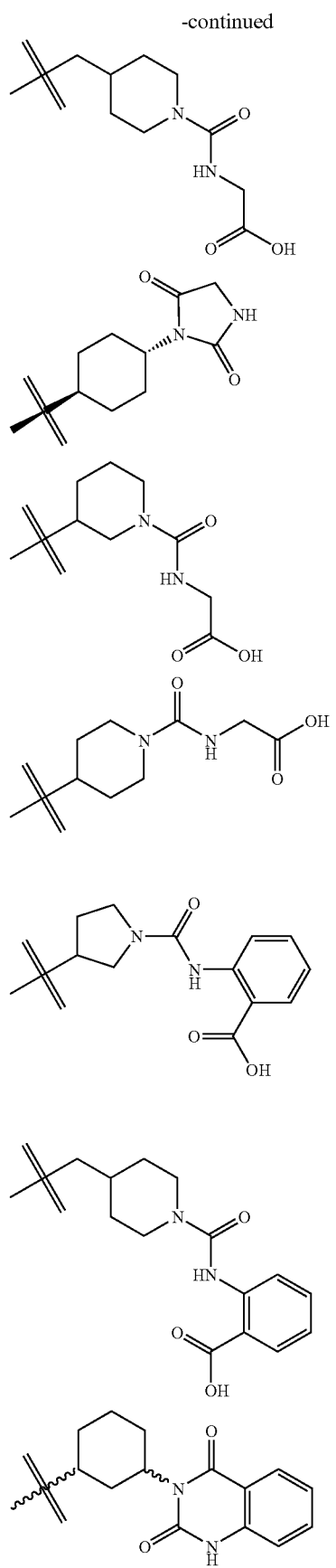

-continued
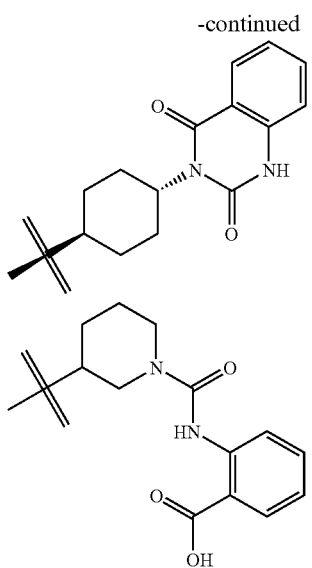
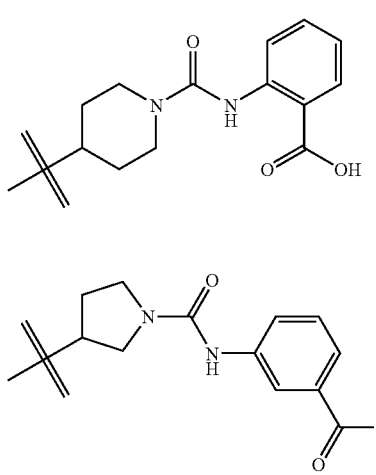
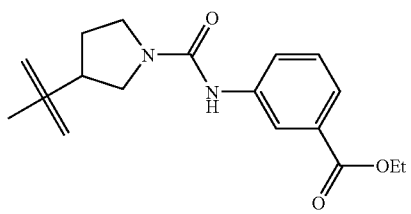
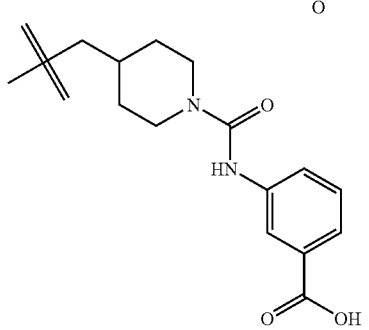
-continued
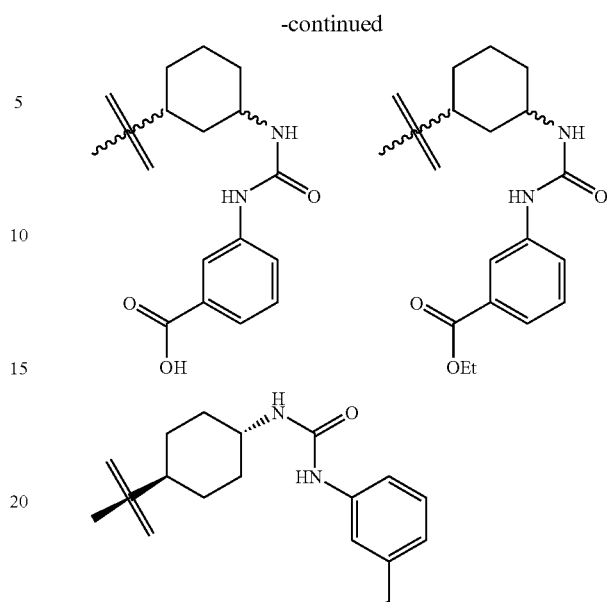
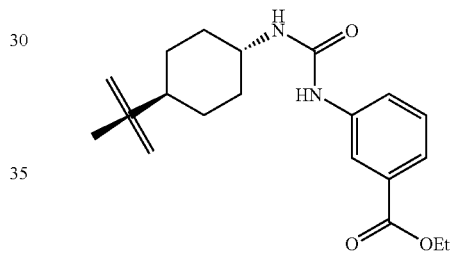
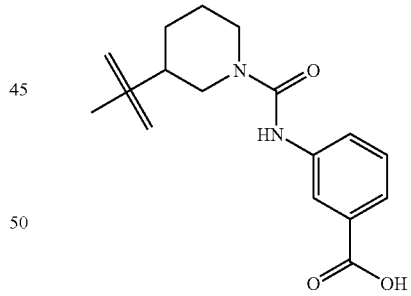
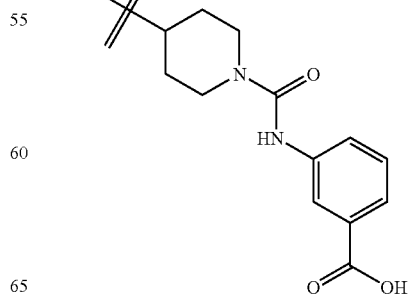

77
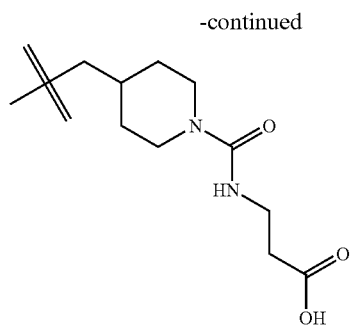
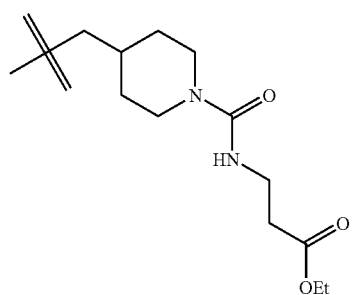
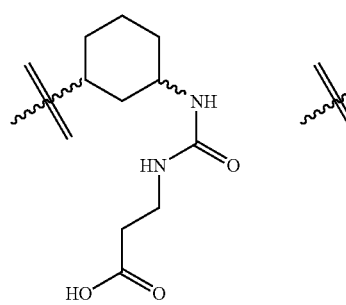
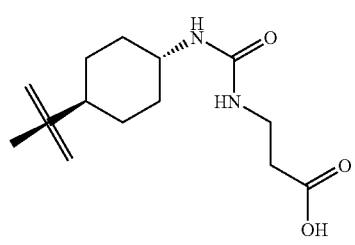
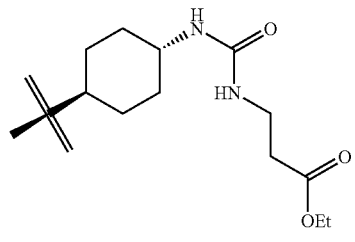
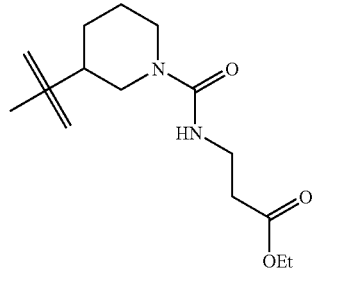
78
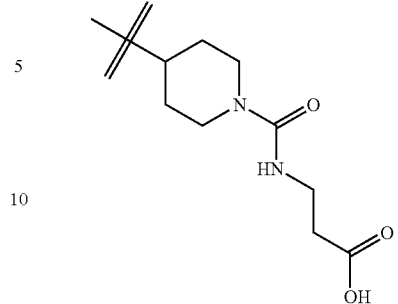
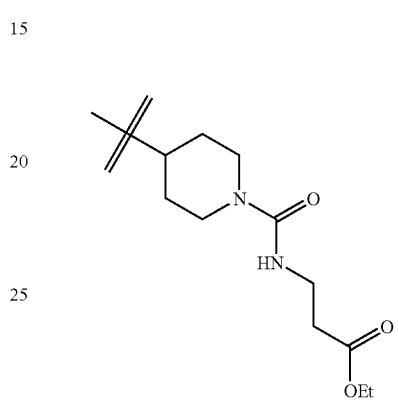
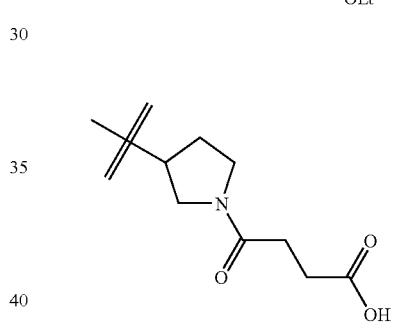
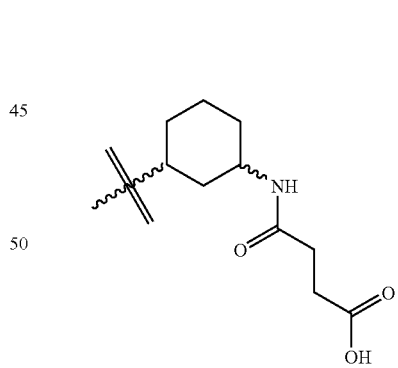
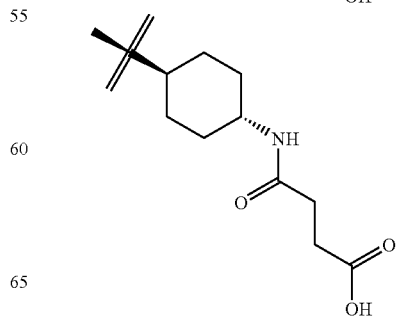

-continued
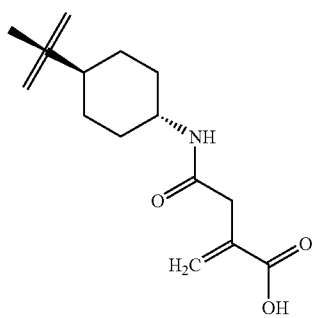
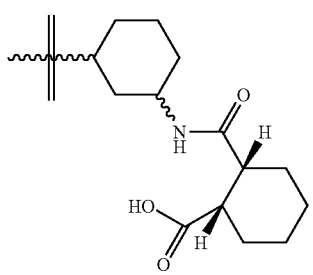
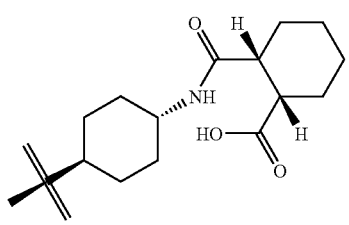
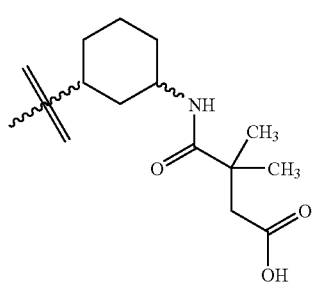
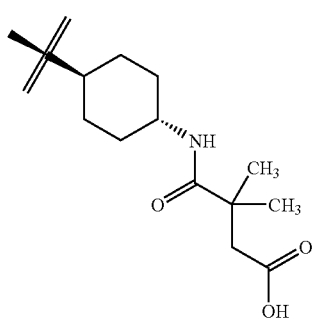
-continued
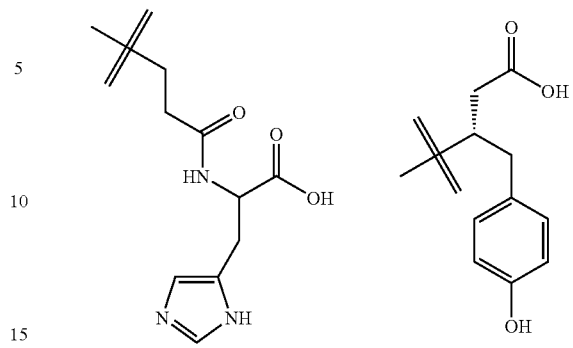
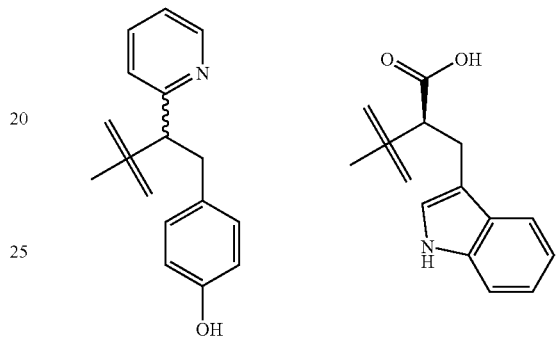
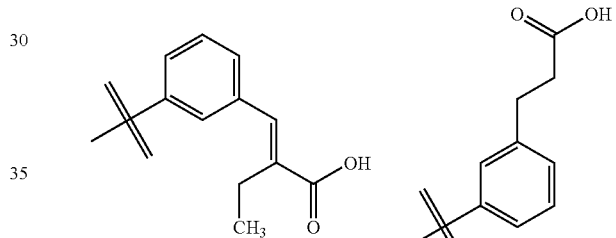
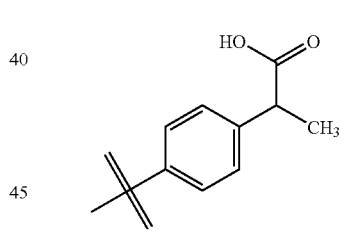
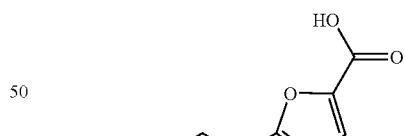
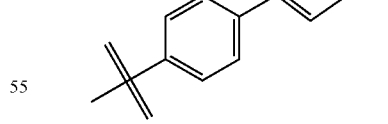
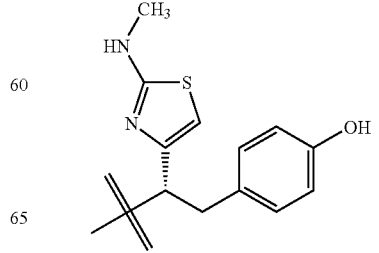

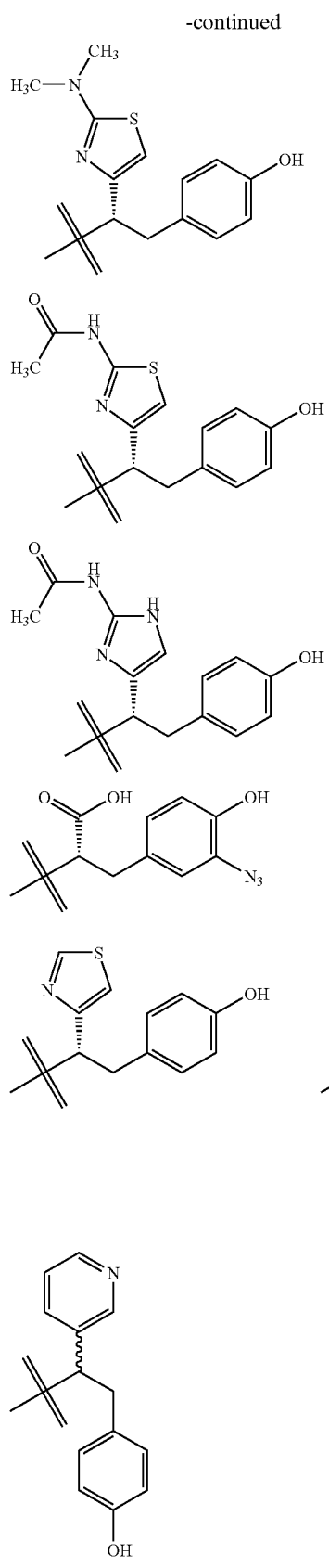
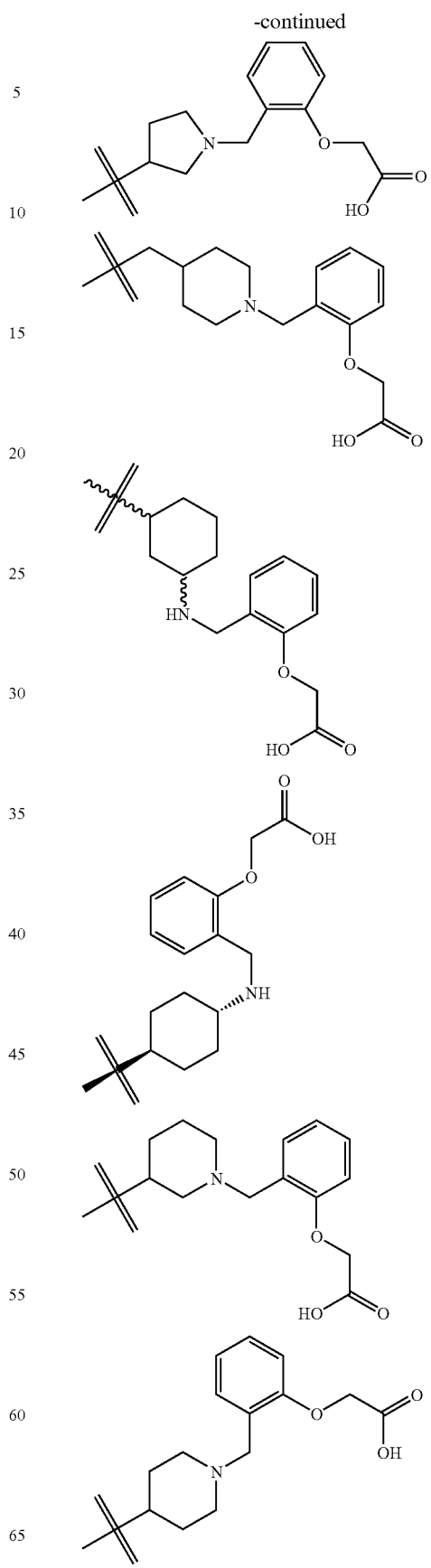

83
-continued
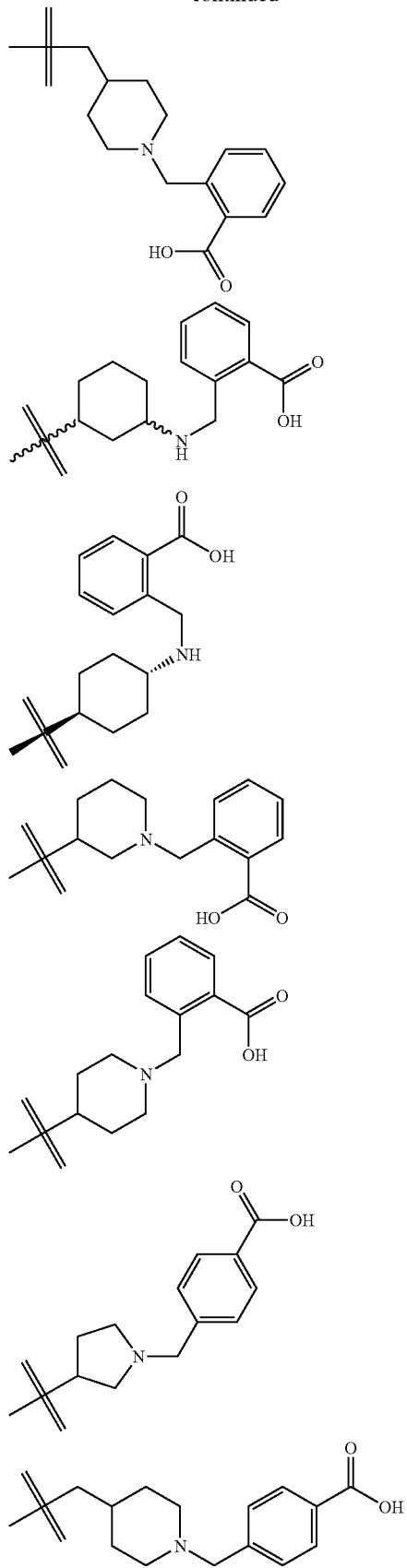
84
-continued
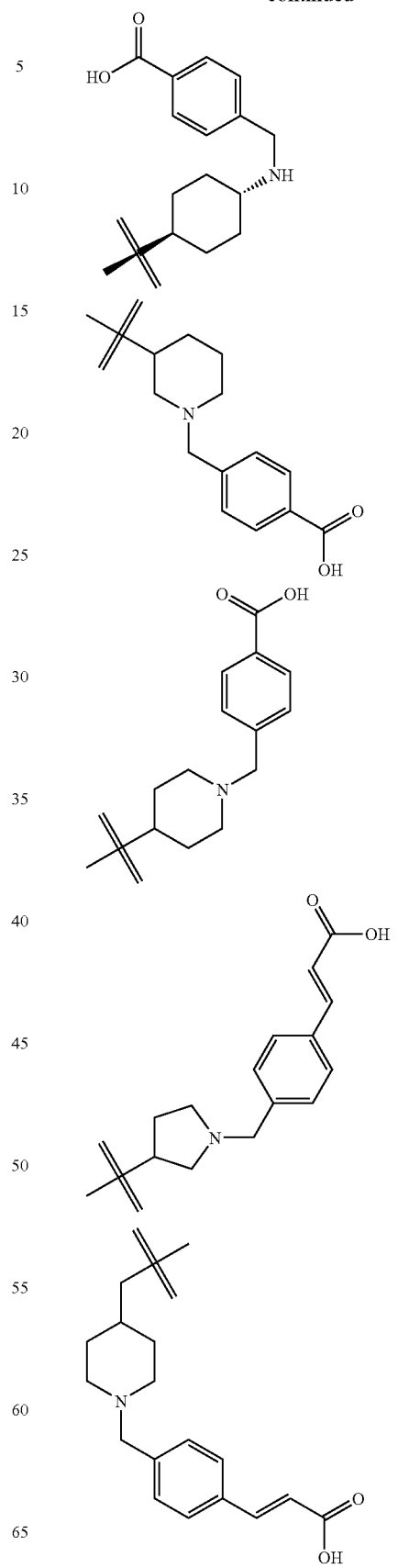

85
-continued
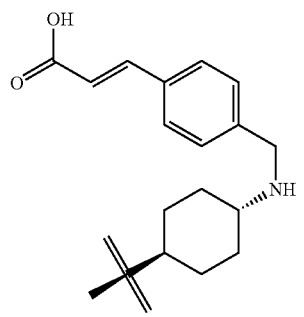
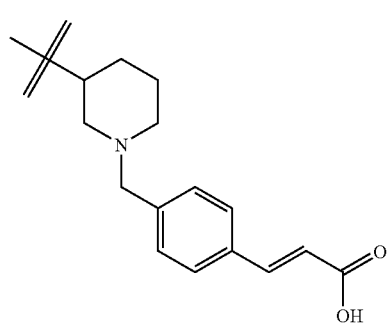
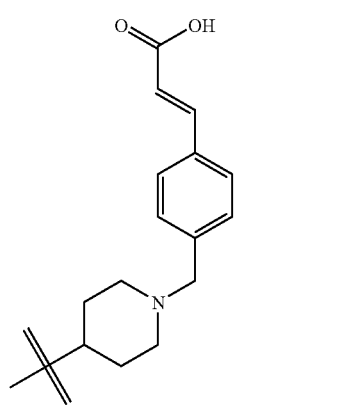
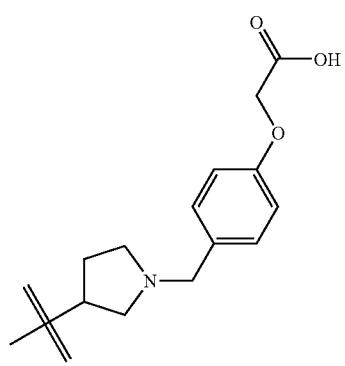
86
-continued
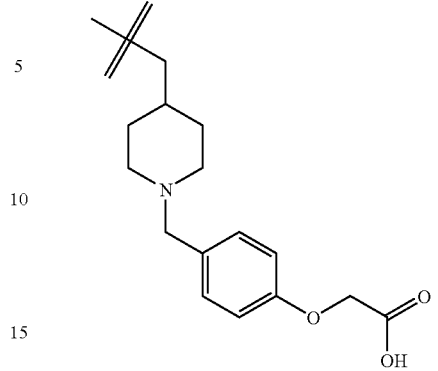
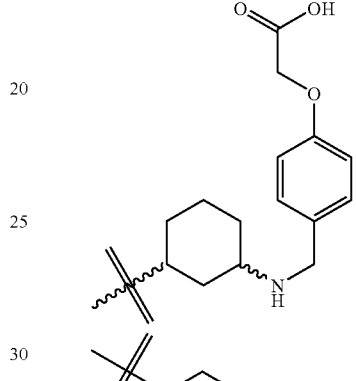
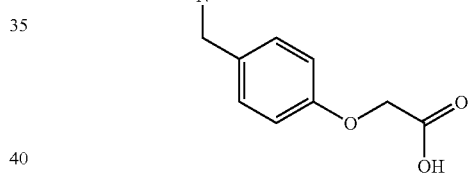

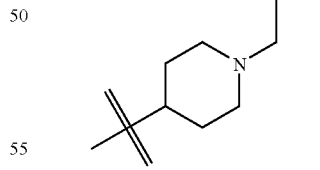
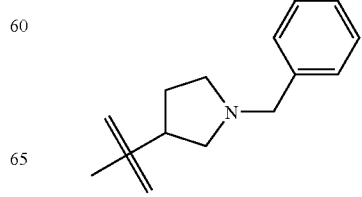

-continued
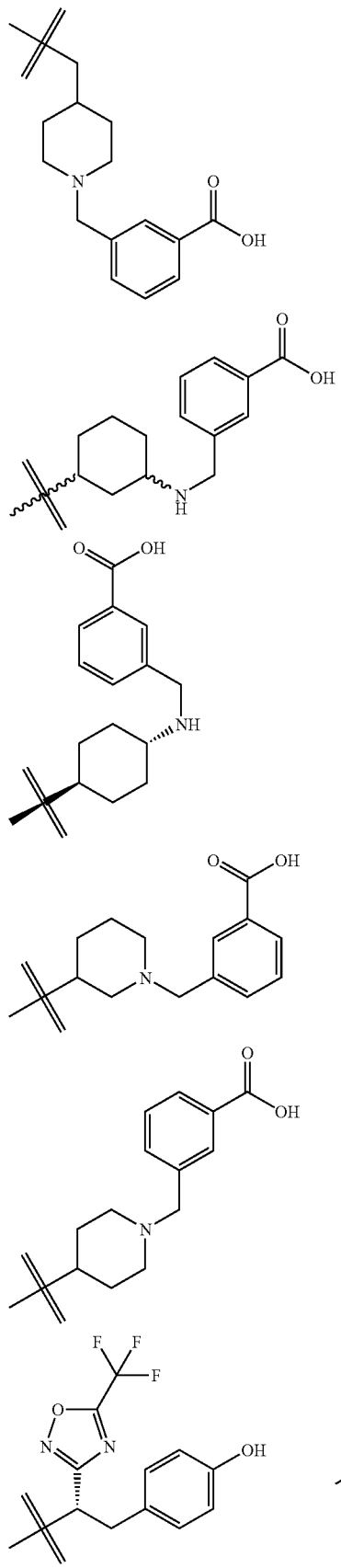
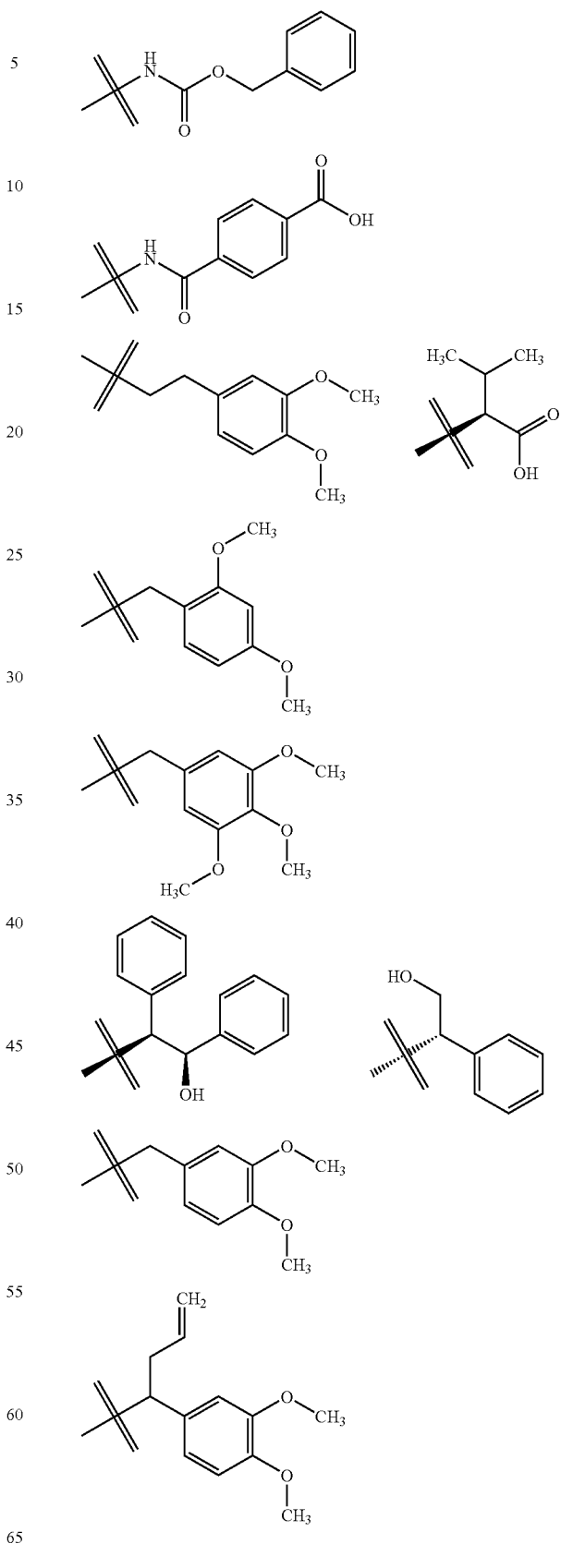

-continued
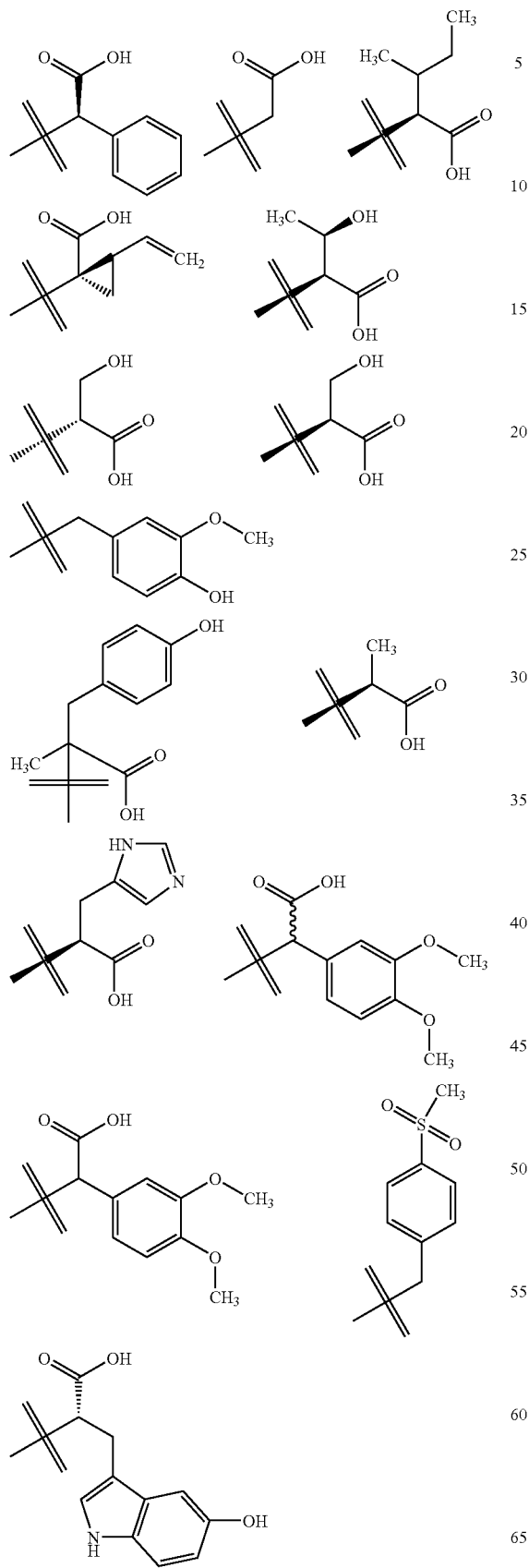
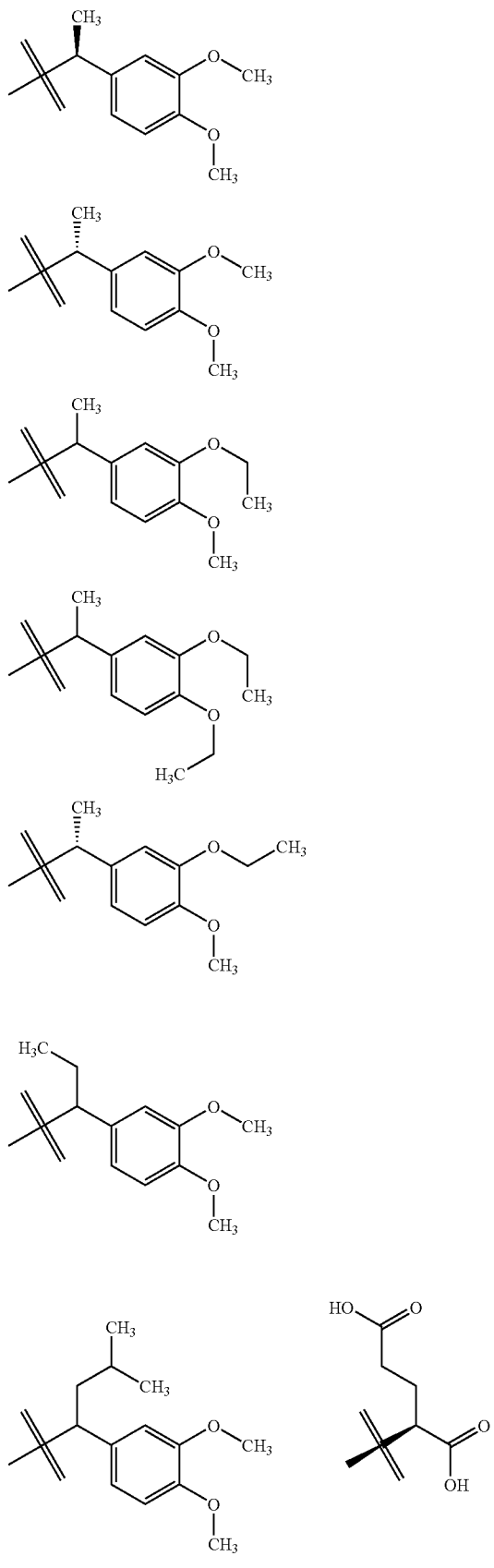

91
-continued
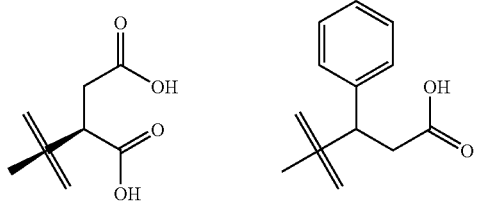
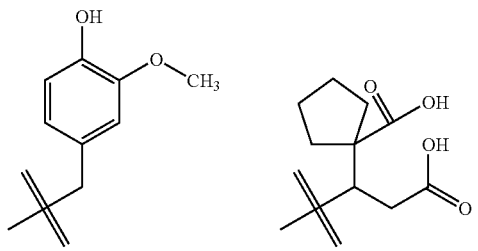
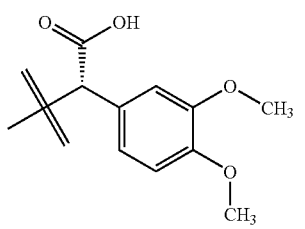
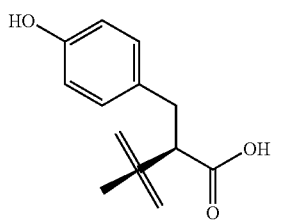
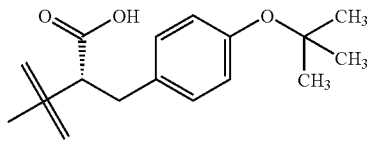
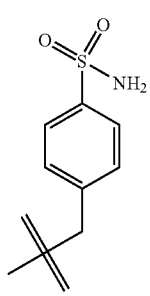
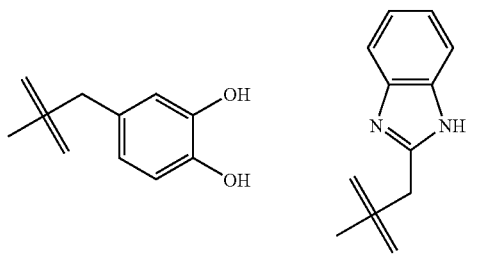
92
-continued
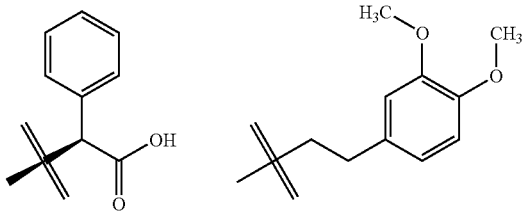
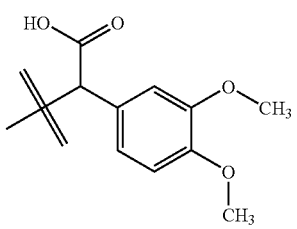
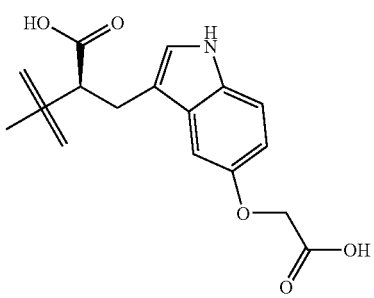
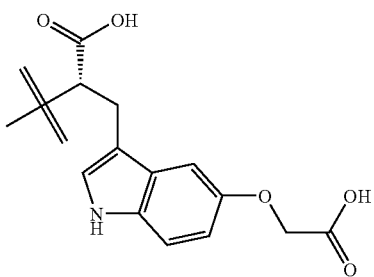
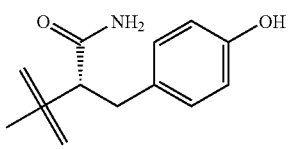
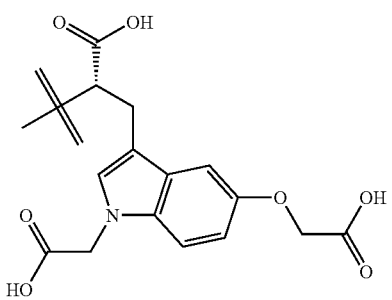

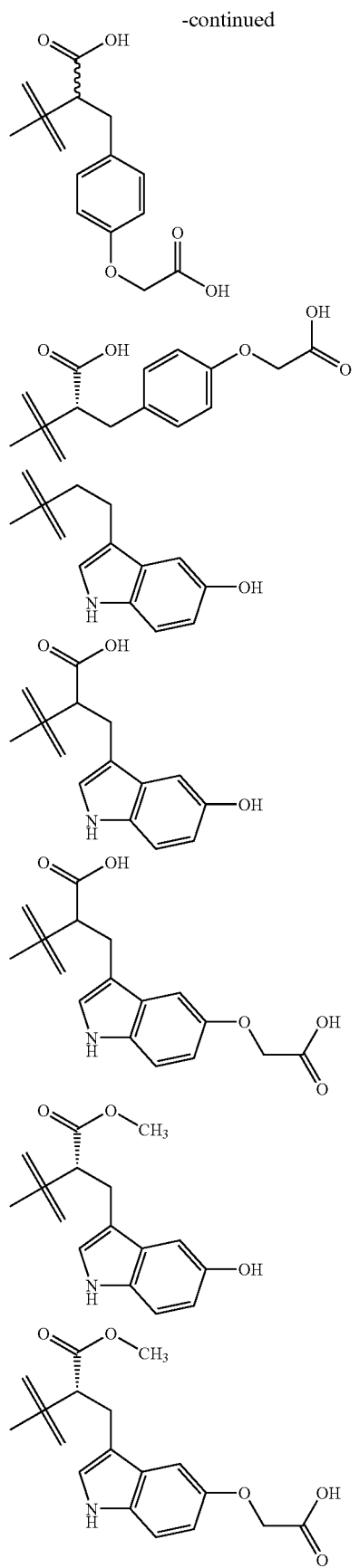
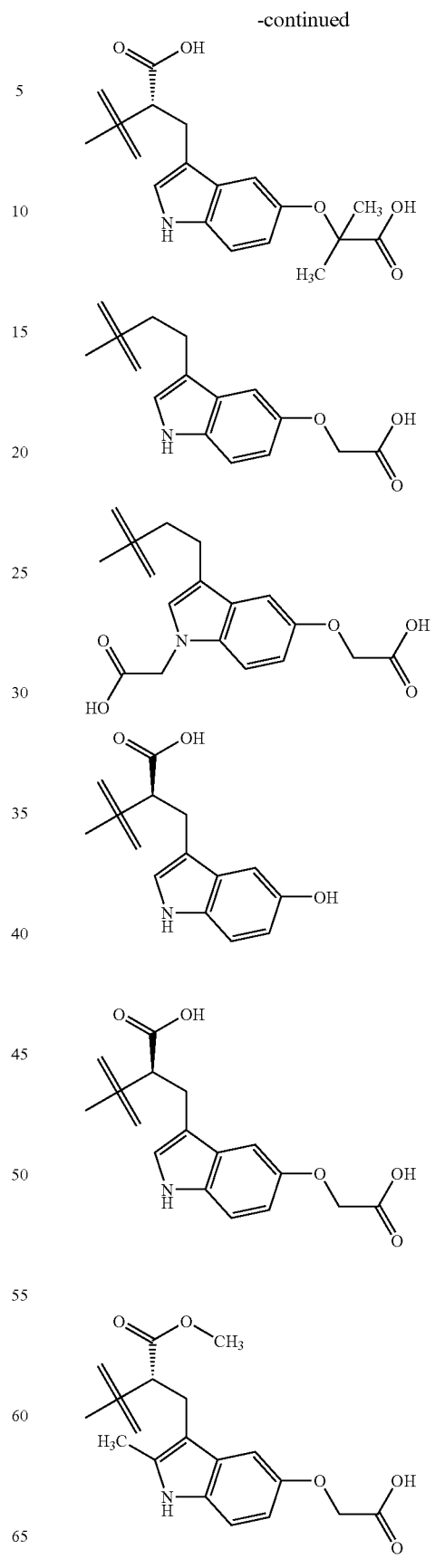

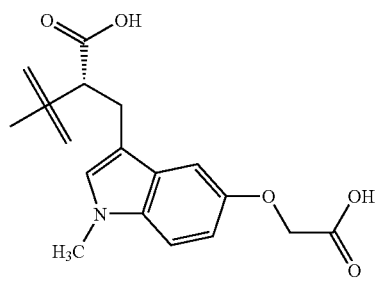
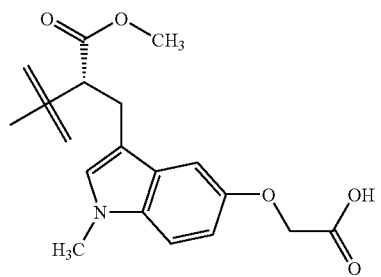
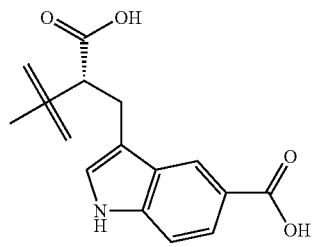
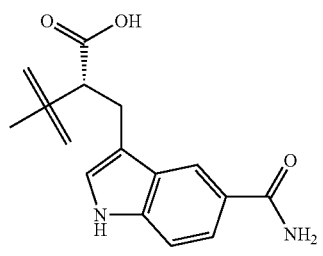
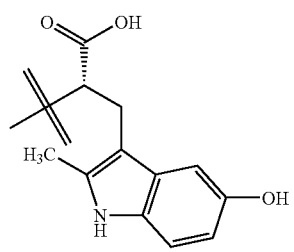
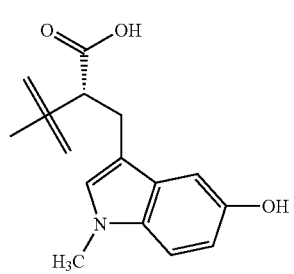
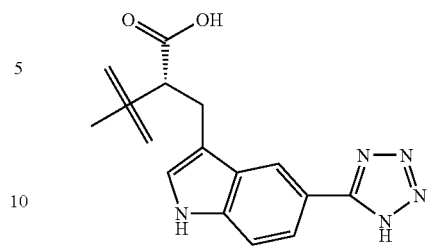
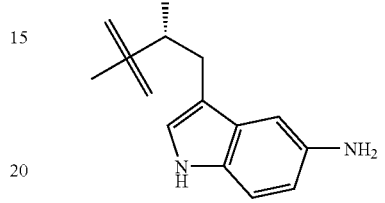
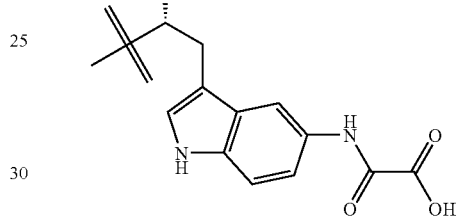
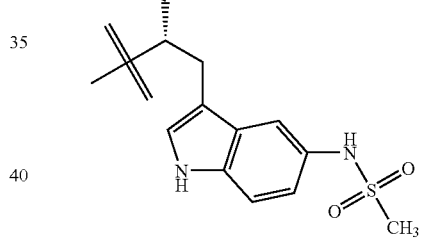
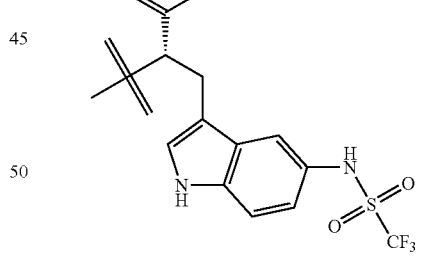
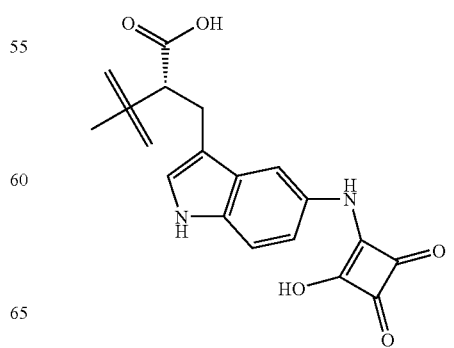

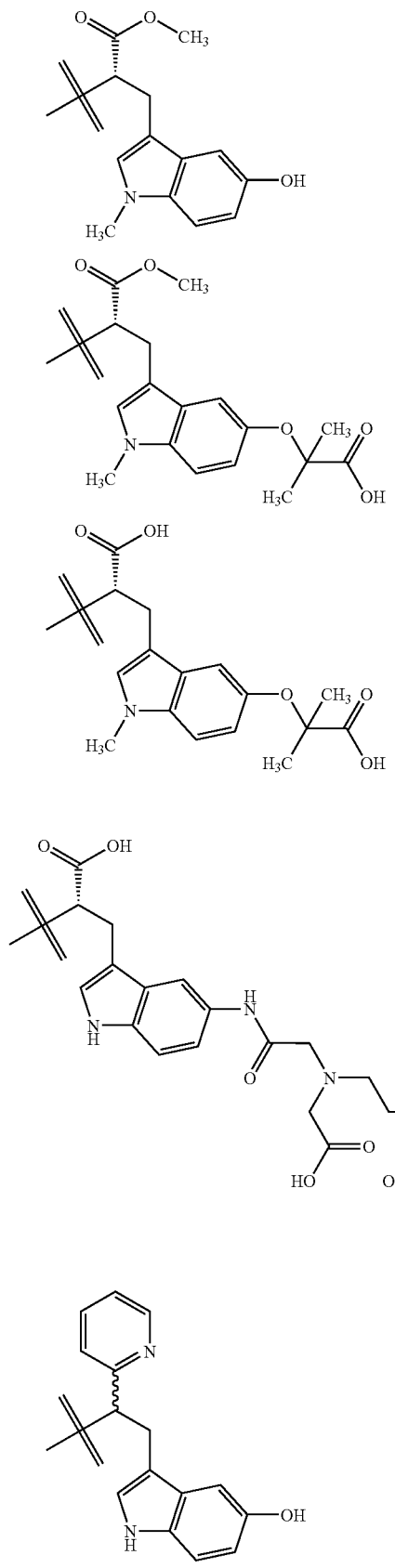
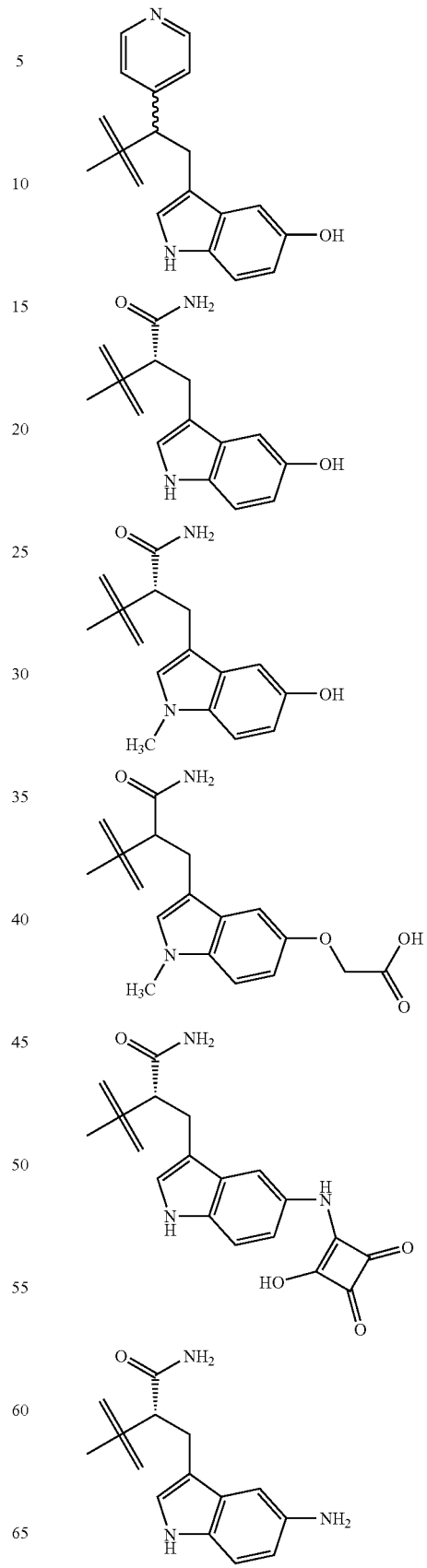

-continued
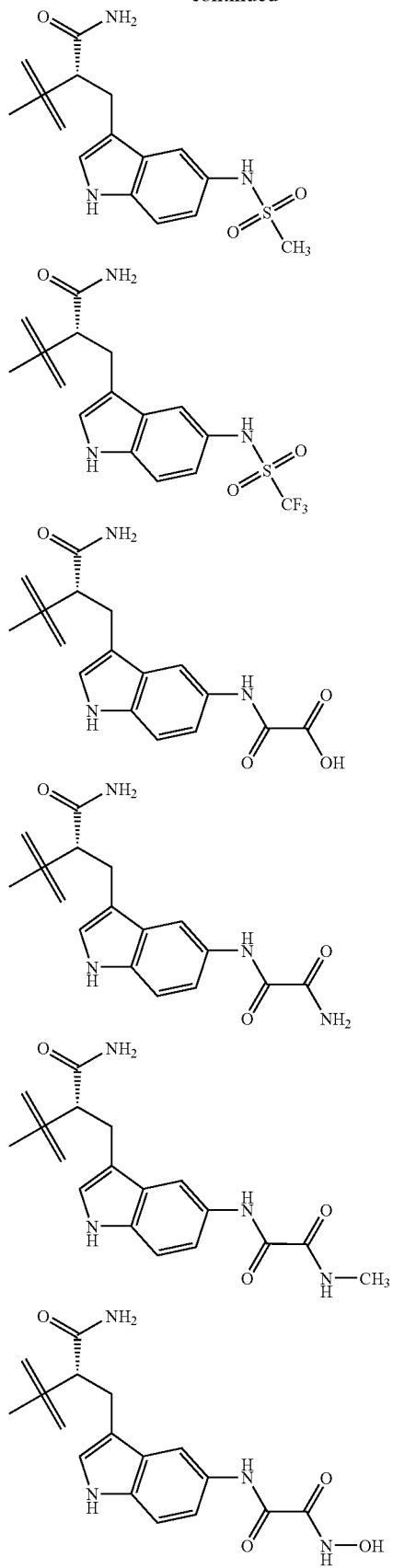
-continued
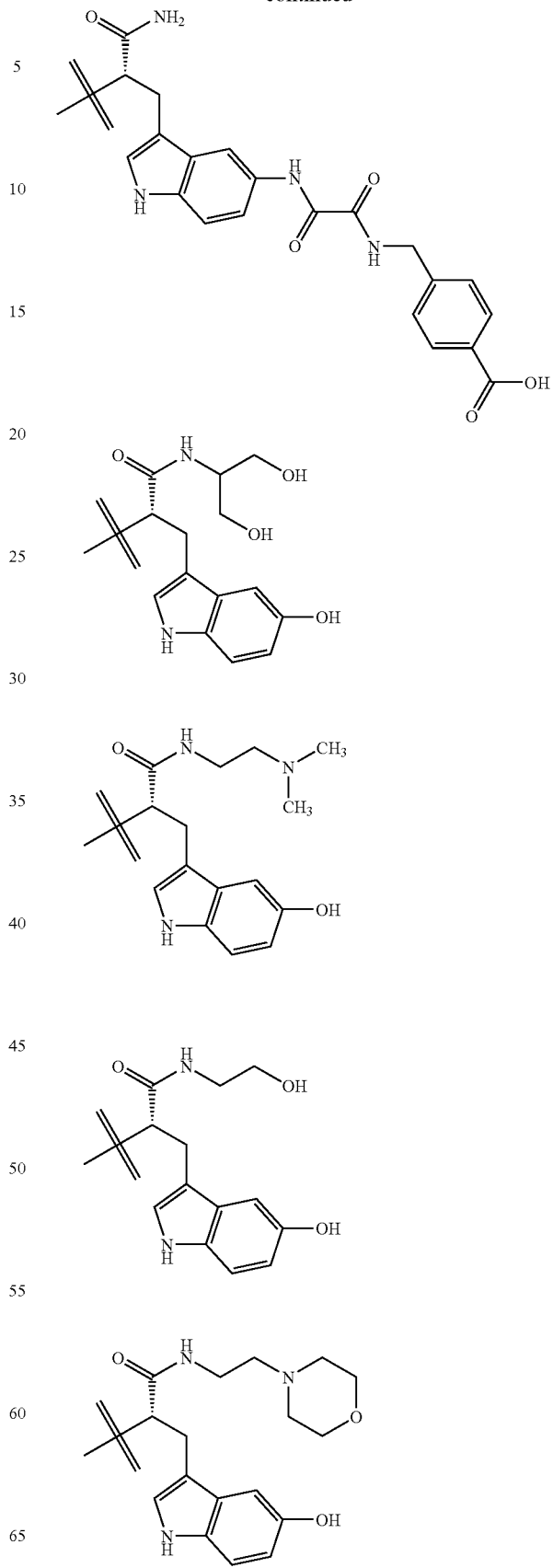

-continued
101
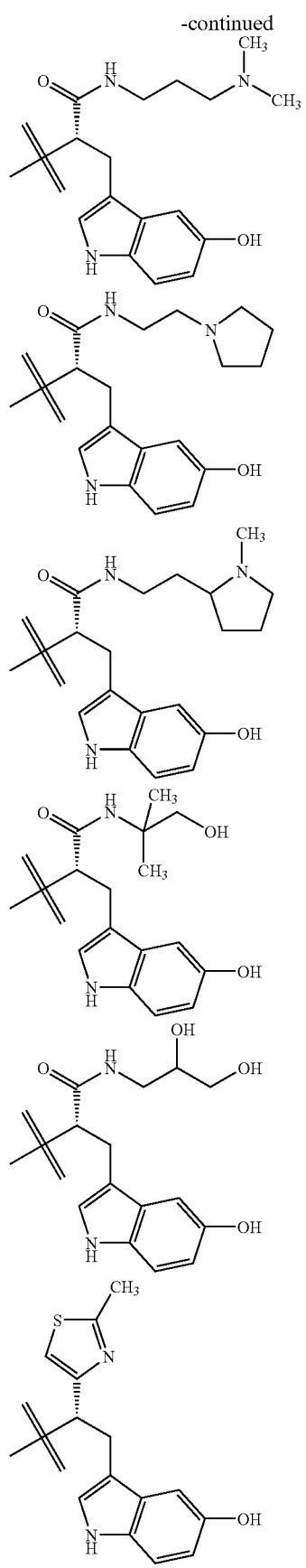
102
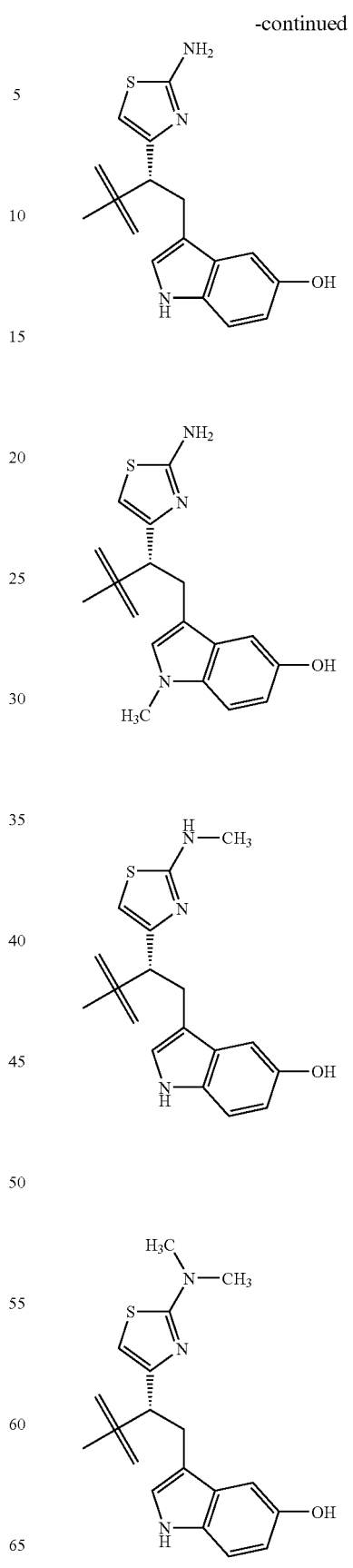

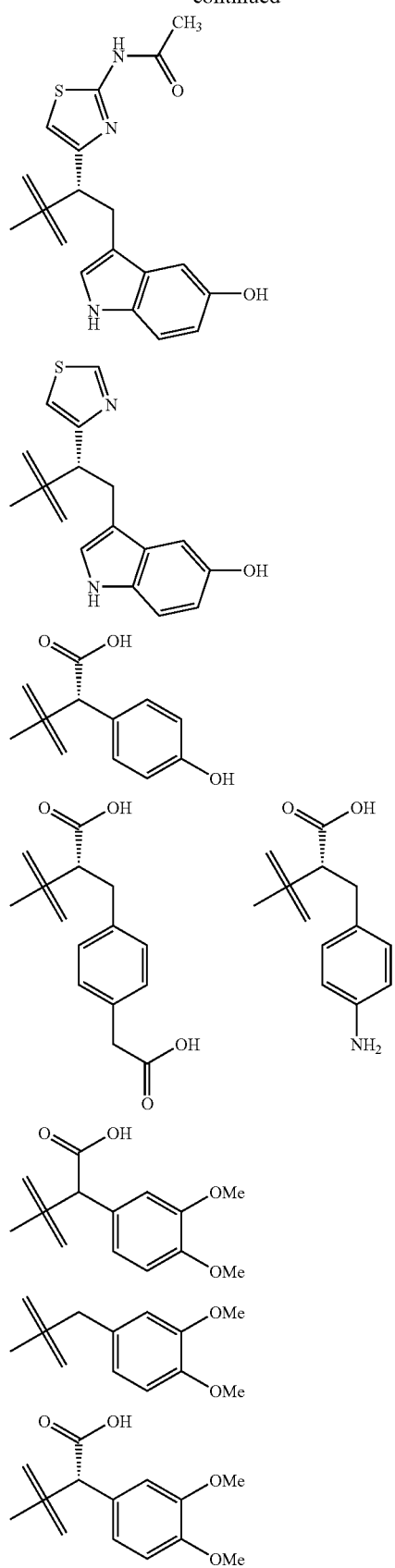
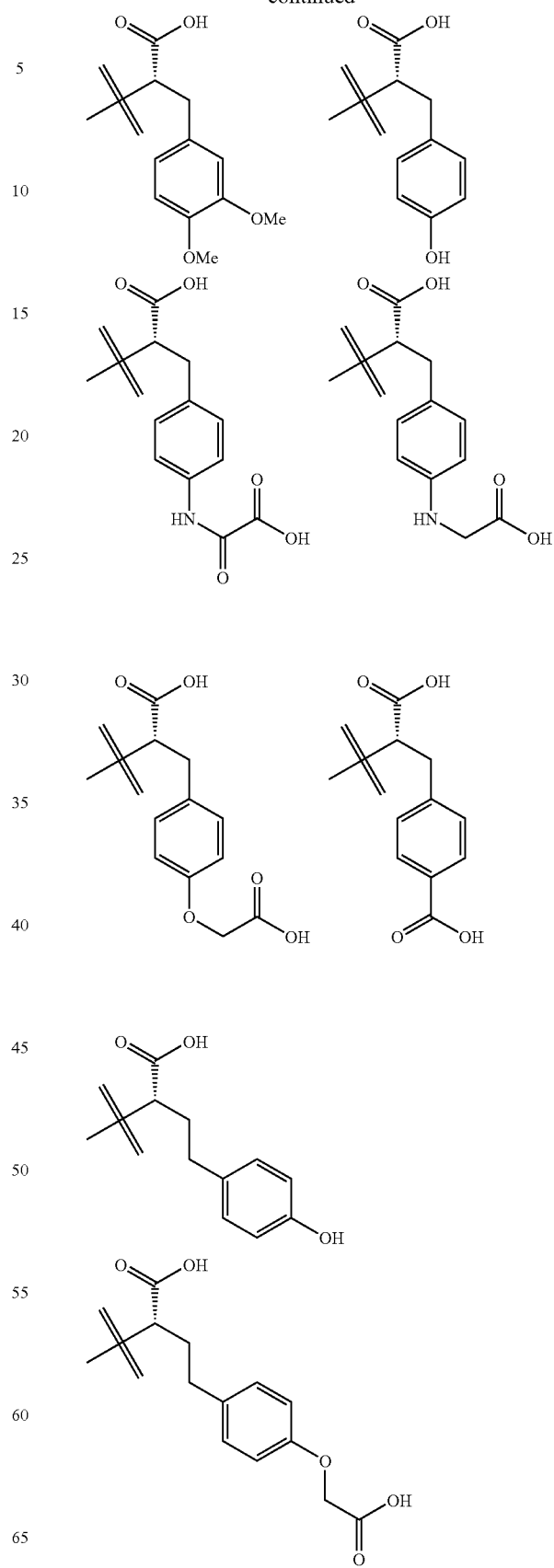

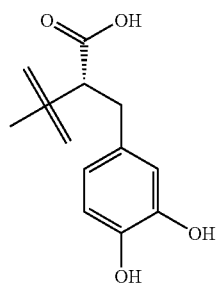
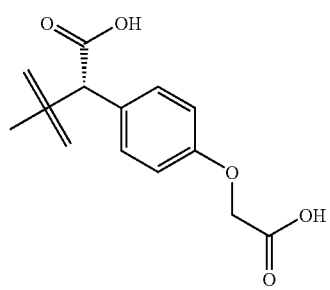
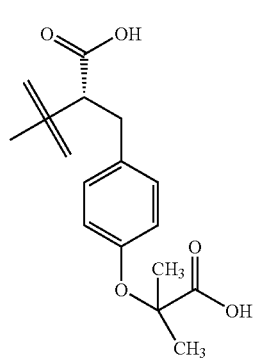
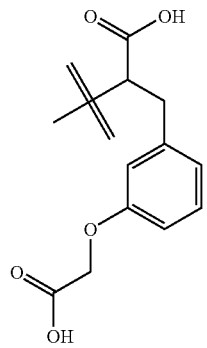
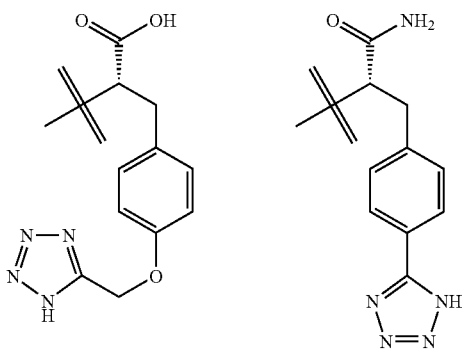
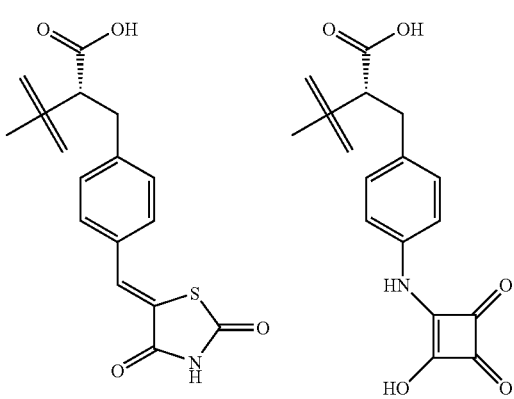
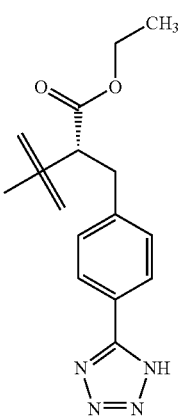
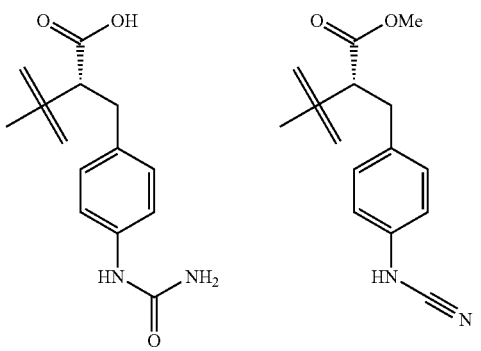
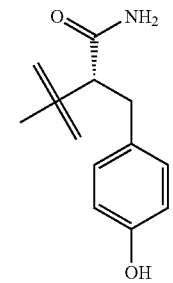
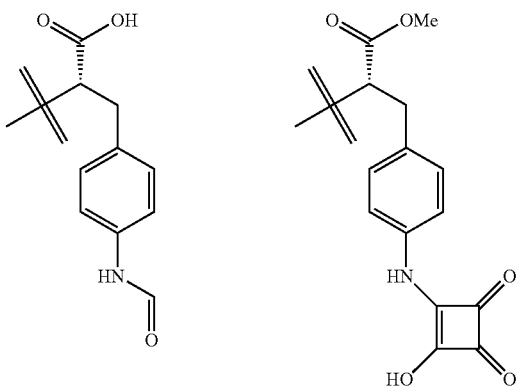

-continued
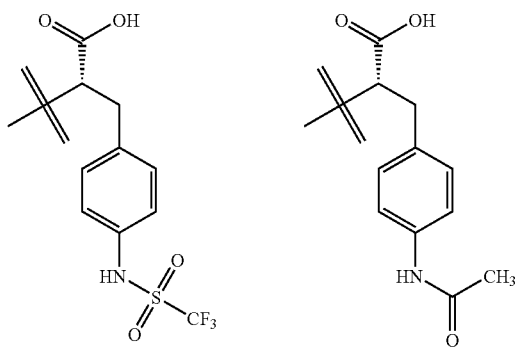
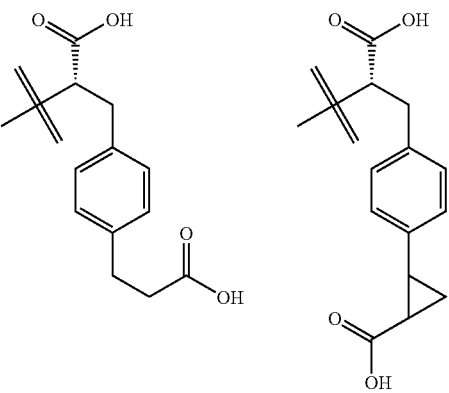
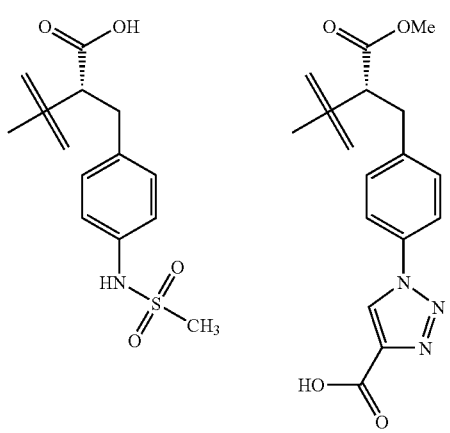
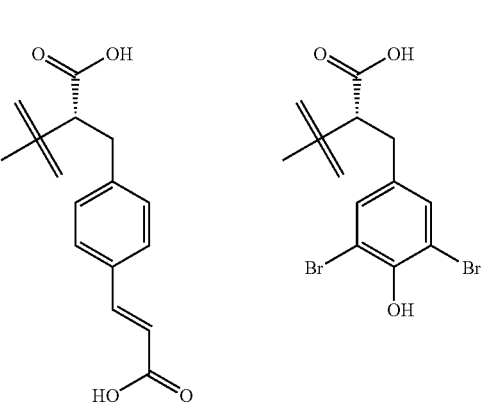
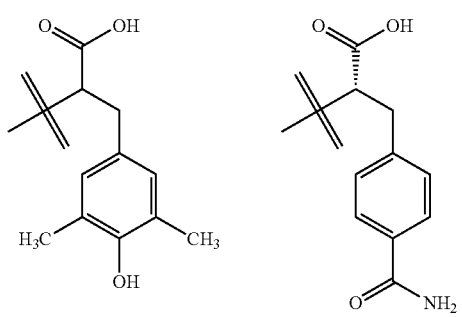
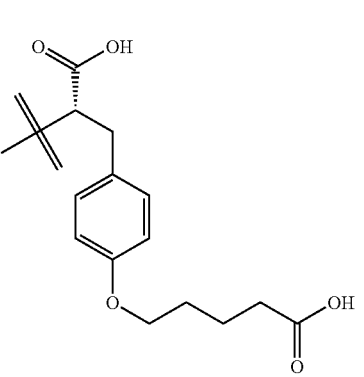
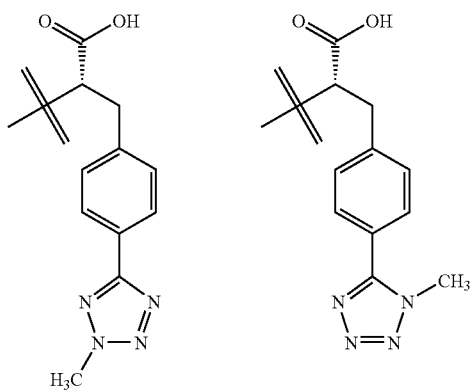
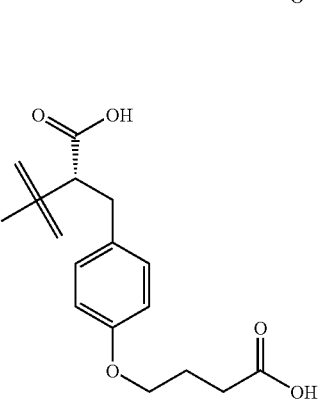

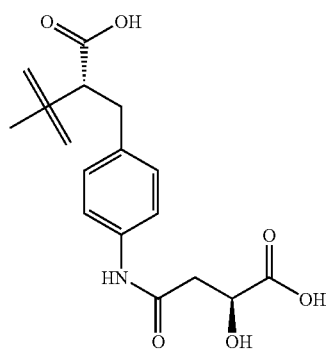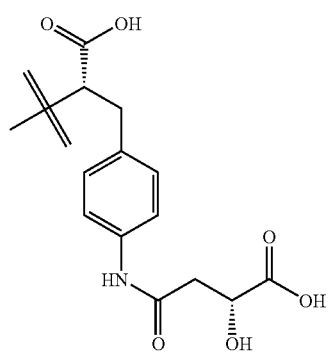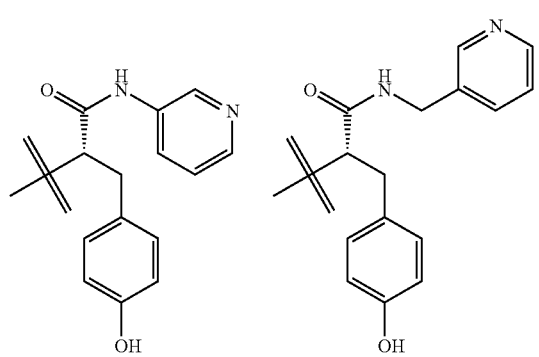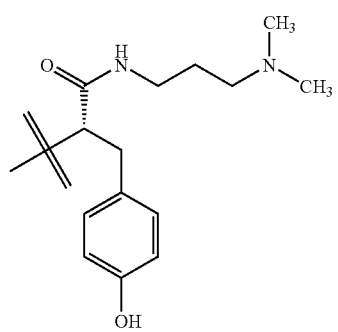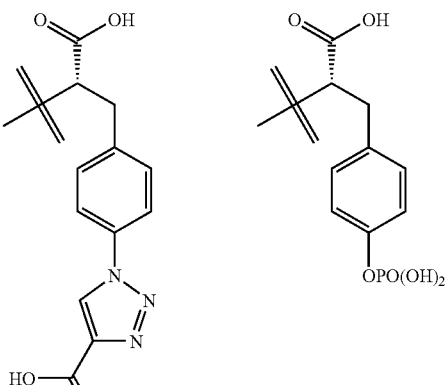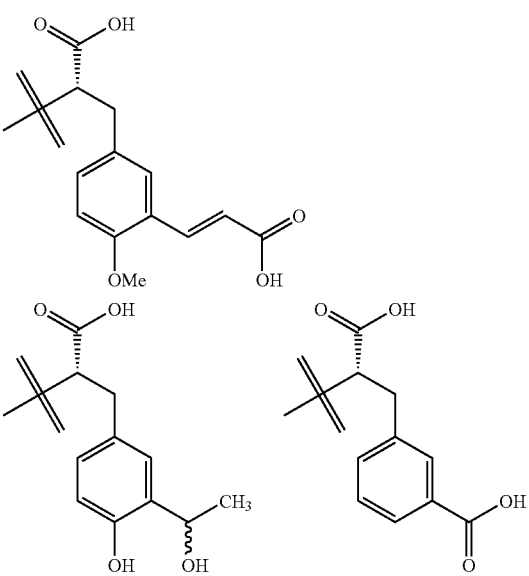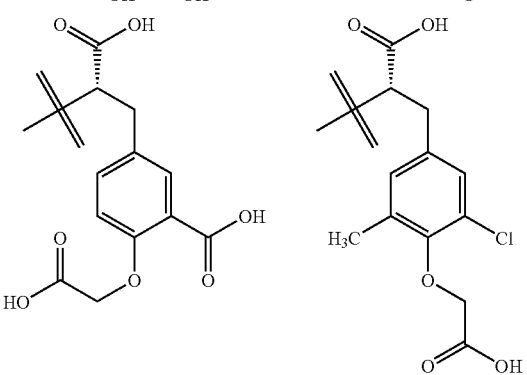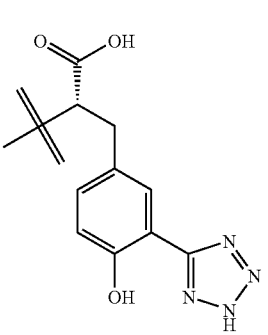

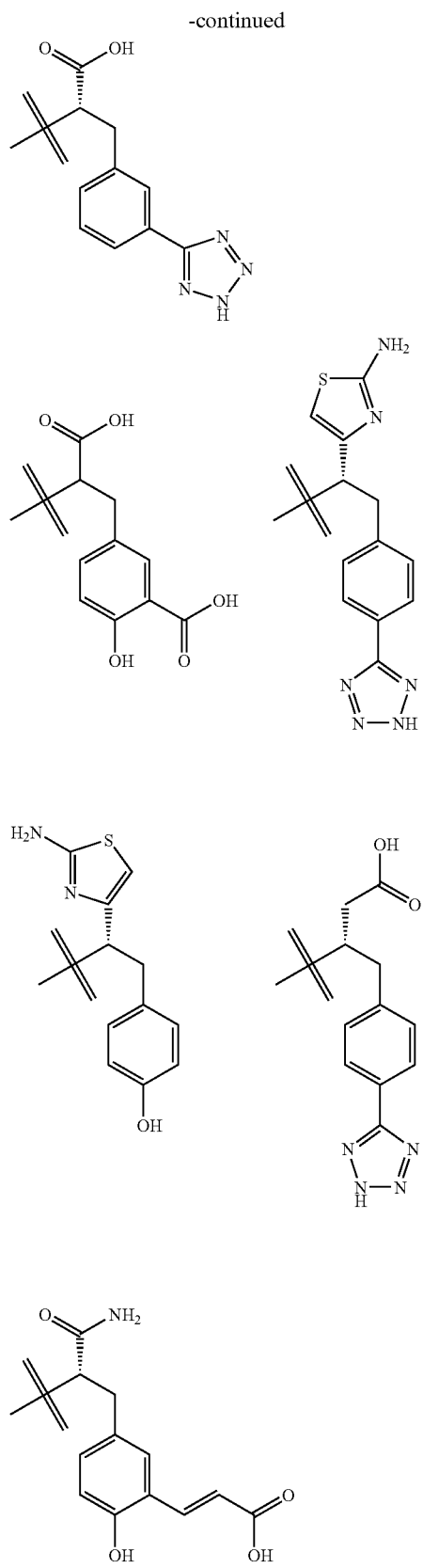
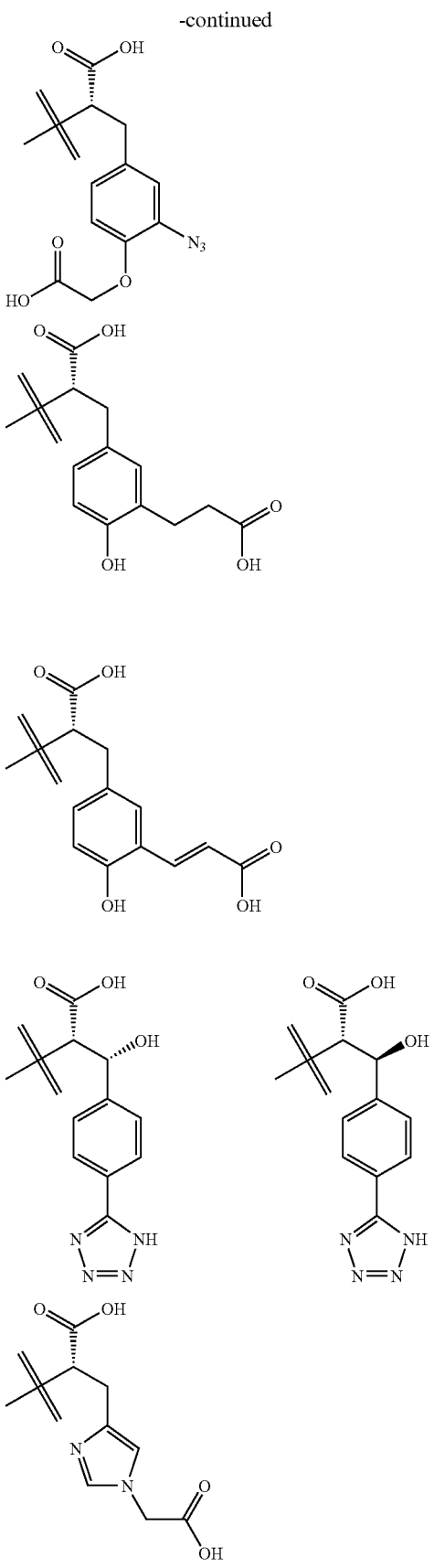

-continued
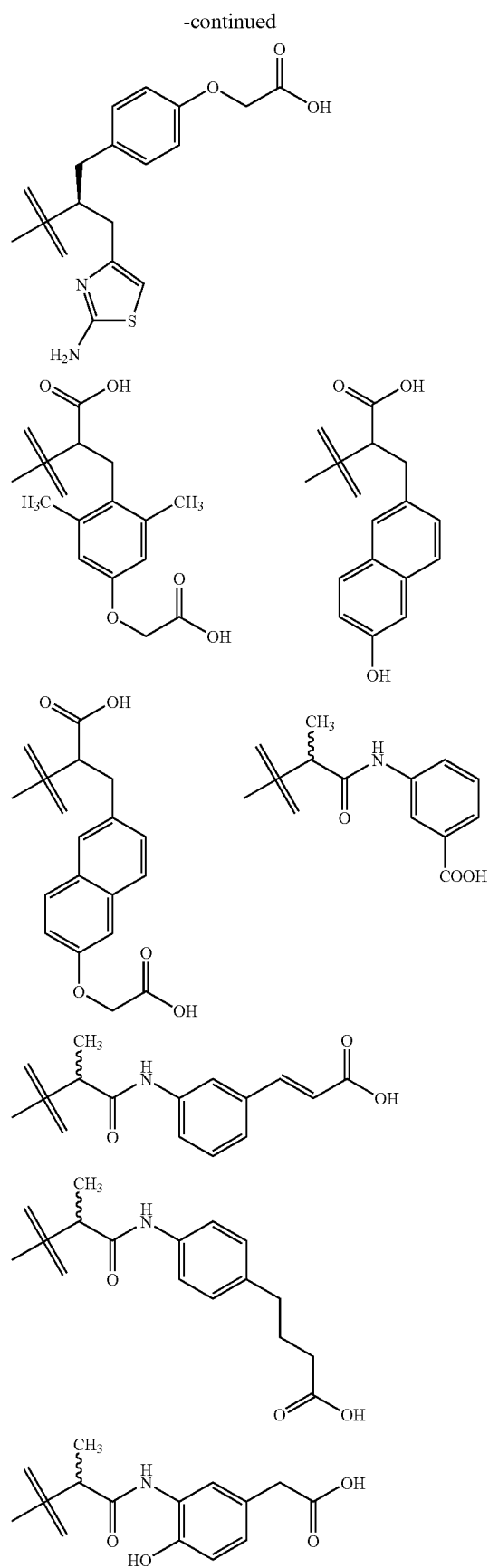
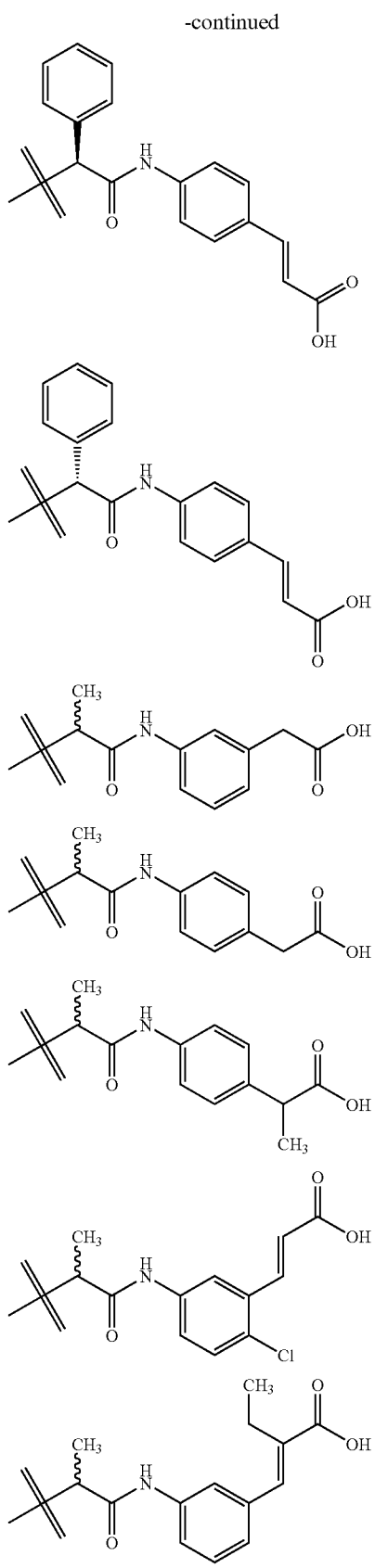

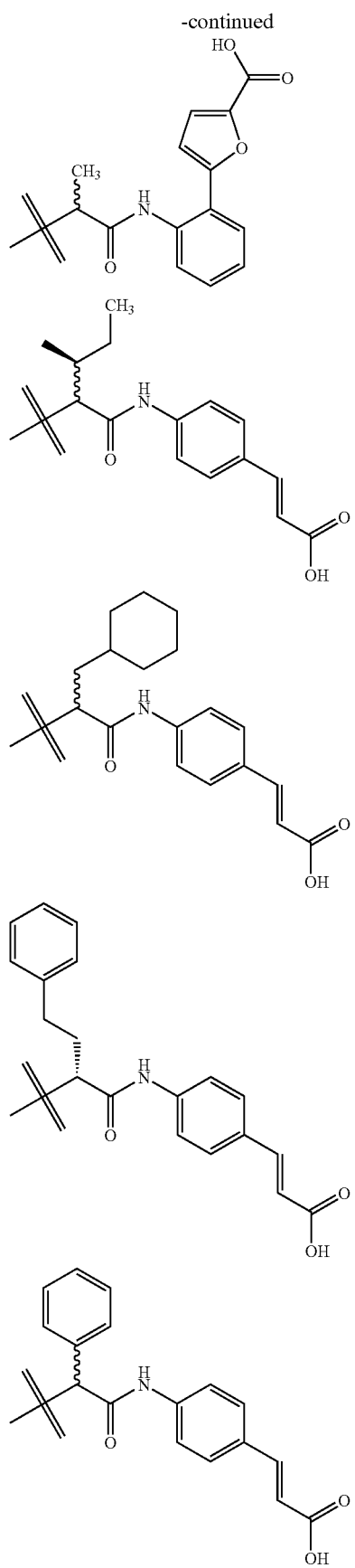
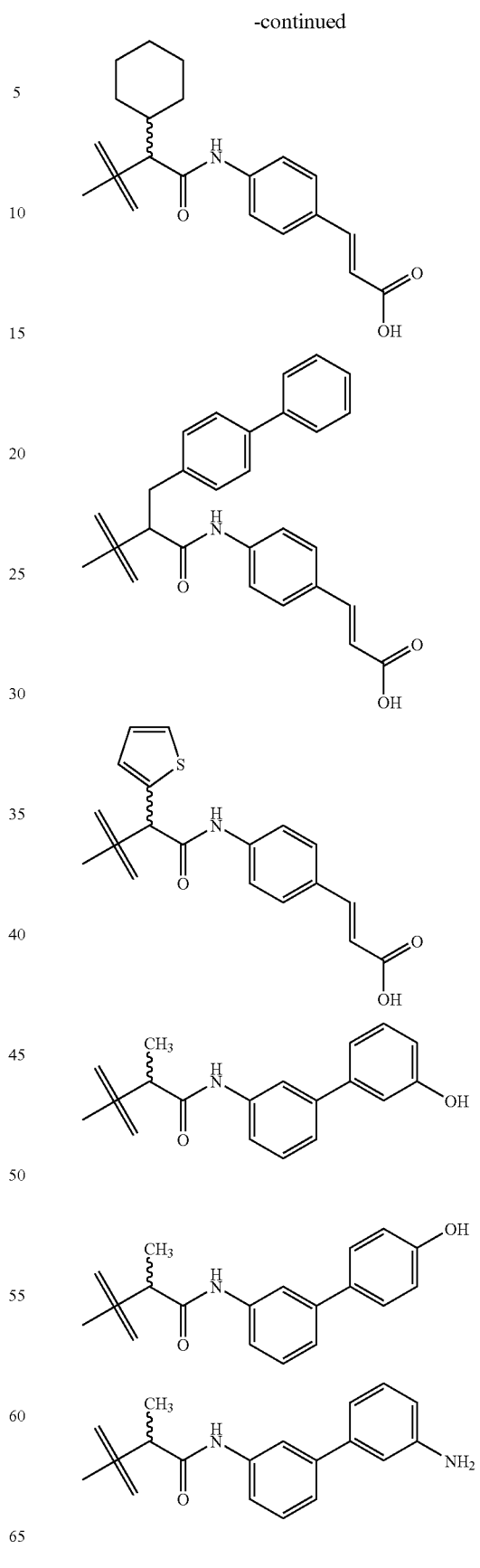

-continued
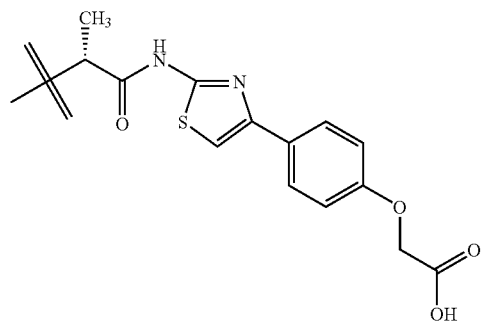
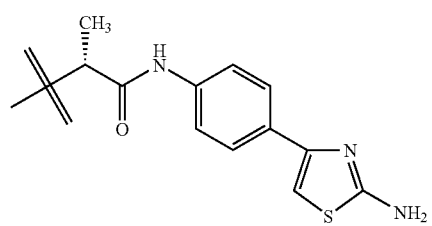
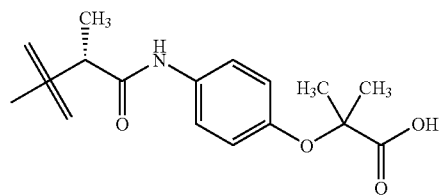
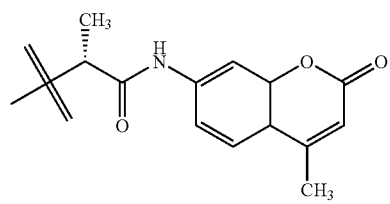
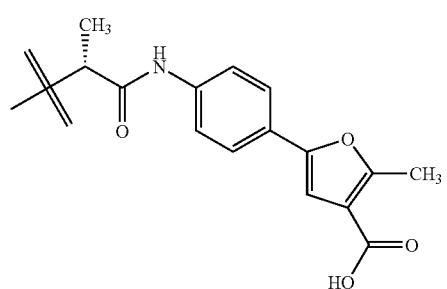
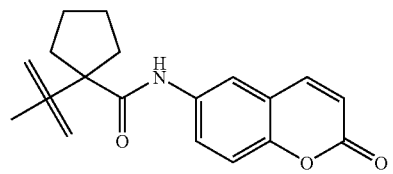
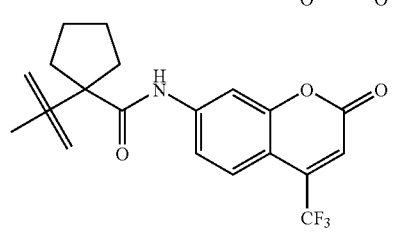
-continued
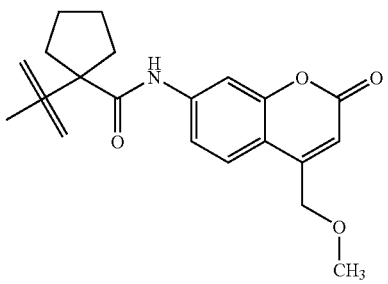
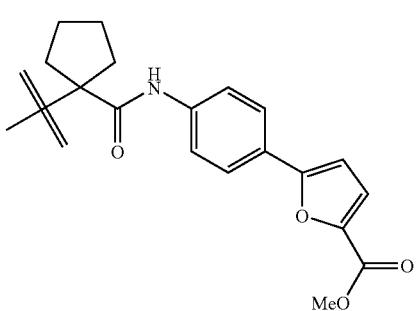
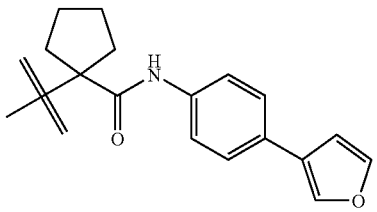
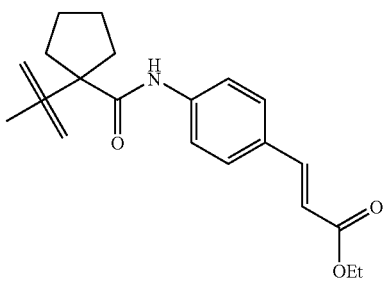
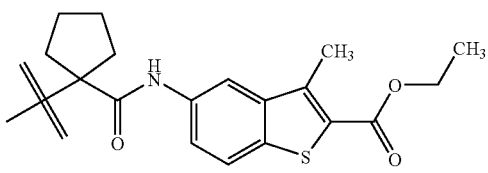
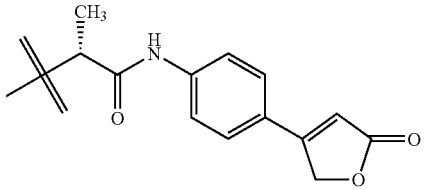
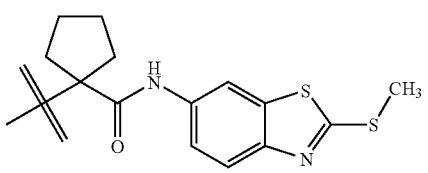

-continued
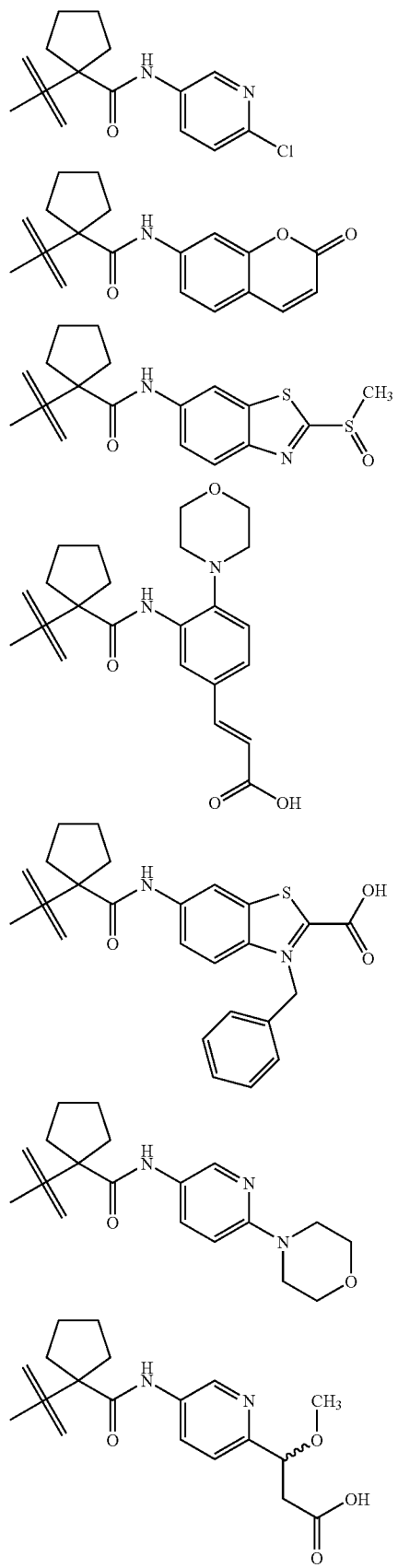
-continued
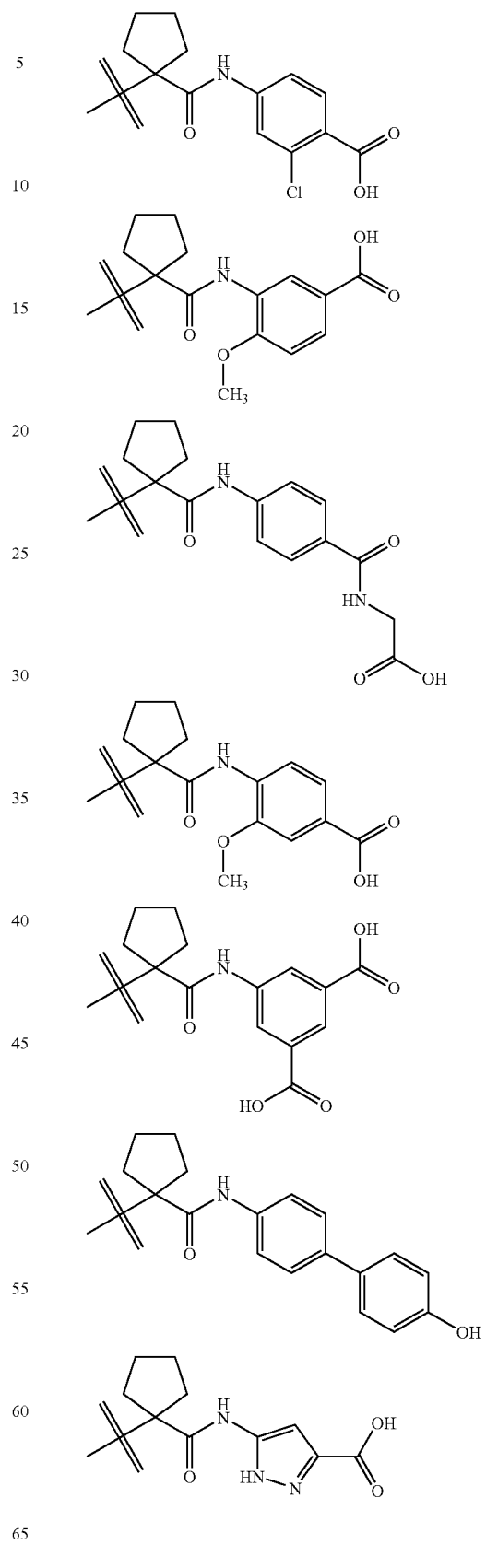

121
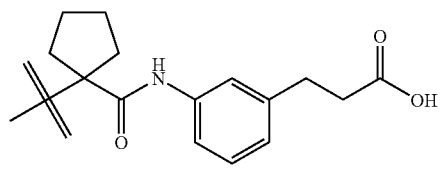
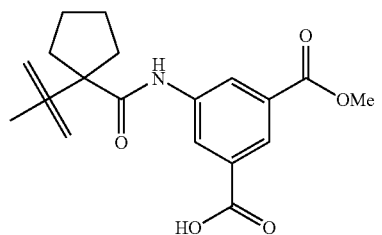
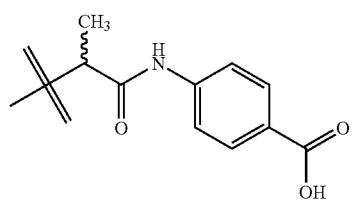
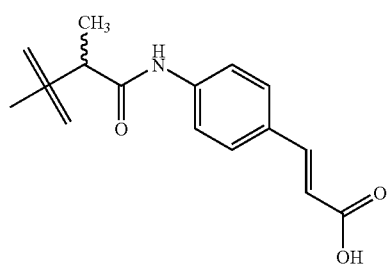
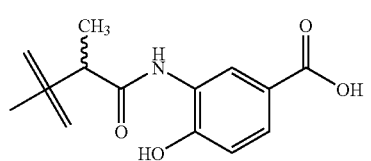
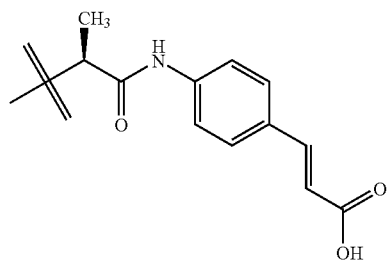
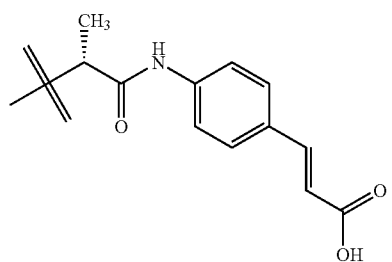
122
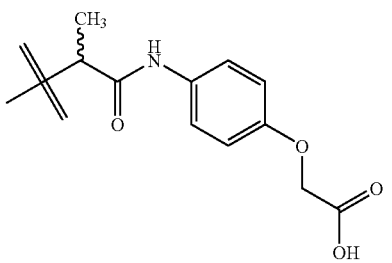
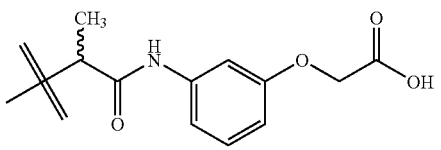
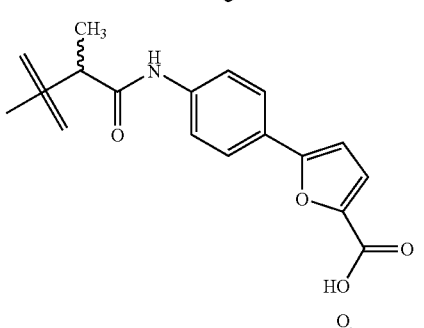
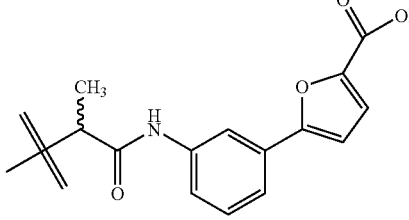
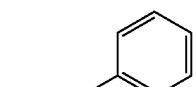
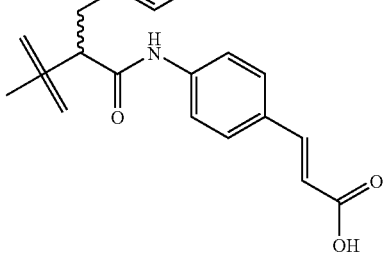
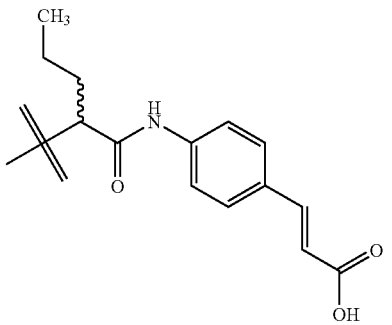

123
-continued
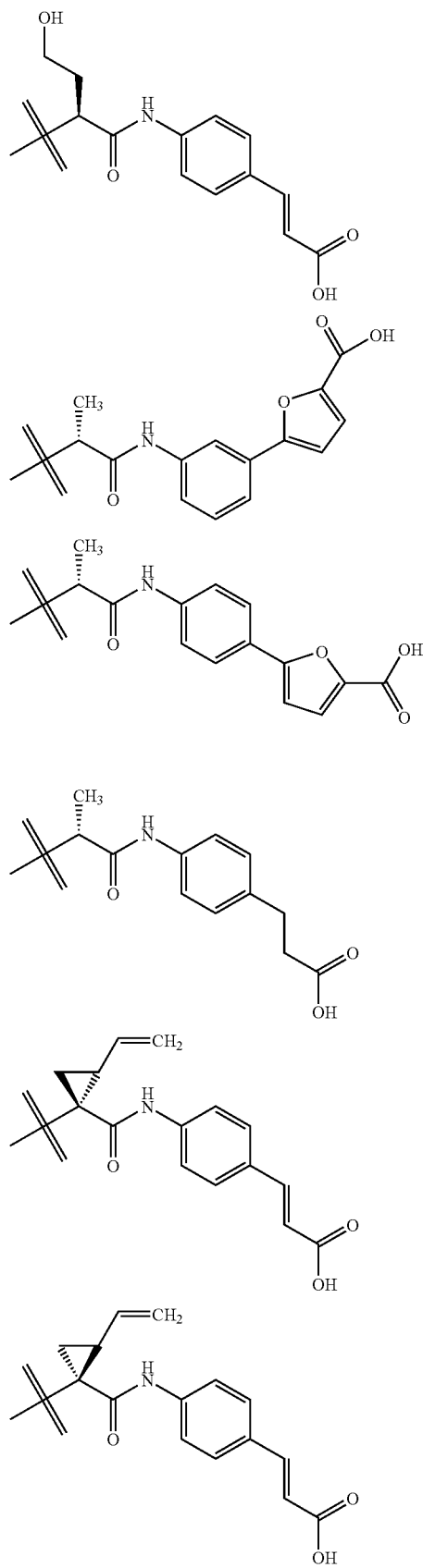
124
-continued
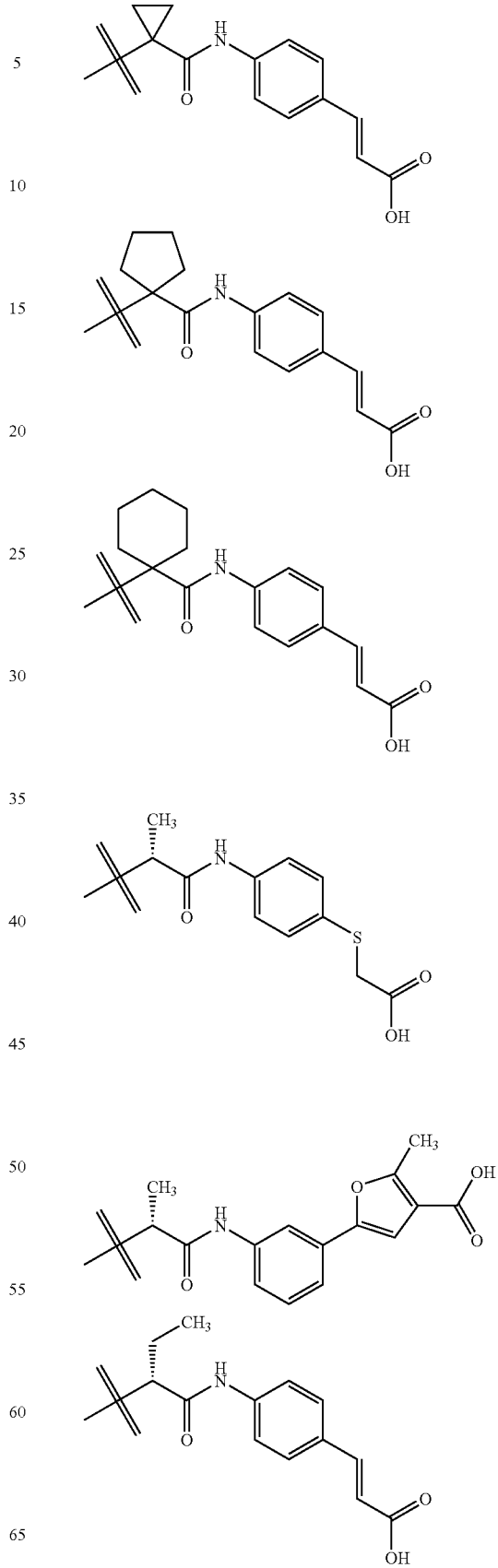

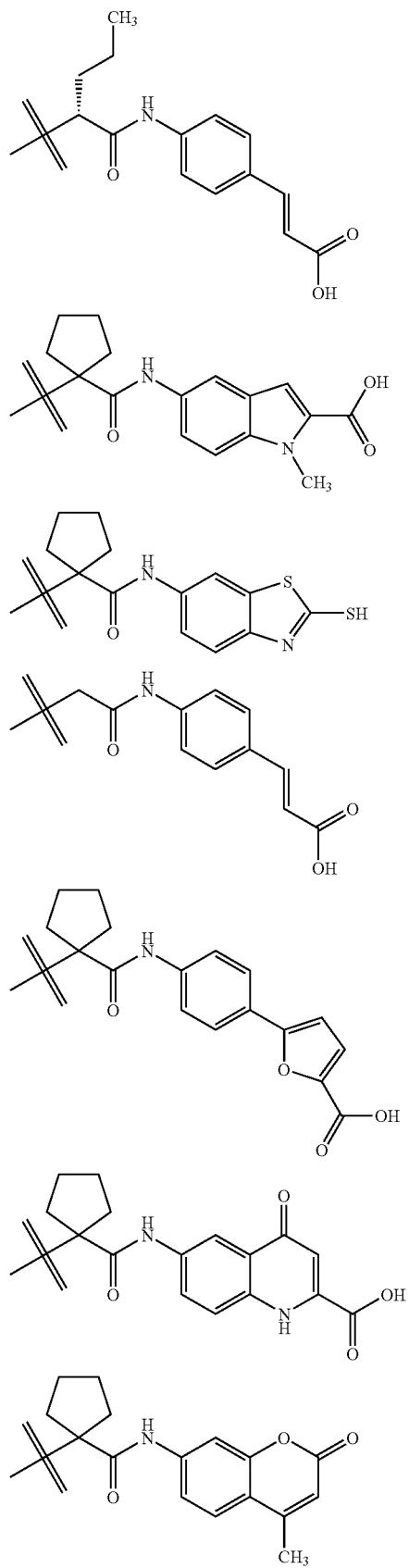
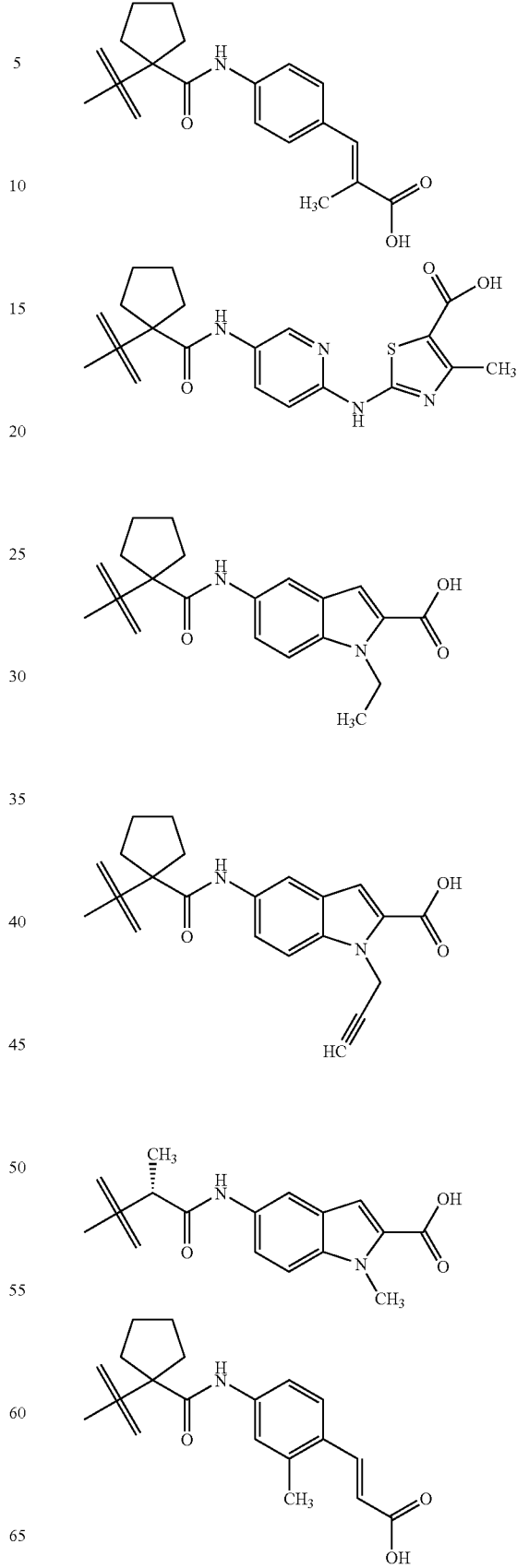

127
-continued
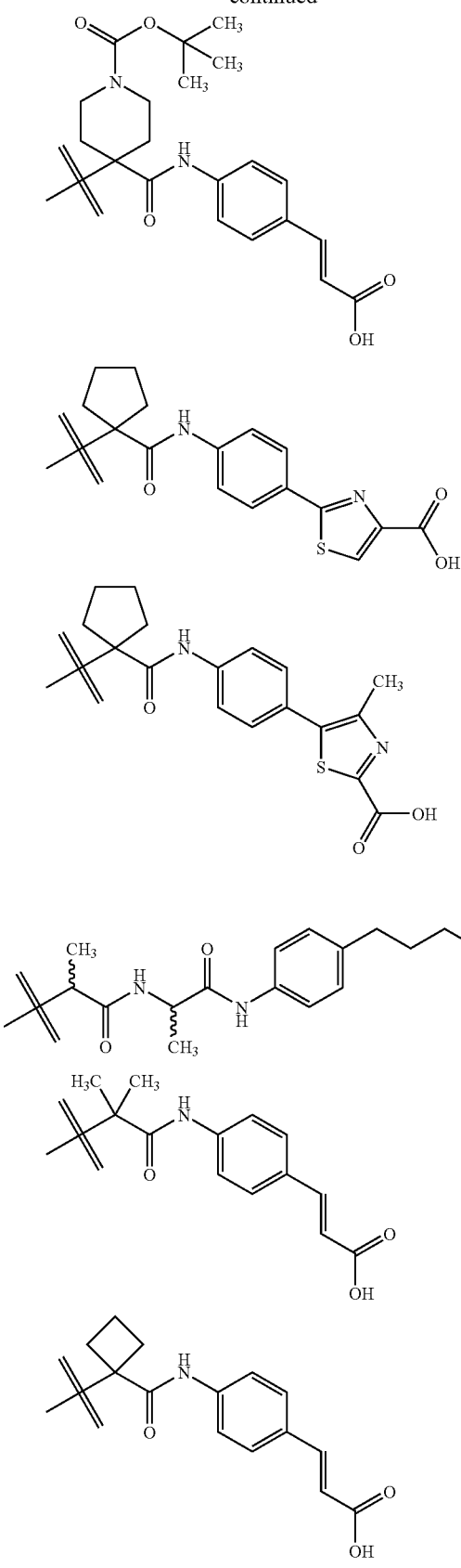
128
-continued
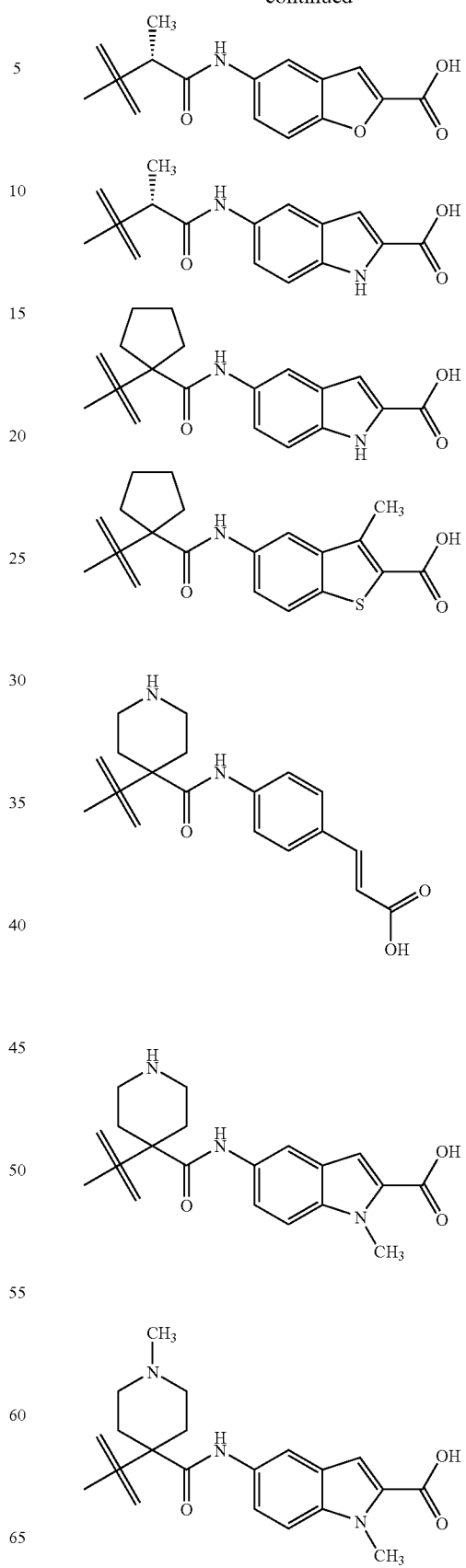

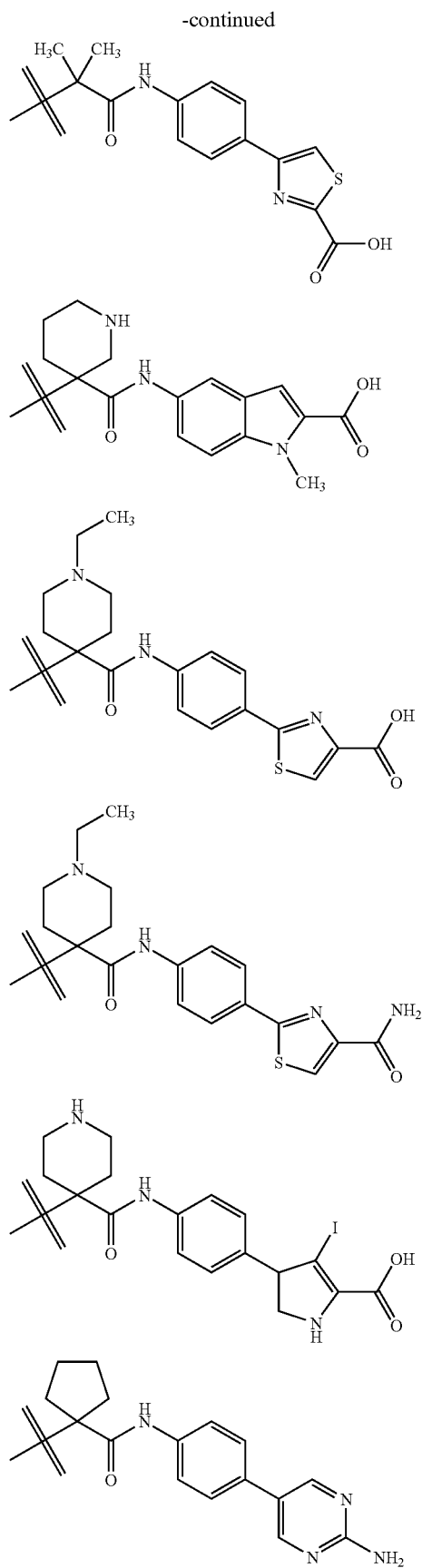
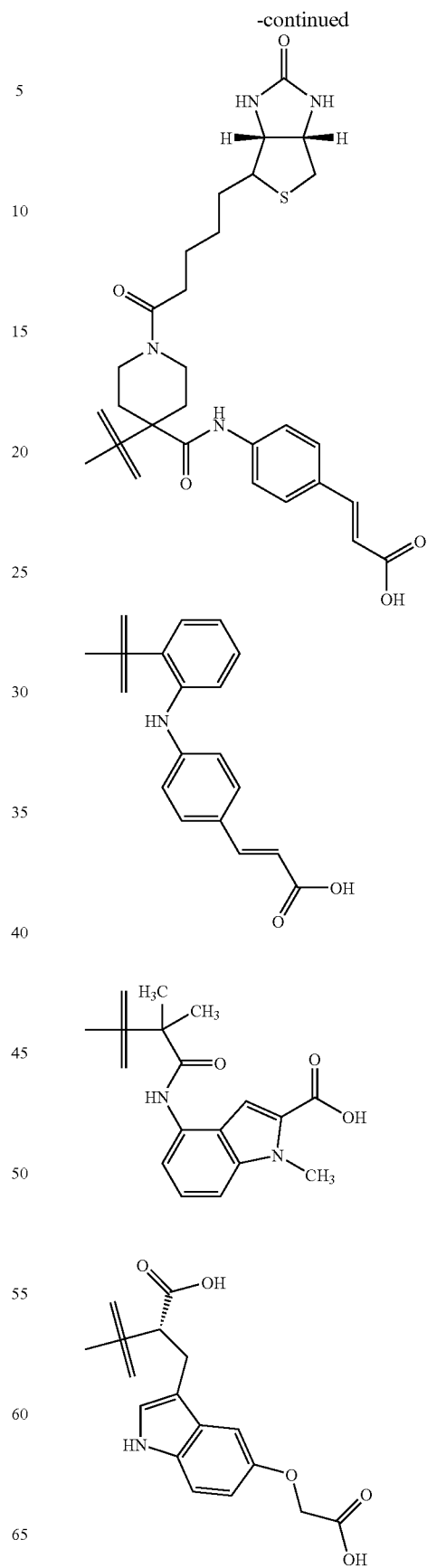

131
-continued
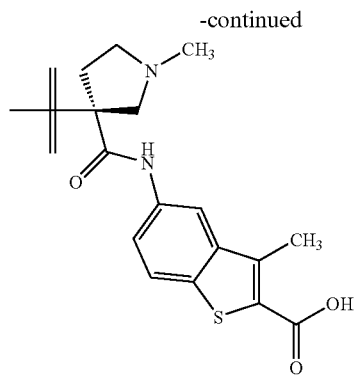
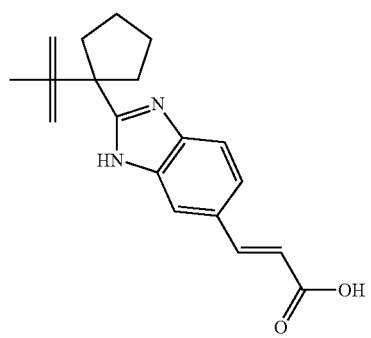
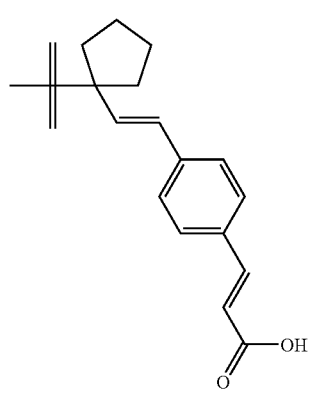
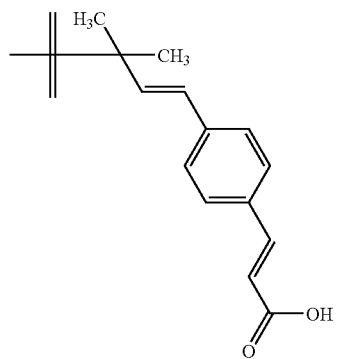
132
-continued
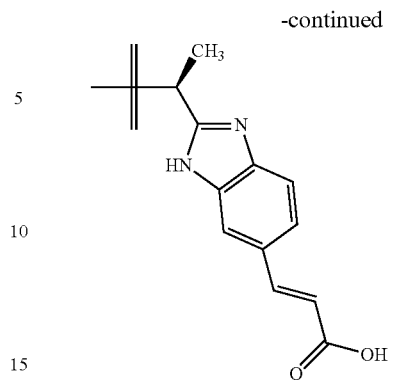
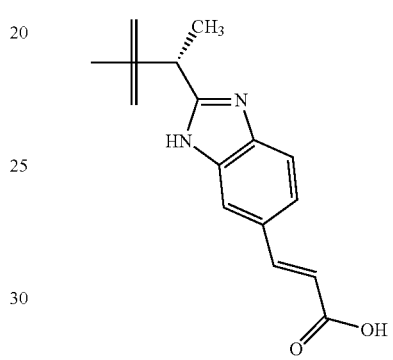
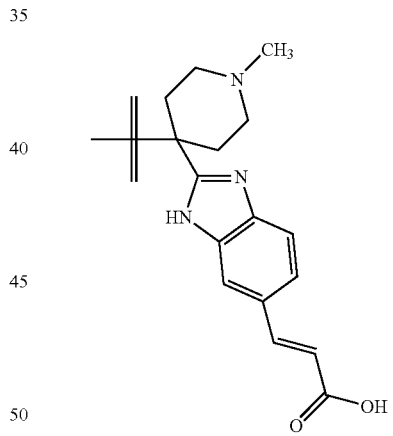
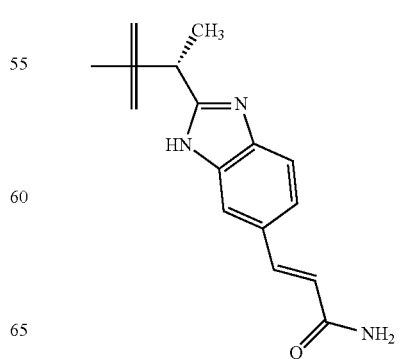

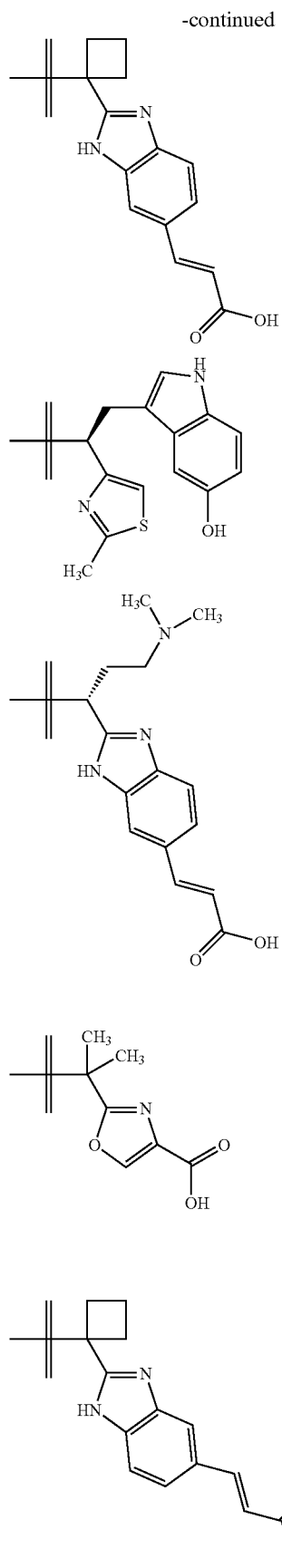
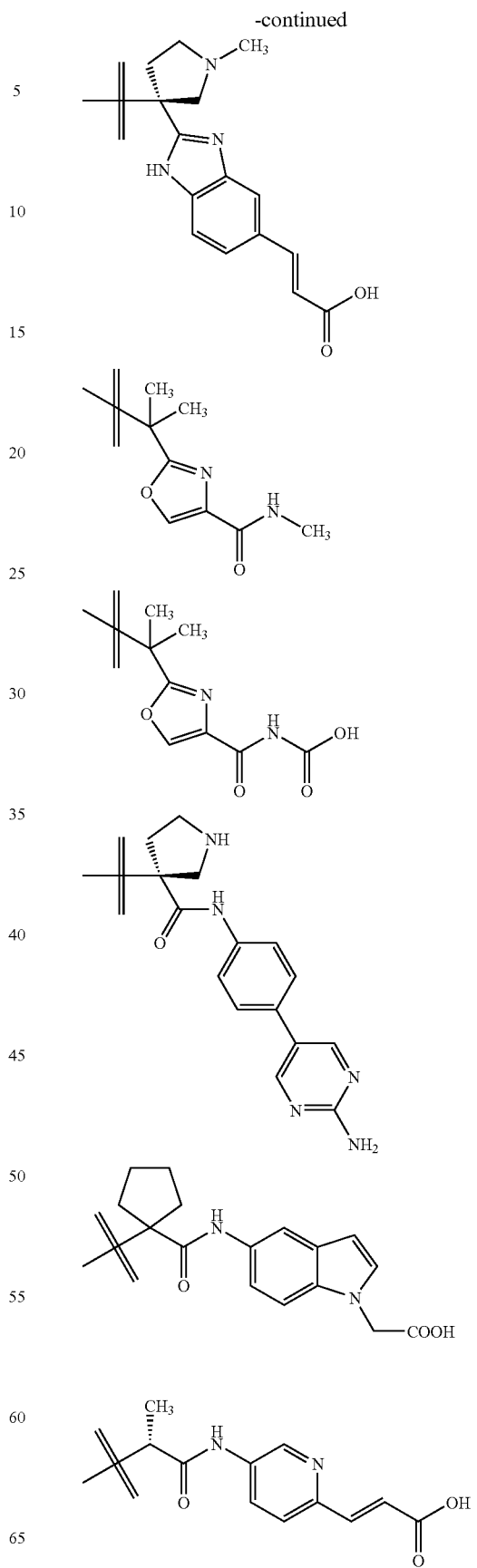

-continued
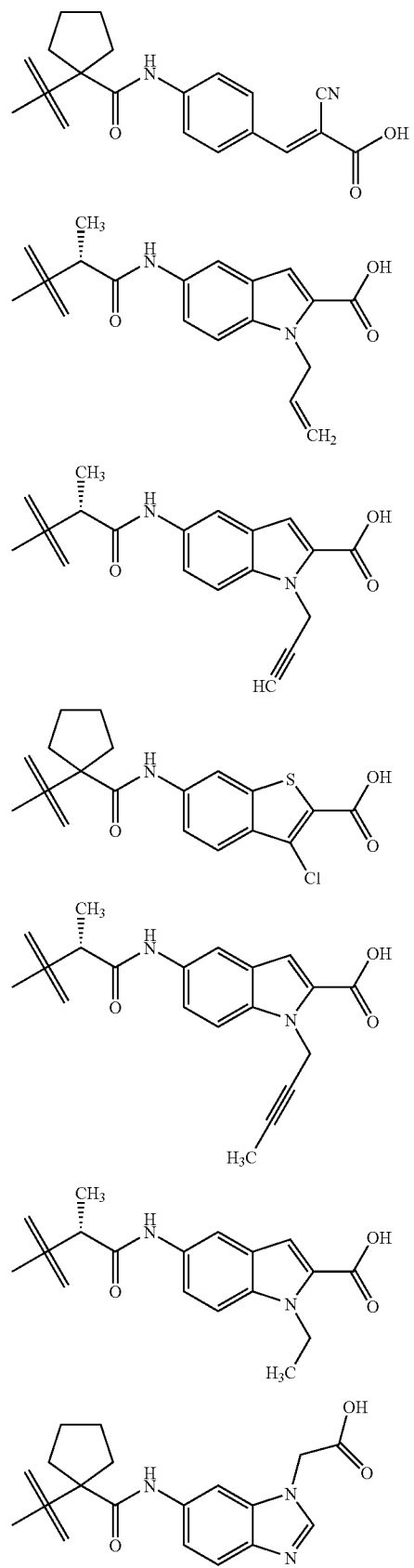
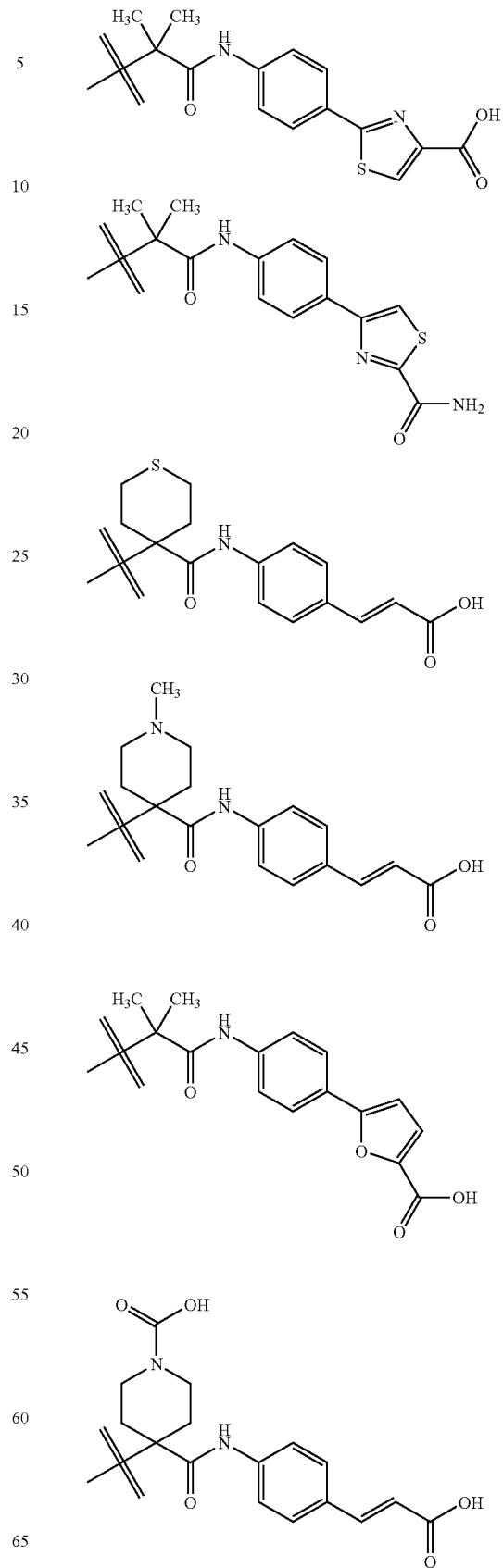

-continued
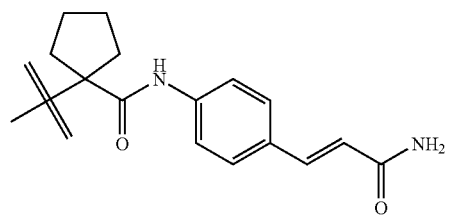
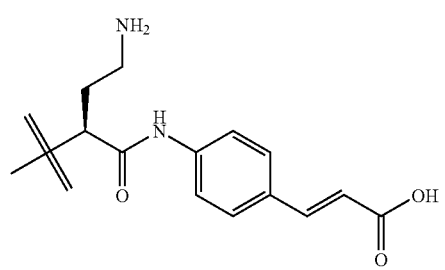
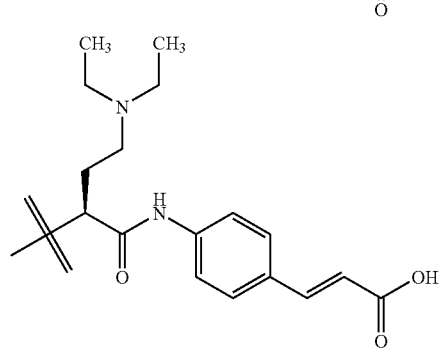
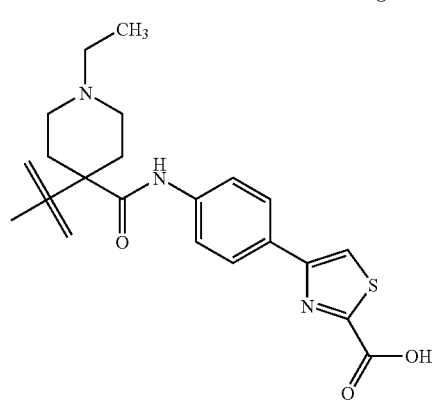
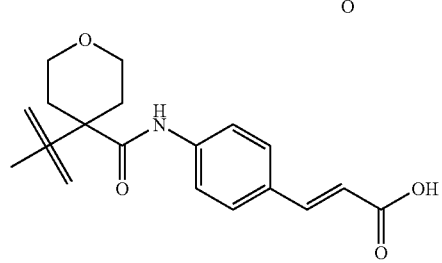
-continued
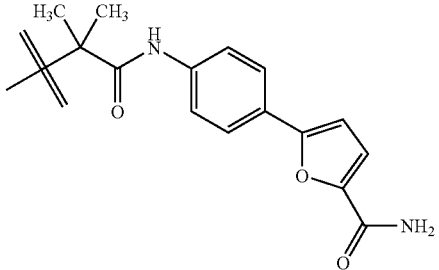
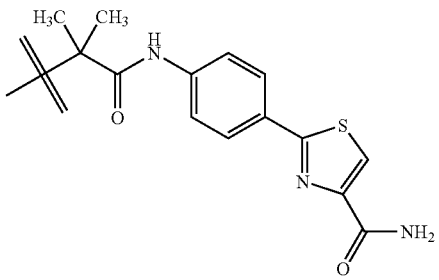
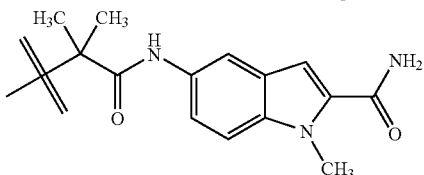
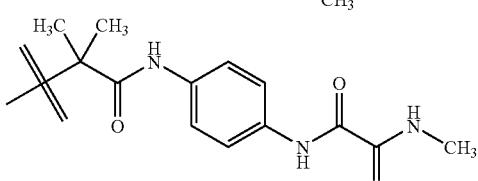
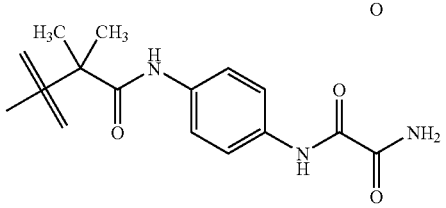
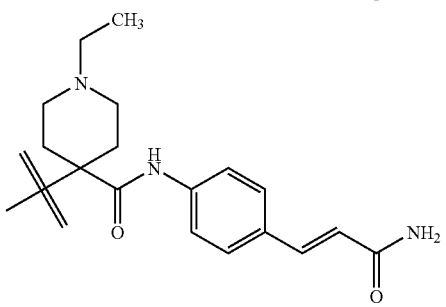
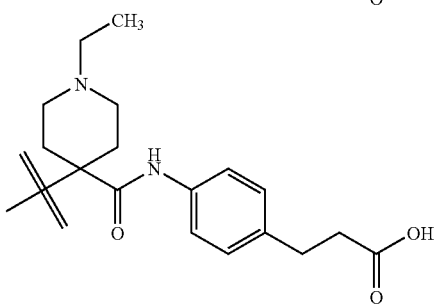

139
-continued
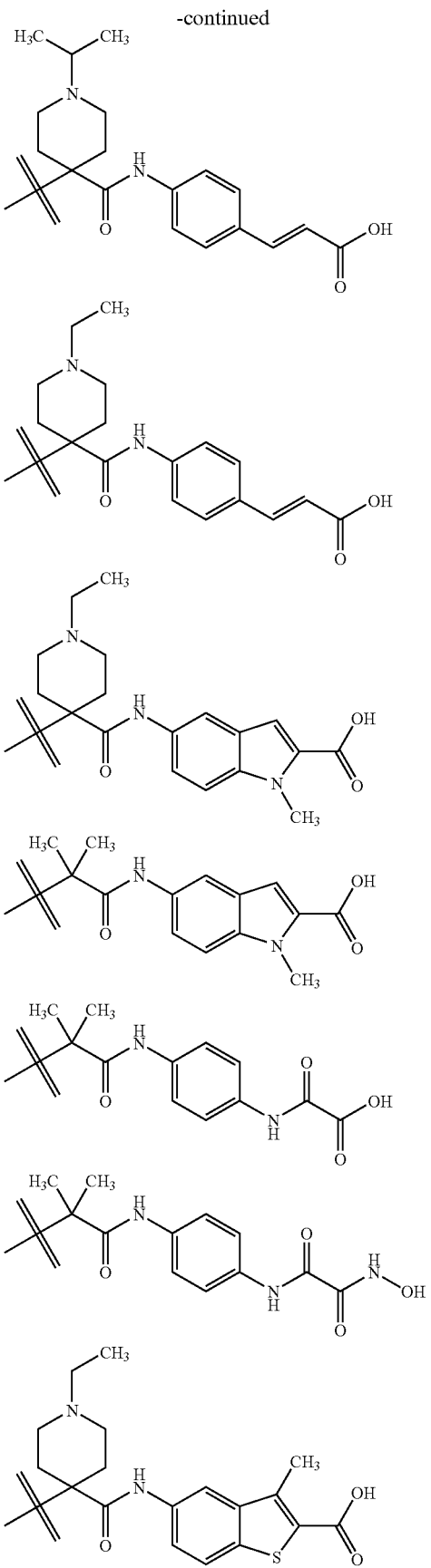
140
-continued
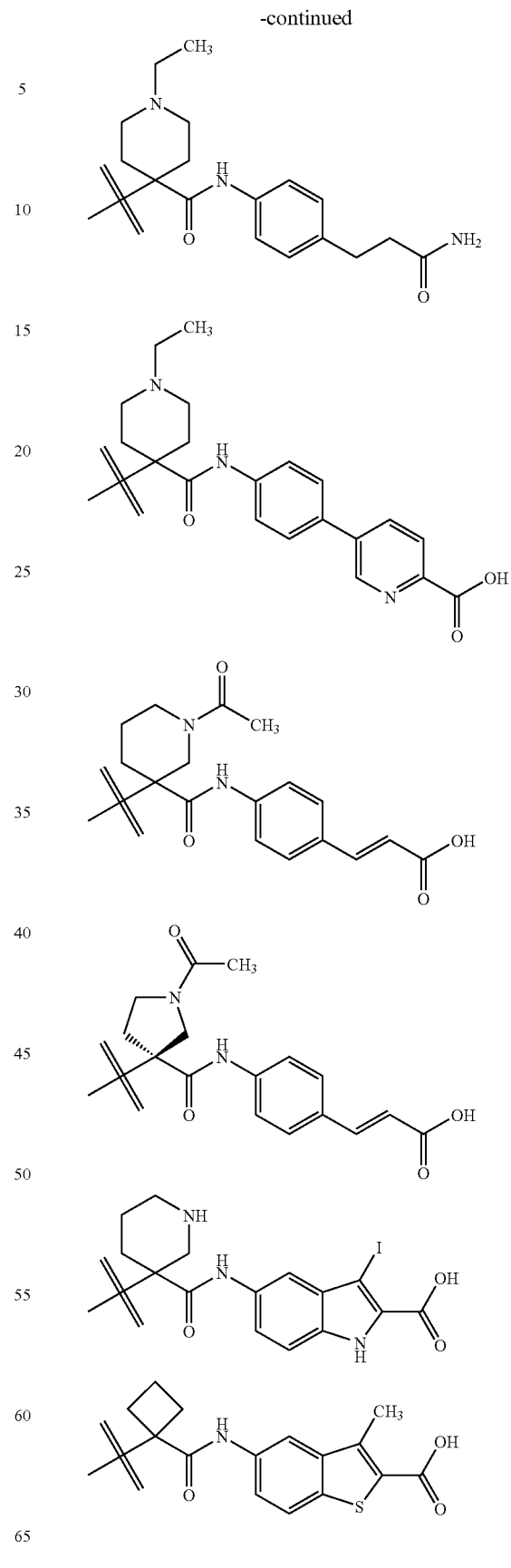

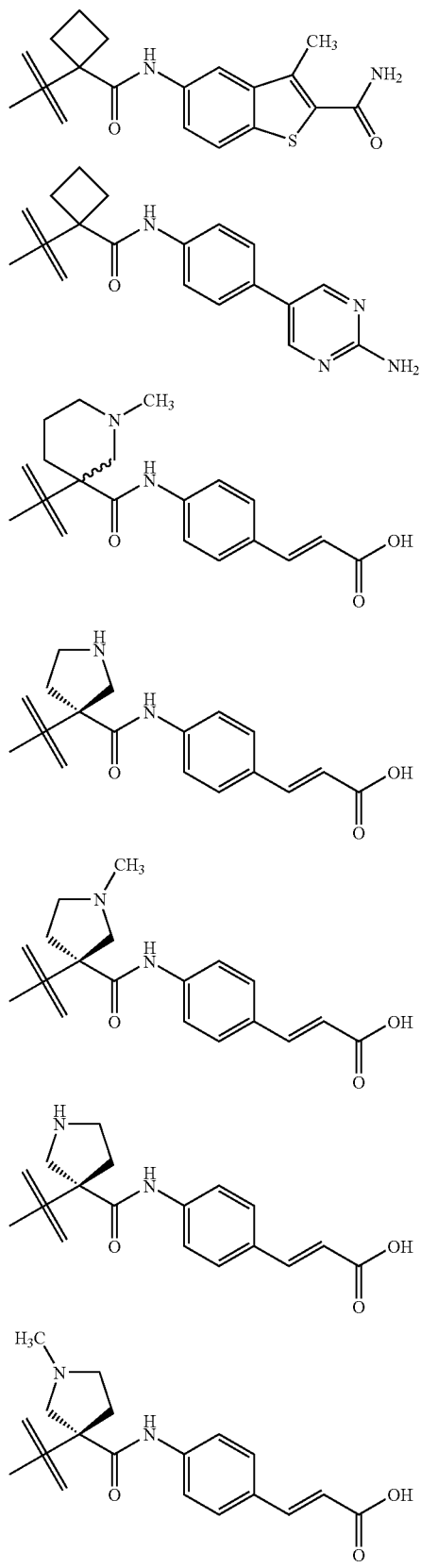
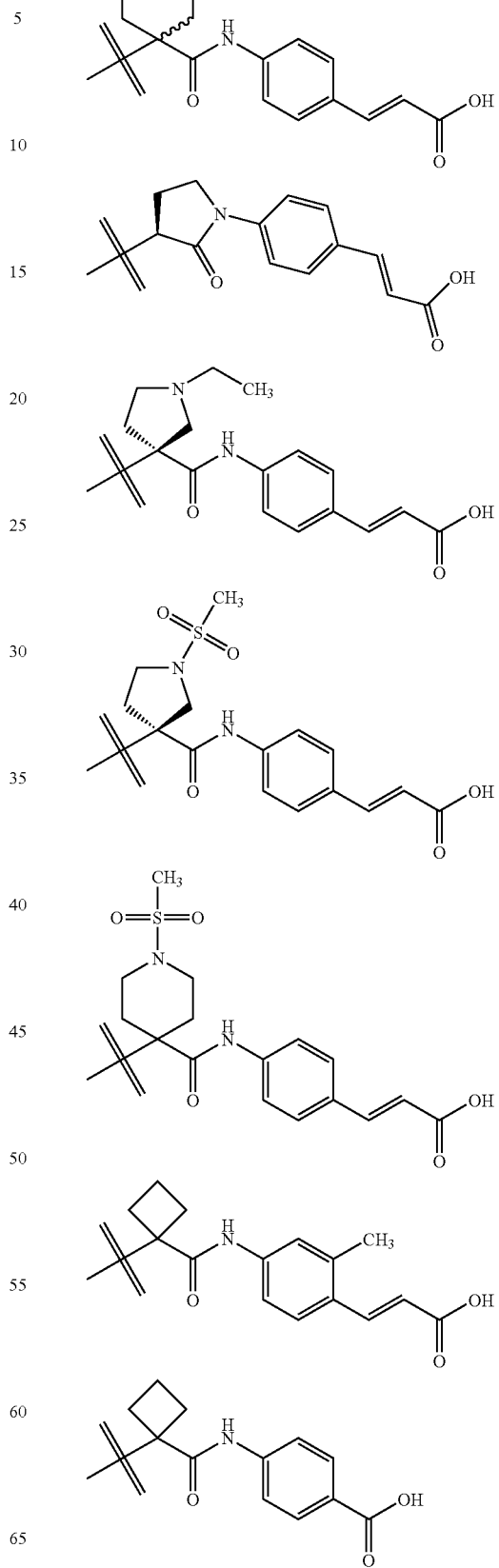

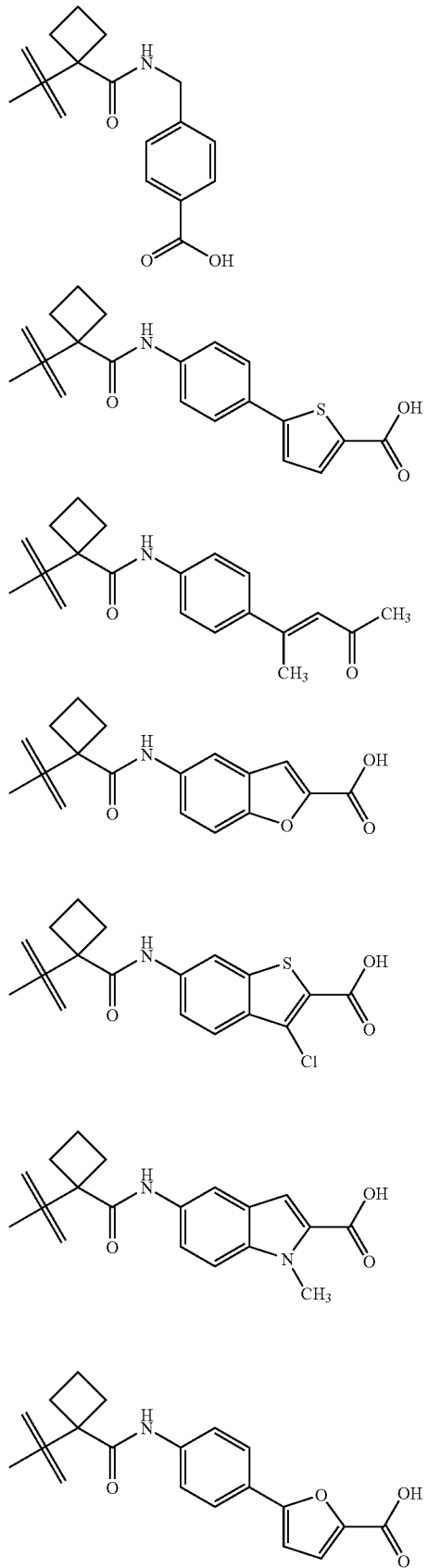
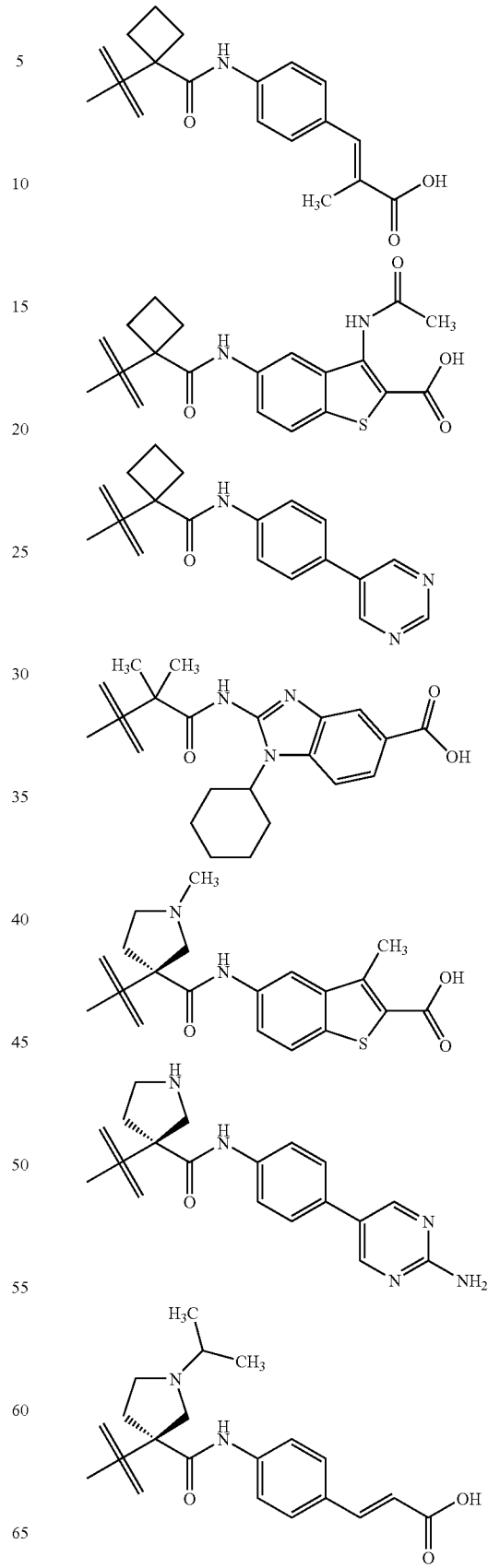

-continued
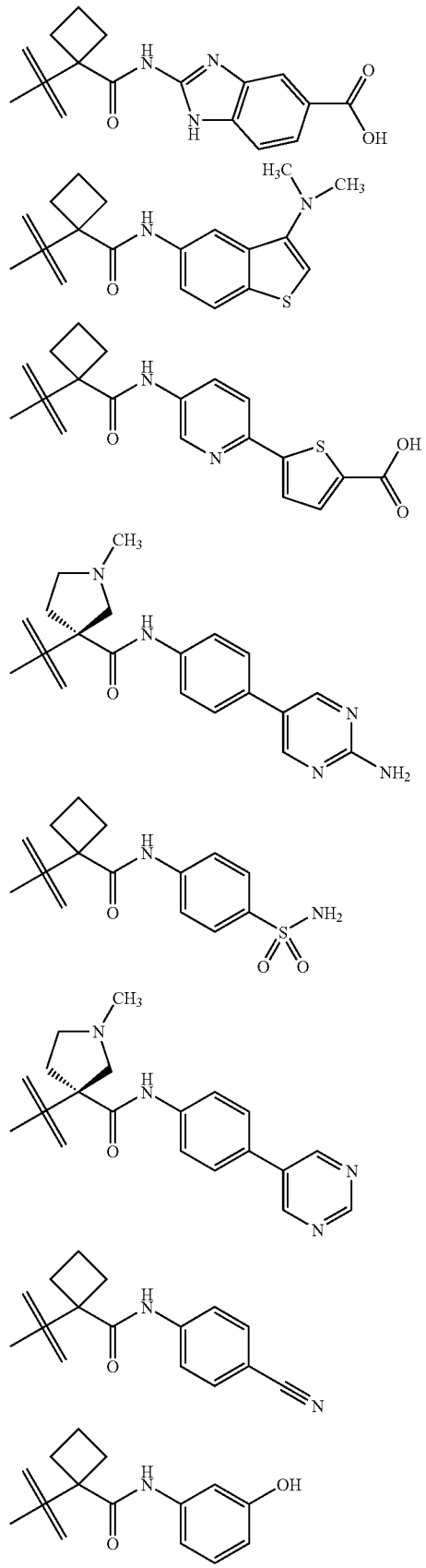
-continued
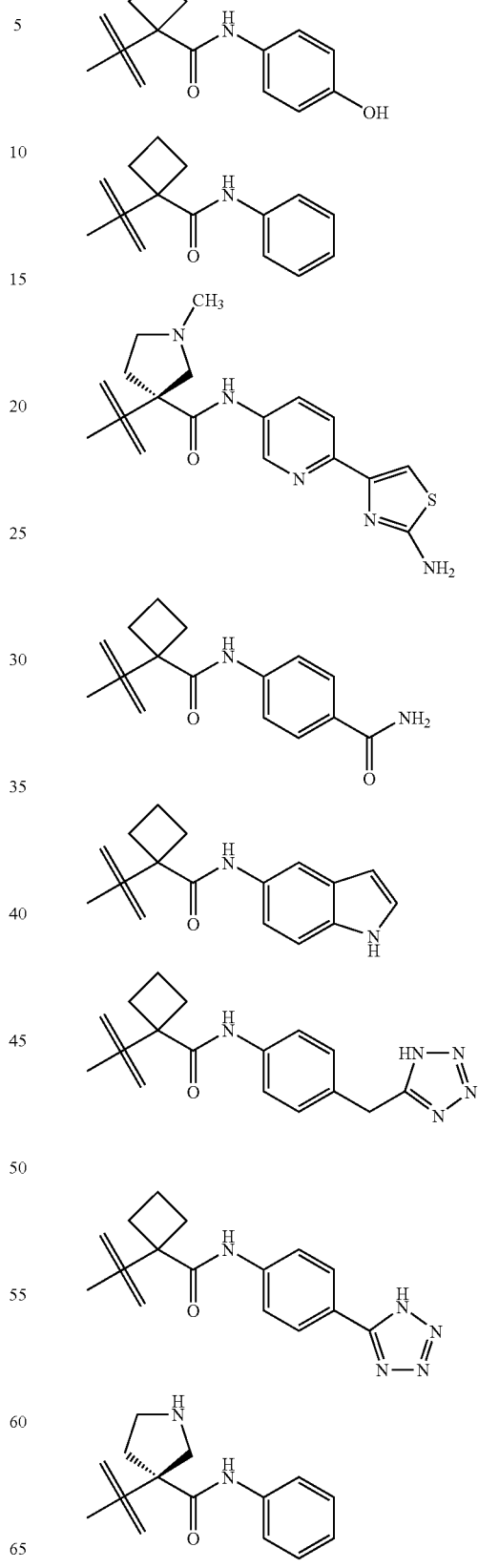

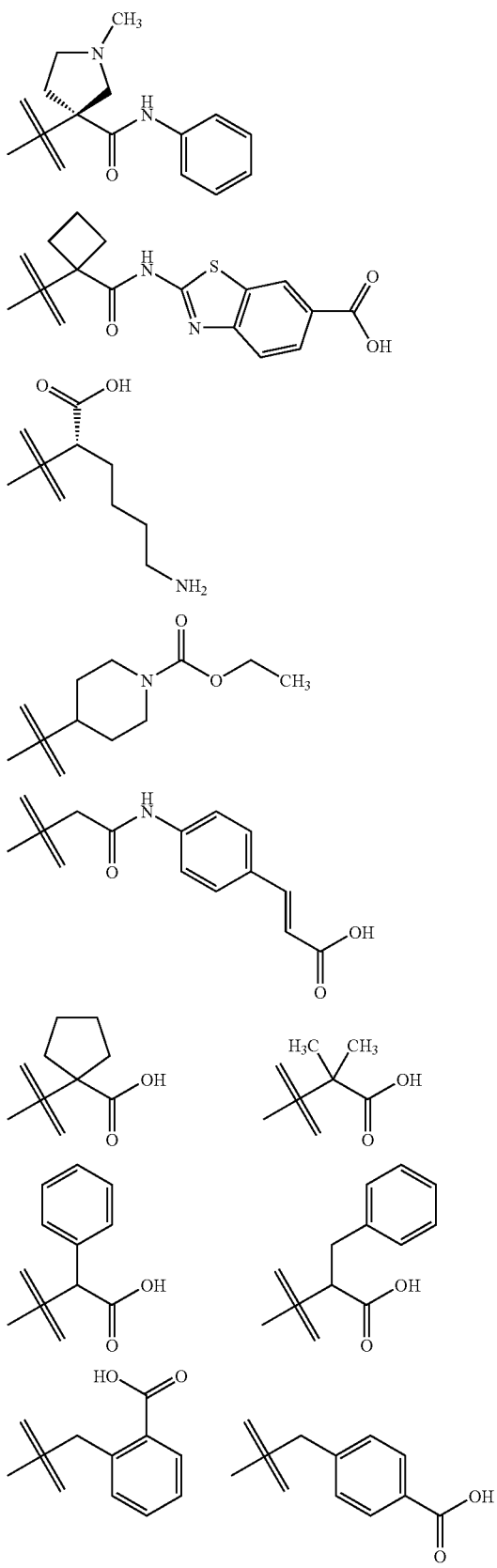
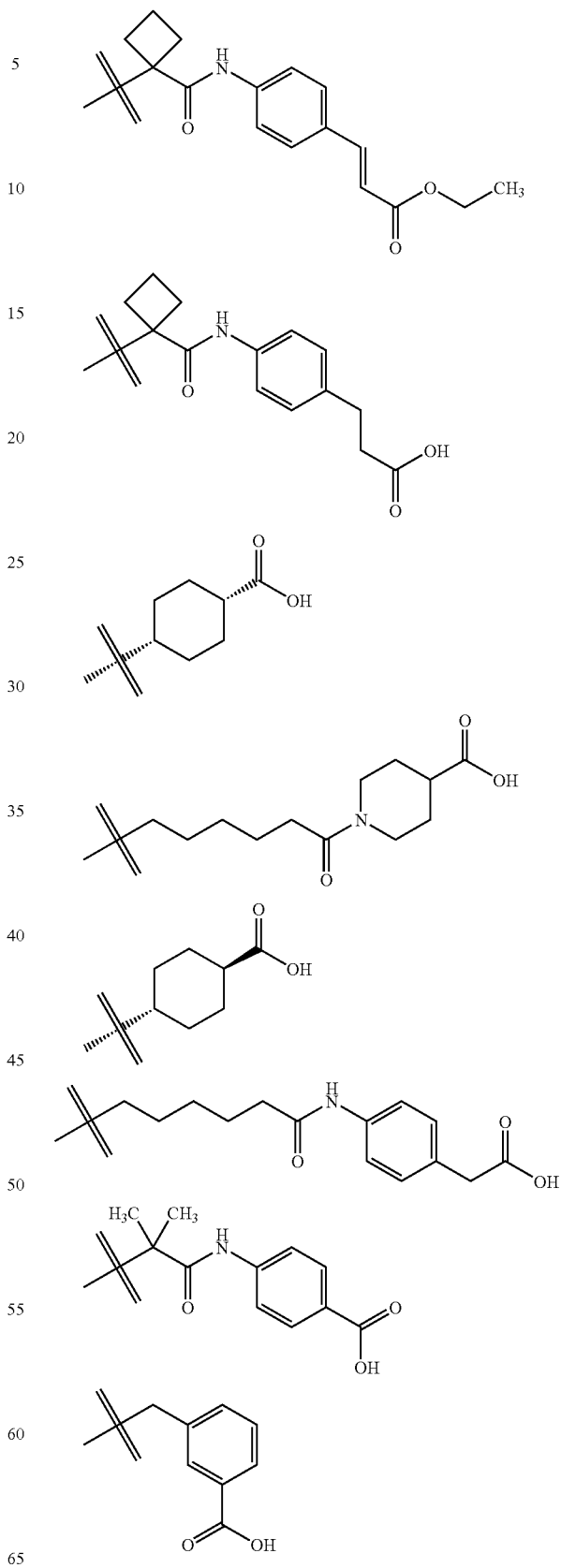

-continued
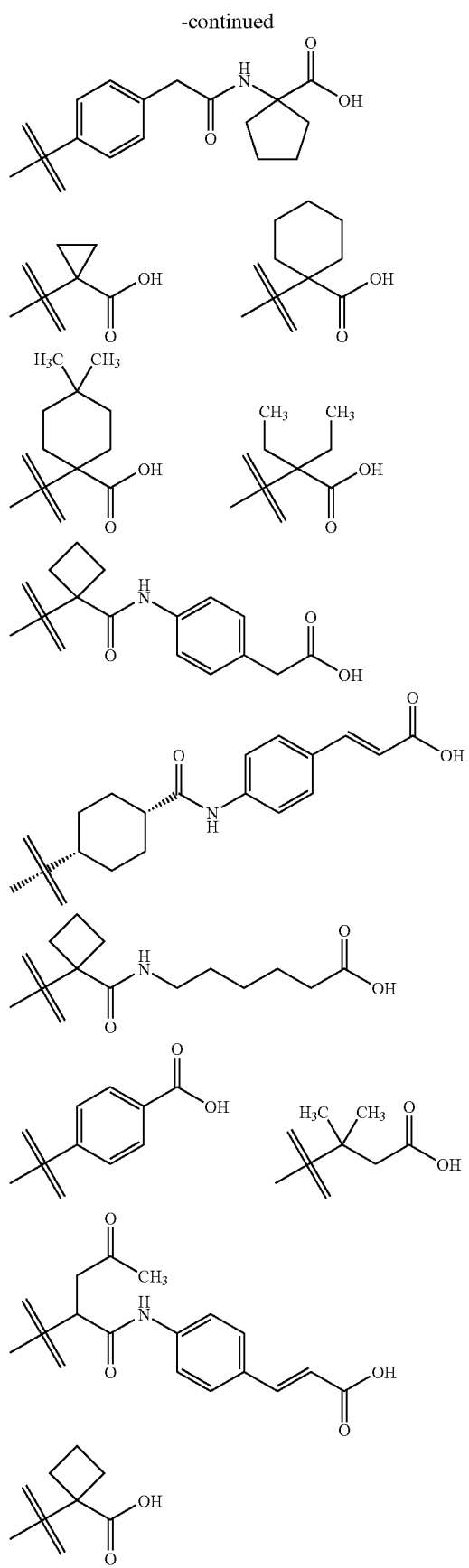
-continued
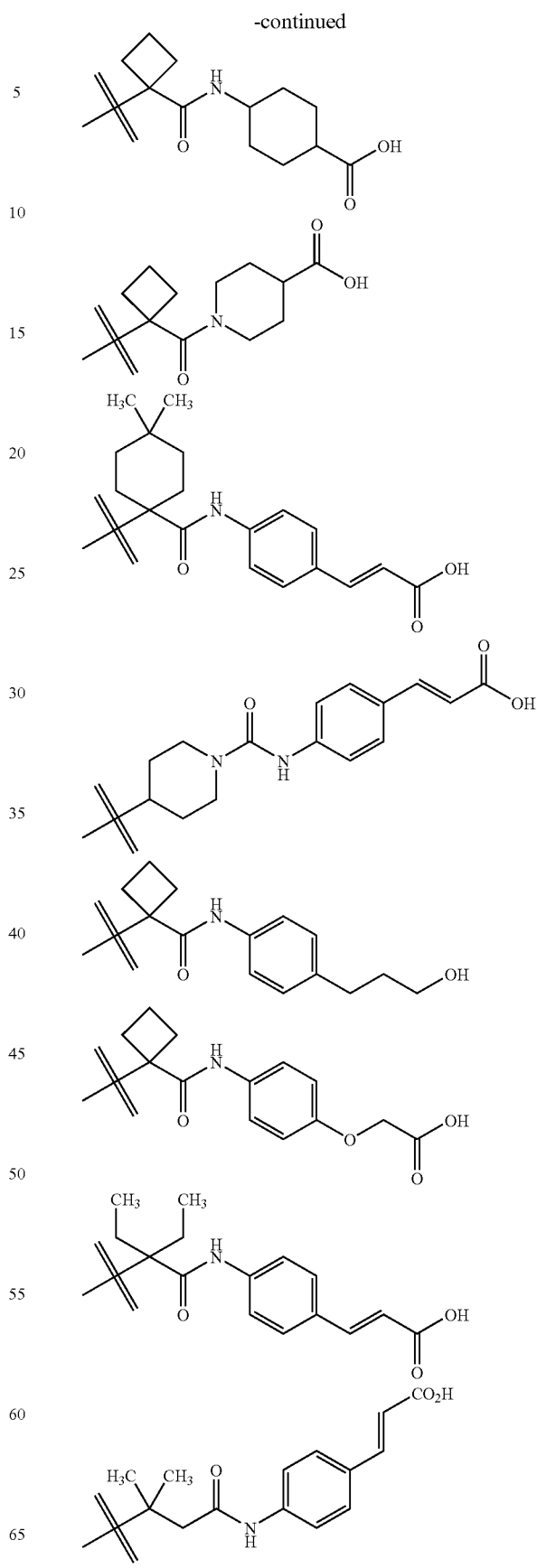

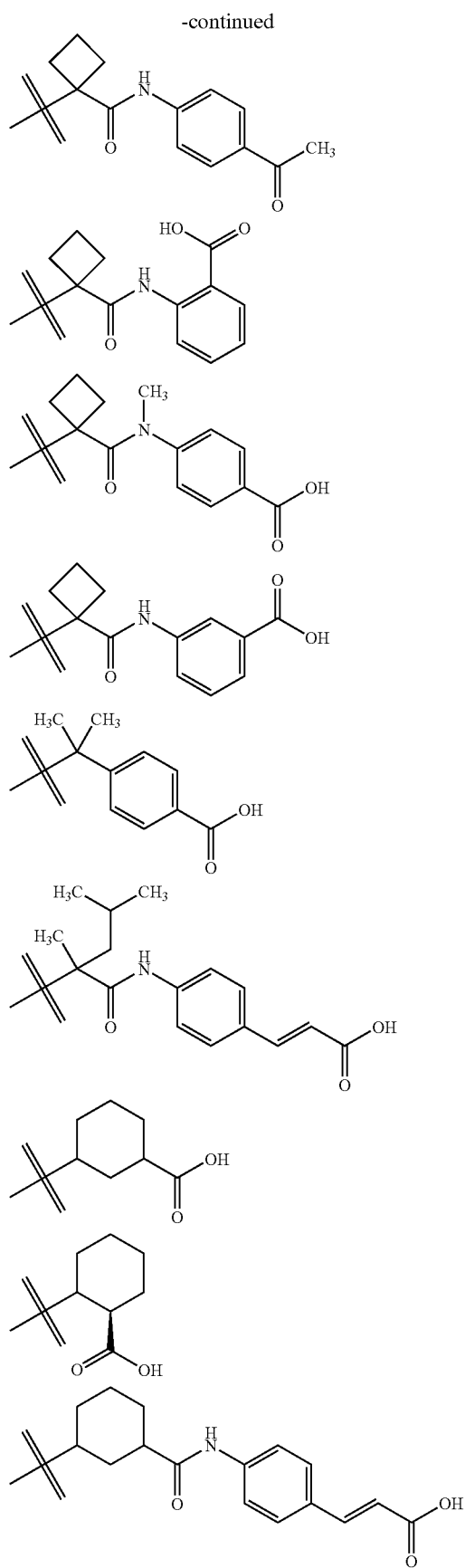
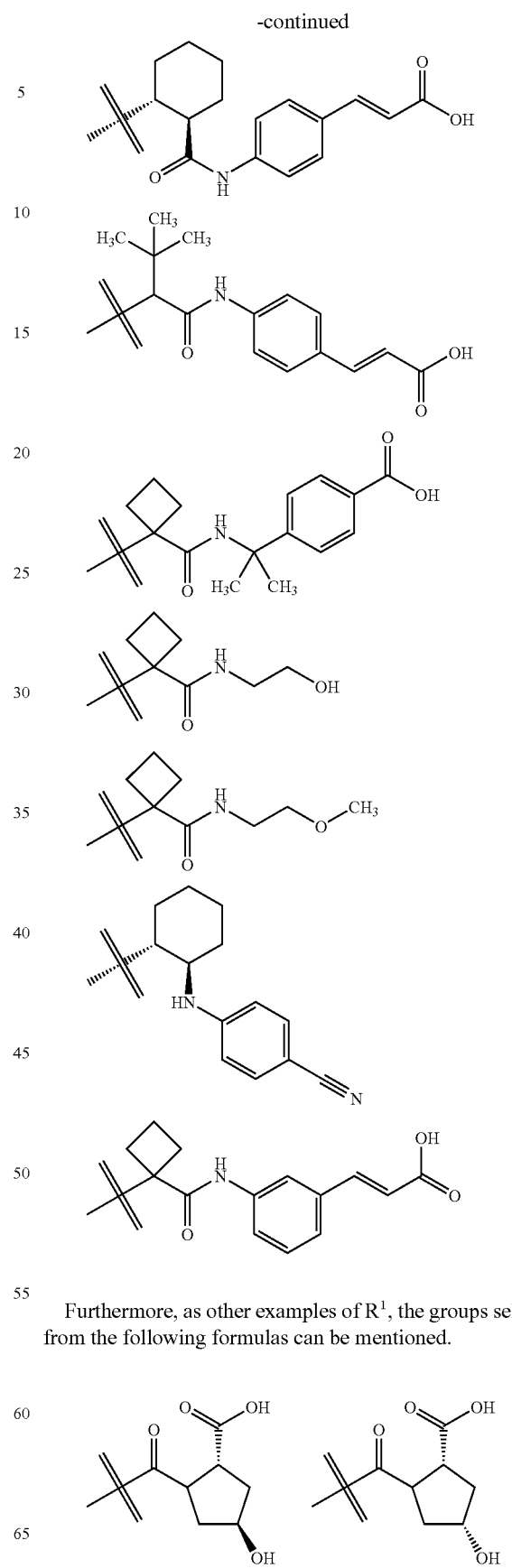
Furthermore, as other examples of R¹, the groups selected from the following formulas can be mentioned.
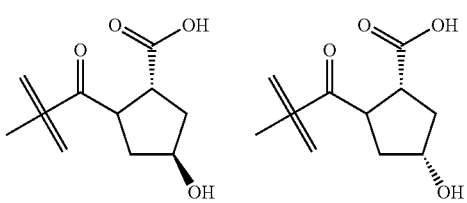

-continued

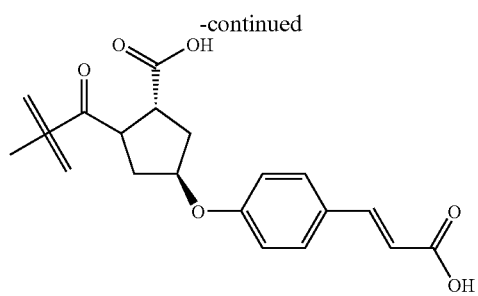
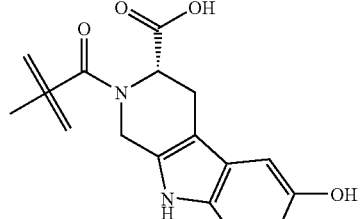
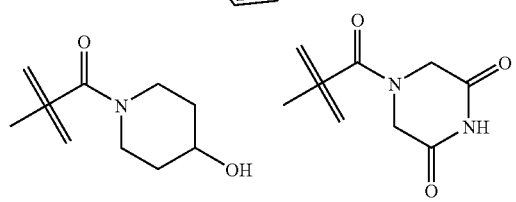
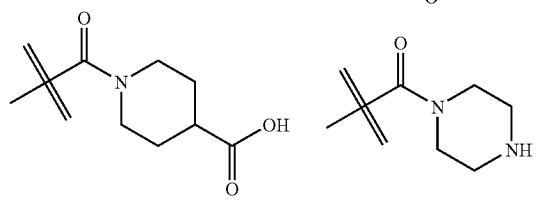
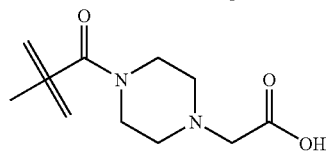
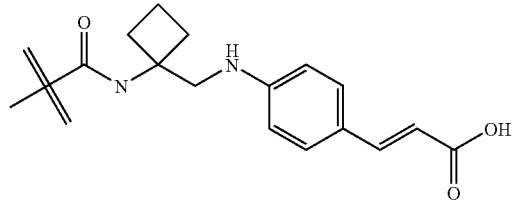
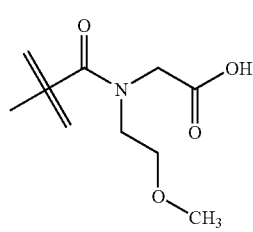

-continued

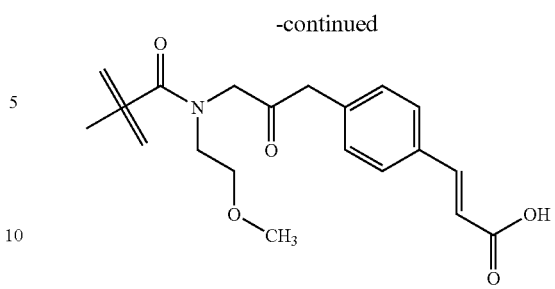
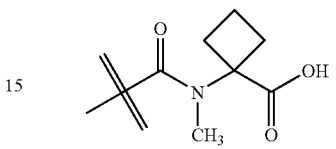

As preferable examples of $R^1$, carboxyl group, methoxycarbonyl group, carbamoyl group,

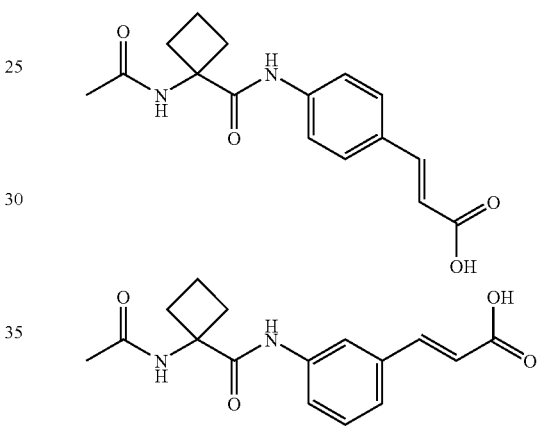

and the like can be mentioned.

For $R^2$, preferred are a hydrogen atom, "a group selected from group E", "a $C_{1-6}$ alkyl group optionally substituted by 1 to 3 substituents selected from group E",

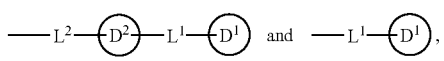

more preferred are a hydrogen atom, "a $C_{1-6}$ alkyl group optionally substituted by 1 to 3 substituents selected from group E" and

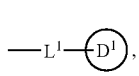

particularly preferably,

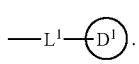

Preferably, $L^1$ and $L^2$ are each independently a bond, $C_{1-6}$ alkylene, —$(CH_2)_{u1}$—$NR^{L1}$—$(CH_2)_{v1}$—, —$(CH_2)_{u1}$—

CO—(CH$_2$)$_{v1}$— or —(CH$_2$)$_{u1}$—CONR$^{L2}$—(CH$_2$)$_{v1}$—, more preferably C$_{1-6}$ alkylene or —(CH$_2$)$_{u1}$—CO—(CH$_2$)$_{v1}$—, particularly preferably C$_{1-6}$ alkylene.

Preferably, u1 and v1 are each independently 0 or an integer of 1 to 3, more preferably 0 or 1, particularly preferably u1 is 1 and v1 is 0.

For R$^{L1}$, preferred is a hydrogen atom, and preferably, ring D$^1$ and ring D$^2$ are each independently "a C$_{6-14}$ aryl group optionally substituted by 1 to 5 substituents selected from group E" or "a heterocyclic group optionally substituted by 1 to 5 substituents selected from group E".

As the "C$_{6-14}$ aryl group" of the "C$_{6-14}$ aryl group optionally substituted by 1 to 5 substituents selected from group E" for ring D$^1$ and ring D$^2$, preferred is a phenyl group.

As the "heterocyclic group" of the "heterocyclic group optionally substituted by 1 to 5 substituents selected from group E" for ring D$^1$ and ring D$^2$, preferred are pyrrolidinyl group, 2-oxopyrrolidinyl group, pyridyl group, piperidyl group, piperazinyl group, morpholinyl group, thiomorpholinyl group, 1,1-dioxomorpholinyl group, azepanyl group, 1,4-diazepanyl group, 1,4-oxazepanyl group and azocanyl group, more preferably, piperidyl group, piperazinyl group, 1,4-oxazepanyl group and azocanyl group.

As the group E in R$^2$, preferred is "—COOR$^{e5}$", when group E is a substituent on ring D$^1$ and ring D$^2$, it may be "a C$_{1-6}$ alkyl group optionally substituted by 1 to 3 substituents selected from group A".

With regard to group E in R$^2$, preferred for R$^{e5}$ is a hydrogen atom or a C$_{1-6}$ alkyl group, when group E is a substituent on ring D$^1$ or ring D$^2$, "a C$_{1-6}$ alkyl group optionally substituted by 1 to 3 substituents selected from group A" is preferably a C$_{1-6}$ alkyl group optionally substituted by "—OR$^{e1}$", more preferably a C$_{1-6}$ alkyl group optionally substituted by a C$_{1-6}$ alkoxy group.

For R$^2$, hydrogen atom, phenylsulfonyl group, benzyloxycarbonyl group, dimethylcarbamoyl group, acetyl group, allyl group, methyl group, ethyl group, isopropyl group, cyclohexyl group, 2,2,2-trifluoroethyl group, cyanomethyl group, nitromethyl group, 2-(2-methoxyethoxy)ethyl group, pivaloylmethyl group, ethoxycarbonylmethyl group, 3-(3-methylureido)propyl group, 2-(methylcarbamoyloxy)ethyl group, 2-(methylsulfanyl)ethyl group, 2-(methanesulfonyl)ethyl group, 2-(methylsulfamoyl)ethyl group, 2-hydroxy-2-methylpropyl group, methanesulfonylcarbamoylmethyl group, 3-(dimethylamino)-2-hydroxypropyl group, carbamoylmethyl group, methylcarbamoylmethyl group, isopropylcarbamoylmethyl group, dimethylcarbamoylmethyl group, 2-(dimethylcarbamoyl)ethyl group, 3-(dimethylcarbamoyl)propyl group, isobutylcarbamoylmethyl group, (1-ethylpropyl)carbamoylmethyl group, tert-butylcarbamoylmethyl group, (2,2-dimethylpropyl)carbamoylmethyl group, (3,3-dimethylbutyl)carbamoylmethyl group, (2,2,2-trifluoroethyl)carbamoylmethyl group, methoxycarbamoylmethyl group, 2-methoxyethylcarbamoylmethyl group, 3-methoxypropylcarbamoylmethyl group, 2-(methylsulfanyl)ethylcarbamoylmethyl group, carboxymethylcarbamoylmethyl group, 2-carboxyethylcarbamoylmethyl group, 3-carboxypropylcarbamoylmethyl group, carbamoylmethylcarbamoylmethyl group, 2-(dimethylamino)ethylcarbamoylmethyl group, N-[2-(dimethylamino)ethyl]-N-methylcarbamoylmethyl group, N-(2-methoxyethyl)-N-methylcarbanoylmethyl group, 3-(dimethylamino)propylcarbamoylmethyl group, 2-(acetylamino)ethylcarbamoylmethyl group, 2-hydroxyethyl group, 3-hydroxypropyl group, 2-methoxyethyl group, 2-(dimethylamino)ethyl group, carboxymethyl group, 2-(acetylamino)ethyl group, 3-(acetylamino)propyl group, 2-(methanesulfonylamino)ethyl group, 3-(methanesulfonylamino)propyl group, 2-[N-(methanesulfonyl)-N-methylamino]ethyl group, 3-(acetylsulfamoyl)propyl group, 2-(3-methyl-2-butenyloxy)ethyl group, 2-(2-methoxyethoxy)ethylcarbamoylmethyl group, 2-(tetrahydropyran-2-yloxy)ethyl group, 2-(4-methylphenoxy)ethyl group, 3-(4-chlorophenylamino)propyl group, 2-(4-methylthiazol-2-ylamino)ethyl group, cyclopropylcarbamoylmethyl group, cyclobutylcarbamoylmethyl group, cyclopentylcarbamoylmethyl group, cyclohexylcarbamoylmethyl group, phenylcarbamoylmethyl group, benzylcarbamoylmethyl group, phenethylcarbamoylmethyl group, N-benzyl-N-methylcarbamoylmethyl group, 3-phenylpropylcarbamoylmethyl group, 4-phenylbutylcarbamoylmethyl group, 2-(3-chlorobenzyloxy)ethyl group, 3-(4-methylbenzylsulfanyl)propyl group, 2-(phenylacetylamino)ethyl group, 2-pyridylmethylcarbamoylmethyl group, 3-pyridylmethylcarbamoylmethyl group, 4-pyridylmethylcarbamoylmethyl group, 2-(pyridin-2-yl)ethylcarbamoylmethyl group, 2-(pyridin-3-yl)ethylcarbamoylmethyl group, 2-(pyridin-4-yl)ethylcarbamoylmethyl group, N-methyl-N-(pyridin-2-ylmethyl)carbamoylmethyl group, N-methyl-N-[2-(pyridin-2-yl)ethyl]carbamoylmethyl group, 3-(imidazol-1-yl)propylcarbamoylmethyl group, benzoylmethyl group, 2-(2,4-dimethylthiazol-5-yl)-2-oxoethyl group, 2-(3-methylisoxazol-4-yl)-2-oxoethyl group, 2-oxo-2-(pyrrolidin-1-yl)ethyl group, 2-(3-methoxypyrrolidin-1-yl)-2-oxoethyl group, 2-(2-carboxypyrrolidin-1-yl)-2-oxoethyl group, 2-(2-carbamoylpyrrolidin-1-yl)-2-oxoethyl group, 2-oxo-2-piperidinoethyl group, 2-morpholino-2-oxoethyl group, 2-(4-methylpiperidin-1-yl)-2-oxoethyl group, 2-(4-ethylpiperidin-1-yl)-2-oxoethyl group, 2-(3-methoxypiperidin-1-yl)-2-oxoethyl group, 2-(4-hydroxypiperidin-1-yl)-2-oxoethyl group, 2-(4-methoxypiperidin-1-yl)-2-oxoethyl group, 2-[4-(tert-butoxycarbonylamino)piperidin-1-yl]-2-oxoethyl group, 2-[4-(dimethylamino)piperidin-1-yl]-2-oxoethyl group, 2-oxo-2-(4-oxopiperidin-1-yl)ethyl group, 2-(4-methylpiperazin-1-yl)-2-oxoethyl group, 2-(4-ethylpiperazin-1-yl)-2-oxoethyl group, 2-(4-isopropylpiperazin-1-yl)-2-oxoethyl group, 2-(4-phenylpiperazin-1-yl)-2-oxoethyl group, 2-(4-acetylpiperazin-1-yl)-2-oxoethyl group, 2-(4-carboxypiperazin-1-yl)-2-oxoethyl group, 2-(4-ethoxycarbonylpiperazin-1-yl)-2-oxoethyl group, 2-[4-(tert-butoxycarbonyl)piperazin-1-yl]-2-oxoethyl group, 2-(4-methanesulfonylpiperazin-1-yl)-2-oxoethyl group, 2-oxo-2-(thiomorpholin-4-yl)ethyl group, 2-oxo-2-(1-oxothiomorpholin-4-yl)ethyl group, 2-(1,1-dioxothiomorpholin-4-yl)-2-oxoethyl group, 2-(azepan-1-yl)-2-oxoethyl group, 2-(1,4-oxazepan-4-yl)-2-oxoethyl group, 2-(4-methyl-1,4-diazepan-1-yl)-2-oxoethyl group, 4-morpholino-4-oxobutyl group, 4-(4-ethylpiperazin-1-yl)-4-oxobutyl group, 2-(thiophen-2-ylcarbonylamino)ethyl group, 2-piperidinoethylcarbamoylmethyl group, 2-morpholinoethylcarbamoylmethyl group, 2-(1-methylpyrrolidin-2-yl)ethylcarbamoylmethyl group, 3-(2-oxopyrrolidin-1-yl)propylcarbamoylmethyl group and 2-(1-benzylpiperidin-4-yl)ethylcarbamoylmethyl group can be specifically mentioned.

As specific examples of R$^2$, moreover, benzyl group, phenethyl group, 3-phenylpropyl group, 2-methoxybenzyl group, 2-(dimethylamino)benzyl group, 3-methoxybenzyl group, 3-(dimethylamino)benzyl group, 3-phenoxybenzyl group, 4-fluorobenzyl group, 4-chlorobenzyl group, 4-methylbenzyl group, 4-hydroxybenzyl group, 4-methoxybenzyl group, 4-cyanobenzyl group, 4-(dimethylamino)benzyl group, 4-(methylcarbamoyl)benzyl group, 4-methanesulfonylbenzyl group, 2-pyridylmethyl group, 3-pyridylmethyl group, 4-pyridylmethyl group, 6-aminopyridin-3-ylmethyl group, 6-acetylaminopyridin-3-ylmethyl group, 2-(pyrrolidin-1-yl)

ethyl group, 2-(2-oxopyrrolidin-1-yl)ethyl group, 2-piperidinoethyl group, 2-(piperazin-1-yl)ethyl group, 2-(4-methylpiperidin-1-yl)ethyl group, 2-(4-ethylpiperidin-1-yl)ethyl group, 2-(1-ethylpiperidin-4-yl)ethyl group, 2-(4-hydroxypiperidin-1-yl)ethyl group, 2-(4-methoxypiperidin-1-yl)ethyl group, 2-(4-phenoxypiperidin-1-yl)ethyl group, 2-[4-(dimethylamino)piperidin-1-yl]ethyl group, 2-(1-acetylpiperidin-4-yl)ethyl group, 2-[1-(tert-butoxycarbonyl)piperidin-4-yl]ethyl group, 2-(1-methanesulfonylpiperidin-4-yl)ethyl group, 2-(4-methylpiperazin-1-yl)ethyl group, 2-(4-ethylpiperazin-1-yl)ethyl group, 2-(4-isopropylpiperazin-1-yl)ethyl group, 2-(4-phenylpiperazin-1-yl)ethyl group, 2-[4-(tert-butoxycarbonyl)piperazin-1-yl]ethyl group, 2-(4-benzoylpiperazin-1-yl)ethyl group, 2-(4-dimethylcarbamoylpiperazin-1-yl)ethyl group, 2-(4-methanesulfonylpiperazin-1-yl)ethyl group, 2-morpholinoethyl group, 2-(thiomorpholin-4-yl)ethyl group, 2-(azepan-1-yl)ethyl group, 2-(1,4-oxazepan-4-yl)ethyl group, 2-(4-methyl-1,4-diazepan-1-yl)ethyl group, 3-morpholinopropyl group, 4-morpholinobutyl group, 1-methylimidazol-2-ylmethyl group, 4-tert-butylthiazol-2-ylmethyl group, 2-methylthiazol-4-ylmethyl group, 3,5-dimethylisoxazol-4-ylmethyl group, 5-methylisoxazol-3-ylmethyl group, [1,2,4]oxadiazol-3-ylmethyl group, 4,4-dimethyl-4,5-dihydrooxazol-2-ylmethyl group, 4-methyl-4H-[1,2,4]triazol-3-ylmethyl group, 1-methyl-1H-tetrazol-5-ylmethyl group, 2-methylpyrimidin-5-ylmethyl group, 5-methylthiophen-2-ylmethyl group, 2,5-dimethyloxazol-4-ylmethyl group, 5-methyl-4-methylcarbamoyloxazol-2-ylmethyl group, 2-methoxymethyl-5-methyloxazol-4-ylmethyl group, 2-(2-dimethylaminothiazol-4-yl)ethyl group, 2-phenyl-4-methylthiazol-5-ylmethyl group, 5-(dimethylaminomethyl)-[1,2,4]oxadiazol-3-ylmethyl group, 5-(acetylaminomethyl)-[1,2,4]oxadiazol-3-ylmethyl group, 2-(dimethylcarbamoylmethyl)-2H-tetrazol-5-ylmethyl group, 1-methylindol-3-ylmethyl group, phenylpyridin-2-ylmethyl group, benzhydrylcarbamoylmethyl group, 4-styrylbenzyl group, 2-(2-morpholino-2-oxoethoxy)ethyl group, 2-oxo-2-[4-(piperidinoacetyl)piperazino)ethyl group, 2-oxo-2-[4-(pyrrolidin-1-yl)piperidin-1-yl]ethyl group, 2-(2-phenoxyethylamino)ethyl group, 4-(morpholinocarbonyl)benzyl group, 3-(3-morpholinophenyl)propyl group, 3-ethynyloxybenzyl group, 2-(N-[3-(dimethylaminoacetylamino)benzyl]-N-methylamino}ethyl group, 2-(dibenzylamino)ethylcarbamoylmethyl group, 4-(2-dibenzylaminomethyl)cyclohexylmethyl group, 2-(morpholinoacetylamino)ethoxycarbonylmethyl group, 3-{1-[2-(2-methoxyethoxy)phenylacetyl)piperidin-4-ylmethylcarbamoyl}benzyl group, 2-(2-morpholinoethoxy)-5-{N-methyl-N-[4-(4-nitrophenylsulfonyl)benzoyl]amino}benzyl group, 2-[N-(2-pyridylmethyl)amino]ethyl group and 2-[N-(2-methoxyethyl)-N-methylaminolethyl group can be mentioned.

As specific examples of $R^2$,
3-oxo-3-piperidinopropyl group,
3-morpholino-3-oxopropyl group,
3-(4-methylpiperazin-1-yl)-3-oxopropyl group,
3-(4-ethylpiperazin-1-yl)-3-oxopropyl group,
3-(4-acetylpiperazin-1-yl)-3-oxopropyl group,
3-(4-methanesblfonylpiperazin-1-yl)-3-oxopropyl group,
3-(4-methoxypiperazin-1-yl)-3-oxopropyl group,
3-(4-methoxycarbonylpiperazin-1-yl)-3-oxopropyl group,
3-piperidinopropyl group,
3-(4-methylpiperazin-1-yl)propyl group,
3-(4-ethylpiperazin-1-yl)propyl group,
3-(4-acetylpiperazin-1-yl)propyl group,
3-(4-methanesulfonylpiperazin-1-yl)propyl group,
3-(4-methoxypiperazin-1-yl)propyl group,
3-(4-methoxycarbonylpiperazin-1-yl)propyl group,
(tetrahydropyran-4-yl)methyl group,
2-(tetrahydropyran-4-yl)ethyl group,
(1-methylpiperidin-4-yl)methyl group,
(1-ethylpiperidin-4-yl)methyl group,
(1-acetylpiperidin-4-yl)methyl group,
(1-methanesulfonylpiperidin-4-yl)methyl group,
(1-methoxypiperidin-4-yl)methyl group,
(1-methoxycarbonylpiperidin-4-yl)methyl group,
2-(tetrahydropyran-3-yl)ethyl group,
2-(1-methylpiperidin-3-yl)ethyl group,
2-(1-ethylpiperidin-3-yl)ethyl group,
2-(1-acetylpiperidin-3-yl)ethyl group,
2-(1-methanesulfonylpiperidin-3-yl)ethyl group,
2-(1-methoxypiperidin-3-yl)ethyl group,
2-(1-methoxycarbonylpiperidin-3-yl)ethyl group,
(tetrahydropyran-3-yl)methyl group,
(1-methylpiperidin-3-yl)methyl group,
(1-ethylpiperidin-3-yl)methyl group,
(1-acetylpiperidin-3-yl)methyl group,
(1-methanesulfonylpiperidin-3-yl)methyl group,
(1-methoxypiperidin-3-yl)methyl group,
(1-methoxycarbonylpiperidin-3-yl)methyl group,
2-(tetrahydropyran-2-yl)ethyl group,
2-(1-methylpiperidin-2-yl)ethyl group,
2-(1-ethylpiperidin-2-yl)ethyl group,
2-(1-acetylpiperidin-2-yl)ethyl group,
2-(1-methanesulfonylpiperidin-2-yl)ethyl group,
2-(1-methoxypiperidin-2-yl)ethyl group,
2-(1-methoxycarbonylpiperidin-2-yl)ethyl group,
(tetrahydropyran-2-yl)methyl group,
(1-methylpiperidin-2-yl)methyl group,
(1-ethylpiperidin-2-yl)methyl group,
(1-acetylpiperidin-2-yl)methyl group,
(1-methanesulfonylpiperidin-2-yl)methyl group,
(1-methoxypiperidin-2-yl)methyl group,
(1-methoxycarbonylpiperidin-2-yl)methyl group,
2-(2-oxopiperidin-1-yl)ethyl group,
2-(3-oxomorpholin-4-yl)ethyl group,
2-(4-methyl-2-oxopiperazin-1-yl)ethyl group,
2-(4-ethyl-2-oxopiperazin-1-yl)ethyl group,
2-(4-acetyl-2-oxopiperazin-1-yl)ethyl group,
2-(4-methanesulfonyl-2-oxopiperazin-1-yl)ethyl group,
2-(4-methoxy-2-oxopiperazin-1-yl)ethyl group,
3-(4-methoxycarbonyl-2-oxopiperazin-1-yl)ethyl group,
2-(4-ethylidenepiperidin-1-yl)ethyl group,
2-(4-methylenepiperidin-1-yl)ethyl group,
2-(4-isopropylidenepiperidin-1-yl)ethyl group,
2-(1-methylpiperidin-4-ylidene)ethyl group,
2-(1-ethylpiperidin-4-ylidene)ethyl group,
2-(1-acetylpiperidin-4-ylidene)ethyl group,
2-(1-methanesulfonylpiperidin-4-ylidene)ethyl group,
2-(1-methoxypiperidin-4-ylidene)ethyl group,
2-(1-methoxycarbonylpiperidin-4-ylidene)ethyl group,
2-cyclohexyloxyethyl group,
2-(tetrahydropyran-4-yloxy)ethyl group,
2-(1-methylpiperidin-4-yloxy)ethyl group,
2-(1-ethylpiperidin-4-yloxy)ethyl group,
2-(1-acetylpiperidin-4-yloxy)ethyl group,
2-(1-methaneplfonylpiperidin-4-yloxy)ethyl group,
2-(1-methoxypiperidin-4-yloxy)ethyl group,
2-(1-methoxycarbonylpiperidin-4-yloxy)ethyl group,
2-isopropoxyethyl group,
2-(2-thiazolyl)ethyl group,
2-(2-methylimidazol-1-yl)ethyl group,
2-(2-pyridyl)ethyl group,
2-(3-pyridyl)ethyl group, 2-(4-pyridyl)ethyl group,
2-(2-dimethylaminothiazol-4-yl)ethyl group,
(2-thiazolyl)methyl group,
(2-methylimidazol-1-yl)methyl group,
(2-pyridyl)methyl group,
(3-pyridyl)methyl group,
(4-pyridyl)methyl group,
(2-dimethylaminothiazol-4-yl)methyl group,
2-(4-ethyl-1,4-diazepan-1-yl)-2-oxoethyl group,
2-(3-hydroxypiperidin-1-yl)-2-oxoethyl group,
2-(3-methoxypiperidin-1-yl)-2-oxoethyl group,
2-(3-methylpiperidin-1-yl)-2-oxoethyl group,
2-(azocan-1-yl)-2-oxoethyl group,
2-(azonan-1-yl)-2-oxoethyl group,
2-oxo-2-(1,2,3,4-tetrahydroquinolin-1-yl)ethyl group,
2-oxo-2-(1,2,3,4-tetrahydroisoquinolin-2-yl)ethyl group,
2-(octahydrocyclopenta[c]pyrrol-2-yl)-2-oxoethyl group,
2-oxo-2-(4-trifluoromethylpiperidin-1-yl)ethyl group,
2-oxo-2-(4-propylpiperidin-1-yl)ethyl group,
2-(4-isopropylpiperidin-1-yl)-2-oxoethyl group,
2-(4,4-dimethylpiperidin-1-yl)-2-oxoethyl group,
2-oxo-2-(2,2,6,6-tetramethylpiperidin-1-yl)ethyl group,
2-oxo-2-(1,2,3,6-tetrahydropyridin-1-yl)ethyl group,
2-(isoindolin-2-yl)-2-oxoethyl group,
2-(octahydroisoindol-2-yl)-2-oxoethyl group,
1-adamantylcarbamoylmethyl group,
2-(2-methylpiperidin-1-yl)-2-oxoethyl group,
diethylcarbamoylmethyl group,
diisopropylcarbamoylmethyl group,
2-(4-ethyl-1,4-diazepan-1-yl)ethyl group,
2-(3-hydroxypiperidin-1-yl)ethyl group,
2-(3-methoxypiperidin-1-yl)ethyl group,
2-(3-methylpiperidin-1-yl)ethyl group,
2-[3-(2-methoxyethyl)piperidin-1-yl]ethyl group,
2-(azocan-1-yl)ethyl group,
2-(azonan-1-yl)ethyl group,
2-(1,2,3,4-tetrahydroquinolin-1-yl)ethyl group,
2-(1,2,3,4-tetrahydroisoquinolin-2-yl)ethyl group,
2-(octahydrocyclopenta[c]pyrrol-2-yl)ethyl group,
2-(4-trifluoromethylpiperidin-1-yl)ethyl group,
2-(4-propylpiperidin-1-yl)ethyl group,
2-(4-isopropylpiperidin-1-yl)ethyl group,
2-(4,4-dimethylpiperidin-1-yl)ethyl group,
2-(2,2,6,6-tetramethylpiperidin-1-yl)ethyl group,
2-(1,2,3,6-tetrahydropyridin-1-yl)ethyl group,
2-(isoindolin-2-yl)ethyl group,
2-(octahydroisoindol-2-yl)ethyl group,
2-(1-adamantylamino)ethyl group,
2-(2-methylpiperidin-1-yl)ethyl group,
2-(diethylamino)ethyl group,
2-(diisopropylamino)ethyl group,
2-(4-methoxycarbonylpiperazin-1-yl)-2-oxoethyl group,
2-(4-methylcarbamoylpiperazin-1-yl)-2-oxoethyl group,
2-[4-(2-methoxyacetyl)piperazin-1-yl]-2-oxoethyl group,
2-(4-cyclopentyloxycarbonylpiperazin-1-yl)-2-oxoethyl group,
2-(4-benzylpiperazin-1-yl)-2-oxoethyl group,
2-(4-isobutyrylpiperazin-1-yl)-2-oxoethyl group,
2-(4-methoxycarbonylpiperazin-1-yl)ethyl group,
2-(4-methylcarbamoylpiperazin-1-yl)ethyl group,
2-[4-(2-methoxyacetyl)piperazin-1-yl]ethyl group,
2-(4-cyclopentyloxycarbonylpiperazin-1-yl)ethyl group,
2-(4-benzylpiperazin-1-yl)ethyl group,
2-(4-isobutyrylpiperazin-1-yl)ethyl group,
methylcarbamoyl group,
tert-butylcarbamoyl group,
N-tert-butyl-N-methylcarbamoyl group,
cyclohexylcarbamoyl group,
(tetrahydropyran-4-yl)carbamoyl group,
(1-methylpiperidin-4-yl)carbamoyl group,
(1-acetylpiperidin-4-yl)carbamoyl group,
(1-methanesulfonylpiperidin-4-yl)carbamoyl group,
(1-methoxycarbonylpiperidin-4-yl)carbamoyl group,
cyclopentylcarbamoyl group,
(tetrahydrofuran-3-yl)carbamoyl group,
(1-methylpyrrolidin-3-yl)carbamoyl group,
(1-acetylpyrrolidin-3-yl)carbamoyl group,
(1-methanesulfonylpyrrolidin-3-yl)carbamoyl group,
(1-methoxycarbonylpyrrolidin-3-yl)carbamoyl group,
N-cyclohexyl-N-methylcarbamoyl group,
N-methyl-N-(tetrahydropyran-4-yl)carbamoyl group,
N-methyl-N-(1-methylpiperidin-4-yl)carbamoyl group,
N-(1-acetylpiperidin-4-yl)-N-methylcarbamoyl group,
N-(1-methanesulfonylpiperidin-4-yl)-N-methylcarbamoyl group,
N-(1-methoxycarbonylpiperidin-4-yl)-N-methylcarbamoyl group,
N-cyclopentyl-N-methylcarbamoyl group,
N-methyl-N-(tetrahydrofuran-3-yl)carbamoyl group,
N-methyl-N-(1-methylpyrrolidin-3-yl)carbamoyl group,
N-(1-acetylpyrrolidin-3-yl)-N-methylcarbamoyl group,
N-(1-methanesulfonylpyrrolidin-3-yl)-N-methylcarbamoyl group,
N-(1-methoxycarbonylpyrrolidin-3-yl)-N-methylcarbamoyl group,
2-(N-acetyl-N-methylamino)ethyl group,
2-(N-methyl-N-propionylamino)ethyl group,
2-(N-cyclohexanecarbonyl-N-methylamino)ethyl group,
2-[N-methyl-N-(tetrahydropyran-4-carbonyl)amino]ethyl group,
2-[N-methyl-N-(1-methylpiperidine-4-carbonyl)amino]ethyl group,
2-[N-(1-acetylpiperidine-4-carbonyl)-N-methylamino]ethyl group,
2-[N-(1-methanesulfonylpiperidine-4-carbonyl)-N-methylamino]ethyl group,
2-[N-(1-methoxycarbonylpiperidine-4-carbonyl)-N-methylamino]ethyl group,
2-(N-cyclopentanecarbonyl-N-methylamino)ethyl group,
2-[N-methyl-N-(tetrahydrofuran-3-carbonyl)amino]ethyl group,
2-[N-methyl-N-(1-methylpyrrolidine-3-carbonyl)amino]ethyl group,
2-[N-(1-acetylpyrrolidine-3-carbonyl)-N-methylamino)ethyl group,
2-[N-(1-methanesulfonylpyrrolidine-3-carbonyl)-N-methylamino]ethyl group,
2-[N-(1-methoxycarbonylpyrrolidine-3-carbonyl)-N-methylamino]ethyl group,
2-(N-methanesulfonyl-N-methylamino)ethyl group,
2-(N-methoxycarbonyl-N-methylamino)ethyl group,
2-(N-ethoxycarbonyl-N-methylamino)ethyl group,
2-(N-cyclohexyloxycarbonyl-N-methylamino)ethyl group,
2-[N-methyl-N-(tetrahydropyran-4-yloxycarbonyl)amino]ethyl group,
2-[N-methyl-N-(1-methylpiperidin-4-yloxycarbonyl)amino]ethyl group,
2-[N-(1-acetylpiperidin-4-yloxycarbonyl)-N-methylamino]ethyl group,
2-[N-(1-methanesulfonylpiperidin-4-yloxycarbonyl)-N-methylamino]ethyl group,
2-[N-(1-methoxycarbonylpiperidin-4-yloxycarbonyl)-N-methylamino]ethyl group,
2-(N-cyclopentyloxycarbonyl-N-methylamino)ethyl group, 2-[N-methyl-N-(tetrahydrofuran-3-yloxycarbonyl)amino]ethyl group,
2-[N-methyl-N-(1-methylpyrrolidin-3-yloxycarbonyl)amino]ethyl group,
2-[N-(1-acetylpyrrolidin-3-yloxycarbonyl)-N-methylamino]ethyl group,
2-[N-(1-methanesulfonylpyrrolidin-3-yloxycarbonyl)-N-methylamino]ethyl group, and
2-[N-(1-methoxycarbonylpyrrolidin-3-yloxycarbonyl)-N-methylamino]ethyl group can be mentioned.

For $R^2$, preferred are a hydrogen atom, 2-oxo-2-piperidinoethyl group, 2-piperidinoethyl group, 2-[4-(tert-butoxycarbonyl)piperazin-1-yl]-2-oxoethyl group, 2-[4-(tert-butoxycarbonyl)piperazin-1-yl]ethyl group, 2-(4-ethylpiperazin-1-yl)-2-oxoethyl group, 2-(azocan-1-yl)ethyl group, 2-(3-methylpiperidin-1-yl)ethyl group, 2-[3-(2-methoxyethyl)piperidin-1-yl]ethyl group, 2-(1,4-oxazepan-4-yl)ethyl group and the like.

For $R^3$, preferred are a hydrogen atom, a halogen atom, "a $C_{1-6}$ alkyl group optionally substituted by 1 to 3 substituents selected from group A" and —$OR^{101}$ (wherein $R^{101}$ is a hydrogen atom or a group selected from group C), and specifically, hydrogen atom, fluorine atom, chlorine atom, methyl group, methoxy group and the like can be mentioned, which is particularly preferably hydrogen atom.

Preferably, $R^5$ and $R^6$ are each independently a hydrogen atom, "a halogen atom", "a $C_{1-6}$ alkyl group optionally substituted by 1 to 3 substituents selected from group A" or "—$OR^{120}$", which is specifically hydrogen atom, fluorine atom, methyl group, ethyl group or trifluoromethyl group, more preferably hydrogen atom.

As another preferable embodiment of $R^5$ and $R^6$, a combination of —$NR^{121}R^{122}$ for $R^5$ and hydrogen atom for $R^6$ can be mentioned. $R^{121}$ and $R^{122}$ are preferably each independently heterocycle $C_{1-6}$ alkyl group optionally substituted by 1 to 5 substituents selected from group B. As the "heterocycle" moiety of the "heterocycle $C_{1-6}$ alkyl group optionally substituted by 1 to 5 substituents selected from group B", preferred are pyridyl group, pyrrolidinyl group, piperidyl group, piperazinyl group, morpholinyl group, thiomorpholinyl group, azepanyl group, azocanyl group, azonanyl group, tetrahydropyranyl group, 1,4-oxazepanyl group, 8-azaspiro[4.5]decanyl group, 1,2,3,4-tetrahydroisoquinolyl group and the like, and more preferred are piperidyl group and morpholinyl group. As the "$C_{1-6}$ alkyl" moiety of the "heterocycle $C_{1-6}$ alkyl group optionally substituted by 1 to 5 substituents selected from group B", preferred is ethyl group. As group B of the "heterocycle $C_{1-6}$ alkyl group optionally substituted by 1 to 5 substituents selected from group B", preferred are halogen atom, $C_{1-6}$ alkyl group, halogenated $C_{1-6}$ alkyl group and —$(CH_2)_r$—$OR^{b1}$ (wherein each symbol is as defined above).

For ring Cy, preferred are a $C_{3-10}$ cycloalkyl group and a $C_{3-10}$ cycloalkenyl group, more preferred are cyclohexyl group and cyclohexenyl group, particularly preferred is cyclohexyl group.

For X, preferred are a group selected from group D and

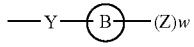

wherein each symbol is as defined above.

When X is a group selected from group D, preferred are hydrogen atom, halogen atom, "$C_{1-6}$ alkyl group optionally substituted by 1 to 3 substituents selected from group A" and "—$(CH_2)_t$—$OR^{d1}$", more preferred are hydrogen atom, halogen atom, "$C_{1-6}$ alkyl group optionally substituted by 1 to 3 substituents selected from group A" and "—$OR^{d1}$", further preferred are hydrogen atom, halogen atom, $C_{1-6}$ alkyl group and "—$OR^{d1}$". As $R^{d1}$ here, preferred are hydrogen atom and $C_{1-6}$ alkyl group optionally substituted by 1 to 3 substituents selected from group A, more preferred are hydrogen atom and $C_{1-6}$ alkyl group.

For Y, preferred is —$(CH_2)_m$—O—$(CH_2)_n$— (wherein each symbol is as defined above), more preferred are —O—$CH_2$— and —O—, still more preferred is —O—$CH_2$—.

For ring B, preferred are a $C_{6-14}$ aryl group and "a heterocyclic group comprising 1 to 4 heteroatoms selected from oxygen atom, nitrogen atom and sulfur atom", more preferred are phenyl group and piperidyl group, and still more preferred is phenyl group.

For Z, preferred are 1 to 3 substituents selected from
(1) a hydrogen atom,
(2) a heterocyclic group optionally substituted by 1 to 5 substituents selected from group D,
(3) —$(CH_2)_t$—$S(O)_q$—$R^{d2}$ and
(4) —$(CH_2)_t$—$COOR^{d5}$ wherein each symbol is as defined above.

The "heterocyclic group" of the "heterocyclic group optionally substituted by 1 to 5 substituents selected from group D" for Z is preferably pyrrolidinyl group, 2-oxopyrrolidinyl group, piperidinyl group, piperazinyl group or morpholinyl group, more preferably 2-oxopyrrolidinyl group, piperazinyl group or morpholinyl group.

When Z is "a heterocyclic group optionally substituted by 1 to 5 substituents selected from group D", the group D is preferably a hydrogen atom or "—$(CH_2)_t$—$S(O)_q$—$R^{d2}$".

With regard to group D in Z, for $R^{d2}$, preferred are a hydrogen atom and a $C_{1-6}$ alkyl group, for $R^{d5}$, preferred are a hydrogen atom and a $C_{1-6}$ alkyl group.

For w, preferred is 1 or 2, as r and t, preferred is 0, 1 or 2, particularly preferred is 0 or 1, further preferred is 0, as p, preferred is 1, as q, preferred is 0 or 2, and particularly preferred is 2.

X is specifically hydrogen atom, methyl group, ethyl group, isopropyl group, tert-butyl group, fluorine atom, chlorine atom, bromine atom, trifluoromethyl group, hydroxyl group, methoxy group, ethoxy group, methylsulfanyl group or the like.

As X,

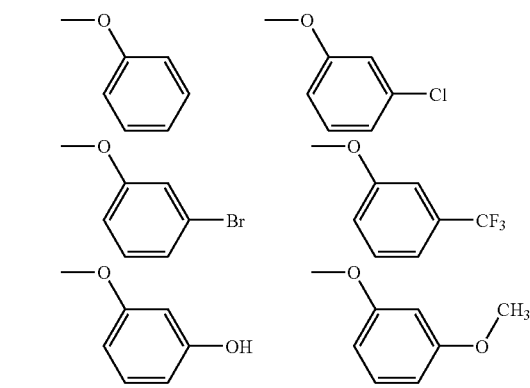

-continued
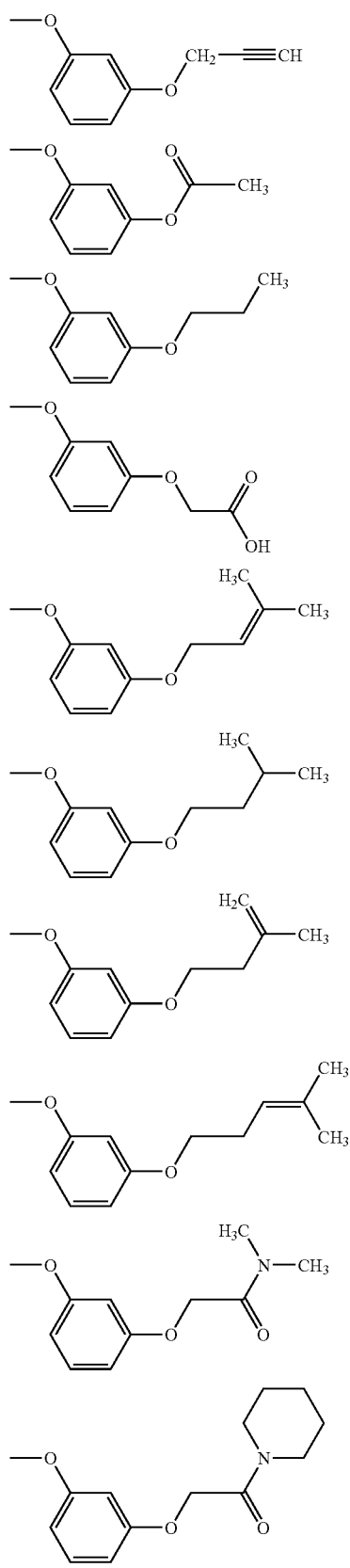
-continued
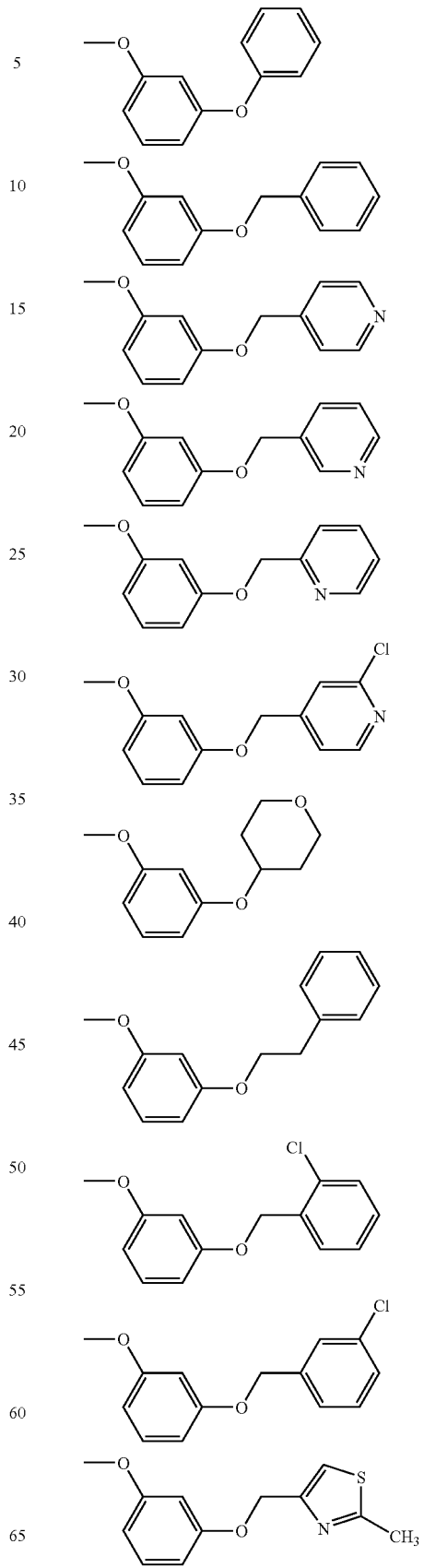

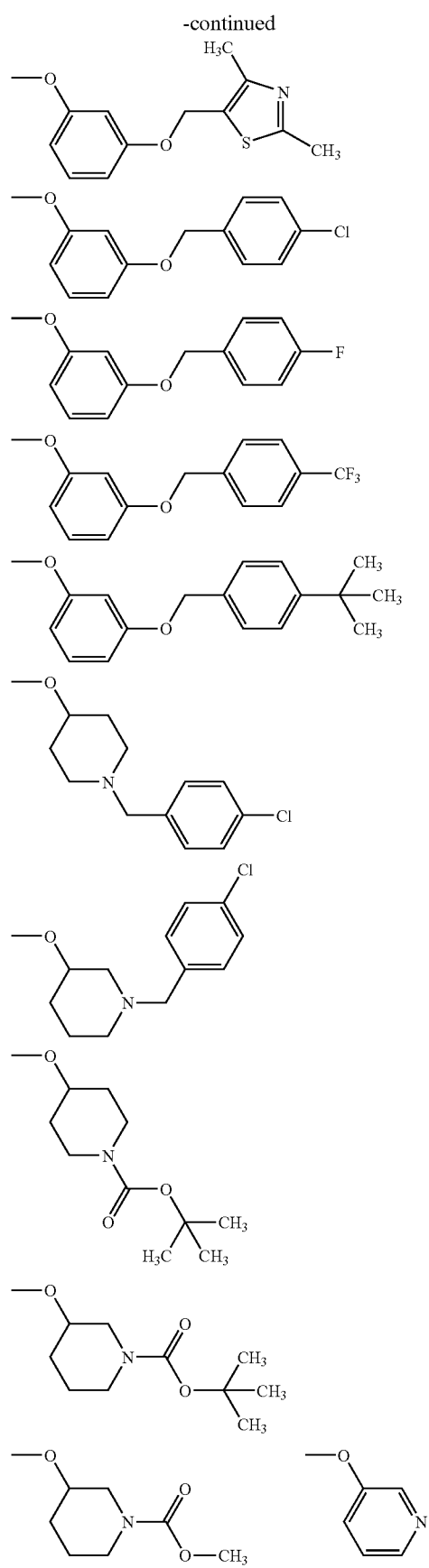
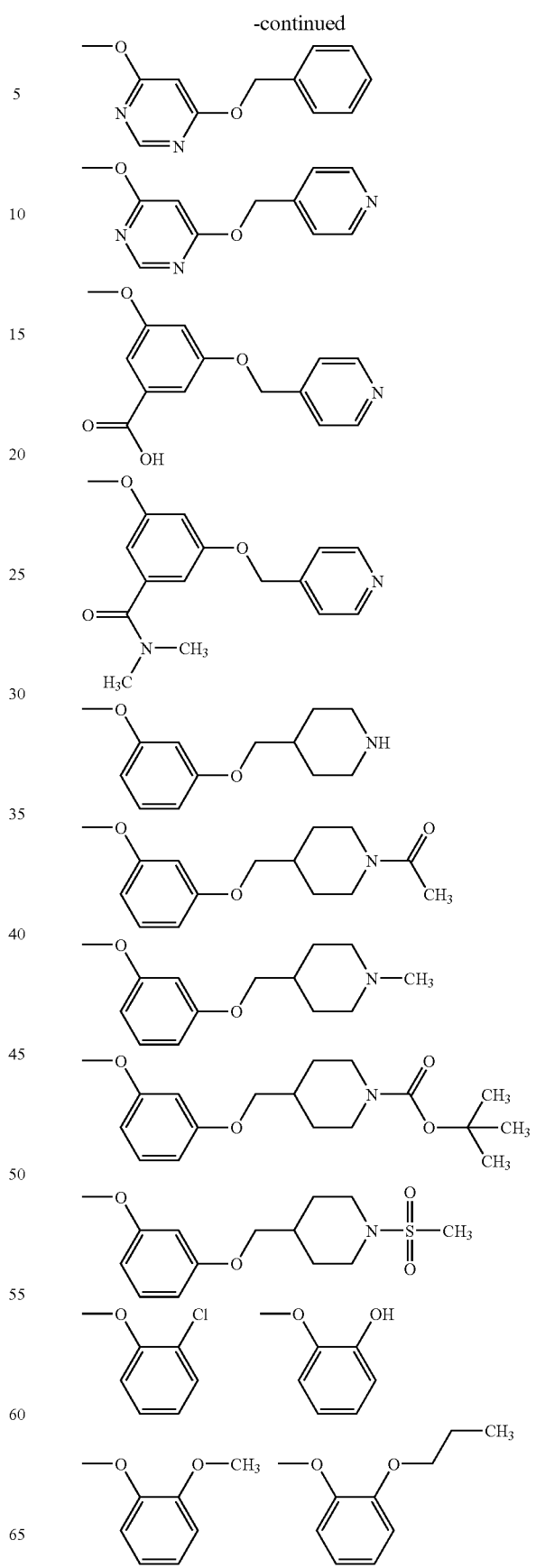

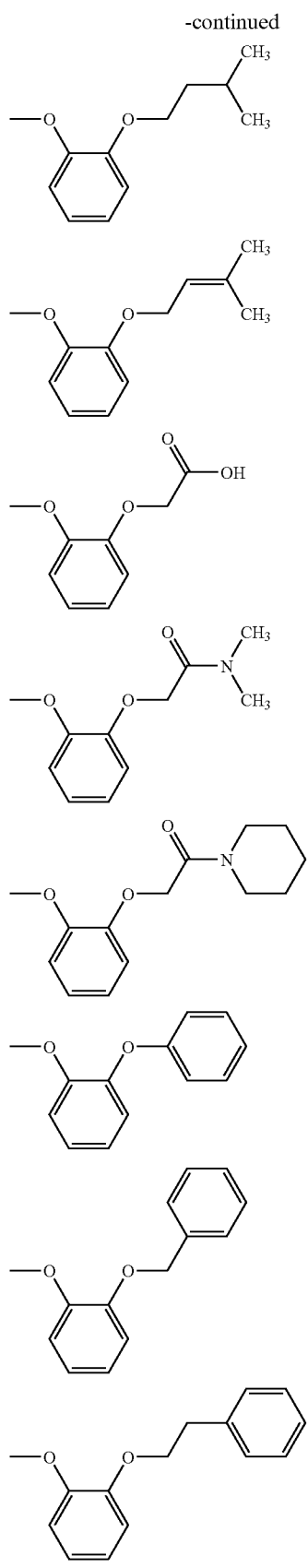
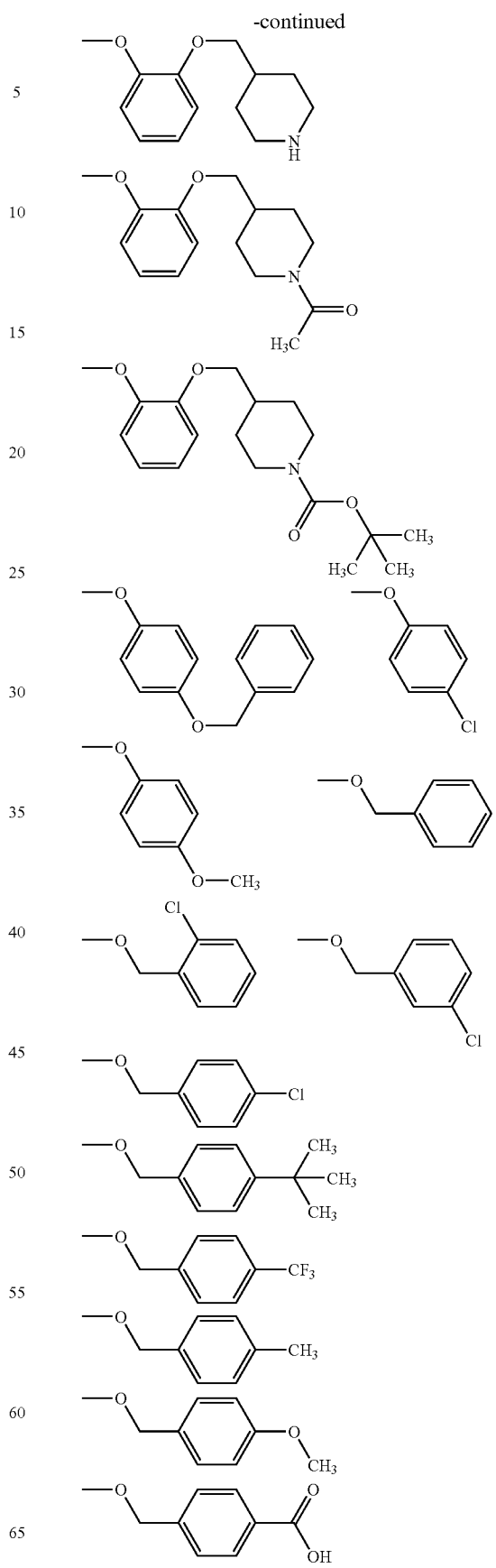

-continued
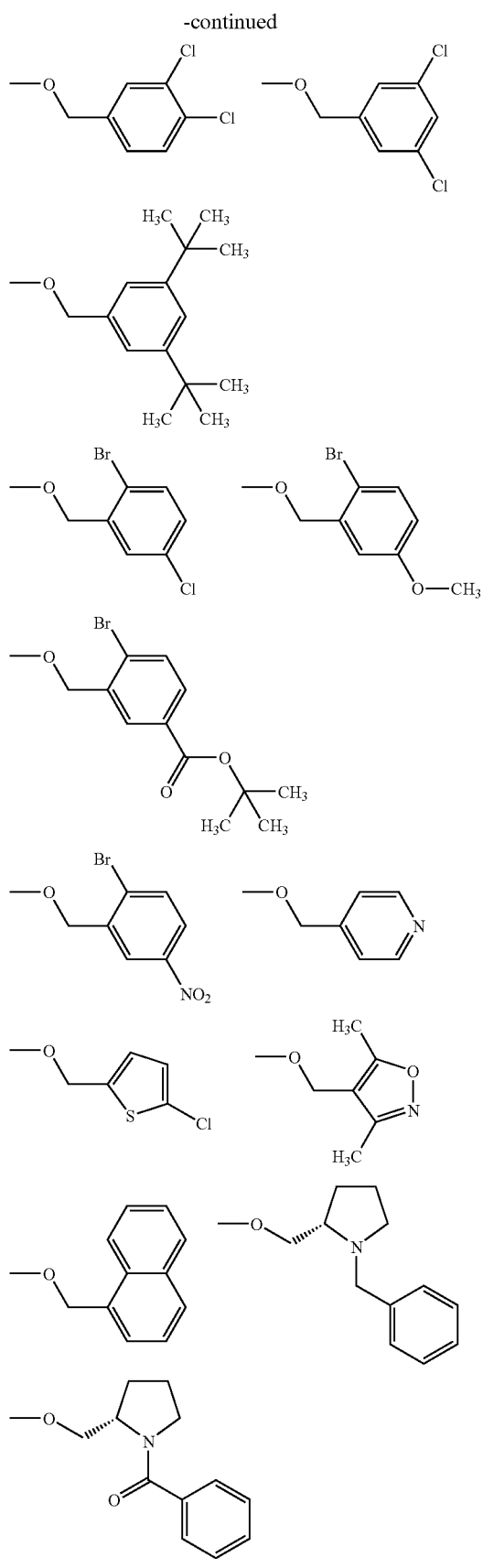
-continued
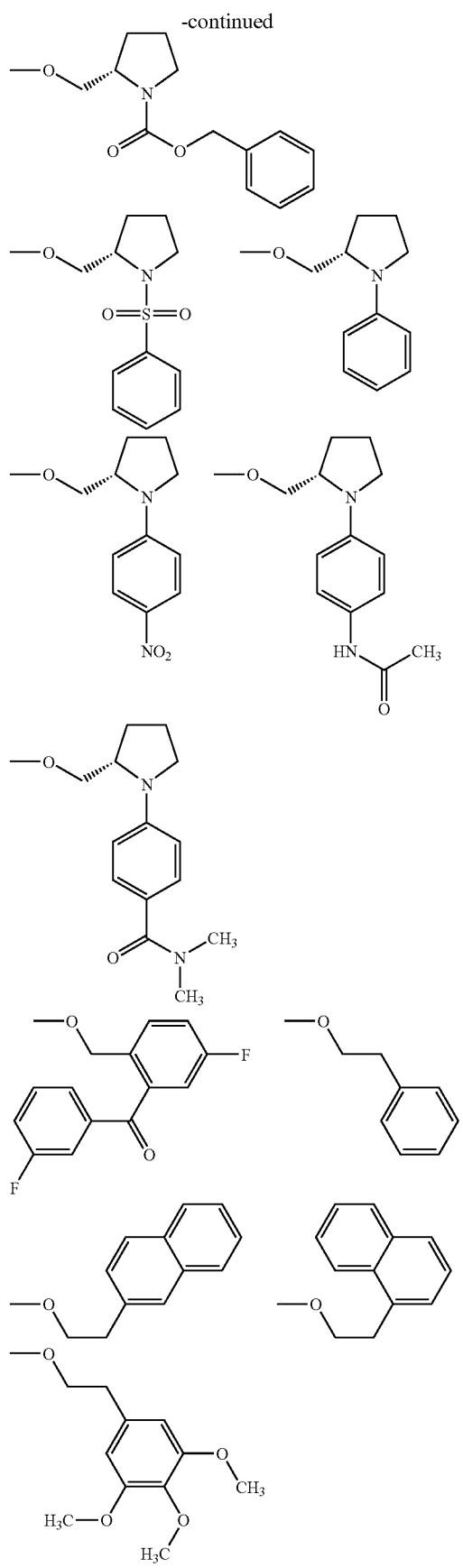

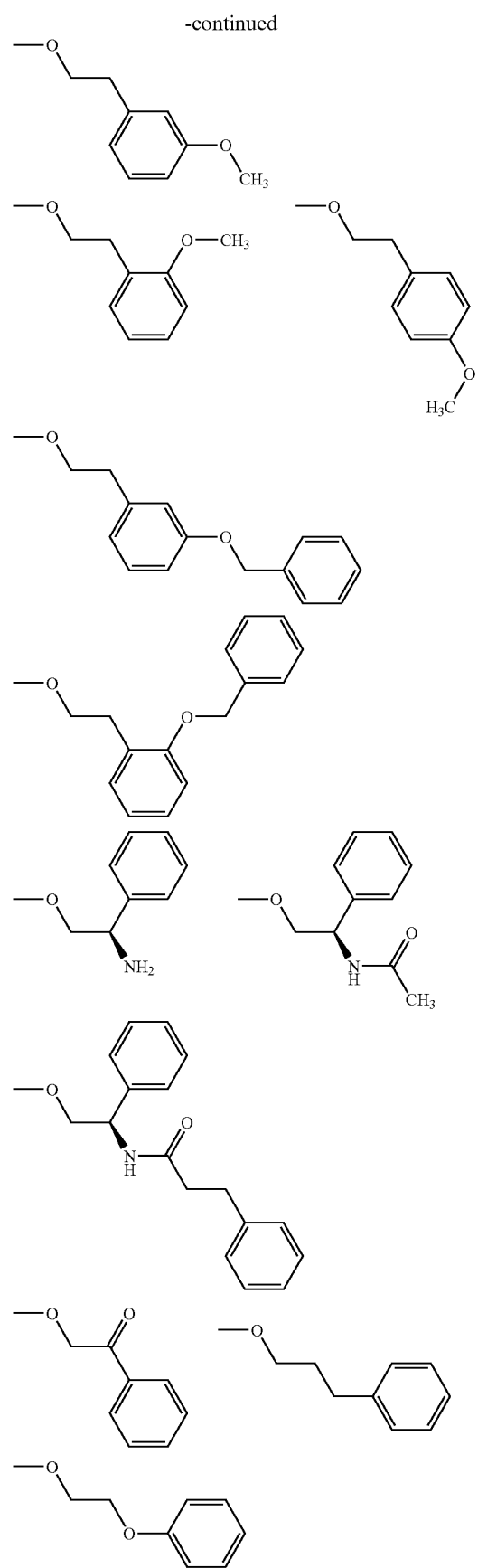
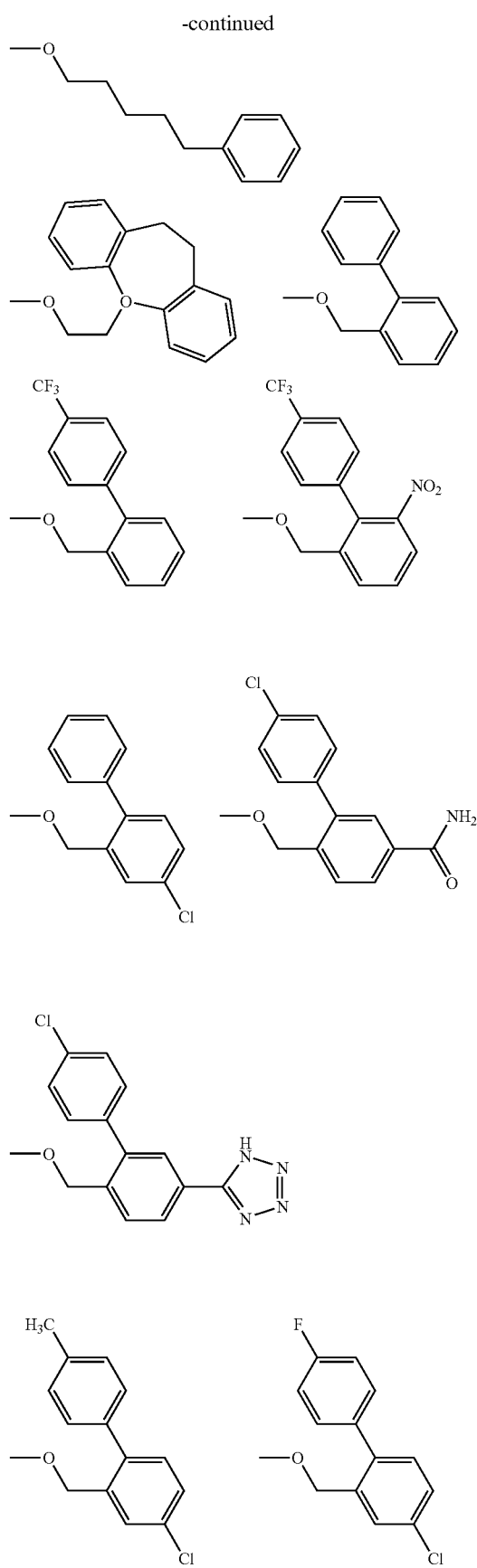

-continued
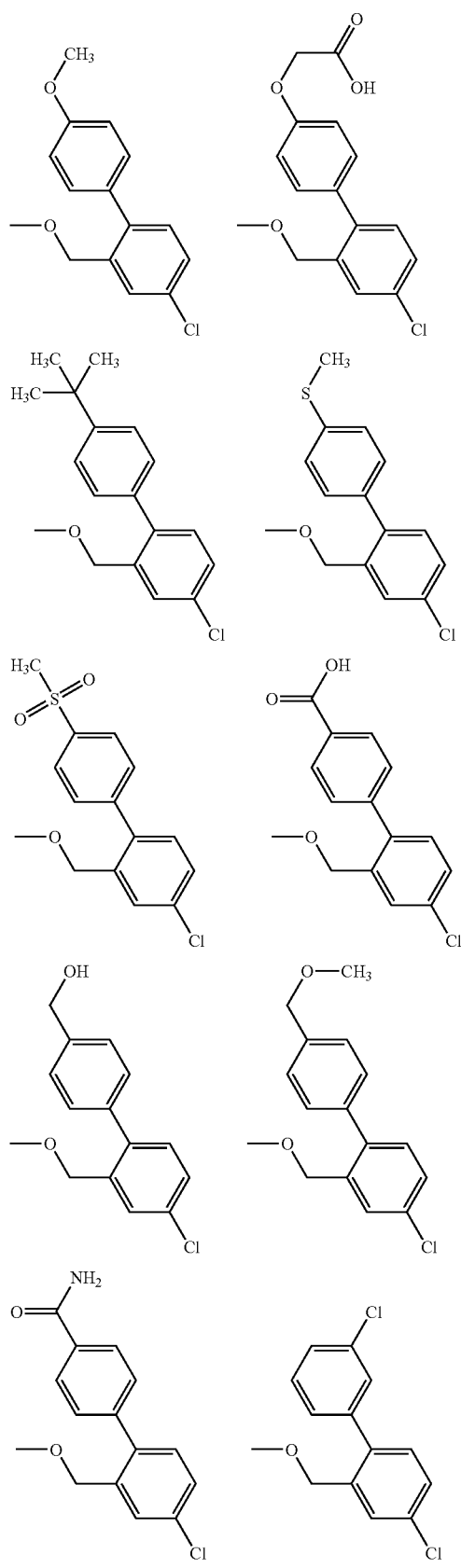
-continued
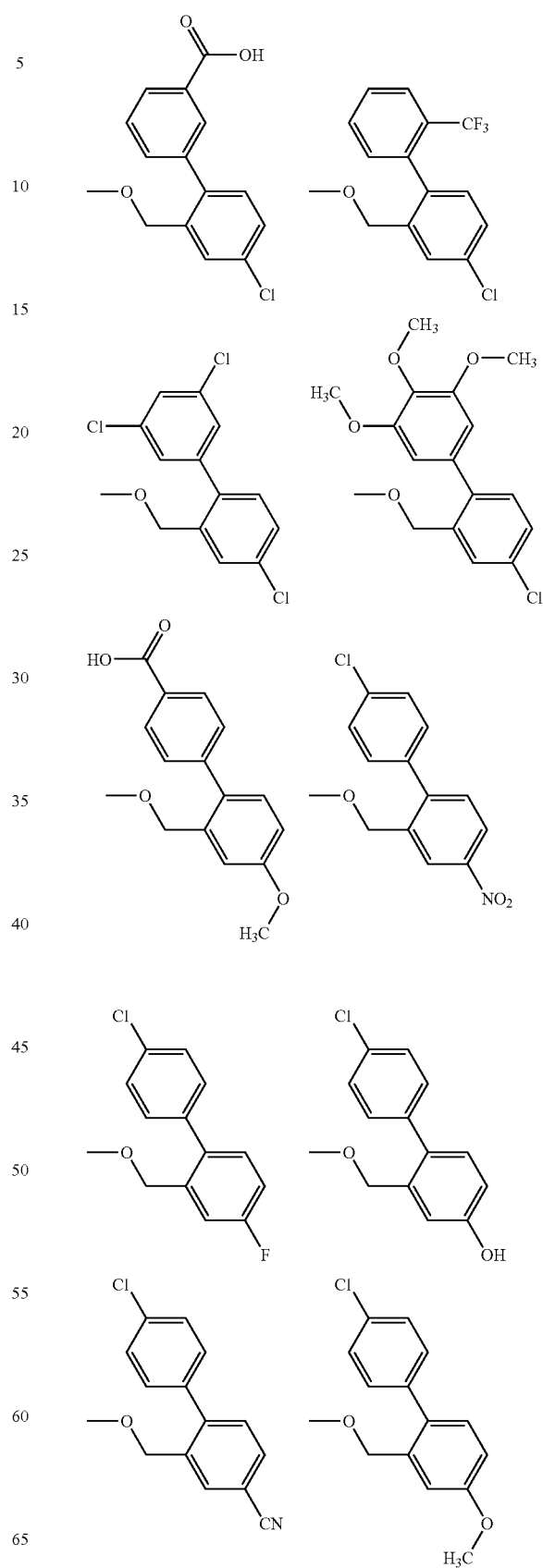

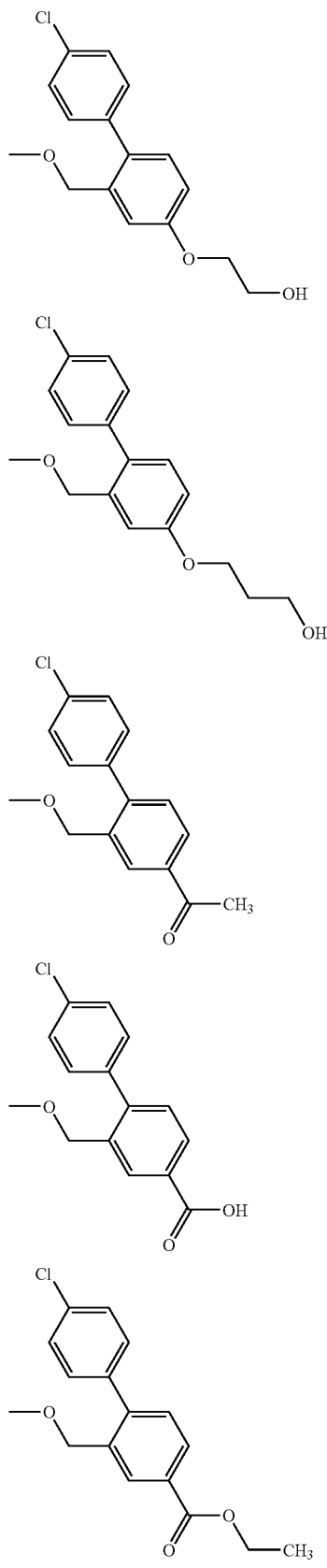
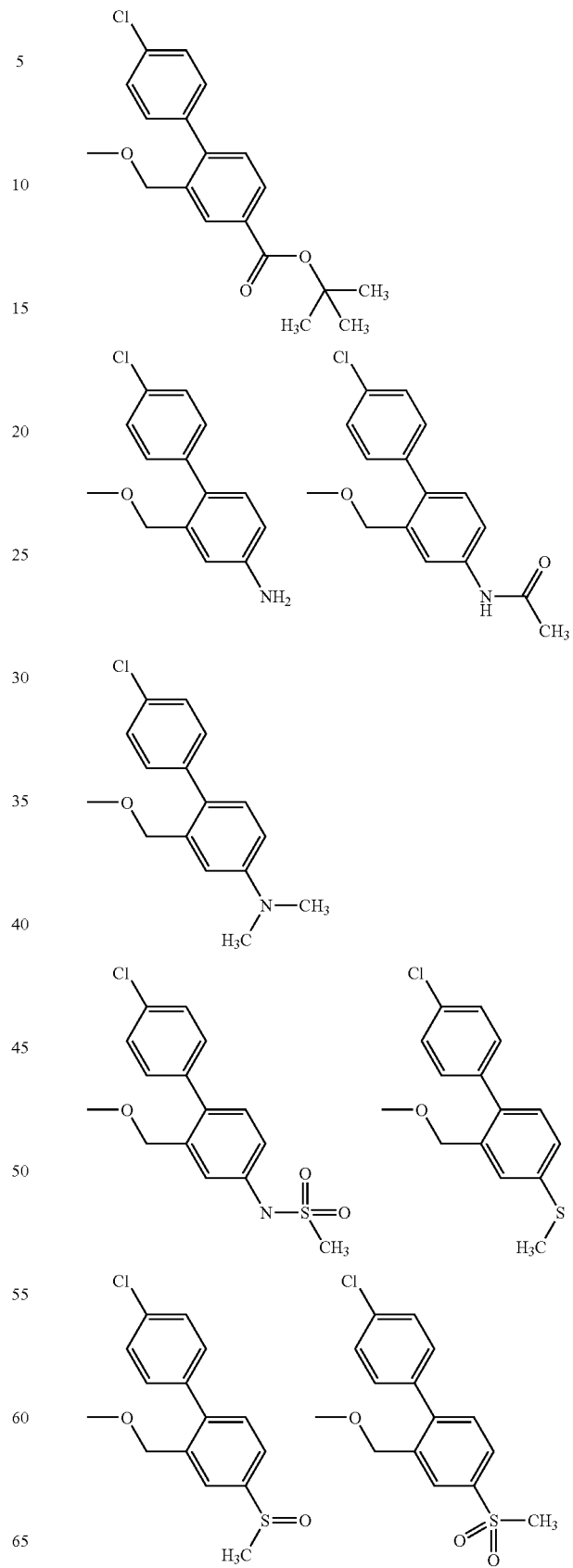

177
-continued
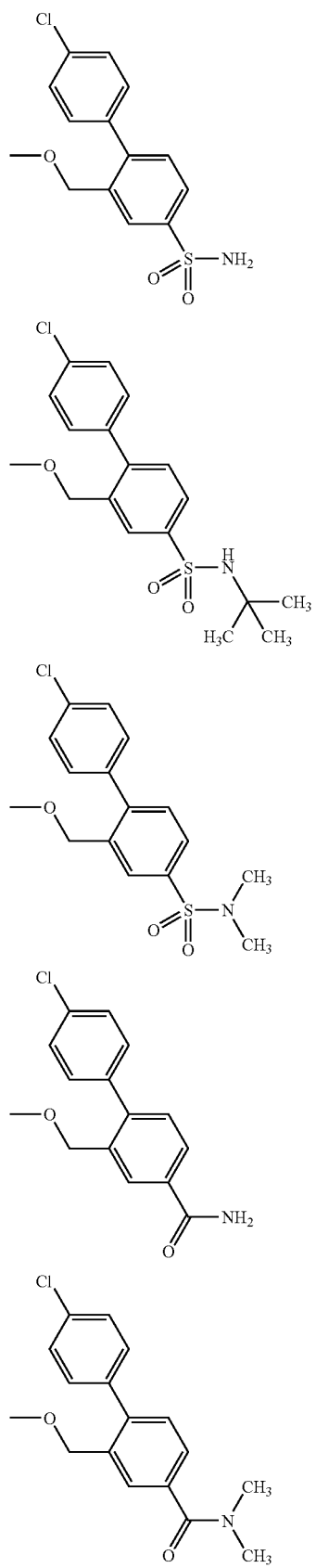
178
-continued
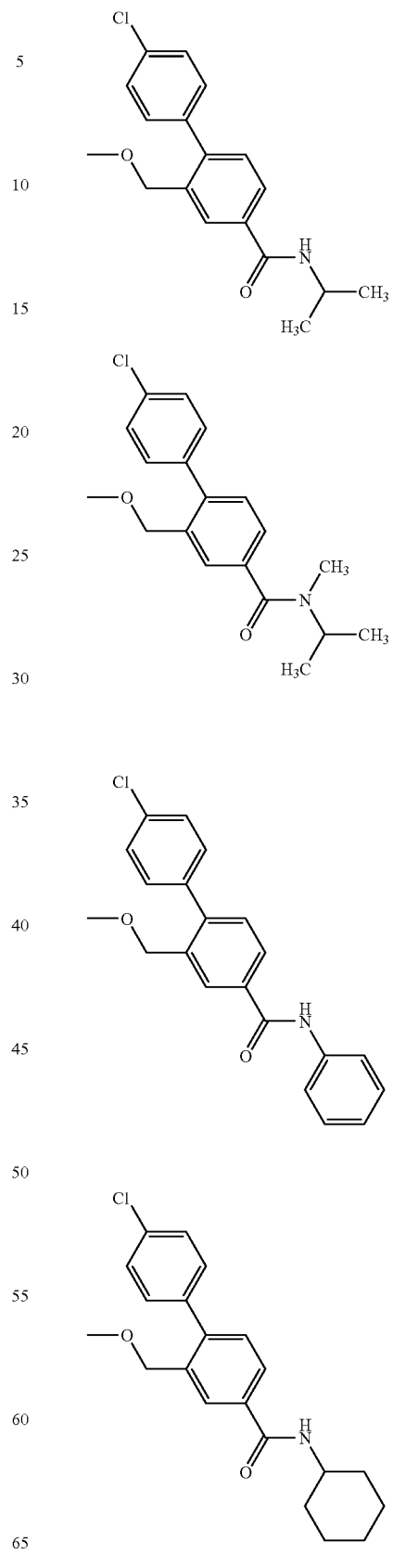

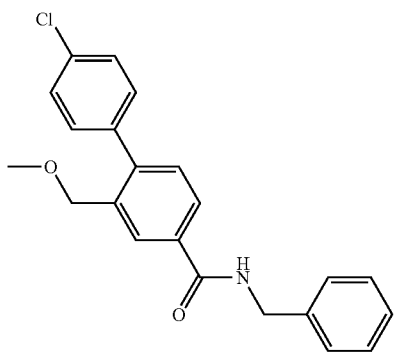
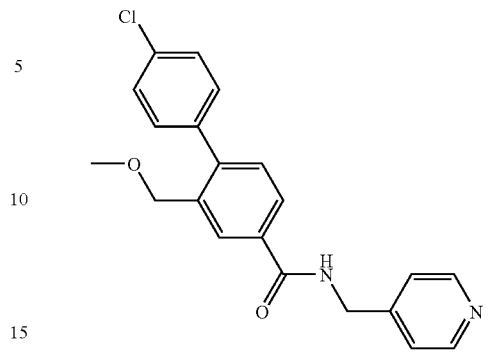
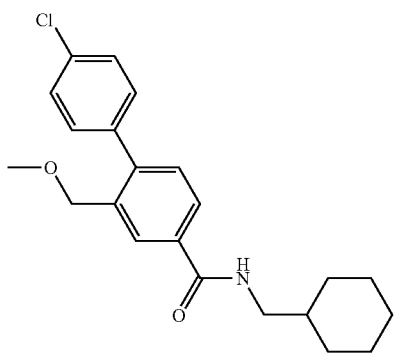
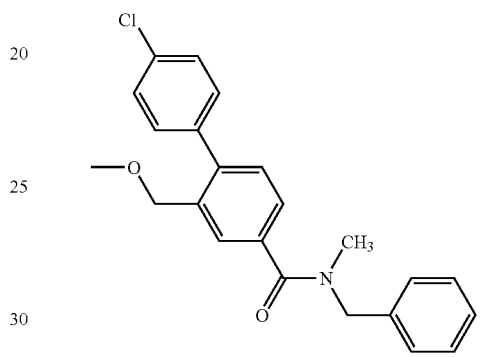
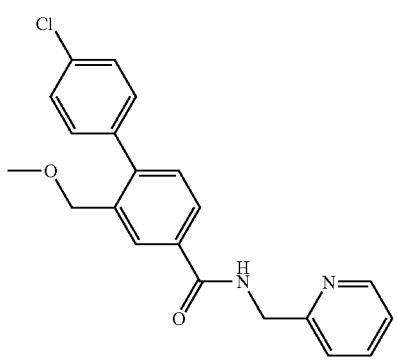
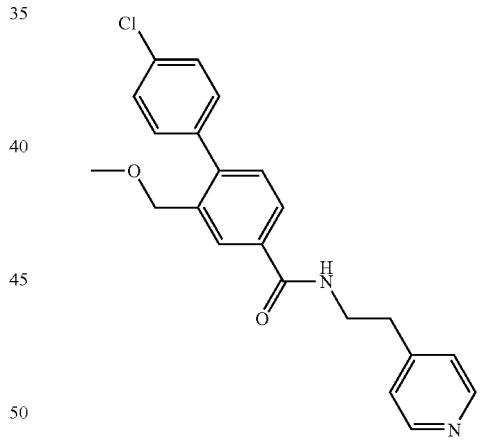
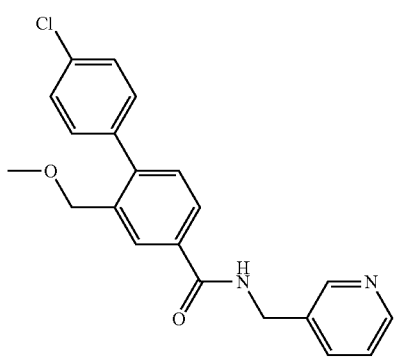
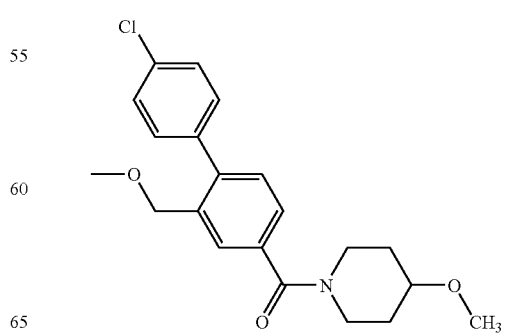

181
-continued
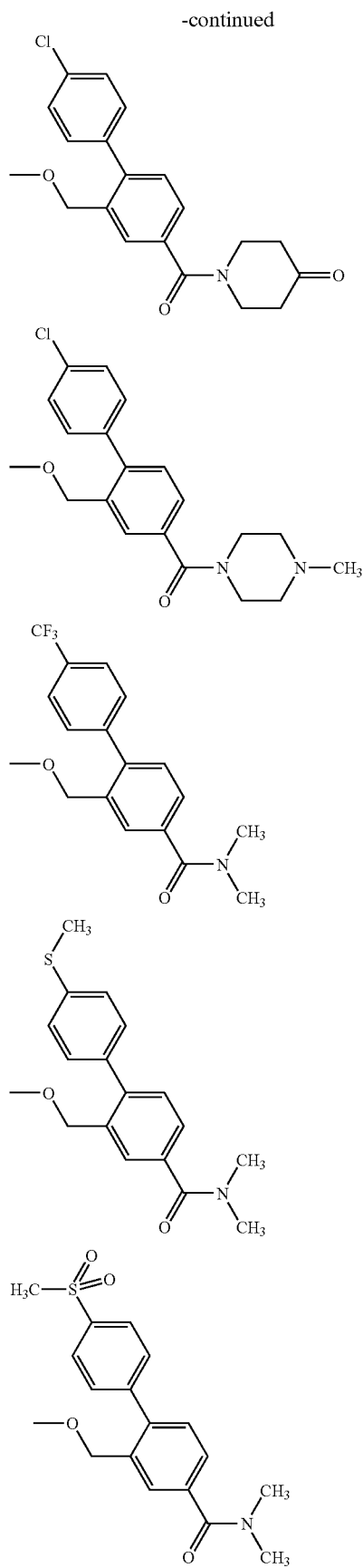
182
-continued
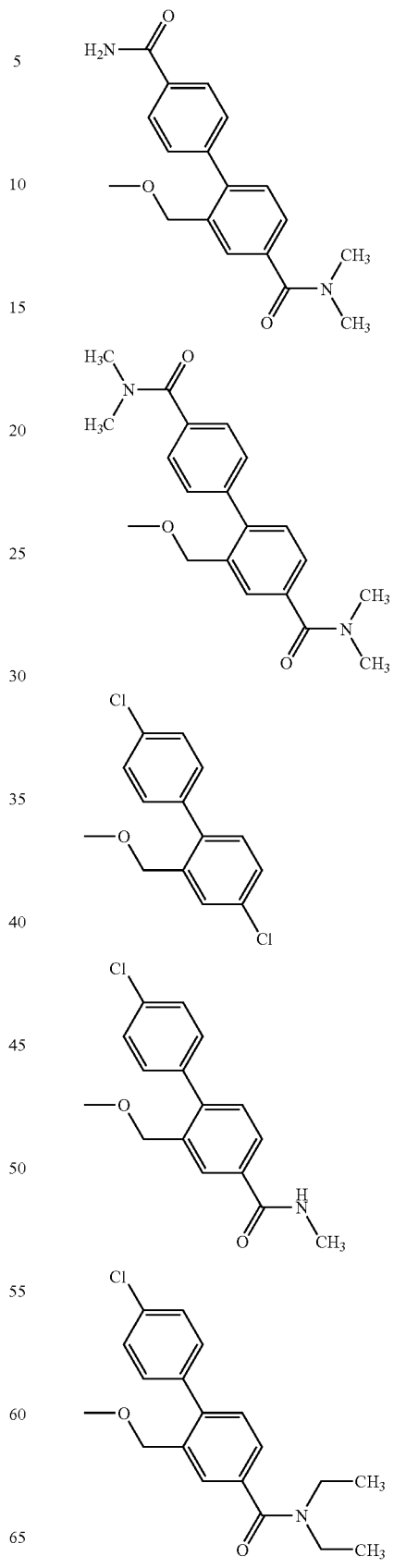

183
-continued
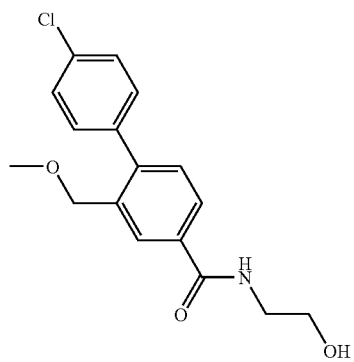
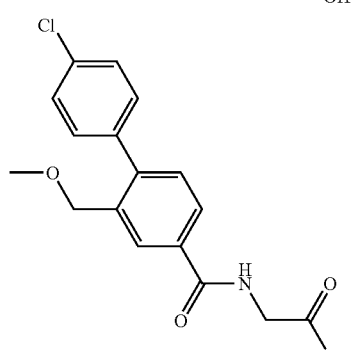
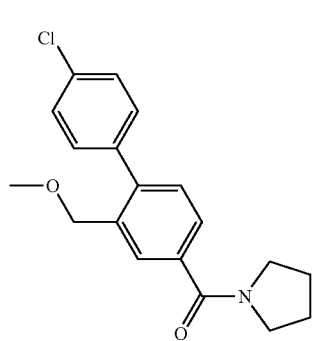
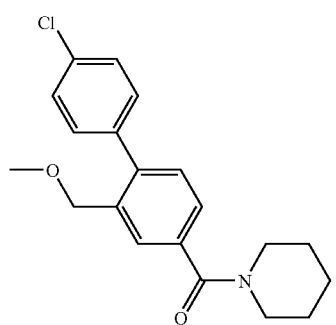
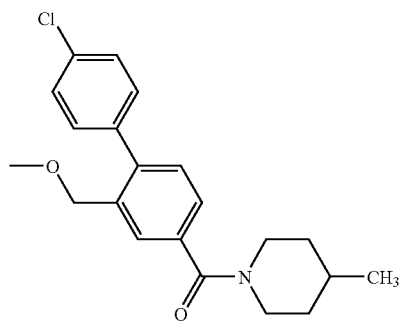
184
-continued
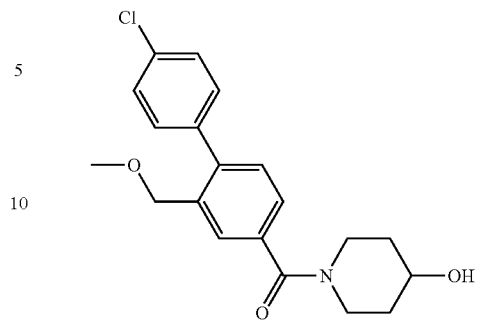
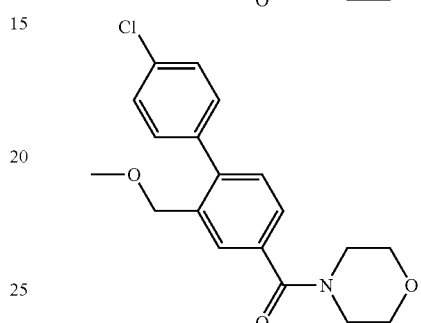
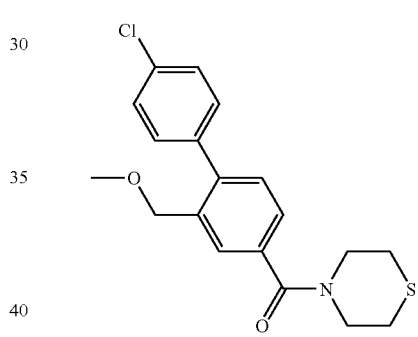
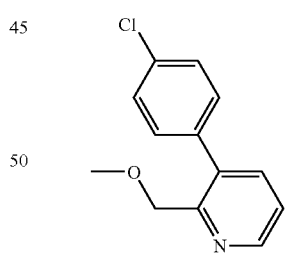
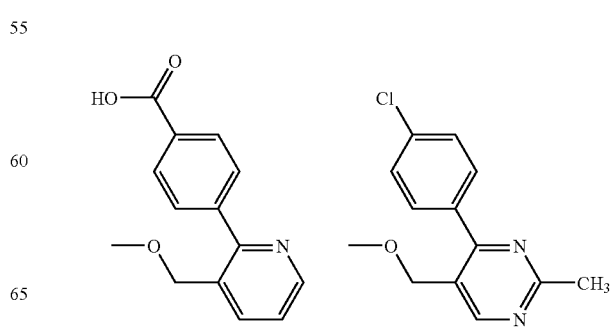

-continued
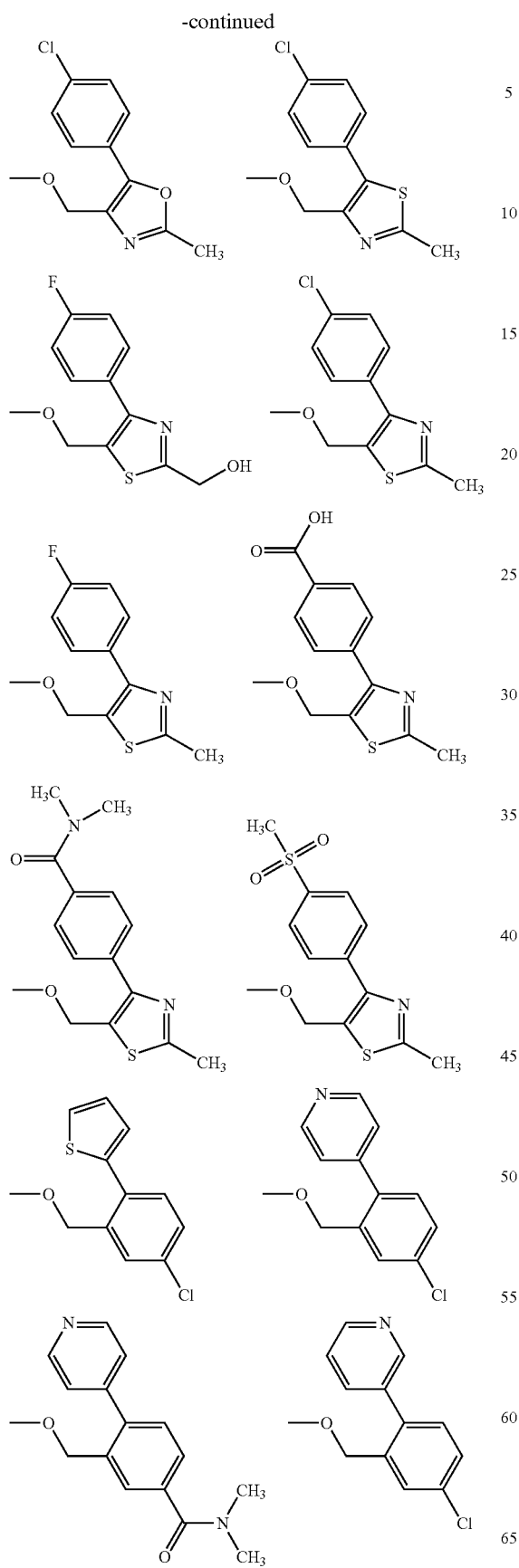
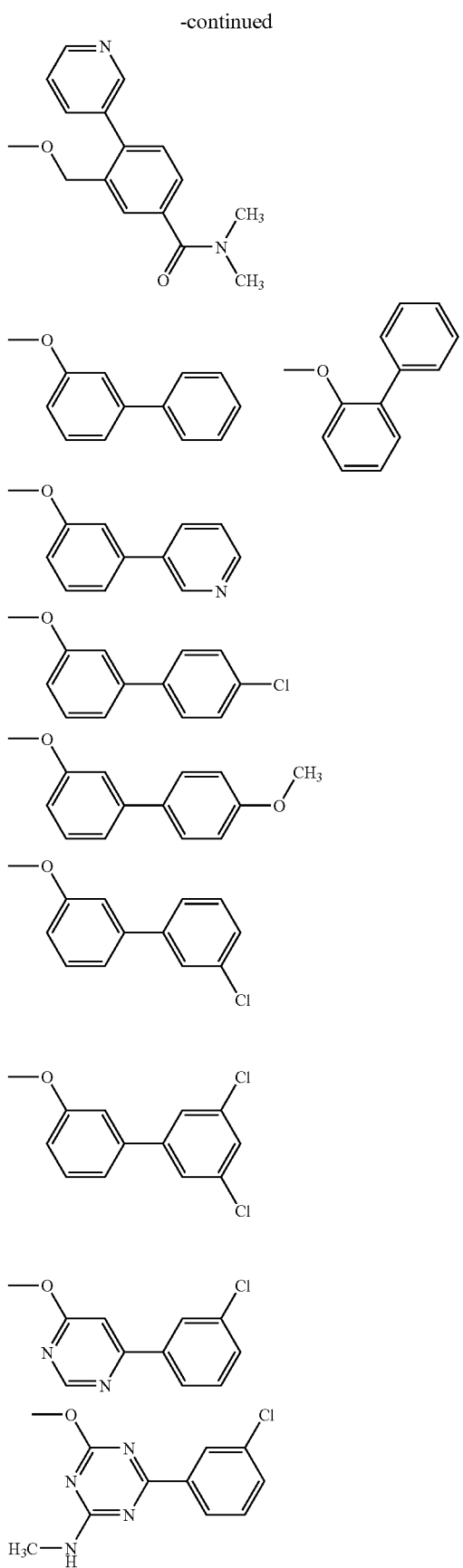

-continued
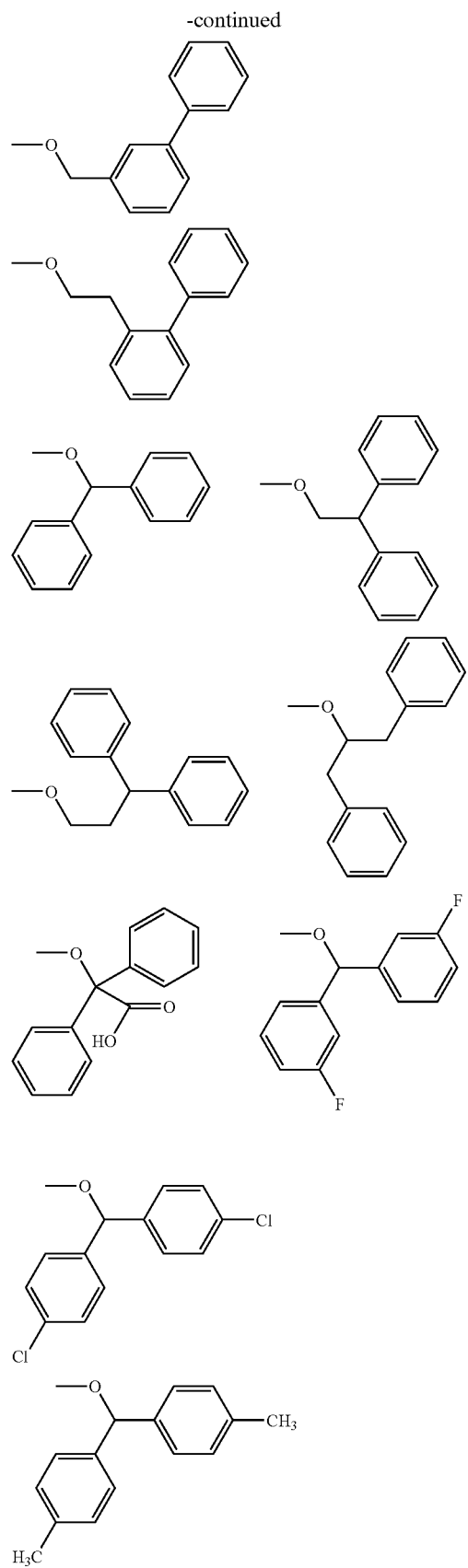
-continued
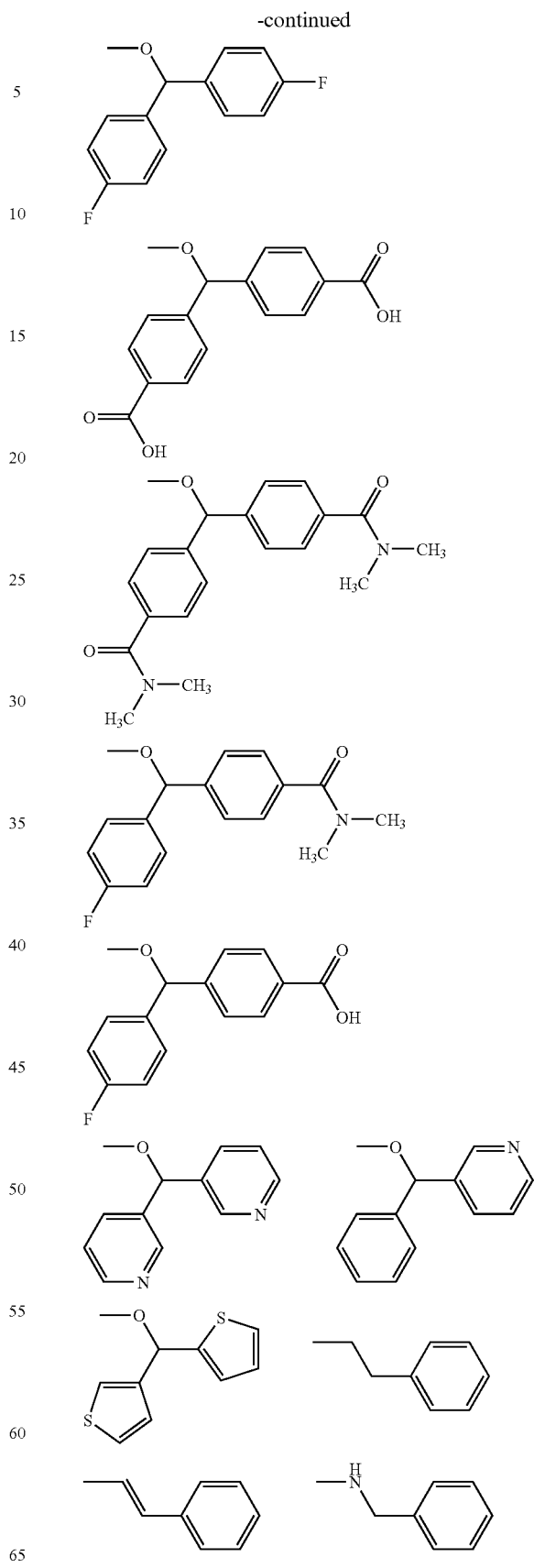

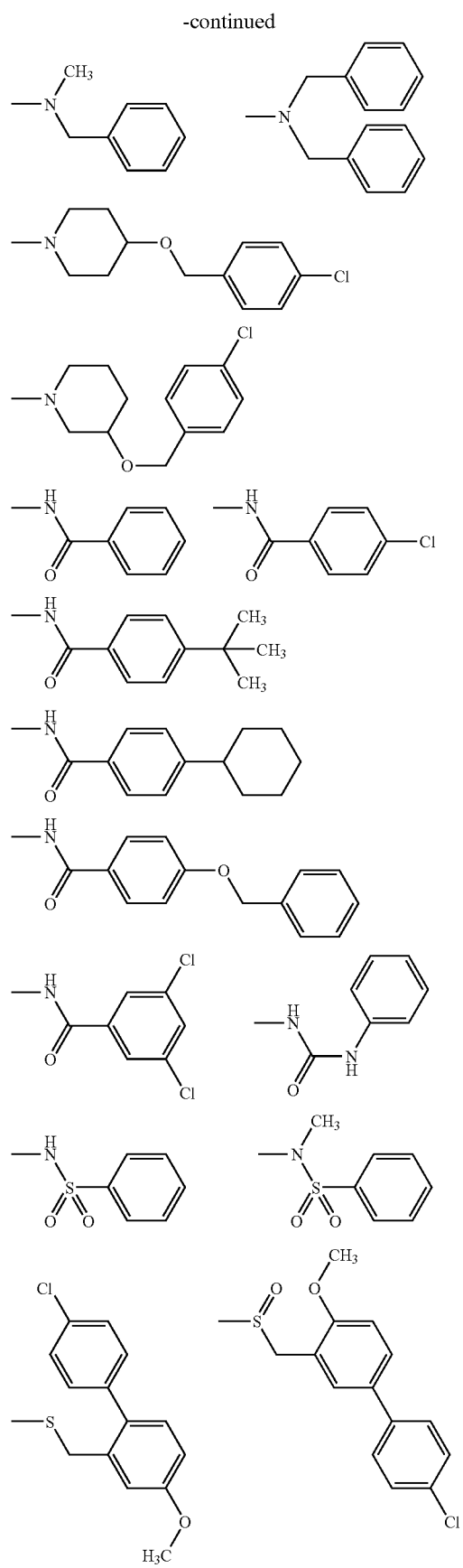
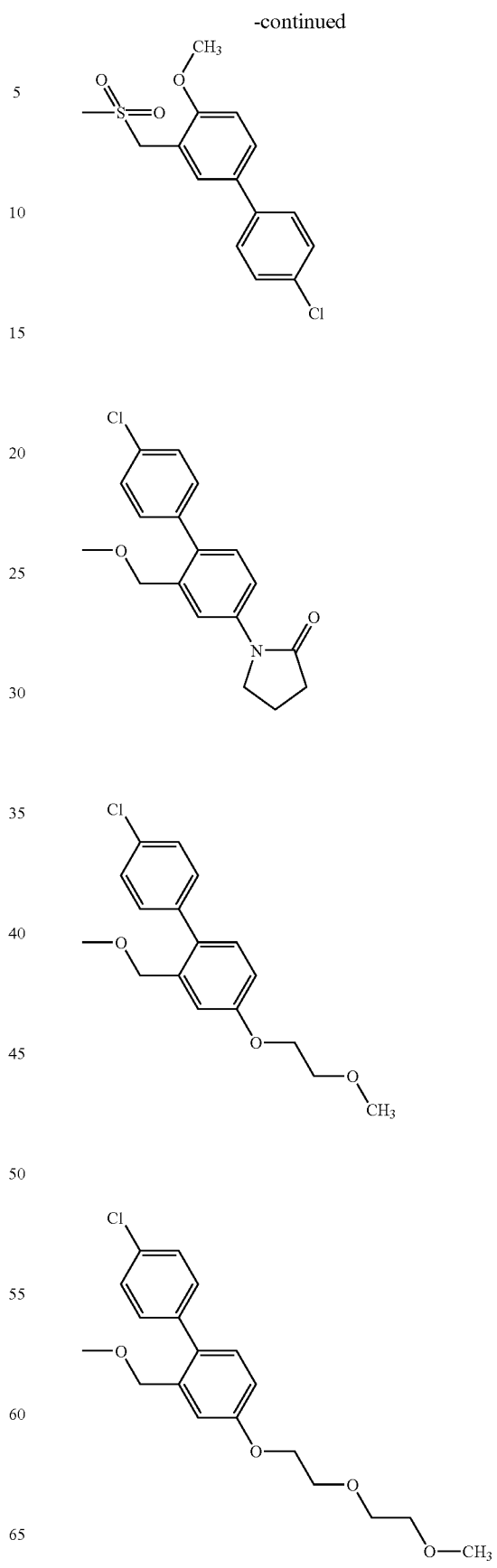

191
-continued
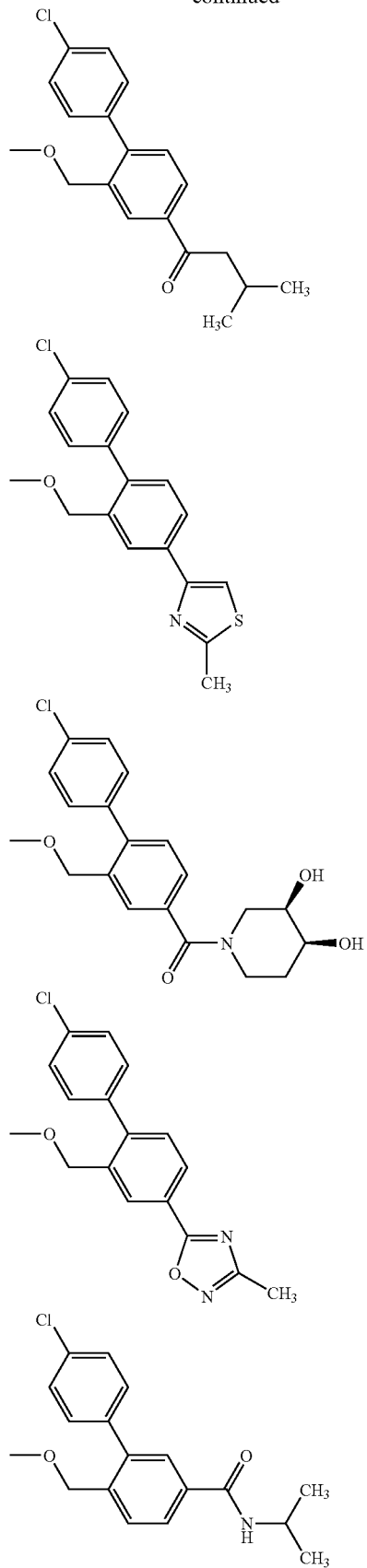
192
-continued
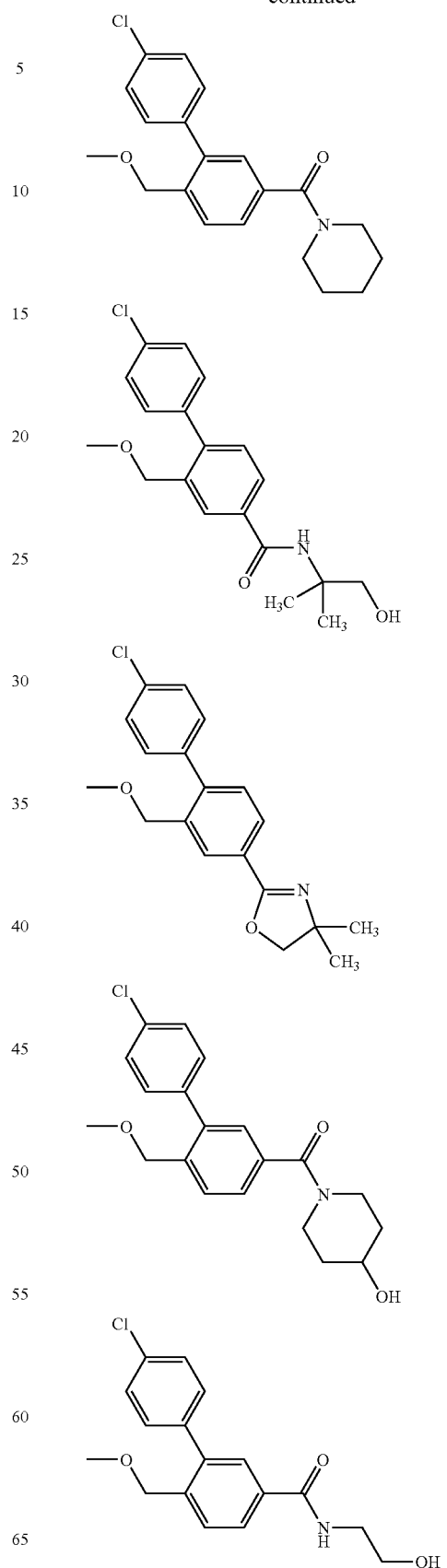

193
-continued
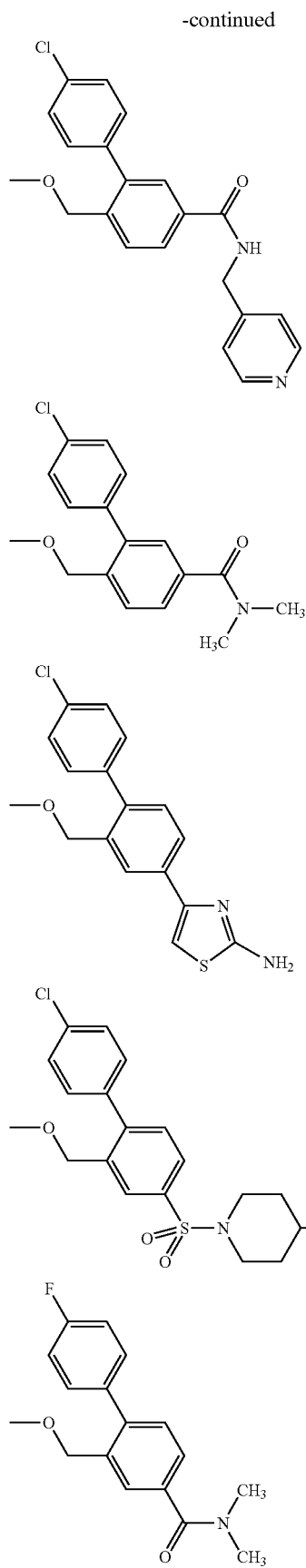
194
-continued
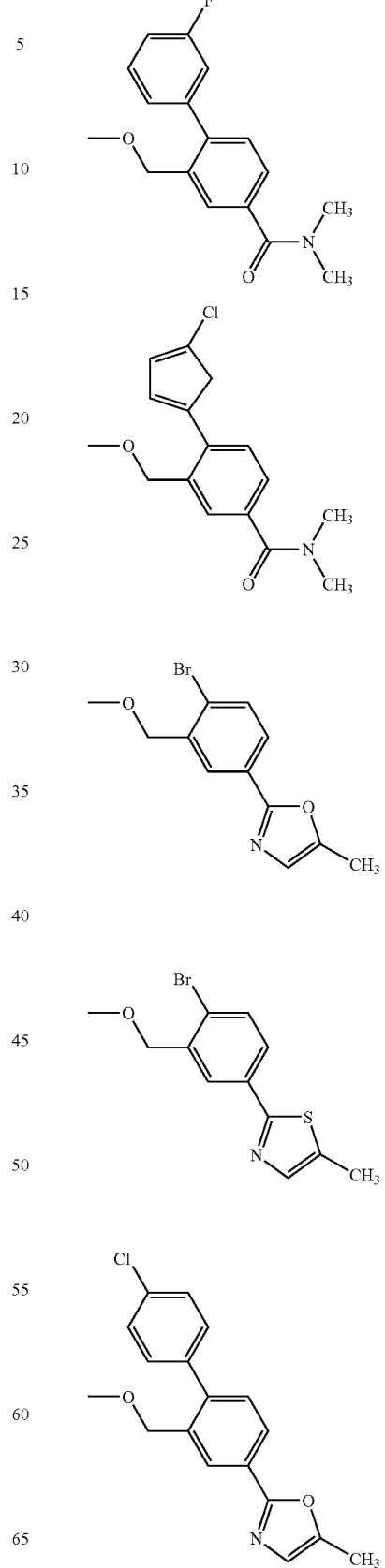

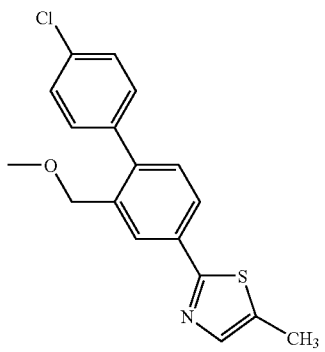
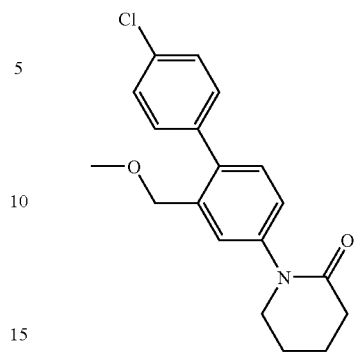
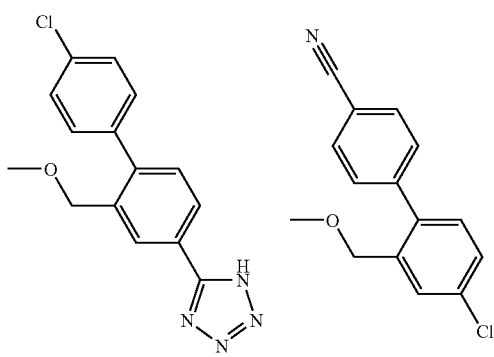
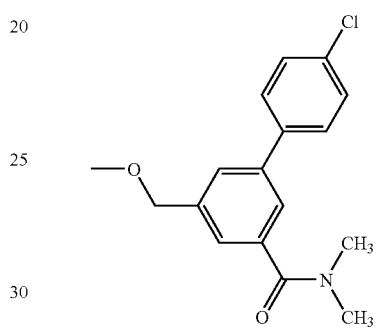
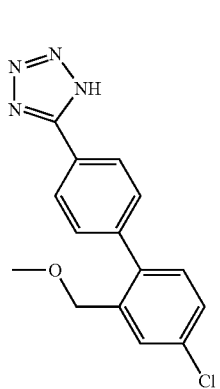
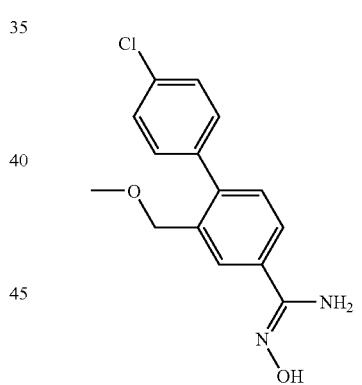
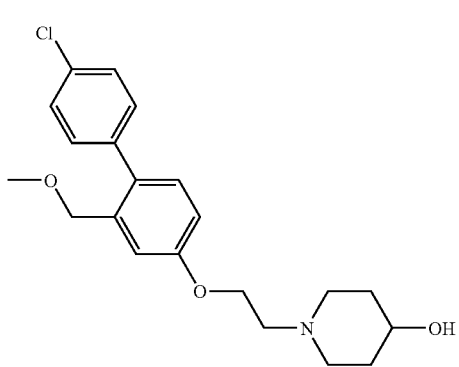
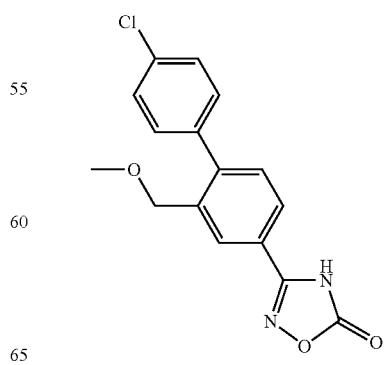

197
-continued
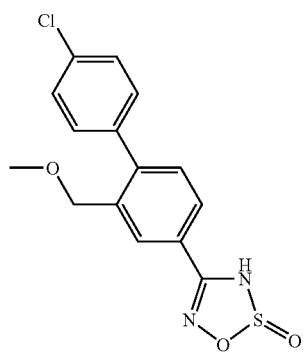
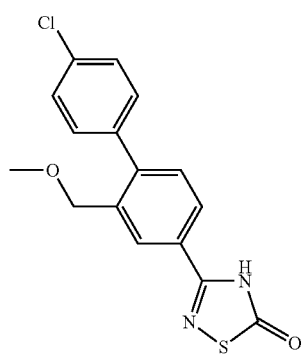
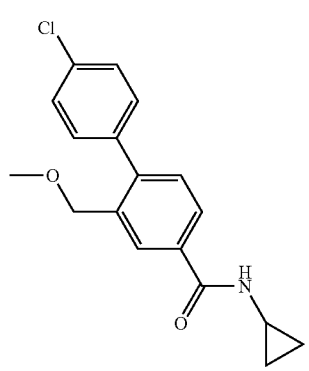
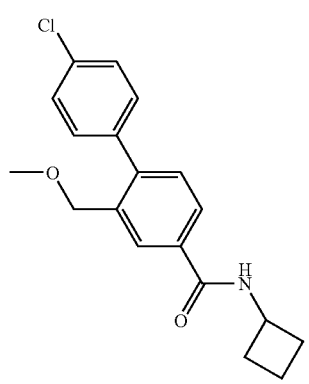
198
-continued
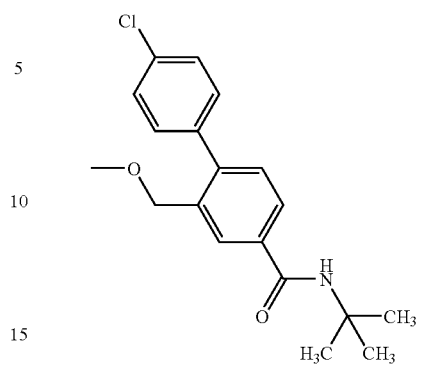
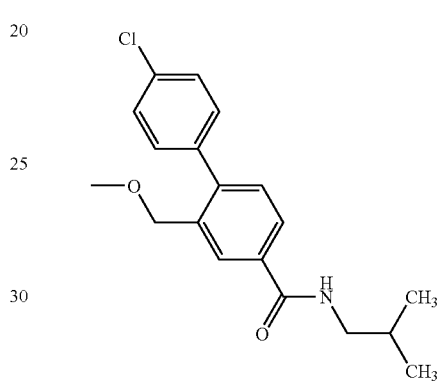
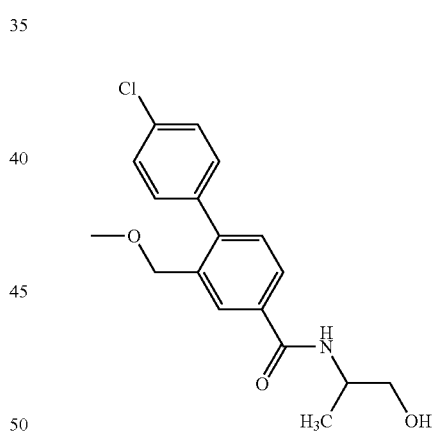
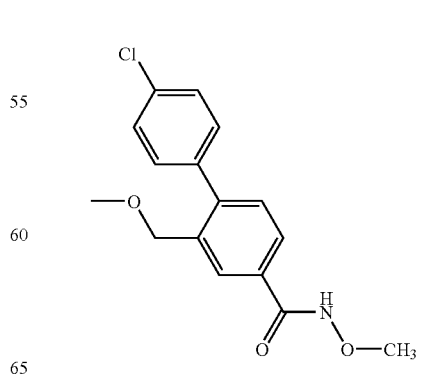

199
-continued
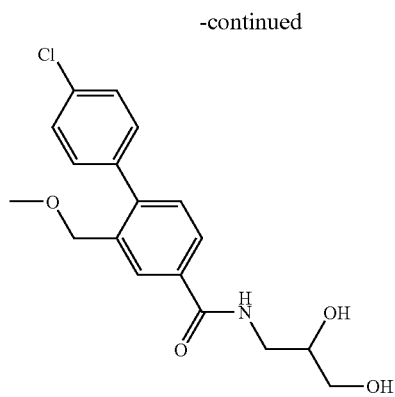
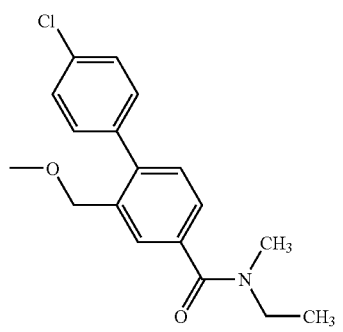
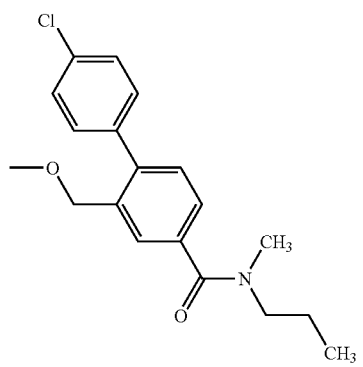
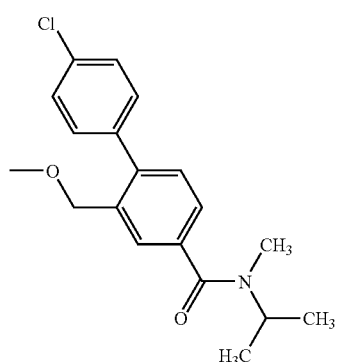
200
-continued
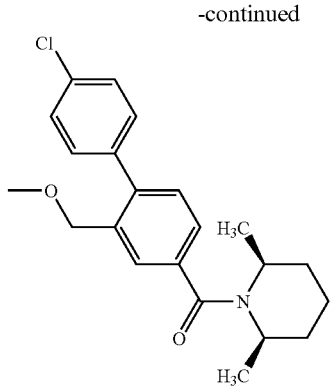
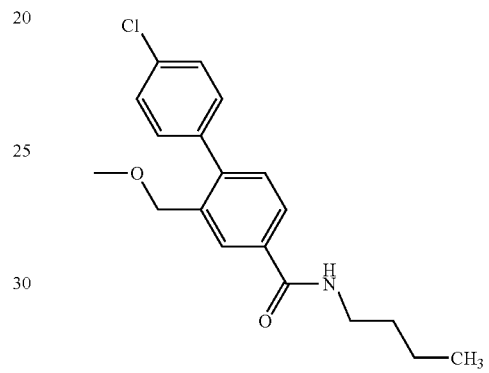
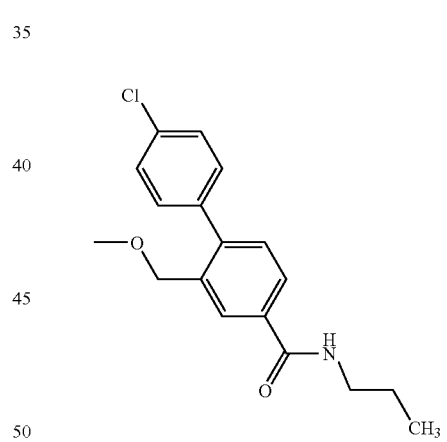
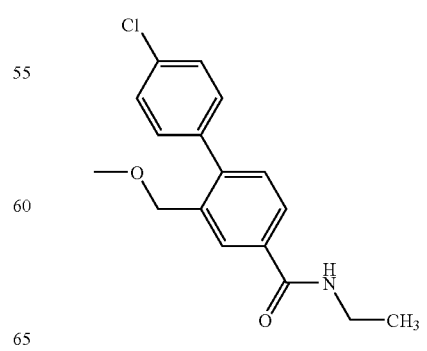

201
-continued
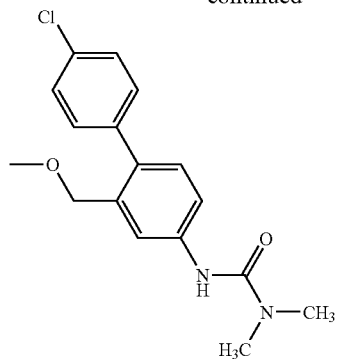
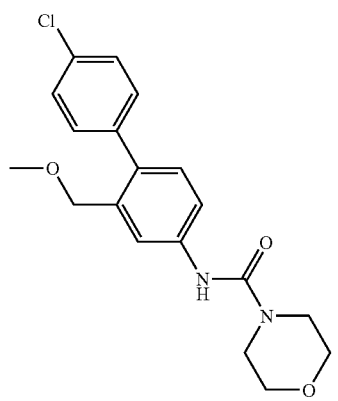
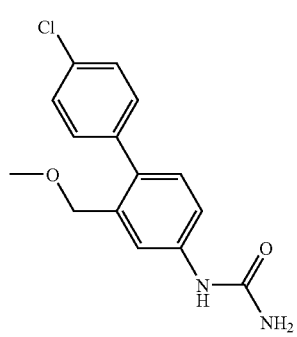
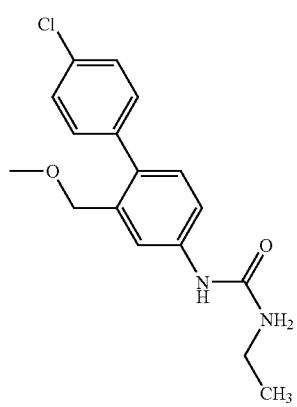
202
-continued
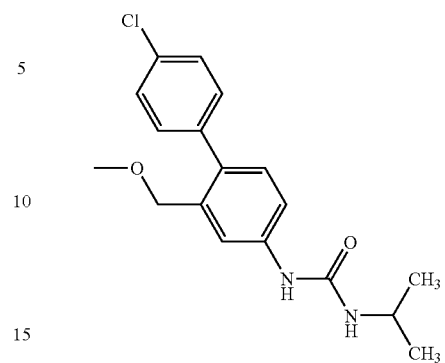
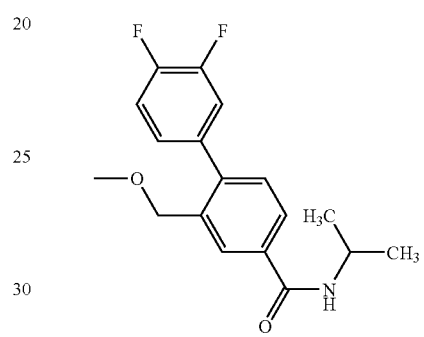
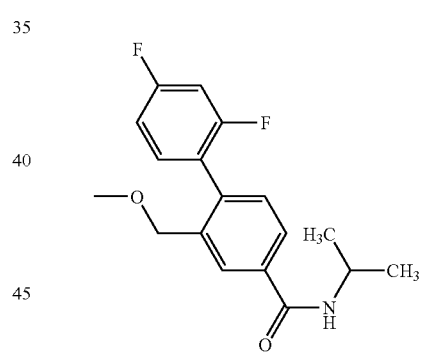
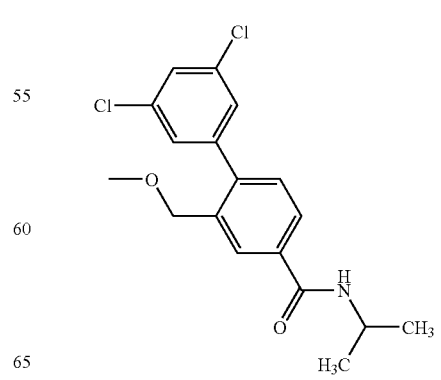

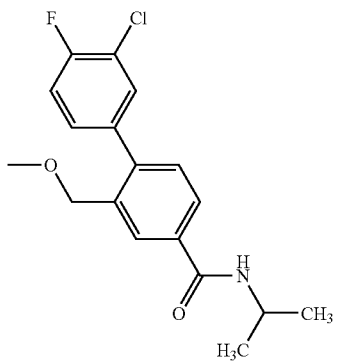
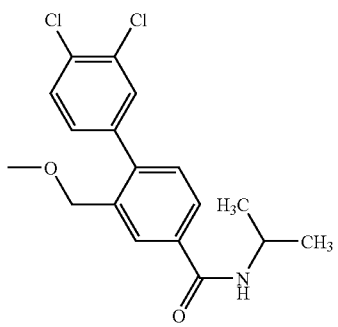
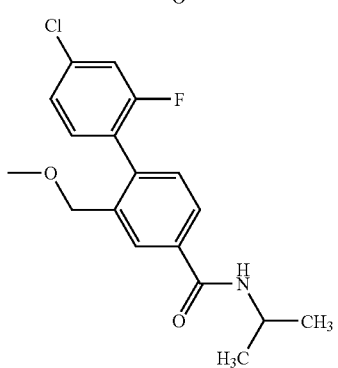
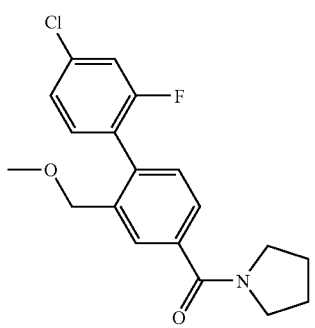
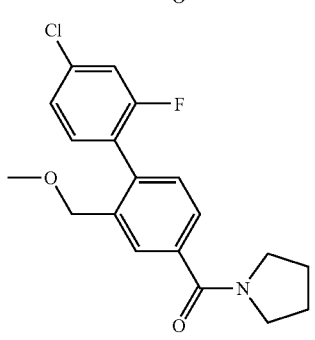
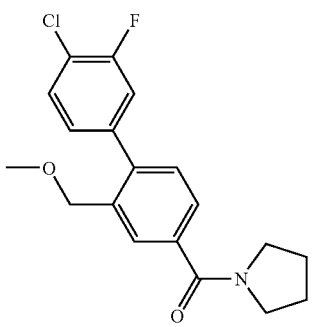
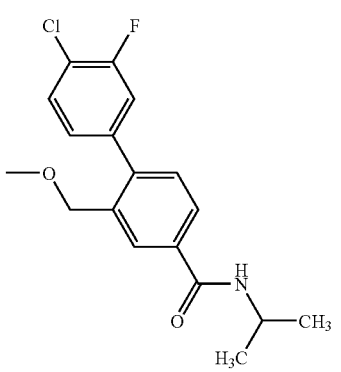
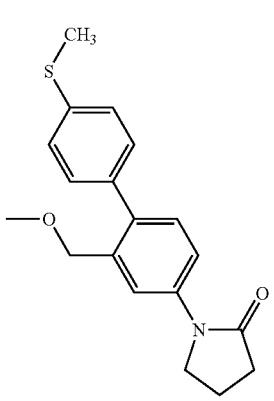
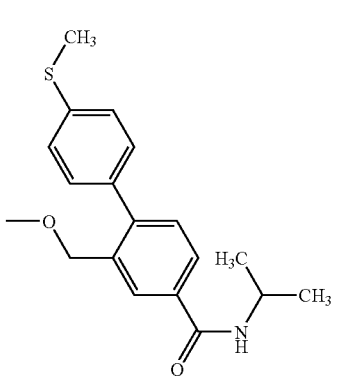

205
-continued
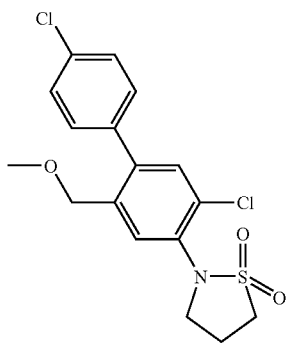
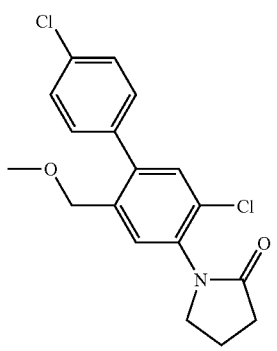
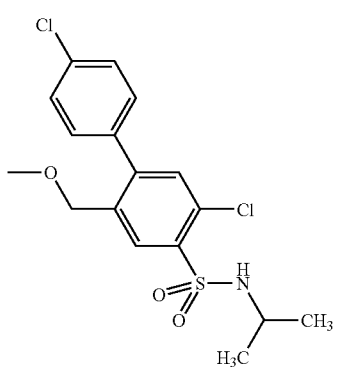
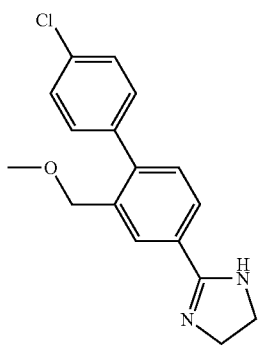
206
-continued
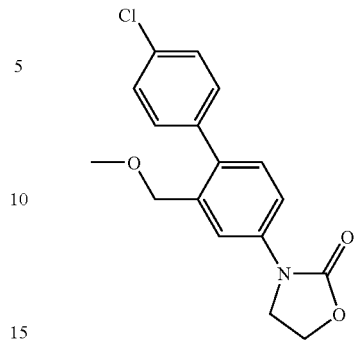
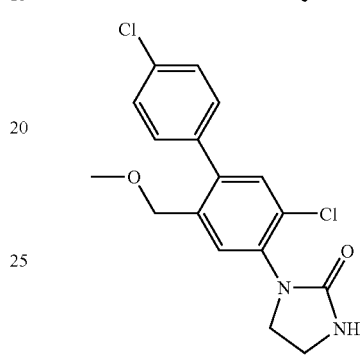
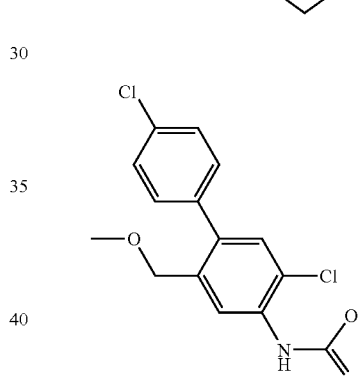
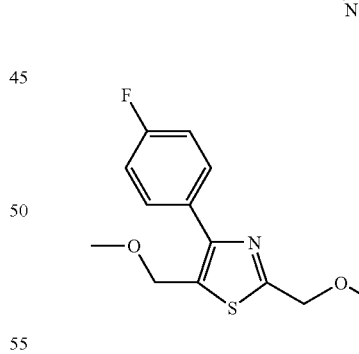
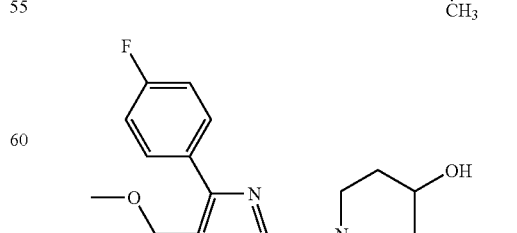

207
-continued
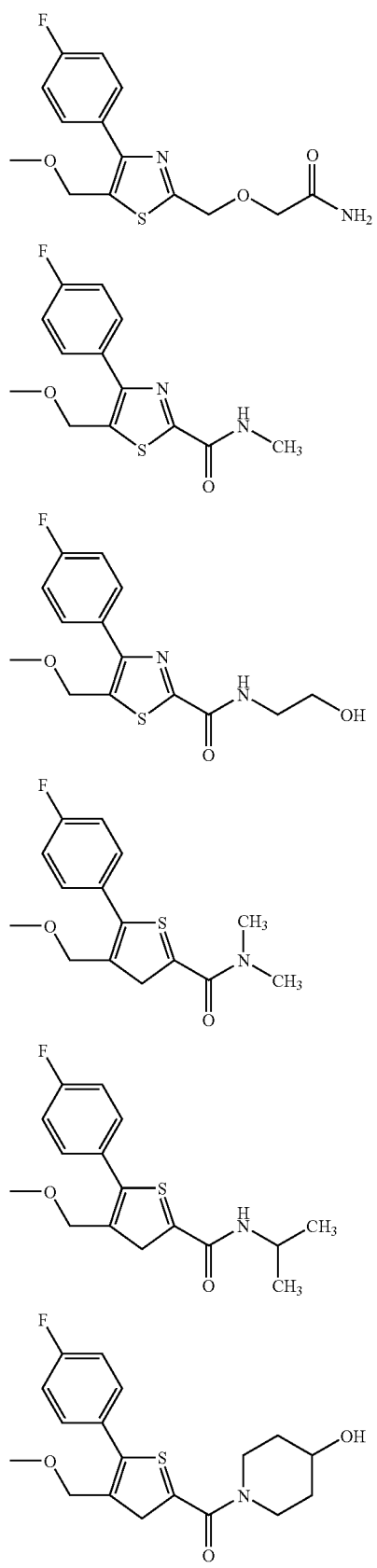
208
-continued
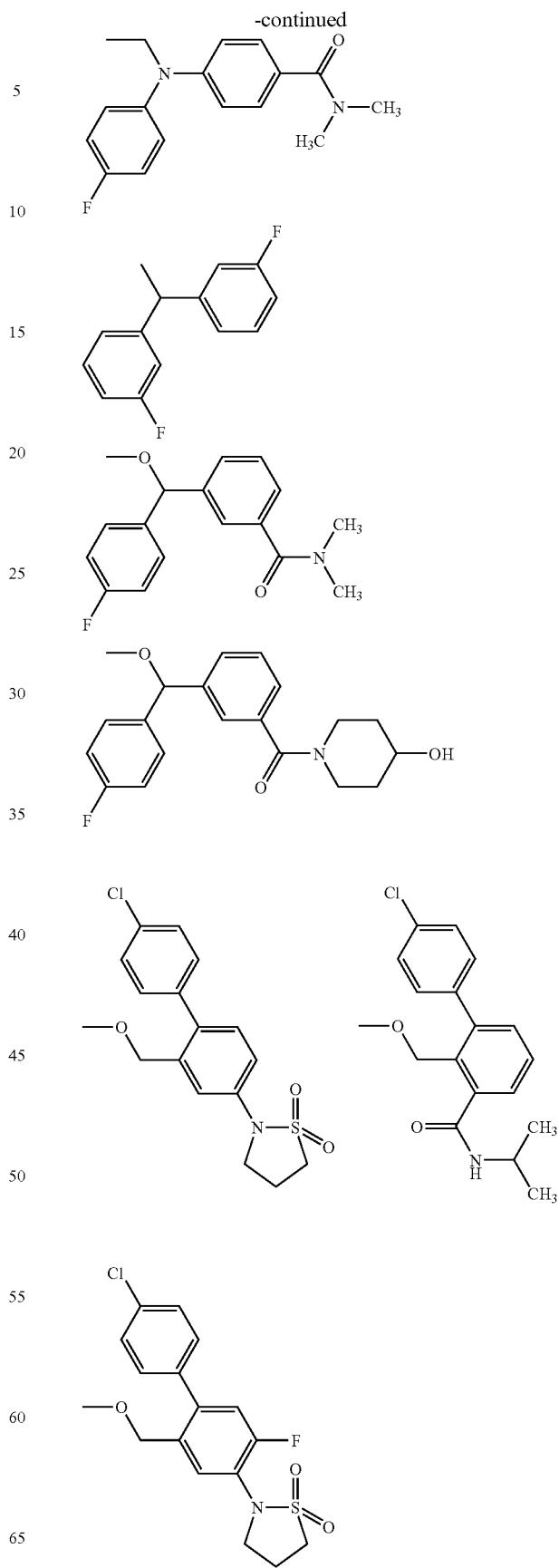

-continued
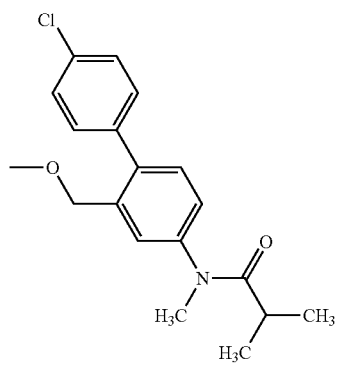
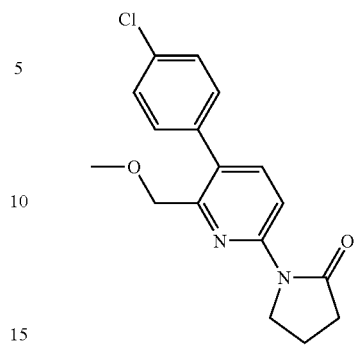
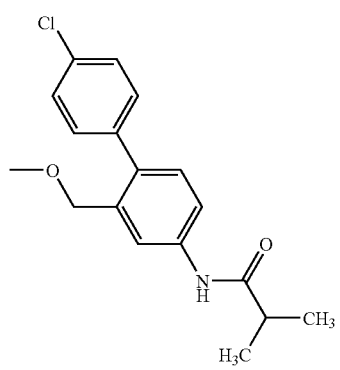
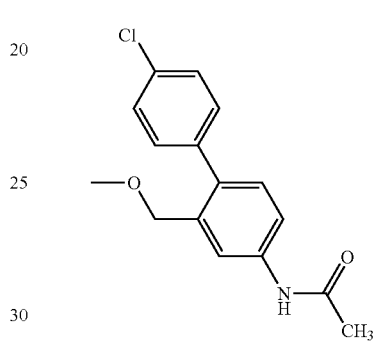
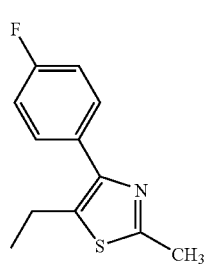
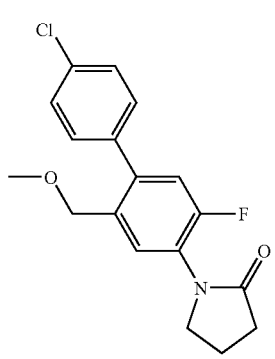
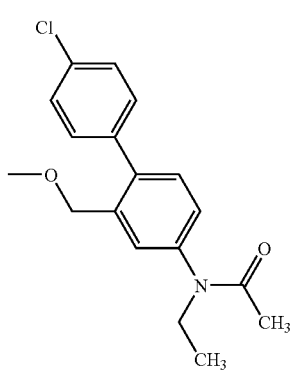
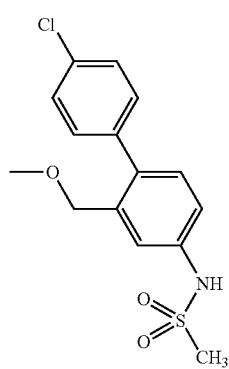
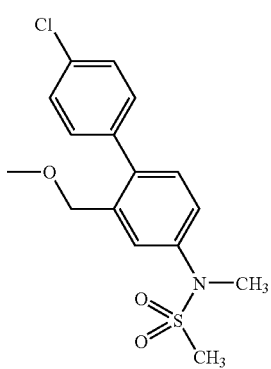
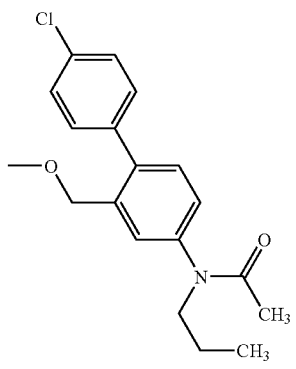

211
-continued
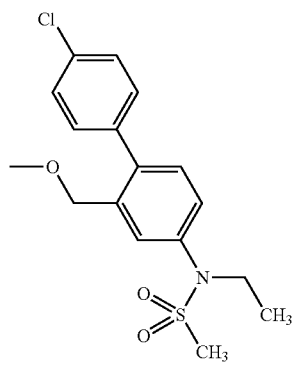
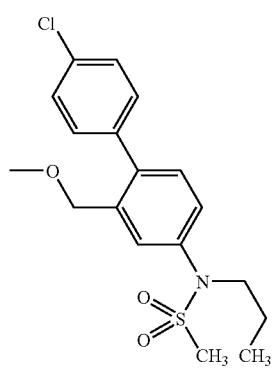
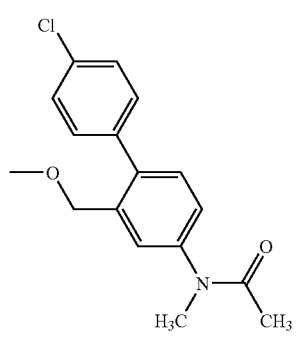
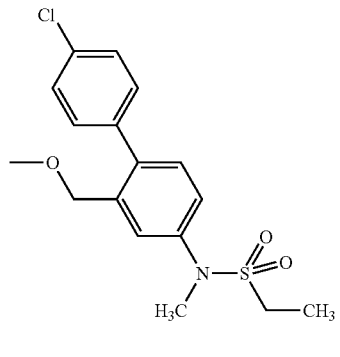
212
-continued
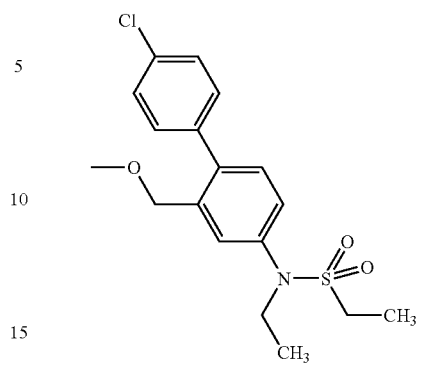
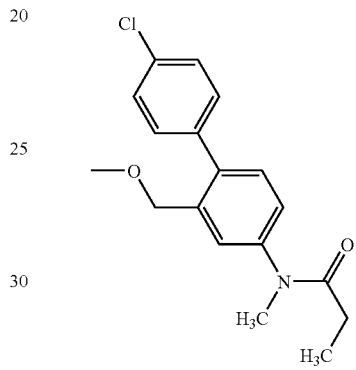
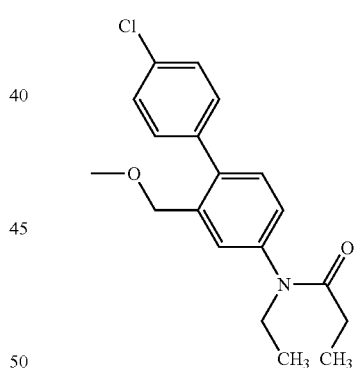
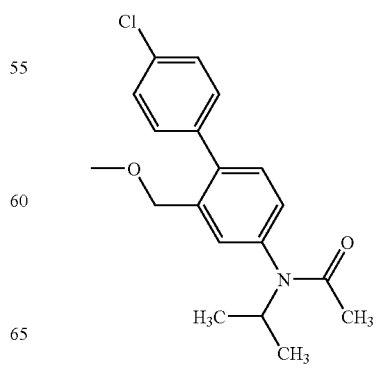

-continued
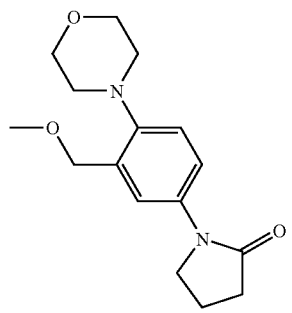
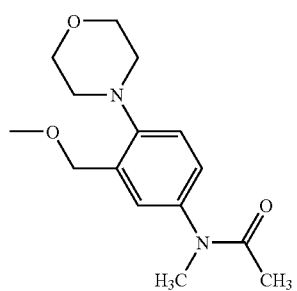
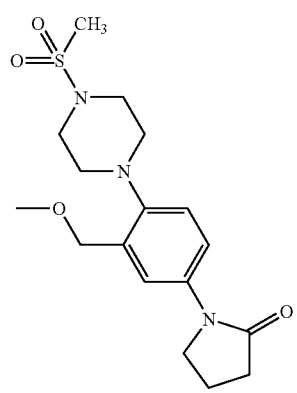
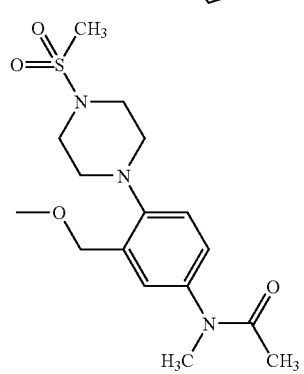
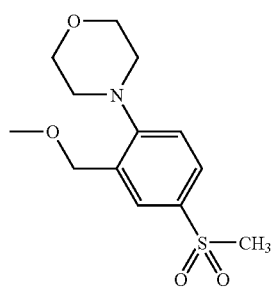
-continued
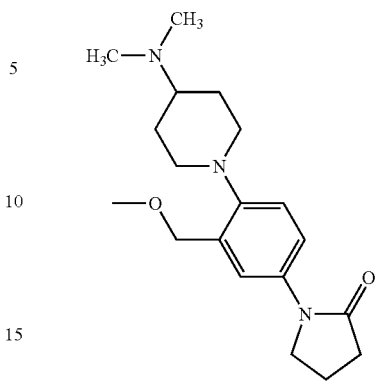
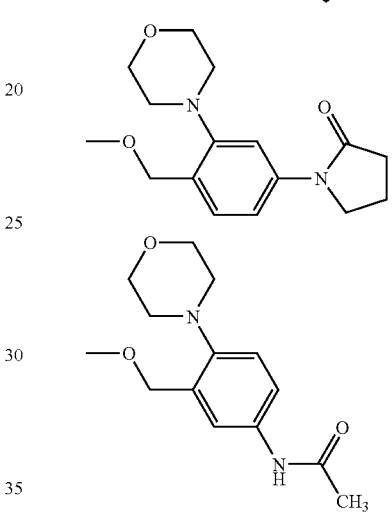
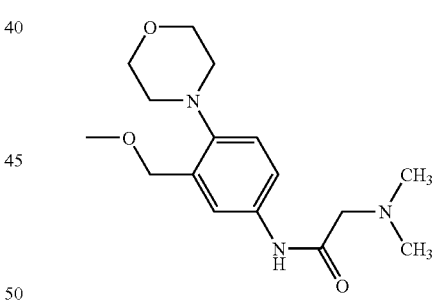
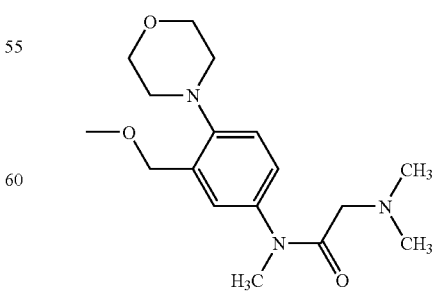

-continued

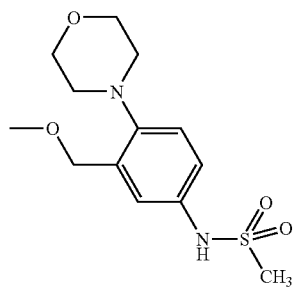

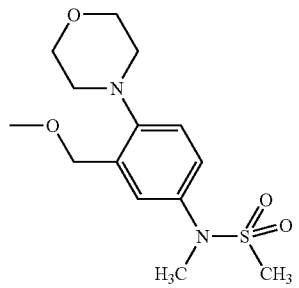

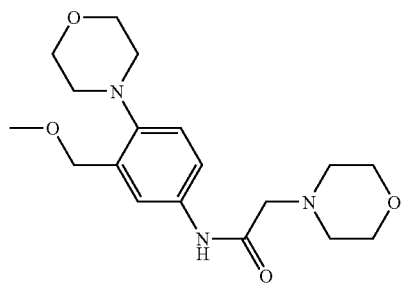

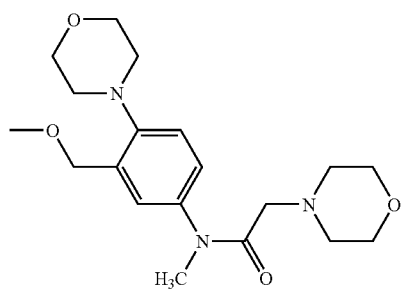

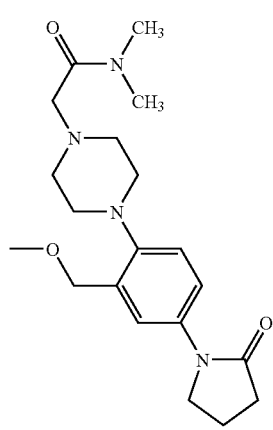

-continued

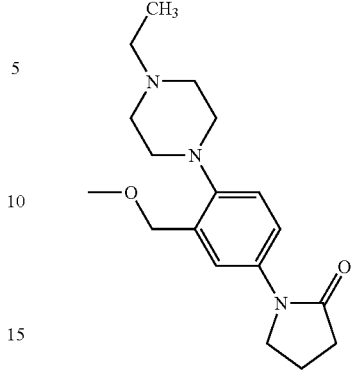

and the like can be more specifically mentioned.

In the formula [I], moreover, a compound represented by the following formula [I-a], [I-b], [I-c] or [I-d] is particularly preferable.

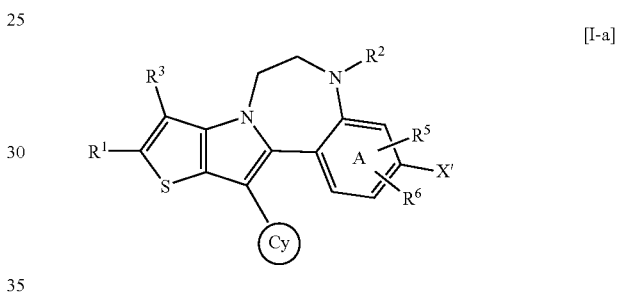

[I-a]

wherein X' is a hydrogen atom, a halogen atom, "a $C_{1-6}$ alkyl group optionally substituted by 1 to 3 substituents selected from group A" or "—$OR^{d1}$", and other symbols are as defined above.

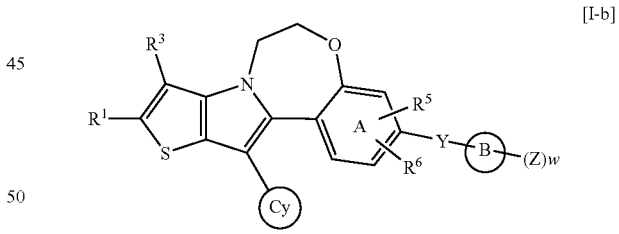

[I-b]

wherein each symbol is as defined above.

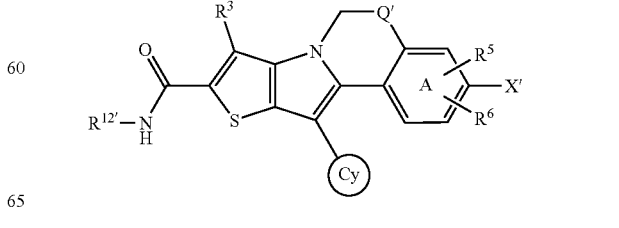

[I-c]

wherein

Q' is —CH$_2$—O—# or —CH$_2$—N(R$^{2"}$)-# wherein # shows the side to be bonded to ring A, R$^{2"}$ is a hydrogen atom or "a C$_{1-6}$ alkyl group optionally substituted by 1 to 3 substituents selected from group A", X' is a hydrogen atom, a halogen atom, "a C$_{1-6}$ alkyl group optionally substituted by 1 to 3 substituents selected from group A" or "—OR$^{d1}$", R$^{12'}$ is

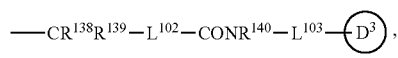

and other symbols are as defined above.

[I-d]

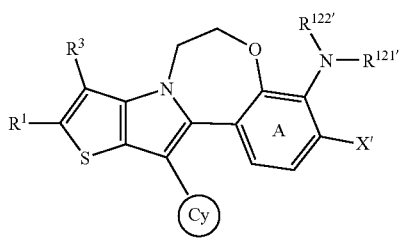

wherein

R$^{121'}$ and R$^{122'}$ are each independently "a heterocycle C$_{1-6}$ alkyl group optionally substituted by 1 to 5 substituents selected from group B", X' is a hydrogen atom, a halogen atom, "a C$_{1-6}$ alkyl group optionally substituted by 1 to 3 substituents selected from group A" or "—OR$^{d1}$", and other symbols are as defined above.

The "carboxyl-protecting group" only needs to be suitable for reaction conditions, and is capable of protecting and deprotecting and may be, for example, methyl; substituted methyl group such as methoxymethyl, methylthiomethyl, 2-tetrahydropyranyl, methoxyethoxymethyl, benzyloxymethyl, phenacyl, diacylmethyl, phthalimidomethyl etc.; ethyl; substituted ethyl group such as 2,2,2-trichloroethyl, 2-chloroethyl, 2-(trimethylsilyl)ethyl, 2-methylthioethyl, 2-(p-toluenesulfonyl)ethyl, t-butyl etc.; benzyl; substituted benzyl group such as diphenylmethyl, triphenylmethyl, p-nitrobenzyl, 4-picolyl, p-methoxybenzyl, 2-(9,10-dioxo)anthrylmethyl etc.; silyl group such as trimethylsilyl, t-butyldimethylsilyl, phenyldimethylsilyl etc.; and the like.

The "pharmaceutically acceptable salt" may be any as long as it forms a non-toxic salt with a compound of the above-mentioned formula [I]. Such salt can be obtained by reacting the compound with an inorganic acid, such as hydrochloric acid, sulfuric acid, phosphoric acid, hydrobromic acid and the like; or an organic acid, such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid, meglumine acid and the like; or an inorganic base, such as sodium hydroxide, potassium hydroxide, calcium hydroxide, magnesium hydroxide, ammonium hydroxide and the like; or an organic base, such as methylamine, diethylamine, triethylamine, triethanolamine, ethylenediamine, tris (hydroxymethyl)methylamine, guanidine, choline, cinchonine and the like; with an amino acid, such as lysine, arginine, alanine and the like. The present invention encompasses water-retaining product, hydrate and solvate of each compound.

The compounds of the above-mentioned formula [I] have various isomers. For example, E compound and Z compound are present as geometric isomers, and when the compound has asymmetric carbon(s), an enantiomer and a diastereomer are present as a stereoisomer due to the asymmetric carbon(s). When an axial chirality exists, a stereoisomer based thereon exists. A tautomer may be also present. The present invention encompasses all of these isomers and mixtures thereof.

The present invention also encompasses a prodrug and a metabolite of each compound.

A "prodrug" means a derivative of the compound of the present invention, which is capable of chemical or metabolic decomposition, which shows inherent efficacy by reverting to the original compound after administration to a body, and which includes salts and complexes without a covalent bond.

A prodrug is utilized for, for example, improving absorption by oral administration, or targeting of a target site.

As the modification moiety, a functional group having high reactivity in the compound of the present invention can be mentioned such as hydroxyl group, carboxyl group, amino group, thiol group and the like.

As preferable embodiments of the compound of the present invention, a compound having fine pharmacological activity (e.g., a compound having strong polymerase inhibitory activity, a compound having strong inhibitory activity on enzyme complex comprising polymerase, a compound having strong HCV replicon-inhibitory activity, a compound having high anti-HCV activity in HCV infected cells and the like), a compound having fine bioavailability (e.g., a compound showing high oral absorbability, a compound having high cell-permeability, a compound stable to metabolic enzyme, a compound with low binding ability to protein and the like), a highly safe compound (e.g., a compound free of immunogenicity or showing low allergic response, a compound free of or low in increase in bilirubin value, a compound showing low P450 (CYP)-inhibitory activity and the like) and the like can be mentioned.

When the inventive compound is used as a pharmaceutical preparation, the inventive compound is generally admixed with pharmaceutically acceptable carriers, excipients, diluents, binders, disintegrators, stabilizers, preservatives, buffers, emulsifiers, aromatics, coloring agents, sweeteners, thickeners, correctives, solubilizers known per se, and other additives such as water, vegetable oil, alcohol such as ethanol, benzyl alcohol and the like, polyethylene glycol, glycerol triacetate, gelatin, lactose, carbohydrate such as starch and the like, magnesium stearate, talc, lanolin, petrolatum and the like, and prepared into a dosage form of tablets, pills, powders, granules, suppositories, injections, eye drops, liquids, capsules, troches, aerosols, elixirs, suspensions, emulsions, syrups and the like, which can be administered systemically or topically and orally or parenterally.

While the dose varies depending on the age, body weight, general condition, treatment effect, administration route and the like, it is from 0.01 mg to 3 g for an adult per dose, which is given one to several times a day.

The "prophylaxis of hepatitis C" means, for example, administration of a pharmaceutical agent to an individual found to carry an HCV by a test and the like but without a symptom of hepatitis C, or to an individual who shows an improved disease state of hepatitis after a treatment of hepatitis C, but who still carries an HCV and is associated with a risk of recurrence of hepatitis.

The compound of the present invention is expected to provide a synergistic effect when concurrently used with other antiviral agents, antiinflammatory agents or immunostimulants.

The medicaments with the prospect of synergistic effect include, for example, interferon-α, interferon-β, interferon-γ, interleukin-2, interleukin-8, interleukin-10, interleukin-12, TNFα, recombinant or modified products thereof, agonists, antibodies, vaccines, ribozymes, antisense nucleotides and the like.

As evidenced in the combination therapy of anti-HIV agents, which is also called a cocktail therapy, the combined use of various anti-virus agents against viruses showing frequent genetic mutations is expected to show effect for suppressing emergence and increase of drug tolerant viruses. For example, two or three agents from HCV-IRES inhibitors, HCV-NS3 protease inhibitors, HCV-NS2NS3 protease inhibitors, HCV-NS5A inhibitors and HCV polymerase inhibitor may be used in combination. Specifically, the combined use with Ribavirin(R), interferon-α (IFN-α, Roferon (R), IntronA(R), Sumiferon(R), MultiFeron(R), Infergen(R), Omniferon(R), Pegasys(R), PEG-Intron A(R)), interferon-β (Frone(R), Rebif(R), AvoneX(R), IFNβMOCHIDA(R)), interferon-ω, 1-β-L-ribofuranosyl-1H-1,2,4-triazole-3-carboxamide, 16α-bromo-3β-hydroxy-5α-androstan-17-one, 1H-imidazole-4-ethanamide dihydrochloride, HCV ribozyme Heptazyme(R), polyclonal antibody Civacir(R), lactoferrin GPX-400, (1S,2R,8R,8aR)-1,2,8-trihydroxyoctahydroindolizidinium chloride, HCV vaccine (MTH-68/B, Innivax C(R), Engerix B(R)), antisense oligonucleotide ISIS-14803, HCV-RNA transcriptase inhibitor VP-50406, tetrachlorodecaoxide (high concentration Oxoferin(R)), tetrahydrofuran-3-yl (S)—N-3-[3-(3-methoxy-4-oxazol-5-ylphenyl)ureido]benzylcarbamate, 4-amino-2-ethoxymethyl-α,α-dimethyl-1H-imidazo[4,5-c]quinoline-1-ethanol, interleukin-2 (Proleukin(R)), thymosin α1 and the like is exemplified, wherein (R) shows product names.

Furthermore, the combined use with the compounds disclosed in JP-A-08-268890, JP-A-10-101591, JP-A-07-069899, WO99/61613 and the like as HCV-IRES inhibitors; the compounds disclosed in WO98/22496, WO99/07733, WO99/07734, WO00/09543, WO00/09558, WO01/59929, WO98/17679, EP932617, WO99/50230, WO00/74768, WO97/43310, U.S. Pat. No. 5,990,276, WO01/58929, WO01/77113, WO02/8198, WO02/8187, WO02/8244, WO02/8256, WO01/07407, WO01/40262, WO01/64678, WO98/46630, JP-A-11-292840, JP-A-10-298151, JP-A-11-127861, JP-A-2001-103993, WO98/46597, WO99/64442, WO0/31129, WO01/32961, WO93/15730, U.S. Pat. No. 7,832,236, WO00/200400, WO02/8251, WO01/16379, WO02/7761 and the like as HCV protease inhibitors; the compounds disclosed in WO97/36554, U.S. Pat. No. 5,830,905, WO97/36866, U.S. Pat. No. 5,633,388, WO01/07027, WO00/24725 and the like as HCV helicase inhibitors; the compounds disclosed in WO00/10573, WO00/13708, WO00/18231, WO00/06529, WO02/06246, WO01/32153, WO01/60315, WO01/77091, WO02/04425, WO02/20497, WO00/04141 and the like as HCV polymerase inhibitors; the compounds disclosed in WO01/58877, JP-A-11-180981, WO01/12214 and the like as interferon agonists or enhancers; and the like is also exemplified.

In the case of combined administration, the compound of the present invention can be administered simultaneously with a pharmaceutical agent to be used in combination (hereinafter combination drug) or administered at certain time intervals. In the case of combined administration, a pharmaceutical composition containing the compound of the present invention and a combination drug can be administered. Alternatively, a pharmaceutical composition containing the compound of the present invention and a pharmaceutical composition containing a combination drug may be administered separately. The administration route of the compound of the present invention and that of the combination drug may be the same or different.

In the case of a combined administration, the compound of the present invention can be administered once a day or several times a day in a single dose of 0.1 mg to 1 g, or may be administered at a smaller dose. The combination drug can be administered at a dose generally used for the prevention or treatment of hepatitis C, for example, at a single dose of 0.2 mg to 0.8 mg. Alternatively, it may be administered at a smaller dose.

Inasmuch as HCV is known to be a virus associated with many genetic mutations, a compound effective for many genotypes is one of the preferable modes. If a compound ensures high blood concentration and sustention thereof when administered as a pharmaceutical agent to an animal infected with HCV, it is also one of the preferable modes. From these aspects, a compound having high inhibitory activity on both HCV type 1a and type 1b and high blood concentration is particularly preferable.

Examples of the production method of the compound to be used for the practice of the present invention are given in the following. However, the production method of the compound of the present invention is not limited to these examples.

Even if no directly corresponding disclosure is found in the following Production Methods, the steps may be modified for efficient production of the compound, such as introduction of a protecting group into a functional group with deprotection in a subsequent step, and changing the order of Production Methods and steps.

The treatment after reaction in each step may be conventional ones, for which typical methods, such as isolation and purification, crystallization, recrystallization, silica gel chromatography, preparative HPLC and the like, can be appropriately selected and combined.

REFERENCE EXAMPLE 1

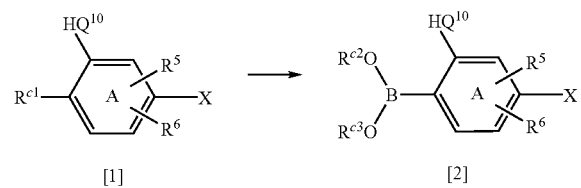

wherein $Q^{10}$ is O or NH, $R^{c1}$ is a leaving group such as bromine atom, iodine atom, —OTf (trifluoromethylsulfonyloxy group) and the like, —B(OR$^{c2}$) (OR$^{c3}$) is —B(OH)$_2$ or 4,4,5,5-tetramethyl-1,3,2-dioxaborolan-2-yl group, and other symbols are as defined above.

Compound [2] can be obtained from commercially available compound [1] or compound [1] obtained by a conventional method and a boric acid ester in the presence of a catalyst and a base.

As the boric acid ester, pinacolborane, bis(pinacolato)diboron and the like can be mentioned.

As the catalyst, palladium catalysts such as Pd(PPh$_3$)$_4$, Pd(dppb)Cl$_2$, PdCl$_2$(dppf)CH$_2$Cl$_2$, PdCl$_2$(PPh$_3$)$_2$, Pd(OAc)$_2$, PdCl$_2$, palladium black, palladium carbon and the like can be mentioned. As the ligand, triphenylphosphine, tri(2-tolyl)phosphine, (2-biphenyl)dicyclohexylphosphine and the like may be added.

As the base, strong bases such as ethylenediamine, sodium carbonate, barium hydroxide, potassium phosphate, cesium carbonate, sodium hydrogen carbonate, sodium tert-butoxide, potassium tert-butoxide, triethylamine, potassium acetate and the like are generally preferable.

In addition, compound [1] may be reacted with a boric acid ester such as triisopropyl borate, trimethyl borate and the like in the presence of n-butyllithium. Where necessary, a protecting group may be introduced into -$Q^{10}$H and the protected compound may be subjected to the reaction.

As a solvent, 1,4-dioxane, THF (tetrahydrofuran), toluene, DME (1,2-dimethoxyethane), water and the like can be mentioned.

REFERENCE EXAMPLE 2

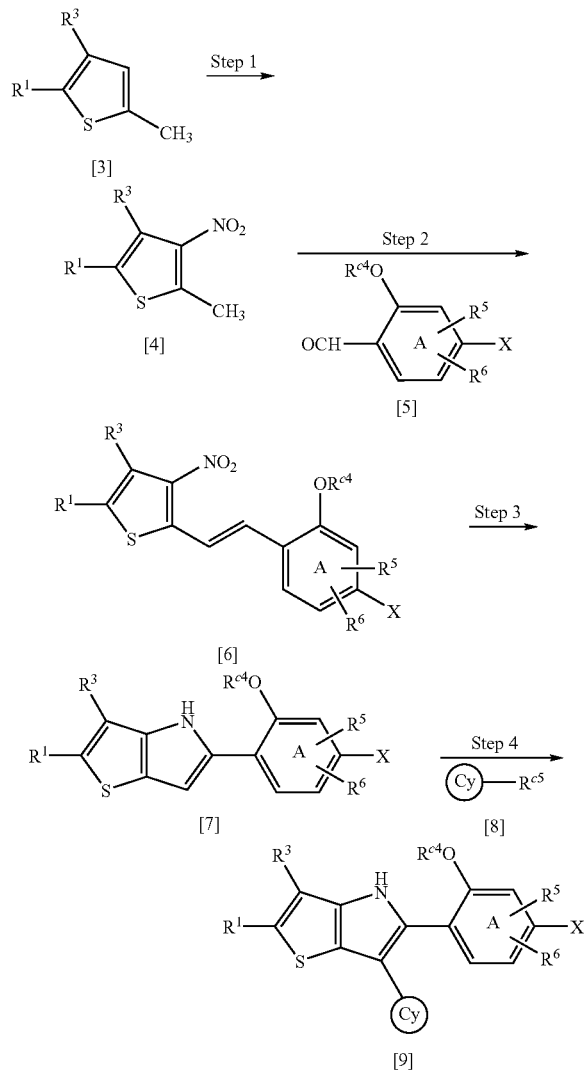

2-tetrahydropyranyl group and the like, $R^{c5}$ is a leaving group such as halogen atom (e.g., chlorine atom, bromine atom and the like), sulfonate (e.g., mesyloxy group, tosyloxy group and the like) and the like, and other symbols are as defined above.

Step 1

Compound [4] can be obtained by nitrating commercially available compound [3] or compound [3] obtained by a conventional method with a nitrating agent such as nitric acid, fuming nitric acid, mixed acid of conc. nitric acid and conc. sulfuric acid, and the like at room temperature or under cooling.

Step 2

Compound [6] can be obtained by reacting compound [4] with aldehyde compound [5] in a solvent such as methanol, ethanol, DMF (N,N-dimethylformamide), DMSO (dimethyl sulfoxide), THF, 1,4-dioxane, toluene etc., in the presence of a base such as pyrrolidine, diethylamine, potassium carbonate, sodium hydride, sodium methoxide, sodium ethoxide, potassium tert-butoxide etc. at room temperature or under heating.

Step 3

Compound [7] can be obtained by cyclizing compound [6] by heating in a solvent such as ethanol, methanol, toluene, DMF, DMSO, pyridine, naphthalene, chloroform, acetic acid, mesitylene etc. or without solvent in the presence of phosphorous acid ester such as triethyl phosphite etc.

Step 4

Compound [9] can be obtained by reacting compound [7] with compound [8] in a solvent such as DMF, DMSO, 1,4-dioxane, acetonitrile, ethanol, THF etc., in the presence of a base such as sodium hydride, sodium hydroxide, potassium hydroxide, potassium carbonate, cesium carbonate, sodium ethoxide, potassium tert-butoxide etc. under ice-cooling to heating.

REFERENCE EXAMPLE 3

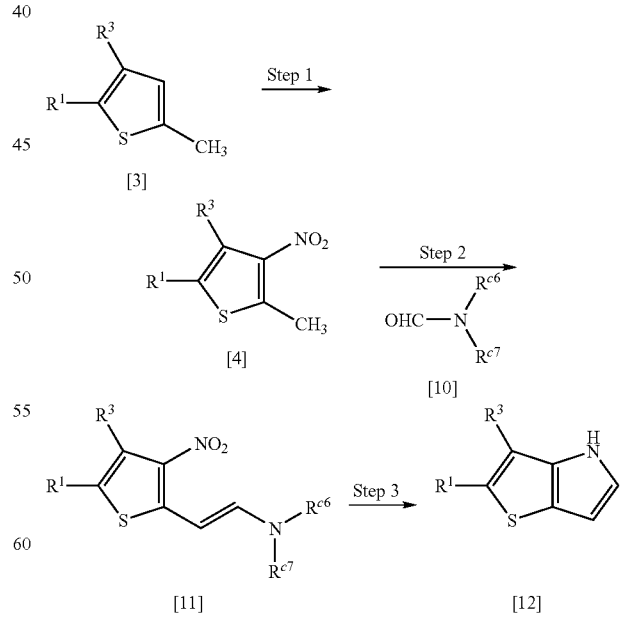

wherein $R^{c4}$ is a hydrogen atom or hydroxyl-protecting group such as tert-butyldimethylsilyl group, acetyl group, benzyl group, methoxymethyl group, methoxyethoxymethyl group, wherein $R^{c6}$ and $R^{c7}$ are $C_{1-6}$ alkyl groups such as methyl group, ethyl group etc., and other symbols are as defined above.

223

Step 1

Compound [4] can be obtained by nitrating compound [3] in the same manner as in Step 1 of Reference Example 2.

Step 2

Compound [11] can be obtained by reacting compound [4] with aldehyde compound [10] or its acetal form in a solvent such as methanol, ethanol, DMF, DMSO, THF, 1,4-dioxane, toluene etc. or without solvent, at room temperature or under heating.

Step 3

Compound [12] can be obtained by cyclizing compound [11] by heating in a solvent such as methanol, ethanol, THF, ethyl acetate, acetic acid, water etc. or in a mixed solvent thereof, in the presence of a catalyst such as palladium carbon, palladium hydroxide, platinum oxide, Raney-nickel etc. at room temperature or under heating.

REFERENCE EXAMPLE 4

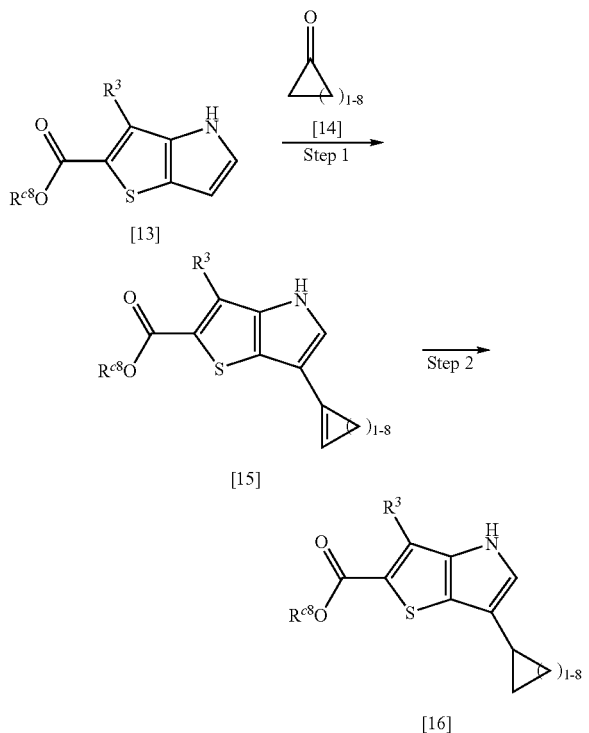

wherein $R^{c8}$ is a hydrogen atom or carboxyl-protecting group such as methyl group, ethyl group, tert-butyl group, benzyl group and the like, and compound [14] is, for example, a compound wherein cycloalkyl group having 3 to 10 carbon atoms is substituted by oxo group, such as cyclopentanone, cyclohexanone and the like.

Step 1

Compound [15] can be obtained by reacting commercially available compound [13] or compound [13] obtained by a conventional method with compound [14] in the presence of a base, or under aldol reaction conditions.

As the base, preferably, sodium methoxide, sodium ethoxide, lithium diisopropylamide, sodium hydroxide, potassium hydroxide, sodium hydride and the like can be mentioned.

224

As a solvent, alcohol solvent such as methanol, ethanol and the like, THF, 1,4-dioxane, DMF, DMSO, DMA (dimethylacetamide), water and a mixed solvent thereof and the like can be mentioned.

As the reaction temperature, $-20°$ C. to $120°$ C. is preferable.

In addition, for a reaction under acidic conditions, in a mixed solvent of acetic acid and phosphoric acid, they may be treated at a reaction temperature of from $15°$ C. to $120°$ C.

Step 2

Compound [16] can be obtained by hydrogenation of compound [15] in a solvent such as methanol, ethanol, THF, ethyl acetate, acetic acid, formic acid, water and a mixed solvent thereof and the like, in the presence of a catalyst such as palladium carbon, palladium hydroxide, palladium hydroxide on carbon, platinum oxide, Raney-nickel and the like, at room temperature or under heating.

REFERENCE EXAMPLE 5

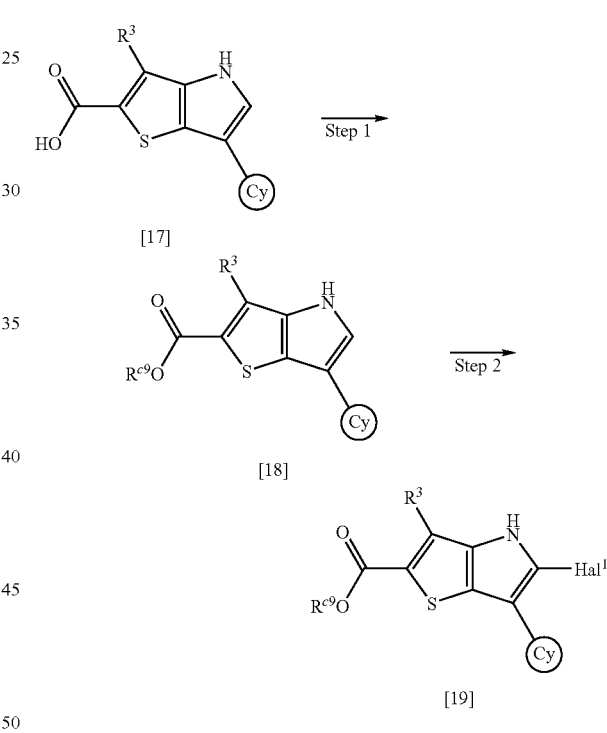

wherein $R^{c9}$ is carboxyl-protecting group such as methyl group, ethyl group, tert-butyl group, benzyl group and the like, $Hal^1$ is halogen atom such as bromine atom, iodine atom and the like, and other symbols are as defined above.

Step 1

Compound [18] can be obtained by introducing a protecting group into a carboxyl group of compound [17] obtained by a conventional method or in the same manner as in Reference Example 4.

Where necessary, a protecting group may be introduced into a nitrogen atom of thienopyrrole.

Step 2

Compound [19] can be obtained by halogenating compound [18] with a halogenating agent.

As the halogenating agent, bromine, N-bromosuccinimide, pyridine tribromide, dibromohydantoin, pyridinium hydrobromide perbromide, an iodide thereof and the like can be mentioned.

As a solvent, halogenated hydrocarbon solvents (dichloromethane, chloroform, carbon tetrachloride etc.), hydrocarbon solvents (toluene etc.), ether solvents (1,4-dioxane, DME, THF etc.), acetic acid, ethyl acetate, isopropyl alcohol or a mixed solvent thereof and the like can be mentioned.

As the reaction temperature, from −40° C. to 100° C. is preferable.

Production Method 1-1

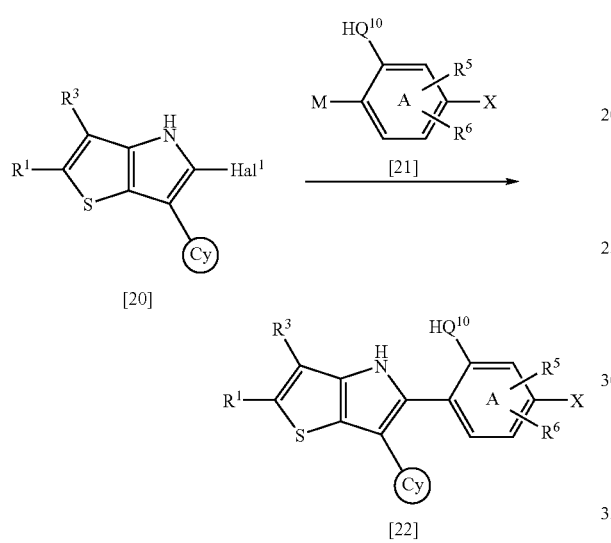

Production Method 1-2

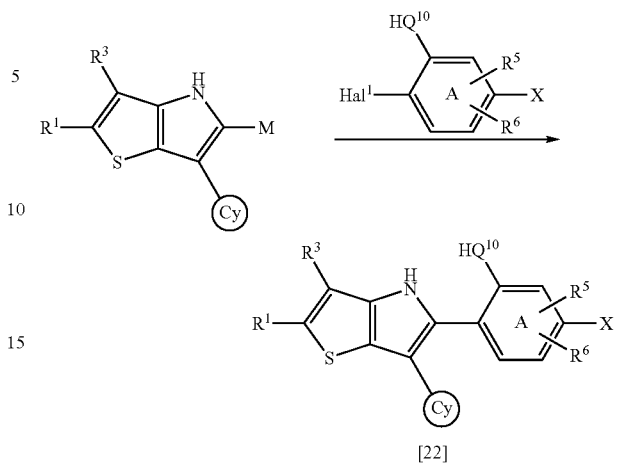

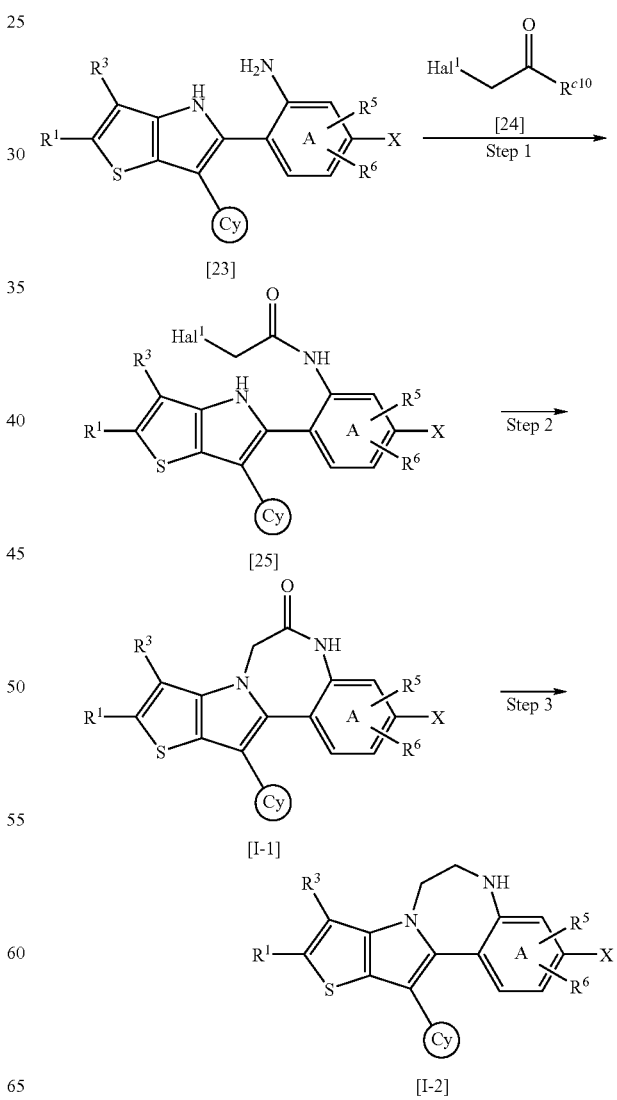

wherein compound [21] is a metal compound, wherein the metal moiety M includes boron, zinc, tin, magnesium, lithium and the like, for example, phenylboronic acid derivative, and other symbols are as defined above.

Compound [22] can be obtained by reacting compound [20] obtained by a conventional method or in the same manner as in Reference Example 5 with compound [21] obtained by a conventional method or in the same manner as in Reference Example 1 using a Suzuki reaction.

For example, compound [22] can be obtained by a reaction in a solvent such as DMF, acetonitrile, alcohol solvents (methanol, ethanol etc.), DME, THF, toluene, water, or a mixed solvent thereof and the like in the presence of a palladium catalyst such as tetrakis(triphenylphosphine)palladium, bis(triphenylphosphine)palladium(II) dichloride, palladium acetate—triphenylphosphine and the like, a nickel catalyst such as nickel chloride, 1,3-bis(diphenylphosphino)propane nickel(II) chloride and the like and a base such as sodium carbonate, potassium carbonate, potassium hydrogen carbonate, sodium hydrogen carbonate, potassium phosphate, triethylamine, potassium fluoride, cesium fluoride, sodium hydrogen phosphate, cesium carbonate and the like, at room temperature or under heating.

The reactivity may be increased by adding lithium chloride and the like.

In addition, the following compounds may be used instead of the above-mentioned compounds [20] and [21].

wherein $R^{c10}$ is halogen atom such as chlorine atom, bromine atom and the like or hydroxyl group, and other symbols are as defined above.

Step 1

Compound [25] can be obtained by reacting compound [23] with compound [24].

When $R^{c10}$ is a hydroxyl group, compound [23] is condensed with carboxylic acid compound [24] in a solvent such as DMF, acetonitrile, THF, chloroform, ethyl acetate, methylene chloride, toluene and the like by adding a condensing agent such as dicyclohexylcarbodiimide, 1-ethyl-3-(3-dimethylaminopropyl)carbodiimide hydrochloride, diphenylphosphoryl azide, benzotriazol-1-yloxytripyrrolidinophosphonium hexafluorophosphate and the like and, where necessary, N-hydroxysuccinimide, 1-hydroxybenzotriazole and the like to give amide compound [25]. The condensation may be carried out in the presence of a base such as triethylamine, diisopropylethylamine, pyridine and the like. Alternatively, amide compound [25] can be obtained from compound [24] as follows. The carboxylic acid compound [24] is converted to an acid halide with thionyl chloride, oxalyl chloride and the like (a catalytic amount of DMF may be added), or to an active ester of compound [24] (e.g., converting to a mixed acid anhydride with ethyl chlorocarbonate and the like), which is then reacted with compound [23] in the presence of a base, such as triethylamine, potassium carbonate, pyridine and the like, or in an amine solvent such as pyridine and the like, to give amide compound [25]. For the reaction of active ester with compound [23], dimethylaminopyridine may be added.

When $R^{c10}$ is halogen atom such as chlorine atom, bromine atom and the like, compound [24] is reacted with compound [23] in the presence or absence of a base such as triethylamine, potassium carbonate, pyridine and the like, or in an amine solvent such as pyridine and the like to give amide compound [25].

To increase selectivity of reaction with amino group, acetic acid and sodium acetate may be added at an equivalent ratio.

Step 2

Compound [I-1] can be obtained by condensation cyclization of compound [25] in a solvent such as ethanol, DMF, DMA, DMSO, acetone, acetonitrile, 1,4-dioxane, THF, toluene, water and the like, in the presence or absence of a base such as potassium hydroxide, sodium hydride, potassium carbonate, triethylamine, sodium ethoxide, potassium tert-butoxide and the like, under cooling to under heating.

Step 3

Compound [I-2] can be obtained by reducing compound [I-1] by a conventional method.

For example, reduction is carried out using a borohydride (e.g., sodium borohydride, sodium triacetoxyborohydride and the like), borane-THF complex and the like as a reducing agent. In this case, an acid such as acetic acid, hydrochloric acid and the like may be added.

As a preferable solvent, ether solvents (1,4-dioxane, THF etc.), alcohol solvents (methanol, ethanol etc.), polar solvents (DMF, DMSO, acetonitrile etc.), halogenated hydrocarbon solvents (dichloromethane, chloroform etc.), hydrocarbon solvents (benzene, toluene etc.), ester solvents (ethyl acetate, butyl acetate etc.), water, or a mixed solvent thereof and the like can be mentioned.

Production Method 2

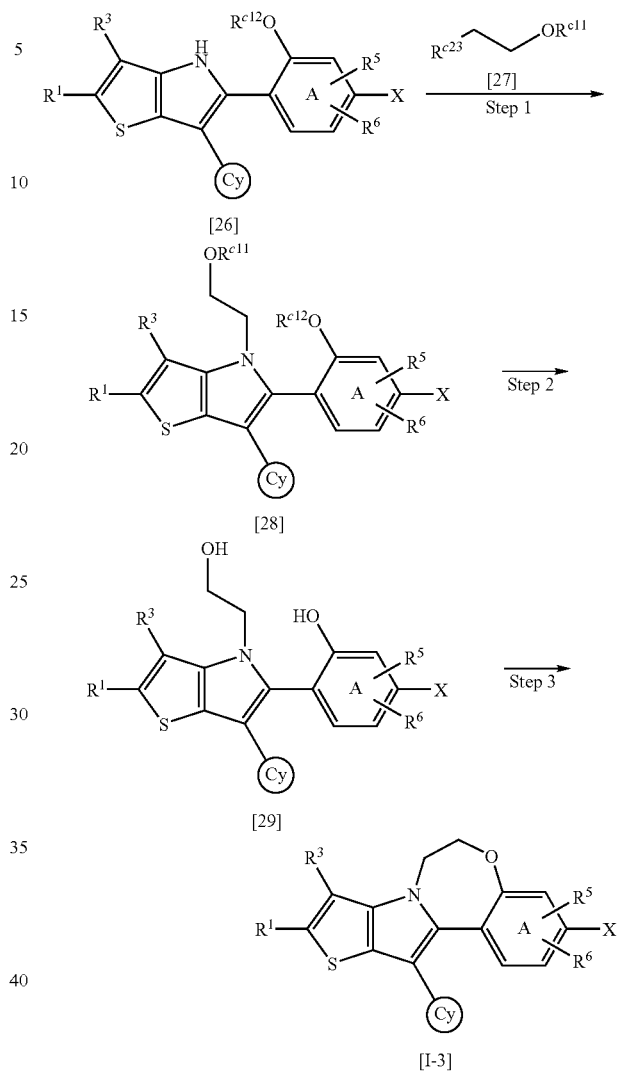

wherein $R^{c11}$ and $R^{c12}$ are the same or different and each is hydroxyl-protecting group, $R^{c23}$ is a leaving group such as halogen atom (e.g., chlorine atom, bromine atom, iodine atom and the like), sulfonate (e.g., mesyloxy group, tosyloxy group and the like) and the like, and other symbols are as defined above.

Step 1

Compound [28] can be obtained by reacting compound [26] with compound [27] in the same manner as in Production Method 1-2, Step 2.

Step 2

Compound [29] can be obtained by removing hydroxyl-protecting group of compound [28] by a conventional method.

As the hydroxyl-protecting group, tert-butyldimethylsilyl group, acetyl group, benzyl group, methoxymethyl group, methoxyethoxymethyl group, 2-tetrahydropyranyl group and the like can be mentioned.

For example, when $R^{c11}$ and $R^{c12}$ are methoxyethoxymethyl group or 2-tetrahydropyranyl group, deprotection is conducted by a method such as treatment with hydrochloric acid at room temperature in a mixed solvent of tetrahydrofuran and methanol and the like.

In addition, when $R^{c11}$ and $R^{c12}$ are benzyl groups, deprotection is conducted by a method such as treatment with a palladium catalyst at room temperature in a mixed solvent of tetrahydrofuran and methanol under a hydrogen atmosphere, treatment under acidic conditions of hydrobromide/acetic acid and the like, or reaction with an acid such as hydrochloric acid, sulfuric acid, hydrobromic acid and the like in an acetic acid solvent, and the like.

Step 3

Compound [I-3] can be obtained by Mitsunobu reaction using compound [29] in a solvent such as DMF, acetonitrile, THF and the like, using triphenylphosphine-diethyl azodicarboxylate, triphenylphosphine-diisopropyl azodicarboxylate and the like.

In addition, compound [I-3] can be also obtained by mesylation, tosylation, trifluoromethylsulfonylation of hydroxyl group of compound [29], followed by reaction in the presence of a strong base such as sodium hydride, potassium hydride and the like.

Production Method 3 is ring $D^1$ containing NH as a component constituting a ring such as piperidine, piperazine, pyrrolidine, morpholine, thiomorpholine, azepane and the like, u1' is an integer of 1 to 6, and other symbols are as defined above.

Step 1

Compound [I-4] can be obtained by reacting compound [I-2] obtained by the above-mentioned Production Method with compound [30] in a solvent such as DMF, DMSO, acetonitrile, ethanol, THF and the like or a mixed solvent thereof, in the presence of a base such as sodium hydride, sodium hydroxide, potassium hydroxide, potassium carbonate, sodium ethoxide, potassium tert-butoxide and the like, under ice-cooling to under heating. In addition, potassium iodide or tetrabutylammonium iodide may be used to increase reactivity.

In this Production Method, $R^{2'}$ may be any group as long as it is bonded to nitrogen atom of fused ring via carbon atom, wherein $C_{1-6}$ alkyl group optionally substituted by 1 to 3 substituents selected from group E, as well as, for example, $L^2$ of $-L^2$-ring $D^2$-$L^1$-ring $D^1$ and -$L^2$-$CH_2$-$L^1$-ring $D^1$, and $L^1$ of -$L^1$-$(CH_2)_u$-$L^3$-$(CH_2)_v$-ring $D^1$ and -$L^1$-ring $D^1$ may be $C_{1-6}$ alkylene, $C_{2-6}$ alkenylene, —$(CH_2)_{u1}$—, —O—$(CH_2)_{v1}$—, —$(CH_2)_{u1}$—, —S—$(CH_2)_{v1}$—, —$(CH_2)_{u1}$, —$NR^{L1}$—

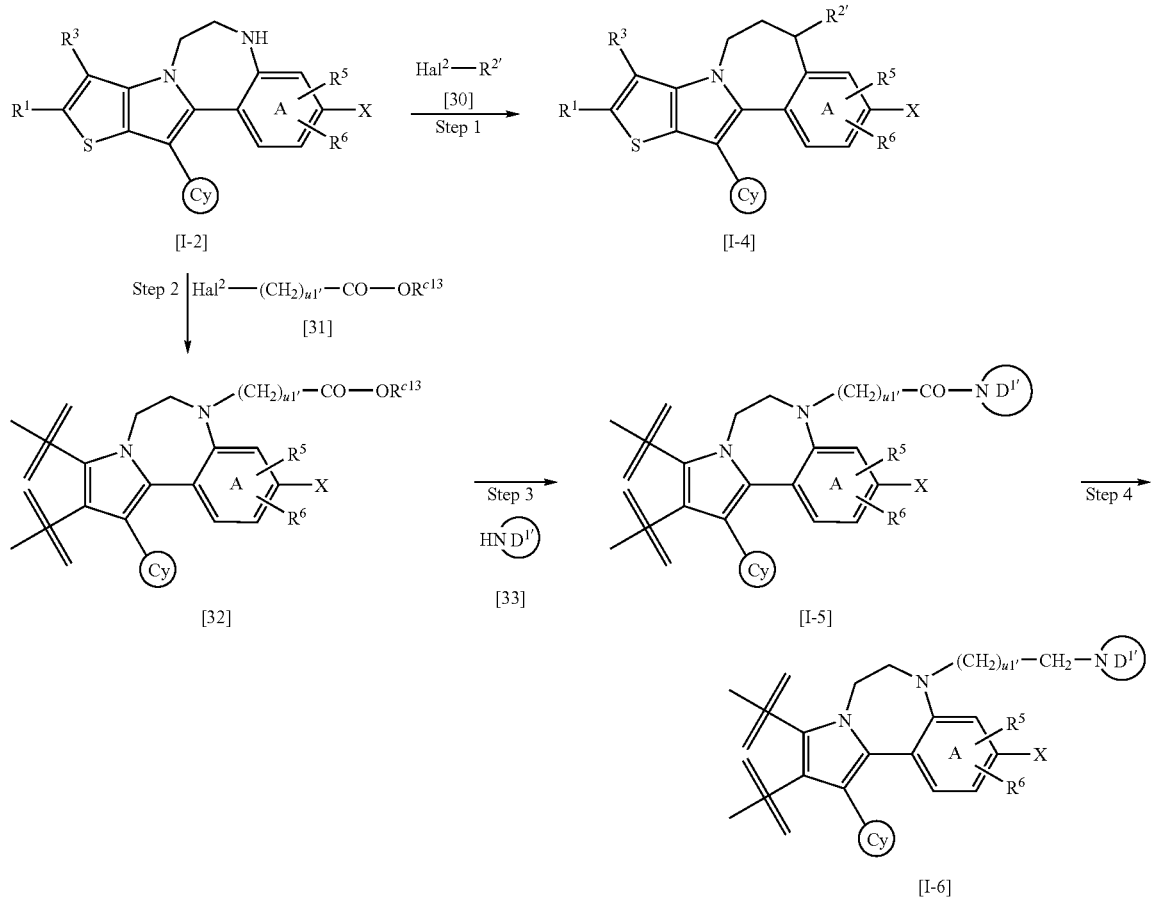

wherein $R^{2'}$ is $C_{1-6}$ alkyl group optionally substituted by 1 to 3 substituents selected from group E and the like, $Hal^2$ is halogen atom such as chlorine atom, bromine atom, iodine atom and the like, $R^{c13}$ is carboxyl-protecting group, ring $D^{1'}$ $(CH_2)_{v1}$—, —$(CH_2)_{u1}$, —CO—$(CH_2)_{v1}$—, —$(CH_2)_{u1}$, —$CONR^{L2}$—$(CH_2)_{v1}$—, —$(CH_2)_{u1}$, —$NR^{L2}CO_2$— $(CH_2)_{v1}$—, —$(CH_2)_{u1}$, —$NR^{L2}CONR^{L3}(CH_2)_{v1}$—, —$(CH_2)_{u1}$, —$NR^{L2}CO$—$(CH_2)_{v1}$, —$(CH_2)_{u1}$, —NR$^{L2}$SO$_2$—(CH$_2$)$_{v1}$—, —(CH$_2$)$_{u1}$, —SO$_2$—(CH$_2$)$_{v1}$—, —(CH$_2$)$_{u1}$, —SO$_2$NR$^{L2}$—(CH$_2$)$_{v1}$— or —(CH$_2$)$_{u1}$—N$^+$R$^{L2}$R$^{L2'}$—(CH$_2$)$_{v1}$— wherein each symbol is as defined above.

In addition, Hal$^2$-R$^{2\cdot}$ may be Hal$^2$-ring D$^1$ or Hal$^2$-ring D$^2$-L$^1$-ring D$^1$.

Step 2

Compound [32] can be obtained by reacting compound [I-2] with compound [31] in the same manner as in Step 1 above.

Step 3

Compound [I-5] can be obtained by eliminating carboxyl-protecting group R$^{c13}$ of compound [32] by a conventional method, and then reacting the resulting compound [32] with compound [33] in the same manner as in Production Method 1-2, Step 1.

For example, when R$^{c13}$ is tert-butyl group, deprotection can be conducted by treatment with trifluoroacetic acid in a solvent such as methylene chloride, chloroform and the like.

Step 4

Compound [I-6] can be obtained by reducing compound [I-5] in the same manner as in Production Method 1-2, Step 3.

Production Method 4

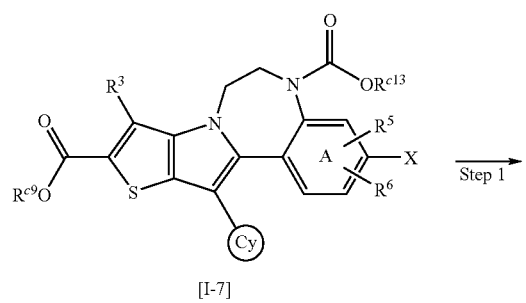

[I-7]

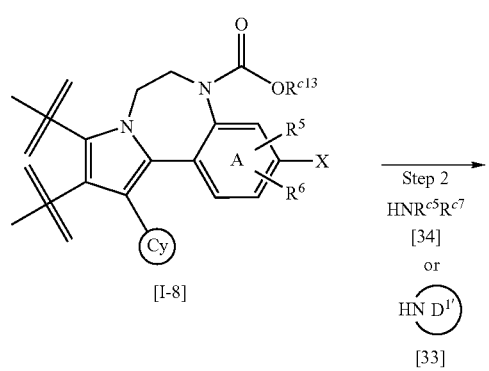

[I-8]

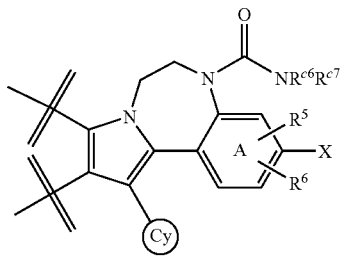

[I-9]

or

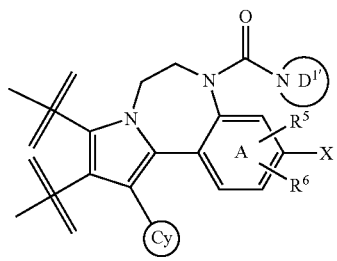

[I-10]

wherein each symbol is as defined above.

Step 1

Compound [I-8] can be obtained by deprotection of carboxyl-protecting group R$^{c13}$ of compound [I-7] obtained by the above-mentioned Production Method, by a conventional method.

Here, a reaction under conditions free from deprotection of R$^{c9}$ is preferable. For example, when R$^{c9}$ is methyl group or ethyl group and R$^{c13}$ is tert-butyl group, deprotection can be conducted by treatment with trifluoroacetic acid in a solvent such as methylene chloride, chloroform and the like.

Step 2

Compounds [I-9] and [I-10] can be obtained by reacting compound [I-8] with compounds [34] and [33], respectively, in the same manner as in Production Method 1-2, Step 1.

Production Method 5

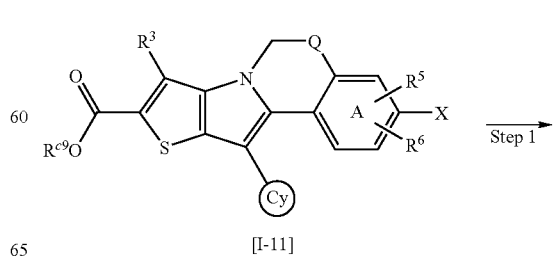

[I-11]

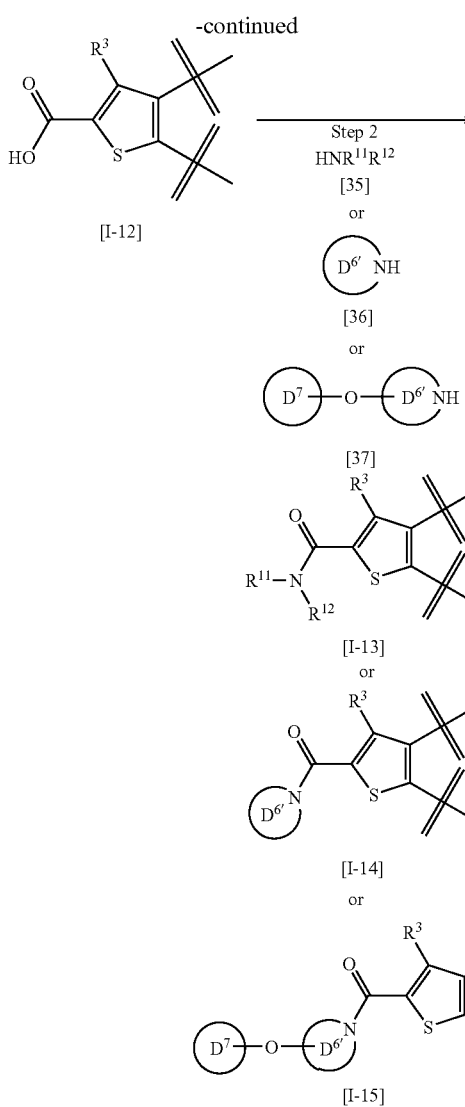

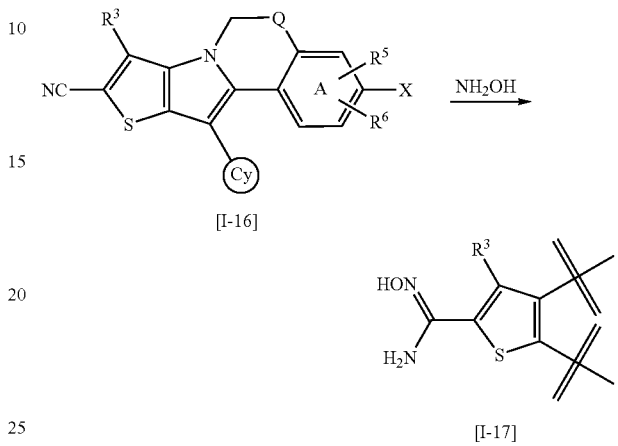

Production Method 6

In this Production Method, conversion of the substituent $R^1$ on the fused ring is shown. This production method can also be used for conversion of $R^2$ or $R^3$.

Production Method 6-1

Conversion of cyano group to substituted amidino group wherein each symbol is as defined above.

The compound [I-16] obtained in the same manner as in the above-mentioned Production Method is reacted with hydroxylamine in a solvent such as water, methanol, ethanol, THF, DMF and the like to give compound [I-17]. When a salt of hydroxylamine such as hydrochloride and the like-is used, the reaction is carried out in the presence of a base such as sodium hydrogen carbonate, sodium hydroxide, triethylamine and the like.

Production Method 6-2

Conversion of sulfonic acid ester moiety to sulfonic acid

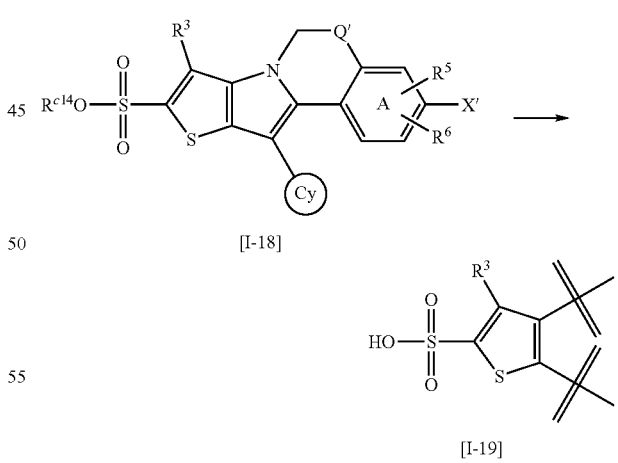

wherein ring $D^6$ is ring $D^6$ containing NH as a component constituting a ring such as piperidine, piperazine, pyrrolidine and the like, and each symbol is as defined above.

Step 1

Compound [I-12] can be obtained by hydrolysis of compound [I-11] obtained in the same manner as in the above-mentioned lo Production Methods, in a solvent such as methanol, ethanol, THF, 1,4-dioxane, water and the like, or a mixed solvent thereof under basic conditions of sodium hydroxide, potassium hydroxide, potassium carbonate, lithium hydroxide and the like or acidic conditions of hydrochloric acid, sulfuric acid and the like.

Step 2

Compounds [I-13], [I-14] and [I-15] can be obtained by reacting compound [I-12] with compounds [35], [36] and [37], respectively, in the same manner as in Production Method 1-2, Step 1.

For compounds [35], [36] and [37], commercially available products or compounds obtained by conventional methods or compounds obtained by the methods described in WO02/04425, WO03/007945, WO03/010141 and WO2005/080399 can be used.

wherein $R^{c14}$ is $C_{1-6}$ alkyl, and other symbols are as defined above.

The compound [I-18] obtained in the same manner as in the above-mentioned Production Method is reacted with iodide salt such as sodium iodide, lithium iodide and the like, bromide salt such as sodium bromide, tetrabutylammonium bromide and the like, amine such as pyridine, trimethylamine, triazole and the like, phosphine such as triphenylphosphine and the like in a solvent such as DMF, DMSO, acetonitrile, methanol, ethanol, water and the like with heating to give compound [I-19].

Production Method 7

This Production Method relates to conversion of the substituent X on the ring A.

Production Method 7-1

Conversion of hydroxyl group to ether

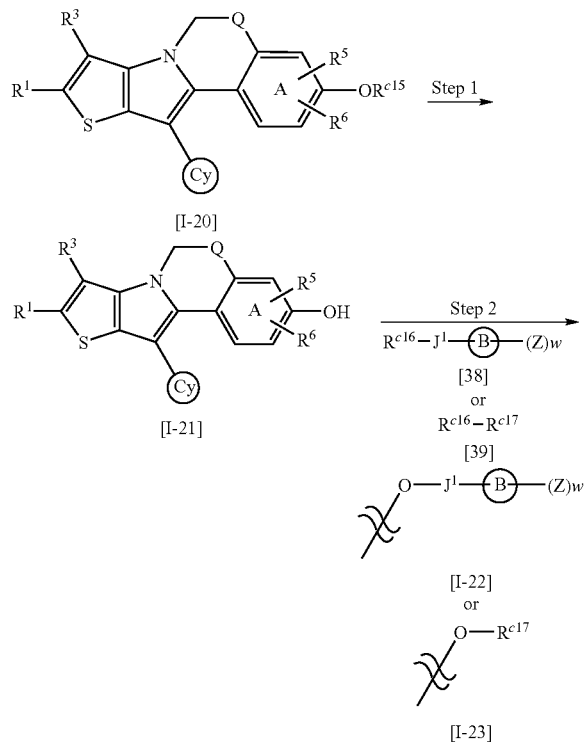

wherein $R^{c15}$ is hydroxyl-protecting group such as acetyl, benzyl and the like, Rc16 is halogen atom such as chlorine atom, bromine atom, iodine atom and the like, hydroxyl group or leaving group such as sulfonate (e.g., mesyloxy group, tosyloxy group and the like), and the like, $R^{c17}$ is a group selected from group F, a $C_{2-6}$ alkenyl group optionally substituted by 1 to 3 substituents selected from group A or a $C_{2-6}$ alkynyl group optionally substituted by 1 to 3 substituents selected from group A corresponding to $R^{d1}$, $J^1$ is a bond, $C_{1-6}$ alkylene, $C_{2-6}$ alkenylene or *—$(CH_2)_m$—$Y^2$—$(CH_2)_n$—, wherein * shows the side to be bonded to $R^{c16}$, m is an integer of 1 to 6, and other symbols are as defined above.

Step 1

Compound [I-21] can be obtained by deprotection of compound [I-20] obtained in the same manner as in the above-mentioned Production Method, by a conventional method.

For example, when $R^{c15}$ is acetyl group, compound [I-20] is hydrolyzed, in a solvent such as methanol, ethanol, THF, 1,4-dioxane and the like, or a mixed solvent thereof, or a mixed solvent of such solvent and water, under basic conditions of sodium hydroxide, potassium hydroxide, potassium carbonate, lithium hydroxide, sodium methoxide, sodium ethoxide and the like or acidic conditions of hydrochloric acid, sulfuric acid and the like to give compound [I-21].

When $R^{c15}$ is benzyl group, compound [I-20] is subjected to catalytic reduction in a solvent such as methanol, ethanol, THF, ethyl acetate, acetic acid, water and the like in the presence of palladium carbon, or by reacting with an acid such as hydrobromic acid and the like in a solvent such as acetic acid to give compound [I-21].

Step 2

When $R^{c16}$ of compound [38] is halogen atom, mesyloxy group or tosyloxy group, compound [I-21] is reacted with compound [38] in a solvent such as DMF, DMSO, acetonitrile, ethanol, THF and the like in the presence of a base such as sodium hydride, sodium hydroxide, potassium hydroxide, potassium carbonate, sodium ethoxide, potassium tert-butoxide and the like at room temperature or with heating to give compound [I-22]. The reaction may be accelerated by adding sodium iodide, potassium iodide or tetrabutylammonium iodide.

When $R^{c16}$ of compound [38] is hydroxyl group, the hydroxyl group of compound [38] is converted to halogen atom with thionyl chloride, phosphorus trichloride, phosphorus tribromide, carbon tetrabromide—triphenylphosphine, N-bromosuccinimide and the like and reacted with compound [I-21] by the aforementioned method to give compound [I-22]. In this case, compound [I-21] may be subjected to Mitsunobu reaction with compound [38] in a solvent such as DMF, acetonitrile, THF and the like using triphenylphosphine—diethyl azodicarboxylate and the like to give compound [I-22].

The compound [I-23] can be obtained in the same manner as above from compound [I-21] and compound [39].

Production Method 7-2

Conversion of nitro group to substituted amino group

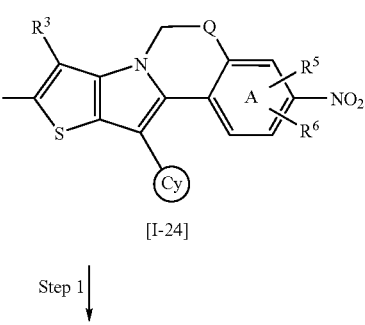

Step 1

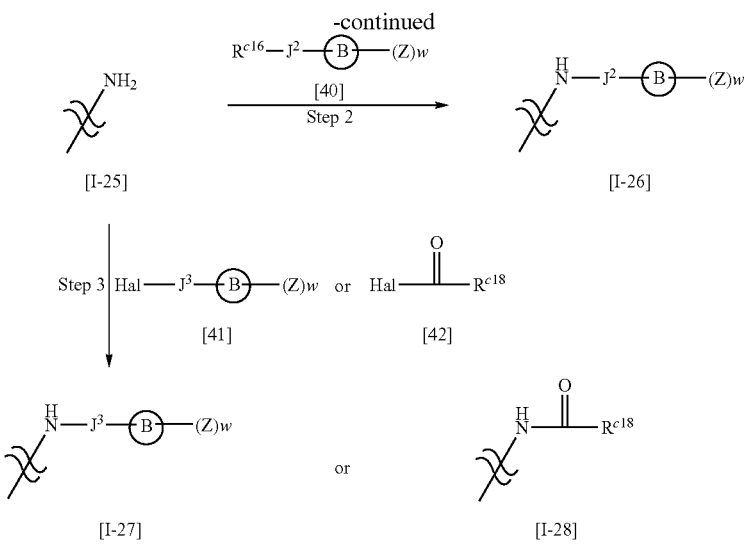

wherein Hal is halogen atom such as chlorine atom, bromine atom and the like, $R^{c18}$ is a $C_{1-6}$ alkyl group, $J^2$ is —$(CH_2)_n$— or *—$(CH_2)_m$—$Y^2$—$(CH_2)_n$— and m is an integer of 1 to 6, wherein * shows the side to be bonded to $R^{c16}$, $J^3$ is *—CO—$(CH_2)_m$—$Y^2$—$(CH_2)_n$—, *—$CO_2$—$(CH_2)_m$—$Y^2$—$(CH_2)_n$—, *—$CONR^{y3}$—$(CH_2)_m$—$Y^2$—$(CH_2)_n$—, *—$SO_2$—$(CH_2)_m$—$Y^2$—$(CH_2)_n$—, *—CO—$(CH_2)_n$—, *—$CO_2$—$(CH_2)_n$—, *—$CONR^{y3}$—$(CH_2)_n$— or *—$SO_2$—$(CH_2)_n$—, wherein * shows the side to be bonded to Hal, and other symbols are as defined above.

Step 1

The compound [I-24] obtained in the same manner as in the above-mentioned Production Method, is hydrogenated in a solvent such as methanol, ethanol, THF, ethyl acetate, acetic acid, water and the like in the presence of a catalyst such as palladium carbon, palladium hydroxide, platinum oxide, Raney nickel and the like at room temperature or with heating to give compound [I-25]. In addition, compound [I-24] is reduced with a reducing agent such as zinc, iron, tin(II) chloride, sodium sulfite and the like, or reacted with hydrazine in the presence of iron(III) chloride to give compound [I-25]. The compound [I-25] can be also obtained by reacting compound [I-24] with sodium hydrosulfite under alkaline conditions.

Step 2

The compound [I-25] is alkylated with compound [40] in the same manner as in Step 2 of Production Method 7-1 to give compound [I-26].

Step 3

When $J^3$ of compound [41] is *—CO—$(CH_2)_m$—$Y^2$—$(CH_2)_n$—, *—$CO_2$—$(CH_2)_m$—$Y^2$—$(CH_2)_n$—, *—$CONR^{y3}$—$(CH_2)_m$—$Y^2$—$(CH_2)_n$—, *—CO—$(CH_2)_n$—, *—$CO_2$—$(CH_2)_n$— or *—$CONR^{y3}$—$(CH_2)_n$—, compound [I-25] is reacted with compound [41] in a solvent such as DMF, acetonitrile, THF, chloroform, ethyl acetate, methylene chloride, toluene and the like in the presence of a base such as triethylamine, potassium carbonate, pyridine and the like, or in an amine solvent such as pyridine in the presence of acetic acid and sodium acetate in an equivalent ratio to give compound [I-27].

When $J^3$ of compound [41] is *—$SO_2$—$(CH_2)_m$—$Y^2$—$(CH_2)_n$— or *—$SO_2$—$(CH_2)_n$—, compound [I-25] is sulfonylated with compound [41] in the same manner as above to give compound [I-27].

The compound [I-25] is acylated with compound [42] in the same manner as above to give compound [I-28].

This Production Method is applied in the same manner as above to give disubstituted compounds (tertiary amine) of compound [I-26], compound [I-27] and compound [I-28].

Production Method 7-3

Conversion of carboxylic acid moiety to amide

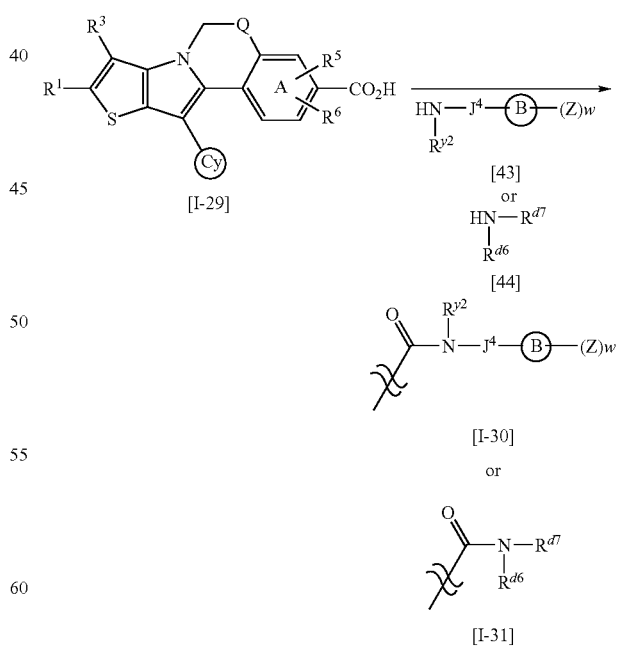

wherein $J^4$ is —$(CH_2)_n$— or #—$(CH_2)_m$—$Y^2$—$(CH_2)_n$— wherein # shows the side to be bonded to amine, and other symbols are as defined above.

The carboxylic acid compound [I-29] obtained in the same manner as in the above-mentioned Production Method is condensed with amine compound [43] in a solvent such as DMF, acetonitrile, THF, chloroform, ethyl acetate, methylene chloride, toluene and the like using a condensing agent such as dicyclohexylcarbodiimide, 1-ethyl-3-(3-dimethylaminopropyl)carbodiimide hydrochloride, diphenylphosphoryl azide and the like and, where necessary, adding N-hydroxysuccinimide, 1-hydroxybenzotriazole and the like to give amide compound [I-30]. Alternatively, amide compound [I-30] can be obtained from compound [I-29] as follows. The carboxylic acid compound [I-29] is converted to an acid halide with thionyl chloride, oxalyl chloride and the like (a catalytic amount of DMF may be added), or to an active ester of carboxylic acid compound [I-29] (e.g., converting to a mixed acid anhydride with ethyl chlorocarbonate and the like), which is then reacted with amine compound [43] in the presence of a base such as triethylamine, potassium carbonate, pyridine and the like, to give amide compound [I-30]. For the reaction of active ester with compound [43], dimethylaminopyridine may be added.

Compound [I-31] can be obtained by reacting carboxylic acid compound [I-29] with amine compound [44] in the same manner as above.

Production Method 8

In this Production Method, additional substituent(s) is(are) introduced into ring B.

Production Method 8-1

Direct bonding of ring Z" to ring B

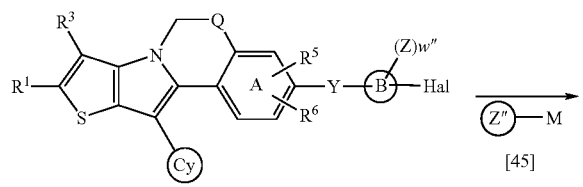

[I-32]

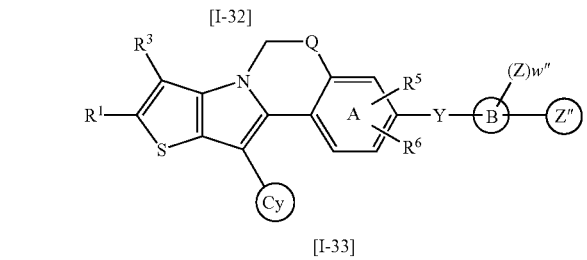

[I-33]

wherein ring Z"-M is aryl metal compound, ring Z" moiety is optionally substituted $C_{6-14}$ aryl or optionally substituted heterocyclic group corresponding to substituent Z, and the metal moiety contains boron, zinc, tin, magnesium and the like, such as phenylboronic acid and 4-chlorophenylboronic acid, w" is 0, 1 or 2, and other symbols are as defined above.

The compound [I-32] obtained in the same manner as in the above-mentioned Production Method is reacted with aryl metal compound [45] in a solvent such as DMF, acetonitrile, 1,2-dimethoxyethane, THF, toluene, water and the like in the presence of a palladium catalyst such as tetrakis(triphenylphosphine)-palladium, bis(triphenylphosphine)palladium(II) dichloride, palladium acetate—triphenylphosphine and the like, a nickel catalyst such as nickel chloride, 1,3-bis(diphenylphosphino)-propane nickel(II) chloride and the like, and a base such as potassium carbonate, potassium hydrogen carbonate, sodium hydrogen carbonate, potassium phosphate, triethylamine, potassium fluoride, sodium hydrogen phosphate, cesium carbonate and the like at room temperature or with heating, to give compound [I-33].

Production Method 8-2

Conversion of hydroxyl group to ether

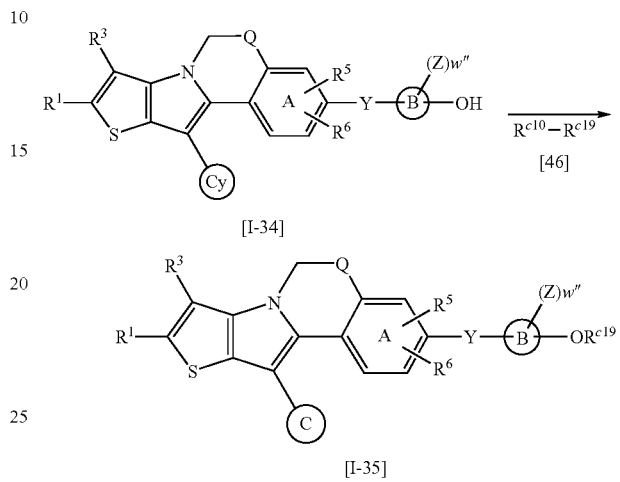

wherein $R^{c19}$ is —$R^{d1}$ or —$(CH_2)_p$—$COR^{d25}$ corresponding to substituent Z, and other symbols are as defined above.

The compound [I-34] obtained in the same manner as in the above-mentioned Production Method is reacted with compound [46] in the same manner as in Step 2 of Production Method 7-1 to give compound [I-35].

Production Method 8-3

Synthesis in advance of ring B part such as compound [38] in Production Method 7-1

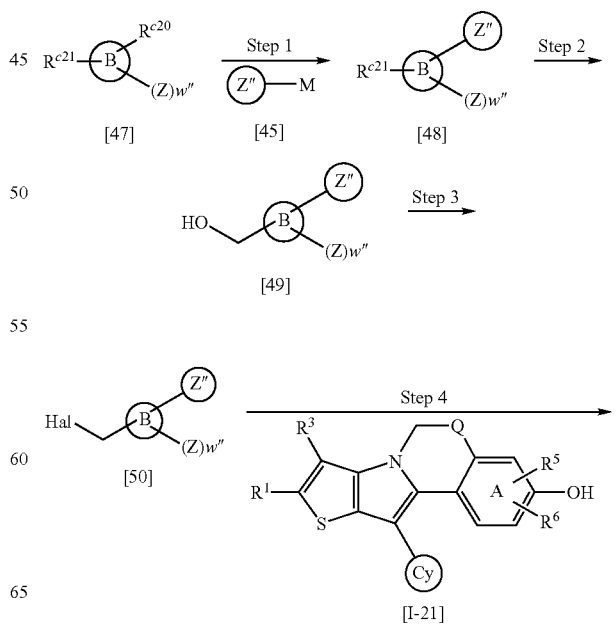

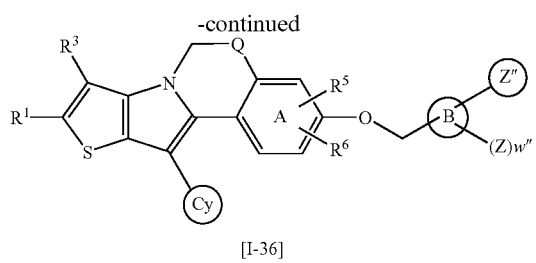

[I-36]

wherein $R^{c20}$ is leaving group such as chlorine atom, bromine atom, iodine atom, trifluoromethanesulfonyloxy, p-toluenesulfonyloxy, methanesulfonyloxy and the like, $R^{c21}$ is formyl, carboxyl or carboxylic acid ester such as methoxycarbonyl, ethoxycarbonyl, tert-butoxycarbonyl and the like, and other symbols are as defined above.

Step 1

Commercially available compound [47] or compound [47] obtained by a conventional method is reacted with aryl metal compound [45] in the same manner as in Production Method 8-1 to give compound [48].

Step 2

The compound [48] obtained in the same manner as in the above-mentioned Production Method is reduced according to a conventional method to give compound [49].

For example, compound [48] is reacted in a solvent such as methanol, ethanol, THF and the like in the presence of a reducing agent such as lithium aluminum hydride, sodium borohydride and the like under cooling to heating to give compound [49].

Step 3

The compound [49] obtained in the same manner as in the above-mentioned Production Method is reacted in a solvent such as 1,4-dioxane, diethyl ether, THF, methylene chloride, chloroform, toluene and the like with a halogenating agent, such as phosphorus halides (e.g., phosphorus pentachloride, phosphorus tribromide and the like), thionyl chloride and the like, to give compound [50]. For an accerelated reaction, the reaction may be carried out in the presence of a tertiary amine such as triethylamine, DMF, pyridine and the like, or under heating.

Step 4

The compound [49] or [50] obtained in the same manner as in the above-mentioned Production Method is reacted with compound [I-21] in the same manner as in Step 2 of Production Method 7-1 to give compound [I-36].

Production Method 8-4

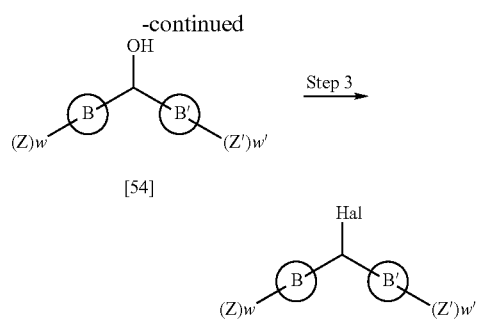

wherein M' is a metal such as magnesium, lithium, zinc and the like, and other symbols are as defined above.

Step 1

Commercially available compound [51] or compound [51] obtained by a conventional method is converted to aryl metal reagent by a conventional method to give compound [52].

For example, when M' is magnesium, magnesium is reacted with compound [51] in a solvent such as THF, diethyl ether, benzene, toluene and the like, preferably THF, from cooling to heating, preferably at −100° C. to 100° C. to give compound [52].

Step 2

The compound [52] obtained in the same manner as in the above-mentioned Production Method is reacted with compound [53] to give compound [54].

The compound [52] is reacted with compound [53] in a solvent such as diethyl ether, benzene, toluene, THF and the like, preferably THF, from cooling to room temperature, preferably at −100° C. to 30° C. to give compound [54].

Step 3

The compound [54] obtained in the same manner as in the above-mentioned Production Method is halogenated in the same manner as in Step 3 of Production Method 8-3 to give compound [55].

The compound [54] is reacted with thionyl chloride and pyridine preferably in toluene solvent to give compound [55].

When compound [55] is symmetric, namely, when the ring B-(Z)w moiety and the ring B'-(Z')w' moiety are the same, compound [52] is reacted with formate such as methyl formate, ethyl formate and the like, preferably ethyl formate, in a solvent such as diethyl ether, benzene, toluene, THF and the like, preferably THF, from cooling to room temperature, preferably at −100° C. to 30° C., to give compound [55].

Production Method 8-5

Method including steps to introduce a protecting group into a functional group

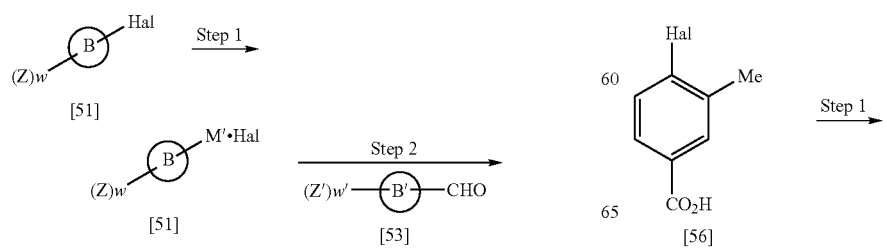

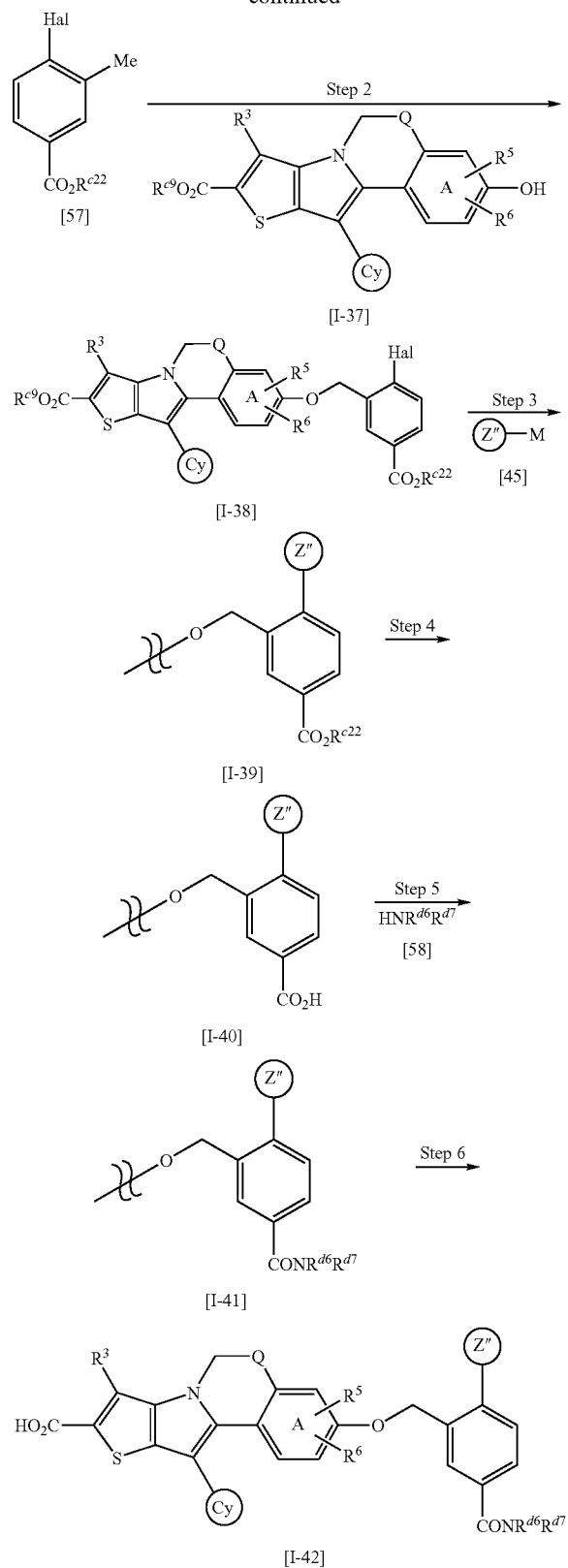

Step 1

Commercially available compound [56] or compound [56] obtained by a known method is protected by a conventional method to give compound [57].

For example, when $R^{c22}$ is tert-butyl, compound [56] is converted to acid halide with thionyl chloride, oxalyl chloride and the like in a solvent such as THF, chloroform, methylene chloride, toluene and the like, and reacted with potassium tert-butoxide to give compound [57].

Step 2

The methyl group of compound [57] obtained in the same manner as in the above-mentioned Production Method is converted to bromomethyl group with N-bromosuccinimide and N,N'-azobisisobutyronitrile and reacted with compound [I-37] in the same manner as in Step 2 of Production Method 7-1 to give compound [I-38].

Step 3

The compound [I-38] obtained in the same manner as in the above-mentioned Production Method is reacted with aryl metal compound [45] in the same manner as in Production Method 8-1 to give compound [I-39].

Step 4

The $R^{c22}$ of the compound [I-39] obtained in the same manner as in the above-mentioned Production Method is removed by a conventional method to give compound [I-40].

The carboxyl-protecting group can be removed by a conventional deprotection method according to the protecting group. In this Step, the conditions free from reaction of $R^{c9}$ are preferable. For example, when $R^{c22}$ is tert-butyl, compound [I-39] is treated with trifluoroacetic acid in a solvent such as methylene chloride, chloroform and the like to give compound [I-40]. In addition, compound [I-39] may be treated with hydrogen chloride or hydrochloric acid in a solvent such as ethyl acetate, 1,4-dioxane, alcohol and the like to give compound [I-40].

Step 5

The compound [I-40] obtained in the same manner as in the above-mentioned Production Method is subjected to amide condensation with compound [58] in the same manner as in Production Method 7-3 to give compound [I-41].

Step 6

The compound [I-41] obtained in the same manner as in the above-mentioned Production Method is deprotected in the same manner as in Step 1 of Production Method 5 to give compound [I-42].

As used herein, $R^{c9}$ is preferably a protecting group that does not react during the Step 1 through Step 5 but removed in this Step.

For example, when $R^{c9}$ is methyl, compound [I-41] is reacted in an alcohol solvent such as methanol, ethanol, n-propanol, isopropanol and the like or a mixed solvent of alcohol solvent and water in the presence of a base such as potassium carbonate, sodium carbonate, lithium hydroxide, sodium hydroxide, potassium hydroxide and the like from cooling to heating for deprotection, followed by acidifying the reaction solution to give compound [I-42].

wherein $R^{c22}$ is carboxyl-protecting group such as tert-butyl and the like, and other symbols are as defined above.

Production Method 8-6

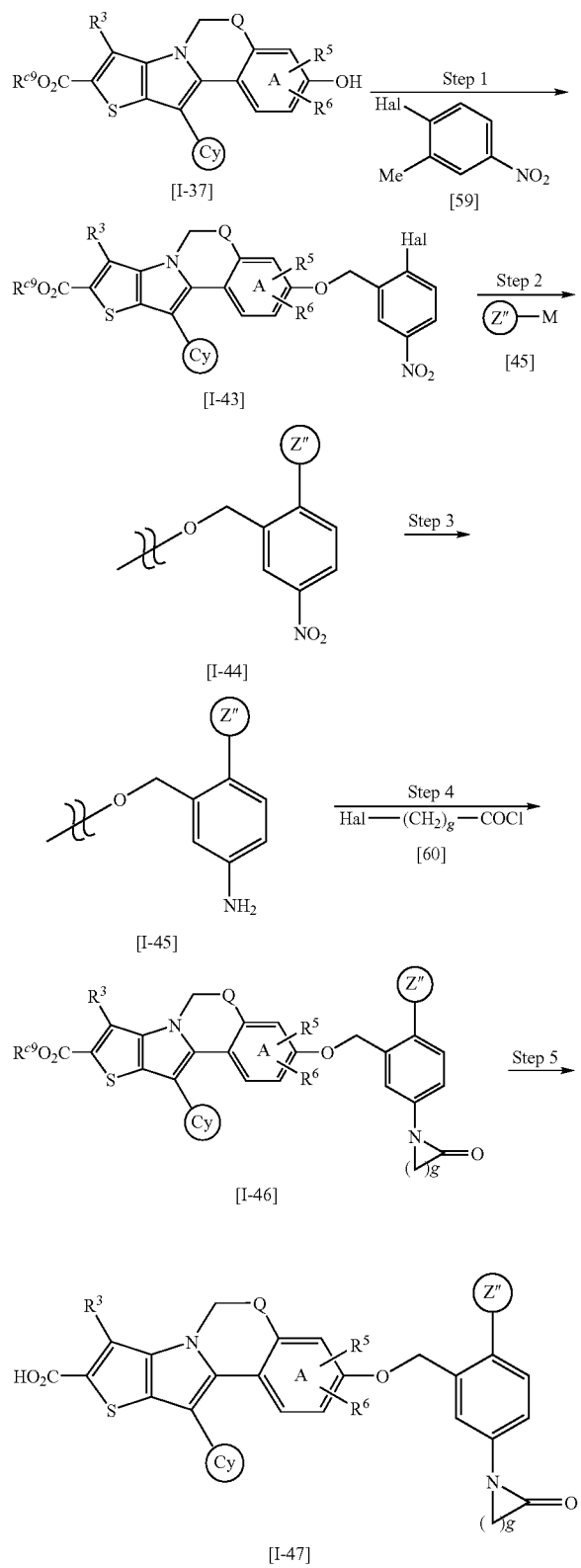

wherein g is an integer of 1 to 5, and other sumbols are as defined above.

Step 1

The compound [I-37] obtained by the above-mentioned Production Method is reacted with toluene derivative [59] in the same manner as in Step 2 of Production Method 8-5 to give compound [I-43].

Step 2

The compound [I-43] obtained by the above-mentioned Production Method is reacted with aryl metal compound [45] in the same manner as in Production Method 8-1 to give compound [I-44].

Step 3

The compound [I-44] obtained by the above-mentioned Production Method is reduced in the same manner as in Step 1 of Production Method 7-2 to give compound [I-45].

Step 4

The compound [I-45] obtained by the above-mentioned Production Method is subjected to amide condensation with compound [60] in the same manner as in Production Method 7-3, which is then subjected to cyclization in a solvent such as DMF, acetonitrile, THF, toluene and the like in the presence or absence of a base such as potassium carbonate, triethylamine, potassium tert-butoxide and the like at room temperature or with heating, to give compound [I-46].

Step 5

The compound [I-46] obtained by the above-mentioned Production Method is deprotected in the same manner as in Step 1 of Production Method 5 to give compound [I-47].

Production Method 8-7

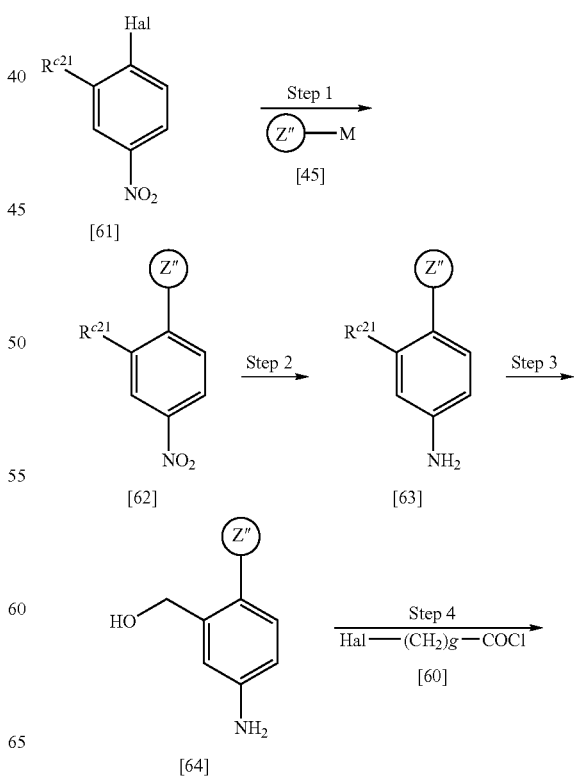

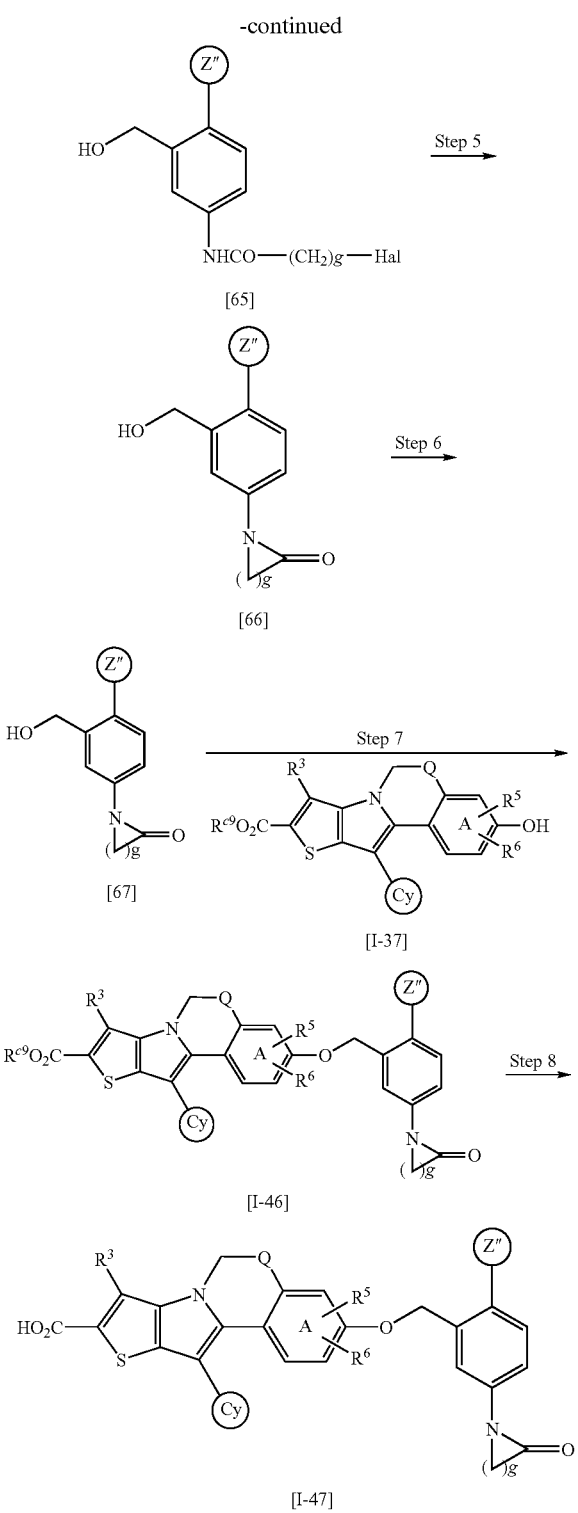

wherein each symbol is as defined above.

Step 1

Commercially available compound [61] or compound [61] obtained by a conventional method is reacted with compound [45] in the same manner as in Production Method 8-1 to give compound [62].

Step 2

The compound [62] obtained in the same manner as in the above-mentioned Production Method is reduced in the same manner as in Step 1 of Production Method 7-2 to give compound [63].

Step 3

The compound [63] obtained in the same manner as in the above-mentioned Production Method is reduced in the same manner as in Step 2 of Production Method 8-3 to give compound [64].

Step 4

The compound [64] obtained in the same manner as in the above-mentioned Production Method is reacted with compound [60] in a solvent such as DMF, acetonitrile, THF, chloroform, ethyl acetate, methylene chloride, toluene and the like to give compound [65]. To enhance the reaction selectivity for amino group, acetic acid and sodium acetate may be added in an equivalent ratio.

Step 5

The compound [65] obtained in the same manner as in the above-mentioned Production Method is subjected to cyclization in a solvent such as ethanol, DMF, acetonitrile, THF, toluene, water and the like in the presence or absence of a base such as potassium hydroxide, potassium carbonate, triethylamine, potassium tert-butoxide and the like at room temperature or with heating, to give compound [66].

Step 6

The compound [66] obtained in the same manner as in the above-mentioned Production Method is halogenated in the same manner as in Step 3 of Production Method 8-3 to give compound [67].

Step 7

The compound [67] obtained in the same manner as in the above-mentioned Production Method is reacted in the same manner as in Step 2 of Production Method 7-1 with compound [I-37] obtained in the same manner as in the above-mentioned Production Method to give compound [I-46].

Step 8

The compound [I-46] obtained in the same manner as in the above-mentioned Production Method is deprotected in the same manner as in Step 1 of Production Method 5 to give compound [I-47].

Production Method 8-8

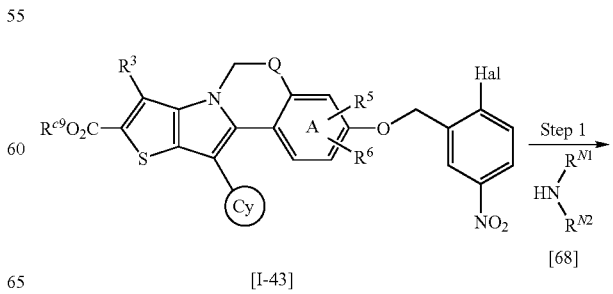

249

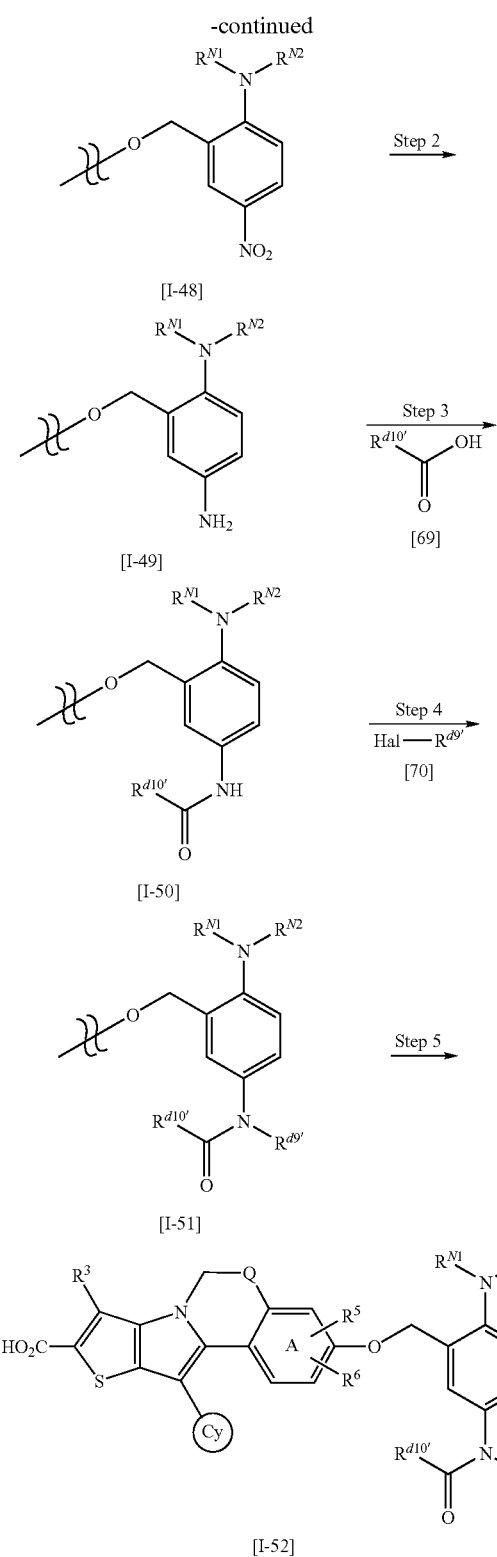

[I-48]

[I-49]

[I-50]

[I-51]

[I-52]

wherein $R^{N1}$ and $R^{N2}$ are the same or different and each is hydrogen atom or a group selected from group F, or $R^{N1}$ and $R^{N2}$ are linked to form a heterocycle containing NH such as piperidino group, 1-piperazinyl group, morpholino group and the like, $R^{d10'}$ is a group selected from group F, $R^{d9'}$ is a $C_{1-6}$

250 alkyl group optionally substituted by 1 to 3 substituents selected from group A, and other symbols are as defined above.

Step 1

The compound [I-43] obtained in the same manner as in the above-mentioned Production Method is reacted with amine compound [68] in a solvent such as DMSO, DMF, acetonitrile, THF, toluene and the like in the presence or absence of a base such as potassium carbonate, triethylamine, potassium tert-butoxide and the like at room temperature or with heating, to give compound [I-48].

Step 2

The compound [I-48] is reduced in the same manner as in Step 1 of Production Method 7-2 to give compound [I-49].

Step 3

The compound [I-49] is reacted with carboxylic acid compound [69] in the same manner as in Production Method 7-3 to give compound [I-50].

Step 4

The compound [I-50] is alkylated with compound [70] in the same manner as in Step 2 of Production Method 7-1 to give compound [I-51].

Step 5

The compound [I-51] is deprotected in the same manner as in Step 1 of Production Method 5 to give compound [I-52].

Production Method 8-9

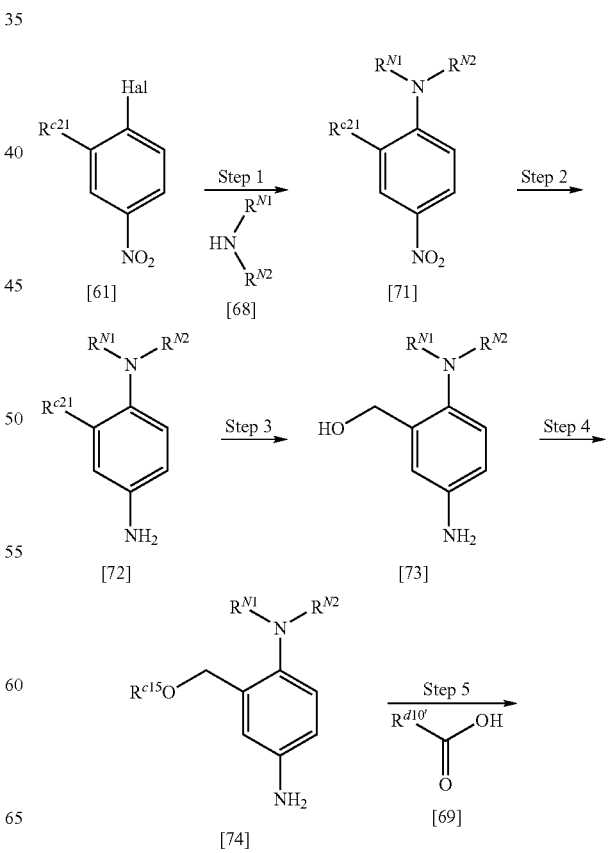

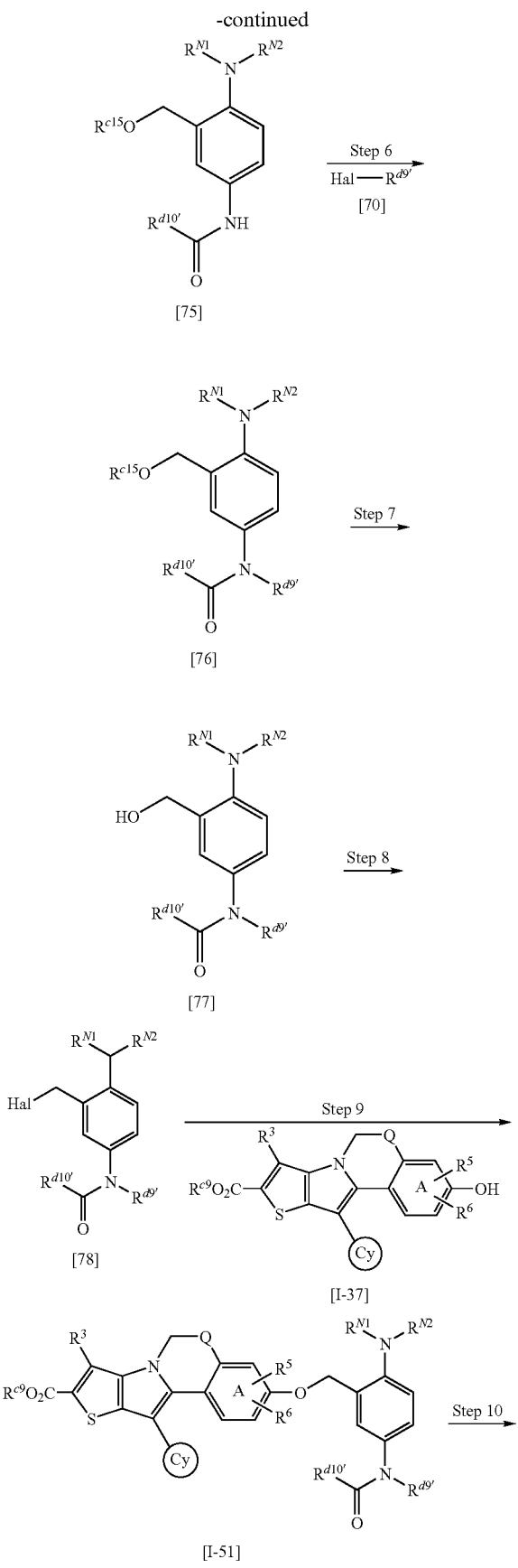

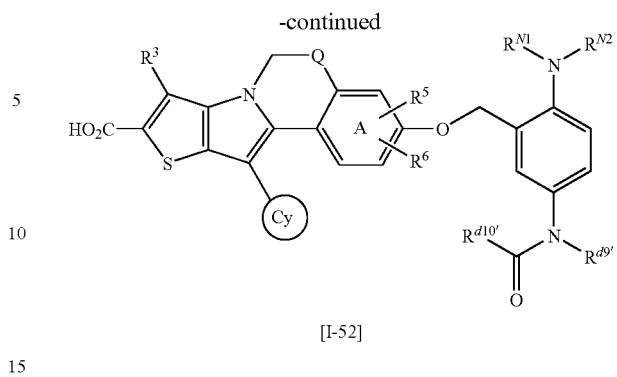

wherein each symbol is as defined above.

Step 1
Commercially available compound [61] or compound [61] obtained by a conventional method is reacted with amine compound [68] in the same manner as in Step I of Production Method 8-8 to give compound [71].

Step 2
The compound [71] is reduced in the same manner as in Step 1 of Production Method 7-2 to give compound [72].

Step 3
The compound [72] is reduced in the same manner as in Step 2 of Production Method 8-3 to give compound [73].

Step 4
The hydroxyl group of the compound [73] is protected by a conventional method to give compound [74].
For protection, for example, when $R^{c15}$ is acetyl group, the compound [73] is reacted with acetic anhydride in the presence of pyridine or tertiary amine at room temperature to heating, when $R^{c15}$ is benzyl group, the compound [73] is heated under reflux with benzyl chloride in benzene in the presence of a base such as potassium hydroxide and the like, when $R^{c15}$ is tert-butyldiphenylsilyl group, the compound [73] is treated with tert-butyldiphenylsilyl chloride and imidazole at room temperature in DMF, and the like.
In addition, desired $R^{d10'}$—CO group may be introduced as a hydroxyl-protecting group in the next Step 5 without going through this step.

Step 5
The compound [74] is reacted with carboxylic acid compound [69] in the same manner as in Production Method 7-3 to give compound [75].

Step 6
The compound [75] is alkylated with compound [70] in the same manner as in Step 2 of Production Method 7-1 to give compound [76].

Step 7
The compound [76] is deprotected in the same manner as in Step 1 of Production Method 7-1 to give compound [77].

Step 8
The compound [77] is halogenated in the same manner as in Step 3 of Production Method 8-3 to give compound [78].

Step 9
The compound [78] is reacted in the same manner as in Step 2 of Production Method 7-1 with compound [I-37] obtained in the same manner as in the above-mentioned Production Method to give compound [I-51].

Step 10

The compound [I-51] is deprotected in the same manner as in Step 1 of Production Method 5 to give compound [I-52].

Production Method 9

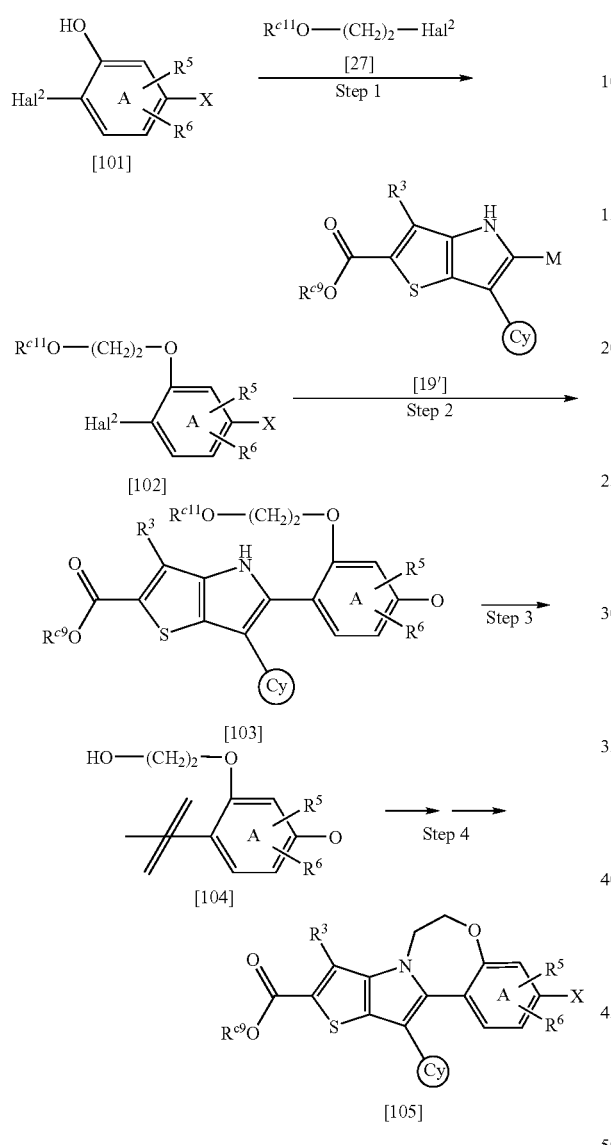

wherein each symbol is as defined above.

Step 1

Compound [102] can be obtained by reacting compound [101] with compound [27] in the same manner as in Production Method 7-1, Step 2.

Step 2

Compound [103] can be obtained by reacting compound [102] with compound [19'] in the same manner as in Production Method 1-1.

Step 3

Compound [104] can be obtained by eliminating a hydroxyl-protecting group of compound [103] by a conventional method.

Step 4

Compound [105] can be obtained converting a hydroxyl group of compound [104] to a leaving group by halogen substitution, mesylation or tosylation by a conventional method, and subjecting the compound to condensation cyclization in the same manner as in Production Method 1-2, Step 2.

Furthermore, a carboxylic acid form can be also obtained by eliminating a carboxyl-protecting group of compound [105] by a conventional method.

Production Method 9-1

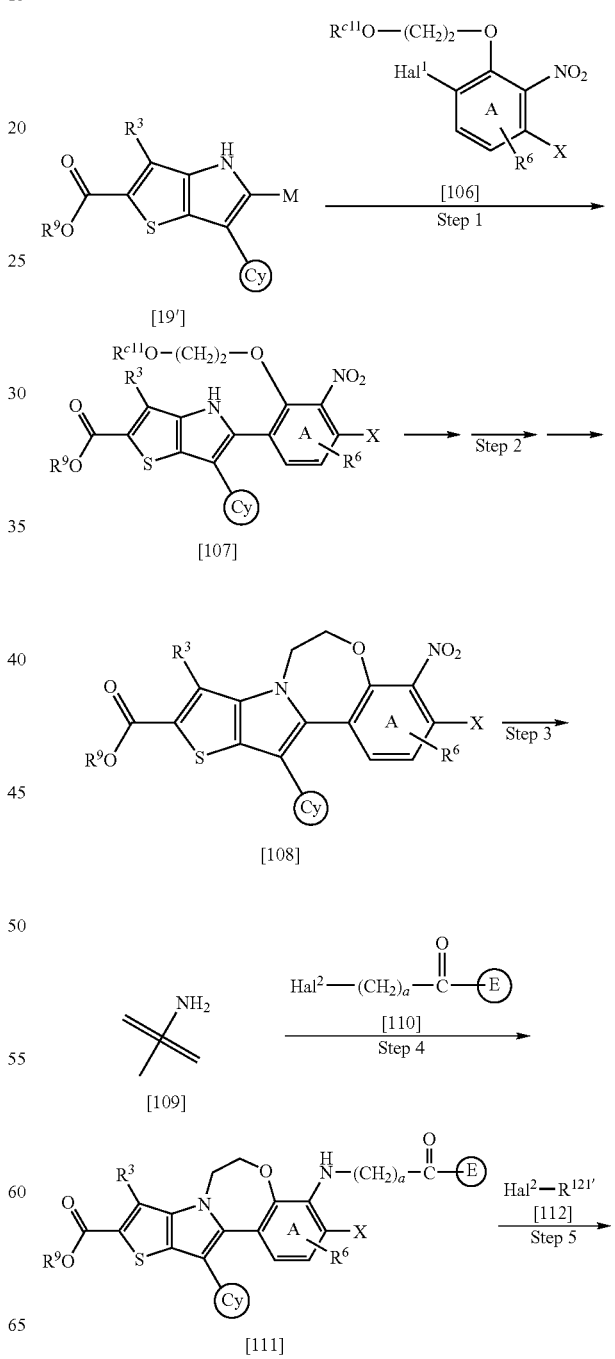

-continued

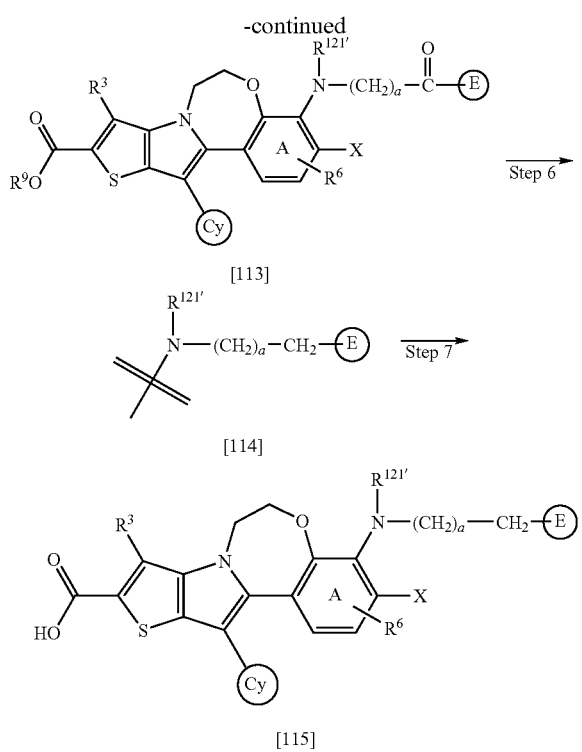

[113]

[114]

[115]

wherein $R^{121'}$ is a $C_{1-6}$ alkanoyl group or a group selected from group C, a is 0 or an integer of 1 to 5, and other symbols are as defined above. The substituent

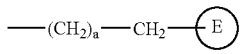

corresponds to "a $C_{6-14}$ aryl $C_{1-6}$ alkyl group optionally substituted by 1 to 5 substituents selected from group B" or "a heterocycle $C_{1-6}$ alkyl group optionally substituted by 1 to 5 substituents selected from group B" represented by $R^{122}$ in the formula [I], and ring E is a $C_{6-14}$ aryl group optionally substituted by 1 to 5 substituents selected from group B or a heterocyclic group optionally substituted by 1 to 5 substituents selected from group B.

Step 1
Compound [107] can be obtained by reacting compound [106] with compound [19'] in the same manner as in Production Method 1-1.

Step 2
Compound [108] can be obtained by eliminating the hydroxyl-protecting group of compound [107], then converting the hydroxyl group to a leaving group by halogen substitution, mesylation or tosylation by a conventional method, and then subjecting the compound to condensation cyclization in the same manner as in Production Method 1-2, Step 2.

Step 3
Compound [109] can be obtained by reducing the nitro group of compound [108] by a conventional method.

Step 4
Compound [111] can be obtained by reacting compound [109] with compound [110] in the same manner as in Production Method 7-1, Step 2.

In this case, a compound wherein amino group is disubstituted by compound [110] may be also obtained. In this event, compound [111] isolated then can be used in the next step.

Step 5
Compound [113] can be obtained by reacting compound [111] with compound [112] in the same manner as in Production Method 7-1, Step 2.

Here, the corresponding substituent can be also introduced by reacting compound [111] with an aldehyde compound or a ketone compound instead of compound [112] in the presence of a reducing agent.

As the reducing agent, borohydrides such as sodium borohydride, sodium cyanoborohydride, sodium triacetoxyborohydride and the like can be mentioned.

As a solvent, THF, 1,4-dioxane, dichloromethane, chloroform, methanol, ethanol, toluene, acetic acid and the like can be mentioned. Acetic acid may be added.

Step 6
Compound [114] can be obtained by reducing carbonyl of compound [113] by a conventional method.

Step 7
Compound [115] can be obtained by hydrolyzing compound [114] in the same manner as in Production Method 5, Step 1.

Production Method 9-2

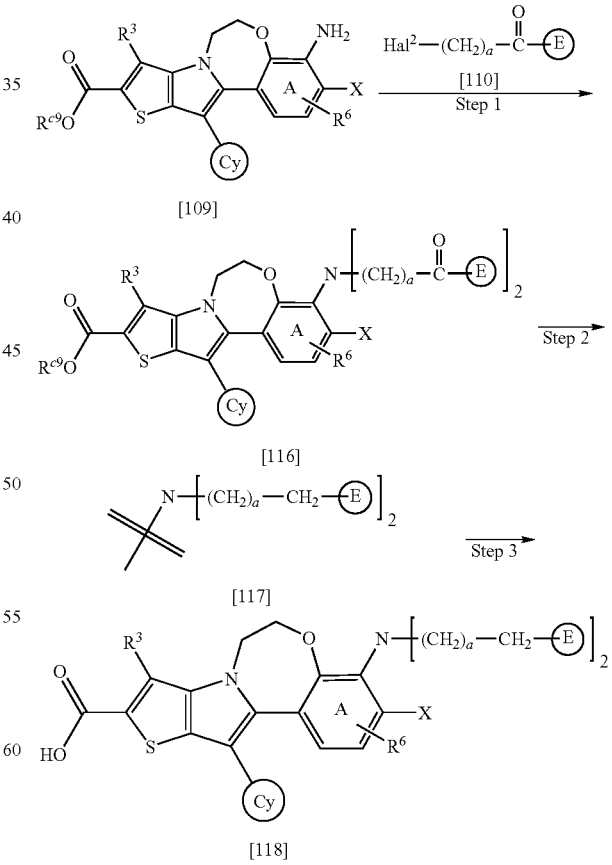

[109]

[116]

[117]

[118]

wherein each symbol is as defined above.

Step 1

Compound [116] can be obtained by reacting compound [109] with compound [110] in the same manner as in Production Method 7-1, Step 2.

Step 2

Compound [117] can be obtained by reducing carbonyl of compound [116] by a conventional method.

Step 3

Compound [118] can be obtained by hydrolyzing compound [117] in the same manner as in Production Method 5, Step 1.

Production Method 10

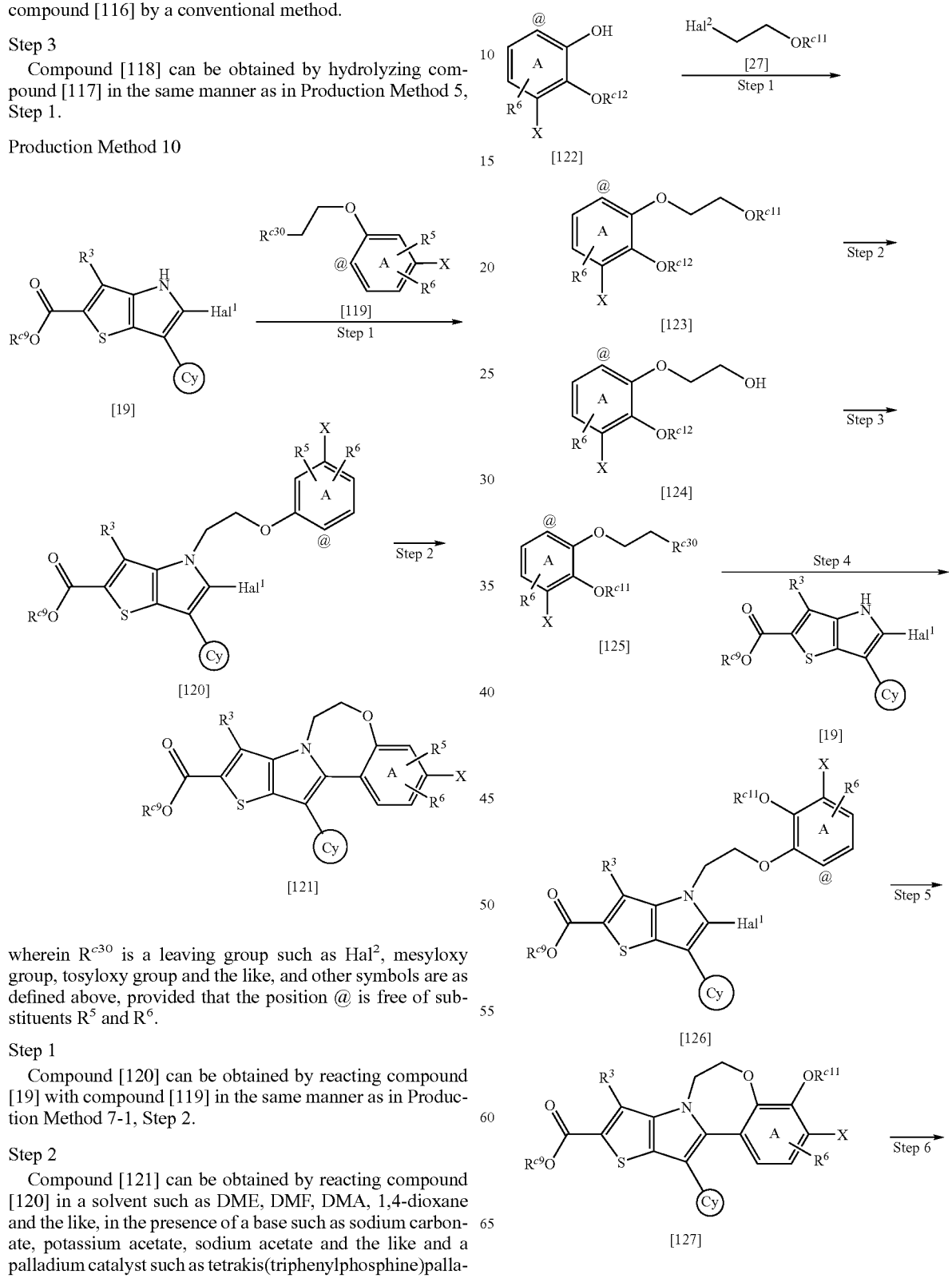

wherein $R^{c30}$ is a leaving group such as $Hal^2$, mesyloxy group, tosyloxy group and the like, and other symbols are as defined above, provided that the position @ is free of substituents $R^5$ and $R^6$.

Step 1

Compound [120] can be obtained by reacting compound [19] with compound [119] in the same manner as in Production Method 7-1, Step 2.

Step 2

Compound [121] can be obtained by reacting compound [120] in a solvent such as DME, DMF, DMA, 1,4-dioxane and the like, in the presence of a base such as sodium carbonate, potassium acetate, sodium acetate and the like and a palladium catalyst such as tetrakis(triphenylphosphine)palladium, bis(triphenylphosphine)palladium(II) dichloride, palladium acetate-triphenylphosphine and the like, at room temperature or under heating.

Production Method 10-1

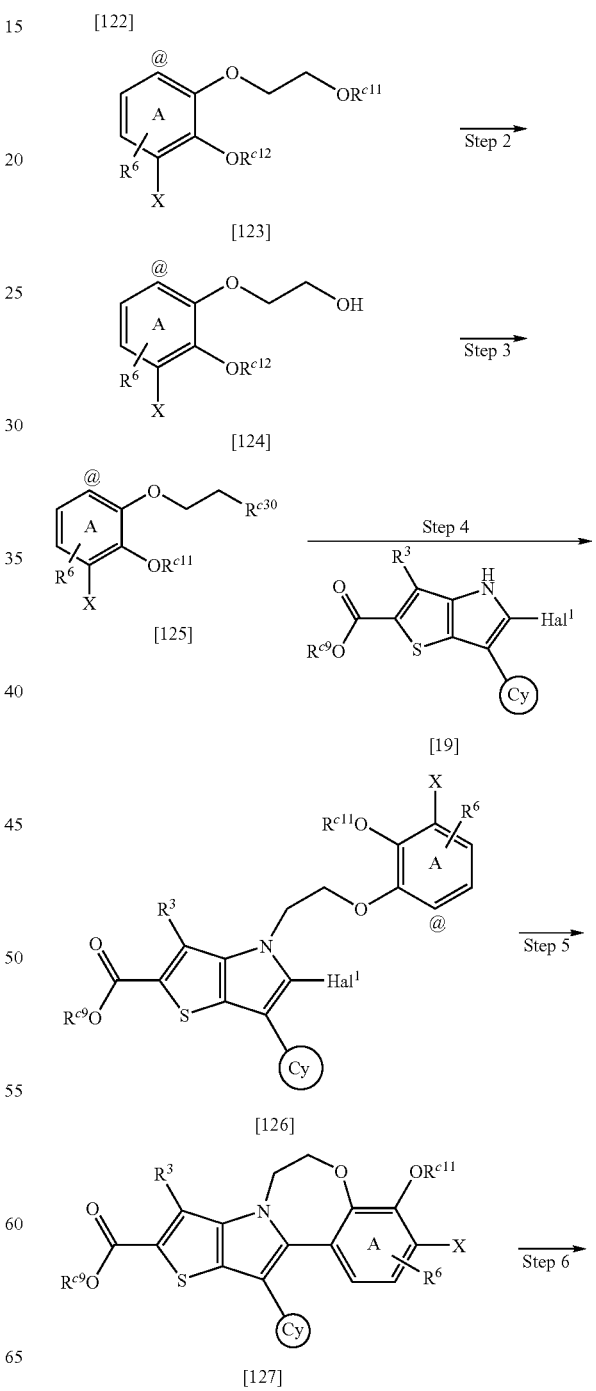

-continued

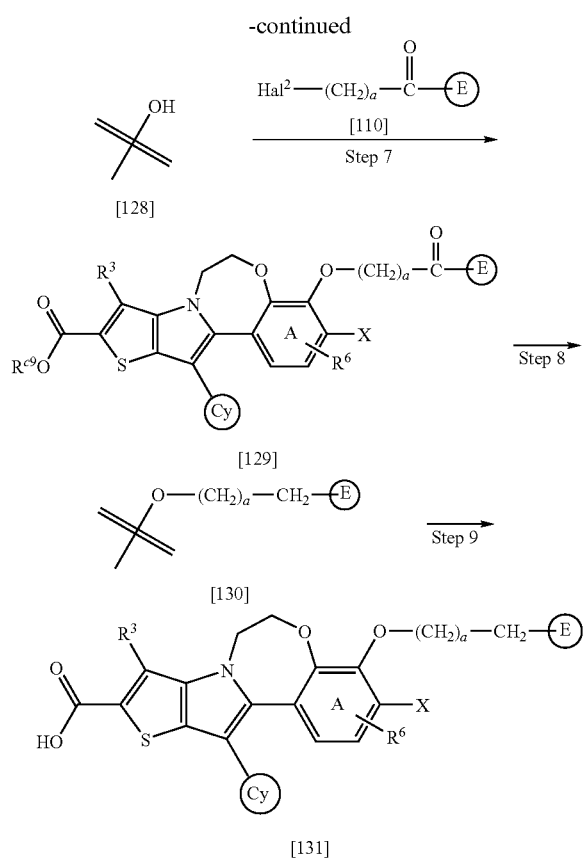

wherein each symbol is as defined above, provided that the position @ is free of substituent $R^6$.

Step 1

Compound [123] can be obtained by reacting compound [122] with compound [27] in the same manner as in Production Method 7-1, Step 2.

Step 2

Compound [124] can be obtained by deprotection of the hydroxyl-protecting group of compound [123] by a conventional method.

Here, conditions for deprotecting $R^{c11}$ without affecting $R^{c12}$ are preferable, as $R^{c11}$, preferred are tetrahydropyran-2-yl group, tert-butyl group, acetyl group and the like, and as $R^{c12}$, preferred are benzyl group, methyl group and the like.

Step 3

Compound [125] can be obtained by converting the hydroxyl group of compound [124] to a leaving group by halogen substitution, mesylation or tosylation by a conventional method.

Step 4

Compound [126] can be obtained by reacting compound [125] with compound [19] in the same manner as in Production Method 7-1, Step 2.

Step 5

Compound [127] can be obtained by subjecting compound [126] to cyclization in the same manner as in Production Method 10, Step 2.

Step 6

Compound [128] can be obtained by eliminating the hydroxyl-protecting group of compound [127] by a conventional method.

Step 7

Compound [129] can be obtained by reacting compound [128] with compound [110] in the same manner as in Production Method 7-1, Step 2.

Step 8

Compound [130] can be obtained by reducing carbonyl of compound [129] by a conventional method.

Step 9

Compound [131] can be obtained by hydrolyzing compound [130] in the same manner as in Production Method 5, Step 1.

Production Method 11

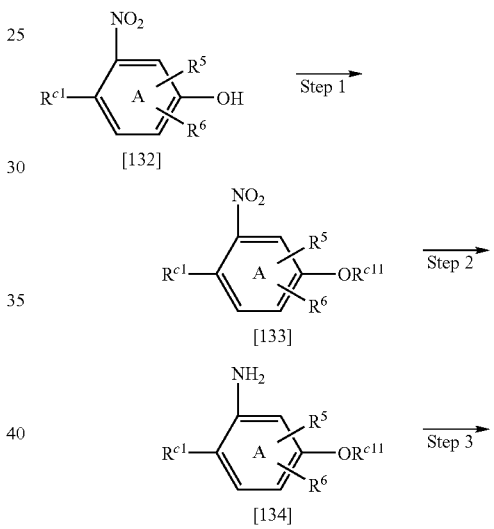

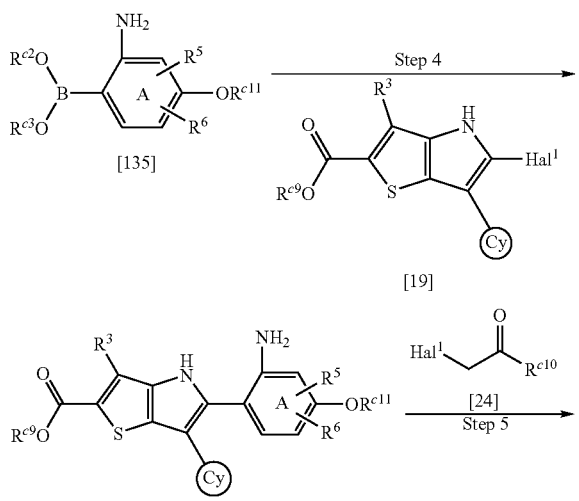

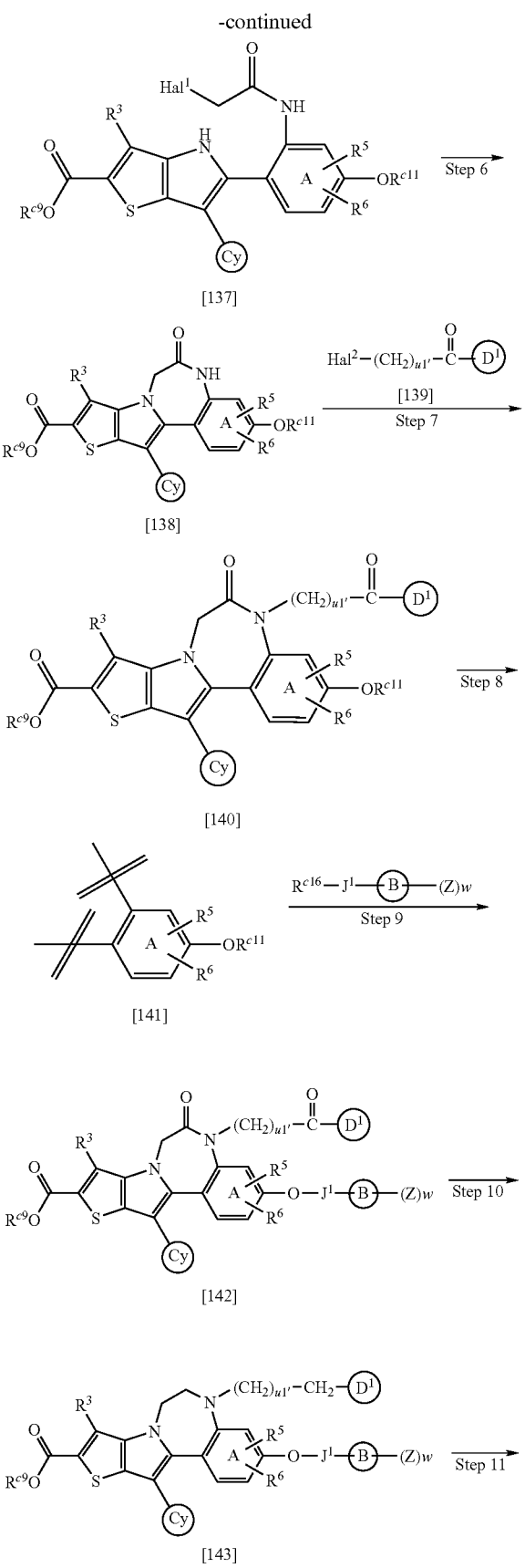

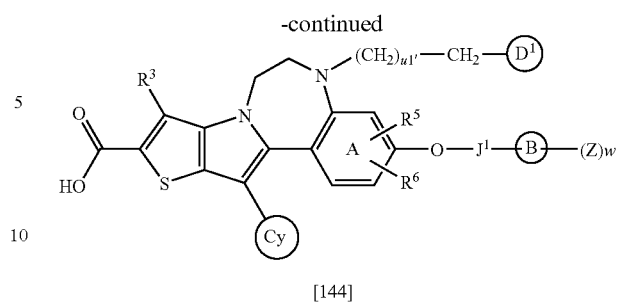

wherein each symbol is as defined above.

Step 1

Compound [133] can be obtained by introducing a hydroxyl-protecting group into compound [132] by a conventional method.

Step 2

Compound [134] can be obtained by reducing the nitro group of compound [133] by a conventional method.

Step 3

Compound [135] can be obtained by reacting compound [134] with boric acid ester in the same manner as in Reference Example 1.

Step 4

Compound [136] can be obtained by reacting compound [135] with compound [19] in the same manner as in Production Method 1-1.

Step 5

Compound [137] can be obtained by reacting compound [136] with compound [24] in the same manner as in Production Method 1-2, Step 1.

Step 6

Compound [138] can be obtained by subjecting compound [137] to condensation cyclization in the same manner as in Production Method 1-2, Step 2.

Step 7

Compound [140] can be obtained by reacting compound [138] with compound [139] in the same manner as in Production Method 3, Step 1. Here, compound [30] (Hal$^2$-R$^{2'}$) or compound [31] (Hal$^2$-(CH$_2$)$_{ul'}$—CO—OR$^{c13}$) may be used instead of compound [139] to introduce other substituents.

Step 8

Compound [141] can be obtained by eliminating the hydroxyl-protecting group of compound [140] by a conventional method.

Step 9

Compound [142] can be obtained by reacting compound [141] with compound [38] in the same manner as in Production Method 7-1, Step 2.

Step 10

Compound [143] can be obtained by reducing carbonyl of compound [142] by a conventional method.

Step 11

Compound [144] can be obtained by hydrolyzing compound [143] in the same manner as in Production Method 5, Step 1.

Production Method 12-1

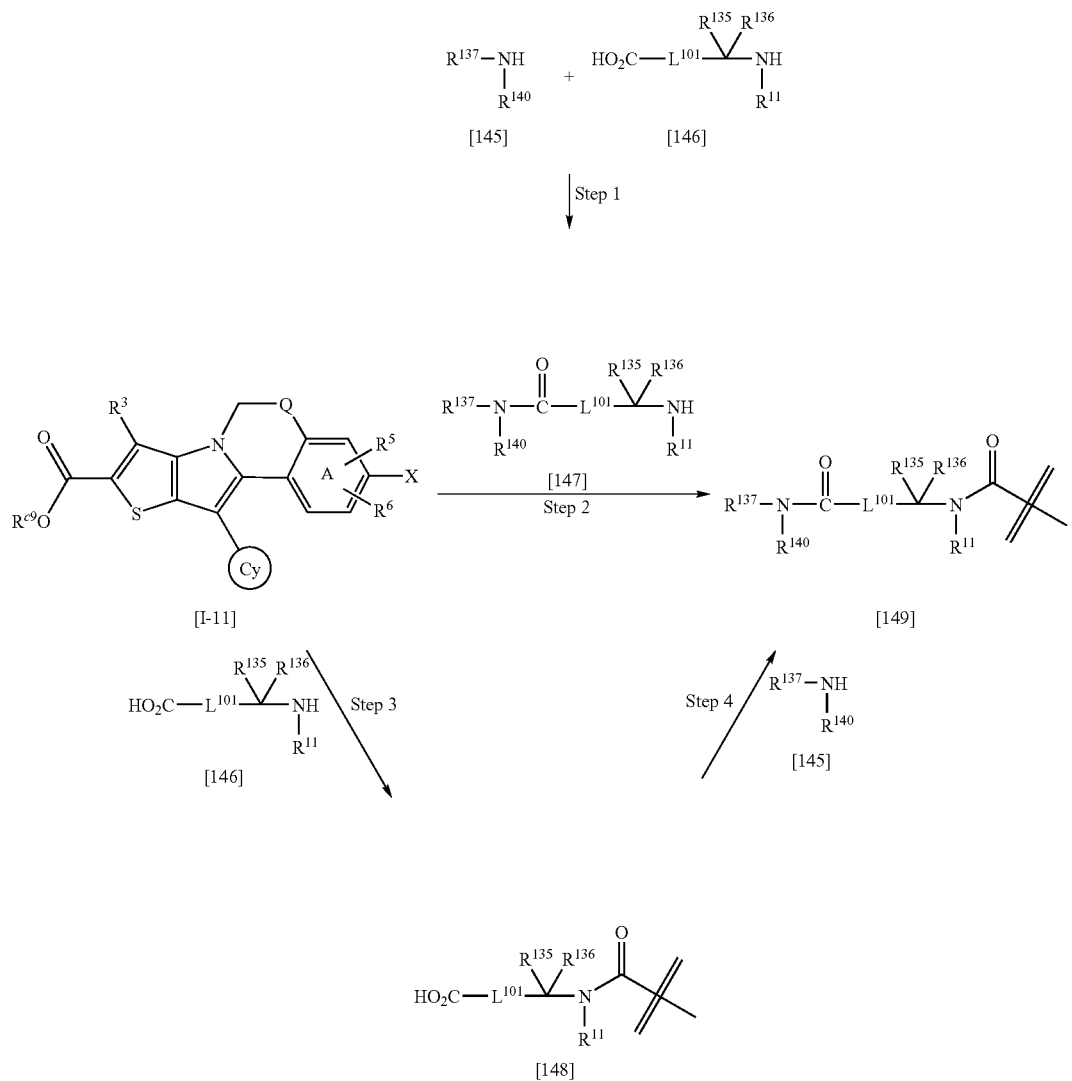

wherein each symbol is as defined above.

Step 1

Compound [147] can be obtained by reacting compound [145] with compound [146] in the same manner as in Production Method 1-2, Step 1.

In general, compound [146], wherein a protecting group has been introduced into an amino group, is used, and after reaction of Step 1, compound [147] obtained by eliminating the amino-protecting group can be used in the next step.

Step 2

Compound [149] can be obtained by reacting compound [I-11] with compound [147] in the same manner as in Production Method 1-2, Step 1.

Compound [I-11] can be used for this step after eliminating the carboxyl-protecting group by hydrolysis in the same manner as in Production Method 5, Step 1.

Step 3

Compound [148] can be obtained by reacting compound [I-11] with compound [146] in the same manner as in Production Method 1-2, Step 1.

Compound [I-11] can be used for this step after eliminating the carboxyl-protecting group by hydrolysis in the same manner as in Production Method 5, Step 1.

In general, compound [146], wherein a protecting group has been introduced into carboxylic acid, is used, and after reaction of Step 3, compound [148] obtained by eliminating the carboxyl-protecting group can be used in the next step.

Step 4

Compound [149] can be obtained by reacting compound [148] with compound [145] in the same manner as in Production Method 1-2, Step 1.

Production Method 12-2
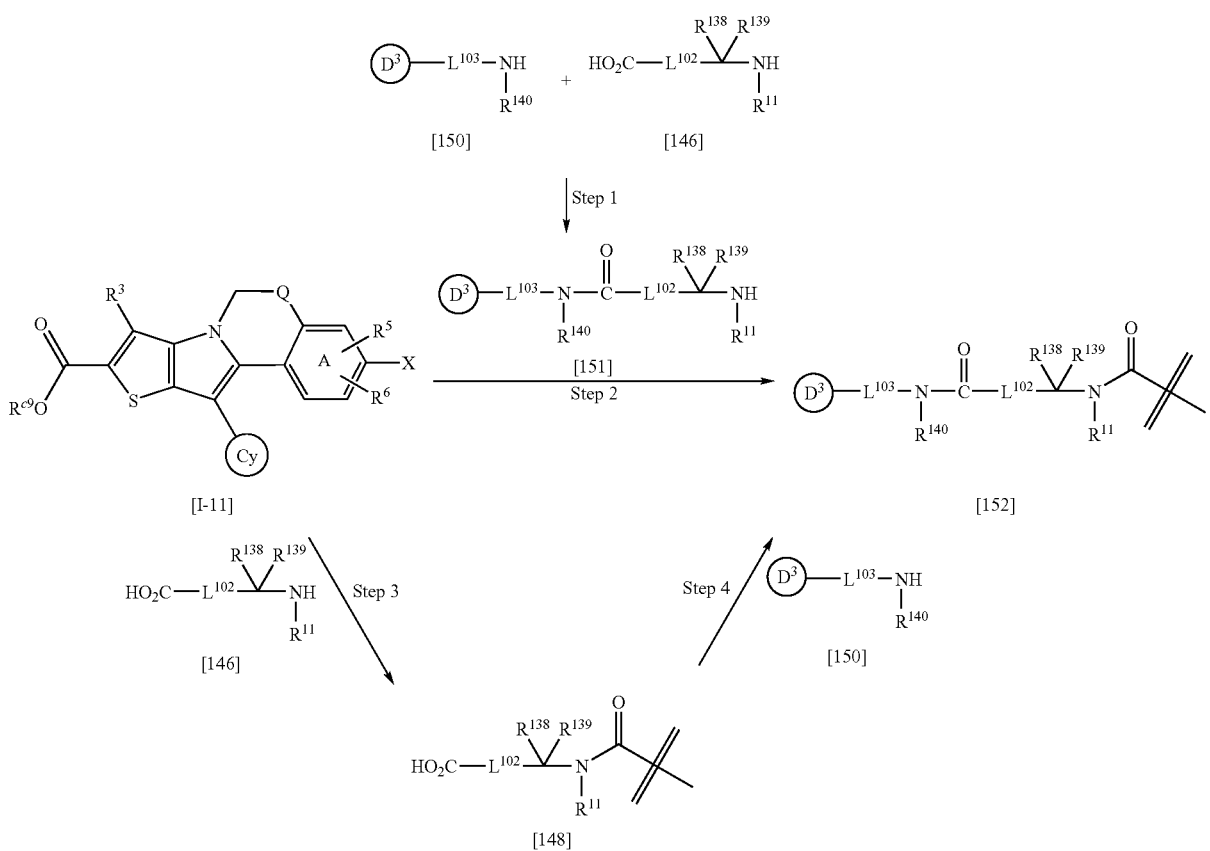
wherein each symbol is as defined above.
Compounds [151] and [152] can be obtained in the same manner as in Production Method 12-1, using compound [150] instead of compound [145].
Production Method 12-3
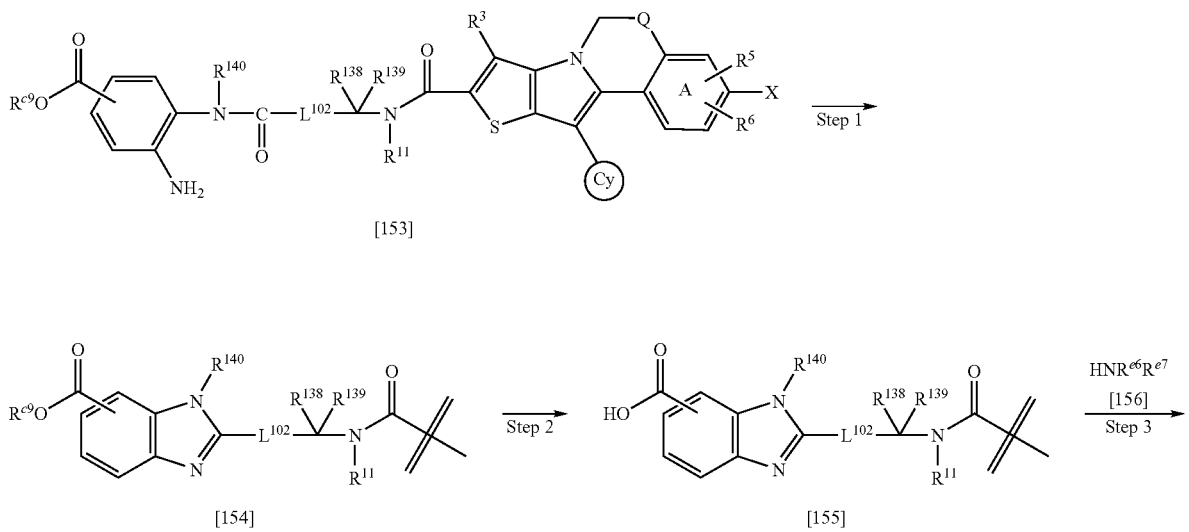

-continued

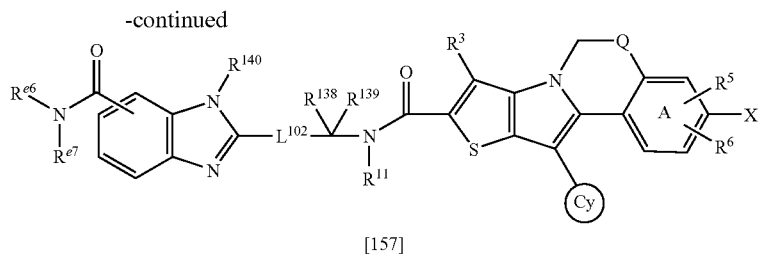

[157]

wherein each symbol is as defined above.

Step 1

Compound [154] can be obtained by subjecting compound [153], obtained in the same manner as in Production Method 12-1 or Production Method 12-2, to condensation cyclization in a solvent such as an alcohol solvent (e.g., methanol, ethanol etc.), toluene, xylene, dichloroethane, chloroform etc., in the presence of an acid catalyst (e.g., p-toluenesulfonic acid, methanesulfonic acid, phosphoric acid, sulfuric acid etc.) or in an acidic solvent (e.g., acetic acid, trifluoroacetic acid, polyphosphoric acid, sulfuric acid etc.), at room temperature or under heating.

Step 2

Compound [155] can be obtained by hydrolyzing compound [154] in the same manner as in Production Method 5, Step 1.

Step 3

Compound [157] can be obtained by reacting compound [155] with compound [156] in the same manner as in Production Method 1-2, Step 1.

Production Method 10-2

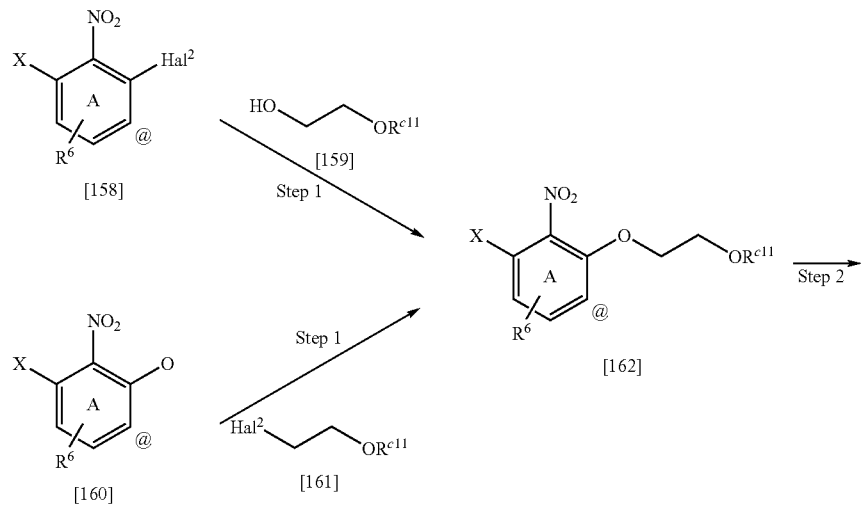

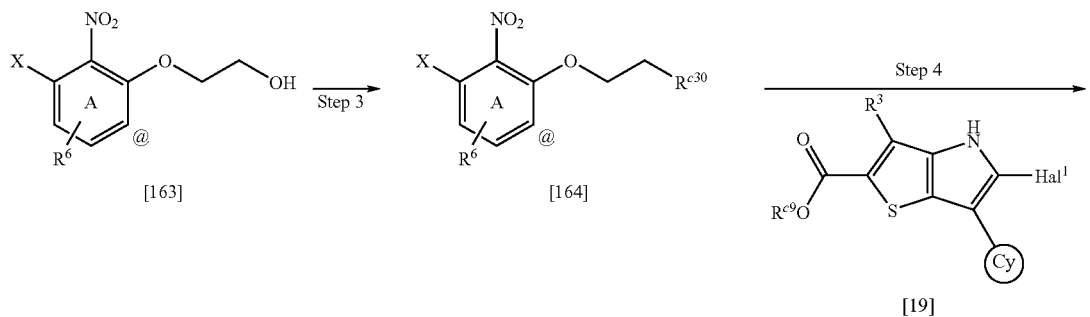

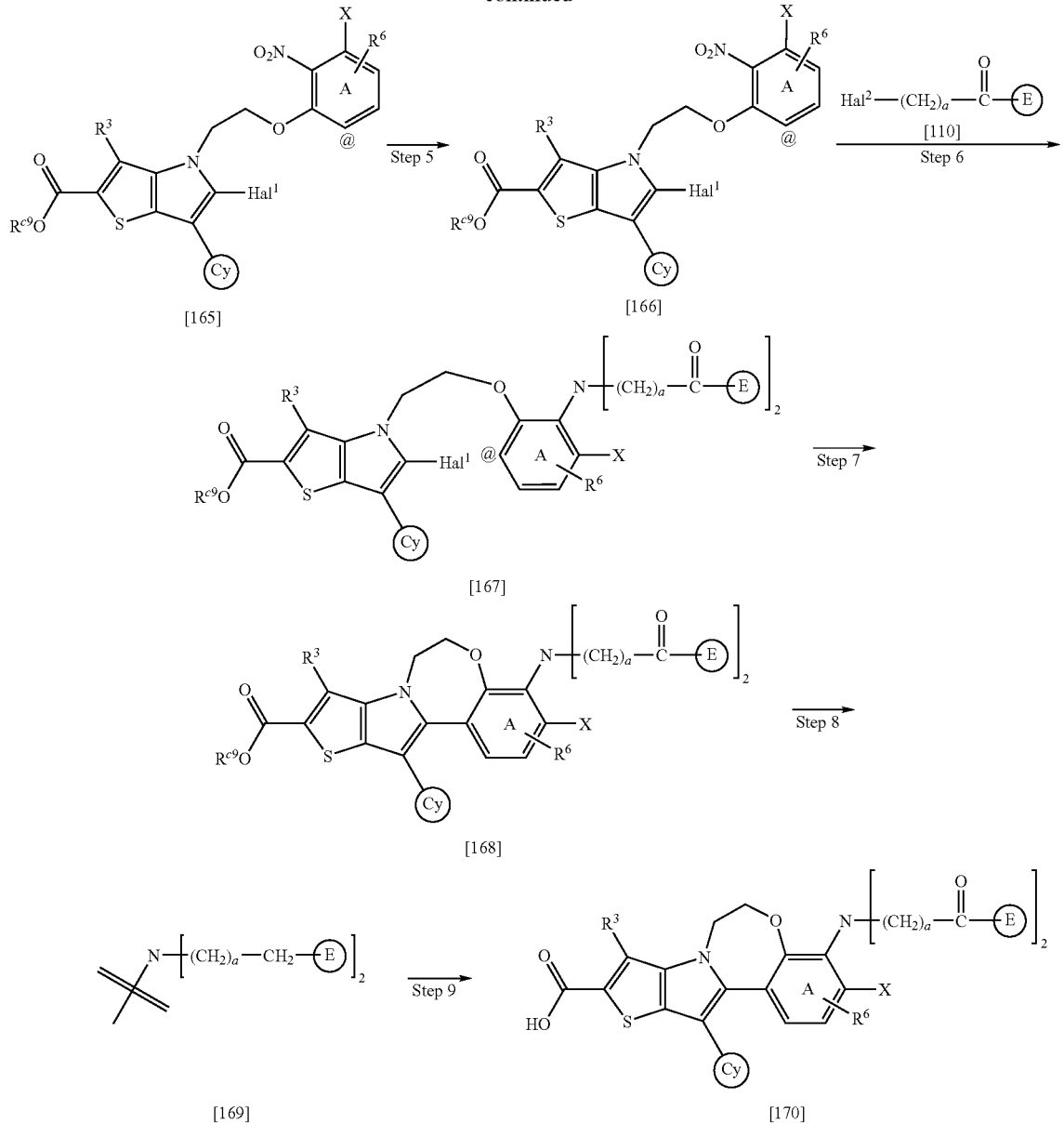

wherein each symbol is as defined above, provided that the position @ is free of substituent $R^6$.

Step 1

Compound [162] can be obtained by reacting compound [158] with compound [159] or compound [160] with compound [161] in a solvent in the presence of a base from under cooling to under heating.

As the solvent, ethanol, DMF, DMA, DMSO, acetone, acetonitrile, 1,4-dioxane, THF, toluene, water and the like can be mentioned.

As the base, sodium hydroxide, potassium hydroxide, potassium carbonate, sodium carbonate, lithium hydroxide, sodium hydride, triethylamine, sodium ethoxide, potassium tert-butoxide and the like can be mentioned.

The reaction may be accelerated by adding sodium iodide or potassium iodide.

Step 2

Compound [163] can be obtained by eliminating the hydroxyl-protecting group of compound [162] by a conventional method.

Step 3

Compound [164] can be obtained by converting the hydroxyl group of compound [163] to a leaving group by a conventional method.

For example, when $R^{c30}$ is a mesyloxy group, a method comprising treatment with mesyl chloride in a solvent such as tetrahydrofuran, chloroform etc. under an argon atmosphere, in the presence of a base such as triethylamine, pyridine, N-methylmorpholine etc. can be employed. Here, dimethylaminopyridine may be added.

Step 4

Compound [165] can be obtained by reacting compound [164] with compound [19] in the same manner as in Production Method 10-2, Step 1.

Step 5

Compound [166] can be obtained by reducing the nitro group of compound [165] by a conventional method.

For example, compound [165] is reduced with a reducing agent such as zinc, iron, tin(II) chloride, sodium sulfite and the like. To be specific, compound [166] can be obtained by reacting compound [165] with hydrazine in the presence of iron(III) chloride or by reacting compound [165] with ammonium chloride in the presence of iron. The compound [166] can be also obtained by reacting compound [165] with sodium hydrosulfite under alkaline conditions.

Step 6

Compound [167] can be obtained by reacting compound [166] with compound [110] in the same manner as in Production Method 10-2, Step 1.

Step 7

Compound [168] can be obtained by reacting compound [167] in a solvent such as DME, DMF, DMA, 1,4-dioxane and the like, in the presence of a base such as sodium carbonate, potassium acetate, sodium acetate and the like and a palladium catalyst such as tetrakis(triphenylphosphine)palladium, bis(triphenylphosphine)palladium(II) dichloride, palladium acetate-triphenylphosphine and the like, at room temperature or under heating.

Step 8

Compound [169] can be obtained by reducing carbonyl of compound [168] by a conventional method.

For example, reduction is carried out using a borohydride (e.g., sodium borohydride, sodium triacetoxyborohydride and the like), borane-THF complex and the like as a reducing agent. In this case, an acid such as acetic acid, hydrochloric acid and the like may be added.

As a preferable solvent, ether solvents (1,4-dioxane, THF etc.), alcohol solvents (methanol, ethanol etc.), polar solvents (DMF, DMSO, acetonitrile etc.), halogenated hydrocarbon solvents (dichloromethane, chloroform etc.), hydrocarbon solvents (benzene, toluene etc.), ester solvents (ethyl acetate, butyl acetate etc.), water, or a mixed solvent thereof and the like can be mentioned.

Step 9

Compound [170] can be obtained by eliminating the carboxyl-protecting group of compound [169] by a conventional method.

As used herein, $R^{c9}$ is preferably a protecting group that does not react during the Step 1 through Step 8 but removed in this step.

For example, when $R^{c9}$ is methyl, compound [169] is reacted in an alcohol solvent such as methanol, ethanol, n-propanol, isopropanol and the like or a mixed solvent such as a mixture of an alcohol solvent and water, a mixture of an alcohol solvent and THF and the like in the presence of a base such as potassium carbonate, sodium carbonate, lithium hydroxide, sodium hydroxide, potassium hydroxide and the like from cooling to heating for deprotection, followed by acidifying the reaction solution to give compound [170].

Production Method 10-3

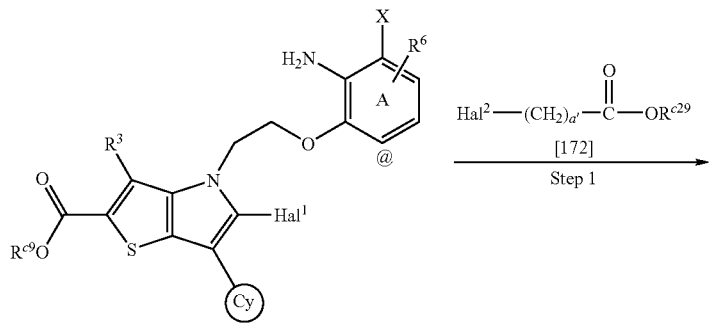

[167]

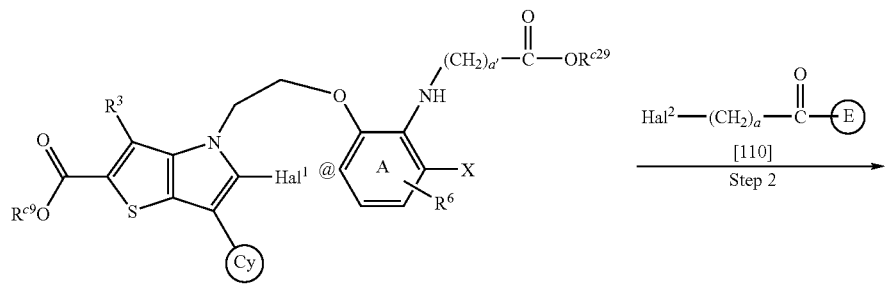

[173]

-continued
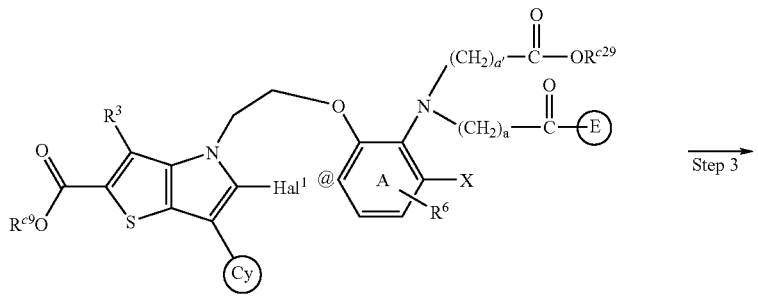
[174]
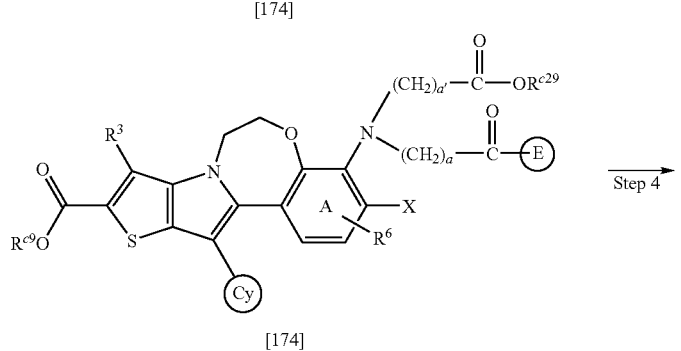
[174]
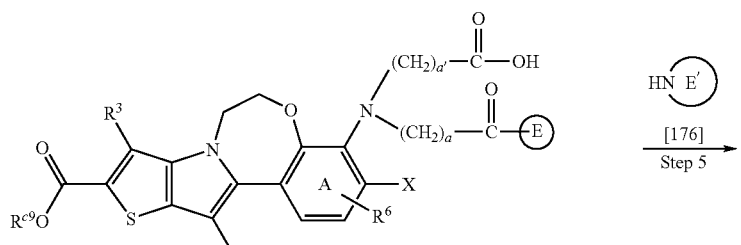
[175]
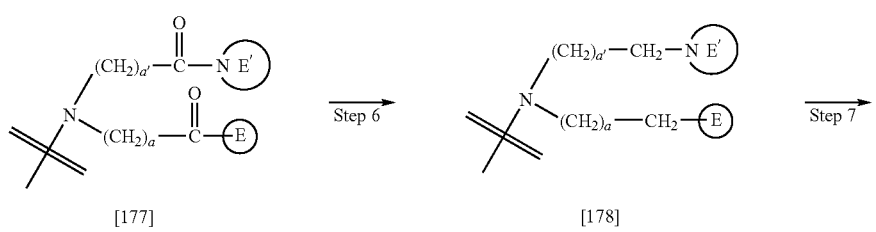
[177]　　　　　　　　　　　[178]
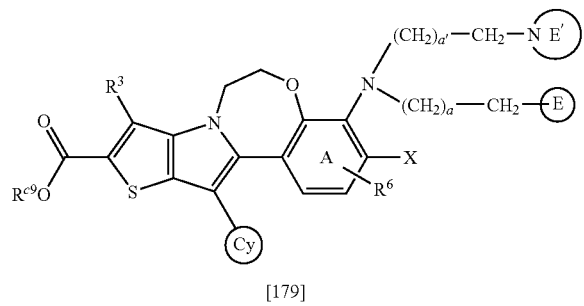
[179]

wherein a' is 0 or an integer of 1 to 5, $R^{c29}$ is carboxyl-protecting group such as tert-butyl group and the like, and other symbols are as defined above. The substituent

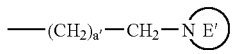

corresponds to "a heterocycle $C_{1-6}$ alkyl group optionally substituted by 1 to 5 substituents selected from group B", which is represented by $R^{121}$ or $R^{122}$ in the formula [I], and ring E' is a heterocycle containing NH as a component constituting the ring such as piperidine, piperazine, pyrrolidine, morpholine, thiomorpholine, azepane, azonane and the like.

Step 1

Compound [172] can be obtained by reacting compound [166] with compound [171] in the same manner as in Production Method 10-2, Step 1.

Step 2

Compound [173] can be obtained by reacting compound [172] with compound [110] in the same manner as in Production Method 10-2, Step 1.

Step 3

Compound [174] can be obtained by subjecting compound [173] to cyclization in the same manner as in Production Method 10-2, Step 7.

Step 4

Compound [175] can be obtained by eliminating the carboxyl-protecting group ($R^{c29}$) of compound [174] by a conventional method.

For example, when $R^{c29}$ is tert-butyl, compound [174] is treated with trifluoroacetic acid in a solvent such as methylene chloride, chloroform and the like to give compound [175]. In addition, compound [174] may be treated with hydrogen chloride or hydrochloric acid in a solvent such as ethyl acetate, 1,4-dioxane, alcohol and the like to give compound [175].

Step 5

Compound [176] is condensed with carboxylic acid compound [175] in a solvent such as DMF, acetonitrile, THF, chloroform, ethyl acetate, methylene chloride, toluene and the like by adding a condensing agent such as dicyclohexylcarbodiimide, 1-ethyl-3-(3-dimethylaminopropyl)carbodiimide hydrochloride, diphenylphosphoryl azide and the like and, where necessary, N-hydroxysuccinimide, 1-hydroxybenzotriazole and the like to give amide compound [177]. Triethylamine may be added.

Alternatively, amide compound [177] can be obtained from compound [175] as follows. The carboxylic acid compound [175] is converted to an acid halide with thionyl chloride, oxalyl chloride and the like (a catalytic amount of DMF may be added), or to an active ester of compound [175] (e.g., converting to a mixed acid anhydride with ethyl chlorocarbonate and the like), which is then reacted with compound [176] in the presence of a base, such as triethylamine, potassium carbonate, pyridine and the like, or in an amine solvent such as pyridine and the like, to give amide compound [177]. For the reaction of active ester with compound [176], dimethylaminopyridine may be added.

Here, compound [177] can also be obtained by reacting compound [166] with compound [110] and a compound of the formula

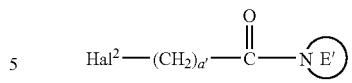

in the same manner as in Steps 1 and 2, and then cyclizing the resulting compound in the same manner as in Step 3.

Step 6

Compound [178] can be obtained by reducing compound [177] by a conventional method.

Step 7

Compound [179] can be obtained by eliminating the carboxyl-protecting group of compound [178] by a conventional method.

Production Method 10-4

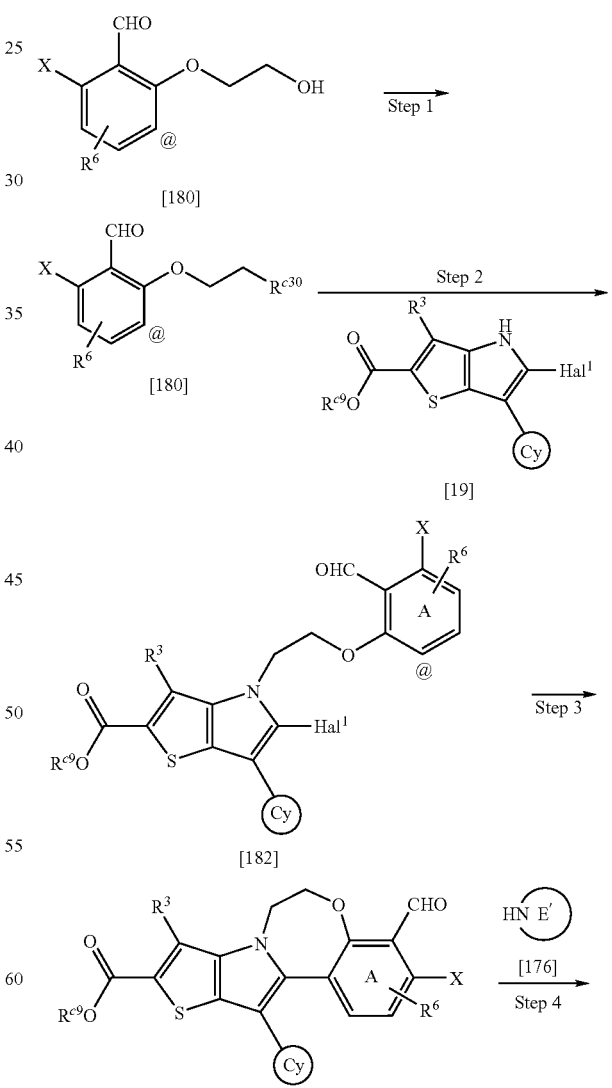

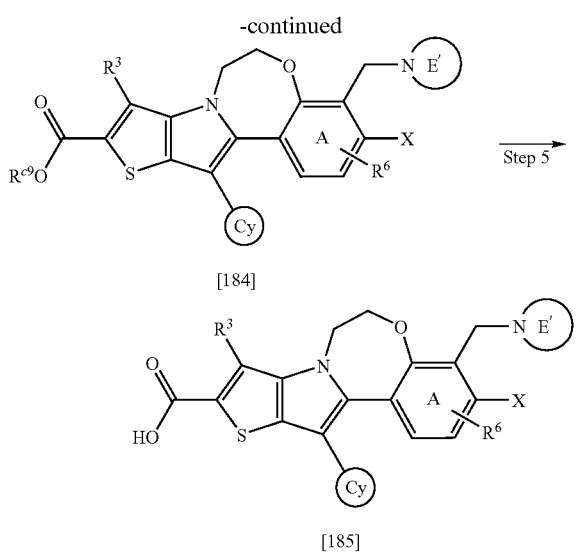

[184]

[185]

wherein each symbol is as defined above.

Step 1

Compound [181] can be obtained by converting the hydroxyl group of compound [180] to a leaving group by a conventional method.

Step 2

Compound [182] can be obtained by reacting compound [181] with compound [19] in the same manner as in Production Method 10-2, Step 1.

Step 3

Compound [183] can be obtained by subjecting compound [182] to cyclization in the same manner as in Production Method 10-2, Step 7.

Step 4

Compound [184] can be obtained by reacting compound [183] with compound [176] in the presence of a reducing agent.

As the reducing agent, borohydrides such as sodium borohydride, sodium cyanoborohydride, sodium triacetoxyborohydride and the like can be mentioned.

As a solvent, THF, 1,4-dioxane, dichloromethane, chloroform, methanol, ethanol, toluene, acetic acid and the like can be mentioned. Acetic acid may be added.

Step 5

Compound [185] can be obtained by eliminating the carboxyl-protecting group of compound [184] by a conventional method.

Production Method 11-1

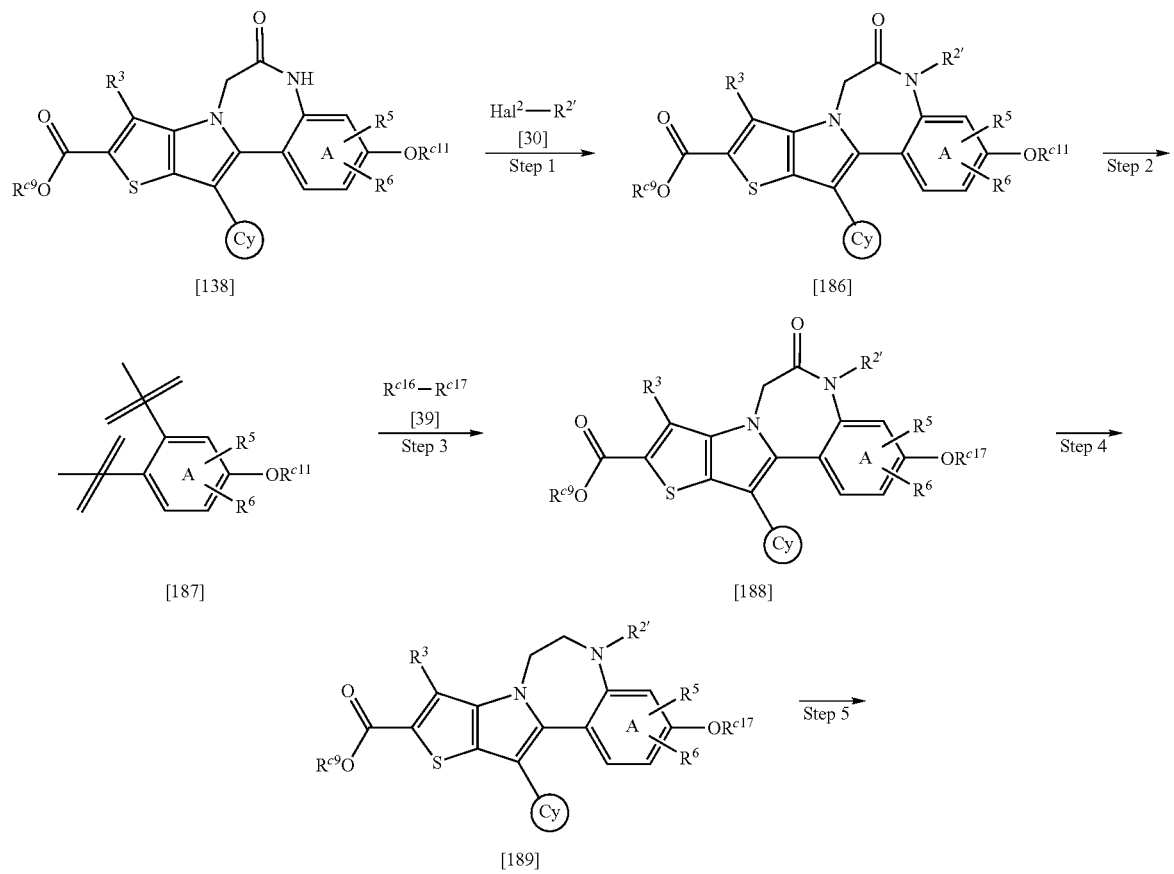

wherein each symbol is as defined above.

Step 1

The compound [138] obtained in the same manner as in Production Method 11 is reacted with compound [30] in the same manner as in Production Method 3, Step 1 to give compound [186].

Step 2

Compound [187] can be obtained by deprotection of the hydroxyl-protecting group of compound [186] by a conventional method.

Step 3

Compound [188] can be obtained by reacting compound [187] with compound [39] in the same manner as in Production Method 7-1, Step 2.

Step 4

Compound [189] can be obtained by reducing carbonyl of compound [188] by a conventional method.

Step 5

Compound [190] can be obtained by hydrolyzing compound [189] in the same manner as in Production Method 5, Step 1.

Step 6

Compound [191] can be obtained by reacting compound [190] with compound [151] in the same manner as in Production Method 12-2, Step 2.

In the above-mentioned Production Method, when Q is —$CH_2$—N($R^2$)-#, $R^2$ can be a substituent other than hydrogen atom, as long as the reaction is not inhibited.

In the compounds of the formula [I], a desired heterocyclic group (including carboxylic acid equivalent) can be formed according to a method similar to the methods disclosed in known publications. Examples of such heterocyclic group and reference publications are recited in the following.

5-oxo-$\Delta^2$-1,2,4-oxadiazolin-3-yl (or 2,5-dihydro-5-oxo-4H-1,2,4-oxadiazol-3-yl), 5-oxo-$\Delta^2$-1,2,4-thiadiazolin-3-yl (or 2,5-dihydro-5-oxo-4H-1,2,4-thiadiazol-3-yl), 2-oxo-$\Delta^3$-1,2,3,5-oxathiadiazolin-4-yl (or 2-oxo-$\Delta^3$-1,2,3,5-oxathiadiazol-4-yl): Journal of Medicinal Chemistry, 39(26), 5228-35, 1996, based on compound [I-17], for example, 5-oxo-$\Delta^2$-1,2,4-oxadiazolin-3-yl, 5-thioxo-$\Delta^2$-1,2,4-oxadiazolin-3-yl can be formed.

5-oxo-$\Delta^2$-1,2,4-triazolin-3-yl: J Org Chem, 61(24), 8397-8401, 1996, 1-oxo-$\Delta^3$-1,2,3,5-thiatriazolin-4-yl: Liebigs Ann Chem, 1376, 1980, 3-oxo-$\Delta^4$-1,2,4-oxadiazolin-5-yl: EP145095, 5-oxo-$\Delta^2$-1,3,4-oxadiazolin-2-yl: J Org Chem, 20, 412, 1955, 5-oxo-$\Delta^3$-1,2,4-dioxazolin-3-yl: J Prakt Chem, 314, 145, 1972, 3-oxo-$\Delta^4$-1,2,4-thiadiazolin-5-yl: JP-A-61-275271, 5-oxo-$\Delta^3$-1,2,4-dithiazolin-3-yl: J Org Chem, 61(19), 6639-6645, 1996, 2-oxo-$\Delta^4$-1,3,4-dioxazolin-5-yl: J Org Chem, 39, 2472, 1974, 2-oxo-$\Delta^4$-1,3,4-oxathiazolin-5-yl: J Med Chem, 35(20), 3691-98, 1992, 5-oxo-$\Delta^2$-1,3,4-thiadiazolin-2-yl: J Prakt Chem, 332(1), 55, 1990, 5-oxo-$\Delta^2$-1,4,2-oxathiazolin-3-yl: J Org Chem, 31, 2417, 1966, 2-oxo-$\Delta^4$-1,3,4-dithiazolin-5-yl: Tetrahedron Lett, 23, 5453, 1982, 2-oxo-$\Delta^4$-1,3,2,4-dioxathiazolin-5-yl: Tetrahedron Lett, 319, 1968, 3,5-dioxoisoxazolidin-4-yl: Helv Chim Acta, 1973, 48, 1965, 2,5-dioxoimidazolidin-4-yl: Heterocycles, 43(1), 49-52, 1996, 5-oxo-2-thioxoimidazolidin-4-yl: J Chem Soc, 4533, 1954, 2,4-dioxooxazolidin-5-yl: J Am Chem Soc, 73, 4752, 1951, 4-oxo-2-thioxooxazolidin-5-yl: Chem Ber, 91, 2537, 1958, 2,4-dioxothiazolidin-5-yl: JP-A-57-123175, 4-oxo-2-thioxothiazolidin-5-yl: Chem Pharm Bull, 30, 3563, 1982.

EXAMPLES

The thienopyrrole compounds of the formula [I] of the present invention and production methods thereof are explained in detail in the following by way of Examples. It is needless to say that the present invention is not limited by these Examples. In the Examples, Me means methyl group, Ac means acetyl group, Bn means benzyl group, THP means 2-tetrahydropyranyl group, and Ms means methanesulfonyl group.

Preparation Example 1

Production of 2-(4,4,5,5-tetramethyl-1,3,2-dioxaborolan-2-yl)phenylamine

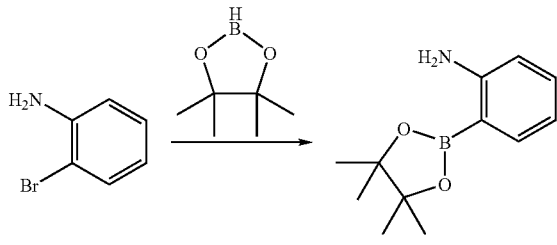

To a solution of 2-bromoaniline (1.0 g, 5.81 mmol) in 1,4-dioxane (15 ml) were added triethylamine (3.24 ml, 23.2 mmol) and [1,1-bis(diphenylphosphino)ferrocene]dichloropalladium(II) dichloromethane complex (PdCl$_2$(dppf) CH$_2$Cl$_2$) (243 mg, 0.30 mmol) at room temperature. To the reaction mixture was added dropwise pinacolborane (2.53 ml, 17.4 mmol), and the reaction mixture was heated to 100° C. and stirred for 3 hr. The reaction mixture was cooled to room temperature and saturated aqueous ammonium chloride solution was added. The mixture was extracted with diethyl ether. The organic layer was washed with saturated brine and dried over anhydrous sodium sulfate. After filtration, the solvent was evaporated under reduced pressure, and the residue was purified by silica gel column chromatography (hexane: ethyl acetate=5:1) to give 2-(4,4,5,5-tetramethyl-1,3,2-dioxaborolan-2-yl)phenylamine (810 mg, yield 63.6%).

$^1$H-NMR (400 MHz, δppm, CDCl$_3$) 7.59(1H, dd, J=7.2, 1.6 Hz), 7.20(1H, ddd, J=15.2, 7.2, 2.0 Hz), 6.66(1H, t, J=7.4 Hz), 6.58(1H, d, J=8.0 Hz), 4.72(2H, brs), 1.33(12H, s).

Example 1

Production of methyl 11-cyclohexyl-8-hydroxy-4,5-dihydro-6-oxa-1-thia-3b-azabenzo[e]cyclopenta[a]azulene-2-carboxylate Step 1:

Production of methyl 5-methylthiophene-2-carboxylate

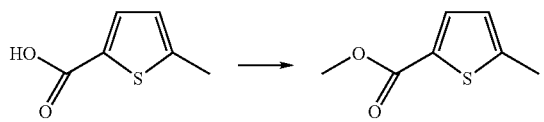

To a solution of 5-methylthiophene-2-carboxylic acid (40.3 g, 282 mmol) in N,N-dimethylformamide (500 ml) were added potassium carbonate (43 g, 310 mmol) and methyl iodide (19.3 ml, 310 mmol). After stirring at room temperature for 4 hr, diethyl ether (1.0 L) was added, and the organic layer was washed successively with water (500 ml×3) and saturated brine (200 ml) and dried over magnesium sulfate. After filtration and concentration, methyl 5-methylthiophene-2-carboxylate (40.8 g, yield 93%) was obtained.

$^1$H-NMR (300 MHz, δppm, CDCl$_3$) 7.61(1H, d, J=3.6 Hz), 6.76(1H, d, J=3.6 Hz), 3.85(3H, s), 2.52(3H, s).

Step 2:

Production of methyl 4-nitro-5-methylthiophene-2-carboxylate

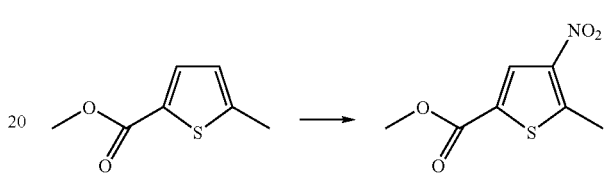

To a solution of methyl 5-methylthiophene-2-carboxylate (40.8 g, 260 mmol) in conc. sulfuric acid (400 ml) was added dropwise a solution of fuming nitric acid (16.5 ml, 391 mmol) in conc. sulfuric acid (100 ml) under ice-cooling in such a manner that the inside temperature did not exceed 5° C. After the completion of the dropwise addition, the mixture was stirred under ice-cooling for 30 min, and poured slowly into ice (1 kg). The precipitated solid was washed with water (500 ml×6) and dried under reduced pressure to give methyl 4-nitro-5-methylthiophene-2-carboxylate (35.1 g, yield 67%).

$^1$H-NMR (300 MHz, δppm, CDCl$_3$) 8.20(1H, s), 3.91(3H, s), 2.84(3H, s).

Step 3:

Production of 2,4-bisbenzyloxybenzaldehyde

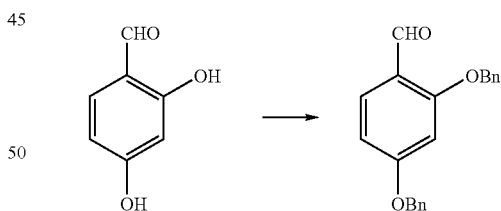

To a solution of 2,4-dihydroxybenzaldehyde (5.00 g, 36.2 mmol) in N,N-dimethylformamide (30 ml) were added potassium carbonate (12.0 g, 86.9 mmol) and benzyl bromide (9.48 ml, 79.6 mmol). After stirring at room temperature for 3 hr 30 min, water (100 ml) and hexane (50 ml) were added, and the precipitated solid was collected by filtration. The solid was washed with water (3 ml×3) and hexane (5 ml) and dried under reduced pressure to give 2,4-bisbenzyloxybenzaldehyde (9.67 g, yield 84%).

$^1$H-NMR (400 MHz, δppm, DMSO-d$_6$) 10.23(1H, s), 7.68 (1H, d, J=8.4 Hz), 7.50-7.32(10H, m), 6.92(1H, d, J=2.0 Hz), 6.75(1H, dd, J=8.8, 2.0 Hz), 5.27(2H, s), 5.21(2H, s).

Step 4:

Production of methyl (E)-5-[2-(2,4-bisbenzyloxyphenyl)vinyl]-4-nitrothiophene-2-carboxylate

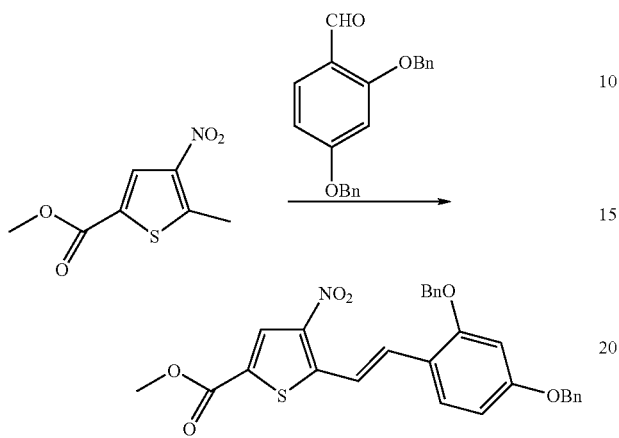

To a solution of methyl 4-nitro-5-methylthiophene-2-carboxylate (1.50 g, 7.46 mmol) in ethanol (7.5 ml) were added 2,4-bisbenzyloxybenzaldehyde (2.49 g, 7.83 mmol) and pyrrolidine (0.65 ml, 7.83 mmol). After stirring for 1 hr with heating under reflux, the reaction mixture was allowed to cool to room temperature. The precipitated solid was collected by filtration. The solid was washed with ethanol (3 ml×3), and dried under reduced pressure to give methyl (E)-5-[2-(2,4-bisbenzyloxyphenyl)vinyl]-4-nitrothiophene-2-carboxylate (3.08 g, yield 82%).

$^1$H-NMR (400 MHz, δppm, DMSO-$d_6$) 8.08(1H, s), 8.04 (1H, d, J=16.0 Hz), 7.64(1H, d, J=8.8 Hz), 7.60(1H, d, J=16.0 Hz), 7.50-7.32(10H, m), 6.87(1H, d, J=2.0 Hz), 6.73(1H, dd, J=8.8, 2.4 Hz), 5.26(2H, s), 5.17(2H, s), 3.86(3H, s).

Step 5:

Production of methyl 5-(2,4-bisbenzyloxyphenyl)-4H-thieno[3,2-b]pyrrole-2-carboxylate

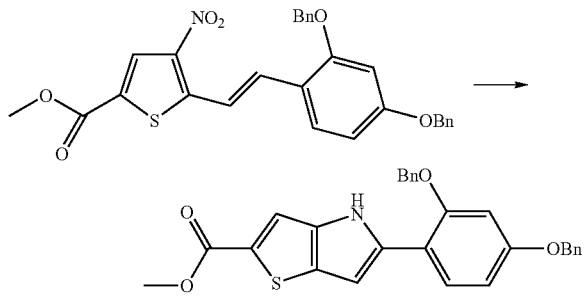

To a solution of methyl (E)-5-[2-(2,4-bisbenzyloxyphenyl)vinyl]-4-nitrothiophene-2-carboxylate (3.08 g, 6.13 mmol) in mesitylene (15 ml) was added triethyl phosphite (3.15 ml, 18.4 mmol), and the mixture was stirred at 160° C. for 43 hr. The reaction mixture was allowed to cool to room temperature, and ethyl acetate (50 ml) was added. The organic layer was washed successively with 1N hydrochloric acid (30 ml), water (30 ml×2) and saturated brine (20 ml), and dried over sodium sulfate. After filtration and concentration, isopropyl alcohol (20 ml) was added to the obtained residue and the precipitated solid was collected by filtration. The solid was washed with isopropyl alcohol (10 ml×3) to give methyl 5-(2,4-bisbenzyloxyphenyl)-4H-thieno[3,2-b]pyrrole-2-carboxylate (1.36 g, yield 47%).

$^1$H-NMR (400 MHz, δppm, DMSO-$d_6$) 11.58(1H, s), 7.62 (1H, d, J=8.4 Hz), 7.62(1H, d, J=0.4 Hz), 7.48-7.29(10H, m), 6.84(1H, s), 6.83(1H, d, J=2.4 Hz), 6.72(1H, dd, J=8.4, 2.4 Hz), 5.31(2H, s), 5.12(2H, s), 3.80(3H, s).

Step 6:

Production of methyl 5-(2,4-bisbenzyloxyphenyl)-6-(cyclohex-2-enyl)-4H-thieno[3,2-b]pyrrole-2-carboxylate

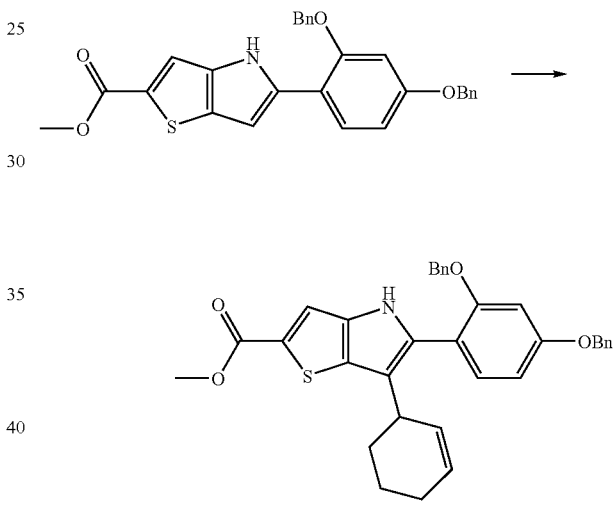

To a solution of methyl 5-(2,4-bisbenzyloxyphenyl)-4H-thieno[3,2-b]pyrrole-2-carboxylate (1.36 g, 2.90 mmol) in N,N-dimethylformamide (15 ml) was added sodium hydride (60% in oil, 127 mg, 3.19 mmol) under ice-cooling and the mixture was stirred for 20 min. 3-Bromocyclohexene (0.34 ml, 2.95 mmol) was added and the mixture was stirred under ice-cooling for 50 min. Ethyl acetate (20 ml) was added to the reaction mixture, and the organic layer was washed successively with water (20 ml×3) and saturated brine (10 ml) and dried over sodium sulfate. After filtration and concentration, a mixed solvent (10 ml) of hexane:ethyl acetate (10:1) was added. The precipitated solid was collected by filtration. The solid was washed with a mixed solvent (5 ml×3) of hexane: ethyl acetate (10:1), and dried under reduced pressure to give methyl 5-(2,4-bisbenzyloxyphenyl)-6-(cyclohex-2-enyl)-4H-thieno[3,2-b]pyrrole-2-carboxylate (1.35 g, yield 85%).

$^1$H-NMR (400 MHz, δppm, DMSO-$d_6$) 11.35(1H, s), 7.56 (1H, s), 7.47-7.26(11H, m), 7.23(1H, d, J=8.4 Hz), 6.85(1H, d, J=2.0 Hz), 6.72(1H, dd, J=2.4, 8.4 Hz), 5.85-5.79(1H, m), 5.54-5.49(1H, m), 5.14(2H, s), 5.13(2H, s), 3.78(3H, s), 3.37-3.32(1H, m), 2.08-1.99(2H, m), 1.74-1.41(4H, m).

Step 7:

Production of methyl 5-(2,4-bisbenzyloxyphenyl)-6-cyclohexyl-4H-thieno[3,2-b]pyrrole-2-carboxylate

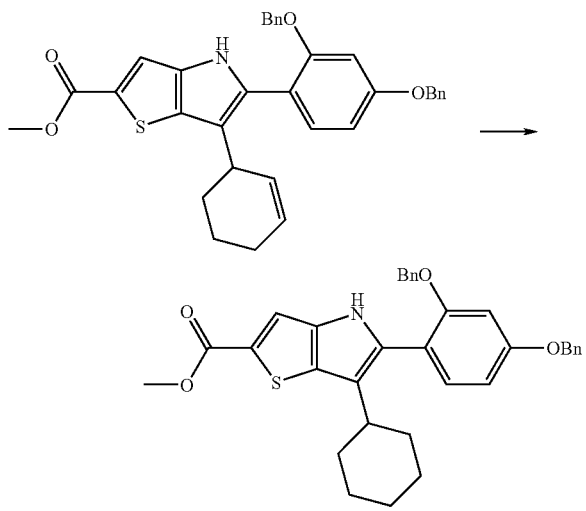

To a solution of methyl 5-(2,4-bisbenzyloxyphenyl)-6-(cyclohex-2-enyl)-4H-thieno[3,2-b]pyrrole-2-carboxylate in a mixture of methanol (6 ml) and tetrahydrofuran (16 ml) was added 20% palladium hydroxide/carbon (400 mg, 0.74 mmol). After stirring for 13 hr under hydrogen atmosphere (3.4 atm) at room temperature, the reaction mixture was filtered through celite, and the filtrate was concentrated. The precipitated solid was collected by filtration. The solid was washed with diisopropyl ether (5 ml×3), and dried under reduced pressure to give methyl 5-(2,4-bisbenzyloxyphenyl)-6-cyclohexyl-4H-thieno[3,2-b]pyrrole-2-carboxylate (1.12 g, yield 82%).

$^1$H-NMR (400 MHz, δppm, DMSO-$d_6$) 11.26(1H, s), 7.57 (1H, s), 7.47-7.25(11H, m), 7.19(1H, d, J=8.4 Hz), 6.84(1H, d, J=2.4 Hz), 6.72(1H, dd, J=8.4, 2.4 Hz), 5.14(2H, s), 5.12 (2H, s), 3.79(3H, s), 2.52-2.47(1H, m), 1.71-1.61(5H, m), 1.56-1.45(2H, m), 1.23-1.15(3H, m).

Step 8:

Production of methyl 4-(2-benzyloxyethyl)-5-(2,4-bisbenzyloxyphenyl)-6-cyclohexyl-4H-thieno[3,2-b]pyrrole-2-carboxylate

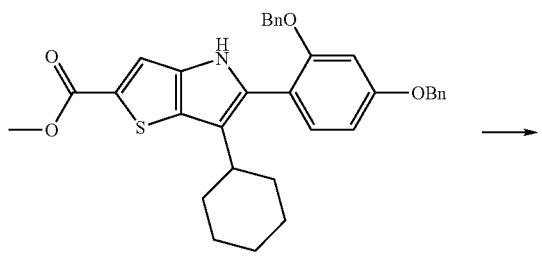

-continued

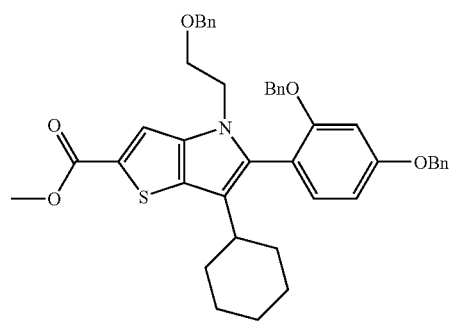

To a solution of methyl 5-(2,4-bisbenzyloxyphenyl)-6-cyclohexyl-4H-thieno[3,2-b]pyrrole-2-carboxylate (1.12 g, 2.03 mmol) in N,N-dimethylformamide (10 ml) was added sodium hydride (60% in oil, 97 mg, 2.43 mmol) under ice-cooling and the mixture was stirred for 10 min. (2-Bromoethoxymethyl)benzene (0.53 ml, 3.24 mmol) was added and the mixture was stirred at room temperature for 4 hr. Ethyl acetate (25 ml) was added to the reaction mixture, and the organic layer was washed successively with water (20 ml×3) and saturated brine (10 ml), and dried over sodium sulfate. After filtration and concentration, the obtained residue was purified by silica gel column chromatography (hexane:ethyl acetate=5:1-2:1) to give methyl 4-(2-benzyloxyethyl)-5-(2,4-bisbenzyloxyphenyl)-6-cyclohexyl-4H-thieno[3,2-b]pyrrole-2-carboxylate (1.21 g, yield 87%).

$^1$H-NMR (400 MHz, δppm, DMSO-$d_6$) 7.86(1H, s), 7.49-7.33(5H, m), 7.28-7.19(8H, m), 7.08(1H, d, J=8.4 Hz), 7.06-7.04(2H, m), 6.85(1H, d, J=2.4 Hz), 6.70(1H, dd, J=8.0, 2.0 Hz), 5.13(1H, d, J=11.2 Hz), 5.12(1H, d, J=12.4 Hz), 5.10 (1H, d, J=11.2 Hz), 5.08(1H, d, J=12.4 Hz), 4.26(2H, s), 4.14-3.93(2H, m), 3.79(3H, s), 3.54-3.40(2H, m), 2.33-2.22 (1H, m), 1.76-1.45(7H, m), 1.21-1.10(3H, m).

Step 9:

Production of methyl 4-(2-acetoxyethyl)-6-cyclohexyl-5-(2,4-dihydroxyphenyl)-4H-thieno[3,2-b]pyrrole-2-carboxylate

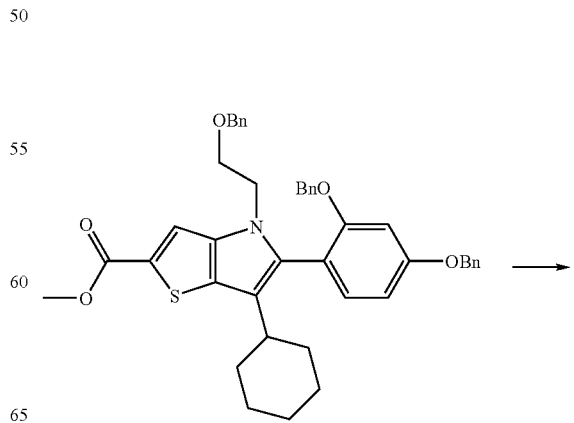

-continued

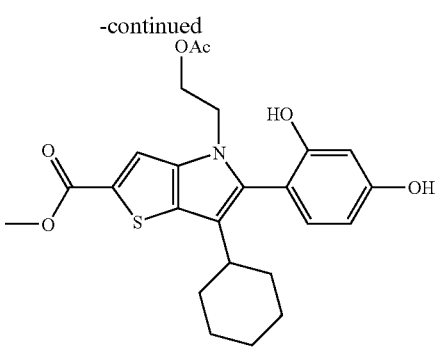

To a solution of methyl 4-(2-benzyloxyethyl)-5-(2,4-bis-benzyloxyphenyl)-6-cyclohexyl-4H-thieno[3,2-b]pyrrole-2-carboxylate (1.21 g, 1.77 mmol) in acetic acid (3 ml) was added 25% hydrogen bromide-acetic acid solution (3 ml), and the mixture was stirred at room temperature for 15 hr. The reaction mixture was concentrated under reduced pressure and the residue was subjected to azeotropic evaporation with toluene (5 ml×2). The obtained residue was purified by silica gel column chromatography (hexane:ethyl acetate=4:1-0:1) to give methyl 4-(2-acetoxyethyl)-6-cyclohexyl-5-(2,4-dihydroxyphenyl)-4H-thieno[3,2-b]pyrrole-2-carboxylate (762 mg, yield 94%).

$^1$H-NMR (400 MHz, δppm, DMSO-$d_6$) 9.54(2H, brs), 7.88 (1H, s), 6.91(1H, d, J=8.4 Hz), 6.41(1H, d, J=2.4 Hz), 6.32 (1H, dd, J=8.4, 2.4 Hz), 4.15-4.04(4H, m), 3.81(3H, s), 2.33-2.25(1H, m), 1.86(3H, s), 1.79-1.41(7H, m), 1.26-1.10(3H, m).

Step 10:

Production of methyl 6-cyclohexyl-5-(2,4-dihydroxyphenyl)-4-(2-hydroxyethyl)-4H-thieno[3,2-b]pyrrole-2-carboxylate

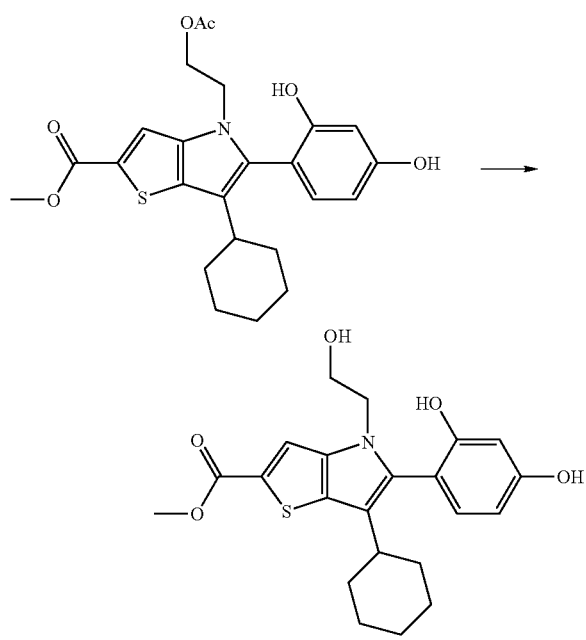

To a solution of methyl 4-(2-acetoxyethyl)-6-cyclohexyl-5-(2,4-dihydroxyphenyl)-4H-thieno[3,2-b]pyrrole-2-carboxylate (505 mg, 1.11 mmol) in methanol (5 ml) was added potassium carbonate (476 mg, 3.44 mmol) and the mixture was stirred at room temperature for 25 min. The reaction mixture was concentration under reduced pressure, and ethyl acetate (5 ml) was added to the residue. The organic layer was washed successively with 1N hydrochloric acid (4 ml) and saturated brine (5 ml×2), and dried over sodium sulfate. Filtration and concentration gave methyl 6-cyclohexyl-5-(2,4-dihydroxyphenyl)-4-(2-hydroxyethyl)-4H-thieno[3,2-b]pyrrole-2-carboxylate as a crude product. The obtained compound was used for Step 11 without further purification.

$^1$H-NMR (400 MHz, δppm, DMSO-$d_6$) 9.53(2H, brs), 7.82 (1H, s), 6.89(1H, d, J=8.4 Hz), 6.40(1H, d, J=2.4 Hz), 6.31 (1H, dd, J=8.4, 2.4 Hz), 3.91-3.81(2H, m), 3.80(3H, s), 3.52-3.35(2H, m), 2.33-2.23(1H, m), 1.76-1.60(5H, m), 1.54-1.41 (2H, m), 1.21-1.11(3H, m).

Step 11:

Production of methyl 11-cyclohexyl-8-hydroxy-4,5-dihydro-6-oxa-1-thia-3b-azabenzo[e]cyclopenta[a]azulene-2-carboxylate

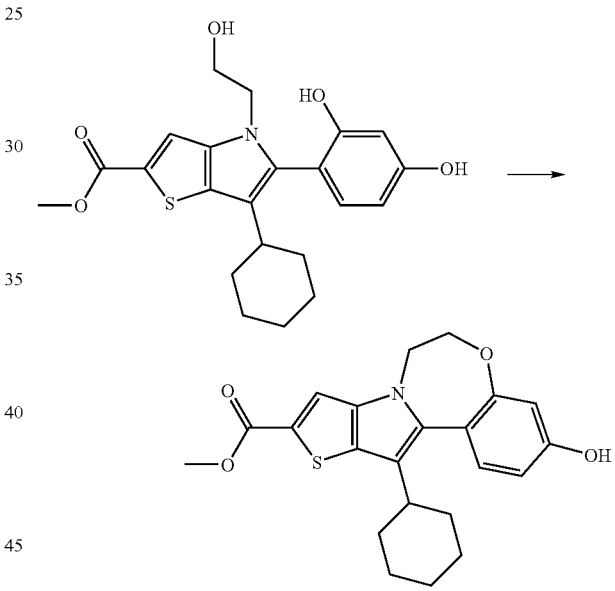

A solution of methyl 6-cyclohexyl-5-(2,4-dihydroxyphenyl)-4-(2-hydroxyethyl)-4H-thieno[3,2-b]pyrrole-2-carboxylate (469 mg, 1.11 mmol) in tetrahydrofuran (5 ml) was cooled in a water bath and triphenylphosphine (582 mg, 2.22 mmol) and diisopropyl azodicarboxylate (0.44 ml, 2.22 mmol) were added with stirring. The mixture was stirred for 2 hr and the reaction mixture was concentrated. The precipitated solid was collected by filtration. The solid was washed with diisopropyl ether (3 ml×3), and dried under reduced pressure to give methyl 11-cyclohexyl-8-hydroxy-4,5-dihydro-6-oxa-1-thia-3b-azabenzo[e]cyclopenta[a]azulene-2-carboxylate (469 mg) as a crude product. The obtained compound was used for Example 2, Step 5 without further purification.

$^1$H-NMR (400 MHz, δppm, DMSO-$d_6$) 9.99(1H, brs), 7.97 (1H, s), 7.19(1H, d, J=8.4 Hz), 6.71(1H, dd, J=8.4, 2.4 Hz), 6.59(1H, d, J=2.4 Hz), 4.41-4.38(2H, m), 4.28-4.25(2H, m), 3.81(3H, s), 2.76-2.66(1H, m), 1.81-1.58(7H, m), 1.38-1.22 (3H, m).

Example 2

Production of methyl 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylate Step 1:

Production of methyl 2-chloro-5-methylsulfanylbenzoate

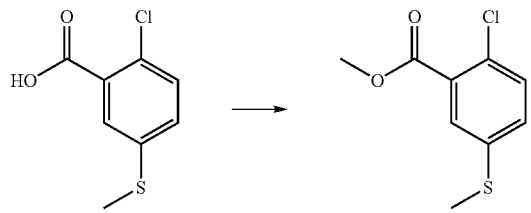

To a solution of 2-chloro-5-methylsulfanylbenzoic acid (20.2 g, 100 mmol) in N,N-dimethylformamide (200 ml) were added potassium carbonate (15.2 g, 110 mmol) and methyl iodide (6.8 ml, 110 mmol). After stirring at room temperature for 3 hr, diethyl ether (300 ml) was added. The organic layer was washed successively with water (200 ml×3) and saturated brine (200 ml), and dried over magnesium sulfate. Filtration and concentration gave methyl 2-chloro-5-methylsulfanylbenzoate (18.5 g, yield 86%).

$^1$H-NMR (400 MHz, δppm, CDCl$_3$) 7.65(1H, d, J=2.6 Hz), 7.33(1H, d, J=8.6 Hz), 7.26(1H, dd, J=8.6, 2.6 Hz), 3.92(3H, s), 2.49(3H, s).

Step 2:

Production of methyl 2-chloro-5-methanesulfonylbenzoate

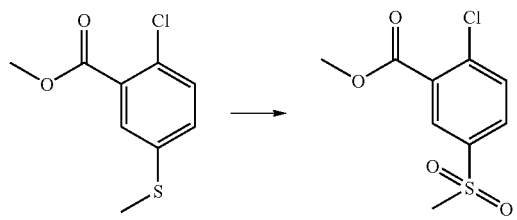

To a solution of methyl 2-chloro-5-methylsulfanylbenzoate (18.5 g, 86 mmol) in chloroform (200 ml) was added 3-chloroperbenzoic acid (46.6 g, 189 mmol) by small portions under ice-cooling. After stirring overnight at room temperature, the reaction mixture was washed with saturated aqueous sodium hydrogen carbonate solution (200 ml×2), and dried over magnesium sulfate. Filtration and concentration gave methyl 2-chloro-5-methanesulfonylbenzoate (23.4 g, yield 100%).

$^1$H-NMR (400 MHz, δppm, CDCl$_3$) 8.39(1H, d, J=2.3 Hz), 7.96(1H, dd, J=8.3, 2.3 Hz), 7.66(1H, d, J=8.3 Hz), 3.97(3H, s), 3.07(3H, s).

Step 3:

Production of methyl 5-methanesulfonyl-2-(morpholin-4-yl)benzoate

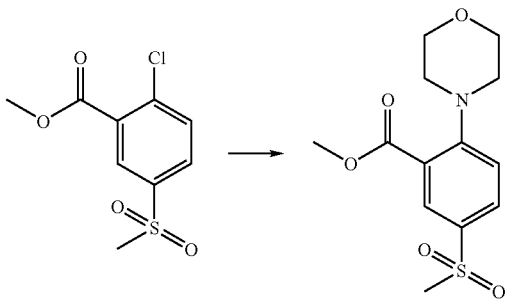

To a solution of methyl 2-chloro-5-methanesulfonylbenzoate (23.4 g, 94 mmol) in toluene (250 ml) were added morpholine (9.8 ml, 113 mmol), cesium carbonate (40 g, 122 mmol), palladium acetate (380 mg, 1.4 mmol) and 2,2'-bis(diphenylphosphino)-1,1'-binaphthyl (1.06 g, 1.7 mmol). After stirring overnight with heating under reflux, ethyl acetate (250 ml) was added. The organic layer was washed successively with water (200 ml×2) and saturated brine (200 ml), and dried over magnesium sulfate. Filtration and concentration gave methyl 5-methanesulfonyl-2-(morpholin-4-yl)benzoate as a crude product. The obtained compound was used for Step 4 without further purification.

$^1$H-NMR (400 MHz, δppm, CDCl$_3$) 8.29(1H, d, J=2.3 Hz), 7.90(1H, dd, J=8.6, 2.3 Hz), 7.05(1H, d, J=8.6 Hz), 3.90(3H, s), 3.88-3.83(4H, m), 3.21-3.16(4H, m), 3.03(3H, s).

Step 4:

Production of 5-methanesulfonyl-2-(morpholin-4-yl)benzyl alcohol

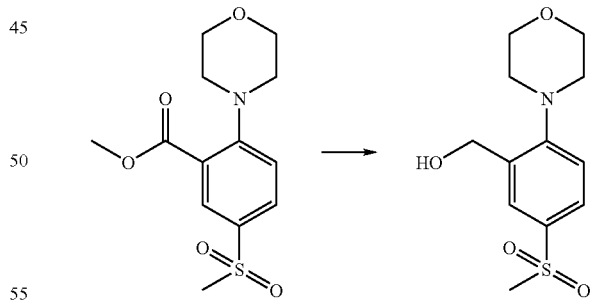

To a solution of methyl 5-methanesulfonyl-2-(morpholin-4-yl)benzoate obtained in Step 3 in tetrahydrofuran (300 ml) was added lithium aluminum hydride (3.6 g, 94 mmol) by small portions under ice-cooling. After stirring under ice-cooling for 1 hr, 1N hydrochloric acid (200 ml) was slowly added and the mixture was stirred at room temperature for 1 hr. After extraction with ethyl acetate (500 ml), the organic layer was washed with saturated brine (200 ml×3), and dried over magnesium sulfate. After filtration and concentration, the resulting solid was collected by filtration. The solid was washed with a mixed solvent (100 ml) of hexane-ethyl acetate (4:1) to give 5-methanesulfonyl-2-(morpholin-4-yl)benzyl alcohol (8.6 g, yield 34%).

$^1$H-NMR (400 MHz, δppm, CDCl$_3$) 7.94(1H, d, J=2.3 Hz), 7.84(1H, dd, J=8.3, 2.3 Hz), 7.22(1H, d, J=8.3 Hz), 4.81(2H, s), 3.90-3.85(4H, m), 3.27(1H, brs), 3.05-3.00(4H, m), 3.04 (1H, s).

Step 5:

Production of methyl 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylate

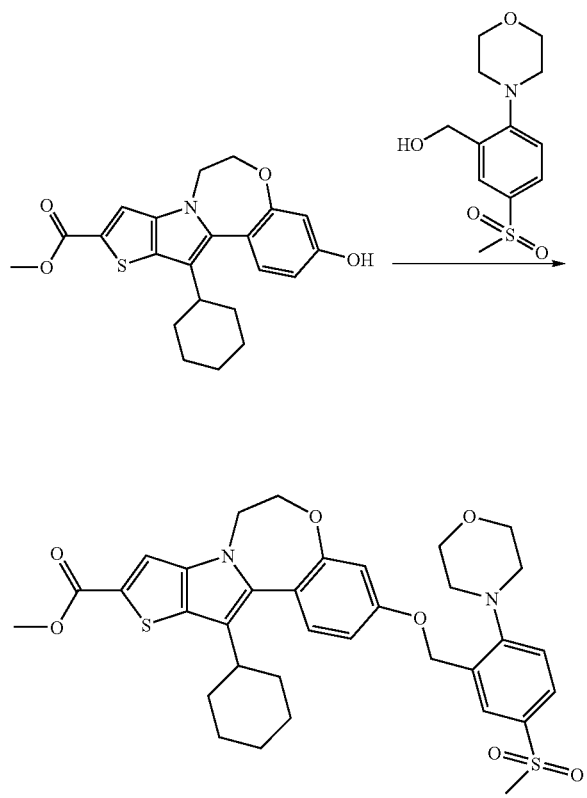

A solution of methyl 11-cyclohexyl-8-hydroxy-4,5-dihydro-6-oxa-1-thia-3b-azabenzo[e]cyclopenta[a]azulene-2-carboxylate (100 mg) in tetrahydrofuran (3 ml) was cooled in a water bath, and 5-methanesulfonyl-2-(morpholin-4-yl)benzyl alcohol (82 mg, 0.30 mmol), triphenylphosphine (99 mg, 0.38 mmol) and diisopropyl azodicarboxylate (0.07 ml, 0.38 mmol) were added with stirring. The reaction mixture was stirred for 16 hr and concentrated. The obtained residue was purified by silica gel column chromatography (chloroform:ethyl acetate=5:1-1:10) to give methyl 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylate (251 mg) as a crude product. The obtained crude product was used for Example 3 without further purification.

Example 3

Production of 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylic acid

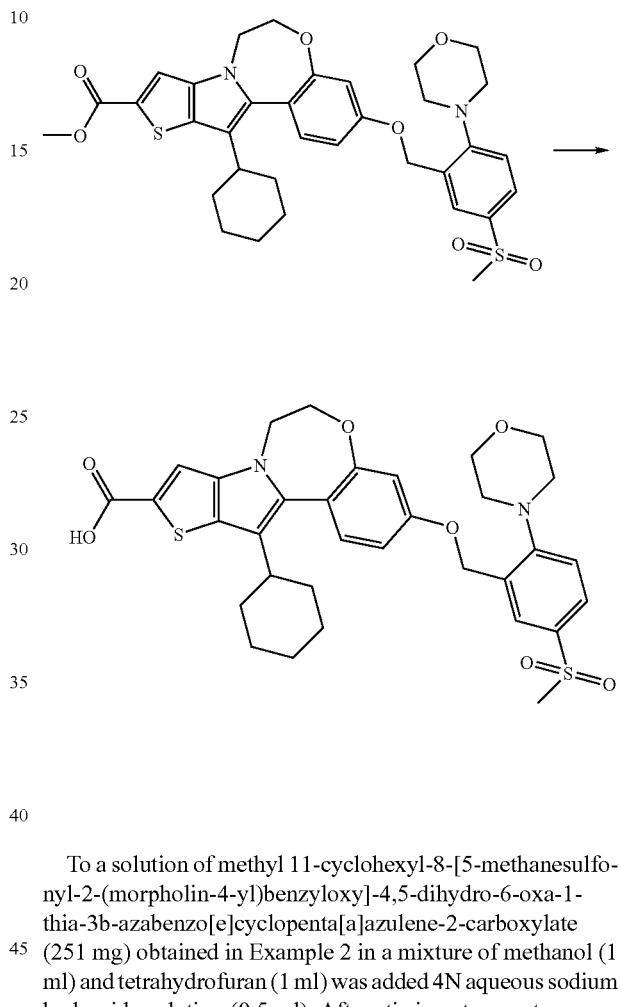

To a solution of methyl 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylate (251 mg) obtained in Example 2 in a mixture of methanol (1 ml) and tetrahydrofuran (1 ml) was added 4N aqueous sodium hydroxide solution (0.5 ml). After stirring at room temperature for 64 hr, the reaction mixture was concentrated. The obtained residue was acidified with 1N hydrochloric acid (2.5 ml). The mixture was extracted with ethyl acetate (5 ml) and the organic layer was washed successively with water (4 ml) and saturated brine (1 ml), and dried over sodium sulfate. After filtration and concentration, the residue was purified by silica gel column chromatography (ethyl acetate:methanol=1:0-5:1) to give 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylic acid (39 mg, yield after 3 steps from Example 1, Step 11: 24%).

$^1$H-NMR (400 MHz, δppm, DMSO-d$_6$) 8.02(1H, d, J=2.4 Hz), 7.88-7.85(2H, m), 7.36(1H, d, J=8.4 Hz), 7.32(1H, d, J=8.4 Hz), 7.02(1H, dd, J=8.4, 2.4 Hz), 6.96(1H, d, J=2.4 Hz), 5.22(2H, s), .4.46-4.42(2H, m), 4.30-4.26(2H, m), 3.80-3.78 (4H, m), 3.19(3H, s), 3.03-3.00(4H, m), 2.76-2.66(1H, m), 1.83-1.75(4H, m), 1.73-1.59(3H, m), 1.38-1.23(3H, m).

MS 637(M+l).

Example 4

Production of 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxamide

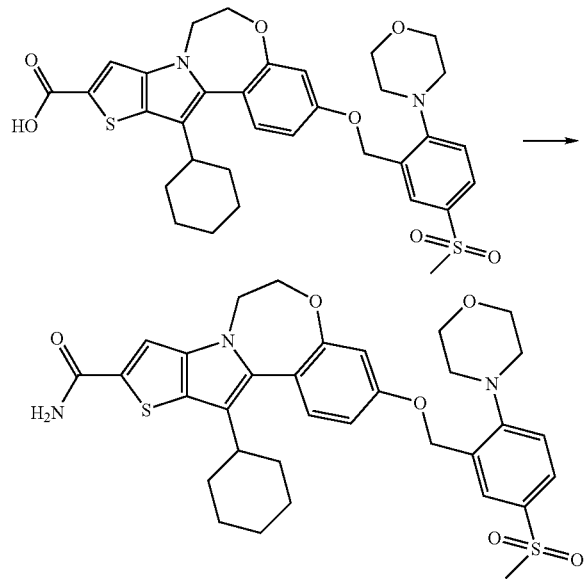

To a solution of 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylic acid (217 mg, 0.34 mmol) in N,N-dimethylformamide (2 ml) were added benzotriazol-1-yloxytripyrrolidinophosphonium hexafluorophosphate (266 mg, 0.51 mmol), 1-hydroxybenzotriazole hydrate (78 mg, 0.51 mmol), diisopropylethylamine (0.24 ml, 1.36 mmol) and ammonium chloride (36 mg, 0.68 mmol). After stirring at room temperature for 2 hr, water (3 ml) was added to the reaction mixture, and the mixture was extracted with ethyl acetate (5 ml). The organic layer was washed successively with water (3 ml×2) and saturated brine (2 ml), and dried over sodium sulfate. After filtration and concentration, a mixed solvent (5 ml) of chloroform:methanol (40:1) was added to the obtained residue and the precipitated solid was collected by filtration. The solid was washed with a mixed solvent (3 ml×3) of chloroform:methanol (40:1) to give 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxamide (112 mg, yield 52%).

$^1$H-NMR (400 MHz, δppm, DMSO-$d_6$) 8.02(1H, d, J=2.4 Hz), 7.87(1H, dd, J=2.4, 8.8 Hz), 7.78(1H, s), 7.36(1H, d, J=8.4 Hz), 7.31(1H, d, J=8.4 Hz), 7.01(1H, dd, J=2.8, 8.4 Hz), 6.95(1H, d, J=2.8 Hz), 5.22(2H, s), 4.45(2H, t, J=5.6 Hz), 4.17(2H, t, J=5.6 Hz), 3.80-3.78(4H, m), 3.19(3H, s), 3.03-3.01(4H, m), 2.76-2.68(1H, m), 1.82-1.75(3H, m), 1.74-1.61(4H, m), 1.38-1.23(3H, m).

MS 636(M+1).

Example 5

Production of methyl 11-cyclohexyl-5-oxo-5,6-dihydro-4H-1-thia-3b,6-diazabenzo[e]cyclopenta[a]azulene-2-carboxylate Step 1:

Production of methyl 5-methylthiophene-2-carboxylate

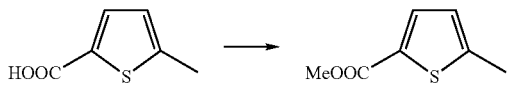

To a solution of 5-methylthiophene-2-carboxylic acid (100 g, 703 mmol) in methanol (1.0 L) was added conc. sulfuric acid (10 ml) and the mixture was heated under reflux for 2 days. The reaction mixture was cooled to room temperature and concentrated under reduced pressure. Diethyl ether (1.0 L) was added to the residue. The mixture was washed successively with water (500 ml×4) and saturated brine (500 ml), and dried over magnesium sulfate. Filtration and concentration under reduced pressure gave methyl 5-methylthiophene-2-carboxylate (109 g, yield 100%).

$^1$H-NMR (400 MHz, δppm, CDCl$_3$) 7.61(1H, d, J=3.6 Hz,), 6.76(1H, d, J=3.6 Hz), 3.85(3H, s), 2.52(3H, s).

Step 2:

Production of methyl 4-nitro-5-methylthiophene-2-carboxylate

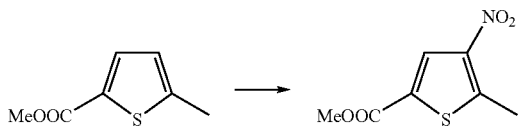

To a solution of methyl 5-methylthiophene-2-carboxylate (109 g, 700 mmol) in conc. sulfuric acid (850 ml) was added dropwise a solution of fuming nitric acid (31 ml, 738 mmol) in conc. sulfuric acid (150 ml) under ice-cooling in such a manner that an inside temperature did not exceed 5° C. After the completion of the dropwise addition, the mixture was stirred under ice-cooling for 30 min, and slowly poured into ice (2 kg). The precipitated solid was collected by filtration, washed with water (500 ml×6) and dried under reduced pressure to give methyl 4-nitro-5-methylthiophene-2-carboxylate (62 g, yield 44%).

$^1$H-NMR (400 MHz, δppm, CDCl$_3$) 8.20(1H, s), 3.91(3H, s), 2.84(3H, s).

Step 3:

Production of methyl (E)-5-(2-dimethylaminovinyl)-4-nitrothiophene-2-carboxylate

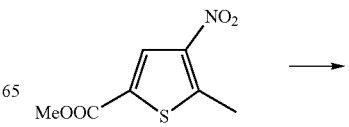

-continued

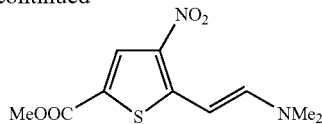

A solution of methyl 4-nitro-5-methylthiophene-2-carboxylate (23 g, 114 mmol) in N,N-dimethylformamide dimethyl acetal (115 ml) was stirred at 110° C. for 1 hr. The reaction mixture was cooled to room temperature, concentrated under reduced pressure to about half amount, and poured into water (500 ml). The precipitated solid was collected by filtration, washed with water (500 ml×2), and dried under reduced pressure to give methyl (E)-5-(2-dimethylaminovinyl)-4-nitrothiophene-2-carboxylate (28 g, yield 96%).

$^1$H-NMR (400 MHz, δppm, CDCl$_3$) 8.10(1H, s), 7.31(1H, d, J=13 Hz), 6.55(1H, d, J=13 Hz), 3.86(3H, s), 3.07(6H, brs).

Step 4:

Production of methyl 4H-thieno[3,2-b]pyrrole-2-carboxylate

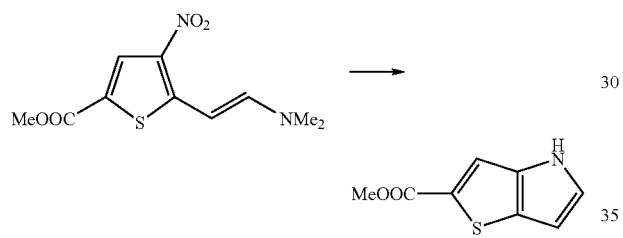

A solution of methyl (E)-5-(2-dimethylaminovinyl)-4-nitrothiophene-2-carboxylate (20 g, 78 mmol), 5% palladium/carbon (2 g) and acetic acid (20 ml) in tetrahydrofuran (300 ml) was stirred under hydrogen atmosphere (3.5 atm) at room temperature for 16 hr. The reaction mixture was filtered through celite and concentrated under reduced pressure. Diethyl ether (300 ml) was added to the residue. The mixture was washed successively with 1N hydrochloric acid (100 ml×2), water (100 ml), saturated aqueous sodium hydrogen carbonate solution (100 ml×2) and saturated brine (100 ml), and dried over magnesium sulfate. Filtration and concentration under reduced pressure gave methyl 4H-thieno[3,2-b]pyrrole-2-carboxylate (12 g, yield 87%).

$^1$H-NMR (400 MHz, δppm, CDCl$_3$) 8.41(1H, brs), 7.71(1H, s), 7.19(1H, t, J=1.2 Hz), 6.49(1H, t, J=1.2 Hz), 3.89(3H, s).

Step 5:

Production of 6-(cyclohex-1-enyl)-4H-thieno[3,2-b]pyrrole-2-carboxylic acid

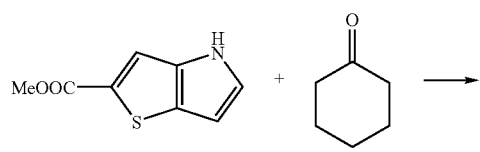

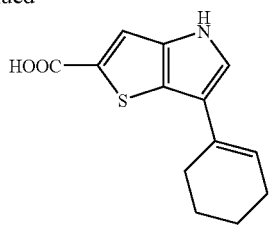

To a solution of methyl 4H-thieno[3,2-b]pyrrole-2-carboxylate (12 g, 68 mmol) and cyclohexanone (21 ml, 204 mmol) in methanol (300 ml) was added 28% sodium methoxide methanol solution (100 ml) and the mixture was stirred with heating under reflux for 2 days. The reaction mixture was cooled to room temperature and concentrated under reduced pressure. 6N Hydrochloric acid (100 ml) was added and the precipitated solid was collected by filtration. The solid was washed successively with water (300 ml×5) and n-hexane (300 ml×3), and dried under reduced pressure to give 6-(cyclohex-1-enyl)-4H-thieno[3,2-b]pyrrole-2-carboxylic acid (17 g, yield 100%).

$^1$H-NMR (400 MHz, δppm, DMSO-d$_6$) 12.73(1H, brs), 11.44(1H, brs), 7.63(1H, s), 7.35(1H, s), 5.81(1H, brs), 2.42-2.36(2H, m), 2.34-2.18(2H, m), 1.76-1.62(4H, m).

Step 6:

Production of 6-cyclohexyl-4H-thieno[3,2-b]pyrrole-2-carboxylic acid

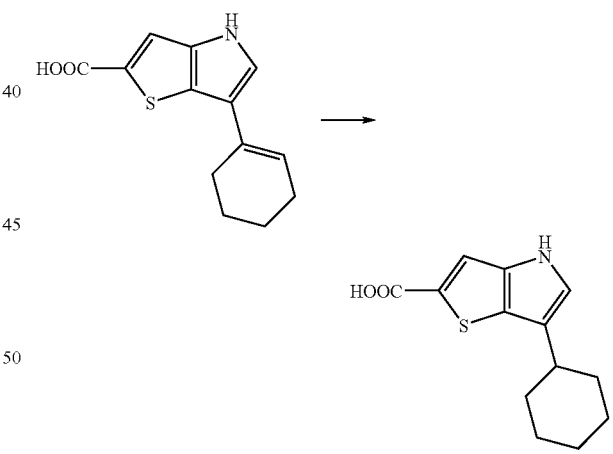

A solution of 6-(cyclohex-1-enyl)-4H-thieno[3,2-b]pyrrole-2-carboxylic acid (17 g, 68 mmol) and 20% palladium hydroxide/carbon (3.4 g) in methanol (100 ml) and tetrahydrofuran (200 ml) was stirred under hydrogen atmosphere (3.5 atm) at room temperature for 18 hr. The reaction mixture was filtered through celite and concentrated under reduced pressure to give a crude product (17 g, yield 100%) of 6-cyclohexyl-4H-thieno[3,2-b]pyrrole-2-carboxylic acid. The obtained compound was used for Step 7 without purification.

$^1$H-NMR (400 MHz, δppm, DMSO-d$_6$) 12.59(1H, brs), 11.14(1H, brs), 7.57(1H, s), 7.08(1H, s), 2.62-2.52(1H, m), 2.02-1.90(2H, m), 1.84-1.66(3H, m), 1.50-1.18(5H, m).

Step 7:

Production of methyl
6-cyclohexyl-4H-thieno[3,2-b]pyrrole-2-carboxylate

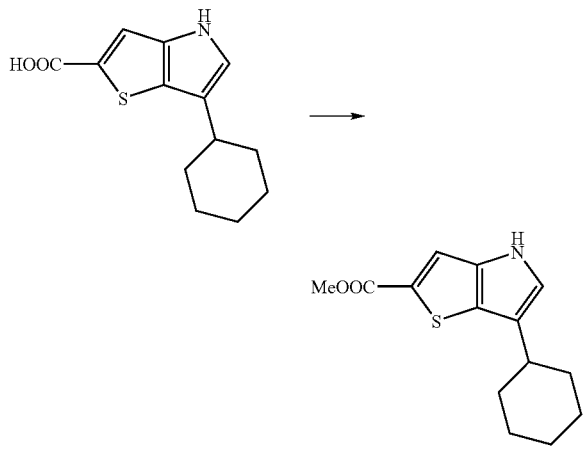

A solution of 6-cyclohexyl-4H-thieno[3,2-b]pyrrole-2-carboxylic acid obtained in Step 6, methyl iodide (4.2 ml, 68 mmol) and potassium carbonate (9.4 g, 68 mmol) in N,N-dimethylformamide (200 ml) was stirred at room temperature for 4 hr. Diethyl ether (500 ml) was added to the reaction mixture and the mixture was washed successively with water (200 ml×3) and saturated brine (200 ml), and dried over magnesium sulfate. Filtration and concentration under reduced pressure gave a crude product (18 g, yield 100%) of methyl 6-cyclohexyl-4H-thieno[3,2-b]pyrrole-2-carboxylate. The obtained compound was used for Step 8 without purification.

$^1$H-NMR (400 MHz, δppm, CDCl$_3$) 8.20(1H, brs), 7.67 (1H, s), 6.95(1H, s), 3.84(3H, s), 2.70-2.60(1H, m), 2.12-2.02 (2H, m), 1.88-1.72(3H, m), 1.58-1.20(5H, m).

Step 8:

Production of methyl 5-bromo-6-cyclohexyl-4H-thieno[3,2-b]pyrrole-2-carboxylate

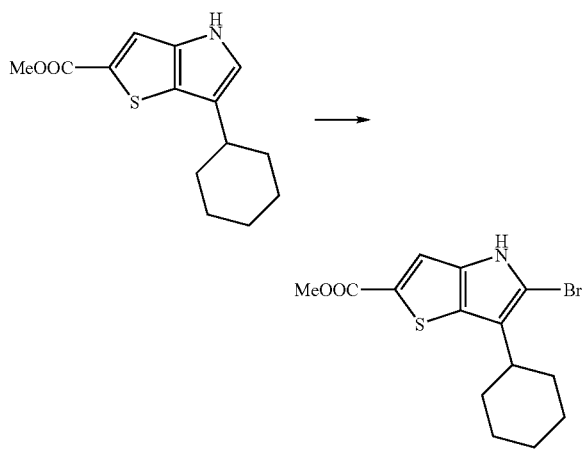

To a solution of methyl 6-cyclohexyl-4H-thieno[3,2-b]pyrrole-2-carboxylate obtained in Step 7 in chloroform (90 ml) and tetrahydrofuran (90 ml) was added pyridinium hydrobromide perbromide (21.7 g, 68 mmol) under ice-cooling. The mixture was stirred under ice-cooling for 2 hr and concentrated under reduced pressure at room temperature. Ethyl acetate (300 ml) was added to the residue, and the mixture was washed successively with 1M aqueous sodium hydrogen sulfite solution (100 ml×3), water (100 ml), saturated aqueous sodium hydrogen carbonate solution (100 ml×2) and saturated brine (100 ml), and dried over magnesium sulfate. The mixture was filtered and concentrated under reduced pressure, and the obtained solid was washed with a mixed solvent (100 ml) of n-hexane:ethyl acetate (25:1). The solid was collected by filtration, and dried under reduced pressure to give methyl 5-bromo-6-cyclohexyl-4H-thieno[3,2-b]pyrrole-2-carboxylate (17 g, yield 73%).

$^1$H-NMR (400 MHz, δppm, CDCl$_3$) 8.56(1H, brs), 7.60 (1H, s), 3.88(3H, s), 2.72-2.60(1H, m), 1.92-1.81(3H, m), 1.80-1.74(1H, m), 1.72-1.56(3H, m), 1.48-1.22(3H, m).

Step 9:

Production of methyl 5-(2-aminophenyl)-6-cyclohexyl-4H-thieno[3,2-b]pyrrole-2-carboxylate

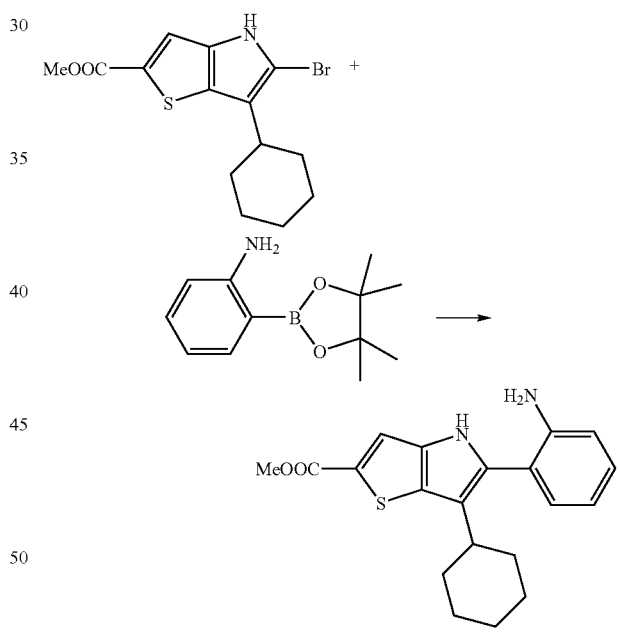

A solution of methyl 5-bromo-6-cyclohexyl-4H-thieno[3,2-b]pyrrole-2-carboxylate (7 g, 20 mmol), 2-(4,4,5,5-tetramethyl-1,3,2-dioxaborolan-2-yl)phenylamine (4.8 g, 22 mmol), sodium hydrogen carbonate (6.7 g, 80 mmol) and tetrakis(triphenylphosphine)palladium (230 mg, 0.2 mmol) in water (20 ml) and ethylene glycol dimethyl ether (50 ml) was stirred with heating under reflux for 4 hr. The reaction mixture was cooled to room temperature and ethyl acetate (200 ml) was added. The mixture was washed successively with water (100 ml), saturated aqueous sodium hydrogen carbonate solution (100 ml) and saturated brine (100 ml), and dried over magnesium sulfate. Filtration and concentration under reduced pressure gave a crude product of methyl 5-(2-

Step 10:

Production of methyl 5-[2-(2-chloroacetylamino)phenyl]-6-cyclohexyl-4H-thieno[3,2-b]pyrrole-2-carboxylate

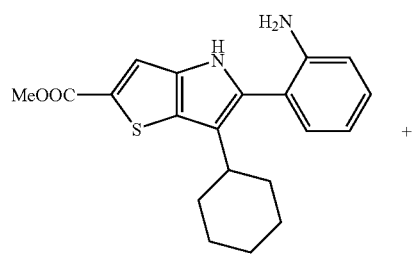

+

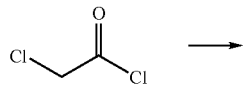

→

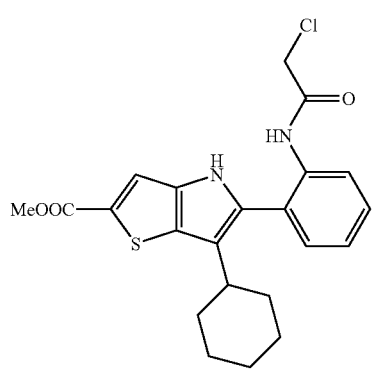

To a solution of methyl 5-(2-aminophenyl)-6-cyclohexyl-4H-thieno[3,2-b]pyrrole-2-carboxylate obtained in Step 9, sodium acetate (2.4 g, 29 mmol) and acetic acid (1.7 ml, 29 mmol) in tetrahydrofuran (70 ml) was added chloroacetyl chloride (2.3 ml, 29 mmol) under ice-cooling. After stirring at room temperature for 2 hr, the reaction mixture was concentrated under reduced pressure. Water (100 ml) was added to the obtained solid. The solid was collected by filtration, washed with diethyl ether (20 ml×2), and dried under reduced pressure to give methyl 5-[2-(2-chloroacetylamino)phenyl]-6-cyclohexyl-4H-thieno[3,2-b]pyrrole-2-carboxylate (5 g, yield after 2 steps from Step 9: 58%).

$^1$H-NMR (300 MHz, δppm, DMSO-$d_6$) 11.51(1H, s), 9.46 (1H, s), 7.85(1H, d, J=8.1 Hz), 7.63(1H, s), 7.43(1H, t, J=8.1 Hz), 7.38-7.24(2H, m), 4.22(2H, s), 3.81(3H, s), 2.45-2.26 (1H, m), 1.85-1.45(7H, m), 1.35-1.04(3H, m).

Step 11:

Production of methyl 11-cyclohexyl-5-oxo-5,6-dihydro-4H-1-thia-3b,6-diazabenzo[e]cyclopenta[a]azulene-2-carboxylate

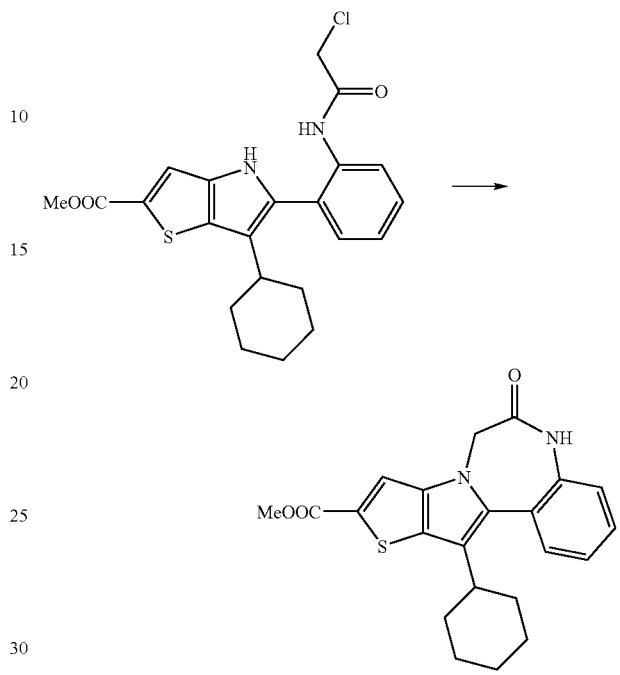

A solution of methyl 5-[2-(2-chloroacetylamino)phenyl]-6-cyclohexyl-4H-thieno[3,2-b]pyrrole-2-carboxylate (5 g, 12 mmol) and potassium carbonate (2.4 g, 17 mmol) in N,N-dimethylformamide (50 ml) was stirred at 90° C. for 1 hr. The reaction mixture was cooled to room temperature and water (200 ml) was added. The precipitated solid was collected by filtration, washed with a mixed solvent (50 ml×2) of n-hexane:diisopropyl ether (4:1), and dried under reduced pressure to give methyl 11-cyclohexyl-5-oxo-5,6-dihydro-4H-1-thia-3b,6-diazabenzo[e]cyclopenta[a]azulene-2-carboxylate (4 g, yield 86%).

$^1$H-NMR (300 MHz, δppm, DMSO-$d_6$) 10.31(1H, s), 8.16 (1H, s), 7.58-7.45(2H, m), 7.40-7.32(1H, m), 7.30-7.22(1H, m), 5.15-4.46(2H, m), 3.83(3H, s), 2.82-2.66(1H, m), 2.15-1.05(10H, m).

Example 6

Production of methyl 11-cyclohexyl-5-oxo-6-[2-oxo-2-(piperidin-1-yl)ethyl]-5,6-dihydro-4H-1-thia-3b,6-diazabenzo[e]cyclopenta[a]azulene-2-carboxylate

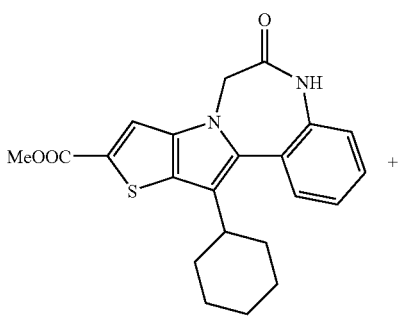

+

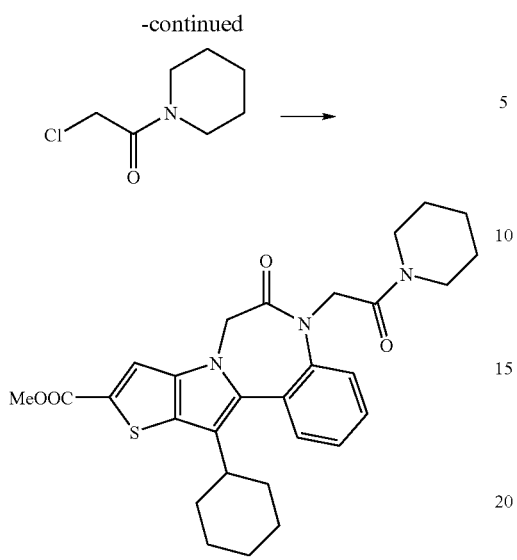

A solution of methyl 11-cyclohexyl-5-oxo-5,6-dihydro-4H-1-thia-3b,6-diazabenzo[e]cyclopenta[a]azulene-2-carboxylate (1.7 g, 4.4 mmol), 2-chloro-1-(piperidin-1-yl)ethanone (0.86 g, 5.3 mmol), potassium carbonate (0.86 g, 6.2 mmol) and potassium iodide (0.073 g, 0.44 mmol) in N,N-dimethylformamide (17 ml) was stirred at 90° C. for 2 hr. The reaction mixture was cooled to room temperature and ethyl acetate (100 ml) was added. The mixture was washed successively with water (50 ml×2), saturated brine (50 ml), and dried over magnesium sulfate. Filtration and concentration under reduced pressure gave a crude product of methyl 11-cyclohexyl-5-oxo-6-[2-oxo-2-(piperidin-1-yl)ethyl]-5,6-dihydro-4H-1-thia-3b,6-diazabenzo[e]cyclopenta[a]azulene-2-carboxylate. The obtained compound was used for Example 7 without purification.

Example 7

Production of methyl 11-cyclohexyl-6-[2-(piperidin-1-yl)ethyl]-5,6-dihydro-4H-1-thia-3b,6-diazabenzo[e]cyclopenta[a]azulene-2-carboxylate

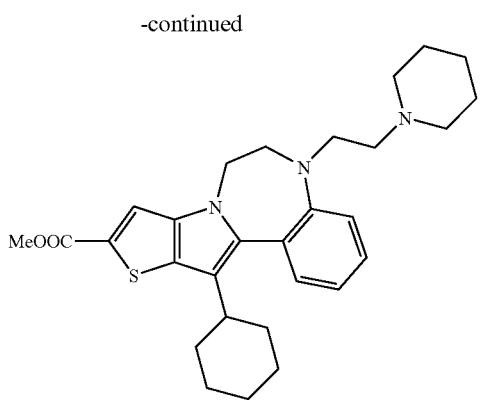

To a solution of methyl 11-cyclohexyl-5-oxo-6-[2-oxo-2-(piperidin-1-yl)ethyl]-5,6-dihydro-4H-1-thia-3b,6-diazabenzo[e]cyclopenta[a]azulene-2-carboxylate obtained in Example 6 in tetrahydrofuran (20 ml) was added a solution (17 ml, 17 mmol) of 1M borane-tetrahydrofuran complex in tetrahydrofuran under ice-cooling. After stirring at room temperature for 14 hr, 2N hydrochloric acid (20 ml) was added and the mixture was stirred at 70° C. for 2 hr. The reaction mixture was cooled to room temperature and basified with 4N aqueous sodium hydroxide solution (10 ml). The mixture was extracted with chloroform (40 ml×4), and the extract was dried over magnesium sulfate. The extract was filtered and concentrated under reduced pressure, and the obtained residue was purified by silica gel column chromatography (chloroform:methanol=10:1) to give methyl 11-cyclohexyl-6-[2-(piperidin-1-yl)ethyl]-5,6-dihydro-4H-1-thia-3b,6-diazabenzo[e]cyclopenta[a]azulene-2-carboxylate (1.1 g, yield after 2 steps from Example 6: 99%).

Example 8

Production of 11-cyclohexyl-6-[2-(piperidin-1-yl)ethyl]-5,6-dihydro-4H-1-thia-3b,6-diazabenzo[e]cyclopenta[a]azulene-2-carboxylic acid dihydrochloride

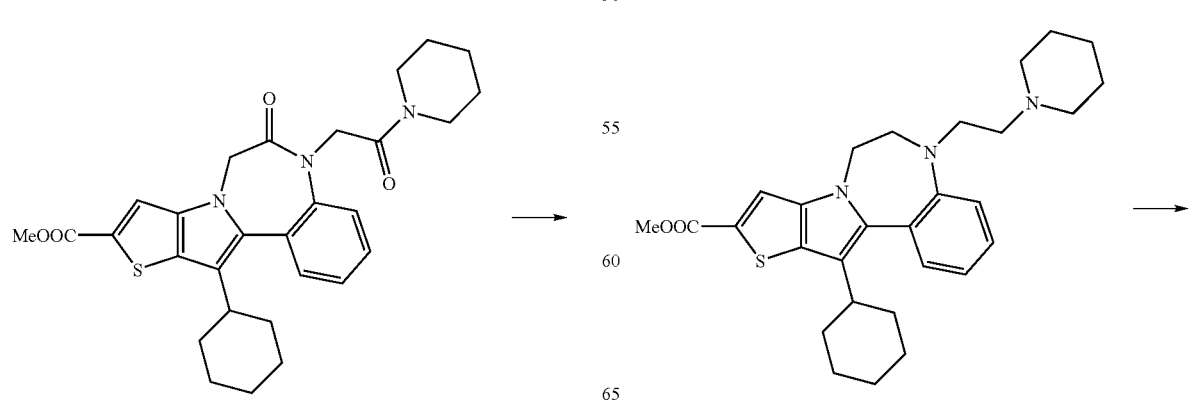

-continued

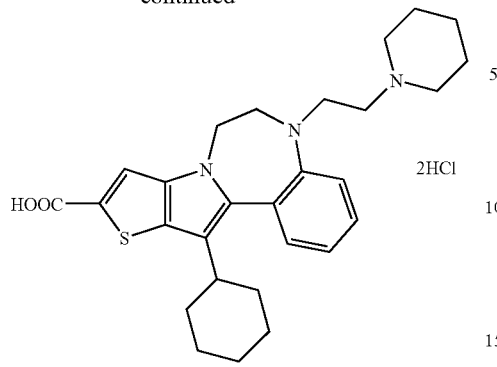

To a solution of methyl 11-cyclohexyl-6-[2-(piperidin-1-yl)ethyl]-5,6-dihydro-4H-1-thia-3b,6-diazabenzo[e]cyclopenta[a]azulene-2-carboxylate (1.1 g, 2.2 mmol) in methanol (10 ml) and tetrahydrofuran (10 ml) was added 4N aqueous sodium hydroxide solution (10 ml) and the mixture was stirred at 70° C. for 1 hr. After stirring at room temperature for 14 hr, the mixture was neutralized with 2N hydrochloric acid (20 ml). The mixture was extracted with chloroform (20 ml×4), and the extract was dried over sodium sulfate. The extract was filtered and concentrated under reduced pressure, and the obtained residue was dissolved in chloroform (10 ml). A 4N HCl-ethyl acetate solution (4 ml) was added and then diethyl ether (10 ml) was added. The resulting solid was collected by filtration, washed with diethyl ether (10 ml), and dried under reduced pressure to give 11-cyclohexyl-6-[2-(piperidin-1-yl) ethyl]-5,6-dihydro-4H-1-thia-3b,6-diazabenzo[e]cyclopenta[a]azulene-2-carboxylic acid dihydrochloride (1.3 g, yield 98%).

$^1$H-NMR (400 MHz, δppm, DMSO-$d_6$) 12.66(1H, brs), 9.60(1H, brs), 7.89(1H, s), 7.45-7.38(1H, m), 7.33-7.25(2H, m), 7.28-7.24(1H, 20 m), 4.23-4.04(2H, m), 3.57-3.46(2H, m), 3.42-3.28(2H, m), 3.15-3.07(2H, m), 3.06-3.00(2H, m), 2.73-2.52(3H, m), 1.82-1.17(16H, m).

MS 478.2(M+1).

Example 9

Production of methyl 6-[2-(4-tert-butoxycarbonylpiperazin-1-yl)-2-oxoethyl]-11-cyclohexyl-5-oxo-5,6-dihydro-4H-1-thia-3b,6-diazabenzo[e]cyclopenta[a]azulene-2-carboxylate

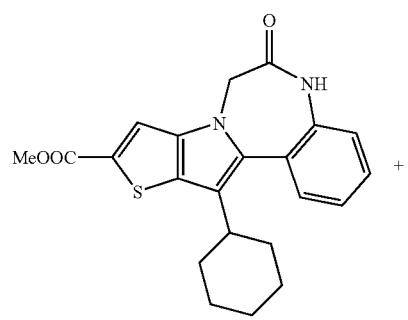

-continued

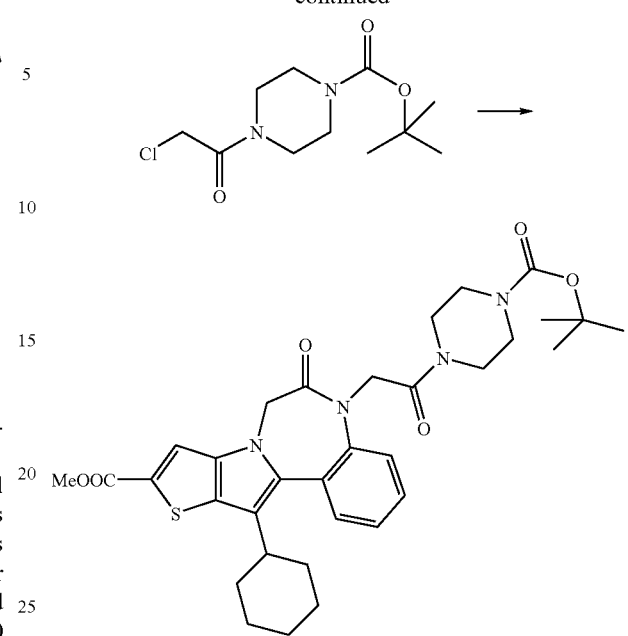

A solution of methyl 11-cyclohexyl-5-oxo-5,6-dihydro-4H-1-thia-3b,6-diazabenzo[e]cyclopenta[a]azulene-2-carboxylate (200 mg, 0.5 mmol), tert-butyl 4-(2-chloroacetyl)piperazine-1-carboxylate (158 mg, 0.6 mmol), potassium carbonate (83 mg, 0.6 mmol) and potassium iodide (17 mg, 0.1 mmol) in N,N-dimethylformamide (5 ml) was stirred at 90° C. for 14 hr. The reaction mixture was cooled to room temperature and water (30 ml) was added. The precipitated solid was collected by filtration and dried under reduced pressure to give methyl 6-[2-(4-tert-butoxycarbonylpiperazin-1-yl)-2-oxoethyl]-11-cyclohexyl-5-oxo-5,6-dihydro-4H-1-thia-3b,6-diazabenzo[e]cyclopenta[a]azulene-2-carboxylate (310 mg, yield 100%).

Example 10

Production of methyl 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylate

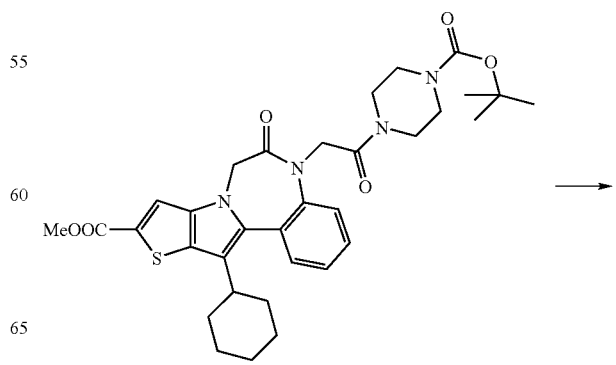

-continued

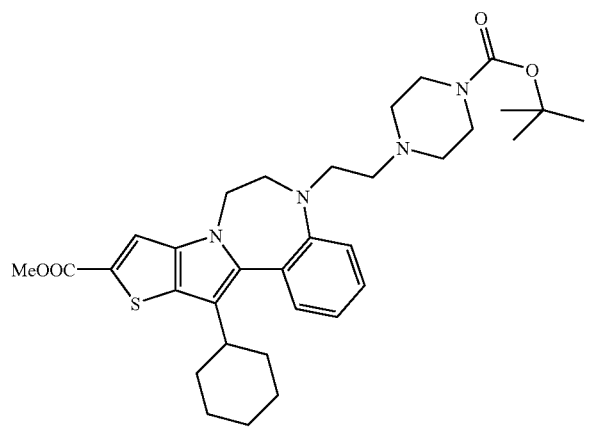

To a solution of methyl 6-[2-(4-tert-butoxycarbonylpiperazin-1-yl)-2-oxoethyl]-11-cyclohexyl-5-oxo-5,6-dihydro-4H-1-thia-3b,6-diazabenzo[e]cyclopenta[a]azulene-2-carboxylate (310 mg, 0.5 mmol) in tetrahydrofuran (10 ml) was added a solution (3 ml, 3 mmol) of 1M borane-tetrahydrofuran complex in tetrahydrofuran under ice-cooling. After stirring at room temperature for 14 hr, 2N hydrochloric acid (5 ml) was added and the mixture was stirred at 70° C. for 2 hr. The reaction mixture was cooled to room temperature and basified with 4N aqueous sodium hydroxide solution (5 ml). Di-tert-butyl dicarbonate (218 mg, 1 mmol) was added, and the mixture was stirred at room temperature for 2 hr. The reaction mixture was extracted with chloroform (20 ml×4), and the extract was dried over magnesium sulfate. The extract was filtered and concentrated under reduced pressure, and the obtained residue was purified by silica gel column chromatography (chloroform:methanol=10:1) to give methyl 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylate (296 mg, yield 100%).

Example 11

Production of 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylic acid hydrochloride -continued

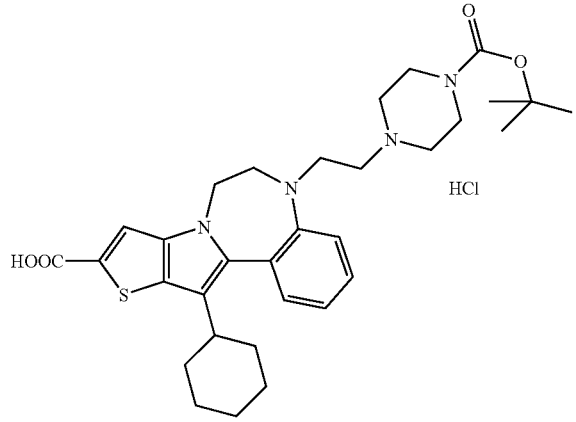

To a solution of methyl 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylate (296 mg, 0.5 mmol) in methanol (5 ml) and tetrahydrofuran (5 ml) was added 4N aqueous sodium hydroxide solution (2 ml), and the mixture was stirred at 70° C. for 1 hr. After stirring at room temperature for 14 hr, the mixture was acidified with 2N hydrochloric acid (5 ml). The mixture was extracted with chloroform (20 ml×4) and the extract was dried over sodium sulfate. The extract was filtered and concentrated under reduced pressure, and the obtained residue was dissolved in chloroform (5 ml). Diethyl ether (5 ml) was added and the resulting solid was collected by filtration. The solid was washed with diethyl ether (5 ml), and dried under reduced pressure to give 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylic acid hydrochloride (131 mg, yield 43%).

$^1$H-NMR (400 MHz, δppm, DMSO-$d_6$) 12.64(1H, brs), 10.51(1H, brs), 7.89(1H, s), 7.45-7.38(1H, m), 7.34-7.18(3H, m), 4.26-4.03(2H, m), 3.68-3.36(6H, m), 3.18-2.97(4H, m), 2.94-2.83(2H, m), 2.73-2.59(3H, m), 1.80-1.53(7H, m), 1.39-1.17(3H, m), 1.32(9H, s).

MS 579.3(M+1).

Example 12

Production of methyl 11-cyclohexyl-5,6-dihydro-4H-1-thia-3b,6-diazabenzo[e]cyclopenta[a]azulene-2-carboxylate

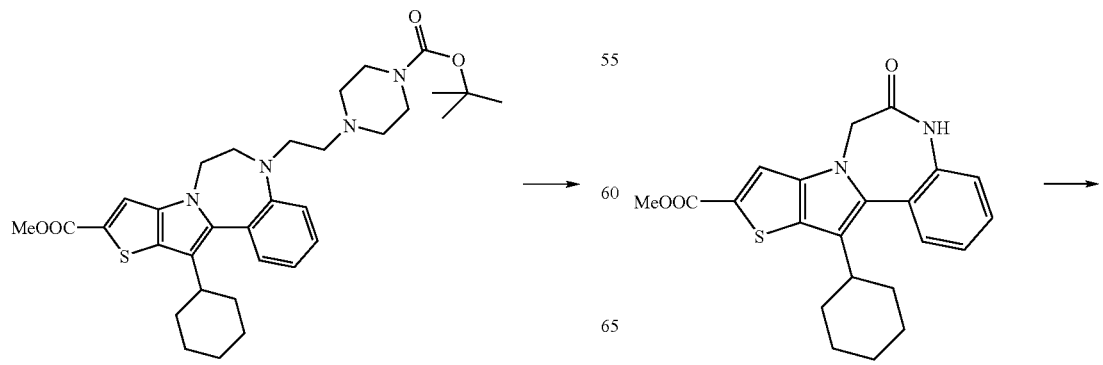

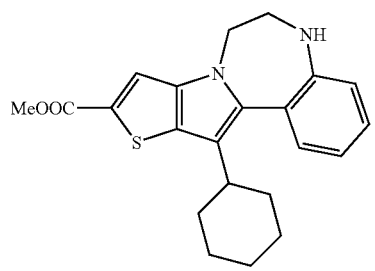

To a solution of methyl 11-cyclohexyl-5-oxo-5,6-dihydro-4H-1-thia-3b,6-diazabenzo[e]cyclopenta[a]azulene-2-carboxylate (200 mg, 0.5 mmol) in tetrahydrofuran (10 ml) was added a solution (3 ml, 3 mmol) of 1M borane-tetrahydrofuran complex in tetrahydrofuran under ice-cooling. After stirring at room temperature for 14 hr, 2N hydrochloric acid (10 ml) was added and the mixture was stirred at 70° C. for 2 hr. The reaction mixture was cooled to room temperature and basified with 4N aqueous sodium hydroxide solution (5 ml). The mixture was extracted with chloroform (40 ml×4), and the extract was dried over magnesium sulfate. Filtration and concentration under reduced pressure gave a crude product (190 mg, yield 100%) of methyl 11-cyclohexyl-5,6-dihydro-4H-1-thia-3b,6-diazabenzo[e]cyclopenta[a]azulene-2-carboxylate. The obtained compound was used for Example 13 without purification.

Example 13

Production of methyl 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylate

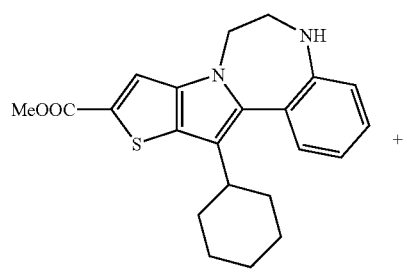

+

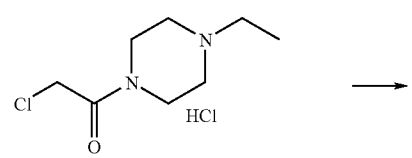

A solution of methyl 11-cyclohexyl-5,6-dihydro-4H-1-thia-3b,6-diazabenzo[e]cyclopenta[a]azulene-2-carboxylate obtained in Example 12, 2-chloro-1-(4-ethylpiperazin-1-yl)ethanone hydrochloride (136 mg, 0.6 mmol), potassium carbonate (166 mg, 1.2 mmol) and potassium iodide (17 mg, 0.1 mmol) in acetonitrile (5 ml) was stirred at 90° C. for 14 hr. The reaction mixture was cooled to room temperature and ethyl acetate (50 ml) was added. The mixture was washed successively with water (20 ml×2), saturated brine (20 ml), and dried over magnesium sulfate. The mixture was filtered and concentrated under reduced pressure, and the obtained residue was purified by silica gel column chromatography (chloroform:methanol=10:1) to give methyl 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylate (132 mg, yield after 2 steps from Example 12: 49%).

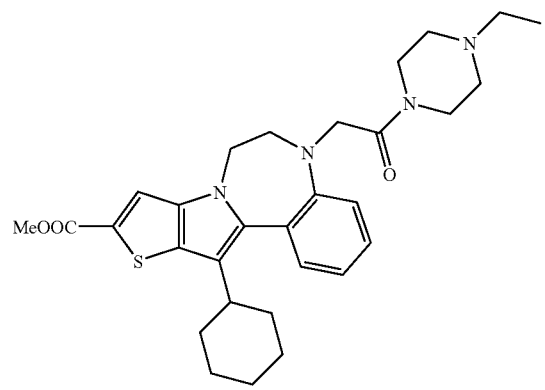

Example 14

Production of 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylic acid dihydrochloride

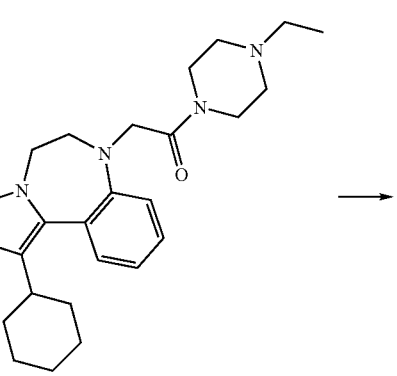

→

-continued

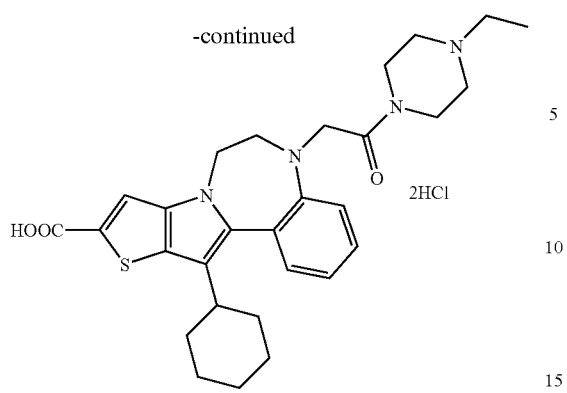

To a solution of methyl 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylate (132 mg, 0.25 mmol) in methanol (5 ml) and tetrahydrofuran (5 ml) was added 4N aqueous sodium hydroxide solution (2 ml) and the mixture was stirred at 70° C. for 1 hr. After stirring at room temperature for 14 hr, the mixture was neutralized with 2N hydrochloric acid (4 ml). The mixture was extracted with chloroform (20 ml×4), and the extract was dried over sodium sulfate. The extract was filtered and concentrated under reduced pressure, and the obtained residue was dissolved in chloroform (5 ml). A 4N HCl-ethyl acetate solution (2 ml) was added and then diethyl ether (5 ml) was added. The resulting solid was collected by filtration, washed with diethyl ether (10 ml), and dried under reduced pressure to give 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylic acid dihydrochloride (85 mg, yield 57%).

$^1$H-NMR (400 MHz, δppm, DMSO-d$_6$) 12.61(1H, brs), 10.71(1H, brs), 7.88(1H, s), 7.32(1H, t, J=7.4 Hz), 7.26(1H, d, J=7.4 Hz), 7.13(1H, t, J=7.4 Hz), 7.08(1H, d, J=7.4 Hz), 4.40-4.25(2H, m), 4.12-3.70(4H, m), 3.62-3.51(1H, m), 3.40-3.10(5H, m), 2.97-2.58(5H, m), 1.92-1.52(7H, m), 1.34-1.14 (3H, m), 1.02(3H, t, J=7.2 Hz).

MS 521.3(M+1).

Example 37

Production of (E)-3-[4-((1-[(11-cyclohexyl-8-methoxy-4,5-dihydro-6-oxa-1-thia-3b-azabenzo[e]cyclopenta[a]azulene-2-carbonyl)amino]cyclobutanecarbonyl)amino)phenyl]acrylic acid Step 1:

Production of methyl 11-cyclohexyl-8-methoxy-4,5-dihydro-6-oxa-1-thia-3b-azabenzo[e]cyclopenta[a]azulene-2-carboxylate

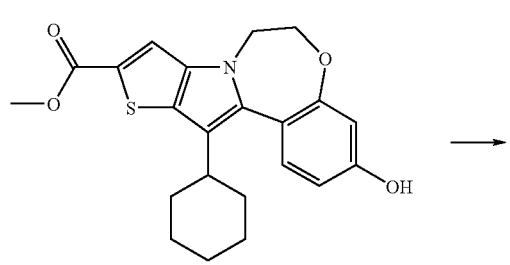

-continued

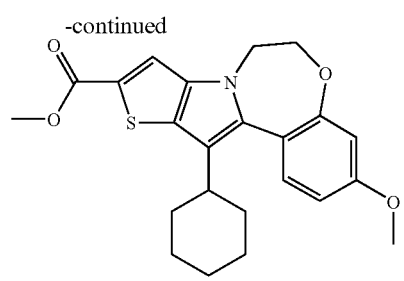

To a solution of methyl 11-cyclohexyl-8-hydroxy-4,5-dihydro-6-oxa-1-thia-3b-azabenzo[e]cyclopenta[a]azulene-2-carboxylate (200 mg, 0.486 mmol) in N,N-dimethylformamide (200 ml) were added potassium carbonate (134 mg, 0.972 mmol) and methyl iodide (45.4 μl, 0.729 mmol). The mixture was stirred overnight at room temperature, and further stirred at 60° C. for 1 hr. The reaction mixture was allowed to cool and water was added to the reaction mixture. The precipitated solid was collected by filtration, washed with water and dried under reduced pressure to give a crude product of methyl 11-cyclohexyl-8-methoxy-4,5-dihydro-6-oxa-1-thia-3b-azabenzo[e]cyclopenta[a]azulene-2-carboxylate (204 mg). The obtained compound was used for Step 2 without further purification.

Step 2:

Production of 11-cyclohexyl-8-methoxy-4,5-dihydro-6-oxa-1-thia-3b-azabenzo[e]cyclopenta[a]azulene-2-carboxylic acid

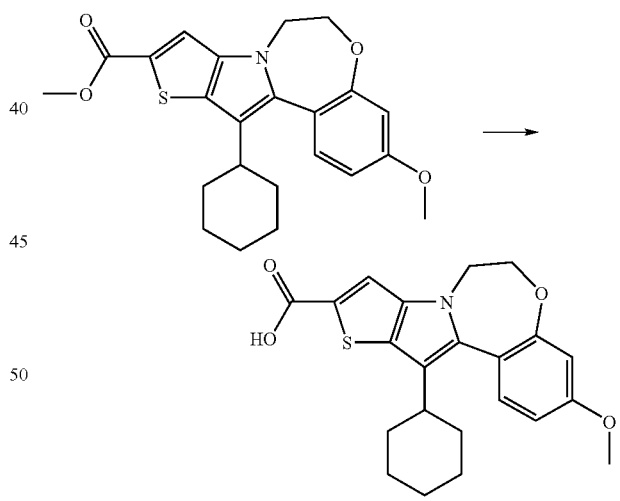

To a solution of methyl 11-cyclohexyl-8-methoxy-4,5-dihydro-6-oxa-1-thia-3b-azabenzo[e]cyclopenta[a]azulene-2-carboxylate (204 mg) obtained in Step 1 in a mixture of methanol (2 ml) and tetrahydrofuran (3 ml) was added 4N aqueous sodium hydroxide solution (1 ml) and the mixture was stirred at 60° C. for 1 hr. The reaction mixture was allowed to cool and 1N hydrochloric acid (5 ml) and water (30 ml) were added. The mixture was stirred at room temperature to allow precipitation of a solid. The precipitated solid was collected by filtration, washed with water and dried under reduced pressure to give 11-cyclohexyl-8-methoxy-4,5-dihydro-6-oxa-1-thia-3b-azabenzo[e]cyclopenta[a]azulene-2-carboxylic acid (189 mg, yield in 2 steps 98%).

$^1$H-NMR (400 MHz, δppm, DMSO-d$_6$) 12.67 (1H, brs), 7.89 (1H, s), 7.31 (1H, d, J=8.6 Hz), 6.91 (1H, dd, J=8.6, 2.8 Hz), 6.80 (1H, d, J=2.8 Hz), 4.44 (2H, brt, J=5.6 Hz), 4.28 (2H, brt, J=5.6 Hz), 3.81 (3H, s), 2.78-2.68 (1H, m), 1.84-1.74 (4H, m), 1.74-1.68 (3H, m), 1.39-1.22 (3H, m).

MS 398.1(M+1).

Step 3:

Production of ethyl (E)-3-[4-({1-[(11-cyclohexyl-8-methoxy-4,5-dihydro-6-oxa-1-thia-3b-azabenzo[e]cyclopenta[a]azulene-2-carbonyl}amino]cyclobutanecarbonyl)amino)phenyl]acrylate added 1-hydroxybenzotriazole monohydrate (21 mg, 0.14 mmol), 1-ethyl-3-(3'-dimethylaminopropyl)carbodiimide hydrochloride (29 mg, 0.15 mmol) and triethylamine (19 μl, 0.14 mmol), and the mixture was stirred overnight at room temperature. A saturated aqueous sodium hydrogen carbonate solution was added to the reaction mixture. The precipitated solid was collected by filtration, washed with water and dried under reduced pressure to give a crude product of ethyl (E)-3-[4-({1-[(11-cyclohexyl-8-methoxy-4,5-dihydro-6-oxa-1-thia-3b-azabenzo[e]cyclopenta[a]azulene-2-carbonyl) amino] cyclobutanecarbonyl}amino) phenyl] acrylate (80 mg). The obtained compound was used for Step 4 without further purification.

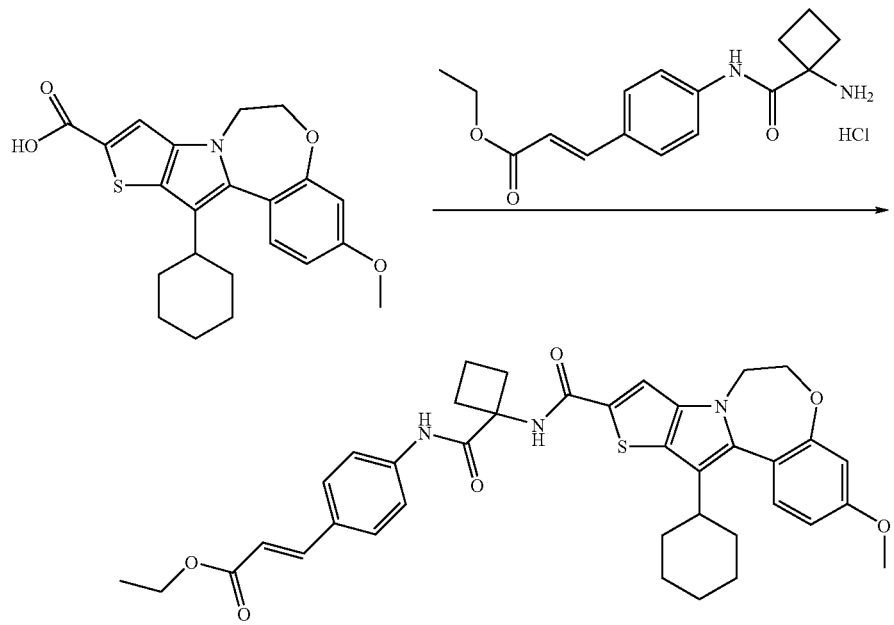

To a solution of 11-cyclohexyl-8-methoxy-4,5-dihydro-6-oxa-1-thia-3b-azabenzo[e]cyclopenta[a]azulene-2-carboxylic acid (50 mg, 0.13 mmol) and ethyl (E)-3-{4-[(1-aminocyclobutanecarbonyl)amino]phenyl}acrylate hydrochloride (45 mg, 0.14 mmol) produced by the method described in WO2005/080399 in N,N-dimethylformamide (2 ml) were Step 4:

Production of (E)-3-[4-({1-[(11-cyclohexyl-8-methoxy-4,5-dihydro-6-oxa-1-thia-3b-azabenzo[e]cyclopenta[a]azulene-2-carbonyl)amino] cyclobutanecarbonyl}amino)phenyl]acrylic acid

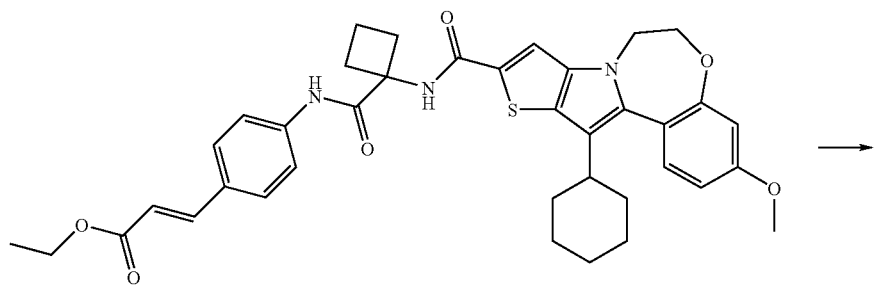

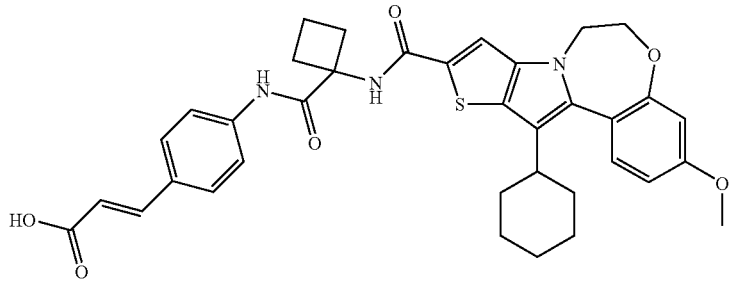

To a solution of ethyl (E)-3-[4-({1-[(11-cyclohexyl-8-methoxy-4,5-dihydro-6-oxa-1-thia-3b-azabenzo[e]cyclopenta[a]azulene-2-carbonyl)amino]cyclobutanecarbonyl}amino)phenyl]acrylate (80 mg) obtained in Step 3 in a mixture of methanol (2 ml) and tetrahydrofuran (4 ml) was added a 4N aqueous sodium hydroxide solution (1 ml), and the mixture was stirred at room temperature for 2 hr. 1N Hydrochloric acid (5 ml) and water (15 ml) were added to the reaction mixture and the precipitated solid was collected by filtration. The solid was washed with water and dried under reduced pressure to give (E)-3-[4-({1-[(11-cyclohexyl-8-methoxy-4,5-dihydro-6-oxa-1-thia-3b-azabenzo[e]cyclopenta[a]azulene-2-carbonyl)amino]cyclobutanecarbonyl}amino)phenyl]acrylic acid (70 mg, yield in 2 steps 86%).

$^1$H-NMR (400 MHz, δppm, DMSO-d$_6$) 12.23 (1H, brs), 9.65 (1H, s), 8.70 (1H, s), 7.98 (1H, s), 7.66 (2H, d, J=9.0 Hz), 7.62 (2H, d, J=9.0 Hz), 7.51 (1H, d, J=16.0 Hz), 7.31 (1H, d, J=8.6 Hz), 6.91 (1H, dd, J=8.6, 2.6 Hz), 6.81 (1H, d, J=2.6 Hz), 6.41 (1H, d, J=16.0 Hz), 4.47 (2H, brt, J=5.6 Hz), 4.21 (2H, brt, J=5.6 Hz), 3.82 (3H, s), 2.77-2.65 (3H, m), 2.35-2.25 (2H, m), 2.04-1.92 (1H, m), 1.92-1.82 (1H, m), 1.82-1.67 (7H, m), 1.39-1.20 (3H, m).

MS 640.3(M+1).

Example 42

Production of 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid trihydrochloride Step 1:

Production of methyl 6-cyclohexyl-5-(4,4,5,5-tetramethyl-1,3,2-dioxaborolan-2-yl)-4H-thieno[3,2-b]pyrrole-2-carboxylate

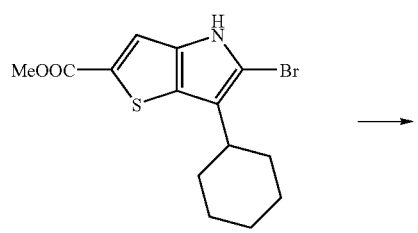

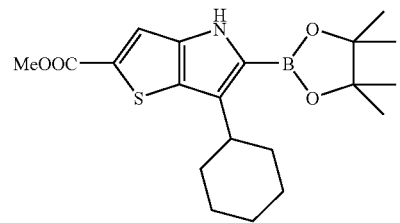

To a solution of methyl 5-bromo-6-cyclohexyl-4H-thieno[3,2-b]pyrrole-2-carboxylate (2.00 g, 5.84 mmol) in 1,4-dioxane (20 ml) was added triethylamine (3.20 ml, 22.9 mmol). 4,4,5,5-Tetramethyl-1,3,2-dioxaborolane (2.50 ml, 17.2 mmol) was added dropwise under an argon stream and the mixture was stirred at room temperature for 30 min. To the mixture were added 2-(dicyclohexylphosphino)biphenyl (245 mg, 0.699 mmol) and palladium acetate(II) (39.0 mg, 0.173 mmol) under an argon stream, and the mixture was stirred at 100° C. for 2 hr. The reaction mixture was allowed to cool to room temperature, and saturated aqueous ammonium chloride solution was added. The mixture was extracted with ethyl acetate, and the organic layer was washed with water and saturated brine in this order, and dried over anhydrous sodium sulfate. After filtration, the solvent was evaporated under reduced pressure. A mixed solvent of hexane-ethyl acetate (10:1) was added to the obtained residue and the precipitated solid was collected by filtration. The obtained solid was dried under reduced pressure to give methyl 6-cyclohexyl-5-(4,4,5,5-tetramethyl-1,3,2-dioxaborolan-2-yl)-4H-thieno[3,2-b]pyrrole-2-carboxylate (1.66 g, yield 74%).

$^1$H-NMR (300 MHz, δppm, CDCl$_3$) 8.60-8.44 (1H, brs), 7.62 (1H, s), 3.90 (3H, s), 3.16 (1H, tt, J=12.1, 3.4 Hz), 1.95-1.70 (3H, m), 1.69-1.59 (2H, m), 1.52-1.35 (2H, m), 1.35-1.28 (2H, m), 1.34 (12H, s).

Step 2:

Production of methyl 6-cyclohexyl-5-{3-nitro-2-[2-(tetrahydropyran-2-yloxy)ethoxy]phenyl}-4H-thieno[3,2-b]pyrrole-2-carboxylate

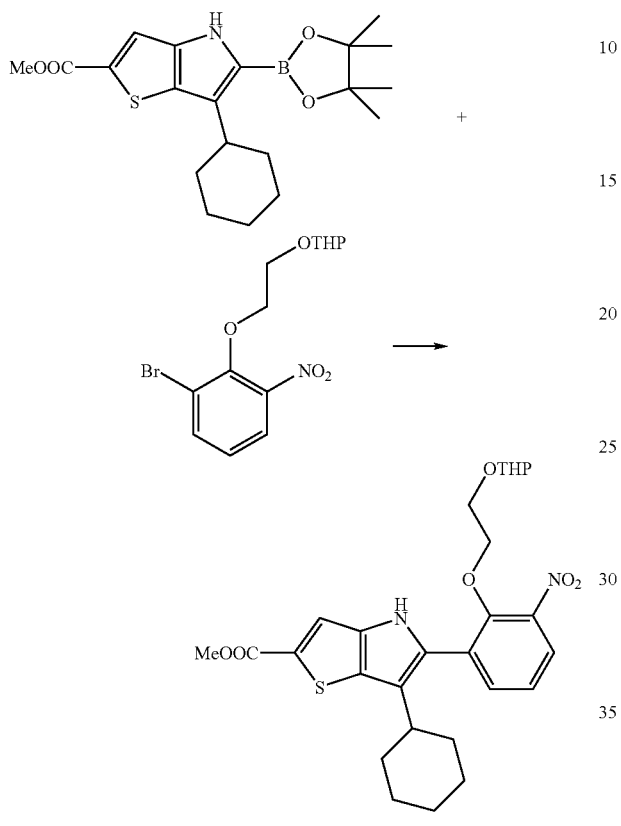

To a solution of 2-[2-(2-bromo-6-nitrophenoxy)ethoxy]tetrahydropyran (1.29 g, 3.72 mmol) in water (10 ml) and ethylene glycol dimethyl ether (20 ml) were added sodium hydrogen carbonate (1.23 g, 14.8 mmol) and tetrakis(triphenylphosphine)palladium (430 mg, 0.372 mmol). Methyl 6-cyclohexyl-5-(4,4,5,5-tetramethyl-1,3,2-dioxaborolan-2-yl)-4H-thieno[3,2-b]pyrrole-2-carboxylate (1.60 g, 4.10 mmol) obtained in Step 1 was divided in 4 portions and added every 30 min while stirring at 90° C. with heating. After the completion of addition, the mixture was further stirred at 90° C. for 4 hr. The reaction mixture was allowed to cool to room temperature and water was added. The mixture was extracted with ethyl acetate and the organic layer was washed with water and saturated brine in this order, and dried over anhydrous sodium sulfate. After filtration, the solvent was evaporated under reduced pressure. The residue was purified by silica gel column chromatography (hexane:ethyl acetate=6:1-3:1) to give methyl 6-cyclohexyl-5-{3-nitro-2-[2-(tetrahydropyran-2-yloxy)ethoxy]phenyl}-4H-thieno[3,2-b]pyrrole-2-carboxylate (863 mg, yield 44%).

$^1$H-NMR (300 MHz, δppm, CDCl$_3$) 9.49 (1H, brs), 7.78 (1H, dd, J=8.1, 1.6 Hz), 7.69 (1H, s), 7.60 (1H, dd, J=7.8, 1.7 Hz), 7.30 (1H, t, J=8.0 Hz), 4.57-4.52 (1H, m), 4.01-3.95 (2H, m), 3.92 (3H, s), 3.82-3.75 (2H, m), 3.68-3.61 (2H, m), 3.51-3.44 (2H, m), 2.80-2.70 (1H, m), 1.91-1.65 (7H, m), 1.60-1.50 (4H, m), 1.40-1.30 (3H, m).

Step 3:

Production of methyl 6-cyclohexyl-5-[2-(2-hydroxyethyloxy)-3-nitrophenyl]-4H-thieno[3,2-b]pyrrole-2-carboxylate

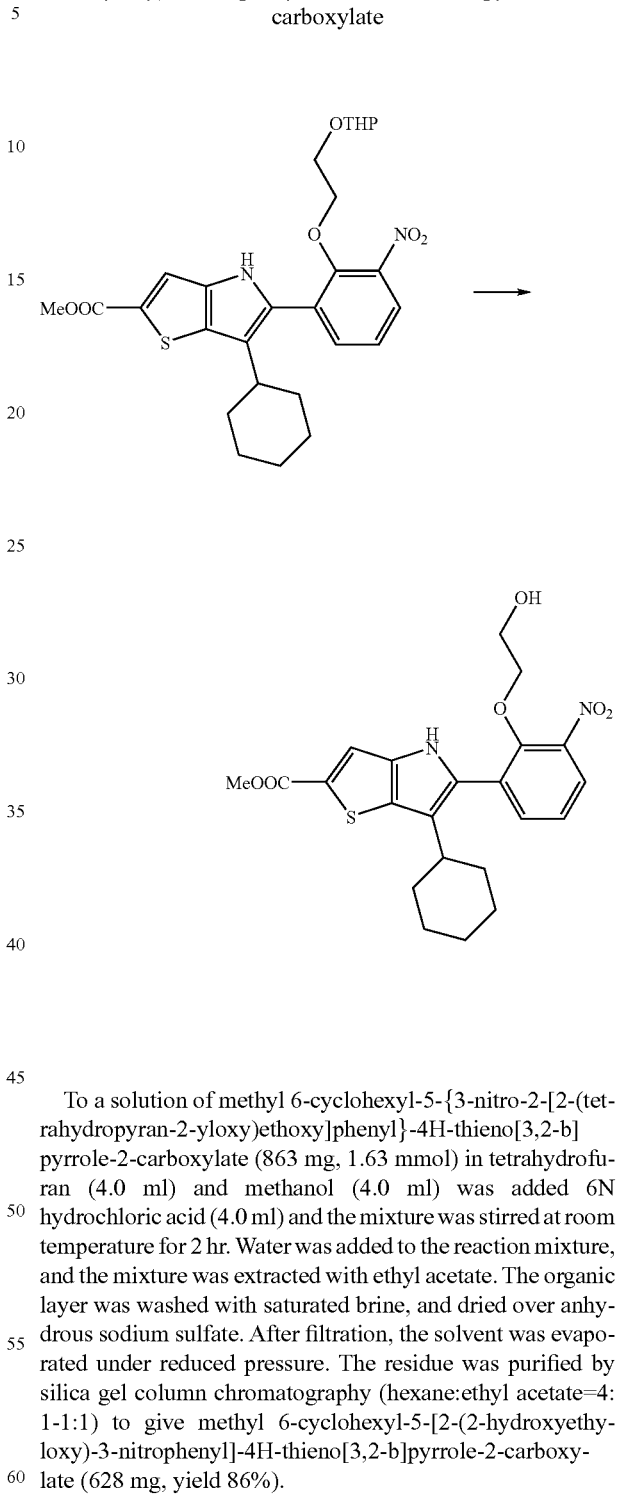

To a solution of methyl 6-cyclohexyl-5-{3-nitro-2-[2-(tetrahydropyran-2-yloxy)ethoxy]phenyl}-4H-thieno[3,2-b]pyrrole-2-carboxylate (863 mg, 1.63 mmol) in tetrahydrofuran (4.0 ml) and methanol (4.0 ml) was added 6N hydrochloric acid (4.0 ml) and the mixture was stirred at room temperature for 2 hr. Water was added to the reaction mixture, and the mixture was extracted with ethyl acetate. The organic layer was washed with saturated brine, and dried over anhydrous sodium sulfate. After filtration, the solvent was evaporated under reduced pressure. The residue was purified by silica gel column chromatography (hexane:ethyl acetate=4:1-1:1) to give methyl 6-cyclohexyl-5-[2-(2-hydroxyethyloxy)-3-nitrophenyl]-4H-thieno[3,2-b]pyrrole-2-carboxylate (628 mg, yield 86%).

$^1$H-NMR (300 MHz, δppm, CDCl$_3$) 9.17 (1H, brs), 7.79 (1H, dd, J=8.3, 1.7 Hz), 7.69 (1H, s), 7.60 (1H, dd, J=7.7, 1.8 Hz), 7.32 (1H, t, J=7.9 Hz), 3.90 (3H, s), 3.87-3.83 (2H, m), 3.78-3.74 (2H, m), 2.80-2.65 (1H, m), 1.90-1.70 (7H, m), 1.42-1.24 (3H, m).

Step 4:

Production of methyl 6-cyclohexyl-5-[2-(2-methanesulfonyloxyethoxy)-3-nitrophenyl]-4H-thieno[3,2-b]pyrrole-2-carboxylate

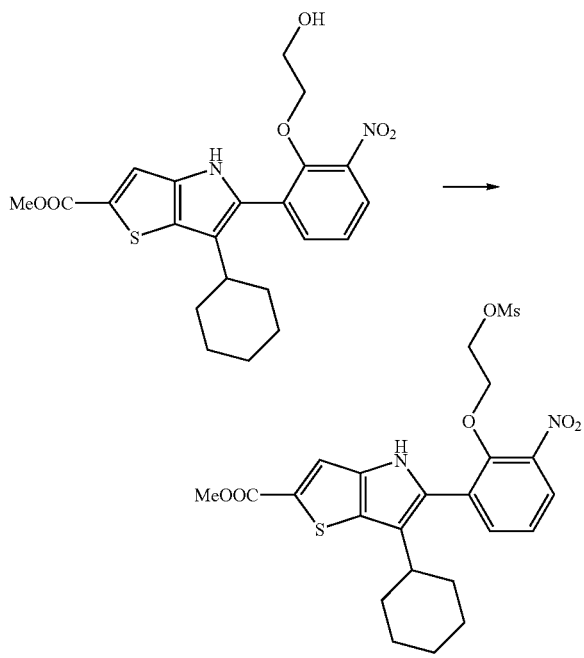

To a solution of methyl 6-cyclohexyl-5-[2-(2-hydroxyethyloxy)-3-nitrophenyl]-4H-thieno[3,2-b]pyrrole-2-carboxylate (628 mg, 1.41 mmol) in chloroform (10 ml) were added triethylamine (0.230 ml, 1.65 mmol) and methanesulfonyl chloride (0.120 ml, 1.55 mmol) in this order under ice-cooling, and the mixture was stirred at room temperature for 1 hr. Water was added to the reaction mixture, and the mixture was extracted with chloroform. The organic layer was washed with 1N hydrochloric acid, saturated aqueous sodium hydrogen carbonate solution and saturated brine in this order, and dried over anhydrous sodium sulfate. After filtration, the solvent was evaporated under reduced pressure. The obtained methyl 6-cyclohexyl-5-[2-(2-methanesulfonyloxyethoxy)-3-nitrophenyl]-4H-thieno[3,2-b]pyrrole-2-carboxylate was used for Step 5 without further purification.

Step 5:

Production of methyl 11-cyclohexyl-7-nitro-4,5-dihydro-6-oxa-1-thia-3b-azabenzo[e]cyclopenta[a]azulene-2-carboxylate

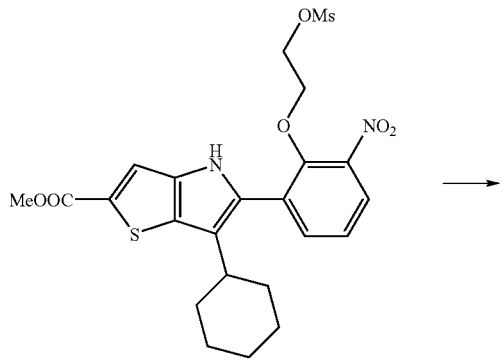

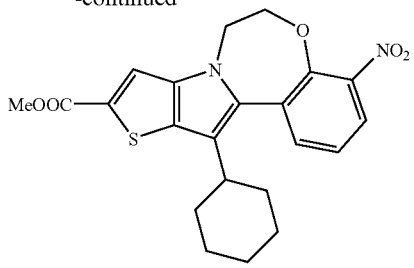

To a solution of methyl 6-cyclohexyl-5-[2-(2-methanesulfonyloxyethoxy)-3-nitrophenyl]-4H-thieno[3,2-b]pyrrole-2-carboxylate obtained in Step 4 as a crude product in N,N-dimethylformamide (20 ml) was added potassium carbonate (389 mg, 2.81 mmol), and the mixture was stirred with heating at 80° C. for 4 hr. The reaction mixture was allowed to cool to room temperature and water was added. The precipitated solid was collected by filtration, and washed with water. The obtained solid was dried under reduced pressure to give methyl 11-cyclohexyl-7-nitro-4,5-dihydro-6-oxa-1-thia-3b-azabenzo[e]cyclopenta[a]azulene-2-carboxylate (535 mg, yield 89%).

$^1$H-NMR (300 MHz, δppm, CDCl$_3$) 7.82 (1H, dd, J=8.1, 1.6 Hz), 7.71 (1H, s), 7.61 (1H, dd, J=7.9, 1.6 Hz), 7.38 (1H, t, J=7.9 Hz), 4.76 (2H, t, J=5.7 Hz), 4.30 (2H, t, J=5.7 Hz), 3.93 (3H, s), 2.81-2.71 (1H, m), 1.92-1.75 (7H, m), 1.41-1.30 (3H, m).

Step 6:

Production of methyl 7-amino-11-cyclohexyl-4,5-dihydro-6-oxa-1-thia-3b-azabenzo[e]cyclopenta[a]azulene-2-carboxylate

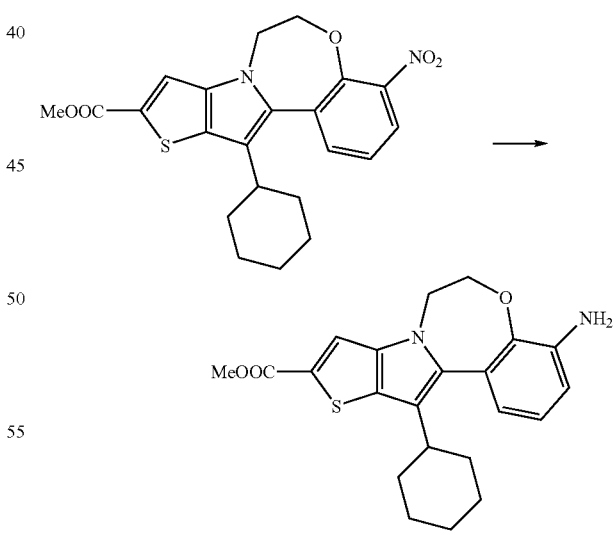

To a solution of methyl 11-cyclohexyl-7-nitro-4,5-dihydro-6-oxa-1-thia-3b-azabenzo[e]cyclopenta[a]azulene-2-carboxylate (535 mg, 1.25 mmol) in tetrahydrofuran (2.5 ml), ethanol (5.0 ml) and water (1.2 ml) were added reduced iron (350 mg, 6.26 mmol) and ammonium chloride (334 mg, 6.24 mmol), and the mixture was stirred with heating at 90° C. for 3 hr. The reaction mixture was allowed to cool to room temperature and filtered through celite. Saturated aqueous sodium hydrogen carbonate solution was added to the filtrate, and the mixture was extracted with ethyl acetate. The organic layer was washed with saturated brine, and dried over anhydrous sodium sulfate. After filtration, the solvent was evaporated under reduced pressure. A mixed solvent of hexane-ethyl acetate (5:1) was added to the residue. The precipitated solid was collected by filtration and the obtained solid was dried under reduced pressure to give methyl 7-amino-11-cyclohexyl-4,5-dihydro-6-oxa-1-thia-3b-azabenzo[e]cyclopenta[a]azulene-2-carboxylate (314 mg, yield 63%).

$^1$H-NMR (300 MHz, δppm, CDCl$_3$) 7.68 (1H, s), 7.05 (1H, t, J=7.8 Hz), 6.82 (1H, dd, J=7.9, 1.4 Hz), 6.79 (1H, dd, J=7.7, 1.4 Hz), 4.53 (2H, t, J=5.8 Hz), 4.19 (2H, t, J=5.8 Hz), 3.91 (3H, s), 2.92-2.82 (1H, m), 1.93-1.70 (7H, m), 1.42-1.25 (3H, m).

Step 7:

Production of methyl 7-(bis[2-oxo-2-(piperidin-1-yl) ethyl]amino)-11-cyclohexyl-4,5-dihydro-6-oxa-1-thia-3b-azabenzo[e]cyclopenta[a]azulene-2-carboxylate

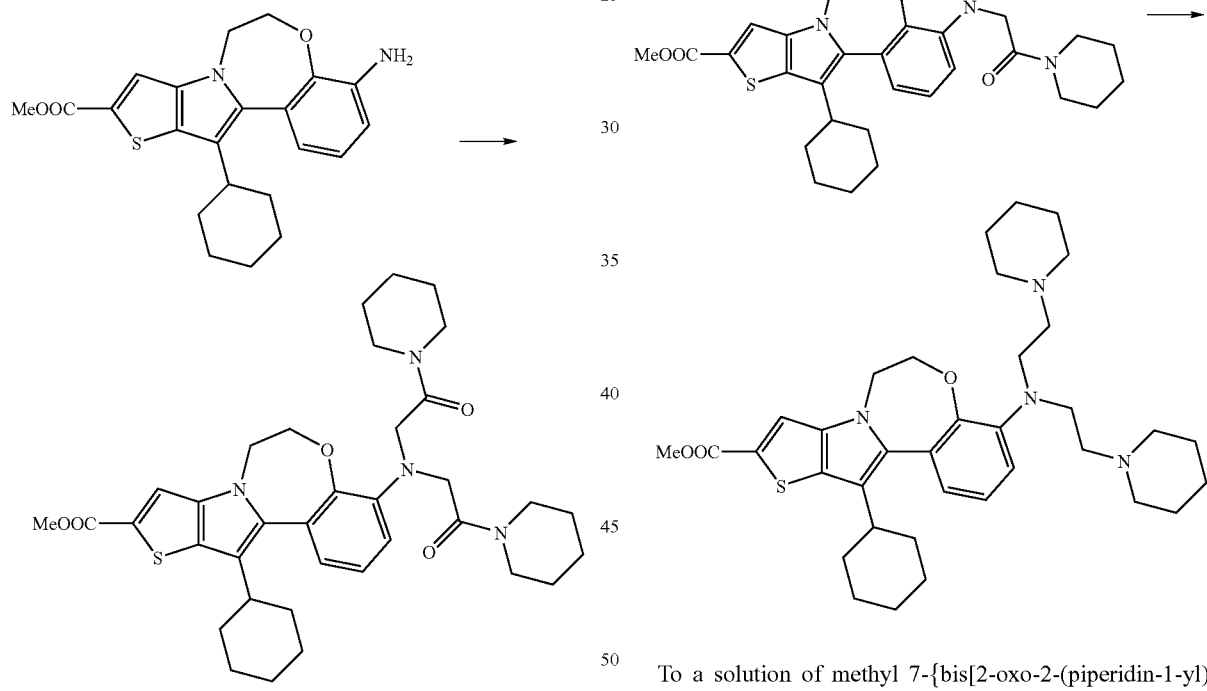

To a solution of 1-(2-bromoacetyl)piperidine (130 mg, 0.630 mmol) in N,N-dimethylformamide (2.0 ml) were added methyl 7-amino-11-cyclohexyl-4,5-dihydro-6-oxa-1-thia-3b-azabenzo[e]cyclopenta[a]azulene-2-carboxylate (100 mg, 0.251 mmol), potassium carbonate (172 mg, 1.24 mmol) and potassium iodide (42.0 mg, 0.253 mmol), and the mixture was stirred with heating at 90° C. for 15 hr. The reaction mixture was allowed to cool to room temperature and water was added. The mixture was extracted with ethyl acetate. The organic layer was washed with water and saturated brine in this order, and dried over anhydrous sodium sulfate. After filtration, the solvent was evaporated under reduced pressure. The residue was purified by silica gel column chromatography (hexane:ethyl acetate=1:1—chloroform:methanol=40:1) to give methyl 7-{bis[2-oxo-2-(piperidin-1-yl)ethyl]amino}-11-cyclohexyl-4,5-dihydro-6-oxa-1-thia-3b-azabenzo[e]cyclopenta[a]azulene-2-carboxylate (144 mg, yield 89%).

$^1$H-NMR (300 MHz, δppm, CDCl$_3$) 7.67 (1H, s), 7.09 (1H, t, J=7.9 Hz), 6.86 (1H, dd, J 7.5, 1.5 Hz), 6.81 (1H, dd, J=8.1, 1.4 Hz), 4.41 (2H, t, J=5.9 Hz), 4.30 (4H, s), 4.08 (2H, t, J=5.9 Hz), 3.91 (3H, s), 3.58 (4H, t, J=5.3 Hz), 3.37 (4H, t, J=5.2 Hz), 2.89-2.75 (1H, m), 1.90-1.70 (6H, m), 1.69-1.49 (10H, m), 1.40-1.25 (6H, m).

Step 8:

Production of methyl 7-{bis[2-(piperidin-1-yl) ethyl]amino}-11-cyclohexyl-4,5-dihydro-6-oxa-1-thia-3b-azabenzo[e]cyclopenta[a]azulene-2-carboxylate

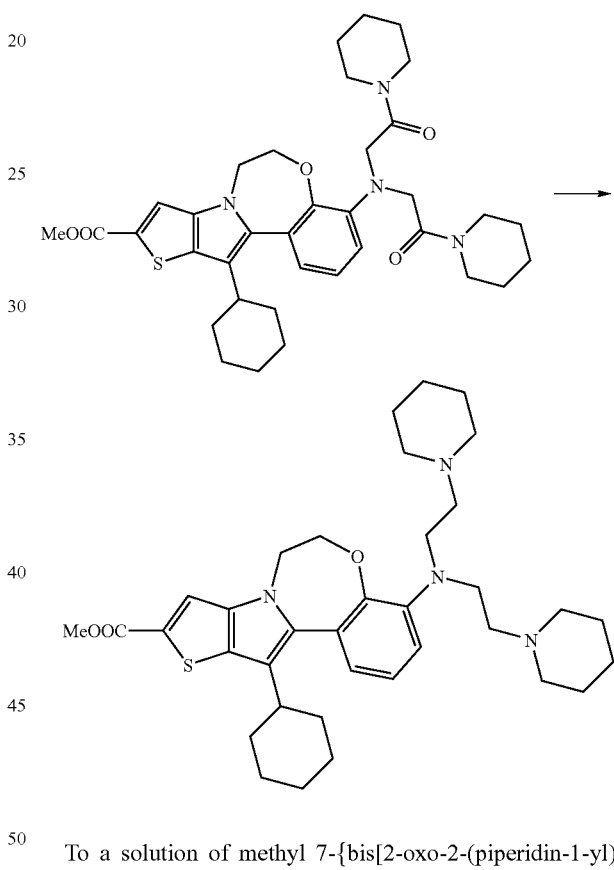

To a solution of methyl 7-{bis[2-oxo-2-(piperidin-1-yl) ethyl]amino}11-cyclohexyl-4,5-dihydro-6-oxa-l-thia-3b-azabenzo[e]cyclopenta[a]azulene-2-carboxylate (144 mg, 0.222 mmol) in tetrahydrofuran (1.0 ml) was added a solution (2.0 ml) of 1M BH$_3$-THF complex in tetrahydrofuran under ice-cooling, and the mixture was stirred at room temperature for 4 hr. 2N Hydrochloric acid was added to the reaction mixture, and the mixture was stirred with heating at 70° C. for 2 hr. The reaction mixture was alkalified with 4N aqueous sodium hydroxide solution and saturated aqueous sodium hydrogen carbonate solution under ice-cooling, and the mixture was extracted with ethyl acetate. The organic layer was washed with saturated brine, and dried over anhydrous sodium sulfate. After filtration, the solvent was evaporated under reduced pressure. The residue was purified by silica gel column chromatography (chloroform:methanol=20:1—5:1) to give methyl 7-(bis[2-(piperidin-1-yl)ethyl]amino}-11-cyclohexyl-4,5-dihydro-6-oxa-1-thia-3b-azabenzo[e]cyclopenta[a]azulene-2-carboxylate (72 mg, yield 52%).

$^1$H-NMR (300 MHz, δppm, CDCl$_3$) 7.68 (1H, s), 7.14 (1H, t, J=7.7 Hz), 7.09 (1H, dd, J=8.1, 1.9 Hz), 6.95 (1H, dd, J=7.4, 1.9 Hz), 4.48 (2H, t, J=5.8 Hz), 4.12 (2H, t, J=5.9 Hz), 3.91 (3H, s), 3.37 (4H, t, J=7.3 Hz), 2.90-2.80 (1H, m), 2.51 (4H, t, J=6.8 Hz), 2.41 (8H, brs), 1.92-1.71 (6H, m), 1.69-1.52 (10H, m), 1.47-1.30 (6H, m).

Step 9:

Production of 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid trihydrochloride

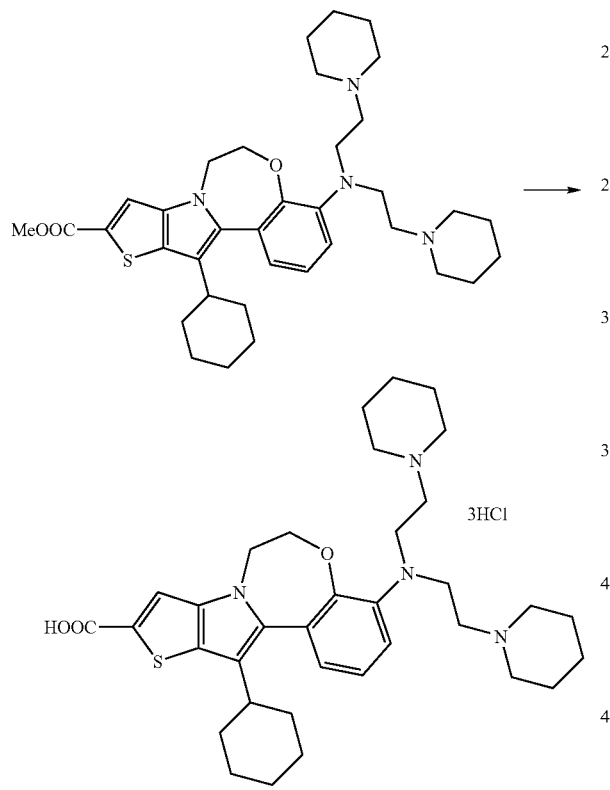

To a solution of methyl 7-(bis[2-(piperidin-1-yl) ethyl] amino)-11-cyclohexyl-4,5-dihydro-6-oxa-1-thia-3b-azabenzo[e]cyclopenta[a]azulene-2-carboxylate (72.0 mg, 0.116 mol) in tetrahydrofuran (1.0 ml) and methanol (1.0 ml) was added 4N aqueous sodium hydroxide solution (1.0 ml), and the mixture was stirred with heating at 70° C. for 3 hr. The reaction mixture was adjusted to pH 7 with 2N hydrochloric acid and extracted with chloroform. The organic layer was dried over anhydrous sodium sulfate. After filtration, the solvent was evaporated under reduced pressure to give 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid. To a solution of the obtained 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid in chloroform (2 ml) was added 4N HCl-ethyl acetate solution (2.0 ml). The reaction mixture was concentrated under reduced pressure, and ethyl acetate was added. The precipitated solid was collected by filtration and the obtained solid was dried under reduced pressure to give 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid trihydrochloride (26.0 mg, yield 31%).

$^1$H-NMR (400 MHz, δppm, DMSO-d$_6$) 10.36 (2H, brs), 7.96 (1H, s), 7.36 (1H, d, J=6.7 Hz), 7.28 (1H, t, J=7.9 Hz), 7.12 (1H, d, J=6.3 Hz), 4.52 (2H, t, J=5.6 Hz), 4.34 (2H, t, J=5.6 Hz), 3.57 (4H, t, J=7.1 Hz), 3.51-3.41 (4H, m), 3.24 (4H, q, J=8.0 Hz), 2.91 (4H, q, J=11.1 Hz), 2.74 (1H, t, J=10.0 Hz), 1.90-1.61 (12H, m), 1.42-1.22 (10H, m).

MS 605.3 (M+1).

Example 45

Production of (E)-3-[4-((1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino]phenyl]acrylic acid Step 1:

Production of methyl 5-(2-amino-4-benzyloxyphenyl)-6-cyclohexyl-4H-thieno[3,2-b]pyrrole-2-carboxylate

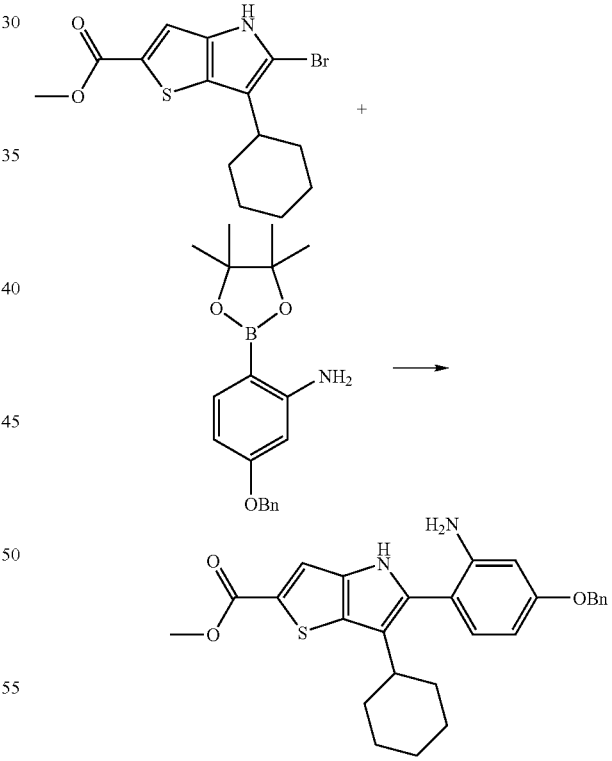

To a suspension of methyl 5-bromo-6-cyclohexyl-4H-thieno[3,2-b]pyrrole-2-carboxylate (4.73 g, 13.8 mmol) and 5-benzyloxy-2-(4,4,5,5-tetramethyl-1,3,2-dioxaborolan-2-yl)phenylamine (5.84 g, 17.9 mmol) produced by the method described in WO2005/080399 in 1,2-dimethoxyethane (50 ml) and water (50 ml) were added sodium hydrogen carbonate (1.72 g, 20.7 mol) and tetrakis(triphenylphosphine)palladium (799 mg, 0.691 mol), and the mixture was stirred overnight with heating at 110° C. The reaction mixture was allowed to cool to room temperature. Water was added to the reaction mixture, and the mixture was extracted with ethyl acetate. The organic layer was washed successively with water and saturated brine, dried over anhydrous magnesium sulfate, and filtered. The solvent was evaporated under reduced pressure and the residue was purified y silica gel column chromatography (hexane:ethyl acetate=3:1) to give methyl 5-(2-amino-4-benzyloxyphenyl)-6-cyclohexyl-4H-thieno[3,2-b]pyrrole-2-carboxylate (5.93 g, yield 93%).

$^1$H-NMR (400 MHz, δppm, CDCl$_3$) 8.17 (1H, brs), 7.67 (1H, s), 7.47-7.34 (5H, m), 7.09 (1H, d, J=8.6 Hz), 6.48 (1H, dd, J=8.6, 2.5 Hz), 6.42 (1H, d, J=2.5 Hz), 5.08 (2H, s), 3.91 (3H, s), 3.82 (2H, brs), 2.60-2.56 (1H, m), 1.78-1.74 (7H, m), 1.33-1.27 (3H, m).

Step 2:

Production of methyl 5-[4-benzyloxy-2-(2-chloro-acetylamino)phenyl]-6-cyclohexyl-4H-thieno[3,2-b]pyrrole-2-carboxylate

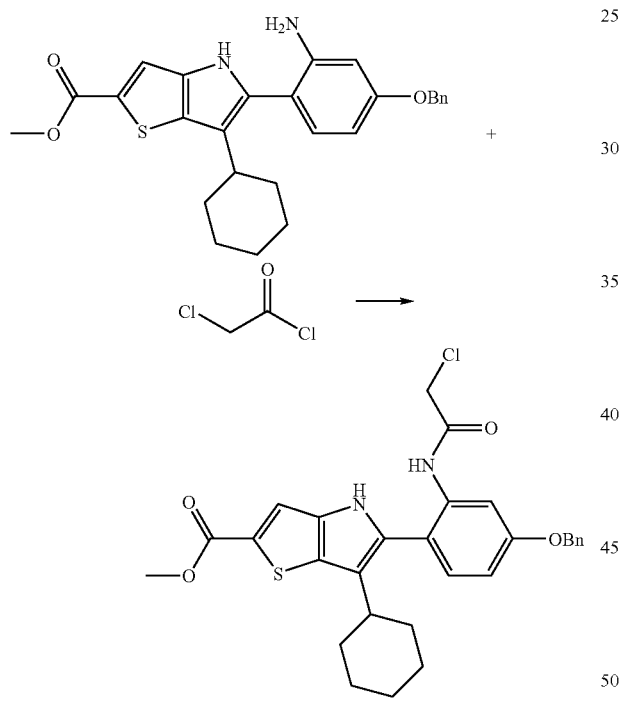

To a suspension of methyl 5-(2-amino-4-benzyloxyphenyl)-6-cyclohexyl-4H-thieno[3,2-b]pyrrole-2-carboxylate (6.30 g, 13.8 mmol), sodium acetate (1.36 g, 16.6 mmol) and acetic acid (0.95 ml, 16.6 mmol) in tetrahydrofuran (100 ml) was added dropwise chloroacetyl chloride (1.32 ml, 16.6 mmol), and the mixture was stirred at room temperature for 2 hr. Water was added to the reaction mixture, and the mixture was extracted with ethyl acetate. The organic layer was washed successively with saturated aqueous sodium hydrogen carbonate solution, saturated brine, and dried over anhydrous magnesium sulfate. After filtration, the solvent was evaporated under reduced pressure. The obtained crude product of methyl 5-[4-benzyloxy-2-(2-chloroacetylamino)phenyl]-6-cyclohexyl-4H-thieno[3,2-b]pyrrole-2-carboxylate (8.22 g) was used for Step 6 without further purification.

$^1$H-NMR (400 MHz, δppm, CDCl$_3$) 8.46 (1H, brs), 8.18 (1H, d, J=2.6 Hz), 8.16 (1H, brs), 7.69 (1H, s), 7.46-7.39 (5H, m), 7.25 (1H, d, J=8.3 Hz), 6.86 (1H, dd, J=8.3, 2.6 Hz), 5.15 (2H, s), 4.04 (2H, s), 3.91 (3H, s), 2.44-2.39 (1H, m), 1.78-1.68 (7H, m) 1.28-1.26 (3H, m).

Step 3:

Production of methyl 8-benzyloxy-11-cyclohexyl-5-oxo-5,6-dihydro-4H-1-thia-3b,6-diazabenzo[e]cyclopenta[a]azulene-2-carboxylate

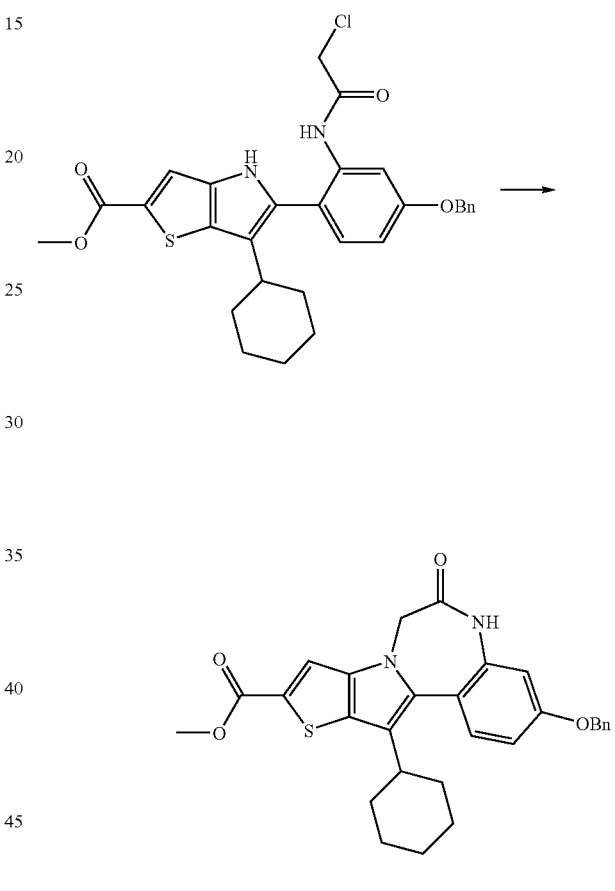

To a solution of methyl 5-[4-benzyloxy-2-(2-chloroacetylamino)phenyl]-6-cyclohexyl-4H-thieno[3,2-b]pyrrole-2-carboxylate (8.22 g, 13.8 mmol) in N,N-dimethylformamide (100 ml) was added potassium carbonate (2.00 g, 14.5 mmol). The mixture was stirred at 60° C. for 3 hr and allowed to cool. Water was added to the reaction mixture, and the precipitated solid was collected by filtration. The solid was washed with water, and then with a mixed solvent of hexane-ethyl acetate (3:1) and dried under reduced pressure to give methyl 8-benzyloxy-11-cyclohexyl-5-oxo-5,6-dihydro-4H-1-thia-3b,6-diazabenzo[e]cyclopenta[a]azulene-2-carboxylate (6.11 g, yield 88%).

$^1$H-NMR (400 MHz, δppm, CDCl$_3$) 7.76 (1H, s), 7.55 (1H, brs), 7.46-7.39 (6H, m), 7.00 (1H, dd, J=8.6, 2.6 Hz), 6.71 (1H, d, J=2.6 Hz), 5.15 (2H, s), 4.63 (2H, s), 3.91 (3H, s), 2.76 (1H, m), 1.86-1.80 (7H, brm), 1.36-1.33 (3H, brm).

Step 4:

Production of methyl 8-benzyloxy-11-cyclohexyl-6-methyl-5-oxo-5,6-dihydro-4H-1-thia-3b,6-diazabenzo[e]cyclopenta[a]azulene-2-carboxylate

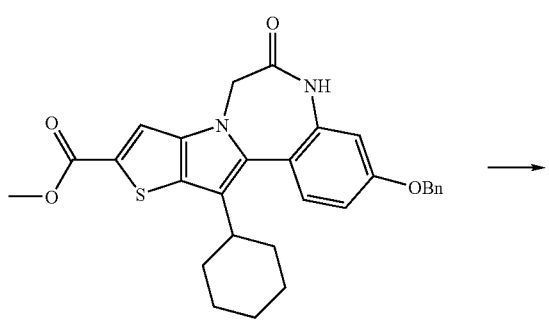

Step 5:

Production of methyl 11-cyclohexyl-8-hydroxy-6-methyl-5-oxo-5,6-dihydro-4H-1-thia-3b,6-diazabenzo[e]cyclopenta[a]azulene-2-carboxylate

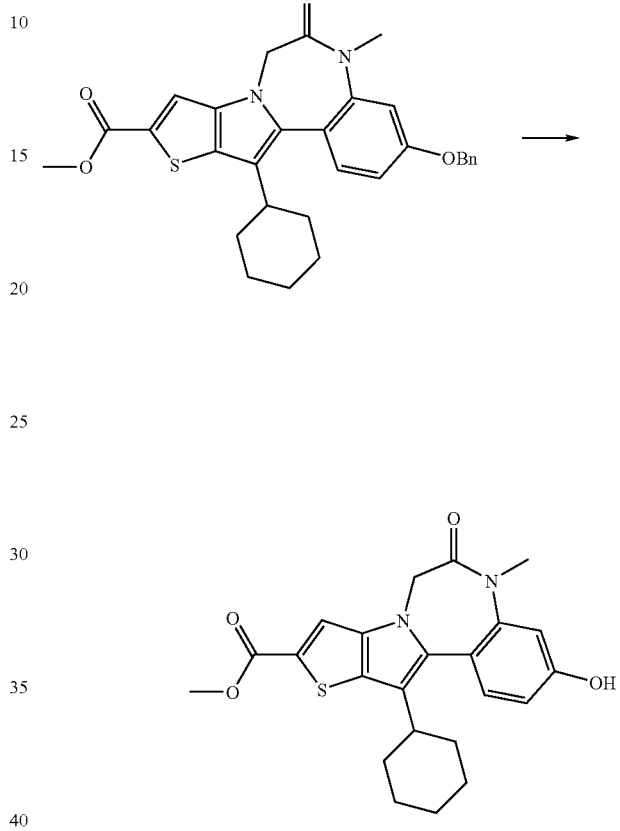

To a solution of methyl 8-benzyloxy-11-cyclohexyl-5-oxo-5,6-dihydro-4H-1-thia-3b,6-diazabenzo[e]cyclopenta[a]azulene-2-carboxylate (3.00 g, 5.99 mmol) in N,N-dimethylformamide (30 ml) were added potassium carbonate (1.08 g, 7.79 mmol) and methyl iodide (0.41 ml, 6.6 mmol). The mixture was stirred at 80° C. for 3 hr, and allowed to cool. Water was added to the reaction mixture and the mixture was extracted with ethyl acetate. The organic layer was washed successively with water and saturated brine, and dried over anhydrous magnesium sulfate. After filtration, the solvent was evaporated under reduced pressure. The obtained crude product was washed with a mixed solvent of hexane-ethyl acetate (1:1), collected by filtration and dried under reduced pressure to give methyl 8-benzyloxy-11-cyclohexyl-6-methyl-5-oxo-5,6-dihydro-4H-1-thia-3b,6-diazabenzo[e]cyclopenta[a]azulene-2-carboxylate (2.70 g, yield 88%).

$^1$H-NMR (400 MHz, δppm, CDCl$_3$) 7.77 (1H, s), 7.50-7.37 (6H, m), 7.01 (1H, dd, J=8.6, 2.6 Hz), 6.97 (1H, d, J=2.6 Hz), 5.16 (2H, s), 4.74 (1H, d, J=14.4 Hz), 4.43 (1H, d, J=14.4 Hz), 3.91 (3H, s), 3.31 (3H, s), 2.82-2.77 (1H, m), 2.03-2.01 (1H, m), 1.94-1.66 (6H, m), 1.42-1.31 (3H, m).

To a solution of methyl 8-benzyloxy-11-cyclohexyl-6-methyl-5-oxo-5,6-dihydro-4H-1-thia-3b,6-diazabenzo[e]cyclopenta[a]azulene-2-carboxylate (2.60 g, 5.05 mmol) in chloroform (5 ml) and acetic acid (5 ml) was added 25% bromic acid-acetic acid solution (15 ml) at room temperature and the mixture was stirred overnight. Water was added to the reaction mixture, and the mixture was extracted with ethyl acetate. The organic layer was washed successively with water, saturated aqueous sodium hydrogen carbonate solution and saturated brine, and dried over anhydrous magnesium sulfate. After filtration, the solvent was evaporated under reduced pressure, and the obtained crude product was washed with a mixed solvent of hexane-ethyl acetate (1:1), collected by filtration, and dried under reduced pressure to give methyl 11-cyclohexyl-8-hydroxy-6-methyl-5-oxo-5,6-dihydro-4H-1-thia-3b,6-diazabenzo[e]cyclopenta[a]azulene-2-carboxylate (1.24 g, yield 58%).

$^1$H-NMR (400 MHz, δppm, DMSO-d$_6$) 10.14 (1H, brs), 8.13 (1H, s), 7.33 (1H, d, J=8.6 Hz), 6.92 (1H, d, J=2.4 Hz), 6.87 (1H, dd, J=8.6, 2.4 Hz), 5.04 (1H, d, J=14.4 Hz), 4.45 (1H, d, J=14.4 Hz), 3.83 (3H, s), 3.20 (3H, s), 2.77-2.75 (1H, m), 2.05-2.02 (1H, m), 1.88-1.85 (1H, m), 1.73-1.59 (5H, m), 1.42-1.40 (1H, m), 1.28-1.26 (2H, m).

Step 6:

Production of methyl 11-cyclohexyl-8-ethoxy-6-methyl-5-oxo-5,6-dihydro-4H-1-thia-3b,6-diazabenzo[e]cyclopenta[a]azulene-2-carboxylate

Step 7:

Production of methyl 11-cyclohexyl-8-ethoxy-6-methyl-5,6-dihydro-4H-1-thia-3b,6-diazabenzo[e]cyclopenta[a]azulene-2-carboxylate

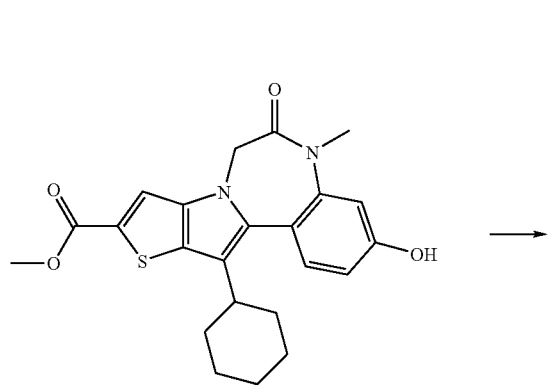

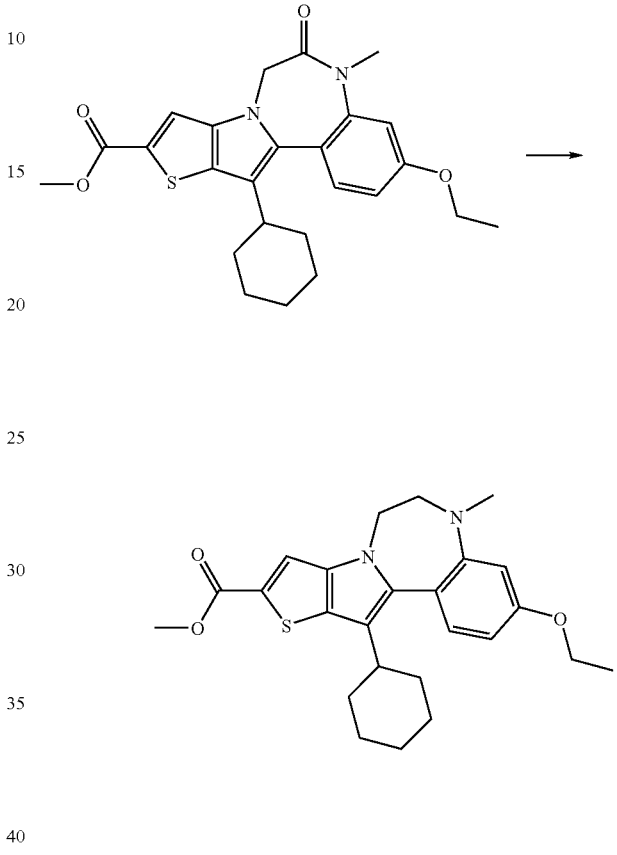

To a solution of methyl 11-cyclohexyl-8-hydroxy-6-methyl-5-oxo-5,6-dihydro-4H-1-thia-3b,6-diazabenzo[e]cyclopenta[a]azulene-2-carboxylate (700 mg, 1.46 mmol) in N,N-dimethylformamide (3 ml) were added potassium carbonate (456 mg, 3.30 mmol) and ethyl iodide (0.20 ml, 2.5 mmol) at room temperature. The reaction mixture was stirred overnight at 80° C. The reaction mixture was allowed to cool and water was added. The precipitated solid was collected by filtration and the obtained solid was washed with water and dried under reduced pressure to give a crude product of methyl 11-cyclohexyl-8-ethoxy-6-methyl-5-oxo-5,6-dihydro-4H-1-thia-3b,6-diazabenzo[e]cyclopenta[a]azulene-2-carboxylate (755 mg). The obtained compound was used for Step 7 without further purification.

$^1$H-NMR (400 MHz, δppm, DMSO-d$_6$) 8.14 (1H, s), 7.43 (1H, d, J=8.7 Hz), 7.12 (1H, d, J=2.6 Hz), 7.05 (1H, dd, J=8.7, 2.6 Hz), 5.07 (1H, d, J=14.6 Hz), 4.46 (1H, d, J=14.4 Hz), 4.16 (2H, q, J=7.0 Hz), 3.84 (3H, s), 3.25 (3H, s), 2.80-2.77 (1H, m), 2.07-2.04 (1H, brm), 1.89-1.85 (1H, brm), 1.73-1.59 (5H, brm) 1.39 (3H, t, J=7.0 Hz), 1.35-1.21 (3H, m).

To a solution of methyl 11-cyclohexyl-8-ethoxy-6-methyl-5-oxo-5,6-dihydro-4H-1-thia-3b,6-diazabenzo[e]cyclopenta[a]azulene-2-carboxylate (746 mg, 1.46 mmol) in tetrahydrofuran (4 ml) was added a solution (7.5 ml) of 1.0M BH$_3$-THF complex in tetrahydrofuran under ice-cooling, and the mixture was stirred overnight at room temperature. 6N Hydrochloric acid (10 ml) was added to the reaction mixture and the mixture was stirred at 80° C. for 6 hr. The reaction mixture was allowed to cool to room temperature and neutralized with 4N aqueous sodium hydroxide solution. Saturated sodium hydrogen carbonate was added and the mixture was extracted with ethyl acetate. The organic layer was washed with saturated brine, and dried over anhydrous magnesium sulfate. After filtration, the solvent was evaporated under reduced pressure. The obtained crude product was washed with a mixed solvent of hexane-ethyl acetate (1:1), collected by filtration, and dried under reduced pressure to give methyl 11-cyclohexyl-8-ethoxy-6-methyl-5,6-dihydro-4H-1-thia-3b,6-diazabenzo[e]cyclopenta[a]azulene-2-carboxylate (469 mg, yield 63%).

$^1$H-NMR (400 MHz, δppm, DMSO-d$_6$) 8.00 (1H, s), 7.18 (1H, d, J=8.4 Hz), 6.71 (1H, dd, J=8.4, 2.5 Hz), 6.64 (1H, d, J=2.5 Hz), 4.20 (4H, brs), 4.10 (2H, q, J=7.0 Hz), 3.82 (3H, s), 2.72 (3H, s), 2.66-2.63 (1H, m), 1.75-1.65 (7H, brm), 1.37 (3H, t, J=7.0 Hz), 1.31-1.27 (3H, brm).

Step 8:

Production of 11-cyclohexyl-8-ethoxy-6-methyl-5,6-dihydro-4H-1-thia-3b,6-diazabenzo[e]cyclopenta[a]azulene-2-carboxylic acid

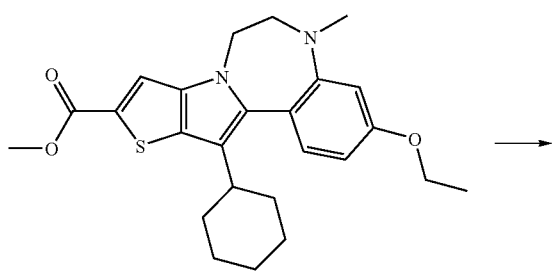

To a solution of methyl 11-cyclohexyl-8-ethoxy-6-methyl-5,6-dihydro-4H-1-thia-3b,6-diazabenzo[e]cyclopenta[a]azulene-2-carboxylate (469 mg, 1.07 mmol) in tetrahydrofuran (5 ml) and methanol (5 ml) was added 4N aqueous sodium hydroxide solution (10 ml), and the mixture was stirred at 60° C. for 2 hr. The reaction mixture was adjusted to pH 7 with 2N hydrochloric acid. The precipitated solid was collected by filtration, washed with water and dried under reduced pressure to give 11-cyclohexyl-8-ethoxy-6-methyl-5,6-dihydro-4H-1-thia-3b,6-diazabenzo[e]cyclopenta[a]azulene-2-carboxylic acid (465 mg, yield 98%).

$^1$H-NMR (400 MHz, δppm, DMSO-$d_6$) 12.61 (1H, brs), 7.88 (1H, s), 7.17 (1H, d, J=8.4 Hz), 6.70 (1H, dd, J=8.4, 2.4 Hz), 6.64 (1H, d, J=2.4 Hz), 4.20-4.17 (4H, brm), 4.10 (2H, q, J=7.0 Hz), 2.72 (3H, s), 2.68-2.61 (1H, m), 1.73-1.66 (7H, brm), 1.37 (3H, t, J=7.0 Hz), 1.30-1.27 (3H, brm).

MS 425.2(M+1).

Step 9:

Production of ethyl (E)-3-[4-({1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino)phenyl]acrylate

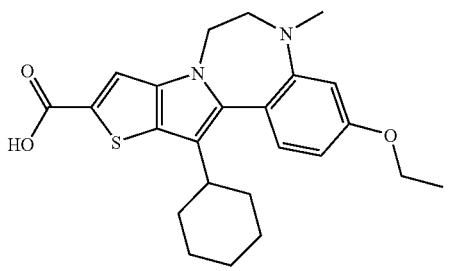

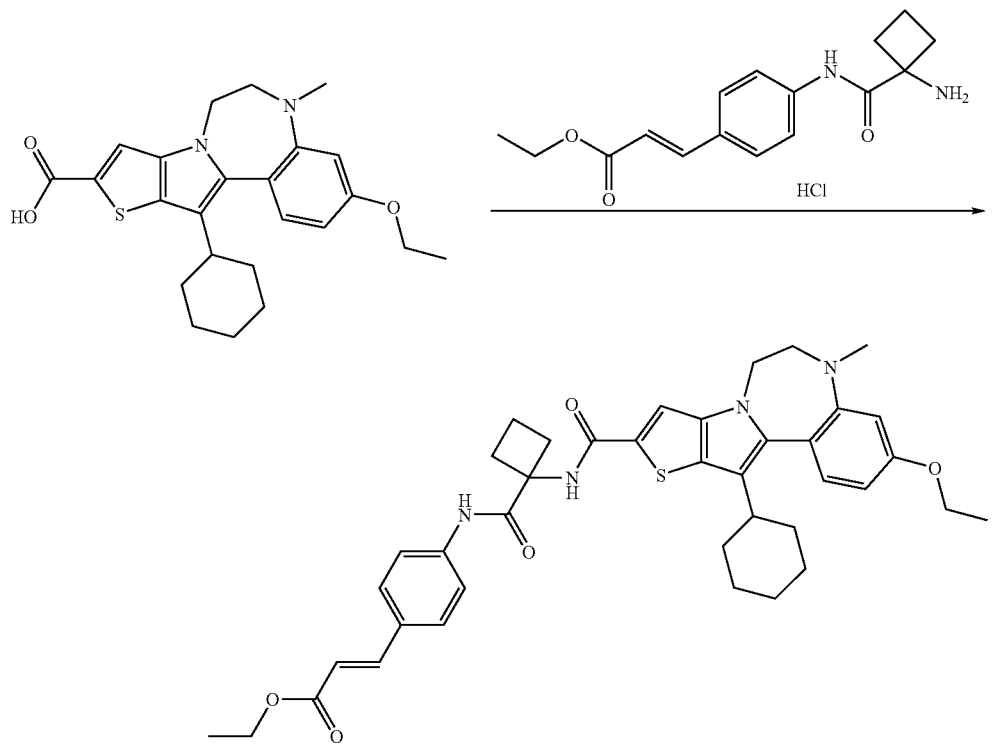

To a solution of 11-cyclohexyl-8-ethoxy-6-methyl-5,6-dihydro-4H-1-thia-3b,6-diazabenzo [e] cyclopenta [a] azulene-2-carboxylic acid (100 mg, 0.236 mmol) and ethyl (E)-3-{4-[(1-aminocyclobutanecarbonyl)amino]phenyl}acrylate hydrochloride (84 mg, 0.26 mmol) produced by the method described in WO2005/080399 in N,N-dimethylformamide (2 ml) were added 1-hydroxybenzotriazole monohydrate (52 mg, 0.34 mmol), 1-ethyl-3-(3'-dimethylaminopropyl)carbodiimide hydrochloride (64 mg, 0.34 mmol) and triethylamine (0.13 ml, 0.94 mmol), and the mixture was stirred overnight at room temperature. Water was added to the reaction mixture, and the mixture was extracted with ethyl acetate. The organic layer was washed successively with water and saturated brine, and dried over anhydrous magnesium sulfate. After filtration, the solvent was evaporated under reduced pressure, and the residue was purified by silica gel column chromatography (hexane:ethyl acetate=2:1) to give ethyl (E)-3-[4-({1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino)phenyl]acrylate (85 mg, yield 56%).

$^1$H-NMR (400 MHz, δppm, DMSO-d$_6$) 9.69 (1H, brs), 8.67 (1H, brs), 7.98 (1H, s), 7.68-7.67 (4H, m), 7.58 (1H, d, J=16.0 Hz), 7.17 (1H, d, J=8.4 Hz), 6.71 (1H, dd, J=8.4, 2.5 Hz), 6.65 (1H, d, J=2.5 Hz), 6.52 (1H, d, J=16.0 Hz), 4.18 (2H, q, J=7.1 Hz), 4.11-4.09 (6H, m), 2.74 (3H, s), 2.71-2.68 (2H, m), 2.65-2.63 (1H, m), 2.34-2.29 (2H, m), 1.96-1.89 (2H, brm), 1.76-1.63 (7H, m), 1.37 (3H, t, J=7.0 Hz), 1.30-1.21 (3H, m).

Step 10:

Production of (E)-3-[4-({1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino)phenyl]acrylic acid

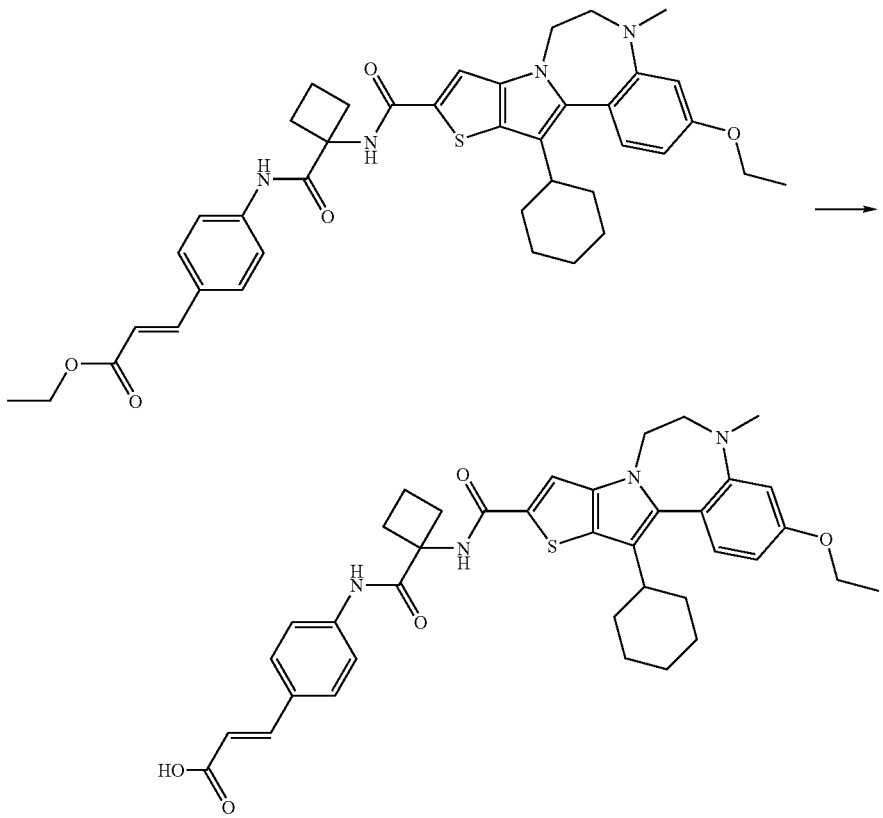

To a solution of ethyl (E)-3-[4-((1-[(11-cyclohexyl-8-ethoxy-6-methyl-5, 6-dihydro-4H-1-thia-3b, 6-diazabenzo [e] cyclopenta [a]azulene-2-carbonyl}amino] cyclobutanecarbonyl}amino)phenyl]acrylate (85 mg, 0.122 mmol) in a mixture of methanol (4 ml) and tetrahydrofuran (4 ml) was added 4N aqueous sodium hydroxide solution (3 ml), and the mixture was stirred at room temperature for 7 hr. 2N Hydrochloric acid (6 ml) was added to the reaction mixture, and the mixture was extracted with ethyl acetate. The organic layer was washed successively with water and saturated brine, and dried over anhydrous magnesium sulfate. After filtration, the solvent was evaporated under reduced pressure, and the residue was purified by silica gel column chromatography (chloroform:methanol=15:1) to give (E)-3-[4-({1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino)phenyl]acrylic acid (62 mg, yield 76%).

$^1$H-NMR (400 MHz, δppm, DMSO-d$_6$) 12.24 (1H, brs)o, 9.70 (1H, m), 8.72 (1H, m)t, 7.99 (1H, r), 7.68-7.61 (4H, m), 7.51 (1H, d, J=16.0 Hz)d, 7.17 (1H, d, J=8.4 Hz), 6.71 (1H, dd, J=8.4, 2.4 Hz), 6.65 (1H, d, J=2.4 Hz), 6.42 (1H, d, J=16.0 Hz), 4.11-4.09 (6H, m), 3.45-3.41 (3H, brs), 2.71-2.69 (2H, m), 2.65-2.62 (1H, m), 2.36-2.28 (2H, m), 2.01-1.84 (3H, m), 1.82-1.60 (5H, m), 1.37 (3H, t, J=7.0 Hz), 1.29-1.23 (3H, m).
MS 667.2(M+1).

In the same manner as in Examples 1 to 14, 37, 42 and 45, and using other conventional methods where necessary, the following compounds of Examples 15 to 36, 38 to 41, 43, 44 and 46 were produced.

11-cyclohexyl-4,5-dihydro-6-oxa-1-thia-3b-azabenzo[e]cyclopenta[a]azulene-2-carboxylic acid (Example 15), 11-cyclohexyl-8-[2-(morpholin-4-yl)-5-(2-oxopyrrolidin-1-yl)benzyloxy]-4,5-dihydro-6-oxa-1-thia-3b-azabenzo[e]cyclopenta[a]azulene-2-carboxylic acid hydrochloride (Example 16), 11-cyclohexyl-8-(1-methoxycarbonylpiperidin-3-yloxy)-4,5-dihydro-6-oxa-1-thia-3b-azabenzo[e]cyclopenta[a]azulene-2-carboxylic acid (Example 17), 11-cyclohexyl-8-[2-(4-methanesulfonylpiperazin-1-yl)-5-(2-oxopyrrolidin-1-yl)benzyloxy]-4,5-dihydro-6-oxa-1-thia-3b-azabenzo[e]cyclopenta[a]azulene-2-carboxylic acid (Example 18), 11-cyclohexyl-8-methyl-6-[2-(piperidin-1-yl)ethyl]-5,6-dihydro-4H-1-thia-3b,6-diazabenzo[e]cyclopenta[a]azulene-2-carboxylic acid dihydrochloride (Example 19), 8-chloro-11-cyclohexyl-6-[2-(piperidin-1-yl)ethyl]-5,6-dihydro-4H-1-thia-3b,6-diazabenzo[e]cyclopenta[a]azulene-2-carboxylic acid dihydrochloride (Example 20), 6-[2-(azocan-1-yl)ethyl]-11-cyclohexyl-5,6-dihydro-4H-1-thia-3b,6-diazabenzo[e]cyclopenta[a]azulene-2-carboxylic acid dihydrochloride (Example 21), 11-cyclohexyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride (Example 22), (S)-11-cyclohexyl-6-{2-[3-(2-methoxyethyl)piperidin-1-yl]ethyl}-5,6-dihydro-4H-1-thia-3b,6-diazabenzo[e]cyclopenta[a]azulene-2-carboxylic acid dihydrochloride (Example 23), 11-cyclohexyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride (Example 24), 6-[2-(azocan-1-yl)ethyl]-11-cyclohexyl-8-methyl-5,6-dihydro-4H-1-thia-3b,6-diazabenzo[e]cyclopenta[a]azulene-2-carboxylic acid dihydrochloride (Example 25), 11-cyclohexyl-8-methyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride (Example 26), (S)-11-cyclohexyl-6-{2-[3-(2-methoxyethyl)piperidin-1-yl]ethyl}-8-methyl-5,6-dihydro-4H-1-thia-3b,6-diazabenzo[e]cyclopenta[a]azulene-2-carboxylic acid dihydrochloride (Example 27), 11-cyclohexyl-8-methyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride (Example 28), 6-[2-(azocan-1-yl)ethyl]-8-chloro-11-cyclohexyl-5,6-dihydro-4H-1-thia-3b,6-diazabenzo[e]cyclopenta[a]azulene-2-carboxylic acid dihydrochloride (Example 29), 8-chloro-11-cyclohexyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride (Example 30), (S)-8-chloro-11-cyclohexyl-6-{2-[3-(2-methoxyethyl)piperidin-1-yl]ethyl}-5,6-dihydro-4H-1-thia-3b,6-diazabenzo[e]cyclopenta[a]azulene-2-carboxylic acid dihydrochloride (Example 31), 8-chloro-11-cyclohexyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride (Example 32), 6-[2-(4-tert-butoxycarbonylpiperazin-1-yl)ethyl]-11-cyclohexyl-8-methyl-5,6-dihydro-4H-1-thia-3b,6-diazabenzo[e]cyclopenta[a]azulene-2-carboxylic acid hydrochloride (Example 33), 6-[2-(4-tert-butoxycarbonylpiperazin-1-yl)ethyl]-8-chloro-11-cyclohexyl-5,6-dihydro-4H-1-thia-3b,6-diazabenzo[e]cyclopenta[a]azulene-2-carboxylic acid hydrochloride (Example 34), 11-cyclohexyl-6-[2-(4-ethylpiperazin-1-yl)-2-oxoethyl]-8-methyl-5,6-dihydro-4H-1-thia-3b,6-diazabenzo[e]cyclopenta[a]azulene-2-carboxylic acid dihydrochloride (Example 35), 8-chloro-11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylic acid dihydrochloride (Example 36), (E)-3-[4-((1-[(11-cyclohexyl-8-methoxy-4,5-dihydro-6-oxa-1-thia-3b-azabenzo[e]cyclopenta[a]azulene-2-carbonyl)amino]cyclobutanecarbonyl}amino)phenyl]acrylic acid (Example 37), (E)-3-[4-({1-[(1-cyclohexyl-6,8-dimethyl-5,6-dihydro-4H-1-thia-3b,6-diazabenzo[e]cyclopenta[a]azulene-2-carbonyl)amino]cyclobutanecarbonyl}amino)phenyl]acrylic acid (Example 38), (E)-3-[4-({1-[(8-chloro-11-cyclohexyl-6-methyl-5,6-dihydro-4H-1-thia-3b,6-diazabenzo[e]cyclopenta[a]azulene-2-carbonyl)amino]cyclobutanecarbonyl}amino)phenyl]acrylic acid (Example 39), (E)-3-[3-({1-[(11-cyclohexyl-8-methoxy-4,5-dihydro-6-oxa-1-thia-3b-azabenzo[e]cyclopenta[a]azulene-2-carbonyl)amino]cyclobutanecarbonyl)amino)phenyl]acrylic acid (Example 40), 11-cyclohexyl-8-ethoxy-4,5-dihydro-6-oxa-1-thia-3b-azabenzo[e]cyclopenta[a]azulene-2-carboxylic acid (Example 41), 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid trihydrochloride (Example 42), (E)-3-[4-({1-[(11-cyclohexyl-8-ethoxy-4,5-dihydro-6-oxa-1-thia-3b-azabenzo[e]cyclopenta[a]azulene-2-carbonyl)amino]cyclobutanecarbonyl)amino)phenyl]acrylic acid (Example 43), 11-cyclohexyl-8-ethoxy-6-methyl-5,6-dihydro-4H-1-thia-3b,6-diazabenzo[e]cyclopenta[a]azulene-2-carboxylic acid (Example 44), (E)-3-[4-({1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino)phenyl]acrylic acid (Example 45), 7-{bis[2-(morpholin-4-yl)ethyl]amino}-11-cyclohexyl-4,5-dihydro-6-oxa-1-thia-3b-azabenzo[e]cyclopenta[a]azulene-2-carboxylic acid trihydrochloride (Example 46).

The structural formulas and physicochemical data of the Example compounds are shown in Tables 1 to 16.

TABLE 1

| Ex. | Formula |
|---|---|
| 1 | (methyl ester thieno-pyrrolo-oxazepine with cyclohexyl and hydroxyphenyl) |
| 2 | (methyl ester thieno-pyrrolo-oxazepine with cyclohexyl, phenyl-O-CH2-(morpholino, methylsulfonyl)phenyl) |
| 3 | (carboxylic acid thieno-pyrrolo-oxazepine with cyclohexyl, phenyl-O-CH2-(morpholino, methylsulfonyl)phenyl) |

TABLE 1-continued

| Ex. | Formula |
|---|---|
| 4 | (carboxamide thieno-pyrrolo-oxazepine with cyclohexyl, phenyl-O-CH2-(morpholino, methylsulfonyl)phenyl) |
| 5 | (methyl ester thieno-pyrrolo-diazepinone with cyclohexyl and fused benzene) |

TABLE 2

| Ex. | Formula |
|---|---|
| 6 | (methyl ester thieno-pyrrolo-benzodiazepinone with cyclohexyl and N-CH2-C(O)-piperidine substituent) |

TABLE 2-continued
| Ex. | Formula |
|---|---|
| 7 | 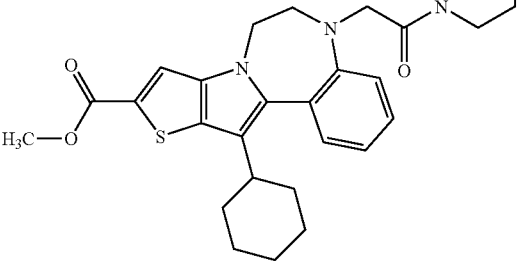 |
| 8 | 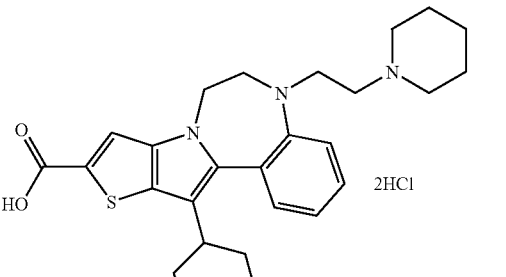 2HCl |
| 9 | 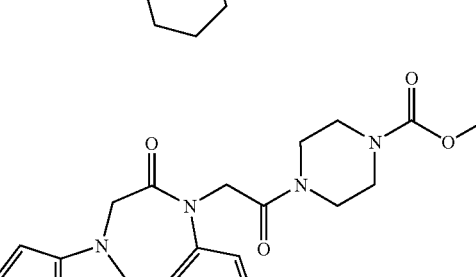 |
TABLE 3
| Ex. | Formula |
|---|---|
| 10 | |

TABLE 3-continued
| Ex. | Formula |
|---|---|
| 11 | 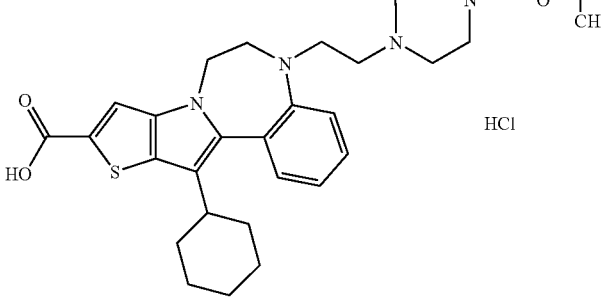 HCl |
| 12 | 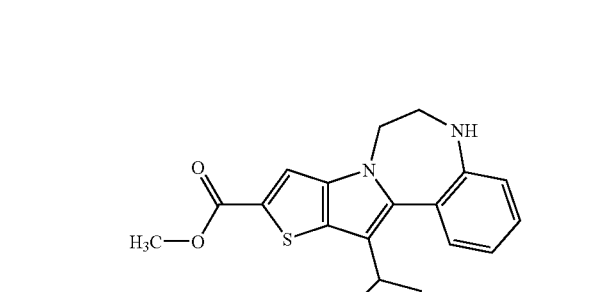 |
| 13 | 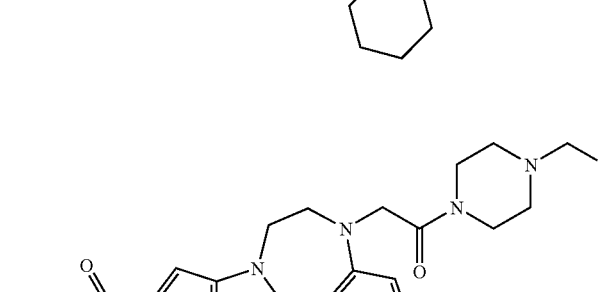 |
TABLE 4
| Ex. | Formula |
|---|---|
| 14 | 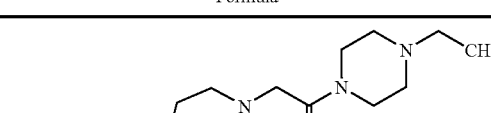 2HCl |

TABLE 5

| Ex. | Formula | ¹H-NMR, δ ppm | MS |
|---|---|---|---|
| 15 | | 400 MHz, DMSO-d6<br>7.65-7.60(1H, m),<br>7.38-7.34(2H, m),<br>7.29(1H, d, J=7.2 Hz),<br>7.18(1H, d, J=9.6 Hz),<br>4.42(2H, t, J=5.6 Hz),<br>4.23(2H, t, J=6.0 Hz),<br>2.78-2.70(1H, m),<br>1.82-1.75(3H, m),<br>1.73-1.62(4H, m),<br>1.37-1.23(3H, m). | 368.1(M + 1) |
| 16 | HCl | 400 MHz, DMSO-d6<br>7.88(1H, s),<br>7.82(1H, d, J=2.4 Hz),<br>7.55(1H, dd, J=2.8, 8.8 Hz),<br>7.29(1H, d, J=8.4 Hz),<br>7.21(1H, d, J=8.8 Hz),<br>6.97(1H, dd, J=2.4, 8.0 Hz),<br>6.93(1H, d, J=2.4 Hz),<br>5.19(2H, s),<br>4.43(2H, t, J=5.2 Hz),<br>4.28(2H, t, J=5.2 Hz),<br>3.81(2H, t, J=7.0 Hz),<br>3.76-3.74(4H, m),<br>2.89-2.87(4H, m),<br>2.76-2.65(1H, m),<br>2.47-2.45(2H, m),<br>2.05(2H, q, J=9.9 Hz),<br>1.82-1.74(3H, m),<br>1.72-1.59(4H, m),<br>1.36-1.23(3H, m). | 642.2(M + 1) |
| 17 | | 400 MHz, DMSO-d6<br>7.67(1H, s),<br>7.26(1H, d, J=8.4 Hz),<br>6.89(1H, dd, J=2.4, 8.4 Hz),<br>6.79(1H, d, J=2.8 Hz),<br>4.50-4.44(1H, m),<br>4.43-4.40(2H, m),<br>4.26-4.20(2H, m),<br>3.65-3.51(4H, m),<br>2.75-2.66(1H, m),<br>2.02-1.93(1H, m),<br>1.82-1.60(9H, m),<br>1.55-1.48(1H, m),<br>1.37-1.23(3H, m). | 525.2(M + 1) |

TABLE 6

| Ex. | Formula | ¹H-NMR, δ ppm | MS |
|---|---|---|---|
| 18 | | 400 MHz, DMSO-d6<br>7.84-7.83(2H, m),<br>7.58-7.55(1H, m),<br>7.30-7.22(2H, m),<br>6.99-6.92(2H, m),<br>5.19(2H, s),<br>4.45-4.42(2H, m),<br>4.29-4.25(2H, m),<br>3.81(2H, t, J=7.4 Hz),<br>3.46-3.43(2H, m),<br>3.30-3.27(4H, m),<br>3.01-2.97(4H, m),<br>2.93(3H, s),<br>2.74-2.66(1H, m),<br>2.48-2.45(2H, m),<br>2.05(2H, q, J=10.0 Hz),<br>1.81-1.74(3H, m),<br>1.72-1.59(4H, m),<br>1.34-1.23(3H, m). | 719.1(M + 1) |

TABLE 6-continued
| Ex. | Formula | ¹H-NMR, δ ppm | MS |
|---|---|---|---|
| 19 | 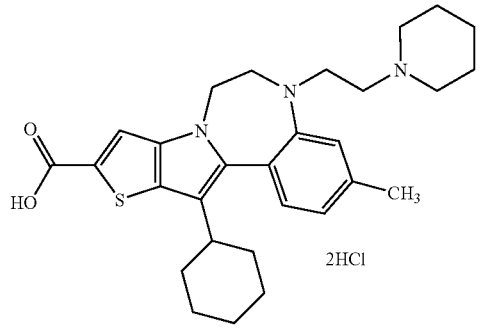 2HCl | 400 MHz, DMSO-d6 10.01(1H, brs), 7.87(1H, s), 7.19(1H, d, J=7.6 Hz), 7.10(1H, s), 7.01(1H, d, J=7.6 Hz), 4.20-4.02(2H, m), 3.58-3.47(2H, m), 3.43-3.29(2H, m), 3.14-3.07(2H, m), 3.04-2.94(2H, m), 2.71-2.50(3H, m), 2.35(3H, s), 1.80-1.17(16H, m). | 492.2(M + 1) |
| 20 | 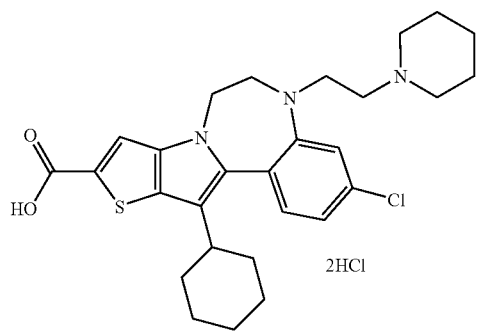 2HCl | 400 MHz, DMSO-d6 12.67(1H, brs), 9.85(1H, brs), 7.89(1H, s), 7.33-7.24(3H, m), 4.24-4.09(2H, m), 3.59-3.51(2H, m), 3.48-3.37(2H, m), 3.17-3.07(2H, m), 3.06-3.00(2H, m), 2.69-2.52(3H, m), 1.81-1.18(16H, m). | 512.2(M + 1) |
TABLE 7
| Ex. | Formula | ¹H-NMR, δ ppm | MS |
|---|---|---|---|
| 21 | 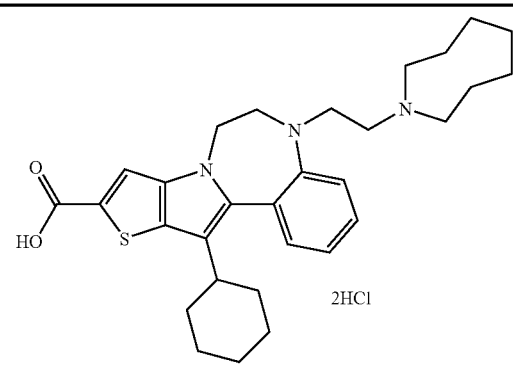 2HCl | 400 MHz, DMSO-d6 12.51(1H, brs), 9.77(1H, brs), 7.88(1H, s), 7.45-7.37(1H, m), 7.33-7.24(2H, m), 7.23-7.18(1H, m), 4.23-4.01(2H, m), 3.80-3.29(5H, m), 3.12-2.97(3H, m), 2.93-2.80(2H, m), 2.71-2.59(1H, m), 1.82-1.55(8H, m), 1.52-1.16(12H, m). | 506.2(M + 1) |
| 22 | 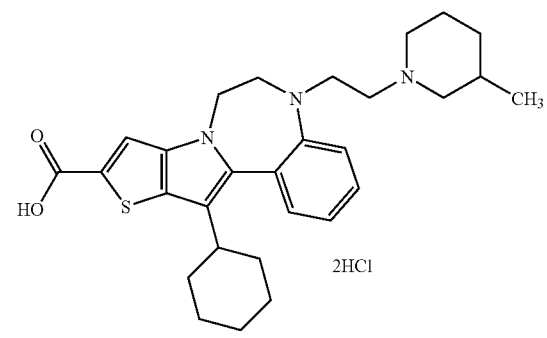 2HCl | 400 MHz, DMSO-d6 12.63(1H, brs), 9.81(1H, brs), 7.88(1H, s), 7.44-7.38(1H, m), 7.33-7.25(2H, m), 7.23-7.18(1H, m), 4.23-4.01(2H, m), 3.75-3.28(4H, m), 3.20-2.93(5H, m), 2.76-2.60(1H, m), 2.31-2.18(1H, m), 1.80-1.41(10H, m), 1.40-1.17(4H, m), 0.86-0.72(1H, m), 0.55(3H, d, J=6.6 Hz). | 492.2(M + 1) |

TABLE 7-continued

| Ex. | Formula | ¹H-NMR, δ ppm | MS |
|---|---|---|---|
| 23 | (structure, 2HCl) | 400 MHz, DMSO-d6 12.65(1H, brs), 9.80(1H, brs), 7.87(1H, s), 7.43-7.37(1H, m), 7.33-7.24(2H, m), 7.23-7.17(1H, m), 4.28-3.88(2H, m), 3.72-3.26(4H, m), 3.19-2.83(6H, m), 3.10(3H, s), 2.74-2.60(1H, m), 2.34-2.22(1H, m), 1.81-1.17(15H, m), 1.14-1.00(2H, m), 0.84-0.74(1H, m). | 536.2(M + 1) |

TABLE 8

| Ex. | Formula | ¹H-NMR, δ ppm | MS |
|---|---|---|---|
| 24 | (structure, 2HCl) | 400 MHz, DMSO-d6 12.62(1H, brs), 10.38(1H, brs), 7.88(1H, s), 7.45-7.38(1H, m), 7.33-7.25(2H, m), 7.24-7.17(1H, m), 4.27-3.99(2H, m), 3.80-2.83(14H, m), 2.71-2.59(1H, m), 1.96-1.82(1H, m), 2.80-1.50(8H, m), 1.33-1.17(3H, m). | 494.2(M + 1) |
| 25 | (structure, 2HCl) | 400 MHz, DMSO-d6 12.59(1H, brs), 9.84(1H, brs), 7.85(1H, s), 7.17(1H, d, J=7.6 Hz), 7.08(1H, s), 7.00(1H, d, J=7.6 Hz), 4.17-4.03(2H, m), 3.55-3.45(2H, m), 3.42-3.27(3H, m), 3.09-2.97(3H, m), 2.92-2.81(2H, m), 2.69-2.58(1H, m), 2.33(3H, s), 1.79-1.52(8H, m), 1.50-1.14(12H, m). | 520.3(M + 1) |
| 26 | (structure, 2HCl) | 400 MHz, DMSO-d6 10.06(1H, brs), 7.85(1H, s), 7.18(1H, d, J=7.6 Hz), 7.09(1H, s), 6.99(1H, d, J=7.6 Hz), 4.21-3.98(2H, m), 3.58-3.45(2H, m), 3.41-3.26(2H, m), 3.17-3.04(3H, m), 3.02-2.93(2H, m), 2.72-2.61(1H, m), 2.33(3H, s), 2.29-2.17(1H, m), 1.79-1.44(8H, m), 1.40-1.31(2H, m), 1.28-1.15(4H, m), 0.84-0.76(1H, m), 0.49(3H, d, J=6.5 Hz). | 506.3(M + 1) |

TABLE 9
| Ex. | Formula | ¹H-NMR, δ ppm | MS |
|---|---|---|---|
| 27 | 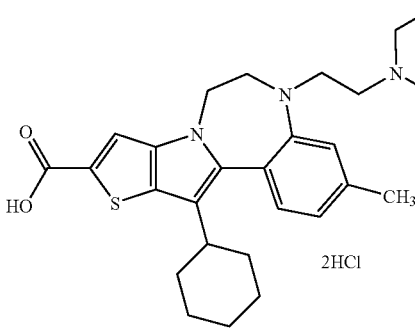 2HCl | 400 MHz, DMSO-d6 10.06(1H, brs), 7.84(1H, s), 7.18(1H, d, J=7.6 Hz), 7.08(1H, s), 6.99(1H, d, J=7.6 Hz), 4.23-3.95(2H, m), 3.61-3.22(4H, m), 3.18-2.88(6H, m), 3.09(3H, s), 2.73-2.59(1H, m), 2.33(3H, s), 2.32-2.19(1H, m), 1.80-1.15(15H, m), 1.06-0.93(2H, m), 0.82-0.74(1H, m). | 550.3(M + 1) |
| 28 | 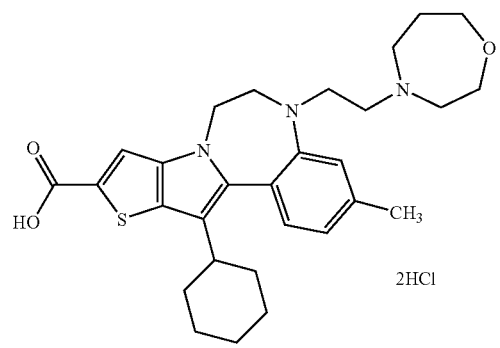 2HCl | 400 MHz, DMSO-d6 12.56(1H, brs), 10.44(1H, brs), 7.86(1H, s), 7.18(1H, d, J=7.6 Hz), 7.10(1H, s), 7.00(1H, d, J=7.6 Hz), 4.22-3.96(2H, m), 3.90-2.81(14H, m), 2.69-2.57(1H, m), 2.34(3H, s), 2.02-1.85(1H, m), 1.82-1.50(8H, m), 1.31-1.15(3H, m). | 508.3(M + 1) |
| 29 | 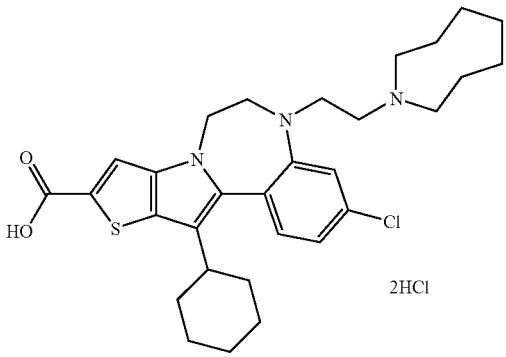 2HCl | 400 MHz, DMSO-d6 12.68(1H, brs), 9.73(1H, brs), 7.88(1H, s), 7.32-7.23(3H, m), 4.24-4.07(2H, m), 3.60-3.49(2H, m), 3.45-3.23(3H, m), 3.14-2.98(3H, m), 2.93-2.82(2H, m), 2.68-2.56(1H, m), 1.81-1.55(8H, m), 1.52-1.15(12H, m). | 540.2(M + 1) |
TABLE 10
| Ex. | Formula | ¹H-NMR, δ ppm | MS |
|---|---|---|---|
| 30 | 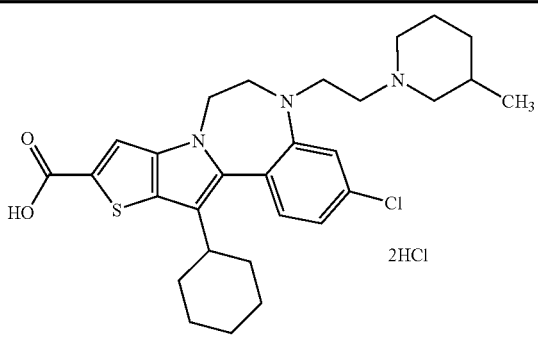 2HCl | 400 MHz, DMSO-d6 12.65(1H, brs), 9.81(1H, brs), 7.88(1H, s), 7.33-7.21(3H, m), 4.23-4.06(2H, m), 3.60-3.49(2H, m), 3.47-3.37(2H, m), 3.17-2.95(5H, m), 2.70-2.59(1H, m), 2.31-2.18(1H, m), 1.80-1.44(8H, m), 1.42-1.34(2H, m), 1.31-1.18(4H, m), 0.50(3H, d, J=6.5 Hz), 0.90-0.72(1H, m). | 526.2(M + 1) |

TABLE 10-continued

| Ex. | Formula | $^1$H-NMR, δ ppm | MS |
|---|---|---|---|
| 31 | 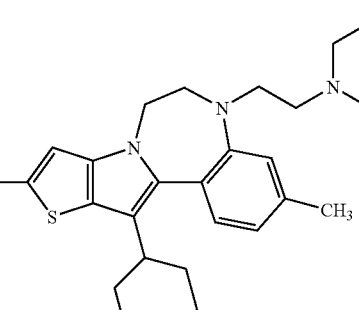<br>2HCl | 400 MHz, DMSO-d6<br>12.66(1H, brs),<br>9.81(1H, brs),<br>7.88(1H, s),<br>7.32-7.22(3H, m),<br>4.32-4.01(2H, m),<br>3.63-3.32(4H, m),<br>3.20-2.90(6H, m),<br>3.10(3H, s),<br>2.71-2.58(1H, m),<br>2.35-2.20(1H, m),<br>1.81-1.12(15H, m),<br>1.09-0.94(2H, m),<br>0.84-0.74(1H, m). | 570.2(M + 1) |
| 32 | 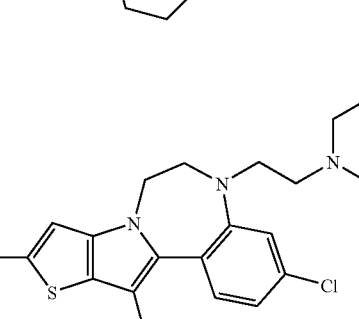<br>2HCl | 400 MHz, DMSO-d6<br>10.66(1H, brs),<br>7.89(1H, s),<br>7.34-7.22(3H, m),<br>4.27-4.03(2H, m),<br>3.65-2.82(14H, m),<br>2.68-2.55(1H, m),<br>2.01-1.87(1H, m),<br>1.80-1.49(8H, m),<br>1.33-1.16(3H, m). | 528.2(M + 1) |

TABLE 11

| Ex. | Formula | $^1$H-NMR, δ ppm | MS |
|---|---|---|---|
| 33 | (structure with Boc-piperazine, cyclohexyl, CH3)<br>HCl | 400 MHz, DMSO-d6<br>12.61(1H, brs),<br>10.55(1H, brs),<br>7.87(1H, s),<br>7.20(1H, d, J=7.6 Hz),<br>7.09(1H, s),<br>7.03(1H, d, J=7.6 Hz),<br>4.22-4.04(2H, m),<br>3.66-3.32(6H, m),<br>3.18-3.00(4H, m),<br>2.95-2.82(2H, m),<br>2.72-2.57(3H, m),<br>2.35(3H, s),<br>1.79-1.52(7H, m),<br>1.39-1.17(3H, m),<br>1.32(9H, s). | 593.3(M + 1) |
| 34 | (structure with Boc-piperazine, cyclohexyl, Cl)<br>HCl | 400 MHz, DMSO-d6<br>12.67(1H, brs),<br>10.50(1H, brs),<br>7.89(1H, s),<br>7.33-7.24(3H, m),<br>4.27-4.06(2H, m),<br>3.64-3.33(6H, m),<br>3.18-3.00(4H, m),<br>2.95-2.83(2H, m),<br>2.73-2.56(3H, m),<br>1.80-1.51(7H, m),<br>1.36-1.14(3H, m),<br>1.32(9H, s). | 613.2(M + 1) |

TABLE 11-continued

| Ex. | Formula | $^1$H-NMR, δ ppm | MS |
|---|---|---|---|
| 35 | 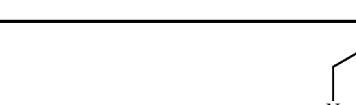 | 400 MHz, DMSO-d6 12.58(1H, brs), 10.68(1H, brs), 7.84(1H, s), 7.15(1H, d, J=7.6 Hz), 6.95(1H, d, J=7.6 Hz), 6.91(1H, s), 4.37-4.24(2H, m), 4.10-4.00(1H, m), 3.92-3.77(2H, m), 3.75-3.66(1H, m), 3.58-3.25(4H, m), 3.19-3.07(2H, m), 2.95-2.84(1H, m), 2.78-2.56(4H, m), 2.28(3H, s), 1.88-1.51(7H, m), 1.33-1.12(3H, m), 1.00(3H, t, J=3.6 Hz). | 535.3(M + 1) |

TABLE 12

| Ex. | Formula | $^1$H-NMR, δ ppm | MS |
|---|---|---|---|
| 36 | 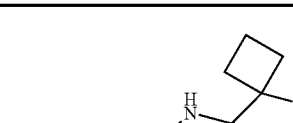 | 400 MHz, DMSO-d6 12.64(1H, brs), 10.53(1H, brs), 7.87(1H, s), 7.26(1H, d, J=8.1 Hz), 7.17(1H, dd, J=8.1, 2.1 Hz), 7.09(1H, d, J=2.1 Hz), 4.42-4.28(2H, m), 4.18-3.93(3H, m), 3.81-3.73(1H, m), 3.60-3.49(1H, m), 3.41-3.15(5H, m), 3.02-2.55(5H, m), 1.86-1.53(7H, m), 1.31-1.16(3H, m), 1.07(3H, t, J=7.3 Hz). | 555.2(M + 1) |

TABLE 13

| Ex. | Formula | $^1$H-NMR, δ ppm | MS |
|---|---|---|---|
| 37 |  | 400 MHz, DMSO-d6 12.23(1H, brs), 9.65(1H, s), 8.70(1H, s), 7.98(1H, s), 7.66(2H, d, J=9.0 Hz), 7.62(2H, d, J=9.0 Hz), 7.51(1H, d, J=16.0 Hz), 7.31(1H, d, J=8.6 Hz), 6.91(1H, dd, J=8.6, 2.6 Hz), 6.81(1H, d, J=2.6 Hz), 6.41(1H, d, J=16.0 Hz), 4.47(2H, brt, J=5.6 Hz), 4.21(2H, brt, J=5.6 Hz), 3.82(3H, s), 2.77-2.65(3H, m), 2.35-2.25(2H, m), 2.04-1.92(1H, m), 1.92-1.82(1H, m), 1.82-1.67(7H, m), 1.39-1.20(3H, m). | 640.3(M + 1) |

TABLE 13-continued

| Ex. | Formula | $^1$H-NMR, δ ppm | MS |
|---|---|---|---|
| 38 | | 400 MHz, DMSO-d6 12.23(1H, brs), 9.66(1H, s), 8.67(1H, s), 7.98(1H, s), 7.66(2H, d, J=8.8 Hz), 7.61(2H, d, J=8.8 Hz), 7.51(1H, d, J=16.0 Hz), 7.15(1H, d, J=7.4 Hz), 6.98-6.90(2H, m), 6.40(1H, d, J=16.0 Hz), 4.13-4.06(2H, m), 3.45-3.36(2H, m), 2.74(3H, s), 2.74-2.69(3H, m), 2.36(3H, s), 2.38-2.26(2H, m), 2.06-1.64(9H, m), 1.85-1.15(3H, m). | 637.3(M + 1) |

TABLE 14

| Ex. | Formula | $^1$H-NMR, δ ppm | MS |
|---|---|---|---|
| 39 | | 400 MHz, DMSO-d6 12.23(1H, brs), 9.65(1H, s), 8.70(1H, s), 7.99(1H, s), 7.66(2H, d, J=8.8 Hz), 7.61(2H, d, J=8.8 Hz), 7.51(1H, d, J=15.8 Hz), 7.26(1H, d, J=7.9 Hz), 7.19-7.10(2H, m), 6.41(1H, d, J=15.8 Hz), 4.20-4.10(2H, m), 3.51-3.40(2H, m), 2.76(3H, s), 2.82-2.56(3H, m), 2.39-2.24(2H, m), 2.05-1.64(9H, m), 1.83-1.15(3H, m). | 657.2(M + 1) |
| 40 | | 400 MHz, DMSO-d6 12.37(1H, brs), 9.54(1H, s), 8.72(1H, s), 7.99(1H, s), 7.87(1H, brs), 7.66(1H, dt, J=7.0, 2.1 Hz), 7.53(1H, d, J=16.0 Hz), 7.38-7.33(2H, m), 7.31(1H, d, J=8.6 Hz), 6.91(1H, dd, J=8.6, 2.6 Hz), 6.81(1H, d, J=2.6 Hz), 6.42(1H, d, J=16.0 Hz), 4.47(2H, brt, J=5.6 Hz), 4.22(2H, brt, J=5.6 Hz), 3.82(3H, s), 2.77-2.65(3H, m), 2.36-2.26(2H, m), 2.04-1.57(9H, m), 1.38-1.19(3H, m). | 640.3(M + 1) |
| 41 | | 400 MHz, DMSO-d6 12.67(1H, brs), 7.90(1H, s), 7.30(1H, d, J=8.6 Hz), 6.90(1H, dd, J=8.6, 2.7 Hz), 6.79(1H, d, J=2.7 Hz), 4.44(2H, t, J=5.4 Hz), 4.29(2H, t, J=5.4 Hz), 4.09(2H, q, J=7.0 Hz), 2.75-2.72(1H, m), 1.84-1.61(7H, m), 1.37(3H, t, J=7.0 Hz), 1.29-1.26(3H, m). | 412.2(M + 1) |

TABLE 15

| Ex. | Formula | $^1$H-NMR, δ ppm | MS |
|---|---|---|---|
| 42 | 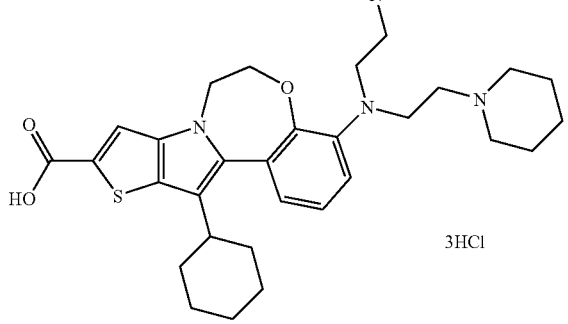<br>3HCl | 400 MHz, DMSO-d6<br>10.36(2H, brs),<br>7.96(1H, s),<br>7.36(1H, d, J=6.7 Hz),<br>7.28(1H, t, J=7.9 Hz),<br>7.12(1H, d, J=6.3 Hz),<br>4.52(2H, t, J=5.6 Hz),<br>4.34(2H, t, J=5.6 Hz),<br>3.57(4H, t, J=7.1 Hz),<br>3.51-3.41(4H, m),<br>3.24(4H, q, J=8.0 Hz),<br>2.91(4H, q, J=11.1 Hz),<br>2.74(1H, t, J=10.0 Hz),<br>1.90-1.61(12H, m),<br>1.42-1.22(10H, m). | 605.3(M + 1) |
| 43 |  | 400 MHz, DMSO-d6<br>12.25(1H, brs),<br>9.70(1H, s), 8.77(1H, s),<br>7.99(1H, s),<br>7.67(2H, d, J=8.8 Hz),<br>7.62(2H, d, J=8.8 Hz),<br>7.51(1H, d, J=15.8 Hz),<br>7.30(1H, d, J=8.3 Hz),<br>6.90(1H, dd, J=8.5, 2.5 Hz),<br>6.80(1H, d, J=2.5 Hz),<br>6.42(1H, d, J=16.0 Hz),<br>4.47(2H, t, J=5.7 Hz),<br>4.22(2H, t, J=5.4 Hz),<br>4.10(2H, q, J=7.0 Hz),<br>2.72-2.68(3H, m),<br>2.35-2.28(2H, m),<br>2.01-1.61(7H, m),<br>1.38(3H, t, J=7.0 Hz),<br>1.29-1.25(3H, m). | 654.3(M + 1) |
| 44 | 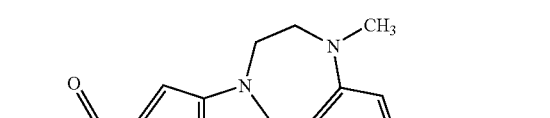 | 400 MHz, DMSO-d6<br>12.61(1H, brs),<br>7.88(1H, s),<br>7.17(1H, d, J=8.4 Hz),<br>6.70(1H, dd, J=8.4, 2.4 Hz),<br>6.64(1H, d, J=2.4 Hz),<br>4.20-4.17(4H, brm),<br>4.10(2H, q, J=7.0 Hz),<br>2.72(3H, s),<br>2.68-2.61(1H, m),<br>1.73-1.66(7H, brm),<br>1.37(3H, t, J=7.0 Hz),<br>1.30-1.27(3H, brm). | 425.2(M + 1) |

TABLE 15

| Ex. | Formula | $^1$H-NMR, δ ppm | MS |
|---|---|---|---|
| 45 | | 400 MHz, DMSO-d6<br>12.24(1H, brs),<br>9.70(1H, s), 8.72(1H, s),<br>7.99(1H, s),<br>7.68-7.61(4H, m),<br>7.51(1H, d, J=16.0 Hz),<br>7.17(1H, d, J=8.4 Hz),<br>6.71(1H, dd, J=8.4, 2.4 Hz),<br>6.65(1H, d, J=2.4 Hz),<br>6.42(1H, d, J=16.0 Hz),<br>4.11-4.09(6H, m),<br>3.45-3.41(3H, brs),<br>2.71-2.69(2H, m),<br>2.65-2.62(1H, m),<br>2.36-2.28(2H, m),<br>2.01-1.84(3H, m),<br>1.82-1.60(5H, m),<br>1.37(3H, t, J=7.0 Hz),<br>1.29-1.23(3H, m). | 667.2(M + 1) |
| 46 | | 400 MHz, DMSO-d6<br>11.31(2H, brs),<br>7.97(1H, s),<br>7.39(1H, d, J=6.7 Hz),<br>7.28(1H, t, J=7.9 Hz),<br>7.13(1H, d, J=7.4 Hz),<br>4.55(2H, t, J=5.6 Hz),<br>4.35(2H, t, J=5.6 Hz),<br>3.97-3.85(8H, brm),<br>3.55-3.39(12H, brm),<br>3.15-3.12(4H, brm),<br>2.76-2.73(1H, m),<br>1.82-1.66(7H, m),<br>1.31-1.29(3H, m). | 609.3(M + 1) |

The evaluation of the HCV polymerase inhibitory activity of the compound of the present invention is explained in the following. This polymerase is an enzyme coded for by the non-structural protein region called NS5B on the genome RNA of HCV (EMBO J., 15:12-22, 1996).

Experimental Example [I]

i) Preparation of enzyme (HCV polymerase)

Using, as a template, a cDNA clone corresponding to the full length genome RNA of HCV BK strain obtained from the blood of a patient with hepatitis C, a region encoding NS5B (J Virol 1991 March, 65(3), 1105-13, 544 amino acids after deletion of 47 amino acids on the C-terminal) was amplified by PCR. The objective gene was prepared by adding a 6 His tag {base pair encoding 6 continuous histidine (His)} to the 3' end thereof and transformed to *Escherichia coli*. The *Escherichia coli* capable of producing the objective protein was cultured. The obtained cells were suspended in a buffer solution and crushed in a microfluidizer. The supernatant was obtained by centrifugation and applied to various column chromatographys {mono-S, Sephacryl S-200 (Pharmacia)}, inclusive of metal chelate chromatography, to give a standard enzyme product.

ii) Synthesis of Substrate RNA

Using a synthetic primer designed based on the sequence of HCV genomic 3' untranslated region, a DNA fragment (148 bp) containing polyU and 3'X sequence was entirely synthesized and cloned into plasmid pBluescript SK II(+) (Stratagene). The cDNA encoding full length NS5B, which was prepared in i) above, was digested with restriction enzyme KpnI to give a cDNA fragment containing the nucleotide sequence of from the restriction enzyme cleavage site to the termination codon. This cDNA fragment was inserted into the upstream of 3' untranslated region of the DNA in pBluescript SK II(+) and ligated. The about 450 bp inserted DNA sequence was used as a template in the preparation of substrate RNA. This plasmid was cleaved immediately after the 3'X sequence, linearized and purified by phenol-chloroform treatment and ethanol precipitation to give DNA.

RNA was synthesized (37° C., 3 hr) by run-off method using this purified DNA as a template, a promoter of pBluescript SK II(+), MEGAscript RNA synthesis kit (Ambion) and T7 RNA polymerase. DNase I was added and the mixture was incubated for 1 hr. The template DNA was removed by decomposition to give a crude RNA product. This crude product was treated with phenol-chloroform and purified by ethanol precipitation to give the objective substrate RNA.

This RNA was applied to formaldehyde denaturation agarose gel electrophoresis to confirm the quality thereof and preserved at −80° C. iii) Assay of enzyme (HCV polymerase) inhibitory activity A test substance (compound of the present invention) and a reaction mixture (30 μl) having the following composition were reacted at 25° C. for 90 min.

10% Trichloroacetic acid at 4° C. and 1% sodium pyrophosphate solution (150 µl) were added to this reaction mixture to stop the reaction. The reaction mixture was left standing in ice for 15 min to insolubilize RNA. This RNA was trapped on a glass filter (Whatman GF/C and the like) upon filtration by suction. This filter was washed with a solution containing 1% trichloroacetic acid and 0.1% sodium pyrophosphate, washed with 90% ethanol and dried. A liquid scintillation cocktail (Packard) was added and the radioactivity of RNA synthesized by the enzyme reaction was measured on a liquid scintillation counter.

The HCV polymerase inhibitory activity ($IC_{50}$) of the compound of the present invention was calculated from the values of radioactivity of the enzyme reaction with and without the 20 test substance.

The results are shown in Tables 17 and 18, wherein each symbol means that $IC_5D$ falls within the following range.

A: $0.1\ \mu M \leqq IC_{50} \leqq 1\ \mu M$
B: $0.01\ \mu M \leqq IC_{50} \leqq 0.1\ \mu M$
C: $IC_{50} < 0.01\ \mu M$ Reaction mixture: HCV polymerase (0.5 µg/ml) obtained in i), substrate RNA (5 µg/ml) obtained in ii), ATP (50 µM), GTP (50 µM), CTP (50 µM), UTP (2 µM), [5,6-$^3$H]UTP (46 Ci/mmol (Amersham), 1 µCi) 20 mM Tris-HCl (pH 7.5), EDTA (1 mM), $MgCl_2$ (5 30 mM), NaCl (50 mM), DTT (1 mM), BSA (0.01%)

TABLE 17

| Example | NS5B 1a $IC_{50}$ | NS5B 1b $IC_{50}$ |
| --- | --- | --- |
| 3 | B | C |
| 4 | B | C |
| 8 | B | B |
| 11 | B | B |
| 14 | B | B |
| 15 | A | B |
| 16 | B | C |
| 17 | B | B |
| 18 | C | C |
| 19 | B | C |
| 20 | B | B |
| 21 | B | C |
| 22 | B | B |
| 23 | B | B |
| 24 | B | B |
| 25 | B | C |
| 26 | B | B |
| 27 | B | B |
| 28 | B | B |
| 29 | B | B |
| 30 | B | C |
| 31 | B | C |
| 32 | B | C |
| 33 | B | B |
| 34 | B | B |
| 35 | B | B |
| 36 | B | B |

TABLE 18

| Example | NS5B 1a $IC_{50}$ | NS5B 1b $IC_{50}$ |
| --- | --- | --- |
| 37 | B | B |
| 38 | B | B |
| 39 | B | B |
| 40 | B | B |
| 41 | B | B |
| 42 | B | C |
| 43 | B | B |
| 44 | B | B |
| 45 | B | B |
| 46 | B | C |

Experimental Example [II]

The test compound was dissolved in DMSO (dimethyl sulfoxide; final concentration 0.5%), and adjusted to a 10-fold concentration of the final concentration with a medium.

Replicon cells (Huh-5-2: manufactured by ReBLikon GmbH) were inoculated on a medium at $5 \times 10^3/90$ µl/well in a 96-well plate.

The medium was changed to a 4% HSA (human serum albumin)-containing medium (90 µl) the next day, and 10 µl of the above-mentioned adjusted product at each concentration was added.

At 48 hr later, luciferase activity was measured with Steady-Glo (manufactured by PROMEGA). The inhibitory rate relative to the control group (0.5% DMSO addition group) was calculated and $EC_{50}$ value was determined by proportional calculation, based on the data of two points across 50%, with the concentration of the compound taken as logarithm. Composition of medium: Dulbecco's modified Eagle's medium (DMEM), 10% fetal bovine serum (FBS), 2 mM L-glutamine, 0.1 mM MEM non-essential amino acid, 100 U/ml penicillin, 0.1 mg/ml streptomycin As in the test, one showing high replication inhibitory, or HCV polymerase inhibitory activity in the presence of a protein is one of the preferable embodiments.

As is evident from the above-mentioned results, the compound of the present invention shows a high inhibitory activity against HCV polymerase.

Therefore, the compound of the present invention can provide a pharmaceutical agent effective for the prophylaxis or treatment of hepatitis C, based on the anti-HCV effect afforded by the HCV polymerase inhibitory activity. When used concurrently with a different anti-HCV agent, such as interferon, and/or an anti-inflammatory agent and the like, it can provide a pharmaceutical agent more effective for the prophylaxis or treatment of hepatitis C. Its high inhibitory activity specific to HCV polymerase suggests the possibility of the compound being a pharmaceutical agent with slight side effects, which can be used safely for humans.

Formulation Example is given in the following. This example is merely for the purpose of exemplification and does not limit the invention.

Formulation Example

| (a) | compound of Example 3 | 10 g |
| --- | --- | --- |
| (b) | lactose | 50 g |
| (c) | corn starch | 15 g |
| (d) | sodium carboxymethylcellulose | 44 g |
| (e) | magnesium stearate | 1 g |

The entire amounts of (a), (b) and (c) and 30 g of (d) are kneaded with water, dried in vacuo and granulated. The obtained granules are mixed with 14 g of (d) and 1 g of (e) and processed into tablets with a tableting machine to give 1000 tablets each containing 10 mg of (a).

This application is based on a patent application No. 2004-329780 filed in Japan, the contents of which are hereby incorporated by reference.

The invention claimed is:

1. A thienopyrrole compound represented by the following formula [I] or a pharmaceutically acceptable salt thereof:

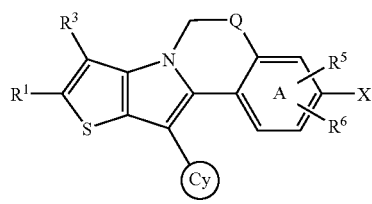

[I]

wherein

Q is (1) —CH$_2$—O-#, (2) —CH$_2$—N(R$^2$)-# or (3) —CO—N(R$^2$)-# wherein # shows the side to be bonded to ring A, ring A is a benzene ring,

R$^1$ is (1) a carboxyl group, (2) a carboxylic acid equivalent selected from the group consisting of —CONHR$^{105'}$
(wherein R$^{105'}$ is hydroxyl, cyano, C$_{1-6}$ alkoxy, or C$_{6-14}$ arloxy), —SO$_2$R$^{106'}$
(wherein R$^{106'}$ is hydroxyl, amino, or C$_{1-6}$ alkylamino), —NHCOR$^{107'}$
(wherein) R$^{107'}$is amino or C$_{1-6}$ alkylamino), —P(=O)(OH)(OR$^{109}$)
(wherein R$^{109}$ is hydrogen or a substituent selected from group C), —P(=O)(OH)NR$^{111}$R$^{112}$
(wherein R$^{111}$ and R$^{112}$ are each independently hydrogen or a substituent selected from group C), —CONHCO—R$^{113}$
wherein R$^{113}$ is a substituent selected from group C), —CONHSO$_2$—R$^{114}$,
(wherein R$^{114}$ is a substituent selected from group C), —SO$_2$NHCO—R$^{115}$
(wherein R$^{115}$ is a substituent selected from group C), and a cyclic substituent selected from the group consisting of

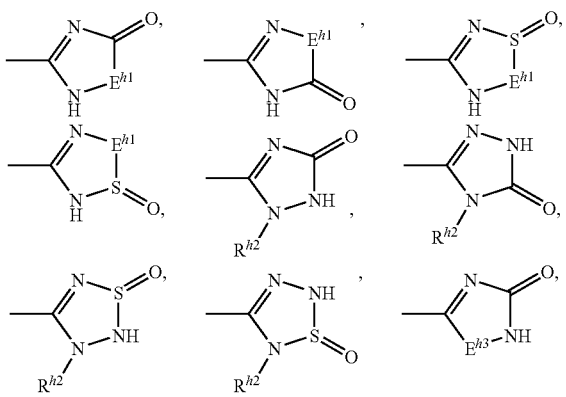

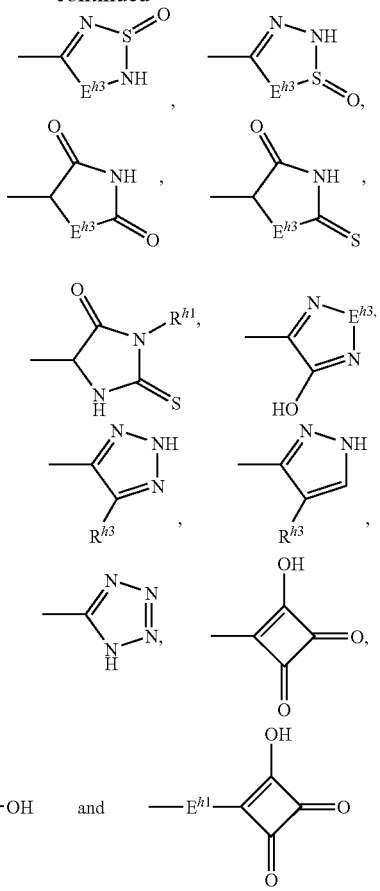

(wherein E$^{h1}$ is O, S, or N(—R$^{h1}$), R$^{h1}$ is hydrogen or C$_{1-6}$ alkyl, E$^{h3}$ is O or S, R$^{h2}$ is C$_{1-6}$ alkyl, R$^{h3}$ is halogen, cyano, C$_{1-6}$ alkyl, trifluoromethyl, formyl, chlorocarbonyl, nitro, acetyl, ethoxycarbonyl, or a carbamoyl), (3) —CONR$^{11}$R$^{12}$ (wherein R$^{11}$ and R$^{12}$ are each independently (1') a hydrogen atom, (2') a C$_{1-6}$ alkyl group optionally substituted by 1 to 3 substituents selected from the following group E, (3') a C$_{2-6}$ alkenyl group optionally substituted by 1 to 3 substituents selected from the following group E, (4') a C$_{6-14}$ aryl group optionally substituted by 1 to 5 substituents selected from the following group E, (5') a heterocyclic group optionally substituted by 1 to 5 substituents selected from the following group E (wherein said heterocyclic group comprises 1 to 4 heteroatoms selected from oxygen atom, nitrogen atom and sulfur atom), (6') a C$_{3-10}$ cycloalkyl group optionally substituted by 1 to 5 substituents selected from the following group E, (7') —NR$^{131}$R$^{132}$, (8') —NHCOOR$^{133}$, (9') —NHCOR$^{134}$ (wherein R$^{131}$, R$^{132}$, R$^{133}$ and R$^{134}$ are each independently a hydrogen atom or a group selected from the following group F), (10') —CR$^{135}$R$^{136}$—L$^{101}$—R$^{137}$, (11') —CR$^{135}$R$^{136}$—L$^{101}$—CONR$^{140}$—R$^{137}$, (12')

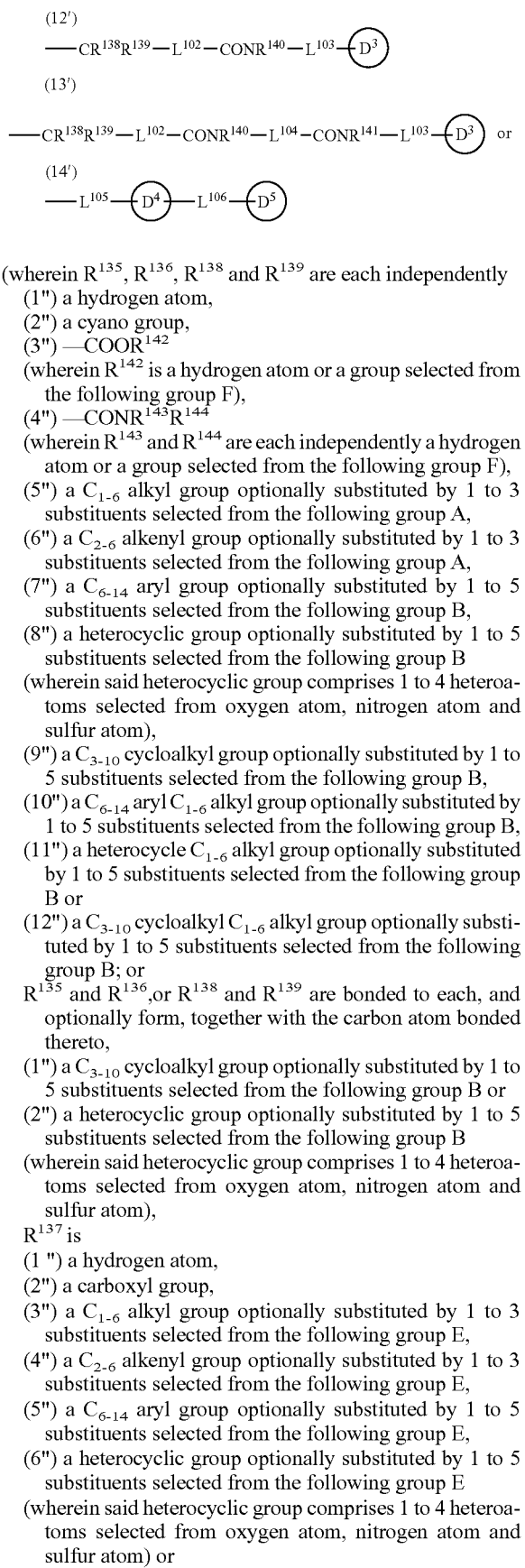

(13')

(14')

(wherein $R^{135}$, $R^{136}$, $R^{138}$ and $R^{139}$ are each independently
(1") a hydrogen atom,
(2") a cyano group,
(3") —COOR$^{142}$
(wherein $R^{142}$ is a hydrogen atom or a group selected from the following group F),
(4") —CONR$^{143}$R$^{144}$
(wherein $R^{143}$ and $R^{144}$ are each independently a hydrogen atom or a group selected from the following group F),
(5") a $C_{1-6}$ alkyl group optionally substituted by 1 to 3 substituents selected from the following group A,
(6") a $C_{2-6}$ alkenyl group optionally substituted by 1 to 3 substituents selected from the following group A,
(7") a $C_{6-14}$ aryl group optionally substituted by 1 to 5 substituents selected from the following group B,
(8") a heterocyclic group optionally substituted by 1 to 5 substituents selected from the following group B
(wherein said heterocyclic group comprises 1 to 4 heteroatoms selected from oxygen atom, nitrogen atom and sulfur atom),
(9") a $C_{3-10}$ cycloalkyl group optionally substituted by 1 to 5 substituents selected from the following group B,
(10") a $C_{6-14}$ aryl $C_{1-6}$ alkyl group optionally substituted by 1 to 5 substituents selected from the following group B,
(11") a heterocycle $C_{1-6}$ alkyl group optionally substituted by 1 to 5 substituents selected from the following group B or
(12") a $C_{3-10}$ cycloalkyl $C_{1-6}$ alkyl group optionally substituted by 1 to 5 substituents selected from the following group B; or
$R^{135}$ and $R^{136}$, or $R^{138}$ and $R^{139}$ are bonded to each, and optionally form, together with the carbon atom bonded thereto,
(1") a $C_{3-10}$ cycloalkyl group optionally substituted by 1 to 5 substituents selected from the following group B or
(2") a heterocyclic group optionally substituted by 1 to 5 substituents selected from the following group B
(wherein said heterocyclic group comprises 1 to 4 heteroatoms selected from oxygen atom, nitrogen atom and sulfur atom),
$R^{137}$ is
(1") a hydrogen atom,
(2") a carboxyl group,
(3") a $C_{1-6}$ alkyl group optionally substituted by 1 to 3 substituents selected from the following group E,
(4") a $C_{2-6}$ alkenyl group optionally substituted by 1 to 3 substituents selected from the following group E,
(5") a $C_{6-14}$ aryl group optionally substituted by 1 to 5 substituents selected from the following group E,
(6") a heterocyclic group optionally substituted by 1 to 5 substituents selected from the following group E
(wherein said heterocyclic group comprises 1 to 4 heteroatoms selected from oxygen atom, nitrogen atom and sulfur atom) or (7") a $C_{3-10}$ cycloalkyl group optionally substituted by 1 to 5 substituents selected from the following group E,
$R^{140}$ and $R^{141}$ are each independently
(1") a hydrogen atom or
(2") a $C_{1-6}$ alkyl group,
$L^{101}$ and $L^{102}$ are each independently
(1") a bond,
(2") —CO—,
(3") a $C_{1-6}$ alkylene optionally substituted by hydroxyl group or
(4") a $C_{2-6}$ alkenylene,
$L^{103}$ is
(1") a bond or
(2") a $C_{1-6}$ alkylene,
$L^{104}$ is a $C_{1-6}$ alkylene,
$L^{105}$ is
(1") a bond or
(2") a $C_{1-6}$ alkylene,
$L^{106}$ is
(1") a bond,
(2") a $C_{1-6}$ alkylene,
(3") —NH—,
(4") —NH—CH$_2$— or
(5") —CH$_2$—CONH—,
ring $D^3$, ring $D^4$ and ring $D^5$ are each independently
(1") a $C_{6-14}$ aryl group optionally substituted by 1 to 5 substituents selected from the following group E,
(2") a $C_{3-10}$ cycloalkyl group optionally substituted by 1 to 5 substituents selected from the following group E or
(3") a heterocyclic group optionally substituted by 1 to 5 substituents selected from the following group E
(wherein said heterocyclic group comprises 1 to 4 heteroatoms selected from oxygen atom, nitrogen atom and sulfur atom))),
(4) —COOR$^{103}$
(wherein $R^{103}$ is a group selected from the following group C or a glucuronic acid residue),

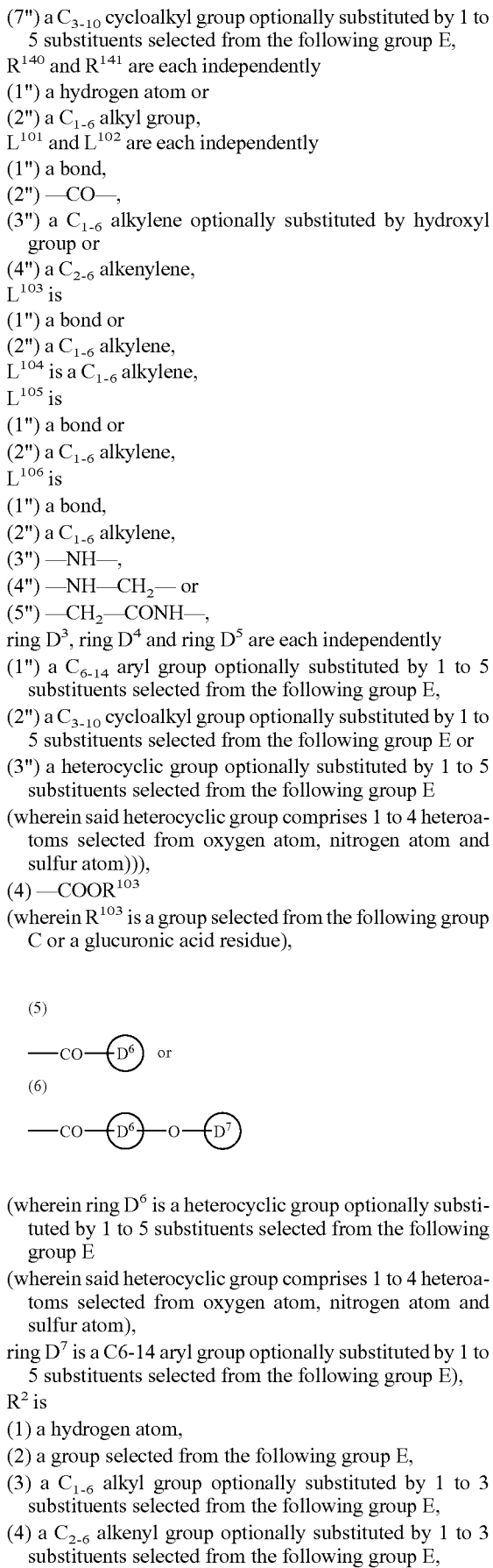

(wherein ring $D^6$ is a heterocyclic group optionally substituted by 1 to 5 substituents selected from the following group E
(wherein said heterocyclic group comprises 1 to 4 heteroatoms selected from oxygen atom, nitrogen atom and sulfur atom),
ring $D^7$ is a C6-14 aryl group optionally substituted by 1 to 5 substituents selected from the following group E),
$R^2$ is
(1) a hydrogen atom,
(2) a group selected from the following group E,
(3) a $C_{1-6}$ alkyl group optionally substituted by 1 to 3 substituents selected from the following group E,
(4) a $C_{2-6}$ alkenyl group optionally substituted by 1 to 3 substituents selected from the following group E,

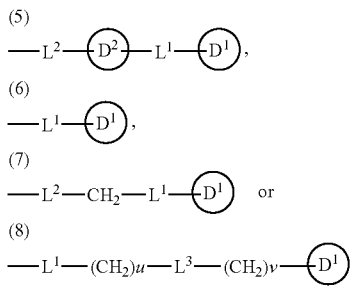

(5) —L²—D²—L¹—D¹, (6) —L¹—D¹, (7) —L²—CH₂—L¹—D¹ or (8) —L¹—(CH₂)u—L³—(CH₂)v—D¹

{wherein u and v are each independently 0 or an integer of 1 to 6, $L^1$ and $L^2$ are each independently (1') a bond, (2') $C_{1-6}$ alkylene, (3') $C_{2-6}$ alkenylene, (4') —(CH₂)$_{u1}$—O—(CH₂)$_{v1}$—, (5') —(CH₂)$_{u1}$—S—(CH₂)$_{v1}$—, (6') —(CH₂)$_{u1}$—NR$^{L1}$—(CH₂)$_{v1}$—, (7') —(CH₂)$_{u1}$—CO—(CH₂)$_{v1}$—, (8') —(CH₂)$_{u1}$—CONR$^{L2}$—(CH₂)$_{v1}$—, (9') —(CH₂)$_{u1}$-NR$^{L2}$CO₂—(CH₂)$_{v1}$—, (10') —(CH₂)$_{u1}$—NR$^{L2}$ CONR$^{L3}$—(CH₂)$_{v1}$—, (11') —(CH₂)$_{u1}$—NR$^{L2}$CO—(CH₂)$_{v1}$—, (12') —(CH₂)$_{u1}$—NR$^{L2}$SO₂—(CH₂)$_{v1}$—, (13') —(CH₂)$_{u1}$—SO₂—(CH₂)$_{v1}$—, (14') —(CH₂)$_{u1}$—SO₂—NR$^{L2}$—(CH₂)$_{v1}$— or (wherein u1 and v1 are each independently 0 or an integer of 1 to 6, $R^{L1}$ is (1") a hydrogen atom, (2") a group selected from the following group C, (3") —COR$^{L11}$, (4") —CONR$^{L11}$R$^{L12}$, (5") —COOR$^{L11}$ or (6") —SO₂R$^{L13}$ (wherein $R^{L11}$ and $R^{L12}$ are each independently a hydrogen atom or a group selected from the following group C, and $R^{L13}$ is a group selected from the following group C), $R^{L2}$, $R^{L2'}$ and $R^{L3}$ are each independently (1") a hydrogen atom, (2") a group selected from the following group C, (3") —COR$^{L11}$ or (4") —SO₂R$^{L13}$ (wherein $R^{L11}$ and $R^{L13}$ are as defined above)), $L^3$ is (1') —CHR$^{L14}$— or (2') —NR$^{L14}$—

(wherein $R^{L14}$ is a group selected from the following group F), ring $D^1$ and ring $D^2$ are each independently (1') a $C_{6-14}$ aryl group optionally substituted by 1 to 5 substituents selected from the following group E, (2') a $C_{3-10}$ cycloalkyl group optionally substituted by 1 to 5 substituents selected from the following group E or (3') a heterocyclic group optionally substituted by 1 to 5 substituents selected from the following group E (wherein said heterocyclic group comprises 1 to 4 heteroatoms selected from oxygen atom, nitrogen atom and sulfur atom)}, $R^3$ is (1) a hydrogen atom, (2) a halogen atom, (3) a $C_{1-6}$ alkanoyl group, (4) a carboxyl group, (5) a cyano group, (6) a nitro group, (7) a $C_{1-6}$ alkyl group optionally substituted by 1 to 3 substituents selected from the following group A, (8) —OR$^{101}$ (wherein $R^{101}$ is a hydrogen atom or a group selected from the following group C), (9) —NR$^{102}$R$^{119}$ (wherein $R^{102}$ and $R^{119}$ are each independently a hydrogen atom, a $C_{1-6}$ alkanoyl group or a $C_{1-6}$ alkylsulfonyl group),

(10) —COOR$^{103}$ (wherein $R^{103}$ is a group selected from the following group C or a glucuronic acid residue),

(11) —CONR$^{104}$R$^{105}$ (wherein $R^{104}$ and $R^{105}$ are each independently a hydrogen atom, a hydroxyl group, a cyano group, a $C_{1-6}$ alkoxy group or a $C_{1-6}$ alkyl group optionally substituted by 1 to 3 substituents selected from the following group A),

(12) —SO₂R$^{106}$ (wherein $R^{106}$ is a hydroxyl group, an amino group, a $C_{1-6}$ alkyl group or a $C_{1-6}$ alkylamino group),

(13) —NHCOR$^{107}$ (wherein $R^{107}$ is an amino group or a $C_{1-6}$ alkylamino group),

(14) —C(=NR$^{108}$)—NH₂

(wherein $R^{108}$ is a hydrogen atom, a $C_{1-6}$ alkyl group optionally substituted by 1 to 3 substituents selected from the following group A, a hydroxyl group or a $C_{1-6}$ alkoxy group),

(15) —P(=O)(OR$^{109}$)₂

(wherein $R^{109}$ are each independently a hydrogen atom or a group selected from the following group C),

(16) —P(=O)(OR$^{110}$)NR$^{111}$R$^{112}$ (wherein $R^{110}$, $R^{111}$ and $R^{112}$ are each independently a hydrogen atom or a group selected from the following group C),

(17) —CONHCO—R$^{113}$ (wherein $R^{113}$ is a group selected from the following group C),

(18) —CONHSO₂—R$^{114}$ (wherein $R^{114}$ is a group selected from the following group C),

(19) —SO₂NHCO—R$^{115}$ (wherein $R^{115}$ is a group selected from the following group C) or

(20) a heterocyclic group optionally substituted by 1 to 5 substituents selected from the following group B (wherein said heterocyclic group comprises 1 to 4 heteroatoms selected from oxygen atom, nitrogen atom and sulfur atom), $R^5$ and $R^6$ are each independently (1) a hydrogen atom, (2) a halogen atom, (3) a $C_{1-6}$ alkyl group optionally substituted by 1 to 3 substituents selected from the following group A, (4) —OR$^{120}$ (wherein $R^{120}$ is a hydrogen atom or a group selected from the following group C) or (5) —NR$^{121}$R$^{122}$ (wherein $R^{121}$ and $R^{122}$ are each independently a hydrogen atom, a $C_{1-6}$ alkanoyl group or a group selected from the following group C), ring Cy is
(1) a $C_{3-10}$ cycloalkyl group optionally substituted by 1 to 5 substituents selected from the following group B,
(2) a $C_{3-10}$ cycloalkenyl group optionally substituted by 1 to 5 substituents selected from the following group B or
(3) a heterocyclic group optionally substituted by 1 to 5 substituents selected from the following group B
(wherein said heterocyclic group comprises 1 to 4 heteroatoms selected from oxygen atom, nitrogen atom and sulfur atom), X is
(1) a group selected from the following group D,
(2) a $C_{2-6}$ alkenyl group optionally substituted by 1 to 3 substituents selected from the following group A or (3)

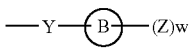

wherein ring B is
(1') a $C_{6-14}$ aryl group,
(2') a $C_{3-10}$ cycloalkyl group or
(3') a heterocyclic group comprising 1 to 4 heteroatoms selected from oxygen atom, nitrogen atom and sulfur atom, each Z is independently
(1') a group selected from the following group D,
(2') a $C_{6-14}$ aryl group optionally substituted by 1 to 5 substituents selected from the following group D,
(3') a $C_{3-10}$ cycloalkyl group optionally substituted by 1 to 5 substituents selected from the following group D,
(4') a $C_{6-14}$ aryl $C_{1-6}$ alkyl group optionally substituted by 1 to 5 substituents selected from the following group D,
(5') a heterocyclic group optionally substituted by 1 to 5 substituents selected from the following group D
(wherein said heterocyclic group comprises 1 to 4 heteroatoms selected from oxygen atom, nitrogen atom and sulfur atom) or
(6') a heterocycle $C_{1-6}$ alkyl group optionally substituted by 1 to 5 substituents selected from the following group D
(wherein said heterocycle $C_{1-6}$ alkyl group is a $C_{1-6}$ alkyl group substituted by "a heterocyclic group optionally substituted by 1 to 5 substituents selected from group D" as defined above), w is an integer of 1 to 3, Y is
(a) $C_{1-6}$ alkylene,
(b) $C_{2-6}$ alkenylene or
(c) $-Y^1-(CH_2)_m-Y^2-(CH_2)_n-$
(wherein m and n are each independently 0 or an integer of 1 to 6, $Y^1$ and $Y^2$ are each independently
(1') a bond,
(2') $-O-$,
(3') $-NR^{y1}-$,
(4') $-S-$,
(5') $-CO-$,
(6') $-SO-$,
(7') $-SO_2-$,
(8') $-CO_2-$,
(9') $-OCO-$,
(10') $-CONR^{y2}-$,
(11') $-NR^{y2}CO-$,
(12') $-SO_2NR^{y2}-$,
(13') $-NR^{y2}SO_2-$,
(14') $-NR^{y2}CO_2-$,
(15') $-OCONR^{y2}-$,
(16') $-NR^{y2}CONR^{y3}-$,
(17') $-CR^{y4}R^{y5}-$ or
(18') $-CH=CH-$
(wherein $R^{y1}$ is
(1") a hydrogen atom,
(2") a group selected from the following group C,
(3") $-COOR^{y11}$,
(4") $-CONR^{y11}R^{y12}$,
(5") $-COR^{y11}$ or
(6") $-SO_2R^{y13}$
(wherein $R^{y11}$ and $R^{y12}$ are each independently a hydrogen atom or a group selected from the following group C, and $R^{y13}$ is a group selected from the following group C), $R^{y2}$ and $R^{y3}$ are each independently
(1") a hydrogen atom,
(2") a group selected from the following group C,
(3") $-COR^{y11}$ or
(4") $-SO_2R^{y13}$ (wherein $R^{y11}$ and $R^{y13}$ are as defined above), $R^{y4}$ and $R^{y5}$ are each independently
(1") a hydrogen atom,
(2") a carboxyl group,
(3") a group selected from group F,
(4") $-OR^{y14}$ or
(5") $-NHR^{y15}$
(wherein $R^{y14}$ is a group selected from the following group C, and $R^{y15}$ is a hydrogen atom, a $C_{1-6}$ alkyl group, a $C_{1-6}$ alkanoyl group or a $C_{6-14}$ aryl $C_{1-6}$ alkyloxycarbonyl group)))

group A:
(1) a halogen atom,
(2) a $C_{1-6}$ alkoxy $C_{1-6}$ alkoxy group,
(3) a cyano group,
(4) $-OR^{a1}$,
(5) $-SR^{a1}$,
(6) $-NR^{a1}R^{a2}$,
(7) $-COOR^{a1}$,
(8) $-CONR^{a1}R^{a2}$,
(9) $-SO_3H$,
(10) $-SO_2NR^{a1}R^{a2}$,
(11) $-NHCOR^{a1}$,
(12) $-NHSO_2R^{a3}$,
(13) $-NHCO_2R^{a4}$ and
(14) $-COR^{a1}$
(wherein $R^{a1}$ and $R^{a2}$ are each a hydrogen atom or a $C_{1-6}$ alkyl group, $R^{a3}$ is a $C_{1-6}$ alkyl group and $R^{a4}$ is a $C_{1-6}$ alkyl group)

group B:
(1) a halogen atom,
(2) a cyano group,
(3) a nitro group,
(4) a $C_{1-6}$ alkyl group,
(5) a $C_{2-6}$ alkenyl group optionally substituted by carboxyl group,
(6) a halogenated $C_{1-6}$ alkyl group,
(7) $-(CH_2)_r-O^{b1}$,
(8) $-(CH_2)_r-SR^{b1}$,
(9) $-(CH_2)_r-NR^{b1}R^{b2}$,
(10) $-(CH_2)_r-COOR^{b1}$,
(11) $-(CH_2)_r-CONR^{b1}R^{b2}$,
(12) $-(CH_2)_r-COR^{b1}$,
(13) $-(CH_2)_r-NR^{b1}-COR^{b2}$,

(14) $-(CH_2)_r-NR^{b1}-SO_2R^{b3}$,
(15) $-(CH_2)_r-SO_2R^{b3}$,
(16) $-(CH_2)_r-SO_2NR^{b1}R^{b2}$,
(17) $-(CH_2)_r-CONR^{b1}-SO_2R^{b3}$,
(18) $-(CH_2)_r-SO_2NR^{b1}-COR^{b2}$,
(19) $-(CH_2)_r-NR^{b1}-COOR^{b3}$,
(20) $-(CH_2)_r-NR^{b1}-CONR^{b2}R^{b4}$,
(21) $-O-(CH_2)_r-COOR^{b1}$ and
(22) $-CO-(CH_2)_r-R^{b5}$
(wherein $R^{b1}$, $R^{b2}$ and $R^{b4}$ are each independently a hydrogen atom or a $C_{1-6}$ alkyl group, $R^{b3}$ is a $C_{1-6}$ alkyl group, and $R^{b5}$ is a heterocyclic group and r is 0 or an integer of 1 to 6)
group C:
(1) a $C_{1-6}$ alkyl group optionally substituted by 1 to 3 substituents selected from the aforementioned group A,
(2) a $C_{6-14}$ aryl group optionally substituted by 1 to 5 substituents selected from the aforementioned group B,
(3) a $C_{6-14}$ aryl $C_{1-6}$ alkyl group optionally substituted by 1 to 5 substituents selected from the aforementioned group B,
(4) a heterocyclic group optionally substituted by 1 to 5 substituents selected from the aforementioned group B and
(5) a heterocycle $C_{1-6}$ alkyl group optionally substituted by 1 to 5 substituents selected from the aforementioned group B
group D:
(a) a hydrogen atom,
(b) a halogen atom,
(c) a cyano group,
(d) a nitro group,
(e) a $C_{1-6}$ alkyl group optionally substituted by 1 to 3 substituents selected from the aforementioned group A,
(f) $-(CH_2)_t-OR^{d1}$,
wherein $R^{d1}$ is
(1) a hydrogen atom,
(2) a group selected from the following group F,
(3) a $C_{2-6}$ alkenyl group optionally substituted by 1 to 3 substituents selected from the aforementioned group A or
(4) a $C_{2-6}$ alkynyl group optionally substituted by 1 to 3 substituents selected from the aforementioned group A,
hereinafter each t is independently 0 or an integer of 1 to 6,
(g) $-(CH_2)_t-S(O)_q-R^{d2}$,
wherein $R^{d2}$ is
(1) a hydrogen atom or
(2) a group selected from the following group F,
q is 0, 1, 2 or 3,
(h) $-(CH_2)_t-NR^{d3}R^{d4}$,
wherein $R^{d3}$ and $R^{d4}$ are each independently
(1) a hydrogen atom or
(2) a group selected from the following group F,
(i) $-(CH_2)_t-COOR^{d5}$,
wherein $R^{d5}$ is
(1) a hydrogen atom or
(2) a group selected from the following group F,
(j) $-(CH_2)_t-CONR^{d6}R^{d7}$,
wherein $R^{d6}$ and $R^{d7}$ are each independently
(1) a hydrogen atom,
(2) a hydroxyl group,
(3) a group selected from the following group F or
(4) a $C_{1-6}$ alkoxy group,
(k) $-(CH_2)_t-COR^{d8}$,
wherein $R^{d8}$ is a group selected from the following group F,
(l) $-(CH_2)_t-NR^{d9}CO-R^{d10}$,
wherein $R^{d9}$ is (1) a hydrogen atom,
(2) a $C_{1-6}$ alkyl group optionally substituted by 1 to 3 substituents selected from the aforementioned group A or
(3) a $C_{1-6}$ alkanoyl group,
$R^{d10}$ is
(1) an amino group,
(2) a $C_{1-6}$ alkylamino group or
(3) a group selected from the following group F,
(m) $-(CH_2)_t-NR^{d11}SO_2-R^{d12}$,
wherein $R^{d11}$ is
(1) a hydrogen atom,
(2) a $C_{1-6}$ alkyl group optionally substituted by 1 to 3 substituents selected from the aforementioned group A or
(3) a $C_{1-6}$ alkanoyl group,
$R^{d12}$ is
(1) a hydrogen atom or
(2) a group selected from the following group F,
(n) $-(CH_2)_t-SO_2-NR^{d13}R^{d14}$,
wherein $R^{d13}$ and $R^{d14}$ are each independently
(1) a hydrogen atom or
(2) a group selected from the following group F,
(o) $-(CH_2)_t-CONR^{d15}-SO_2R^{d16}$,
wherein $R^{d15}$ and $R^{d16}$ are each independently
(1) a hydrogen atom or
(2) a group selected from the following group F,
(p) $-(CH_2)_t-SO_2NR^{d17}-COR^{d18}$,
wherein $R^{d17}$ is
(1) a hydrogen atom or
(2) a group selected from the following group F,
$R^{d18}$ is a group selected from the following group F,
(q) $-(CH_2)_t-NR^{d19}-COOR^{d20}$,
wherein $R^{d19}$ and $R^{d20}$ are each independently
(1) a hydrogen atom or
(2) a group selected from the following group F,
(r) $-(CH_2)_t-NR^{d21}-CONR^{d22}R^{d23}$,
wherein $R^{d21}$, $R^{d22}$ and $R^{d23}$ are each independently
(1) a hydrogen atom or
(2) a group selected from the following group F,
(s) $-(CH_2)_t-C(=NR^{d24})NH_2$,
wherein $R^{d24}$ is
(1) a hydrogen atom,
(2) a hydroxyl group,
(3) a $C_{1-6}$ alkyl group optionally substituted by 1 to 3 substituents selected from the aforementioned group A or
(4) $C_{1-6}$ alkoxy group,
(t) $-(CH_2)_t-O-(CH_2)_p-COR^{d25}$,
wherein $R^{d25}$ is
(1) an amino group,
(2) a $C_{1-6}$ alkylamino group or
(3) a heterocyclic group optionally substituted by 1 to 5 substituents selected from the aforementioned group B,
p is 0 or an integer of 1 to 6, and
(u) a heterocyclic group optionally substituted by 1 to 5 substituents selected from the aforementioned group B
(wherein said heterocyclic group comprises 1 to 4 heteroatoms selected from oxygen atom, nitrogen atom and sulfur atom)
group E:
(a) a halogen atom,
(b) a cyano group,
(c) a nitro group,
(d) an azido group,
(e) $-OP(=O)(OH)_2$,
(f) $-OR^{e1}$, wherein $R^{e1}$ is
(1) a hydrogen atom,
(2) a group selected from the following group F,
(3) a $C_{2-6}$ alkenyl group optionally substituted by 1 to 3 substituents selected from the aforementioned group A or
(4) a $C_{2-6}$ alkynyl group optionally substituted by 1 to 3 substituents selected from the aforementioned group A,
(g) —S(O)$_q$—$R^{e2}$
wherein $R^{e2}$ is
(1) a hydrogen atom or
(2) a group selected from the following group F,
q is 0, 1, 2 or 3,
(h) —NR$^{e3}$R$^{e4}$,
wherein $R^{e3}$ and $R^{e4}$ are each independently
(1) a hydrogen atom,
(2) a cyano group or
(3) a group selected from the following group F,
(i) —COOR$^{e5}$,
wherein $R^{e5}$ is
(1) a hydrogen atom or
(2) a group selected from the following group F,
(j) —CONR$^{e6}$R$^{e7}$,
wherein $R^{e6}$ and $R^{e7}$ are each independently
(1) a hydrogen atom,
(2) a hydroxyl group,
(3) a group selected from the following group F or
(4) a $C_{1-6}$ alkoxy group,
(k) —COR$^{e8}$,
wherein $R^{e8}$ is a group selected from the following group F,
(1) NR$^{e9}$CO—R$^{e10}$,
wherein $R^{e9}$ is
(1) a hydrogen atom,
(2) a $C_{1-6}$ alkyl group or
(3) a $C_{1-6}$ alkanoyl group,
$R^{e10}$ is
(1) a hydrogen atom,
(2) an amino group,
(3) a $C_{1-6}$ alkylamino group,
(4) a $C_{2-6}$ alkenyl group optionally substituted by 1 to 3 substituents selected from the aforementioned group A or
(5) a group selected from the following group F,
(m) —NR$^{e11}$SO$_2$—R$^{e12}$,
wherein $R^{e11}$ is
(1) a hydrogen atom,
(2) a $C_{1-6}$ alkyl group or
(3) a $C_{1-6}$ alkanoyl group,
$R^{e12}$ is
(1) a hydrogen atom or
(2) a group selected from the following group F,
(n) —SO$_2$—NR$^{e13}$R$^{e14}$,
wherein $R^{e13}$ and $R^{e14}$ are each independently
(1) a hydrogen atom or
(2) a group selected from the following group F,
(o) —CONR$^{e15}$—SO$_2$R$^{e16}$,
wherein $R^{e15}$ and $R^{e16}$ are each independently
(1) a hydrogen atom or
(2) a group selected from the following group F,
(p) —SO$_2$NR$^{e17}$—COR$^{e18}$,
wherein $R^{e17}$ is
(1) a hydrogen atom or
(2) a group selected from the following group F,
$R^{e18}$ is a group selected from the following group F,
(q) —NR$^{e19}$—COOR$^{e20}$,
wherein $R^{e19}$ and $R^{e20}$ are each independently
(1) a hydrogen atom or
(2) a group selected from the following group F,
(r) —NR$^{e21}$—CONR$^{e22}$R$^{e23}$
wherein $R^{e21}$, $R^{e22}$ and $R^{e23}$ are each independently
(1) a hydrogen atom or
(2) a group selected from the following group F,
(s) —NHCO—COOR$^{e24}$
wherein $R^{e24}$ is
(1) a hydrogen atom or
(2) a group selected from the following group F,
(t) —NHCO—CONR$^{e25}$R$^{e26}$
wherein $R^{e25}$ and $R^{e26}$ are each independently
(1) a hydrogen atom,
(2) a hydroxyl group or
(3) a group selected from the following group F,
(u) —CONH—COOH, (v)
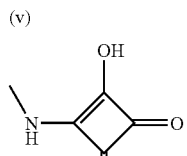

(w)
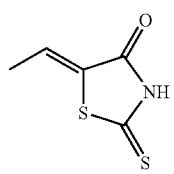

(x)
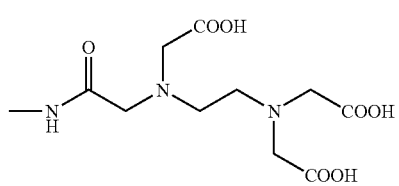

(y) a $C_{6-14}$ aryl group optionally substituted by 1 to 5 substituents selected from the aforementioned group B,
(z) a $C_{3-10}$ cycloalkyl group optionally substituted by 1 to 5 substituents selected from the aforementioned group B,
(aa) a heterocyclic group optionally substituted by 1 to 5 substituents selected from the aforementioned group B (wherein said heterocyclic group comprises 1 to 4 heteroatoms selected from oxygen atom, nitrogen atom and sulfur atom),
(bb) a $C_{3-10}$ cycloalkylidene group optionally substituted by 1 to 5 substituents selected from the aforementioned group B, and
(cc) a heterocycle ylidene group optionally substituted by 1 to 5 substituents selected from the aforementioned group B (wherein said heterocycle ylidene group comprises 1 to 4 heteroatoms selected from oxygen atom, nitrogen atom and sulfur atom),
when group E is a substituent on a $C_{6-14}$ aryl group, a $C_{3-10}$ cycloalkyl group or a heterocyclic group, it may be
(dd) a $C_{1-6}$ alkyl group optionally substituted by 1 to 3 substituents selected from the aforementioned group A,
(ee) a $C_{2-6}$ alkenyl group optionally substituted by 1 to 3 substituents selected from the aforementioned group A, (ff) a $C_{2-6}$ alkynyl group optionally substituted by 1 to 3 substituents selected from the aforementioned group A, (gg) $C_{1-6}$ alkylidene group optionally substituted by 1 to 3 substituents selected from the aforementioned group A, (hh) a $C_{6-14}$ aryl $C_{1-6}$ alkyl group optionally substituted by 1 to 5 substituents selected from the aforementioned group B, (ii) a $C_{3-10}$ cycloalkyl $C_{1-6}$ alkyl group optionally substituted by 1 to 5 substituents selected from the aforementioned group B, or (jj) a heterocycle $C_{1-6}$ alkyl group optionally substituted by 1 to 5 substituents selected from the aforementioned group B group F:

(1) a $C_{1-6}$ alkyl group optionally substituted by 1 to 3 substituents selected from the aforementioned group A, (2) a $C_{6-14}$ aryl group optionally substituted by 1 to 5 substituents selected from the aforementioned group B, (3) a heterocyclic group optionally substituted by 1 to 5 substituents selected from the aforementioned group B (wherein said heterocyclic group comprises 1 to 4 heteroatoms selected from oxygen atom, nitrogen atom and sulfur atom), (4) a $C_{3-10}$ cycloalkyl group optionally substituted by 1 to 5 substituents selected from the aforementioned group B, (5) a $C_{6-14}$ aryl $C_{1-6}$ alkyl group optionally substituted by 1 to 5 substituents selected from the aforementioned group B, (6) a heterocycle $C_{1-6}$ alkyl group optionally substituted by 1 to 5 substituents selected from the aforementioned group B (wherein said heterocycle $C_{1-6}$ alkyl group is a $C_{1-6}$ alkyl group substituted by a heterocyclic group optionally substituted by 1 to 5 substituents selected from group B as defined above) and (7) a $C_{3-10}$ cycloalkyl $C_{1-6}$ alkyl group optionally substituted by 1 to 5 substituents selected from the aforementioned group B.

2. The thienopyrrole compound of claim 1, wherein Q is —$CH_2$—O-# or —$CH_2$—N($R^2$), or a pharmaceutically acceptable salt thereof.

3. The thienopyrrole compound of claim 2, wherein Q is —$CH_2$—O-#, or a pharmaceutically acceptable salt thereof.

4. The thienopyrrole compound of claim 2, wherein Q is —$CH_2$—N($R^2$)-#, or a pharmaceutically acceptable salt thereof.

5. The thienopyrrole compound of claim 1, wherein $R^1$ is a carboxyl group, or a pharmaceutically acceptable salt thereof.

6. The thienopyrrole compound of claim 1, wherein R is —$CONHR^{12}$, or a pharmaceutically acceptable salt thereof.

7. The thienopyrrole compound of claim 6, wherein $R^{12}$ is a hydrogen atom or,

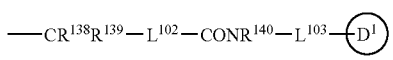

or a pharmaceutically acceptable salt thereof.

8. The thienopyrrole compound of claim 4, wherein $R^2$ is selected from a hydrogen atom, a $C_{1-6}$ alkyl group optionally substituted by 1 to 3 substituents selected from group E and,

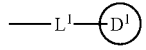

or a pharmaceutically acceptable salt thereof.

9. The thienopyrrole compound of claim 8, wherein $R^2$ is a $C_{1-6}$ alkyl group optionally substituted by 1 to 3 substituents selected from group E, or a pharmaceutically acceptable salt thereof.

10. The thienopyrrole compound of claim 8, wherein $R^2$ is,

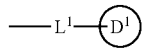

or a pharmaceutically acceptable salt thereof.

11. The thienopyrrole compound of claim 1, wherein $R^3$ is a hydrogen atom, or a pharmaceutically acceptable salt thereof.

12. The thienopyrrole compound of claim 1, wherein $R^5$ and $R^6$ are each a hydrogen atom, or a pharmaceutically acceptable salt thereof.

13. The thienopyrrole compound of claim 1, wherein $R^5$ is —$NR^{121}R^{122}$ wherein $R^{121}$ and $R^{122}$ are each independently a heterocycle $C_{1-6}$ alkyl group optionally substituted by 1 to 5 substituents selected from group B, and $R^6$ is a hydrogen atom, or a pharmaceutically acceptable salt thereof.

14. The thienopyrrole compound of claim 1, wherein ring Cy is a $C_{3-10}$ cycloalkyl group optionally substituted by 1 to 5 substituents selected from group B, or a pharmaceutically acceptable salt thereof.

15. The thienopyrrole compound of claim 1, wherein X is a group selected from group D, or a pharmaceutically acceptable salt thereof.

16. The thienopyrrole compound of claim 15, wherein X is a hydrogen atom, a halogen atom, a $C_{1-6}$ alkyl group optionally substituted by 1 to 3 substituents selected from group A or —$OR^{d1}$, or a pharmaceutically acceptable salt thereof.

17. The thienopyrrole compound of claim 1, wherein X is,

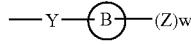

or a pharmaceutically acceptable salt thereof.

18. The thienopyrrole compound of claim 17, wherein Y is —$(CH_2)_m$—O—$(CH_2)_n$—, or a pharmaceutically acceptable salt thereof.

19. The thienopyrrole compound of claim 17, wherein ring B is a $C_{6-14}$ aryl group or a heterocyclic group comprising 1 to 4 heteroatoms selected from oxygen atom, nitrogen atom and sulfur atom, or a pharmaceutically acceptable salt thereof.

20. The thienopyrrole compound of claim 17, wherein Z is 1 to 3 substituents selected from (1) a hydrogen atom, (2) a heterocyclic group optionally substituted by 1 to 5 substituents selected from group D, (3) —$(CH_2)_t$—S(O)$_q$—$R^{d2}$ and (4) —$(CH_2)_t$—$COOR^{d5}$, or a pharmaceutically acceptable salt thereof.

21. The thienopyrrole compound of claim 1 or a pharmaceutically acceptable salt thereof, which is selected from the group consisting of methyl 11-cyclohexyl-8-hydroxy-4,5-dihydro-6-oxa-1-thia-3b-azabenzo[e]cyclopenta[a]azulene-2-carboxylate, methyl 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylate, 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxylic acid, 11-cyclohexyl-8-[5-methanesulfonyl-2-(morpholin-4-yl)benzyloxy]-4,5-dihydro-6-oxa-1-thia-3b-azabenzo[e]cyclopenta[a]azulene-2-carboxamide, methyl 11-cyclohexyl-5-oxo-5,6-dihydro-4H-1-thia-3b,6-diazabenzo[e]cyclopenta[a]azulene-2-carboxylate, methyl 11-cyclohexyl-5-oxo-6-[2-oxo-2-(piperidin-1-yl)ethyl]-5,6-dihydro-4H-1-thia-3b,6-diazabenzo[e]cyclopenta[a]azulene-2-carboxylate, methyl 11-cyclohexyl-6-[2-(piperidin-1-yl)ethyl]-5,6-dihydro-4H-1-thia-3b,6-diazabenzo[e]cyclopenta[a]azulene-2-carboxylate, 11-cyclohexyl-6-[2-(piperidin-1-yl)ethyl]-5,6-dihydro-4H-1-thia-3b,6-diazabenzo[e]cyclopenta[a]azulene-2-carboxylic acid dihydrochloride, methyl 6-[2-(4-tert-butoxycarbonylpiperazin-1-yl)-2-oxoethyl]-11-cyclohexyl-5-oxo-5,6-dihydro-4H-1-thia-3b,6-diazabenzo[e]cyclopenta[a]azulene-2-carboxylate, methyl 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylate, 6-[2-(4-tert-butoxycarbonylpiperazin-1-yl)ethyl]-11-cyclohexyl-5,6-dihydro-4H-1-thia-3b,6-diazabenzo[e]cyclopenta[a]azulene-2-carboxylic acid hydrochloride, methyl 11-cyclohexyl-5,6-dihydro-4H-1-thia-3b,6-diazabenzo[e]cyclopenta[a]azulene-2-carboxylate, methyl 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylate, 11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylic acid dihydrochloride, 11-cyclohexyl-4,5-dihydro-6-oxa-1-thia-3b-azabenzo[e]cyclopenta[a]azulene-2-carboxylic acid, 11-cyclohexyl-8-[2-(morpholin-4-yl)-5-(2-oxopyrrolidin-1-yl)benzyloxy]-4,5-dihydro-6-oxa-1-thia-3b-azabenzo[e]cyclopenta[a]azulene-2-carboxylic acid hydrochloride, 11-cyclohexyl-8-(1-methoxycarbonylpiperidin-3-yloxy)-4,5-dihydro-6-oxa-1-thia-3b-azabenzo[e]cyclopenta[a]azulene-2-carboxylic acid, 11-cyclohexyl-8-[2-(4-methanesulfonylpiperazin-1-yl)-5-(2-oxopyrrolidin-1-yl)benzyloxy]-4,5-dihydro-6-oxa-1-thia-3b-azabenzo[e]cyclopenta[a]azulene-2-carboxylic acid, 11-cyclohexyl-8-methyl-6-[2-(piperidin-1-yl)ethyl]-5,6-dihydro-4H-1-thia-3b,6-diazabenzo[e]cyclopenta[a]azulene-2-carboxylic acid dihydrochloride, 8-chloro-11-cyclohexyl-6-[2-(piperidin-1-yl)ethyl]-5,6-dihydro-4H-1-thia-3b,6-diazabenzo[e]cyclopenta[a]azulene-2-carboxylic acid dihydrochloride, 6-[2-(azocan-1-yl)ethyl]-11-cyclohexyl-5,6-dihydro-4H-1-thia-3b,6-diazabenzo[e]cyclopenta[a]azulene-2-carboxylic acid dihydrochloride, 11-cyclohexyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride, (S)-11-cyclohexyl-6-{2-[3-(2-methoxyethyl)piperidin-1-yl]ethyl}-5,6-dihydro-4H-1-thia-3b,6-diazabenzo[e]cyclopenta[a]azulene-2-carboxylic acid dihydrochloride, 11-cyclohexyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride, 6-[2-(azocan-1-yl)ethyl]-11-cyclohexyl-8-methyl-5,6-dihydro-4H-1-thia-3b,6-diazabenzo[e]cyclopenta[a]azulene-2-carboxylic acid dihydrochloride, 11-cyclohexyl-8-methyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride, (S)-11-cyclohexyl-6-{2-[3-(2-methoxyethyl)piperidin-1-yl]ethyl}-8-methyl-5,6-dihydro-4H-1-thia-3b,6-diazabenzo[e]cyclopenta[a]azulene-2-carboxylic acid dihydrochloride, 11-cyclohexyl-8-methyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride, 6-[2-(azocan-1-yl)ethyl]-8-chloro-11-cyclohexyl-5,6-dihydro-4H-1-thia-3b,6-diazabenzo[e]cyclopenta[a]azulene-2-carboxylic acid dihydrochloride, 8-chloro-11-cyclohexyl-6-[2-(3-methylpiperidin-1-yl)ethyl]-5,6-dihydro-4H-1-thia-3b,6-diazabenzo[e]cyclopenta[a]azulene-2-carboxylic acid dihydrochloride, (S)-8-chloro-11-cyclohexyl-6-{2-[3-(2-methoxyethyl)piperidin-1-yl]ethyl}-5,6-dihydro-4H-1-thia-3b,6-diazabenzo[e]cyclopenta[a]azulene-2-carboxylic acid dihydrochloride, 8-chloro-11-cyclohexyl-6-[2-(1,4-oxazepan-4-yl)ethyl]-5,6-dihydro-4H-1-thia-3b,6-diazabenzo[e]cyclopenta[a]azulene-2-carboxylic acid dihydrochloride, 6-[2-(4-tert-butoxycarbonylpiperazin-1-yl)ethyl]-11-cyclohexyl-8-methyl-5,6-dihydro-4H-1-thia-3b,6-diazabenzo[e]cyclopenta[a]azulene-2-carboxylic acid hydrochloride, 6-[2-(4-tert-butoxycarbonylpiperazin-1-yl)ethyl]-8-chloro-11-cyclohexyl-5,6-dihydro-4H-1-thia-3b,6-diazabenzo[e]cyclopenta[a]azulene-2-carboxylic acid hydrochloride, 11-cyclohexyl-6-[2-(4-ethylpiperazin-1-yl)-2-oxoethyl]-8-methyl-5,6-dihydro-4H-1-thia-3b,6-diazabenzo[e]cyclopenta[a]azulene-2-carboxylic acid dihydrochloride, and 8-chloro-11-cyclohexyl-6-[2-(4-ethylpiperazin-1-yl)-2-oxoethyl]-5,6-dihydro-4H-1-thia-3b,6-diazabenzo[e]cyclopenta[a]azulene-2-carboxylic acid dihydrochloride.

22. The thienopyrrole compound of claim 1 or a pharmaceutically acceptable salt thereof, which is selected from the group consisting of (E)-3-[4-({1-[(11-cyclohexyl-8-methoxy-4,5-dihydro-6-oxa-1-thia-3b-azabenzo[e]cyclopenta[a]azulene-2-carbonyl)amino]cyclobutanecarbonyl}amino)phenyl]acrylic acid, (E)-3-[4-({1-[(11-cyclohexyl-6,8-dimethyl-5,6-dihydro-4H-1-thia-3b,6-diazabenzo[e]cyclopenta[a]azulene-2-carbonyl)amino]cyclobutanecarbonyl}amino)phenyl]acrylic acid, (E)-3-[4-({1 -[(8-chloro-11-cyclohexyl-6-methyl-5,6-dihydro-4H-1-thia-3b,6-diazabenzo[e]cyclopenta[a]azulene-2-carbonyl)amino]cyclobutanecarbonyl}amino)phenyl]acrylic acid, (E)-3-[3-({1-[(11-cyclohexyl-8-methoxy-4,5-dihydro-6-oxa-1-thia-3b-azabenzo[e]cyclopenta[a]azulene-2-carbonyl)amino]cyclobutanecarbonyl}amino)phenyl]acrylic acid, 11-cyclohexyl-8-ethoxy-4,5-dihydro-6-oxa-1-thia-3b-azabenzo[e]cyclopenta[a]azulene-2-carboxylic acid, 7-{bis[2-(piperidin-1-yl)ethyl]amino}-11-cyclohexyl-4,5-dihydro-6-oxa-1-thia-3b-azabenzo[e]cyclopenta[a]azulene-2-carboxylic acid trihydrochloride, (E)-3-[4-({1-[(11-cyclohexyl-8-ethoxy-4,5-dihydro-6-oxa-1-thia-3b-azabenzo[e]cyclopenta[a]azulene-2-carbonyl)amino]cyclobutanecarbonyl}amino)phenyl]acrylic acid, 11-cyclohexyl-8-ethoxy-6-methyl-5,6-dihydro-4H-1-thia-3b,6-diazabenzo[e]cyclopenta[a]azulene-2-carboxylic acid, (E)-3-[4-({1-[(11-cyclohexyl-8-ethoxy-6-methyl-5,6-dihydro-4H-1-thia-3b,6-diazabenzo[e]cyclopenta[a]azulene-2-carbonyl)amino]cyclobutanecarbonyl}amino)phenyl]acrylic acid, and 7-{bis[2-(morpholin-4-yl)ethyl]amino}-1-cyclohexyl-4,5-dihydro-6-oxa-1-thia-3b-azabenzo[e]cyclopenta[a]azulene-2-carboxylic acid trihydrochloride.

23. A pharmaceutical composition comprising a thienopyrrole compound of claims 1-22 or a pharmaceutically acceptable salt thereof, and a pharmaceutically acceptable carrier.

24. A method for treating hepatitis C, which comprises administering an effective amount of a thienopyrrole compound of any one of claims 1-22 or a pharmaceutically acceptable salt thereof to a mammal.

25. A method for inhibiting hepatitis C virus polymerase, which comprises administering an effective amount of a thienopyrrole compound of claim 1 or a pharmaceutically acceptable salt thereof to a mammal.

* * * * *

UNITED STATES PATENT AND TRADEMARK OFFICE
CERTIFICATE OF CORRECTION

PATENT NO. : 7,659,263 B2  Page 1 of 2
APPLICATION NO. : 11/271136
DATED : February 9, 2010
INVENTOR(S) : Mizojiri et al.

It is certified that error appears in the above-identified patent and that said Letters Patent is hereby corrected as shown below:

On the Cover page, (*) Notice: Subject to any disclaimer, the term of this patent is extended or adjusted under 35 USC 154(b) by 383 days.

Delete the phrase "by 383 days" and insert --by 616 days--

Column 361, line 33, "arloxy" should read --aryloxy--

Column 363, line 44, "$R^{135}$ and $R^{136}$, or $R^{138}$ and $R^{139}$ are bonded to each," should read --$R^{135}$ and $R^{136}$, or, $R^{138}$ and $R^{139}$ are bonded to each other--

Column 364, line 58, "C6-14" should read --$C_{6-14}$--

Column 365, line 31, insert --or-- after "(13') -$(CH_2)_{u1}$-$SO_2$-$(CH_2)_{v1}$-,"

Column 365, line 32, delete "or"

Column 365, line 46, "$R^{L2}$, $R^{L2'}$ and $R^{L3}$" should read --$R^{L2}$ and $R^{L3}$--

Column 367, line 46, delete "''"

Column 367, line 47, delete "'''"

Column 368, line 61, "(7) -$(CH_2)_r$-$O^{b1}$," should read --(7) -$(CH_2)_r$-$OR^{b1}$,--

Column 373, line 42, "or -$CH_2$-$N(R^2)$," should read --or -$CH_2$-$N(R^2)$-#,--

Signed and Sealed this

Thirty-first Day of August, 2010

David J. Kappos
*Director of the United States Patent and Trademark Office*

CERTIFICATE OF CORRECTION (continued)
U.S. Pat. No. 7,659,263 B2

Column 373, lines 56-59,

"$—CR^{138}R^{139}—L^{102}—CONR^{140}—L^{103}—(D^1)$" should read $--—CR^{138}R^{139}—L^{102}—CONR^{140}—L^{103}—(D^3)--$, Column 378, line 1, "7-{bis[2-(morpholin-4-yl)ethyl]amino}-1-cyclohexyl-4," should read --7-{bis[2-(morpholin-4-yl)ethyl]amino}-11-cyclohexyl-4,--